United States Patent
Goodman et al.

(10) Patent No.: US 7,749,998 B2
(45) Date of Patent: Jul. 6, 2010

(54) MORPHOLINYL AND PYRROLIDINYL ANALOGS

(75) Inventors: Krista B. Goodman, King of Prussia, PA (US); Michael J. Neeb, King of Prussia, PA (US); Clark A. Sehon, King of Prussia, PA (US); Andrew Q. Viet, King of Prussia, PA (US); Gren Z. Wang, King of Prussia, PA (US)

(73) Assignee: GlaxoSmithKline LLC, Philadelphia, PA (US)

( * ) Notice: Subject to any disclaimer, the term of this patent is extended or adjusted under 35 U.S.C. 154(b) by 0 days.

(21) Appl. No.: 12/373,901

(22) PCT Filed: Jul. 20, 2007

(86) PCT No.: PCT/US2007/073951

§ 371 (c)(1),
(2), (4) Date: Jan. 15, 2009

(87) PCT Pub. No.: WO2008/011551

PCT Pub. Date: Jan. 24, 2008

(65) Prior Publication Data

US 2009/0275571 A1    Nov. 5, 2009

Related U.S. Application Data

(60) Provisional application No. 60/832,176, filed on Jul. 20, 2006, provisional application No. 60/870,202, filed on Dec. 15, 2006.

(51) Int. Cl.
- *C07D 413/12* (2006.01)
- *A61K 31/538* (2006.01)
- *A61P 9/10* (2006.01)
- *A61P 9/04* (2006.01)
- *A61P 13/10* (2006.01)

(52) U.S. Cl. .................. 514/230.5; 544/105
(58) Field of Classification Search ............. 514/230.5; 544/105
See application file for complete search history.

(56) References Cited

U.S. PATENT DOCUMENTS

| | | | |
|---|---|---|---|
| 4,999,359 | A | 3/1991 | Vecchletti et al. |
| 5,087,630 | A | 2/1992 | Colle et al. |
| 6,514,970 | B1 | 2/2003 | Dhanak et al. |
| 6,544,992 | B1 | 4/2003 | Dhanak et al. |
| 6,818,655 | B2 | 11/2004 | Dhanak et al. |
| 6,849,635 | B2 | 2/2005 | Dhanak et al. |
| 7,019,008 | B2 | 3/2006 | Dhanak et al. |
| 7,432,258 | B2 | 10/2008 | Goodman et al. |
| 2003/0100580 | A1 | 5/2003 | Dhanak et al. |
| 2004/0039017 | A1 | 2/2004 | Dhanak et al. |
| 2004/0053963 | A1 | 3/2004 | Dhanak et al. |
| 2004/0142923 | A1 | 7/2004 | Dhanak et al. |
| 2004/0142948 | A1 | 7/2004 | Dhanak et al. |
| 2004/0152692 | A1 | 8/2004 | Dhanak et al. |
| 2004/0152891 | A1 | 8/2004 | Dhanak et al. |
| 2004/0152895 | A1 | 8/2004 | Dhanak et al. |
| 2004/0198979 | A1 | 10/2004 | Dhanak et al. |
| 2005/0043536 | A1 | 2/2005 | Dhanak et al. |
| 2005/0107355 | A1 | 5/2005 | Dolle et al. |

FOREIGN PATENT DOCUMENTS

| | | |
|---|---|---|
| WO | WO02/079188 | 10/2002 |
| WO | WO2004/043366 | 5/2004 |
| WO | WO2004/043368 | 5/2004 |
| WO | WO2004/043369 | 5/2004 |
| WO | WO2004/043463 | 5/2004 |
| WO | WO2004/043917 | 5/2004 |
| WO | WO2004/043948 | 5/2008 |

*Primary Examiner*—Kahsay T Habte
(74) *Attorney, Agent, or Firm*—Linda E. Hall; Robert J. Smith

(57) ABSTRACT

The present invention relates to morpholinyl, and pyrrolidinyl analogs, pharmaceutical compositions containing them, and their use as antagonists of urotensin II.

10 Claims, No Drawings

MORPHOLINYL AND PYRROLIDINYL ANALOGS

This application is a 371 of International Application No. PCT/US2007/073951, filed 20 Jul. 2007, which claims the benefit of 60/832,176, filed 20 Jul. 2006 and 60/870,202 filed 15 Dec. 2006, which are incorporated herein in their entirety.

FIELD OF THE INVENTION

The present invention relates to morpholinyl and pyrrolidinyl analogs, pharmaceutical compositions containing them and their use as urotensin II antagonists.

BACKGROUND OF THE INVENTION

The integrated control of cardiovascular homeostasis is achieved through a combination of both direct neuronal control and systemic neurohormonal activation. Although the resultant release of both contractile and relaxant factors is normally under stringent regulation, an aberration in this status quo can result in cardiohemodynamic dysfunction with pathological consequences.

The principal mammalian vasoactive factors that comprise this neurohumoral axis, namely angiotensin-II, endothelin-1, and norepinephrine, all function via an interaction with specific G-protein coupled receptors (GPCR). The urotensin-II/UT receptor (formerly known as GPR14) system represents a novel member of this neurohumoral axis. As such, inhibitors of this system have the potential to be of utility in the management of a diverse range of diseases.

In studies with human Urotensin-II [Ames et. al. *Nature* 1999, 401, 282-286; Behm et al., 2004, *Naunyn-Schmeid. Arch. Pharmacol.*, 369; 274-280] it was found that it was an extremely potent and efficacious vasoconstrictor in vitro and in vivo; exhibited sustained contractile activity that was extremely resistant to wash out; and had detrimental effects on cardiac performance (myocardial contractility).

Human Urotensin-II was assessed for contractile activity in the rat-isolated aorta and was shown to be the most potent contractile agonist identified to date. Based on the in vitro pharmacology and in vivo hemodynamic profile of human Urotensin-II in the cat [Behm et al., 2004, *Naunyn-Schmeid. Arch. Pharmacol.*, 369; 274-280), monkey [Ames et. al. *Nature* 1999, 401, 282-286] and human [Lim et al., 2004, *Circulation*, 109; 1212-1214] it plays a pathological role in cardiovascular diseases characterized by excessive or abnormal vasoconstriction and myocardial dysfunction [Douglas et al., 2004, *Trends Pharmacol. Sci.*, 25; 76-85].

Compounds that antagonize the Urotensin-II receptor may be useful in the treatment of congestive heart failure, stroke, ischemic heart disease (angina, myocardial ischemia), cardiac arrhythmia, hypertension (essential and pulmonary), COPD, fibrosis (e.g. pulmonary fibrosis), restenosis, atherosclerosis, dyslipidemia, asthma [Hay D W P, Luttmann M A, Douglas S A: 2000, Br J Pharmacol: 131; 10-12, Gilbert et al. 2004, *Curr Opin Investig Drugs*, 5; 276-282 and Douglas et al. 2004, *Trends Pharmacol. Sci.*, 25; 76-85], neurogenic inflammation and metabolic vasculopathies all of which are characterized by abnormal vasoconstriction and/or myocardial dysfunction. Urotensin antagonists may provide end organ protection in hypersensitive cohorts in addition to lowering blood pressure.

Since Urotensin-II (U-II) is expressed within the mammalian CNS [Ames et. al. *Nature* 1999, 401, 282; Chartrel et al., 2004; *J. Neurochem.*, 91; 110-118], U-II antagonists may be useful in the treatment of addiction, schizophrenia, cognitive disorders/Alzheimer's disease, [Gartlon J. Psychopharmacology (Berl) 2001 June; 155(4):426-33], impulsivity, anxiety, stress, depression, pain, migraine, neuromuscular function, Parkinson's, movement disorders, sleep-wake cycle, and incentive motivation [Clark et al. *Brain Research* 923 (2001) 120-127].

Functional U-II receptors are expressed in rhabdomyosarcomas cell lines and therefore U-II antagonists may have oncological indications. [Takahashi et al., 2003, Peptides, 24; 301-306; Matsushita et al., 2003, Endocrinology, 144; 1825-1831; Yoshimoto et al., 2004, Peptides, 25; 1775-1781]. Urotensin II may also be implicated in various metabolic diseases such as diabetes [Ames et. al. *Nature* 1999, 401, 282; Wenyi et al., 2003, *Diabetologia*, 46; 972-976] in various gastrointestinal disorders [Horie et al., 2003, *Neuropharmacology*, 45; 1019-1027], bone, cartilage, and joint disorders/inflammation (e.g. arthritis and osteoporosis; [Bottrill et al., 2000; *Br. J. Pharmacol.*, 130; 1865-1870; Horie et al., 2003, *Neuropharmacology*, 45; 1019-1027; Suga et al., 2004, *J, Biochem.*, 135; 605-613]; and genito-urinary disorders, including overactive bladder [Yano et al., 1994, *Gen. Comp. Endocrinol.*, 96; 412-419]. Therefore, these compounds may be useful for the prevention (treatment) of gastric reflux, gastric motility, ulcers, arthritis, osteoporosis and urinary incontinence [Yano et al., 1994, *Gen. Comp. Endocrinol.*, 96; 412-419] and obesity [Takahashi K, Endocr J. 2004 February; 51(1):1-17].

SUMMARY OF THE INVENTION

In one aspect this invention provides for morpholinyl and pyrrolidinyl analogs and pharmaceutical compositions containing them.

In a second aspect, this invention provides for the use of the compounds of Formula (I) as antagonists of urotensin II and as inhibitors of urotensin II.

In another aspect, this invention provides for the use of the compounds of Formula (I) for treating and preventing conditions associated with urotensin II imbalance.

In yet another aspect, this invention provides for the use of the compounds of Formula (I) for the treatment or prevention of congestive heart failure, stroke, ischemic heart disease (e.g. angina, myocardial ischemia), cardiac arrhythmia, hypertension (e.g. essential and pulmonary), renal disease (acute and chronic renal failure/end stage renal disease, nephrotoxicity) peripheral vascular disease (e.g. male erectile dysfunction, diabetic retinopathy, intermittent claudication/ischemic limb disease) and ischemic/hemorrhagic stroke, COPD, restenosis, asthma, neurogenic inflammation, migraine, metabolic vasculopathies, bone/cartilage/joint diseases (e.g. osteoporosis, arthritis), arthritis, other inflammatory diseases, fibrosis (e.g. pulmonary fibrosis), sepsis, atherosclerosis, thromboembolic disorders, dyslipidemia, addiction, schizophrenia, cognitive disorders/Alzheimer's disease, impulsivity, anxiety, stress, depression, Parkinson's, movement disorders, sleep-wake cycle, incentive motivation, pain, (e.g. inflammatory and visceral pain) neuromuscular function, diabetes, diabetes/metabolic syndrome, eating disorders, gastric reflux, gastric motility disorders, IBS, colitis, ulcers, obesity, overactive bladder, and genitourinary diseases.

The urotensin antagonist may be administered alone or in conjunction with one or more other therapeutic agents, e.g. agents being selected from the group consisting of endothelin receptor antagonists, angiotensin converting enzyme (ACE) inhibitors, A-II receptor antagonists, vasopeptidase inhibitors, diuretics, digoxin, and dual non-selective β-adrenoceptor and α$_1$-adrenoceptor antagonists.

Other aspects and advantages of the present invention are described further in the following detailed description of the preferred embodiments thereof.

DETAILED DESCRIPTION OF THE INVENTION

The present invention provides for compounds of Formula (I):

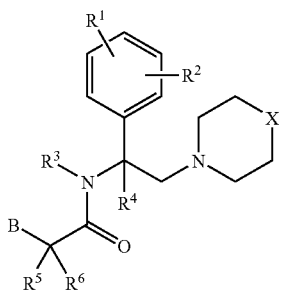

Wherein:

R$^1$ is

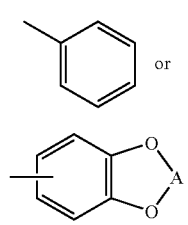

A is (CH$_2$)$_n$;

n is 1 or 2;

the group (a) may be unsubstituted or substituted by one, two, or three substituents chosen from: halo, OC$_{1-3}$ alkyl, OH, CN, C(O)OH, NR$_7$R$_8$, OCF$_3$, C(O)NR$_9$R$_{10}$, SO$_2$C$_{1-3}$ alkyl, SO$_2$C$_{3-6}$ cycloalkyl, SO$_2$-phenyl, SO$_2$NR$_9$R$_{10}$, CF$_3$, and NO$_2$;

R$^2$ is hydrogen, halo, OC$_{1-3}$ alkyl, NHC(O)C$_{1-3}$ alkyl, NHSO$_2$C$_{1-3}$alkyl, NHSO$_2$-phenyl, NHC(O)C$_{3-6}$ cycloalkyl, or NHC(O)-phenyl;

R$^3$ is C$_{1-3}$ alkyl or C$_{3-6}$ cycloalkyl

R$^4$, R$^5$, and R$^6$ are independently hydrogen or CH$_3$;

R$^7$ and R$^8$ are independently hydrogen, C(O)C$_{1-3}$ alkyl, C(O)C$_{3-6}$ cycloalkyl, C(O)-phenyl, C$_{1-6}$ alkyl, phenyl, SO$_2$C$_{1-3}$ alkyl, SO$_2$C$_{3-6}$ cycloalkyl, SO$_2$-phenyl, or C(O)NHC$_{1-3}$ alkyl;

R$^9$ and R$^{10}$ are independently hydrogen, C$_{1-3}$ alkyl, C$_{3-6}$ cycloalkyl, phenyl; or taken together R$^9$ and R$^{10}$ may form a 5 to 7 member ring optionally containing one or two heteroatoms chosen from O, N, and S;

X is O or a bond;

B is:

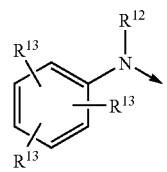

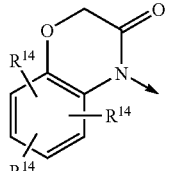

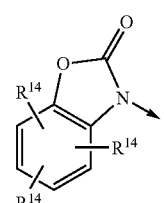

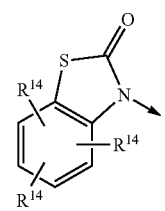

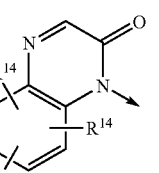

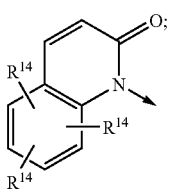

R$^{12}$ is hydrogen, C$_{1-3}$ alkyl, CH$_2$CN, (CH$_2$)$_m$(O)CH$_3$ 5 CH$_2$C(O)NH$_2$, or (CH$_2$)$_m$OH;

R$^{13}$ is hydrogen, halo, C$_{1-3}$ alkyl, CF$_3$, or OC$_{1-3}$ alkyl;

m is 2 or 3;

R$^{14}$ is hydrogen, halo, C$_{1-3}$ alkyl, OC$_{1-3}$ alkyl, OCF$_3$, CF$_3$, C(O)NR$_{15}$R$_{16}$, or C(O)OC$_{1-3}$ alkyl; and R$^{15}$ and R$^{16}$ are independently hydrogen, C$_{1-3}$ alkyl, C$_{3-6}$ cycloalkyl, or phenyl;

or a pharmaceutically acceptable salt thereof.

When used herein, the term "alkyl" includes all straight chain and branched isomers. Representative examples thereof include methyl, ethyl, n-propyl, iso-propyl, n-butyl, sec-butyl, iso-butyl, t-butyl, n-pentyl and n-hexyl.

The term '$C_{3-6}$ cycloalkyl' as used herein refers to a saturated monocyclic hydrocarbon ring of 3 to 6 carbon atoms. Examples of such groups include cyclopropyl, cyclobutyl, cyclopentyl, or cyclohexyl and the like.

When used herein, the terms 'halogen' and 'halo' include fluorine, chlorine, bromine and iodine, and fluoro, chloro, bromo, and iodo, respectively.

With regard to stereoisomers, the compounds of Formula (I) may have one or more asymmetric carbon atom and may occur as racemates, racemic mixtures and as individual enantiomers or diastereomers. All such isomeric forms are included within the present invention, including mixtures thereof.

Examples of heterocycles formed by $R^9$ and $R^{10}$ are: pyrrolidine, morpholine, piperidine, hexahydroazepine, imidazole, thiomorpholine, piperazine, homomorpholine, and homopiperazine.

As used herein, "pharmaceutically acceptable" refers to those compounds, materials, compositions, and dosage forms which are, within the scope of sound medical judgment, suitable for use in contact with the tissues of human beings and animals without excessive toxicity, irritation, or other problem or complication, commensurate with a reasonable benefit/risk ratio.

The skilled artisan will appreciate that pharmaceutically acceptable salts of the compounds according to Formula (I) may be prepared. These pharmaceutically acceptable salts may be prepared in situ during the final isolation and purification of the compound, or by separately reacting the purified compound in its free acid or free base form with a suitable base or acid, respectively.

In certain embodiments, compounds according to Formula (I) may contain an acidic functional group and are, therefore, capable of forming pharmaceutically acceptable base addition salts by treatment with a suitable base. Examples of such bases include a) hydroxides, carbonates, and bicarbonates of sodium, potassium, lithium, calcium, magnesium, aluminium, and zinc; and b) primary, secondary, and tertiary amines including aliphatic amines, aromatic amines, aliphatic diamines, and hydroxy alkylamines such as methylamine, ethylamine, 2-hydroxyethylamine, diethylamine, triethylamine, ethylenediamine, ethanolamine, diethanolamine, and cyclohexylamine.

In certain embodiments, compounds according to Formula (I) may contain a basic functional group and are therefore capable of forming pharmaceutically acceptable acid addition salts by treatment with a suitable acid. Suitable acids include pharmaceutically acceptable inorganic acids and organic acids. Representative pharmaceutically acceptable acids include hydrogen chloride, hydrogen bromide, nitric acid, sulfuric acid, sulfonic acid, phosphoric acid, acetic acid, hydroxyacetic acid, phenylacetic acid, propionic acid, butyric acid, valeric acid, maleic acid, acrylic acid, fumaric acid, malic acid, malonic acid, tartaric acid, citric acid, salicylic acid, benzoic acid, tannic acid, formic acid, stearic acid, lactic acid, ascorbic acid, p-toluenesulfonic acid, oleic acid, lauric acid, and the like.

As used herein, the term "a compound of Formula (I)" or "the compound of Formula (I)" refers to one or more compounds according to Formula (I). The compound of Formula (I) may exist in solid or liquid form. In the solid state, it may exist in crystalline or noncrystalline form, or as a mixture thereof. The skilled artisan will appreciate that pharmaceutically acceptable solvates may be formed for crystalline compounds wherein solvent molecules are incorporated into the crystalline lattice during crystallization. Solvates may involve non-aqueous solvents such as, but not limited to, ethanol, isopropanol, DMSO, acetic acid, ethanolamine, or ethyl acetate, or they may involve water as the solvent that is incorporated into the crystalline lattice. Solvates wherein water is the solvent incorporated into the crystalline lattice are typically referred to as "hydrates." Hydrates include stoichiometric hydrates as well as compositions containing variable amounts of water. The invention includes all such solvates.

In one embodiment:

$R^1$ is phenyl substituted by one or two halo, $OC_{1-3}$alkyl, CN, C(O)OH, $NR^7R^8$, $C(O)NR^9R^{10}$, $SO_2C_{1-3}$ alkyl, or $SO_2NR^{11}R^{12}$;

$R^2$ is hydrogen or halo;

$R^3$ is methyl;

$R^4$ is hydrogen or $CH_3$;

$R^5$ and $R^6$ are hydrogen;

$R^7$ and $R^8$ are independently hydrogen, $C(O)C_{1-3}$alkyl, $C_{1-6}$alkyl, $SO_2C_{1-3}$ alkyl, or $C(O)NHC_{1-3}$alkyl;

$R^9$ and $R^{10}$ are independently hydrogen, $C_{1-3}$alkyl;

or taken together $R^9$ and $R^{10}$ form a pyrrolidine, morpholine, or piperidine group;

X is O or a bond;

B is:

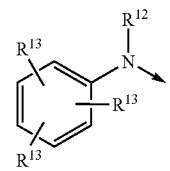

(c)

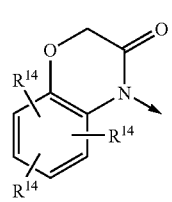

(d)

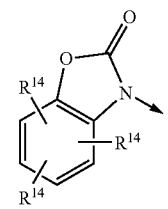

(e)

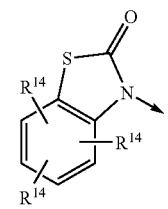

(f)

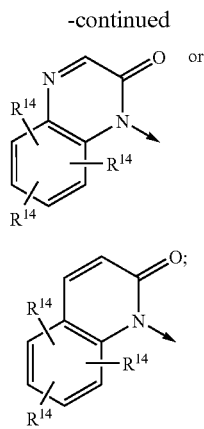

$R^{12}$ is methyl, $CH_2CN$, $(CH_2)_m(O)CH_3$, or $CH_2C(O)NH_2$;

$R^{13}$ is hydrogen or halo;

m is 2; and $R^{14}$ is hydrogen or halo.

In another embodiment:

$R^1$ is phenyl substituted by one or two $OC_{1-3}$alkyl, $C(O)OH$, or $C(O)NR^9R^{10}$;

$R^2$ is hydrogen or halo;

$R^3$ is methyl;

$R^4$ is hydrogen or $CH_3$;

$R^5$ and $R^6$ are hydrogen;

$R^9$ and $R^{10}$ are independently hydrogen, $C_{1-3}$alkyl;

or taken together $R^9$ and $R^{10}$ form a pyrrolidine, morpholine, or piperidine group;

X is O or a bond;

B is:

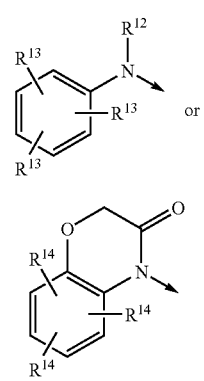

$R^{12}$ is methyl, $CH_2CN$, $(CH_2)_m(O)CH_3$, or $CH_2C(O)NH_2$;

$R^{13}$ is hydrogen or halo;

m is 2; and $R^{14}$ is hydrogen or halo.

Preferably the compound of Formula I is the R enantiomer.

It is to be understood that the present invention covers all combinations of particular groups described hereinabove.

Compounds of Formula (I) include:

$N^1$-[1-(4-biphenylyl)-2-(1-pyrrolidinyl)ethyl]-$N^2$-(3,4-dichlorophenyl)-$N^1$-,$N^2$-dimethylglycinamide;

N-[(1S)-1-(4-biphenylyl)-2-(1-pyrrolidinyl)ethyl]-2-(5-chloro-2-oxo-1,3-benzoxazol-3(2H)-yl)-N-methylacetamide;

N-[1-(4-biphenylyl)-2-(4-morpholinyl)ethyl]-2-(5-chloro-2-oxo-1,3-benzoxazol-3(2H)-yl)-N-methylacetamide;

$N^1$-[1-(4-biphenylyl)-2-(4-morpholinyl)ethyl]-$N^2$-(3,4-dichlorophenyl)-$N^1$,$N^2$-dimethylglycinamide;

$N^1$-[1-(4-biphenylyl)-2-(4-morpholinyl)ethyl]-$N^2$-(cyanomethyl)-$N^2$-(3,4-dichlorophenyl)-$N^1$-methylglycinamide;

N-[1-(4-biphenylyl)-2-(4-morpholinyl)ethyl]-2-(6,7-dimethyl-3-oxo-2,3-dihydro-4H-1,4-benzoxazin-4-yl)-N-methylacetamide;

$N^1$-[1-(4'-chloro-4-biphenylyl)-2-(1-pyrrolidinyl)ethyl]-$N^2$-(3,4-dichlorophenyl)-$N^1$,$N^2$-dimethylglycinamide;

$N^1$-[1-(2'-chloro-4-biphenylyl)-2-(1-pyrrolidinyl)ethyl]-$N^2$-(3,4-dichlorophenyl)-$N^1$,$N^2$-dimethylglycinamide;

$N^1$-[1-(3'-chloro-4-biphenylyl)-2-(1-pyrrolidinyl)ethyl]-$N^2$-(3,4-dichlorophenyl)-$N^1$,$N^2$-dimethylglycinamide;

$N^2$-(3,4-dichlorophenyl)-$N^1$,$N^2$-dimethyl-$N^1$-[1-[3'-(methyloxy)-4-biphenylyl]-2-(1-pyrrolidinyl)ethyl]glycinamide;

$N^2$-(3,4-dichlorophenyl)-$N^1$,$N^2$-dimethyl-$N^1$-[1-[4'-(methyloxy)-4-biphenylyl]-2-(1-pyrrolidinyl)ethyl]glycinamide;

$N^1$-[1-(3',4'-dichloro-4-biphenylyl)-2-(1-pyrrolidinyl)ethyl]-$N^2$-(3,4-dichlorophenyl)-$N^1$,$N^2$-dimethylglycinamide;

$N^1$-[1-(2',3'-dichloro-4-biphenylyl)-2-(1-pyrrolidinyl)ethyl]-$N^2$-(3,4-dichlorophenyl)-$N^1$,$N^2$-dimethylglycinamide;

$N^1$-[1-(2',4'-dichloro-4-biphenylyl)-2-(1-pyrrolidinyl)ethyl]-$N^2$-(3,4-dichlorophenyl)-$N^1$,$N^2$-dimethylglycinamide;

$N^1$-[1-(3',5'-dichloro-4-biphenylyl)-2-(1-pyrrolidinyl)ethyl]-$N^2$-(3,4-dichlorophenyl)-$N^1$,$N^2$-dimethylglycinamide;

$N^1$-[1-(3'-chloro-4'-fluoro-4-biphenylyl)-2-(1-pyrrolidinyl)ethyl]-$N^2$-(3,4-dichlorophenyl)-$N^1$,$N^2$-dimethylglycinamide;

$N^1$-[1-[4-(1,3-benzodioxol-5-yl)phenyl]-2-(1-pyrrolidinyl)ethyl]-$N^2$-(3,4-dichlorophenyl)-$N^1$,$N^2$-dimethylglycinamide;

4'-[1-[[N-(3,4-dichlorophenyl)-N-methylglycyl](methyl)amino]-2-(1-pyrrolidinyl)ethyl]-4-biphenylcarboxylic acid;

$N^2$-(3,4-dichlorophenyl)-$N^1$-[1-(4'-hydroxy-4-biphenylyl)-2-(1-pyrrolidinyl)ethyl]-$N^1$,$N^2$-dimethylglycinamide;

$N^2$-(3,4-dichlorophenyl)-$N^1$,$N^2$-dimethyl-$N^1$-[1-{2'-[(1-methylethyl)oxy]-4-biphenylyl}-2-(1-pyrrolidinyl)ethyl]glycinamide;

$N^2$-(3,4-dichlorophenyl)-$N^1$,$N^2$-dimethyl-$N^1$-[1-{3'-[(1-methylethyl)oxy]-4-biphenylyl}-2-(1-pyrrolidinyl)ethyl]glycinamide;

$N^2$-(3,4-dichlorophenyl)-$N^1$-[1-[3'-(ethyloxy)-4-biphenylyl]-2-(1-pyrrolidinyl)ethyl]-$N^1$,$N^2$-dimethylglycinamide;

$N^2$-(3,4-dichlorophenyl)-$N^1$,$N^2$-dimethyl-$N^1$-(2-(1-pyrrolidinyl)-1-{3'-[(trifluoromethyl)oxy]-4-biphenylyl}ethyl) glycinamide;

$N^2$-(3,4-dichlorophenyl)-$N^1$-[1-[4-(2,3-dihydro-1,4-benzodioxin-5-yl)phenyl]-2-(1-pyrrolidinyl)ethyl]-$N^1$,$N^2$-dimethylglycinamide;

N-cyclopropyl-4'-[1-[[N-(3,4-dichlorophenyl)-N-methylglycyl](methyl)amino]-2-(1-pyrrolidinyl)ethyl]-4-biphenylcarboxamide;

4'-[1-[[N-(3,4-dichlorophenyl)-N-methylglycyl](methyl)amino]-2-(1-pyrrolidinyl)ethyl]-N-(1-methylethyl)-4-biphenylcarboxamide;

3-chloro-4'-[1-[[N-(3,4-dichlorophenyl)-N-methylglycyl](methyl)amino]-2-(1-pyrrolidinyl)ethyl]-4-biphenylcarboxamide;

3-chloro-4'-[1-[[N-(3,4-dichlorophenyl)-N-methylglycyl](methyl)amino]-2-(1-pyrrolidinyl)ethyl]-N-methyl-4-biphenylcarboxamide;

3-chloro-4'-[1-[[N-(3,4-dichlorophenyl)-N-methylglycyl](methyl)amino]-2-(1-pyrrolidinyl)ethyl]-N,N-dimethyl-4-biphenylcarboxamide;

$N^2$-(3,4-dichlorophenyl)-$N^1$,$N^2$-dimethyl-$N^1$-[1-[4'-(4-morpholinylcarbonyl)-4-biphenylyl]-2-(1-pyrrolidinyl)ethyl]glycinamide;

$N^2$-(3,4-dichlorophenyl)-$N^1$,$N^2$-dimethyl-$N^1$-[1-[4'-(1-piperidinylcarbonyl)-4-biphenylyl]-2-(1-pyrrolidinyl)ethyl]glycinamide;

$N^2$-(3,4-dichlorophenyl)-$N^1$-[1-[4'-(ethylsulfonyl)-4-biphenylyl]-2-(1-pyrrolidinyl)ethyl]-$N^1$,$N^2$-dimethylglycinamide;

$N^1$-[1-[4'-(aminosulfonyl)-4-biphenylyl]-2-(1-pyrrolidinyl)ethyl]-$N^2$-(3,4-dichlorophenyl)-$N^1$,$N^2$-dimethylglycinamide;

$N^2$-(3,4-dichlorophenyl)-$N^1$,$N^2$-dimethyl-$N^1$-[1-{4'-[(methylamino)sulfonyl]-4-biphenylyl}-2-(1-pyrrolidinyl)ethyl]glycinamide;

$N^2$-(3,4-dichlorophenyl)-$N^1$-[1-{4'-[(dimethylamino)sulfonyl]-4-biphenylyl}-2-(1-pyrrolidinyl)ethyl]-$N^1$,$N^2$-dimethylglycinamide;

$N^1$-[1-(4'-chloro-3-biphenylyl)-2-(1-pyrrolidinyl)ethyl]-$N^2$-(3,4-dichlorophenyl)-$N^1$,$N^2$-dimethylglycinamide;

$N^2$-(3,4-dichlorophenyl)-$N^1$-[1-[4'-(dimethylamino)-3-biphenylyl]-2-(1-pyrrolidinyl)ethyl]-$N^1$,$N^2$-dimethylglycinamide;

$N^2$-(3,4-dichlorophenyl)-$N^1$,$N^2$-dimethyl-$N^1$-[1-[3'-(methyloxy)-3-biphenylyl]-2-(1-pyrrolidinyl)ethyl]glycinamide;

$N^2$-(3,4-dichlorophenyl)-$N^1$,$N^2$-dimethyl-$N^1$-[1-[2'-(methyloxy)-3-biphenylyl]-2-(1-pyrrolidinyl)ethyl]glycinamide;

$N^2$-(3,4-dichlorophenyl)-$N^1$,$N^2$-dimethyl-$N^1$-[1-[4'-(methyloxy)-3-biphenylyl]-2-(1-pyrrolidinyl)ethyl]glycinamide;

$N^1$-[1-(2'-chloro-3-biphenylyl)-2-(1-pyrrolidinyl)ethyl]-$N^2$-(3,4-dichlorophenyl)-$N^1$,$N^2$-dimethylglycinamide;

N-[1-(3-biphenylyl)-2-(1-pyrrolidinyl)ethyl]-$N^2$-(3,4-dichlorophenyl)-$N^1$,$N^2$-dimethylglycinamide;

N-[1-(3-biphenylyl)-2-(1-pyrrolidinyl)ethyl]-2-(6,7-dichloro-3-oxo-2,3-dihydro-4H-1,4-benzoxazin-4-yl)-N-methylacetamide;

$N^2$-(3,4-dichlorophenyl)-$N^1$-[1-(2'-hydroxy-3-biphenylyl)-2-(1-pyrrolidinyl)ethyl]-$N^1$,$N^2$-dimethylglycinamide;

$N^2$-(3,4-dichlorophenyl)-$N^1$-[1-(4'-hydroxy-3-biphenylyl)-2-(1-pyrrolidinyl)ethyl]-$N^1$,$N^2$-dimethylglycinamide;

2-(6,7-dichloro-3-oxo-2,3-dihydro-4H-1,4-benzoxazin-4-yl)-N-methyl-N-{2-(4-morpholinyl)-1-[4'-(1-pyrrolidinylcarbonyl)-4-biphenylyl]ethyl}acetamide;

3-chloro-4'-[1-[[(6,7-dichloro-3-oxo-2,3-dihydro-4H-1,4-benzoxazin-4-yl)acetyl](methyl)amino]-2-(4-morpholinyl)ethyl]-N-methyl-4-biphenylcarboxamide;

3-chloro-4'-[1-[[(6,7-dichloro-3-oxo-2,3-dihydro-4H-1,4-benzoxazin-4-yl)acetyl](methyl)amino]-2-(4-morpholinyl)ethyl]-N,N-dimethyl-4-biphenylcarboxamide;

2-(6,7-dichloro-3-oxo-2,3-dihydro-4H-1,4-benzoxazin-4-yl)-N-methyl-N-{2-(4-morpholinyl)-1-[2'-(trifluoromethyl)-4-biphenylyl]ethyl}acetamide;

2-(6,7-dichloro-3-oxo-2,3-dihydro-4H-1,4-benzoxazin-4-yl)-N-methyl-N-{2-(4-morpholinyl)-1-[3'-(trifluoromethyl)-4-biphenylyl]ethyl}acetamide;

2-(6,7-dichloro-3-oxo-2,3-dihydro-4H-1,4-benzoxazin-4-yl)-N-methyl-N-{2-(4-morpholinyl)-1-[4'-(trifluoromethyl)-4-biphenylyl]ethyl}acetamide;

2-(6,7-dichloro-3-oxo-2,3-dihydro-4H-1,4-benzoxazin-4-yl)-N-[1-(2'-fluoro-4-biphenylyl)-2-(4-morpholinyl)ethyl]-N-methylacetamide;

2-(6,7-dichloro-3-oxo-2,3-dihydro-4H-1,4-benzoxazin-4-yl)-N-[1-(3'-fluoro-4-biphenylyl)-2-(4-morpholinyl)ethyl]-N-methylacetamide;

2-(6,7-dichloro-3-oxo-2,3-dihydro-4H-1,4-benzoxazin-4-yl)-N-[1-(4'-fluoro-4-biphenylyl)-2-(4-morpholinyl)ethyl]-N-methylacetamide;

2-[(2-amino-2-oxoethyl)(3,4-dichlorophenyl)amino]-N-methyl-N-[1-[3'-(methyloxy)-4-biphenylyl]-2-(4-morpholinyl)ethyl]acetamide;

2-[(2-amino-2-oxoethyl)(3,4-dichlorophenyl)amino]-N-[1-(3'-cyano-4-biphenylyl)-2-(4-morpholinyl)ethyl]-N-methylacetamide;

2-[(2-amino-2-oxoethyl)(3,4-dichlorophenyl)amino]-N-[1-[4'-(dimethylamino)-4-biphenylyl]-2-(4-morpholinyl)ethyl]-N-methylacetamide;

2-[(2-amino-2-oxoethyl)(3,4-dichlorophenyl)amino]-N-[1-[2',3'-bis(methyloxy)-4-biphenylyl]-2-(4-morpholinyl)ethyl]-N-methylacetamide;

N-[1-(4-biphenylyl)-2-(4-morpholinyl)ethyl]-2-(6,7-dimethyl-3-oxo-2,3-dihydro-4H-1,4-benzoxazin-4-yl)-N-methylacetamide;

N-[1-(3'-cyano-4-biphenylyl)-2-(4-morpholinyl)ethyl]-2-(6,7-dichloro-3-oxo-2,3-dihydro-4H-1,4-benzoxazin-4-yl)-N-methylacetamide;

N-cyclopropyl-4'-[1-[[(6,7-dichloro-3-oxo-2,3-dihydro-4H-1,4-benzoxazin-4-yl)acetyl](methyl)amino]-2-(4-morpholinyl)ethyl]-4-biphenylcarboxamide;

4'-[1-[[(6,7-dichloro-3-oxo-2,3-dihydro-4H-1,4-benzoxazin-4-yl)acetyl](methyl)amino]-2-(4-morpholinyl)ethyl]-N-(1-methylethyl)-4-biphenylcarboxamide;

3-chloro-4'-[1-[[(6,7-dichloro-3-oxo-2,3-dihydro-4H-1,4-benzoxazin-4-yl)acetyl](methyl)amino]-2-(4-morpholinyl)ethyl]-4-biphenylcarboxamide;

2-(6,7-dichloro-3-oxo-2,3-dihydro-4H-1,4-benzoxazin-4-yl)-N-methyl-N-{2-(4-morpholinyl)-1-[4'-(1-piperidinylcarbonyl)-4-biphenylyl]ethyl}acetamide;

2-(6,7-dichloro-3-oxo-2,3-dihydro-4H-1,4-benzoxazin-4-yl)-N-methyl-N-[1-[4-(4-methyl-3,4-dihydro-2H-1,4-benzoxazin-7-yl)phenyl]-2-(4-morpholinyl)ethyl]acetamide;

N-[1-[4'-(aminosulfonyl)-4-biphenylyl]-2-(4-morpholinyl)ethyl]-2-(6,7-dichloro-3-oxo-2,3-dihydro-4H-1,4-benzoxazin-4-yl)-N-methylacetamide;

N-[1-(3'-cyano-3-biphenylyl)-2-(4-morpholinyl)ethyl]-2-(6,7-dichloro-3-oxo-2,3-dihydro-4H-1,4-benzoxazin-4-yl)-N-methylacetamide;

N-[1-(3-biphenylyl)-2-(4-morpholinyl)ethyl]-2-(6,7-dichloro-3-oxo-2,3-dihydro-4H-1,4-benzoxazin-4-yl)-N-methylacetamide;

2-(6,7-dichloro-3-oxo-2,3-dihydro-4H-1,4-benzoxazin-4-yl)-N-[1-{4'-[(dimethylamino)sulfonyl]-3-biphenylyl}-2-(4-morpholinyl)ethyl]-N-methylacetamide;

2-(6,7-dichloro-3-oxo-2,3-dihydro-4H-1,4-benzoxazin-4-yl)-N-[1-[4'-(dimethylamino)-3-biphenylyl]-2-(4-morpholinyl)ethyl]-N-methylacetamide;

2-(6,7-dichloro-3-oxo-2,3-dihydro-4H-1,4-benzoxazin-4-yl)-N-methyl-N-{2-(4-morpholinyl)-1-[3'-(1-piperidinylcarbonyl)-3-biphenylyl]ethyl}acetamide;

2-(6,7-dichloro-3-oxo-2,3-dihydro-4H-1,4-benzoxazin-4-yl)-N-methyl-N-[2-(4-morpholinyl)-1-(3'-nitro-3-biphenylyl)ethyl]acetamide;

N-[1-(4-biphenylyl)-2-(4-morpholinyl)ethyl]-2-(6,7-dimethyl-3-oxo-2,3-dihydro-4H-1,4-benzoxazin-4-yl)-N-methylacetamide;

N-[1-[4'-(dimethylamino)-4-biphenylyl]-2-(4-morpholinyl)ethyl]-2-(6,7-dimethyl-3-oxo-2,3-dihydro-4H-1,4-benzoxazin-4-yl)-N-methylacetamide;

2-(6,7-dichloro-3-oxo-2,3-dihydro-4H-1,4-benzoxazin-4-yl)-N-methyl-N-[1-{3'-[(1-methylethyl)oxy]-4-biphenylyl}-2-(4-morpholinyl)ethyl]acetamide;

1,1-dimethylethyl {4'-[1-[[(6,7-dichloro-3-oxo-2,3-dihydro-4H-1,4-benzoxazin-4-yl)acetyl](methyl)amino]-2-(4-morpholinyl)ethyl]-4-biphenylyl}carbamate;

[N-[1-(4-biphenylyl)-2-(1-pyrrolidinyl)ethyl]-N-methyl-2-[7-methyl-6-(methyloxy)-3-oxo-2,3-dihydro-4H-1,4-benzoxazin-4-yl]acetamide;

N-[1-(4-biphenylyl)-2-(4-morpholinyl)ethyl]-N-methyl-2-[7-methyl-6-(methyloxy)-3-oxo-2,3-dihydro-4H-1,4-benzoxazin-4-yl]acetamide;

N-[1-(4-biphenylyl)-2-(1-pyrrolidinyl)ethyl]-N-methyl-2-[6-methyl-5-(methyloxy)-2-oxo-1,3-benzoxazol-3(2H)-yl]acetamide;

N-[1-(4-biphenylyl)-2-(4-morpholinyl)ethyl]-N-methyl-2-[6-methyl-5-(methyloxy)-2-oxo-1,3-benzoxazol-3(2H)-yl]acetamide;

N-[1-(4-biphenylyl)-1-methyl-2-(1-pyrrolidinyl)ethyl]-2-(5-chloro-2-oxo-1,3-benzoxazol-3(2H)-yl)-N-methylacetamide;

N1-[1-(4-biphenylyl)-1-methyl-2-(1-pyrrolidinyl)ethyl]-N2-(cyanomethyl)-N2-(3,4-dichlorophenyl)-N1-methylglycinamide;

N-[1-(4-biphenylyl)-1-methyl-2-(1-pyrrolidinyl)ethyl]-2-(6,7-dichloro-3-oxo-2,3-dihydro-4H-1,4-benzoxazin-4-yl)-N-methylacetamide;

N-[1-(4-biphenylyl)-1-methyl-2-(1-pyrrolidinyl)ethyl]-2-(5-chloro-2-oxo-1,3-benzothiazol-3(2H)-yl)-N-methylacetamide;

N-[1-(4-biphenylyl)-2-(1-pyrrolidinyl)ethyl]-N-methyl-2-[6-(methyloxy)-2-oxo-1,3-benzoxazol-3(2H)-yl]acetamide;

$N^1$-[1-(4-biphenylyl)-2-(1-pyrrolidinyl)ethyl]-$N^2$-(3,4-dichlorophenyl)-$N^1$-methyl-$N^2$-[2-(methyloxy)ethyl]glycinamide;

$N^1$-[1-(4-biphenylyl)-2-(1-pyrrolidinyl)ethyl]-$N^2$-(3,4-dichlorophenyl)-$N^1$,2-dimethylalaninamide;

(S)N-[1-(4-biphenylyl)-2-(4-morpholinyl)ethyl]-2-(6,7-dichloro-3-oxo-2,3-dihydro-4H-1,4-benzoxazin-4-yl)-N-methylacetamide;

Ethyl 4-{2-[[1-(4-biphenylyl)-2-(1-pyrrolidinyl)ethyl](methyl)amino]-2-oxoethyl}-3-oxo-3,4-dihydro-2H-1,4-benzoxazine-6-carboxylate;

Ethyl 4-{2-[[1-(4-biphenylyl)-2-(4-morpholinyl)ethyl](methyl)amino]-2-oxoethyl}-3-oxo-3,4-dihydro-2H-1,4-benzoxazine-6-carboxylate;

4-{2-[[1-(4-biphenylyl)-2-(1-pyrrolidinyl)ethyl] (methyl)amino]-2-oxoethyl}-N-methyl-3-oxo-3,4-dihydro-2H-1,4-benzoxazine-6-carboxamide;

4-{2-[[1-(4-biphenylyl)-2-(1-pyrrolidinyl)ethyl] (methyl)amino]-2-oxoethyl}-N,N-dimethyl-3-oxo-3,4-dihydro-2H-1,4-benzoxazine-6-carboxamide;

4-{2-[[1-(4-biphenylyl)-2-(1-pyrrolidinyl)ethyl] (methyl)amino]-2-oxoethyl}-N-ethyl-3-oxo-3,4-dihydro-2H-1,4-benzoxazine-6-carboxamide;

4-{2-[[1-(4-biphenylyl)-2-(1-pyrrolidinyl)ethyl] (methyl)amino]-2-oxoethyl}-3-oxo-3,4-dihydro-2H-1,4-benzoxazine-6-carboxamide;

4-{2-[[1-(4-biphenylyl)-2-(4-morpholinyl)ethyl] (methyl)amino]-2-oxoethyl}-3-oxo-3,4-dihydro-2H-1,4-benzoxazine-6-carboxamide;

2-(6,7-dichloro-3-oxo-2,3-dihydro-4H-1,4-benzoxazin-4-yl)-N-[1-(3-fluoro-4-biphenylyl)-2-(4-morpholinyl)ethyl]-N-methylacetamide;

N-[1-(3-chloro-4-biphenylyl)-2-(4-morpholinyl)ethyl]-2-(6,7-dichloro-3-oxo-2,3-dihydro-4H-1,4-benzoxazin-4-yl)-N-methylacetamide;

N-[1-(4-biphenylyl)-2-(4-morpholinyl)ethyl]-N-methyl-2-{3-oxo-6-[(trifluoromethyl)oxy]-2,3-dihydro-4H-1,4-benzoxazin-4-yl}acetamide;

N-[1-(4-biphenylyl)-2-(1-pyrrolidinyl)ethyl]-N-methyl-2-[7-(methyloxy)-3-oxo-6-(trifluoromethyl)-2,3-dihydro-4H-1,4-benzoxazin-4-yl]acetamide;

N-[1-(4-biphenylyl)-2-(4-morpholinyl)ethyl]-2-(5,6-dimethyl-2-oxo-1(2H)-quinolinyl)-N-methylacetamide;

N-[1-(4-biphenylyl)-2-(1-pyrrolidinyl)ethyl]-N-methyl-2-(2-oxo-1,3-benzoxazol-3(2H)-yl)acetamide;

N-[1-(4-biphenylyl)-2-(1-pyrrolidinyl)ethyl]-2-(5-chloro-2-oxo-1,3-benzoxazol-3(2H)-yl)-N-methylacetamide;

$N^1$-[1-(4-biphenylyl)-2-(1-pyrrolidinyl)ethyl]-$N^2$-(cyanomethyl)-$N^2$-(3,4-dichlorophenyl)-$N^1$-methylglycinamide;

N-[1-(4-biphenylyl)-2-(1-pyrrolidinyl)ethyl]-2-(6,7-dichloro-2-oxo-1(2H)-quinoxalinyl)-N-methylacetamide;

N-[1-(4-biphenylyl)-2-(1-pyrrolidinyl)ethyl]-2-(5-chloro-2-oxo-1,3-benzothiazol-3(2H)-yl)-N-methylacetamide;

N-[1-(4-biphenylyl)-2-(1-pyrrolidinyl)ethyl]-2-(6,7-dichloro-3-oxo-2,3-dihydro-4H-1,4-benzoxazin-4-yl)-N-methylacetamide;

N-(1-biphenyl-4-yl-2-pyrrolidin-1-ylethyl)-2-(6,7-dibromo-3-oxo-2,3-dihydro-4H-1,4-benzoxazin-4-yl)-N-methylacetamide;

N-[1-(4-biphenylyl)-2-(1-pyrrolidinyl)ethyl]-2-(6,7-dimethyl-3-oxo-2,3-dihydro-4H-1,4-benzoxazin-4-yl)-N-methylacetamide;

N-[(1R)-1-(4-biphenylyl)-2-(1-pyrrolidinyl)ethyl]-2-(5-chloro-2-oxo-1,3-benzoxazol-3(2H)-yl)-N-methylacetamide;

(N-[1-(4-biphenylyl)-2-(4-morpholinyl)ethyl]-2-(6,7-dibromo-3-oxo-2,3-dihydro-4H-1,4-benzoxazin-4-yl)-N-methylacetamide;

N-[1-(4-biphenylyl)-2-(4-morpholinyl)ethyl]-2-(6,7-dichloro-3-oxo-2,3-dihydro-4H-1,4-benzoxazin-4-yl)-N-methylacetamide;

N-[1-(4-biphenylyl)-2-(4-morpholinyl)ethyl]-2-(5-chloro-2-oxo-1,3-benzothiazol-3(2H)-yl)-N-methylacetamide;

N-[1-(4-biphenylyl)-2-(4-morpholinyl)ethyl]-2-(6,7-dichloro-2-oxo-1(2H)-quinoxalinyl)-N-methylacetamide;

N-[1-(4-biphenylyl)-2-(4-morpholinyl)ethyl]-2-(6,7-dichloro-2-oxo-1(2H)-quinolinyl)-N-methylacetamide;

$N^2$-(3,4-dichlorophenyl)-$N^1$,$N^2$-dimethyl-$N^1$-[1-[2'-(methyloxy)-4-biphenylyl]-2-(1-pyrrolidinyl)ethyl]glycinamide;

$N^2$-(3,4-dichlorophenyl)-$N^1$-[1-(3'-hydroxy-4-biphenylyl)-2-(1-pyrrolidinyl)ethyl]-$N^1$,$N^2$-dimethylglycinamide;

$N^1$-[1-(3'-cyano-4-biphenylyl)-2-(1-pyrrolidinyl)ethyl]-$N^2$-(3,4-dichlorophenyl)-$N^1$,$N^2$-dimethylglycinamide;

$N^1$-[1-(4'-cyano-4-biphenylyl)-2-(1-pyrrolidinyl)ethyl]-$N^2$-(3,4-dichlorophenyl)-$N^1$,$N^2$-dimethylglycinamide;

$N^2$-(3,4-dichlorophenyl)-$N^1$,$N^2$-dimethyl-$N^1$-[1-{4'-[(methylsulfonyl)amino]-4-biphenylyl}-2-(1-pyrrolidinyl)ethyl]glycinamide;

N1-[1-[2',3'-bis(methyloxy)-4-biphenylyl]-2-(1-pyrrolidinyl)ethyl]-N2-(3,4-dichlorophenyl)-N1,N2-dimethylglycinamide;

$N^1$-[1-[3'-(acetylamino)-4-biphenylyl]-2-(1-pyrrolidinyl)ethyl]-$N^2$-(3,4-dichlorophenyl)-$N^1$,$N^2$-dimethylglycinamide;

$N^1$-[1-[4'-(acetylamino)-4-biphenylyl]-2-(1-pyrrolidinyl)ethyl]-$N^2$-(3,4-dichlorophenyl)-$N^1$,$N^2$-dimethylglycinamide;

$N^2$-(3,4-dichlorophenyl)-$N^1$-[1-(2'-hydroxy-4-biphenylyl)-2-(1-pyrrolidinyl)ethyl]-$N^1$,$N^2$-dimethylglycinamide;

$N^2$-(3,4-dichlorophenyl)-$N^1$-[1-[3'-(dimethylamino)-4-biphenylyl]-2-(1-pyrrolidinyl)ethyl]-$N^1$,$N^2$-dimethylglycinamide;

$N^1$-[1-[2'-(acetylamino)-4-biphenylyl]-2-(1-pyrrolidinyl)ethyl]-$N^2$-(3,4-dichlorophenyl)-$N^1$,$N^2$-dimethylglycinamide;

$N^2$-(3,4-dichlorophenyl)-$N^1$-[1-[4'-(dimethylamino)-4-biphenylyl]-2-(1-pyrrolidinyl)ethyl]-$N^1$,$N^2$-dimethylglycinamide;

$N^2$-(3,4-dichlorophenyl)-$N^1$,$N^2$-dimethyl-$N^1$-[1-{3'-[(methylsulfonyl)amino]-4-biphenylyl}-2-(1-pyrrolidinyl)ethyl]glycinamide;

$N^1$-[1-[3',4'-bis(methyloxy)-4-biphenylyl]-2-(1-pyrrolidinyl)ethyl]-$N^2$-(3,4-dichlorophenyl)-$N^1$,$N^2$-dimethylglycinamide;

$N^1$-[1-(3'-amino-4-biphenylyl)-2-(1-pyrrolidinyl)ethyl]-$N^2$-(3,4-dichlorophenyl)-$N^1$,$N^2$-dimethylglycinamide;

N-cyclopropyl-4'-[1-[[N-(3,4-dichlorophenyl)-N-methylglycyl](methyl)amino]-2-(1-pyrrolidinyl)ethyl]-3-biphenylcarboxamide;

4'-[1-[[N-(3,4-dichlorophenyl)-N-methylglycyl](methyl)amino]-2-(1-pyrrolidinyl)ethyl]-N-(1-methylethyl)-3-biphenylcarboxamide;

4'-[1-[[N-(3,4-dichlorophenyl)-N-methylglycyl](methyl)amino]-2-(1-pyrrolidinyl)ethyl]-5-fluoro-N-methyl-3-biphenylcarboxamide;

$N^2$-(3,4-dichlorophenyl)-$N^1$,$N^2$-dimethyl-$N^1$-{2-(1-pyrrolidinyl)-1-[4'-(1-pyrrolidinylcarbonyl)-4-biphenylyl]ethyl}glycinamide;

$N^2$-(3,4-dichlorophenyl)-$N^1$,$N^2$-dimethyl-$N^1$-[1-[3'-(4-morpholinylcarbonyl)-4-biphenylyl]-2-(1-pyrrolidinyl)ethyl]glycinamide;

$N^2$-(3,4-dichlorophenyl)-$N^1$,$N^2$-dimethyl-$N^1$-[1-{2'-[(methylsulfonyl)amino]-4-biphenylyl}-2-(1-pyrrolidinyl)ethyl]glycinamide;

$N^2$-(3,4-dichlorophenyl)-$N^1$-[1-{2'-[(dimethylamino)sulfonyl]-4-biphenylyl}-2-(1-pyrrolidinyl)ethyl]-$N^1$,$N^2$-dimethylglycinamide;

$N^2$-(3,4-dichlorophenyl)-$N^1$,$N^2$-dimethyl-$N^1$-[1-[4'-(methylsulfonyl)-4-biphenylyl]-2-(1-pyrrolidinyl)ethyl]glycinamide;

N-[1-[3',4'-bis(methyloxy)-4-biphenylyl]-2-(1-pyrrolidinyl)ethyl]-2-(6,7-dichloro-3-oxo-2,3-dihydro-4H-1,4-benzoxazin-4-yl)-N-methylacetamide;

4'-[1-[[(6,7-dichloro-3-oxo-2,3-dihydro-4H-1,4-benzoxazin-4-yl)acetyl](methyl)amino]-2-(1-pyrrolidinyl)ethyl]-4-biphenylcarboxylic acid;

2-(6,7-dichloro-3-oxo-2,3-dihydro-4H-1,4-benzoxazin-4-yl)-N-methyl-N-[1-{3'-[(1-methylethyl)oxy]-4-biphenylyl}-2-(1-pyrrolidinyl)ethyl]acetamide;

2-(6,7-dichloro-3-oxo-2,3-dihydro-4H-1,4-benzoxazin-4-yl)-N-methyl-N-[1-{3'-[(methylsulfonyl)amino]-4-biphenylyl}-2-(1-pyrrolidinyl)ethyl]acetamide;

2-(6,7-dichloro-3-oxo-2,3-dihydro-4H-1,4-benzoxazin-4-yl)-N-methyl-N-[1-[4'-(dimethylamino)-4-biphenylyl]-2-(1-pyrrolidinyl)ethyl]-N-methylacetamide;

N-[1-[4'-(acetylamino)-4-biphenylyl]-2-(1-pyrrolidinyl)ethyl]-2-(6,7-dichloro-3-oxo-2,3-dihydro-4H-1,4-benzoxazin-4-yl)-N-methylacetamide;

2-(6,7-dichloro-3-oxo-2,3-dihydro-4H-1,4-benzoxazin-4-yl)-N-methyl-N-[1-[3'-(methyloxy)-4-biphenylyl]-2-(1-pyrrolidinyl)ethyl]acetamide;

4'-[1-[[(6,7-dimethyl-3-oxo-2,3-dihydro-4H-1,4-benzoxazin-4-yl)acetyl](methyl)amino]-2-(1-pyrrolidinyl)ethyl]-4-biphenylcarboxylic acid;

2-(6,7-dimethyl-3-oxo-2,3-dihydro-4H-1,4-benzoxazin-4-yl)-N-methyl-N-[1-{3'-[(1-methylethyl)oxy]-4-biphenylyl}-2-(1-pyrrolidinyl)ethyl]acetamide;

2-(6,7-dimethyl-3-oxo-2,3-dihydro-4H-1,4-benzoxazin-4-yl)-N-methyl-N-[1-{3'-[(methylsulfonyl)amino]-4-biphenylyl}-2-(1-pyrrolidinyl)ethyl]acetamide;

N-[1-[4'-(dimethylamino)-4-biphenylyl]-2-(1-pyrrolidinyl)ethyl]-2-(6,7-dimethyl-3-oxo-2,3-dihydro-4H-1,4-benzoxazin-4-yl)-N-methylacetamide;

N-[1-[4'-(acetylamino)-4-biphenylyl]-2-(1-pyrrolidinyl)ethyl]-2-(6,7-dimethyl-3-oxo-2,3-dihydro-4H-1,4-benzoxazin-4-yl)-N-methylacetamide;

2-(6,7-dimethyl-3-oxo-2,3-dihydro-4H-1,4-benzoxazin-4-yl)-N-methyl-N-[1-[3'-(methyloxy)-4-biphenylyl]-2-(1-pyrrolidinyl)ethyl]acetamide;

N-[1-[3',4'-bis(methyloxy)-4-biphenylyl]-2-(1-pyrrolidinyl)ethyl]-2-(6,7-dimethyl-3-oxo-2,3-dihydro-4H-1,4-benzoxazin-4-yl)-N-methylacetamide;

4'-[1-[[N-(cyanomethyl)-N-(3,4-dichlorophenyl)glycyl](methyl)amino]-2-(1-pyrrolidinyl)ethyl]-4-biphenylcarboxylic acid;

$N^2$-(cyanomethyl)-$N^2$-(3,4-dichlorophenyl)-$N^1$-methyl-$N^1$-[1-{3'-[(1-methylethyl)oxy]-4-biphenylyl}-2-(1-pyrrolidinyl)ethyl]glycinamide;

$N^2$-(cyanomethyl)-$N^2$-(3,4-dichlorophenyl)-$N^1$-methyl-$N^1$-[1-{3'-[(methylsulfonyl)amino]-4-biphenylyl}-2-(1-pyrrolidinyl)ethyl]glycinamide;

$N^2$-(cyanomethyl)-$N^2$-(3,4-dichlorophenyl)-$N^1$-[1-[4'-(dimethylamino)-4-biphenylyl]-2-(1-pyrrolidinyl)ethyl]-$N^1$-methylglycinamide;

$N^1$-[1-[4'-(acetylamino)-4-biphenylyl]-2-(1-pyrrolidinyl)ethyl]-$N^2$-(cyanomethyl)-$N^2$-(3,4-dichlorophenyl)-$N^1$-methylglycinamide;

$N^2$-(cyanomethyl)-$N^2$-(3,4-dichlorophenyl)-$N^1$-methyl-$N^1$-[1-[3'-(methyloxy)-4-biphenylyl]-2-(1-pyrrolidinyl)ethyl]glycinamide;

$N^1$-[1-[3',4'-bis(methyloxy)-4-biphenylyl]-2-(1-pyrrolidinyl)ethyl]-$N^2$-(cyanomethyl)-$N^2$-(3,4-dichlorophenyl)-$N^1$-methylglycinamide;

4'-[1-[[N-(3,4-dichlorophenyl)-N-methylglycyl](methyl)amino]-2-(1-pyrrolidinyl)ethyl]-2-biphenylcarboxamide;

4'-[1-[[N-(3,4-dichlorophenyl)-N-methylglycyl](methyl)amino]-2-(1-pyrrolidinyl)ethyl]-3-biphenylcarboxamide;

4'-[1-[[N-(3,4-dichlorophenyl)-N-methylglycyl](methyl)amino]-2-(1-pyrrolidinyl)ethyl]-4-biphenylcarboxamide-Trifluoroacetate;

4'-[1-[[N-(3,4-dichlorophenyl)-N-methylglycyl](methyl)amino]-2-(1-pyrrolidinyl)ethyl]-N-methyl-3-biphenylcarboxamide;

4'-[1-[[N-(3,4-dichlorophenyl)-N-methylglycyl](methyl)amino]-2-(1-pyrrolidinyl)ethyl]-N-methyl-4-biphenylcarboxamide;

4'-[1-[[N-(3,4-dichlorophenyl)-N-methylglycyl](methyl)amino]-2-(1-pyrrolidinyl)ethyl]-N,N-dimethyl-3-biphenylcarboxamide;

4'-[1-[[N-(3,4-dichlorophenyl)-N-methylglycyl](methyl)amino]-2-(1-pyrrolidinyl)ethyl]-N,N-dimethyl-4-biphenylcarboxamide;

N-[1-(4'-chloro-3-biphenylyl)-2-(1-pyrrolidinyl)ethyl]-2-(6,7-dichloro-3-oxo-2,3-dihydro-4H-1,4-benzoxazin-4-yl)-N-methylacetamide;

2-(6,7-dichloro-3-oxo-2,3-dihydro-4H-1,4-benzoxazin-4-yl)-N-[1-[4'-(dimethylamino)-3-biphenylyl]-2-(1-pyrrolidinyl)ethyl]-N-methylacetamide;

2-(6,7-dichloro-3-oxo-2,3-dihydro-4H-1,4-benzoxazin-4-yl)-N-methyl-N-[1-[3'-(methyloxy)-3-biphenylyl]-2-(1-pyrrolidinyl)ethyl]acetamide;

2-(6,7-dichloro-3-oxo-2,3-dihydro-4H-1,4-benzoxazin-4-yl)-N-[1-(2'-hydroxy-3-biphenylyl)-2-(1-pyrrolidinyl)ethyl]-N-methylacetamide;

2-(6,7-dichloro-3-oxo-2,3-dihydro-4H-1,4-benzoxazin-4-yl)-N-[1-(4'-hydroxy-3-biphenylyl)-2-(1-pyrrolidinyl)ethyl]-N-methylacetamide;

N-[1-[4'-(acetylamino)-3-biphenylyl]-2-(1-pyrrolidinyl)ethyl]-2-(6,7-dichloro-3-oxo-2,3-dihydro-4H-1,4-benzoxazin-4-yl)-N-methylacetamide;

2-(6,7-dichloro-3-oxo-2,3-dihydro-4H-1,4-benzoxazin-4-yl)-N-methyl-N-[1-{4'-[(methylsulfonyl)amino]-4-biphenylyl}-2-(4-morpholinyl)ethyl]acetamide;

2-(6,7-dichloro-3-oxo-2,3-dihydro-4H-1,4-benzoxazin-4-yl)-N-methyl-N-[1-[4'-(methylsulfonyl)-4-biphenylyl]-2-(4-morpholinyl)ethyl]acetamide;

N-{1-[3'-(acetylamino)biphenyl-4-yl]-2-morpholin-4-yl-ethyl}-2-(6,7-dichloro-3-oxo-2,3-dihydro-4H-1,4-benzoxazin-4-yl)-N-methylacetamide;

2-(6,7-dichloro-3-oxo-2,3-dihydro-4H-1,4-benzoxazin-4-yl)-N-methyl-N-[1-{2'-[(methylsulfonyl)amino]-4-biphenylyl}-2-(4-morpholinyl)ethyl]acetamide;

2-(6,7-dichloro-3-oxo-2,3-dihydro-4H-1,4-benzoxazin-4-yl)-N-[1-[4'-(ethylsulfonyl)-4-biphenylyl]-2-(4-morpholinyl)ethyl]-N-methylacetamide;

2-(6,7-dichloro-3-oxo-2,3-dihydro-4H-1,4-benzoxazin-4-yl)-N-methyl-N-{2-(4-morpholinyl)-1-[3'-(1-piperidinylcarbonyl)-4-biphenylyl]ethyl}acetamide;

2-(6,7-dichloro-3-oxo-2,3-dihydro-4H-1,4-benzoxazin-4-yl)-N-methyl-N-{2-(4-morpholinyl)-1-[4'-(4-morpholinylcarbonyl)-4-biphenylyl]ethyl}acetamide;

2-(6,7-dichloro-3-oxo-2,3-dihydro-4H-1,4-benzoxazin-4-yl)-N-methyl-N-{2-(4-morpholinyl)-1-[3'-(4-morpholinylcarbonyl)-4-biphenylyl]ethyl}acetamide;

2-(6,7-dichloro-3-oxo-2,3-dihydro-4H-1,4-benzoxazin-4-yl)-N-methyl-N-[1-[3'-(ethyloxy)-4-biphenylyl]-2-(4-morpholinyl)ethyl]-N-methylacetamide;

2-(6,7-dichloro-3-oxo-2,3-dihydro-4H-1,4-benzoxazin-4-yl)-N-[1-[5'-(ethyloxy)-2'-fluoro-4-biphenylyl]-2-(4-morpholinyl)ethyl]-N-methylacetamide;

2-(6,7-dichloro-3-oxo-2,3-dihydro-4H-1,4-benzoxazin-4-yl)-N-[1-[4'-(dimethylamino)-4-biphenylyl]-2-(4-morpholinyl)ethyl]-N-methylacetamide;

N-[1-[2',3'-bis(methyloxy)-4-biphenylyl]-2-(4-morpholinyl)ethyl]-2-(6,7-dichloro-3-oxo-2,3-dihydro-4H-1,4-benzoxazin-4-yl)-N-methylacetamide;

4'-[1-[[(6,7-dichloro-3-oxo-2,3-dihydro-4H-1,4-benzoxazin-4-yl)acetyl](methyl)amino]-2-(4-morpholinyl)ethyl]-3-biphenylcarboxamide;

4'-[1-[[(6,7-dichloro-3-oxo-2,3-dihydro-4H-1,4-benzoxazin-4-yl)acetyl](methyl)amino]-2-(4-morpholinyl)ethyl]-N-methyl-3-biphenylcarboxamide;

4'-[1-[[(6,7-dichloro-3-oxo-2,3-dihydro-4H-1,4-benzoxazin-4-yl)acetyl](methyl)amino]-2-(4-morpholinyl)ethyl]-N,N-dimethyl-3-biphenylcarboxamide;

2-(6,7-dichloro-3-oxo-2,3-dihydro-4H-1,4-benzoxazin-4-yl)-N-methyl-N-[1-{3'-[(methylsulfonyl)amino]-4-biphenylyl}-2-(4-morpholinyl)ethyl]acetamide;

4'-[1-[[(6,7-dichloro-3-oxo-2,3-dihydro-4H-1,4-benzoxazin-4-yl)acetyl](methyl)amino]-2-(4-morpholinyl)ethyl]-2-biphenylcarboxamide;

4'-[1-[[(6,7-dichloro-3-oxo-2,3-dihydro-4H-1,4-benzoxazin-4-yl)acetyl](methyl)amino]-2-(4-morpholinyl)ethyl]-4-biphenylcarboxamide;

4'-[1-[[(6,7-dichloro-3-oxo-2,3-dihydro-4H-1,4-benzoxazin-4-yl)acetyl](methyl)amino]-2-(4-morpholinyl)ethyl]-N-methyl-4-biphenylcarboxamide;

4'-[1-[[(6,7-dichloro-3-oxo-2,3-dihydro-4H-1,4-benzoxazin-4-yl)acetyl](methyl)amino]-2-(4-morpholinyl)ethyl]-N,N-dimethyl-4-biphenylcarboxamide;

N-cyclopropyl-4'-[1-[[(6,7-dichloro-3-oxo-2,3-dihydro-4H-1,4-benzoxazin-4-yl)acetyl](methyl)amino]-2-(4-morpholinyl)ethyl]-3-biphenylcarboxamide;

4'-[1-[[(6,7-dichloro-3-oxo-2,3-dihydro-4H-1,4-benzoxazin-4-yl)acetyl](methyl)amino]-2-(4-morpholinyl)ethyl]-N-(1-methylethyl)-3-biphenylcarboxamide;

4'-[1-[[(6,7-dichloro-3-oxo-2,3-dihydro-4H-1,4-benzoxazin-4-yl)acetyl](methyl)amino]-2-(4-morpholinyl)ethyl]-5-fluoro-N-methyl-3-biphenylcarboxamide;

2-(6,7-dichloro-3-oxo-2,3-dihydro-4H-1,4-benzoxazin-4-yl)-N-methyl-N-{2-(4-morpholinyl)-1-[3'-(1-pyrrolidinylcarbonyl)-4-biphenylyl]ethyl}acetamide;

N-[1-[2'-(acetylamino)-4-biphenylyl]-2-(4-morpholinyl)ethyl]-2-(6,7-dichloro-3-oxo-2,3-dihydro-4H-1,4-benzoxazin-4-yl)-N-methylacetamide;

2-(6,7-dichloro-3-oxo-2,3-dihydro-4H-1,4-benzoxazin-4-yl)-N-methyl-N-[1-{4'-[(methylamino)sulfonyl]-4-biphenylyl}-2-(4-morpholinyl)ethyl]acetamide;

2-(6,7-dichloro-3-oxo-2,3-dihydro-4H-1,4-benzoxazin-4-yl)-N-[1-{4'-[(dimethylamino)sulfonyl]-4-biphenylyl}-2-(4-morpholinyl)ethyl]-N-methylacetamide;

2-(6,7-dichloro-3-oxo-2,3-dihydro-4H-1,4-benzoxazin-4-yl)-N-[1-{2'-[(dimethylamino)sulfonyl]-4-biphenylyl}-2-(4-morpholinyl)ethyl]-N-methylacetamide;

2-(6,7-dichloro-3-oxo-2,3-dihydro-4H-1,4-benzoxazin-4-yl)-N-methyl-N-{2-(4-morpholinyl)-1-[3'-(1-piperidinylcarbonyl)-3-biphenylyl]ethyl}acetamide;

N-[1-[3',4'-bis(methyloxy)-3-biphenylyl]-2-(4-morpholinyl)ethyl]-2-(6,7-dichloro-3-oxo-2,3-dihydro-4H-1,4-benzoxazin-4-yl)-N-methylacetamide;

2-(6,7-dichloro-3-oxo-2,3-dihydro-4H-1,4-benzoxazin-4-yl)-N-methyl-N-[1-{4'-[(methylsulfonyl)amino]-3-biphenylyl}-2-(4-morpholinyl)ethyl]acetamide;

N-[1-[4'-(acetylamino)-3-biphenylyl]-2-(4-morpholinyl)ethyl]-2-(6,7-dichloro-3-oxo-2,3-dihydro-4H-1,4-benzoxazin-4-yl)-N-methylacetamide;

2-(6,7-dichloro-3-oxo-2,3-dihydro-4H-1,4-benzoxazin-4-yl)-N-methyl-N-[1-[4'-(methylsulfonyl)-3-biphenylyl]-2-(4-morpholinyl)ethyl]acetamide;

N-[1-[3'-(acetylamino)-3-biphenylyl]-2-(4-morpholinyl)ethyl]-2-(6,7-dichloro-3-oxo-2,3-dihydro-4H-1,4-benzoxazin-4-yl)-N-methylacetamide;

3'-[1-[[(6,7-dichloro-3-oxo-2,3-dihydro-4H-1,4-benzoxazin-4-yl)acetyl](methyl)amino]-2-(4-morpholinyl)ethyl]-3-biphenylcarboxamide;

N-[1-[2'-(acetylamino)-3-biphenylyl]-2-(4-morpholinyl)ethyl]-2-(6,7-dichloro-3-oxo-2,3-dihydro-4H-1,4-benzoxazin-4-yl)-N-methylacetamide;

N-[1-(4'-cyano-3-biphenylyl)-2-(4-morpholinyl)ethyl]-2-(6,7-dichloro-3-oxo-2,3-dihydro-4H-1,4-benzoxazin-4-yl)-N-methylacetamide;

2-(6,7-dichloro-3-oxo-2,3-dihydro-4H-1,4-benzoxazin-4-yl)-N-methyl-N-[1-{3'-[(methylsulfonyl)amino]-3-biphenylyl}-2-(4-morpholinyl)ethyl]acetamide;

3'-[1-[[(6,7-dichloro-3-oxo-2,3-dihydro-4H-1,4-benzoxazin-4-yl)acetyl](methyl)amino]-2-(4-morpholinyl)ethyl]-2-biphenylcarboxamide;

N-[1-(2'-cyano-3-biphenylyl)-2-(4-morpholinyl)ethyl]-2-(6,7-dichloro-3-oxo-2,3-dihydro-4H-1,4-benzoxazin-4-yl)-N-methylacetamide;

2-(6,7-dichloro-3-oxo-2,3-dihydro-4H-1,4-benzoxazin-4-yl)-N-[1-[4'-(ethylsulfonyl)-3-biphenylyl]-2-(4-morpholinyl)ethyl]-N-methylacetamide;

3'-[1-[[(6,7-dichloro-3-oxo-2,3-dihydro-4H-1,4-benzoxazin-4-yl)acetyl](methyl)amino]-2-(4-morpholinyl)ethyl]-N-methyl-4-biphenylcarboxamide;

3'-[1-[[(6,7-dichloro-3-oxo-2,3-dihydro-4H-1,4-benzoxazin-4-yl)acetyl](methyl)amino]-2-(4-morpholinyl)ethyl]-N,N-dimethyl-4-biphenylcarboxamide;

2-(6,7-dichloro-3-oxo-2,3-dihydro-4H-1,4-benzoxazin-4-yl)-N-methyl-N-[1-{2'-[(methylsulfonyl)amino]-3-biphenylyl}-2-(4-morpholinyl)ethyl]acetamide;

N-[1-[4'-(aminosulfonyl)-3-biphenylyl]-2-(4-morpholinyl)ethyl]-2-(6,7-dichloro-3-oxo-2,3-dihydro-4H-1,4-benzoxazin-4-yl)-N-methylacetamide;

3'-[1-[[(6,7-dichloro-3-oxo-2,3-dihydro-4H-1,4-benzoxazin-4-yl)acetyl](methyl)amino]-2-(4-morpholinyl)ethyl]-4-biphenylcarboxamide;

3'-[1-[[(6,7-dichloro-3-oxo-2,3-dihydro-4H-1,4-benzoxazin-4-yl)acetyl](methyl)amino]-2-(4-morpholinyl)ethyl]-N,N-dimethyl-3-biphenylcarboxamide;

3'-[1-[[(6,7-dichloro-3-oxo-2,3-dihydro-4H-1,4-benzoxazin-4-yl)acetyl](methyl)amino]-2-(4-morpholinyl)ethyl]-N-methyl-3-biphenylcarboxamide;

2-(6,7-dichloro-3-oxo-2,3-dihydro-4H-1,4-benzoxazin-4-yl)-N-methyl-N-{2-(4-morpholinyl)-1-[4'-(1-pyrrolidinylcarbonyl)-3-biphenylyl]ethyl}acetamide;

2-(6,7-dichloro-3-oxo-2,3-dihydro-4H-1,4-benzoxazin-4-yl)-N-methyl-N-{2-(4-morpholinyl)-1-[4'-(4-morpholinylcarbonyl)-3-biphenylyl]ethyl}acetamide;

2-(6,7-dichloro-3-oxo-2,3-dihydro-4H-1,4-benzoxazin-4-yl)-N-[1-[3'-(dimethylamino)-3-biphenylyl]-2-(4-morpholinyl)ethyl]-N-methylacetamide;

2-(6,7-dichloro-3-oxo-2,3-dihydro-4H-1,4-benzoxazin-4-yl)-N-[1-{2'-[(dimethylamino)sulfonyl]-3-biphenylyl}-2-(4-morpholinyl)ethyl]-N-methylacetamide;

2-(6,7-dichloro-3-oxo-2,3-dihydro-4H-1,4-benzoxazin-4-yl)-N-methyl-N-{2-(4-morpholinyl)-1-[3'-(1-pyrrolidinylcarbonyl)-3-biphenylyl]ethyl}acetamide;

2-(6,7-dichloro-3-oxo-2,3-dihydro-4H-1,4-benzoxazin-4-yl)-N-methyl-N-{2-(4-morpholinyl)-1-[4'-(1-piperidinylcarbonyl)-3-biphenylyl]ethyl}acetamide;

2-(6,7-dichloro-3-oxo-2,3-dihydro-4H-1,4-benzoxazin-4-yl)-N-methyl-N-[1-[3'-(methylsulfonyl)-3-biphenylyl]-2-(4-morpholinyl)ethyl]acetamide;

3-chloro-3'-[1-[[(6,7-dichloro-3-oxo-2,3-dihydro-4H-1,4-benzoxazin-4-yl)acetyl](methyl)amino]-2-(4-morpholinyl)ethyl]-4-biphenylcarboxamide;

N-cyclopropyl-3'-[1-[[(6,7-dichloro-3-oxo-2,3-dihydro-4H-1,4-benzoxazin-4-yl)acetyl](methyl)amino]-2-(4-morpholinyl)ethyl]-4-biphenylcarboxamide;

3'-[1-[[(6,7-dichloro-3-oxo-2,3-dihydro-4H-1,4-benzoxazin-4-yl)acetyl](methyl)amino]-2-(4-morpholinyl)ethyl]-N-(1-methylethyl)-3-biphenylcarboxamide;

3'-[1-[[(6,7-dichloro-3-oxo-2,3-dihydro-4H-1,4-benzoxazin-4-yl)acetyl](methyl)amino]-2-(4-morpholinyl)ethyl]-4-biphenylcarboxylic acid;

2-(6,7-dimethyl-3-oxo-2,3-dihydro-4H-1,4-benzoxazin-4-yl)-N-methyl-N-[1-{3'-[(1-methylethyl)oxy]-4-biphenylyl}-2-(4-morpholinyl)ethyl]acetamide;

2-(6,7-dimethyl-3-oxo-2,3-dihydro-4H-1,4-benzoxazin-4-yl)-N-methyl-N-[1-{3'-[(methylsulfonyl)amino]-4-biphenylyl}-2-(4-morpholinyl)ethyl]acetamide;

N-[1-[3',4'-bis(methyloxy)-4-biphenylyl]-2-(4-morpholinyl)ethyl]-2-(6,7-dimethyl-3-oxo-2,3-dihydro-4H-1,4-benzoxazin-4-yl)-N-methylacetamide;

2-(6,7-dichloro-3-oxo-2,3-dihydro-4H-1,4-benzoxazin-4-yl)-N-methyl-N-[1-[3'-(methyloxy)-4-biphenylyl]-2-(4-morpholinyl)ethyl]acetamide;

N-[1-[3',4'-bis(methyloxy)-4-biphenylyl]-2-(4-morpholinyl)ethyl]-2-(6,7-dichloro-3-oxo-2,3-dihydro-4H-1,4-benzoxazin-4-yl)-N-methylacetamide;

4'-[1-[[(6,7-dichloro-3-oxo-2,3-dihydro-4H-1,4-benzoxazin-4-yl)acetyl](methyl)amino]-2-(4-morpholinyl)ethyl]-4-biphenylcarboxylic acid;

N-[1-[4'-(acetylamino)-4-biphenylyl]-2-(4-morpholinyl)ethyl]-2-(6,7-dichloro-3-oxo-2,3-dihydro-4H-1,4-benzoxazin-4-yl)-N-methylacetamide;

N-[1-(4'-amino-4-biphenylyl)-2-(4-morpholinyl)ethyl]-2-(6,7-dichloro-3-oxo-2,3-dihydro-4H-1,4-benzoxazin-4-yl)-N-methylacetamide;

N-{4'-[1-[[(6,7-dichloro-3-oxo-2,3-dihydro-4H-1,4-benzoxazin-4-yl)acetyl](methyl)amino]-2-(4-morpholinyl)ethyl]-4-biphenylyl}propanamide;

2-(6,7-dichloro-3-oxo-2,3-dihydro-4H-1,4-benzoxazin-4-yl)-N-[1-{4'-[(ethylsulfonyl)amino]-4-biphenylyl}-2-(4-morpholinyl)ethyl]-N-methylacetamide;

2-(6,7-dichloro-3-oxo-2,3-dihydro-4H-1,4-benzoxazin-4-yl)-N-[1-(4'-{[(ethylamino)carbonyl]amino}-4-biphenylyl)-2-(4-morpholinyl)ethyl]-N-methylacetamide;

N-[1-(4-biphenylyl)-2-(1-pyrrolidinyl)ethyl]-N-methyl-2-[7-(methyloxy)-3-oxo-2,3-dihydro-4H-1,4-benzoxazin-4-yl]acetamide;

(R)N-[1-(4-biphenylyl)-2-(4-morpholinyl)ethyl]-2-(6,7-dichloro-3-oxo-2,3-dihydro-4H-1,4-benzoxazin-4-yl)-N-methylacetamide;

N-[1-(4-biphenylyl)-2-(1-pyrrolidinyl)ethyl]-N-methyl-2-[6-(methyloxy)-3-oxo-2,3-dihydro-4H-1,4-benzoxazin-4-yl]acetamide;

N-[1-(4-biphenylyl)-2-(1-pyrrolidinyl)ethyl]-N-methyl-2-{3-oxo-6-[(trifluoromethyl)oxy]-2,3-dihydro-4H-1,4-benzoxazin-4-yl}acetamide;

N-[1-(4-biphenylyl)-2-(1-pyrrolidinyl)ethyl]-N-methyl-2-[5-(methyloxy)-2-oxo-1,3-benzoxazol-3(2H)-yl]acetamide;

N-[1-(4-biphenylyl)-2-(1-pyrrolidinyl)ethyl]-N-methyl-2-[2-oxo-5-[(trifluoromethyl)oxy]-1,3-benzoxazol-3(2H)-yl]acetamide;

N-[1-(4-biphenylyl)-2-(4-morpholinyl)ethyl]-2-(5,6-dichloro-2-oxo-1(2H)-quinolinyl)-N-methylacetamide;

N-[1-(4-biphenylyl)-2-(4-morpholinyl)ethyl]-2-(6,7-dimethyl-2-oxo-1(2H)-quinolinyl)-N-methylacetamide; and N-[1-(4-biphenylyl)-2-(4-morpholinyl)ethyl]-2-(6,7-dimethyl-2-oxo-1(2H)-quinoxalinyl)-N-methylacetamide;

and pharmaceutically acceptable salts thereof.
Further compounds include:

4'-[(1R)-1-[[(6,7-dichloro-3-oxo-2,3-dihydro-4H-1,4-benzoxazin-4-yl)acetyl](methyl)amino]-2-(4-morpholinyl)ethyl]-4-biphenylcarboxylic acid;

4'-[(1R)-1-[[(6,7-dichloro-3-oxo-2,3-dihydro-4H-1,4-benzoxazin-4-yl)acetyl](methyl)amino]-2-(1-pyrrolidinyl)ethyl]-3-biphenylcarboxamide; and 4'-[(1R)-1-[[(6,7-dichloro-3-oxo-2,3-dihydro-4H-1,4-benzoxazin-4-yl)acetyl](methyl)amino]-2-(1-pyrrolidinyl)ethyl]-4-biphenylcarboxamide;

and pharmaceutically acceptable salts thereof.

Further compounds include:

4'-[(1R)-1-[[(6,7-dichloro-3-oxo-2,3-dihydro-4H-1,4-benzoxazin-4-yl)acetyl](methyl)amino]-2-(4-morpholinyl)ethyl]-4-biphenylcarboxylic acid HCl salt;

4'-[(1R)-1-[[(6,7-dichloro-3-oxo-2,3-dihydro-4H-1,4-benzoxazin-4-yl)acetyl](methyl)amino]-2-(4-morpholinyl)ethyl]-4-biphenylcarboxylic acid TFA salt;

4'-[(1R)-1-[[(6,7-dichloro-3-oxo-2,3-dihydro-4H-1,4-benzoxazin-4-yl)acetyl](methyl)amino]-2-(1-pyrrolidinyl)ethyl]-3-biphenylcarboxamide TFA salt; and 4'-[(1R)-1-[[(6,7-dichloro-3-oxo-2,3-dihydro-4H-1,4-benzoxazin-4-yl)acetyl](methyl)amino]-2-(1-pyrrolidinyl)ethyl]-4-biphenylcarboxamide TFA salt.

The compounds of Formula (I) and pharmaceutically acceptable derivatives and salts thereof may be prepared by the processes described hereinafter, said processes constituting a further aspect of the invention. In the following description, the groups are as defined above for compounds of formula (I) unless otherwise indicated.

When $R^1$ is phenyl, target molecules can be prepared from the bromomethyl ketone (scheme 1). The bromo is displaced with morpholine or pyrrolidine which is followed by reductive amination to give the benzylic amine. Acylation provides the desired compounds.

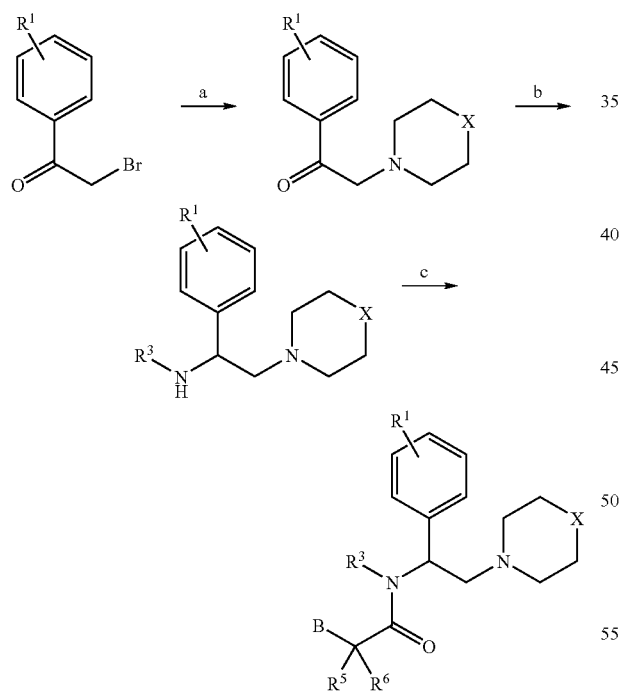

Conditions: a) morpholine or pyrrolidine, ether; b) MeNH$_2$, NaCNBH$_3$, HOAc, MeOH; c) BOP reagent, NEt$_3$, DMF.

When $R^1$ is substituted phenyl, target molecules can be prepared from 2-bromo-1-(bromophenyl)ethanone (scheme 2). The bromo is displaced with morpholine or pyrrolidine which is followed by reductive amination to give the benzylic amines. Acylation provides the amides and palladium catalyzed cross coupling reaction affords the target molecules.

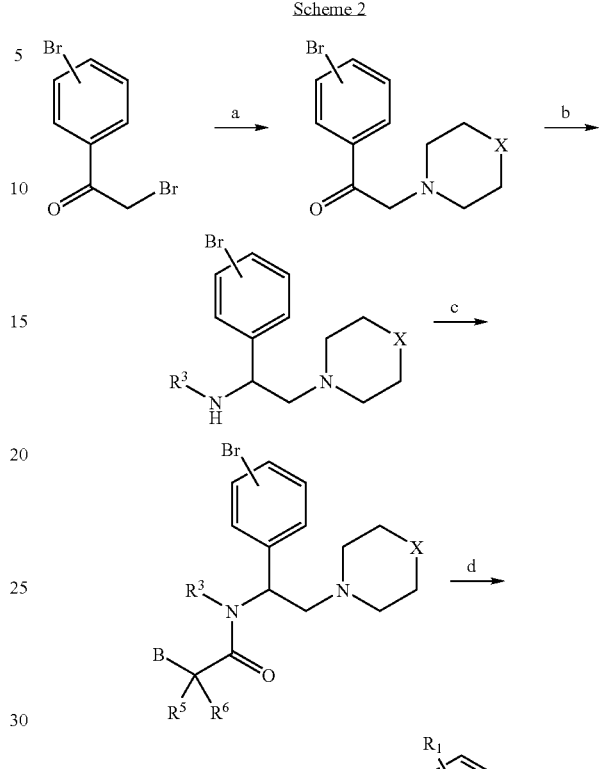

Conditions: a) morpholine or pyrrolidine, ether; b) MeNH$_2$, NaCNBH$_3$, HOAc, MeOH; c) Pd source, ArB(OH)$_2$, K$_2$CO$_3$, microwave or conventional heating; d) BOP reagent, NEt$_3$, DMF.

When $R^2$ is other than H, compounds are prepared starting with substituted benzoic acids (Scheme 3). Conversion to the morpholine amide is followed by reaction with methyl magnesium bromide to provide the acetophenones. Bromination affords the bromomethyl ketone. Target molecules are then completed as in scheme 2.

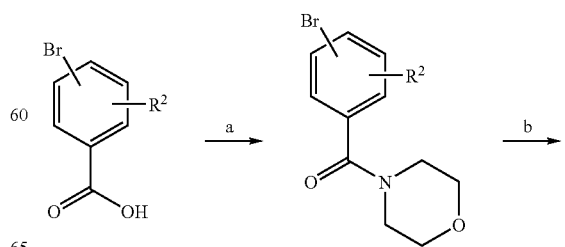

-continued

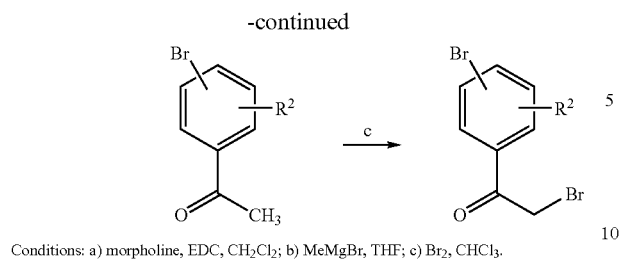

Conditions: a) morpholine, EDC, CH₂Cl₂; b) MeMgBr, THF; c) Br₂, CHCl₃.

When $R^4$ is methyl, compounds are prepared starting with 1-(bromophenyl)ethanamine (Scheme 4). Initial Boc protection is followed by palladium catalyzed cross coupling to provide the biphenyl compound. A second Boc protection to give the bis Boc compound is followed by a base promoted rearrangement to provide the tert-butyl ester. Boc deprotection along with tert-butyl ester hydrolysis is followed immediately be reesterification in acidic methanol. Two stage functional group manipulation provides the Boc protected amino acid. Amide formation followed by reduction gives the diamine and then amidation furnished the target molecule.

Scheme 4

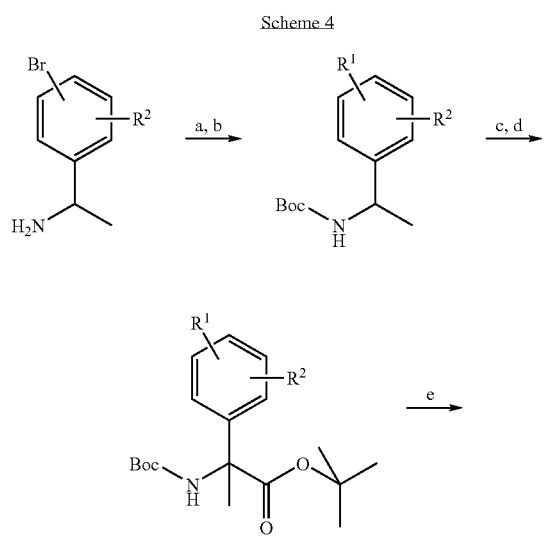

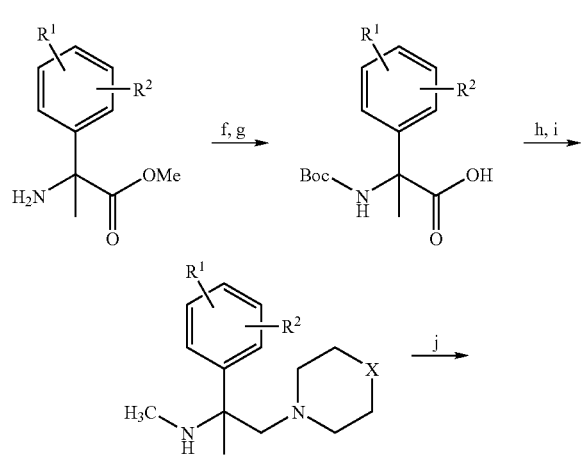

-continued

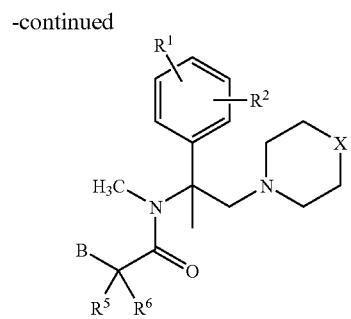

Conditions: a) (Boc)₂O, CH₂Cl₂, b) Pd source, ArB(OH)₂, K₂CO₃, 100° C.; c) (Boc)₂O, 80° C. (melt); d) n-BuLi, t-BuOK, (i-Pr)2NH, THF, -78° C.; e) HCl, dioxane, then MeOH, HCl; f) (Boc)₂O, CHCl₃; g) LiOH, THF; h) BOP reagent, amine, NEt₃, DMF; i) LAH, THF, heating; j) BOP reagent, acid NEt₃, DMF.

The carboxylic acids corresponding to groups B are prepared in various ways. 2-Anilino acids are prepared starting with the appropriate aniline and alkylating with 2-bromo esters (scheme 5). A second alkylation provides the tertiary aniline. Hydrolysis furnishes the desired acid.

Scheme 5

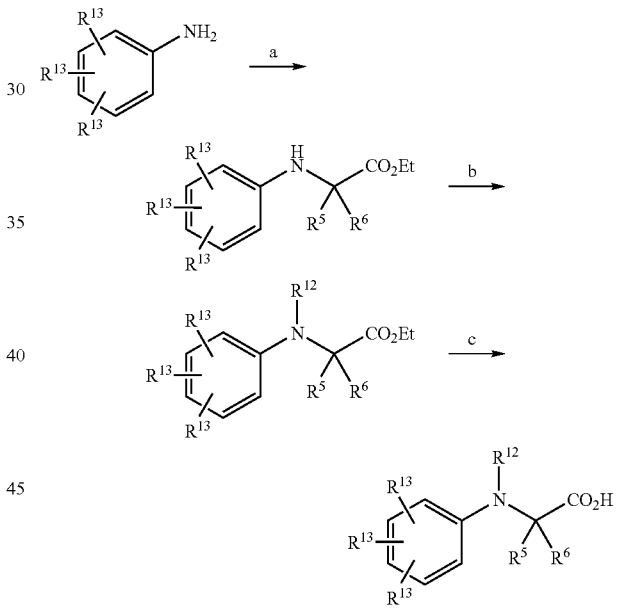

Conditions: a) base, BrC(R₅R₆)CO₂Et; b) base, dimethylsulfate or R₁₂Br; c) LiOH, THF.

Alternative B groups and their corresponding carboxylic acids, when not commercially available, can be prepared from amino phenols by condensation with bromoacetyl bromide (scheme 6). Alkylation with an alkyl bromoacetate followed by hydrolysis furnishes the desired acids.

Scheme 6

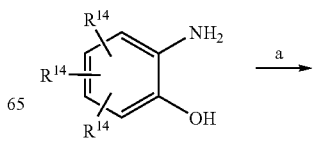

-continued

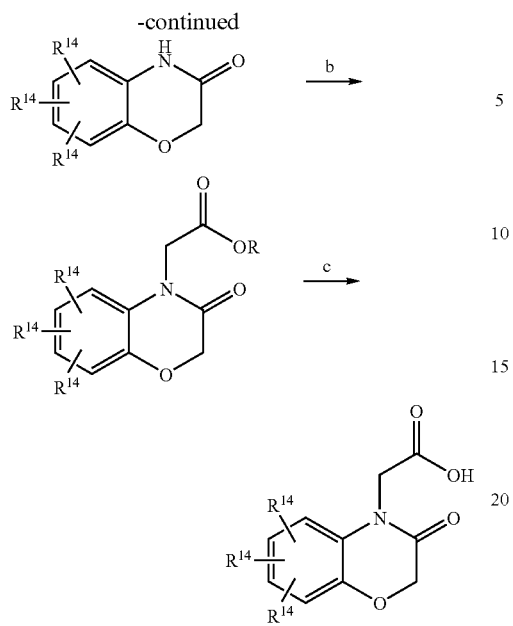

Conditions: a) NaHCO₃, bromoacetyl bromide, CHCl₃; b) BrCH₂COOR, NaH, DMF; c) LiOH, THF (R = Me, Et), or acid (R = t-Bu).

The heterocyclic group can also be made starting with substituted fluoro nitrobenzenes (scheme 7). Nucleophilic addition of ethyl glycolate provides an aryl ether. Reduction of the nitro group to an aniline is accompanied by ring closure to the benzoxazinone.

Scheme 7

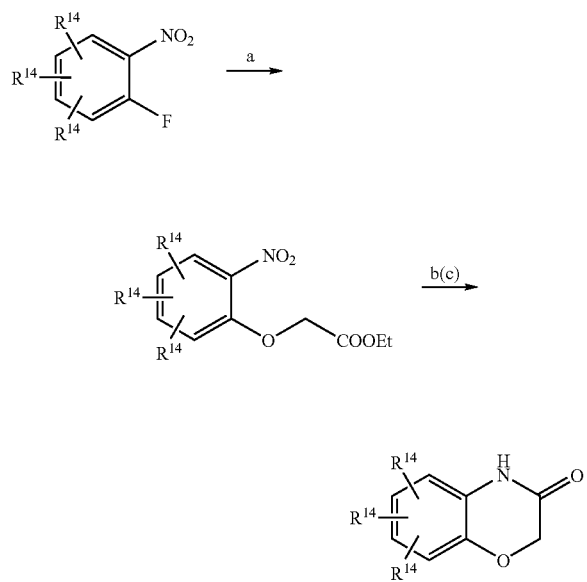

Conditions: a) ethyl glycolate, NaF, dioxane; b) SnCl₂·2H₂O, EtOH, 85° C.;

Other B-group carboxylic acids are prepared starting with phenylene diamines (scheme 8). Condensation with ethyl glyoxylate furnishes the heterocycle. Alkylation with an alkyl bromoacetate followed by hydrolysis furnishes the desired acids.

Scheme 8

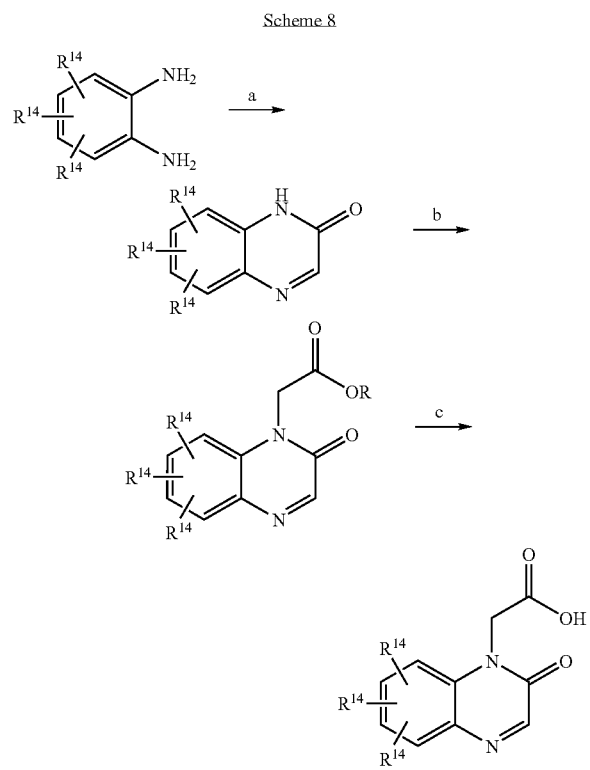

Conditions: a) HCOCO₂Et, tol, EtOH; b) BrCH₂COOR, NaH, DMF; c) LiOH, THF (R = Me, Et), or acid (R = t-Bu).

With appropriate manipulation, including the use of alternative nitrogen protecting group(s), the synthesis of the remaining compounds of Formula (I) may be accomplished by methods analogous to those above and to those described in the Experimental section.

Separation of diastereoisomers or cis and trans isomers may be achieved by conventional techniques, e.g. by fractional crystallisation, chromatography or H.P.L.C. of a stereoisomeric mixture of the agent may also be prepared from a corresponding optically pure intermediate or by resolution, such as H.P.L.C. of the corresponding racemate using a suitable chiral support or by fractional crystallisation of the diastereoisomeric salts formed by reaction of the corresponding racemate with a suitable optically active acid or base, as appropriate.

In order to use a compound of the Formula (I) or a pharmaceutically acceptable salt thereof for the treatment of humans and other mammals it is normally formulated in accordance with standard pharmaceutical practice as a pharmaceutical composition.

Compounds of Formula (I) and their pharmaceutically acceptable salts may be administered in a standard manner for the treatment of the indicated diseases, for example orally, parenterally, sub-lingually, transdermally, rectally, via inhalation or via buccal administration.

Compounds of Formula (I) and their pharmaceutically acceptable salts which are active when given orally can be formulated as syrups, tablets, capsules and lozenges. A syrup formulation will generally consist of a suspension or solution of the compound or salt in a liquid carrier for example, ethanol, peanut oil, olive oil, glycerine or water with a flavoring or coloring agent. Where the composition is in the form of a tablet, any pharmaceutical carrier routinely used for preparing solid formulations may be used. Examples of such carriers include magnesium stearate, terra alba, talc, gelatin, agar, pectin, acacia, stearic acid, starch, lactose and sucrose. Where the composition is in the form of a capsule, any routine encapsulation is suitable, for example using the aforementioned carriers in a hard gelatin capsule shell. Where the composition is in the form of a soft gelatin shell capsule any pharmaceutical carrier routinely used for preparing dispersions or suspensions may be considered, for example aqueous gums, celluloses, silicates or oils and are incorporated in a soft gelatin capsule shell.

Typical parenteral compositions consist of a solution or suspension of the compound or salt in a sterile aqueous or non-aqueous carrier, for example polyethylene glycol, and polyvinylpyrrolidone; optionally containing a parenterally acceptable oil, such as lecithin, arachis oil, or sesame oil.

Typical compositions for inhalation are in the form of a solution, suspension or emulsion that may be administered as a dry powder or in the form of an aerosol using a conventional propellant such as dichlorodifluoromethane or trichlorofluoromethane.

A typical suppository formulation comprises a compound of Formula (I) or a pharmaceutically acceptable salt thereof which is active when administered in this way, with a binding and/or lubricating agent, for example polymeric glycols, gelatins, cocoa-butter or other low melting vegetable waxes or fats or their synthetic analogues.

Typical transdermal formulations comprise a conventional aqueous or non-aqueous vehicle, for example a cream, ointment, lotion or paste or are in the form of a medicated plaster, patch or membrane.

Preferably the composition is in unit dosage form, for example a tablet, capsule or metered aerosol dose, so that the patient may administer to themselves a single dose.

Each dosage unit for oral administration contains suitably from 0.1 mg to 500 mg/Kg, and preferably from 1 mg to 200 mg/Kg, and each dosage unit for parenteral administration contains suitably from 0.1 mg to 200 mg, of a compound of Formula (I) or a pharmaceutically acceptable salt thereof calculated as the free acid or base. Each dosage unit for intranasal administration contains suitably 1-400 mg and preferably 10 to 200 mg per person. A topical formulation contains suitably 0.01 to 1.0% of a compound of Formula (I).

The daily dosage regimen for oral administration is suitably about 0.01 mg/Kg to 40 mg/Kg, of a compound of Formula (I) or a pharmaceutically acceptable salt thereof calculated as the free acid. The daily dosage regimen for parenteral administration is suitably about 0.001 mg/Kg to 100 mg/Kg, of a compound of the Formula (I) or a pharmaceutically acceptable salt thereof calculated as the free acid. The daily dosage regimen for intranasal administration and oral inhalation is suitably about 10 to about 500 mg/person. The active ingredient may be administered from 1 to 6 times a day, sufficient to exhibit the desired activity.

These compounds may be used for the treatment or prevention of congestive heart failure, stroke, ischemic heart disease (e.g. angina, myocardial ischemia), cardiac arrhythmia, hypertension (e.g. essential and pulmonary), renal disease (acute and chronic renal failure/end stage renal disease, nephrotoxicity) peripheral vascular disease (e.g. male erectile dysfunction, diabetic retinopathy, intermittent claudication/ischemic limb disease) and ischemic/hemorrhagic stroke, COPD, restenosis, asthma, neurogenic inflammation, migraine, metabolic vasculopathies, bone/cartilage/joint diseases (e.g. osteoporosis, arthritis), arthritis, other inflammatory diseases, fibrosis (e.g. pulmonary fibrosis), sepsis, atherosclerosis, thromboembolic disorders, dyslipidemia, addiction, schizophrenia, cognitive disorders/Alzheimer's disease, impulsivity, anxiety, stress, depression, Parkinson's, movement disorders, sleep-wake cycle, incentive motivation, pain, (e.g. inflammatory and visceral pain) neuromuscular function, diabetes, diabetes/metabolic syndrome, eating disorders, gastric reflux, gastric motility disorders, IBS, colitis, ulcers, obesity, overactive bladder, and genitourinary diseases.

The urotensin antagonist may be administered alone or in conjunction with one or more other therapeutic agents, said agents being selected from the group consisting of endothelin receptor antagonists, angiotensin converting enzyme (ACE) inhibitors, A-II receptor antagonists, vasopeptidase inhibitors, diuretics, digoxin, and dual non-selective $\alpha$-adrenoceptor and $\alpha_1$-adrenoceptor antagonists.

The biological activity of the compounds of Formula (I) are demonstrated by the following tests. Compounds of the examples had a Ki of 0.1-30 nM in the human rhabdomyosarcoma cell line Ki Determination for UT Antagonists in Native Cells The human rhabdomyosarcoma cell line (SJRH30), obtained from American Type Culture Collection (ATCC; Manassas, Va.), is cultured in accordance with the supplier's specific recommendations.

Binding of [$^{125}$I]hU-II to SJRH30 cells is measured using a whole cell binding assay. Cells are split into 6-well plates and incubated 48 h at 37° C. Growth media is aspirated, and the cells are washed with binding buffer DPBS$^+$ (Dulbecco's phosphate-buffered saline with 10 mM $MgCl_2$, 0.7 mM $CaCl_2$, 1.4 mM glucose and 0.2% bovine serum albumin).

[$^{125}$I]hU-II binding to SJRH30 cells is performed at 37° C. for 30 min in 1 ml DPBS$^+$. Nonspecific binding is defined in the presence of 1 µM unlabeled hU-II. The assay is done in duplicate. Competition binding is performed using 200 pM of [$^{125}$I]hU-II and different concentrations of competing ligands. Drug (0.1 nM to 10 µM) is made in DMSO at 50-fold excess concentration.

After incubation, the cells are washed with cold DPBS$^+$ (4×1 ml) and then solubilized with 1 ml of 1 M NaOH and transferred to 12×75 mm glass tubes. Radioactivity is then measured in a Packard gamma counter (>85% efficiency). The experiment is repeated at least three times.

Affinity constant ($K_i$s) from competition binding experiments are calculated using the interactive non-linear curve-fitting program of GRAPHPAD Prism (San Diego, Calif.).

$Ca^{2+}$-Mobilization:

Compounds of the invention are further characterised in a functional assay using FLIPR technology for the determination of their effect to inhibit the intracellular calcium increase induced by Urotensin II. A HEK293 cell line with stably expressed human Urotensin receptor (GPR14) is used in the studies. 20K cells/well are seeded in 384 well Greiner Bio-one plate coated with poly-D-lysine in culture medium (EMEM with 10% FBS), and incubated overnight in $CO_2$ at 37° C. After aspirating the medium, the cells are loaded with 4 uM of cytoplasmic calcium indicator Fluor-3 dye (Molecular Devices Co.) in 50 ul/well EMEM and incubated in $CO_2$ at 37° C. for 60 minutes. After incubating, the dye is aspirated off and the cells are washed one time with 50 ul/well of assay buffer (10× Kreb's Henseleit Ringer's Solution with 15 mM Hepes, 1 mM $MgCl_2$ and 1 mM $CaCl_2$). 50 ul/well of assay buffer is added to the cells and 25 ul/well of assay buffer containing different concentrations of compounds is then added to the cells for another 30-minutes incubation at 37° C. Finally, 25 ul/well urotensin-II in assay buffer containing 0.1% BSA is added to the cells and the fluorescence signal is read on a FLIPR system. IC50 values of each compound are determined by an 11-point 3x-dilution inhibition curve. The potency of the antagonist (fpK$_i$ value or pK$_B$ value) is calculated from pIC50 by the Cheng-Prusoff equation or calculated from Schild's analysis.

pA$_2$ Determination of UT Receptor Antagonists in the Rat Isolated Thoracic Aorta Male Sprague-Dawley rats (350-500 g) are anesthetized with inhaled isoflurane (5% in $O_2$) and killed by cervical dislocation. Thoracic aorta are isolated, cleaned of adherent tissue and cut into 3 mm rings. Following denudation by rubbing with a fine forceps, each ring is suspended in 10 ml organ baths containing Krebs solution of the following composition (mM): NaCl, 112.0; KCl, 4.7; $KH_2PO_4$, 1.2; $MgSO_4$, 1.2; $CaCl_2$, 2.5; $NaHCO_3$, 25.0; dextrose, 11.0; indomethacin, 0.01. The Krebs solution is maintained at 37±1° C. and aerated with 95% $O_2$:5% $CO_2$ (pH 7.4). Changes in isometric force are measured isometrically under 1.0 g optimal resting tension using force-displacement transducers (MLT0201/D; Letica Scientific Instruments) and recorded using Chart 5.0 software (ADInstruments). Following a 60 min equilibration period, arteries are treated with standard concentrations of KCl (60 mM) and phenylephrine (1 µM) to which subsequent agonist-induced responses are normalized. Once the contractile response to phenylephrine had plateaued, carbachol (10 µM) is added to vessels in order to evaluate endothelial integrity. Following a 30-min pretreatment with either vehicle (DMSO) or antagonist (300, 1,000 or 3,000 nM), cumulative concentration-response curves to hU-II (0.1 nM-10 µM) are obtained for each vessel by adding the spasmogen to the tissue bath at half-10 g increments. Each response is allowed to plateau before the addition of subsequent agonist concentrations.

Kb Determination of UT Receptor Antagonists in the Rat Isolated Thoracic Aorta

Male Sprague-Dawley rats (350-500 g) are anesthetized with inhaled isoflurane (5% in $O_2$) and killed by cervical dislocation. Thoracic aorta are isolated, cleaned of adherent tissue and cut into 3 mm rings. Following denudation by rubbing with a fine forceps, each ring is suspended in 10 ml organ baths containing Krebs solution of the following composition (mM): NaCl, 112.0; KCl, 4.7; $KH_2PO_4$, 1.2; $MgSO_4$, 1.2; $CaCl_2$, 2.5; $NaHCO_3$, 25.0; dextrose, 11.0; indomethacin, 0.01. Krebs solution is maintained at 37±1° C. and aerated with 95% $O_2$:5% $CO_2$ (pH 7.4). Changes in isometric force are measured isometrically under 1.0 g optimal resting tension using force-displacement transducers (MLT0201/D; Letica Scientific Instruments) and recorded using Chart 5.0 software (ADInstruments). Following a 60 min equilibration period, arteries are treated with standard concentrations of KCl (60 mM) and phenylephrine (1 µM) to which subsequent agonist-induced responses are normalized. Once the contractile response to phenylephrine plateaued, carbachol (10 µM) is added to vessels in order to evaluate endothelial integrity. Following a 30-min pretreatment with either vehicle (DMSO) or antagonist (typically either 1 or 10 µM depending on the compounds binding affinity), cumulative concentration-response curves to hU-II (0.1 nM-10 µM) are obtained for each vessel by adding the spasmogen to the tissue bath at half-10 g increments. Each response is allowed to plateau before the addition of subsequent agonist concentrations.

Kb Determination of UT Receptor Antagonists in Cat Isolated Femoral Artery and Thoracic Aorta Following sodium pentobarbital overdose, the thoracic aorta and left femoral artery are isolated from adult male cats (3-5 kg; Liberty Research Inc., Waverly, N.Y.). Vessels are cleaned of adherent tissue, cut into 3 mm rings and denuded of endothelium by rubbing with a fine forceps. Each ring is suspended in 10 ml organ baths containing Krebs Solution of the following composition (mM): NaCl, 112.0; KCl, 4.7; $KH_2PO_4$, 1.2; $MgSO_4$, 1.2; $CaCl_2$, 2.5; $NaHCO_3$, 25.0; dextrose, 11.0; indomethacin, 0.01. Krebs solution is maintained at 37±1° C. and aerated with 95% $O_2$:5% $CO_2$ (pH 7.4). Changes in isometric force are measured isometrically under 2.0 g optimal resting tension using force-displacement transducers (MLT0201/D; Letica Scientific Instruments) and recorded using Chart 5.0 software (ADInstruments). Following a 60 min equilibration period, arteries are treated with standard concentrations of KCl (60 mM) and phenylephrine (1 µM) to which subsequent agonist-induced responses are normalized. Once the contractile response to phenylephrine had plateaued, carbachol (10 µM) is added to vessels in order to evaluate endothelial integrity. Following a 30-min pretreatment with either vehicle (DMSO) or antagonist (typically either 1 or 10 µM depending on the compounds binding affinity), cumulative concentration-response curves to hU-II (0.01 nM-10 µM) are obtained for each vessel by adding the spasmogen to the tissue bath at half-10 g increments. Each response is allowed to plateau before the addition of subsequent agonist concentrations.

The following Examples are illustrative but not limiting embodiments of the present invention.

In the Examples:

1H NMR spectra were recorded on a Bruker Advance 400 megahertz NMR spectrometer. Chemical shifts are expressed in parts per million (ppm, units). Coupling constants (J) are in units of hertz (Hz). Splitting patterns describe apparent multiplicities and are designated as s (singlet), d (doublet), t (triplet), q (quartet), dd (double doublet), dt (double triplet), m (multiplet), br (broad).

MS and liquid chromatography MS were recorded on a MDS Sciex liquid chromatography/mass spectroscopy system. All mass spectra were performed under electrospray ionization (ESI), chemical ionization (CI), electron impact (EI) or by fast atom bombardment (FAB) methods.

HPLC data was recorded on an Agilent 1100 series HPLC system with C-18 reverse phase column (Eclipse XDB-C18, 4.6×250 mm, 5 micron) running a gradient of 1-99% MeCN/H2O (+0.1% TFA) over 12 minutes.

All reactions were monitored by thin-layer chromatography on 0.25 mm E. Merck silica gel plates (60F-254), visualized with UV light, 5% ethanolic phosphomolybdic acid, p-anisaldehyde solution, aqueous potassium permanganate or potassium iodide/platinum chloride solution in water.

Flash column chromatography was performed on silica gel.

The naming program used is ACD Name Pro 6.02.

Diamines are prepared from acetophenones or further advanced intermediates by bromination, and displacement of the resulting bromide with an amine to give an aminoketone.

Example 1

N-(3,4-dichlorophenyl)-N-methylglycine, lithium salt

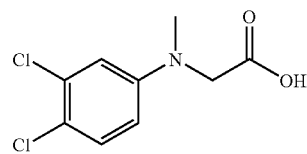

a) Ethyl N-(3,4-dichlorophenyl)glycinate

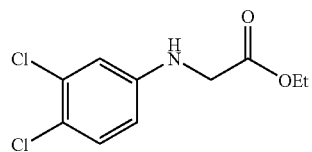

3,4-Dichloroaniline (100 g, 0.617 mol), ethyl bromoacetate (68.4 mL, 0.617 mol), and diisopropylethylamine (129.0 mL, 0.740 mol) were combined in 300 mL of dry NMP and stirred at room temperature for 18 h. HPLC (Eclipse XDB-C18, 4.6×250 mm, 5 micron, 1-99% $CH_3CN/H_2O$ with 0.1% trifluoroacetic acid) after 18 h at room temperature showed that most of the starting material ($R_t$=5.2 min) was consumed and that a new peak had formed ($R_t$=7.9 min). The reaction was heated to 90° C. for 1 h, at which point HPLC indicated that conversion was complete. The reaction was allowed to cool to room temperature and then poured onto 2.5 L of ice, 1.5 L of water, and 240 g of $NaHCO_3$. A tan precipitate formed immediately, the suspension was stirred vigorously for 10 minutes and then filtered through a fritted glass funnel. The tan solid was air-dried for 20 h in a crystallizing dish and then transferred to a 1 L flask and dried by rotary evaporation to remove the bulk of the remaining water. The tan solid was further dried under high vacuum to give 148 g (97%) of the title compound. LC/MS (APCI) m/e 248 [M+H]$^+$.

b) ethyl N-(3,4-dichlorophenyl)-N-methylglycinate

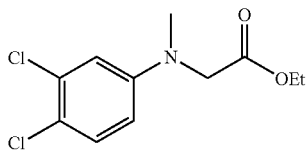

The product from step a) (20 g, 80.6 mmol) was dissolved in 20 mL of N-methylpyrrolidinone and treated with dimethyl sulfate (15.3 mL, 161 mmol) and sodium bicarbonate (13.5 g, 161 mmol). The reaction was stirred for 68 hours at room temperature, after which time HPLC (Eclipse XDB-C18, 4.6×250 mm, 5 micron, 1-99% $CH_3CN/H_2O$ with 0.1% trifluoroacetic acid) indicated that the reaction mixture was comprised of approximately two-thirds product ($R_t$=8.4 min) and one third starting material ($R_t$=7.8 min). The reaction was heated to 100° C. and monitored periodically by HPLC. Additional dimethyl sulfate and sodium bicarbonate were added as needed. In this case, an additional 3 equivalents (23 mL, 242 mmol) of dimethyl sulfate and 0.5 equivalents (3.5 g, 40.3 mmol) of sodium bicarbonate were added over the course of 24 hours while maintaining the temperature at 100° C., which brought the reaction to approximately 90% completion. The reaction was allowed to cool to room temperature and was poured into 500 mL of water. The aqueous phase was extracted with ether (3×250 mL). The combined organic layers were washed with water (3×250 mL) and saturated NaCl (1×300 mL), dried over magnesium sulfate, filtered and concentrated to a brown oil which was purified by silica gel chromatography (330 g silica gel 60, isocratic elution with 10% ethyl acetate/90% hexanes over 75 minutes) to give ethyl N-(3,4-dichlorophenyl)-N-methylglycinate (9.18 g, 35.0 mmol, 43%) as a colorless oil. LC/MS (APCI) m/e 262 [M+H]$^+$.

c) N-(3,4-dichlorophenyl)-N-methylglycine, lithium salt

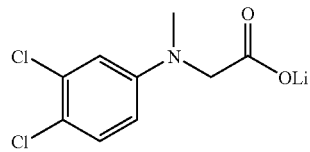

The product of step b) (9.18 g, 35.0 mmol) was dissolved in 50 mL of THF and treated with LiOH (0.838 g, 35.0 mmol) dissolved in 5 mL of water. After two hours, HPLC (Eclipse XDB-C18, 4.6×250 mm, 5 micron, 1-99% $CH_3CN/H_2O$ with 0.1% trifluoroacetic acid) indicated that all of the starting material ($R_t$=8.4 min) had been converted to the desired product ($R_t$=6.7 min). The volatiles were removed under reduced pressure and then placed under high vacuum for 24 hours to provide the lithium salt of N-(3,4-dichlorophenyl)-N-methylglycine (8.4 g, quantitative yield) as a white solid. LC/MS (APCI) m/e 234 [M+H]$^+$.

Example 2

((3,4-Dichlorophenyl){2-oxo-2-[(cis)-3-phenyl-2-(1-pyrrolidinylmethyl)-1-piperidinyl]ethyl}amino)acetonitrile

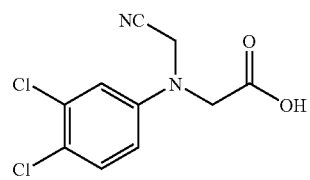

a) Ethyl N-(cyanomethyl)-N-(3,4-dichlorophenyl)glycinate

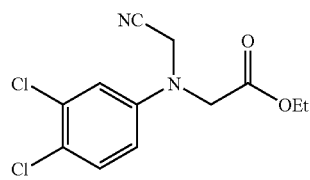

Ethyl N-(3,4-dichlorophenyl)glycinate (4.0 g, 16.1 mmol), diisopropylethylamine (3.37 mL, 19.3 mmol), bromoacetonitrile (1.23 mL, 17.7 mmol) and sodium iodide (2.41 g, 16.1 mmol) were dissolved in 25 mL of dry NMP and heated to 120° C. After 20 h, HPLC (Eclipse XDB-C18, 4.6×250 mm, 5 micron, 1-99% $CH_3CN/H_2O$ with 0.1% trifluoroacetic acid) showed that approximately half of the starting material ($R_t$=7.8 min) was consumed and that a new peak had formed ($R_t$=7.6 min). The reaction was monitored periodically by HPLC and additional bromoacetonitrile was added as needed to achieve complete conversion. In this case, an additional 1.5 equivalents (1.68 mL, 24.1 mmol) of bromoacetonitrile was added and the reaction was heated for an additional 28 h, after which time the HPLC indicated that the reaction was complete. The reaction mixture was poured into 400 mL of 50% saturated ammonium chloride and extracted with 500 mL of ethyl acetate. The layers were separated and the organic layer was washed with 50% saturated sodium bicarbonate (400 mL), water (400 mL), and saturated NaCl (400 mL). The organic extracts were dried over magnesium sulfate, filtered, and concentrated to a black oil which was adsorbed onto approximately 15 g of silica gel. The crude residue was purified by column chromatography (300 g silica gel 40 um, gradient elution from 30-70-100% EtOAc/hexanes over 40 minutes) to give the title compound as a yellow solid (2.59 g, 9.02 mmol, 56%). LC/MS (APCI) m/e 260 [M−CN]+.

b) N-(Cyanomethyl)-N-(3,4-dichlorophenyl)glycine

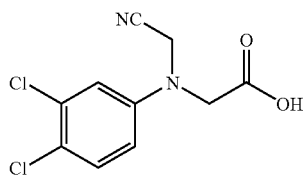

Ethyl N-(cyanomethyl)-N-(3,4-dichlorophenyl)glycinate (1.00 g, 3.48 mmol) was dissolved in 10 mL of THF and treated with LiOH (83.4 mg, 3.48 mmol) dissolved in 2 mL of water. After 2 h, HPLC (Eclipse XDB-C18, 4.6×250 mm, 5 micron, 1-99% $CH_3CN/H_2O$ with 0.1% trifluoroacetic acid) showed that all of the starting material ($R_t$=7.6 min) was gone and that a single new peak ($R_t$=6.2 min) had formed. The reaction mixture was treated with a solution of 4.0M HCl in dioxane (1.74 mL, 6.96 mmol) and then the solvent was removed by rotary evaporation followed by high vacuum to give 870 mg (3.36 mmol, 96%) of N-(cyanomethyl)-N-(3,4-dichlorophenyl)glycine as a white solid which was used in subsequent chemistry without further purification. LC/MS (APCI) m/e 232 [M−CN]+.

Example 3

(6,7-dichloro-3-oxo-2,3-dihydro-4H-1,4-benzoxazin-4-yl)acetic acid

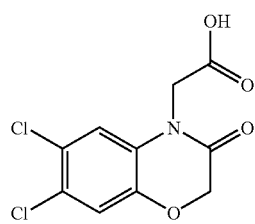

a) ethyl[(4,5-dichloro-2-nitrophenyl)oxy]acetate

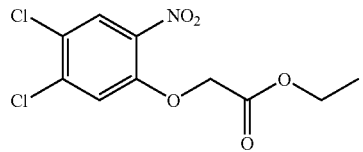

1,2-dichloro-4-fluoro-5-nitrobenzene (50 g, 0.238 mol), ethyl glycolate (90.1 mL, 0.952 mol), and potassium fluoride (76.1 g, 1.31 mol) were added to a 1 L round-bottom flask containing 200 mL of anhydrous dioxane. The mixture was magnetically stirred and heated to 100° C. in an oil bath. After two hours, HPLC (Eclipse XDB-C18, 4.6×250 mm, 5 micron, 1-99% $CH_3CN/H_2O$ with 0.1% trifluoroacetic acid) showed that all of the starting material ($R_t$=7.5 min) was gone and that one major peak ($R_t$=7.8 min) had formed. The reaction mixture was poured into 4 L of water, which resulted in precipitation of the product. The solid was filtered off and dried under vacuum to give ethyl[(4,5-dichloro-2-nitrophenyl)oxy]acetate (67.4 g, 0.229 mol, 96%) as a tan solid. MS (ES) m/e 294 [M+H]+.

b) 6,7-dichloro-2H-1,4-benzoxazin-3(4H)-one

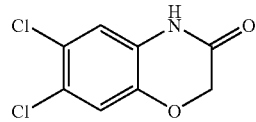

Ethyl[(4,5-dichloro-2-nitrophenyl)oxy]acetate (36.0 g, 0.122 mol) was dissolved in 400 mL of ethanol and treated with $SnCl_2.2H_2O$ (138.0 g, 0.612 mol). This mixture was magnetically stirred and heated to 85° C. in an oil bath. After 20 hours, HPLC (Eclipse XDB-C18, 4.6×250 mm, 5 micron, 1-99% $CH_3CN/H_2O$ with 0.1% trifluoroacetic acid) showed that all of the starting material ($R_t$=7.8 min) was gone and that two new compounds had formed: the desired product ($R_t$=6.2 min) and the hydroxamic acid of the desired product ($R_t$=5.9 min). An additional 138.0 g of $SnCl_2.2H_2O$ (0.612 mol) and 90 mL of concentrated HCl were added and stirred at 85° C. for seven hours, after which time HPLC showed that only the desired product remained. The reaction mixture was poured into 5.5 L of 5% aqueous HCl and stirred for 20 minutes, resulting in precipitation of the product. The solid was filtered off and air-dried on a vacuum funnel for one hour. The solid was transferred to a 1 L round bottom flask and suspended in 500 mL of absolute ethanol. The solvent was removed by rotary evaporation to azeotrope off the last traces of water and the resulting white solid was dried under high vacuum to give 6,7-dichloro-2H-1,4-benzoxazin-3(4H)-one (22.2 g, 0.102 mol, 83%) as a fine white powder. MS (ES) m/e 218 [M+H]+.

c) ethyl (6,7-dichloro-3-oxo-2,3-dihydro-4H-1,4-benzoxazin-4-yl)acetate

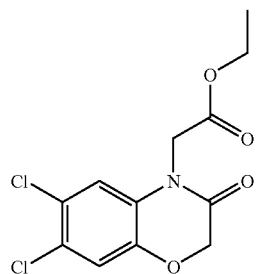

A 1 L round-bottom flask was purged with argon and charged with sodium hydride (6.94 g of a 60% dispersion of NaH in mineral oil, 0.174 mol) and 60 mL of anhydrous DMF. This suspension was magnetically stirred and cooled to 0° C. in an ice-bath and then treated slowly with a suspension of 6,7-dichloro-2H-1,4-benzoxazin-3(4H)-one (22.2 g. 0.102 mol) in 140 mL of anhydrous DMF. The reaction mixture was maintained at 0° C. for one hour and then treated slowly with ethyl bromoacetate (29.4 mL, 0.265 mol) over a period of 5-10 minutes. This reaction mixture was maintained at 0° C. for thirty minutes, allowed to warm to room temperature, and then was maintained at room temperature for thirty minutes. HPLC (Eclipse XDB-C18, 4.6×250 mm, 5 micron, 1-99% $CH_3CN/H_2O$ with 0.1% trifluoroacetic acid) showed that all of the starting material ($R_t$=6.2 min) was gone and that a new compound had formed ($R_t$=7.5 min). The reaction mixture was poured into 5.5 L of 5% aqueous HCl and the product precipitated immediately as a yellow solid. The suspension was stirred for 10 minutes and the solid was filtered off to give a yellow filter cake. The solid was rinsed with ice-cold ethanol (3×200 mL) and hexanes (3×200 mL) and then dried under high vacuum to give ethyl (6,7-dichloro-3-oxo-2,3-dihydro-4H-1,4-benzoxazin-4-yl)acetate (26.0 g, 0.085 mol, 84%) as a white powder. MS (ES) m/e 304 $[M+H]^+$.

d) (6,7-dichloro-3-oxo-2,3-dihydro-4H-1,4-benzoxazin-4-yl)acetic acid

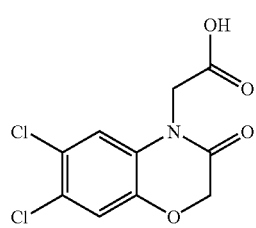

Ethyl (6,7-dichloro-3-oxo-2,3-dihydro-4H-1,4-benzoxazin-4-yl)acetate (22.0 g, 0.072 mol) was suspended in 400 mL of THF and treated with LiOH (3.46 g, 0.144 mol) dissolved in 80 mL of water at room temperature. The reaction was magnetically stirred and maintained at room temperature for 20 hours. The reaction was then quenched with 30 mL of concentrated HCl and stirred for 20 minutes. HPLC (Eclipse XDB-C18, 4.6×250 mm, 5 micron, 1-99% $CH_3CN/H_2O$ with 0.1% trifluoroacetic acid) showed that all of the starting material ($R_t$=7.5 min) was gone and that a single product ($R_t$=6.0 min) had formed. The solvent was removed by rotary evaporation to give an off-white solid that was further dried under high vacuum to give 24.5 g of a mixture of the title compound (77% by mass) and LiCl (23% by mass) which was used in subsequent reactions without further purification. Actual product yield is 18.9 g (0.068 mol, 95%). MS (ES) m/e 276 $[M+H]^+$.

Example 4

(6,7-dibromo-3-oxo-2,3-dihydro-4H-1,4-benzoxazin-4-yl)acetic acid

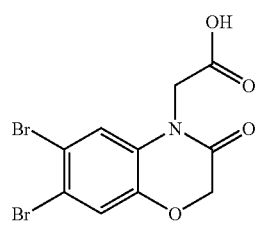

Following the procedure in example 3c and 3d except replacing 6,7-dichloro-2H-1,4-benzoxazin-3(4H)-one with 6,7-bromo-2H-1,4-benzoxazin-3(4H)-one, the title compound was prepared.

Example 5

(6,7-dimethyl-3-oxo-2,3-dihydro-4H-1,4-benzoxazin-4-yl)acetic acid

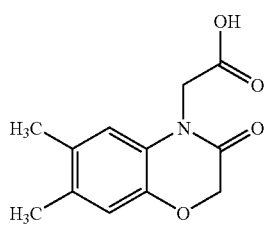

a) 6,7-dimethyl-2H-1,4-benzoxazin-3(4H)-one

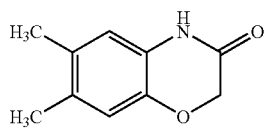

A solution of 4,5-dimethyl-2-aminophenol (1.73 g, 12.6 mmol) in chloroform (50 mL) was added to a rapidly stirred saturated solution of sodium bicarbonate. Bromoacetyl bromide (1.1 mL, 2.54 g, 12.6 mmol) in chloroform (15 mL) was added dropwise to the rapidly stirring mixture. Stirring continued for 2 h. EtOAc was added. Layers separated and the EtOAc solution washed with $H_2O$ (1×), brine (1×), dried ($MgSO_4$) and concentrated to give a brown solid, which was dissolved in DMF (85 mL). $CsCO_3$ (4.1 g, 12.6 mmol) was added and the mixture heated at 80 deg. C. for 1 h, then poured into ice-H$_2$O (200 mL). The crystallized product was collected, washed with H$_2$O, and dried to give a tan solid (1.78 g, 80%). MS (ES) m/e 178[M+H]$^+$.

b) (6,7-dimethyl-3-oxo-2,3-dihydro-4H-1,4-benzoxazin-4-yl)acetic acid

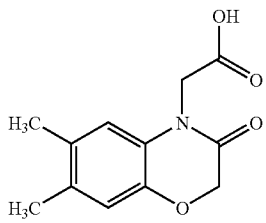

Following the procedure in example 3c and 3d except replacing 6,7-dichloro-2H-1,4-benzoxazin-3(4H)-one with 6,7-dimethyl-2H-1,4-benzoxazin-3(4H)-one, the title compound was prepared.

Example 6

(6,7-dichloro-2-oxo-1(2H)-quinoxalinyl)acetic acid

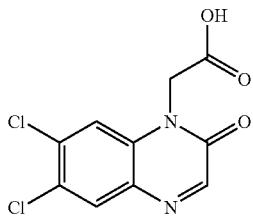

a) 6,7-dichloro-2(1H)-quinoxalinone

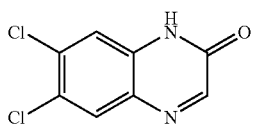

4,5-Dichlorophenylenediamine (26.0 g, 147 mmol) and 50% ethyl glyoxylate in toluene (32 mL, 161 mmol) in ethanol (250 mL) was refluxed for 18 h. The reaction was cooled and the crystallized brown product was collected by filtration, then washed with ethanol (50 mL). The obtained product (25.5 g, 81%) was 96% pure via LC/MS. MS (ES) m/e 215 [M+H]$^+$.

b) (6,7-dichloro-2-oxo-1(2H)-quinoxalinyl)acetic acid

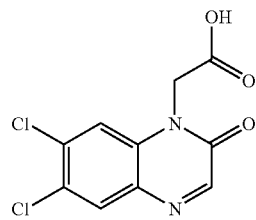

Following the procedure in example 3c and 3d except replacing 6,7-dichloro-2H-1,4-benzoxazin-3(4H)-one with 6,7-dichloro-2(1H)-quinoxalinone, the title compound was prepared.

Example 7

(2-Oxo-1,3-benzoxazol-3(2H)-yl)acetic acid

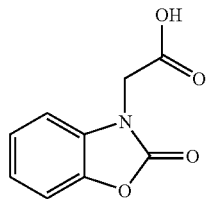

a) Ethyl (2-oxo-1,3-benzoxazol-3(2H)-yl)acetate

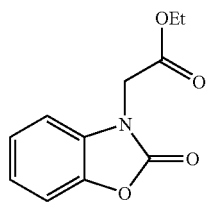

A solution of 1,3-benzoxazol-2(3H)-one (676 mg, 5.0 mmol) in (5 mL) was added to a suspension of NaH (220 mg, 5.5 mmol) in DMF (5 mL) at room temperature, and the resulting solution was stirred for 1 h. Ethyl bromoacetate (0.55 mL, 5.0 mmol) was added to the reaction mixture, and stirring was continued for 2 h. The reaction was quenched with water (10 mL) and extracted with EtOAc (2×20 mL). The organic extracts were combined and washed with water, brine, and dried (Na$_2$SO$_4$). The solvent was removed under b) (2-Oxo-1,3-benzoxazol-3(2H)-yl)acetic acid

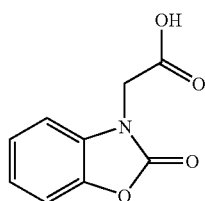

The product from Step a) (94 mg, 0.43 mmol) was dissolved in THF (4 mL) and a solution of LiOH.H$_2$O (20 mg, 0.47 mmol) in THF (1 mL) was added. The reaction mixture was stirred at room temperature for 3 hours, acidified to pH ~1 with 2 N HCl, and extracted with EtOAc (2×10 mL). The organic extracts were combined and washed with water, brine, and dried (Na$_2$SO$_4$). The solvent was removed under reduced pressure to give the title compound (81 mg, 98%) as a brown solid. MS (ES) m/e 194 [M+H]$^+$.

Examples 8 and 9

Following the procedure in example G except replacing 1,3-benzoxazol-2(3H)-one with 5-chloro-1,3-benzothiazol-2(3H)-one or 5-chloro-1,3-benzoxazol-2(3H)-one, the following compounds were prepared.

| Ex # | Structure | Name |
|---|---|---|
| 8 | 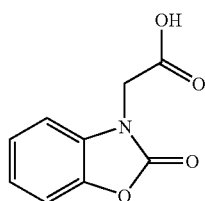 | (5-chloro-2-oxo-1,3-benzothiazol-3(2H)-yl)acetic acid |
| 9 | 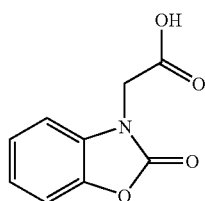 | (5-chloro-2-oxo-1,3-benzoxazol-3(2H)-yl)acetic acid |

Example 10A and 10B (6,7-dichloro-2-oxo-1(2H)-quinolinyl)acetic acid (A), (5,6-dichloro-2-oxo-1(2H)-quinolinyl)acetic acid (B)

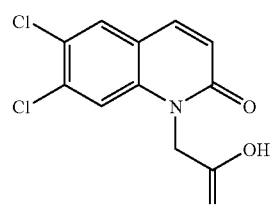
A

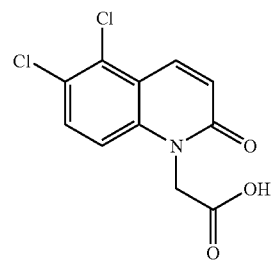
B a) (2E)-N-(3,4-dichlorophenyl)-3-phenyl-2-propenamide

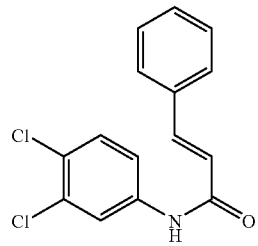

3,4-Dichloroaniline (5.41 g, 33.6 mmol) and triethylamine (1.5 mL) were dissolved in 160 mL of THF and treated with trans-cinnamoyl chloride (6.71 g, 40.3 mmol) with vigorous stirring at room temperature for 2 h, and then quenched with 10 mL of H$_2$O. The reaction mixture was extracted with EtOAc (3×100 mL). The combined organics were washed with saturated solution of Na$_2$CO$_3$, brine, dried over MgSO$_4$ and then concentrated in vacuo to yield the title compound as a white crystalline solid (6.2 g, 63%), MS (ES) m/e 293 [M+H]$^+$.

b) 6,7-Dichloro-2(1H)-quinolinone (A) 5,6-dichloro-2(1H)-quinolinone (B)

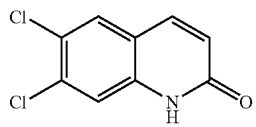
A

-continued

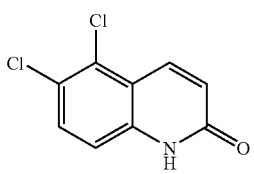
B

A mixture of (2E)-N-(3,4-dichlorophenyl)-3-phenyl-2-propenamide (4.0 g, 13.7 mmol) and AlCl$_3$ (9.1 g, 68.5 mmol) was heated slowly until the mixture became liquefied and then subsequently congealed to form a solid cake. Ice was slowly added to break up the hardened material. The mixture was vigorously stirred for 2 h. The precipitate was collected and washed with 2 N HCl solution, water, and ether to obtain a white mixture of product A and B above (2.8 g, 96%), MS (ES) m/e 215 [M+H]$^+$.

c) Methyl (6,7-dichloro-2-oxo-1(2H)-quinolinyl)acetate (A) methyl (5,6-dichloro-2-oxo-1(2H)-quinolinyl)acetate (B)

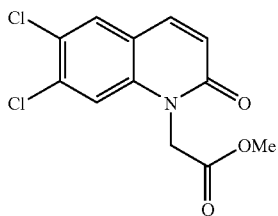
A

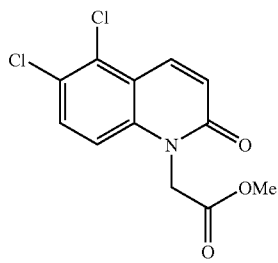
B

A suspension of NaH (1.20 g, 29.9 mmol) in mineral oil (60%) was added to a mixture of 6,7-dichloro-2(1H)-quinolinone (A) and 5,6-dichloro-2(1H)-quinolinone (B) (3.2 g, 14.9 mmol) in THF. The mixture was stirred for 0.5 h and a solution of methyl bromoacetate (2.74 g, 17.9 mmol) was added. The reaction mixture was continued stirring for 3 h, quenched with H$_2$O and then concentrated in vacuo. The residue was extracted with EtOAc (2×100 mL), washed with a saturated solution of Na$_2$CO$_3$, brine, dried over MgSO$_4$ and then concentrated in vacuo to yield the title compounds as a white crystalline solid (3.5 g, 82%), MS (ES) m/e 287 [M+H]$^+$.

d) (6,7-dichloro-2-oxo-1(2H)-quinolinyl)acetic acid (A) (5,6-dichloro-2-oxo-1(2H)-quinolinyl)acetic acid (B)

LiOH.H$_2$O (1.5 g, 61 mmol) was added to a solution of (6,7-dichloro-2-oxo-1(2H)-quinolinyl)acetic acid (A) and (5,6-dichloro-2-oxo-1(2H)-quinolinyl)acetic acid (B) (3.5 g, 12 mmol) in MeOH. The resulting reaction mixture was heated at reflux for 2 h and then concentrated in vacuo. The residue was washed with H$_2$O several times and purified by preparative HPLC (YMC CombiPrep ODS-A, 50×20 mm, 20 mL/min, A: acetonitrile B: water, A: 10 to 90% over 10 min, UV detection at 214 nm) to give the title compounds A (0.8 g 24%), B (0.3 g, 9%), MS (ES) m/e 272 [M+H]$^+$.

Example 11

N$^1$-[1-(4-biphenylyl)-2-(1-pyrrolidinyl)ethyl]-N$^2$-(3,4-dichlorophenyl)-N$^1$-,N$^2$-dimethylglycinamide

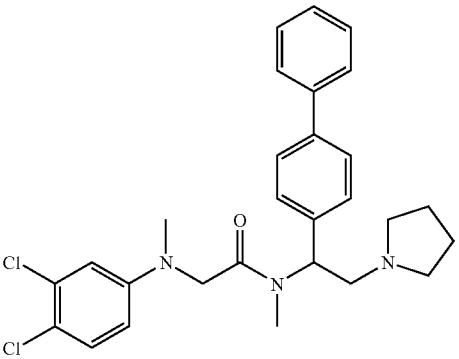

[1-(4-biphenylyl)-2-(1-pyrrolidinyl)ethyl]methylamine (50 mg, 0.18 mmol) was added to a solution of N-(3,4-dichlorophenyl)-N-methylglycine (49 mg, 0.21 mmol), (benzotriazol-1-yloxy) tris(dimethylamino) phosphonium-hexafluorophosphate (BOP) (118 mg, 0.27 mmol) and triethylamine (TEA) (54 mg, 0.54 mmol) in dichloromethane (DCM) (2.0 mL), The reaction mixture was stirred at room temperature for 3 h and was then concentrated in vacuo. To the residue was added 4 mL of saturated solution of Na$_2$CO$_3$ and then extracted by ethyl acetate (2×3 mL). The combined organic layers were concentrated in vacuo to give a brown solid, which was purified by using a Gilson preparative HPLC system (Phenomenex 75×30 mm column, 40 mL/min flow rate, A: 0.1% TFA in acetonitrile B: 0.1% TFA in water, A: 10 to 100% over 15 min, UV detection at 215 nm) to yield the title compound (52 mg, 58%). MS (ES) m/e 496 [M+H]+.

Examples 12-19

Proceeding in a similar manner as in example 11, but replacing N-(3,4-dichlorophenyl)-N-methylglycine with the appropriate carboxylic acids, the compounds listed in table 1 were prepared. As is appreciated by those skilled in the art, these analogous examples may involve variations in synthetic procedure.

TABLE 1

| Ex # | Structure | Name | MS [M + H]+ |
|---|---|---|---|
| 12 | 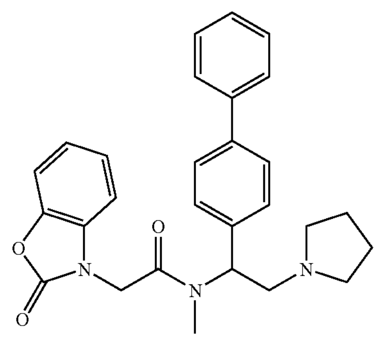 | N-[1-(4-biphenylyl)-2-(1-pyrrolidinyl)ethyl]-N-methyl-2-(2-oxo-1,3-benzoxazol-3(2H)-yl)acetamide | 455 |
| 13 | 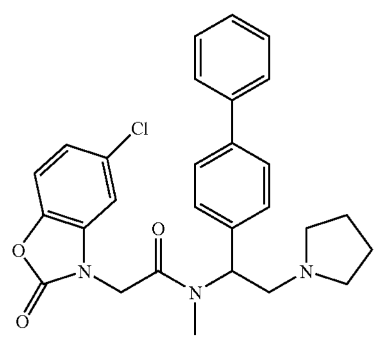 | N-[1-(4-biphenylyl)-2-(1-pyrrolidinyl)ethyl]-2-(5-chloro-2-oxo-1,3-benzoxazol-3(2H)-yl)-N-methylacetamide | 490 |
| 14 | 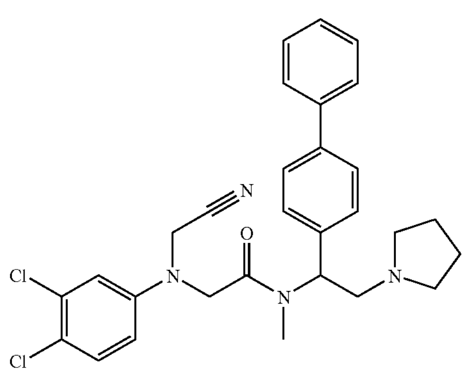 | N$^1$-[1-(4-biphenylyl)-2-(1-pyrrolidinyl)ethyl]-N$^2$-(cyanomethyl)-N$^2$-(3,4-dichlorophenyl)-N$^1$-methylglycinamide | 521 |

TABLE 1-continued

| Ex # | Structure | Name | MS [M + H]+ |
|---|---|---|---|
| 15 | 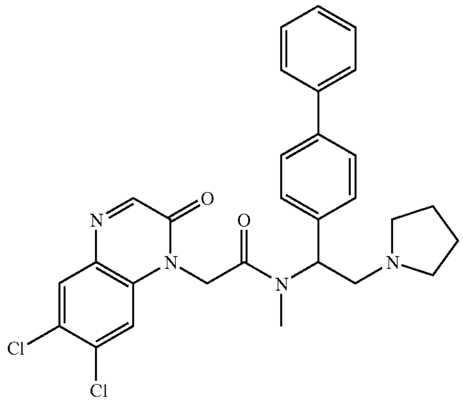 | N-[1-(4-biphenylyl)-2-(1-pyrrolidinyl)ethyl]-2-(6,7-dichloro-2-oxo-1(2H)-quinoxalinyl)-N-methylacetamide | 535 |
| 16 | 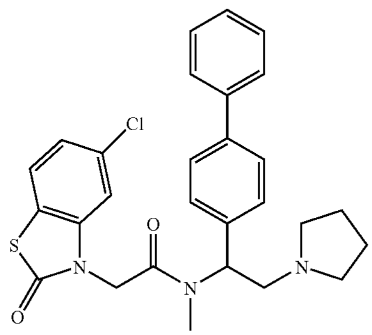 | N-[1-(4-biphenylyl)-2-(1-pyrrolidinyl)ethyl]-2-(5-chloro-2-oxo-1,3-benzothiazol-3(2H)-yl)-N-methylacetamide | 506 |
| 17 | 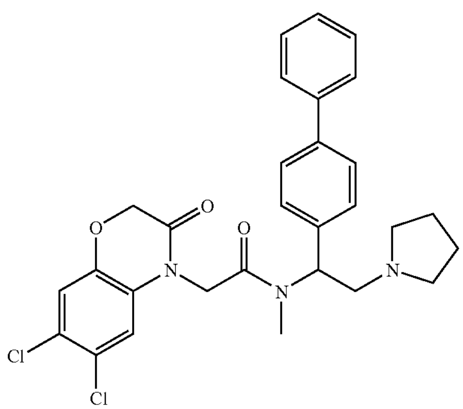 | N-[1-(4-biphenylyl)-2-(1-pyrrolidinyl)ethyl]-2-(6,7-dichloro-3-oxo-2,3-dihydro-4H-1,4-benzoxazin-4-yl)-N-methylacetamide | 538 |
| 18 | 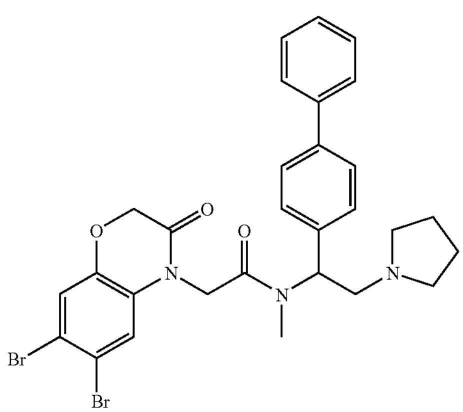 | N-(1-biphenyl-4-yl-2-pyrrolidin-1-ylethyl)-2-(6,7-dibromo-3-oxo-2,3-dihydro-4H-1,4-benzoxazin-4-yl)-N-methylacetamide | 627 |

TABLE 1-continued

| Ex # | Structure | Name | MS [M + H]+ |
|---|---|---|---|
| 19 | 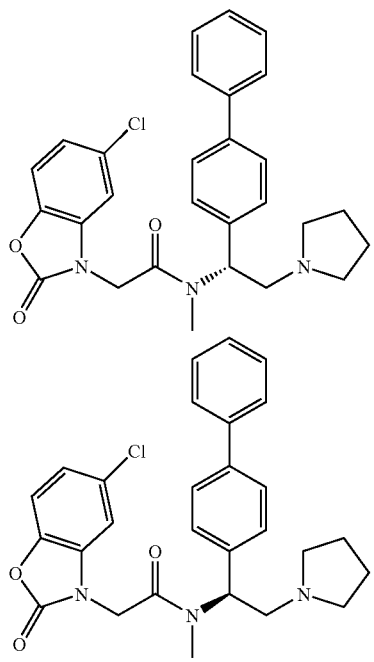 | N-[1-(4-biphenylyl)-2-(1-pyrrolidinyl)ethyl]-2-(6,7-dimethyl-3-oxo-2,3-dihydro-4H-1,4-benzoxazin-4-yl)-N-methylacetamide | 498 |

Examples 20 and 21

N-[(1R)-1-(4-biphenylyl)-2-(1-pyrrolidinyl)ethyl]-2-(5-chloro-2-oxo-1,3-benzoxazol-3(2H)-yl)-N-methylacetamide and N-[(1S)-1-(4-biphenylyl)-2-(1-pyrrolidinyl)ethyl]-2-(5-chloro-2-oxo-1,3-benzoxazol-3(2H)-yl)-N-methylacetamide 128 mg of racemic N-[1-(4-biphenylyl)-2-(1-pyrrolidinyl)ethyl]-2-(5-chloro-2-oxo-1,3-benzoxazol-3(2H)-yl)-N-methylacetamide was separated into the N-[(1R)-1-(4-biphenylyl)-2-(1-pyrrolidinyl)ethyl]-2-(5-chloro-2-oxo-1,3-benzoxazol-3(2H)-yl)-N-methylacetamide and N-[(1S)-1-(4-biphenylyl)-2-(1-pyrrolidinyl)ethyl]-2-(5-chloro-2-oxo-1,3-benzoxazol-3(2H)-yl)-N-methylacetamide enantiomer by using chiral HPLC on a Chiralpak® AD-H column (250× 4.6 mm), with a mobile phase of Heptane/isopropanol/triethylamine-50/50/0.1, a flow rate of 8.0 mL/min, and detection at 254 nm UV at 25° C. 36 mg of each isomer was obtained. MS (ES) m/e 490 [M+H]+.

Example 22

(N-[1-(4-biphenylyl)-2-(4-morpholinyl)ethyl]-2-(6,7-dibromo-3-oxo-2,3-dihydro-4H-1,4-benzoxazin-4-yl)-N-methylacetamide

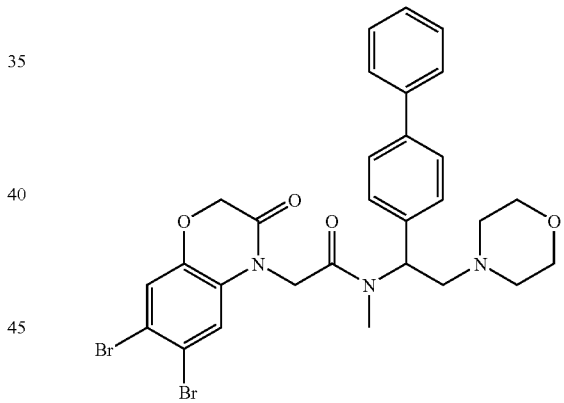

a) 1-(4-Biphenylyl)-2-(4-morpholinyl)ethanone

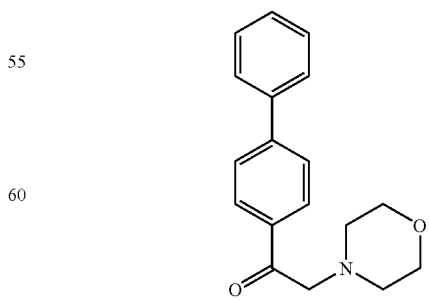

Morpholine (1.67 g, 19.1 mmol) in anhydrous ether (20 mL) was added dropwise to a solution of 1-(4-biphenylyl)-2- bromoethanone (2.63 g, 9.56 mmol) and triethylamine (TEA) (2.90 g, 28.68 mmol) in anhydrous ether (50 mL) at 0° C. over 30 min. The reaction mixture was then warmed to room temperature. After stirring for 2 h, water (80 mL) was added and the aqueous layer was extracted with ethyl acetate (2×60 mL). The combined organic layer was dried over $MgSO_4$ and concentrated to yield the title compound as a light yellow solid (2.52 g, 93%), which was used without further purification. MS (ES) m/e 281 [M+H]+.

b) [1-(4-biphenylyl)-2-(4-morpholinyl)ethyl]methylamine

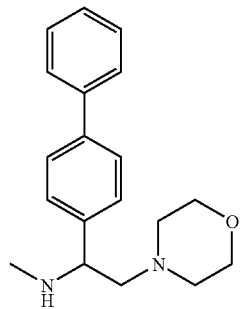

2.0 M methylamine solution in THF (18 mL, 36.0 mmol) was added to a solution of 1-(4-biphenylyl)-2-(4-morpholinyl)ethanone (2.52 g, 8.93 mmol) in anhydrous THF (20 mL), The reaction mixture was stirred at room temperature for 1 h and then sodium cyanoborohydride (1.68 g, 26.79 mmol) and acetic acid (1 mL) were added. The resulting mixture was stirred at room temperature for 72 h until the starting material was consumed completely. At this point, saturated $K_2CO_3$ solution (40 mL) was added to and after stirring for 15 min, the solution was extracted with ethyl acetate (2×50 mL). The combined organic layer was dried over $Na_2SO_4$ and concentrated. The resulting residue was isolated by column chromatography on silica gel (MeOH/EtOAc, 1:10) to yield [1-(4-biphenylyl)-2-(4-morpholinyl)ethyl]methylamine as an off-white solid (1.40 g, 53%), MS (ES) m/e 296[M+H]+.

c) (N-[1-(4-biphenylyl)-2-(4-morpholinyl)ethyl]-2-(6,7-dibromo-3-oxo-2,3-dihydro-4H-1,4-benzoxazin-4-yl)-N-methylacetamide

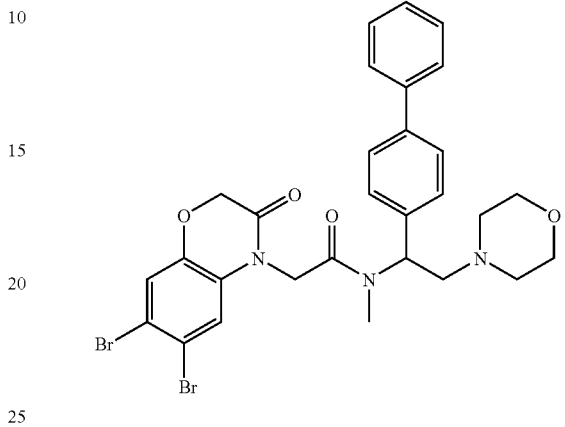

The title compound was prepared according to the procedure described in example 11 replacing N-(3,4-dichlorophenyl)-N-methylglycine with (6,7-dibromo-3-oxo-2,3-dihydro-4H-1,4-benzoxazin-4-yl)acetic acid, and [1-(4-biphenylyl)-2-(1-pyrrolidinyl)ethyl]methylamine with the product from step b) above to give the title compound (52 mg, 58%). MS (ES) m/e 643 [M+H]+.

Examples 23-30

Proceeding in a similar manner as in example 22, but replacing (6,7-dibromo-3-oxo-2,3-dihydro-4H-1,4-benzoxazin-4-yl)acetic acid with the appropriate carboxylic acids, the compounds listed in table 2 were prepared. As is appreciated by those skilled in the art, these analogous examples may involve variations in synthetic procedure.

TABLE 2

| Ex # | Structure | Name | MS [M + H]+ |
|---|---|---|---|
| 23 | 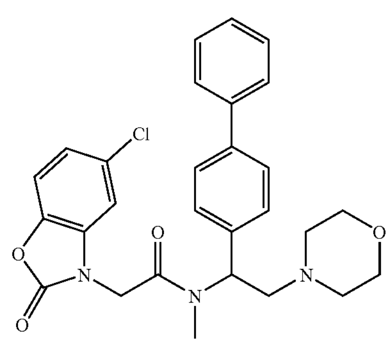 | N-[1-(4-biphenylyl)-2-(4-morpholinyl)ethyl]-2-(5-chloro-2-oxo-1,3-benzoxazol-3(2H)-yl)-N-methylacetamide | 506 |

TABLE 2-continued

| Ex # | Structure | Name | MS [M + H]+ |
|---|---|---|---|
| 24 | 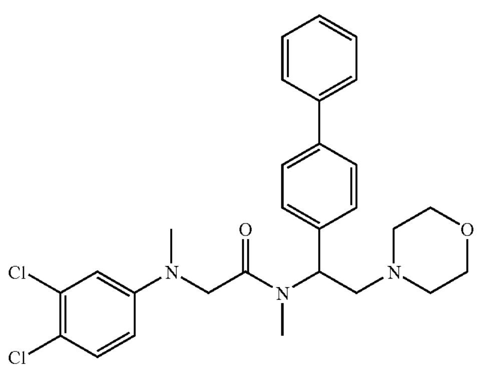 | N¹-[1-(4-biphenylyl)-2-(4-morpholinyl)ethyl]-N²-(3,4-dichlorophenyl)-N¹,N²-dimethylglycinamide | 512 |
| 25 | 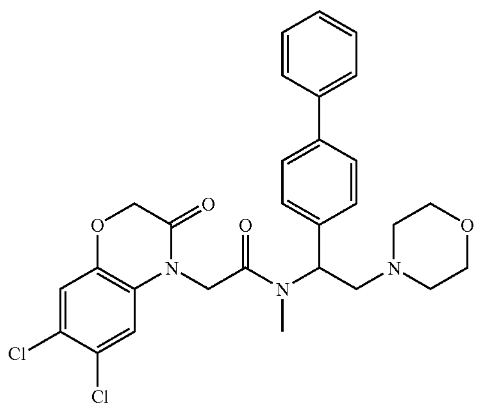 | N-[1-(4-biphenylyl)-2-(4-morpholinyl)ethyl]-2-(6,7-dichloro-3-oxo-2,3-dihydro-4H-1,4-benzoxazin-4-yl)-N-methylacetamide | 554 |
| 26 | 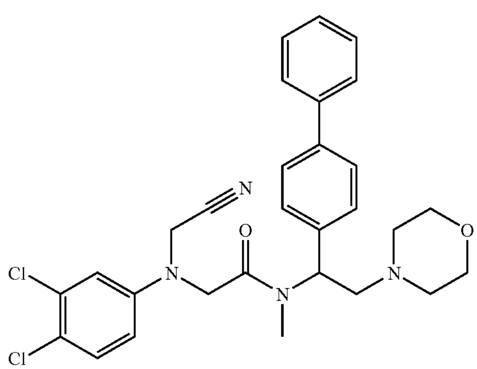 | N¹-[1-(4-biphenylyl)-2-(4-morpholinyl)ethyl]-N²-(cyanomethyl)-N²-(3,4-dichlorophenyl)-N¹-methylglycinamide | 537 |
| 27 | 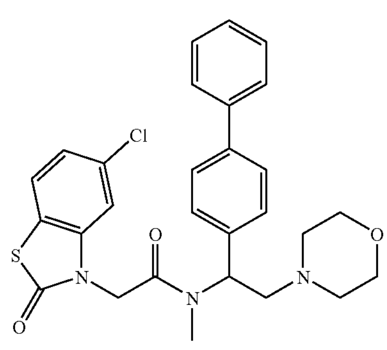 | N-[1-(4-biphenylyl)-2-(4-morpholinyl)ethyl]-2-(5-chloro-2-oxo-1,3-benzothiazol-3(2H)-yl)-N-methylacetamide | 522 |

TABLE 2-continued

| Ex # | Structure | Name | MS [M + H]+ |
|---|---|---|---|
| 28 | 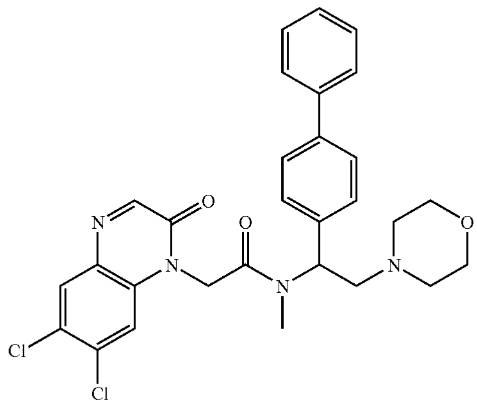 | N-[1-(4-biphenylyl)-2-(4-morpholinyl)ethyl]-2-(6,7-dichloro-2-oxo-1(2H)-quinoxalinyl)-N-methylacetamide | 551 |
| 29 | 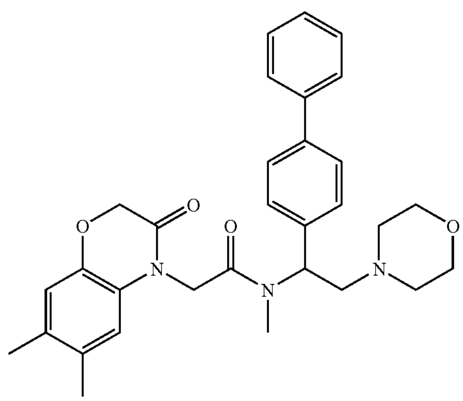 | N-[1-(4-biphenylyl)-2-(4-morpholinyl)ethyl]-2-(6,7-dimethyl-3-oxo-2,3-dihydro-4H-1,4-benzoxazin-4-yl)-N-methylacetamide | 514 |
| 30 | 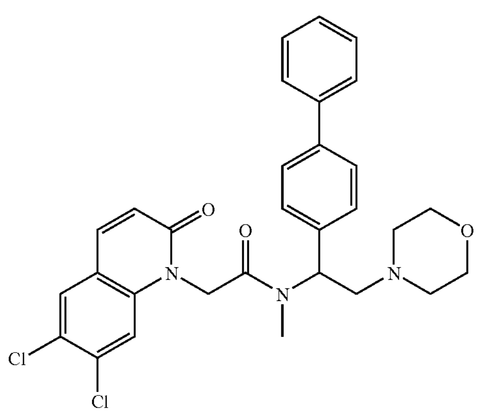 | N-[1-(4-biphenylyl)-2-(4-morpholinyl)ethyl]-2-(6,7-dichloro-2-oxo-1(2H)-quinolinyl)-N-methylacetamide | 550 |

Example 31

1-(4-bromophenyl)-N-methyl-2-(1-pyrrolidinyl)ethanamine

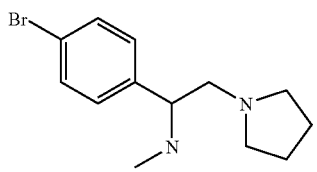

a) 1-(4-bromophenyl)-2-(1-pyrrolidinyl)ethanone

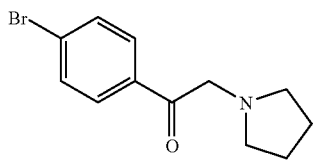

2-bromo-1-(4-bromophenyl)ethanone (5.0 g, 18 mmol) was dissolved in 10 mL diethyl ether and added dropwise over 15 min to a solution of pyrrolidine (3.0 mL, 36 mmol) in 20 mL diethyl ether cooled to 0° C. in an ice bath. The resulting solution was allowed to warm to room temperature and maintained for 1 h. The solvent was removed under reduced pressure. The residue was dissolved in 100 mL of EtOAc and washed with sodium bicarbonate (100 mL) and then brine (100 mL). The organic layer was dried over Na$_2$SO$_4$, filtered, and concentrated under reduced pressure to give 4.6 g (96%) of the title compound as a yellow/orange solid. MS (ES) m/e 268/270 [M+H]$^+$.

b) 1-(4-bromophenyl)-N-methyl-2-(1-pyrrolidinyl)ethanamine

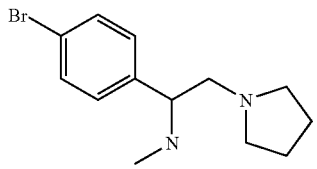

1-(4-Bromophenyl)-2-(1-pyrrolidinyl)ethanone (4.45 g, 16.6 mmol) and methyl amine (33 mL, 66.4 mmol of 2 M solution in THF) were dissolved in 75 mL THF and maintained for 15 minutes at room temperature. NaBH$_3$CN (3.13 g, 49.8 mmol) was added and the reaction mixture was treated with 1 mL acetic acid and stirred at room temperature for 4 days. The solvent was removed under reduced pressure. The residue was dissolved in 100 mL of EtOAc and washed with sodium bicarbonate (100 mL) and then brine (100 mL). The organic layer was dried over Na$_2$SO$_4$, filtered, and concentrated under reduced pressure to give 4.7 g (99%) of the title compound as a yellow oil. MS (ES) m/e 284 [M+H]$^+$.

Example 32 a) N$^1$-[1-(4-bromophenyl)-2-(1-pyrrolidinyl)ethyl]-N$^2$-(3,4-dichlorophenyl)-N$^1$,N$^2$-dimethylglycinamide

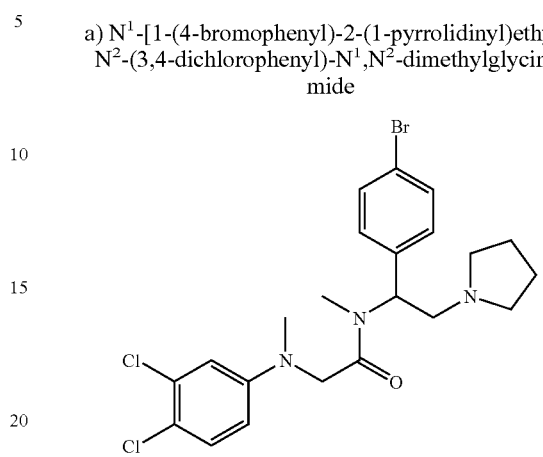

1-(4-bromophenyl)-N-methyl-2-(1-pyrrolidinyl)ethanamine (4.7 g, 17 mmol) was dissolved in 150 mL of methylene chloride and treated with N-(3,4-dichlorophenyl)-N-methylglycine (4.02 g, 16.6 mmol), EDC (3.5 g, 18 mmol), HOBt (2.47 g, 18.2 mmol), and triethylamine (2.55 mL, 18.3 mmol). The reaction mixture was stirred at room temperature for 18 h. Methylene chloride (50 mL) was added and the reaction mixture was washed with sodium bicarbonate (100 mL) and then brine (100 mL). The organic layer was dried over Na$_2$SO$_4$, filtered, and concentrated under reduced pressure. The residue was dissolved in 15 mL of DMSO and purified by preparative HPLC (Phenomenex 75×30 mm column, 15 injections, 40 mL/min flow rate, A: 0.1% TFA in acetonitrile B: 0.1% TFA in water, A: 10 to 100% over 15 min, UV detection at 215 nm) to give 4.01 g (48%) of the title compound as a light yellow solid. MS (ES) m/e 500 [M+H]$^+$.

Example 33 b) N$^1$-[1-(4'-chloro-4-biphenylyl)-2-(1-pyrrolidinyl)ethyl]-N$^2$-(3,4-dichlorophenyl)-N$^1$,N$^2$-dimethylglycinamide

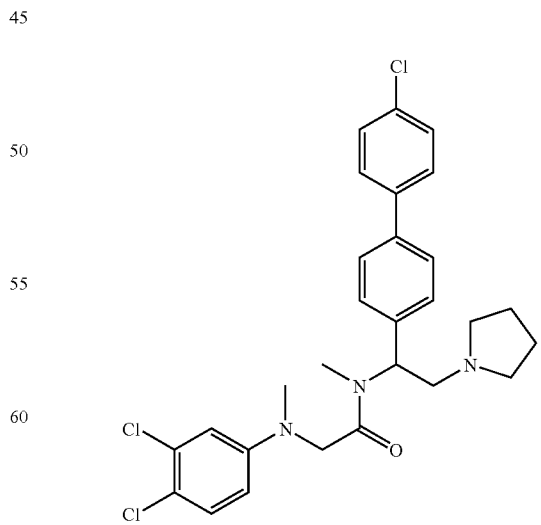

N$^1$-[1-(4-bromophenyl)-2-(1-pyrrolidinyl)ethyl]-N$^2$-(3,4-dichlorophenyl)-N$^1$,N$^2$-dimethylglycinamide (50 mg, 0.100 mmol) was dissolved in 500 uL of 1,4-Dioxane and combined with (4-chlorophenyl)boronic acid (23 mg, 0.150 mmol), Pd(dppf)$_2$Cl$_2$ (2 mg, 0.003 mmol), and 300 uL of 1M Na$_2$CO$_3$ in water in a glass reaction tube (0.5-2.0 mL Smith Process Vial) that was equipped with a magnetic stir bar. The tube was fitted with a rubber septum and hermetically sealed with a crimped metal foil seal. Using a Personal Chemistry Emrys Optimizer microwave unit, the reaction mixture was magnetically stirred and irradiated with microwave energy of dynamically adjusted power in order to maintain a temperature of 185° C. for 360 seconds. Ethyl acetate (2 mL) and brine (2 mL) were added and the reaction mixture was filtered. The organic layer was separated and the solvent was removed under reduced pressure. The residue was dissolved in 1.0 mL DMSO and purified by preparative HPLC (Phenomenex 75×30 mm column, 40 mL/min flow rate, A: 0.1% TFA in acetonitrile B: 0.1% TFA in water, A: 10 to 100% over 15 min, UV detection at 215 nm) to give 25 mg (47%) of the title compound as a tan solid. MS (ES) m/e 530/532 [M+H]$^+$.

Examples 34-84

Proceeding in a similar manner to example 33, but replacing (4-chlorophenyl)boronic acid with the appropriate boronic acids or esters, the compounds listed in table 3 were prepared. As is appreciated by those skilled in the art, these analogous examples may involve variations in synthetic procedure.

TABLE 3

| Ex # | Structure | Name | MS [M + H]$^+$ |
|---|---|---|---|
| 34 | 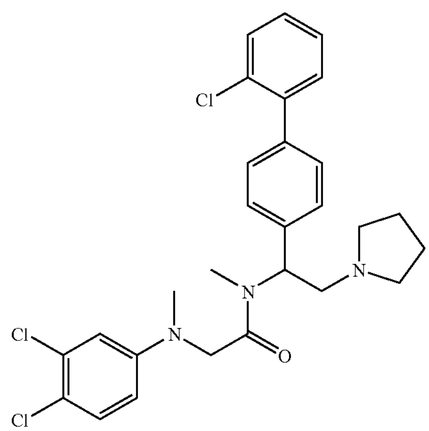 | N$^1$-[1-(2'-chloro-4-biphenylyl)-2-(1-pyrrolidinyl)ethyl]-N$^2$-(3,4-dichlorophenyl)-N$^1$,N$^2$-dimethylglycinamide | 530/532 |
| 35 | 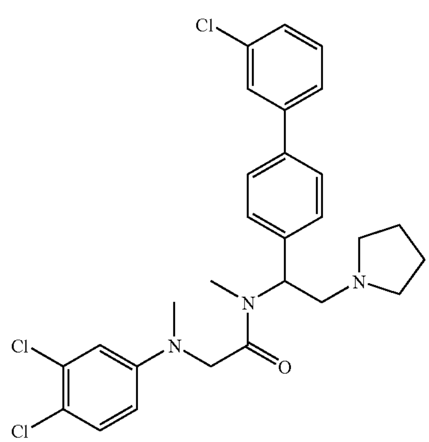 | N$^1$-[1-(3'-chloro-4-biphenylyl)-2-(1-pyrrolidinyl)ethyl]-N$^2$-(3,4-dichlorophenyl)-N$^1$,N$^2$-dimethylglycinamide | 530/532 |

TABLE 3-continued

| Ex # | Structure | Name | MS [M + H]+ |
|---|---|---|---|
| 36 | 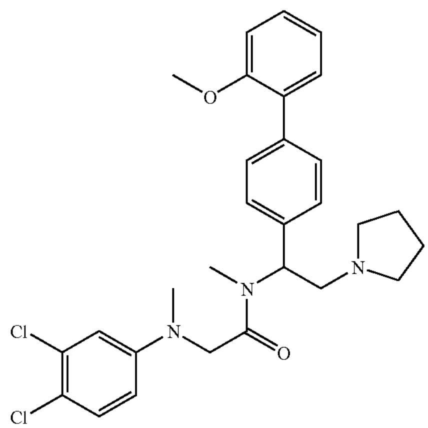 | N²-(3,4-dichlorophenyl)-N¹,N²-dimethyl-N¹-[1-[2'-(methyloxy)-4-biphenylyl]-2-(1-pyrrolidinyl)ethyl]glycinamide | 526/528 |
| 37 | 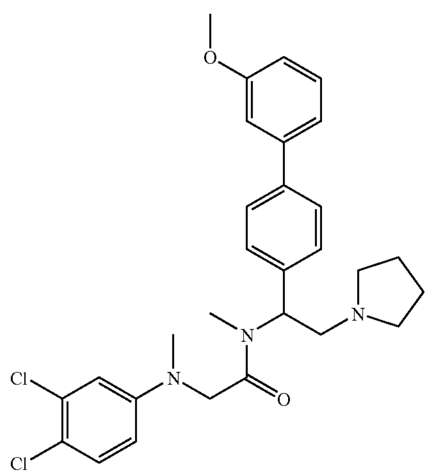 | N²-(3,4-dichlorophenyl)-N¹,N²-dimethyl-N¹-[1-[3'-(methyloxy)-4-biphenylyl]-2-(1-pyrrolidinyl)ethyl]glycinamide | 526/528 |
| 38 | 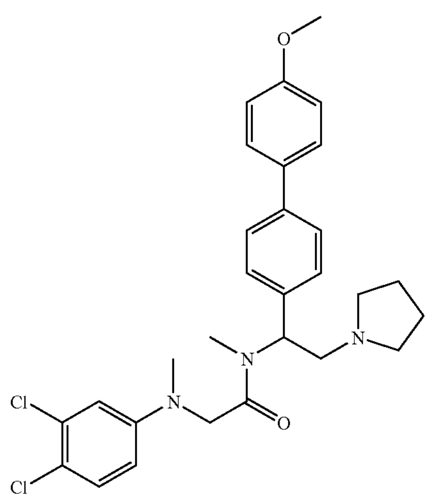 | N²-(3,4-dichlorophenyl)-N¹,N²-dimethyl-N¹-[1-[4'-(methyloxy)-4-biphenylyl]-2-(1-pyrrolidinyl)ethyl]glycinamide | 526/528 |

TABLE 3-continued

| Ex # | Structure | Name | MS [M + H]+ |
|---|---|---|---|
| 39 | 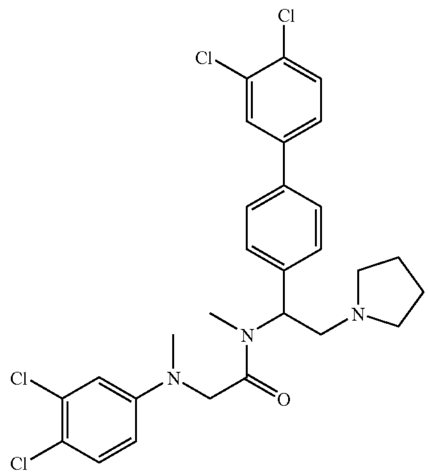 | $N^1$-[1-(3',4'-dichloro-4-biphenylyl)-2-(1-pyrrolidinyl)ethyl]-$N^2$-(3,4-dichlorophenyl)-$N^1$,$N^2$-dimethylglycinamide | 566 |
| 40 | 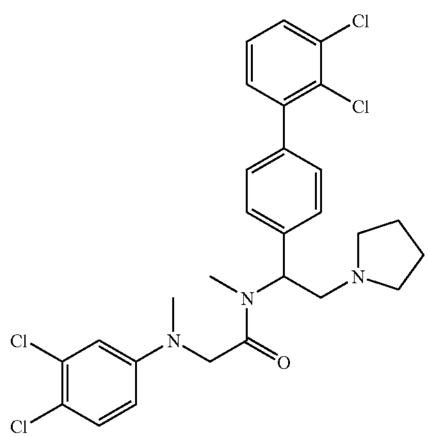 | $N^1$-[1-(2',3'-dichloro-4-biphenylyl)-2-(1-pyrrolidinyl)ethyl]-$N^2$-(3,4-dichlorophenyl)-$N^1$,$N^2$-dimethylglycinamide | 566 |
| 41 | 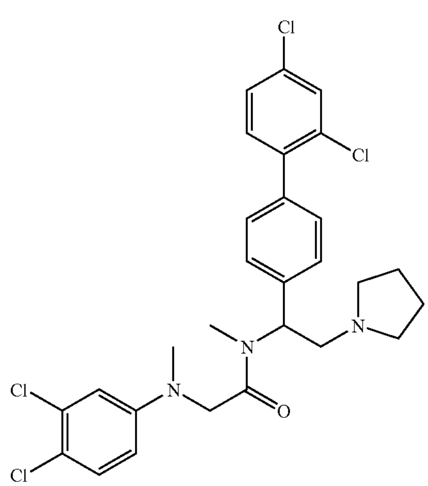 | $N^1$-[1-(2',4'-dichloro-4-biphenylyl)-2-(1-pyrrolidinyl)ethyl]-$N^2$-(3,4-dichlorophenyl)-$N^1$,$N^2$-dimethylglycinamide | 566 |

TABLE 3-continued

| Ex # | Structure | Name | MS [M + H]+ |
|---|---|---|---|
| 42 | 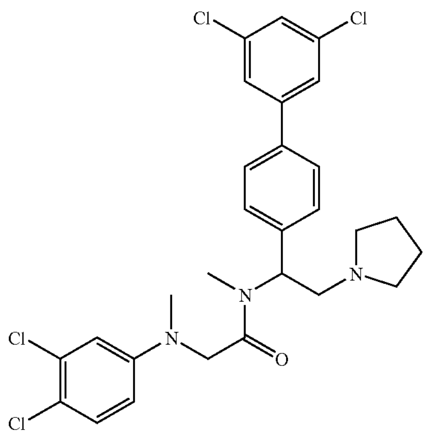 | $N^1$-[1-(3',5'-dichloro-4-biphenylyl)-2-(1-pyrrolidinyl)ethyl]-$N^2$-(3,4-dichlorophenyl)-$N^1$,$N^2$-dimethylglycinamide | 566 |
| 43 | 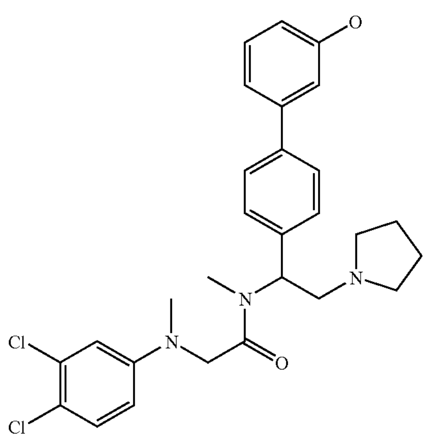 | $N^2$-(3,4-dichlorophenyl)-$N^1$-[1-(3'-hydroxy-4-biphenylyl)-2-(1-pyrrolidinyl)ethyl]-$N^1$,$N^2$-dimethylglycinamide | 512/514 |
| 44 | 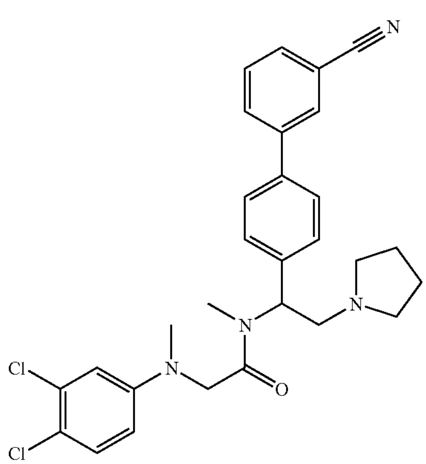 | $N^1$-[1-(3'-cyano-4-biphenylyl)-2-(1-pyrrolidinyl)ethyl]-$N^2$-(3,4-dichlorophenyl)-$N^1$,$N^2$-dimethylglycinamide | 521/523 |

TABLE 3-continued

| Ex # | Structure | Name | MS [M + H]+ |
|---|---|---|---|
| 45 | 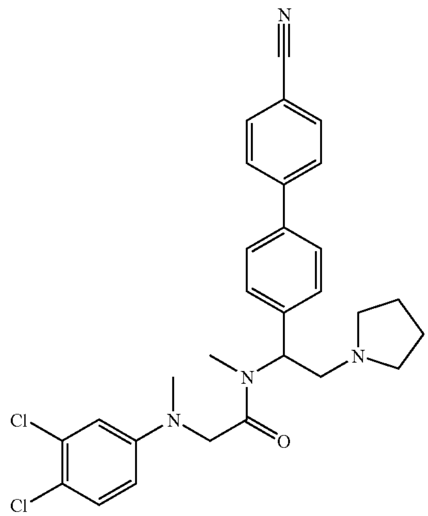 | N1-[1-(4'-cyano-4-biphenylyl)-2-(1-pyrrolidinyl)ethyl]-N2-(3,4-dichlorophenyl)-N1,N2-dimethylglycinamide | 521/523 |
| 46 | 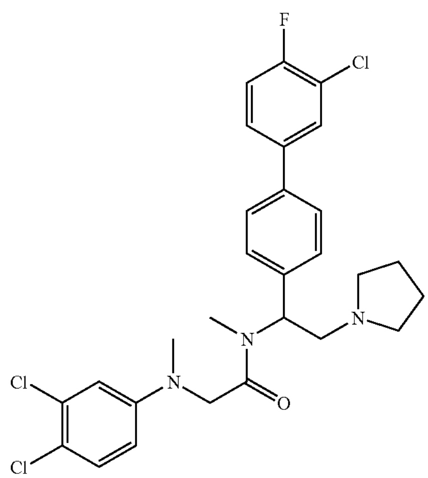 | N1-[1-(3'-chloro-4'-fluoro-4-biphenylyl)-2-(1-pyrrolidinyl)ethyl]-N2-(3,4-dichlorophenyl)-N1,N2-dimethylglycinamide | 548/550 |
| 47 | 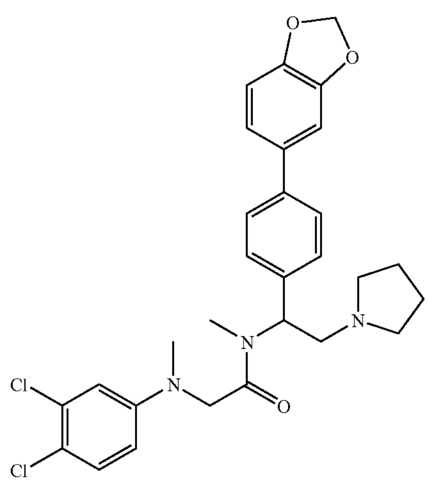 | N1-[1-[4-(1,3-benzodioxol-5-yl)phenyl]-2-(1-pyrrolidinyl)ethyl]-N2-(3,4-dichlorophenyl)-N1,N2-dimethylglycinamide | 540/542 |

TABLE 3-continued

| Ex # | Structure | Name | MS [M + H]+ |
|---|---|---|---|
| 48 | 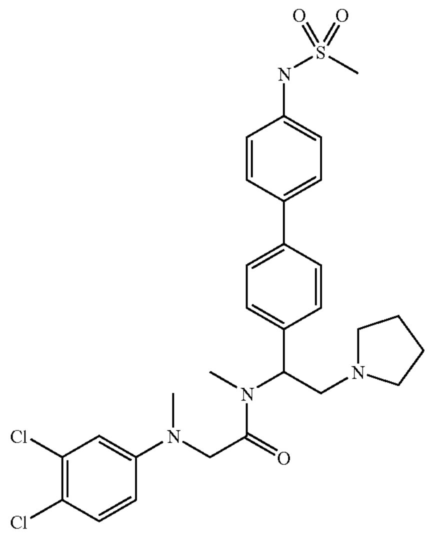 | N²-(3,4-dichlorophenyl)-N¹,N²-dimethyl-N¹-[1-{4'-[(methylsulfonyl)amino]-4-biphenylyl}-2-(1-pyrrolidinyl)ethyl]glycinamide | 589/591 |
| 49 | 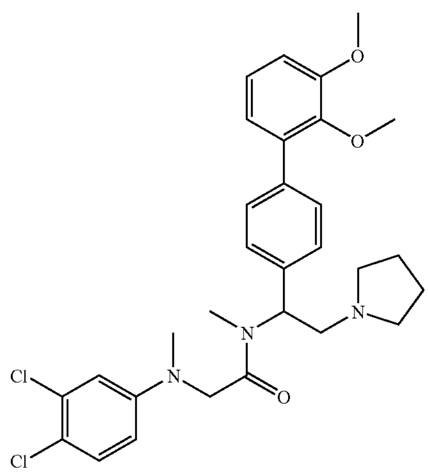 | N¹-[1-[2',3'-bis(methyloxy)-4-biphenylyl]-2-(1-pyrrolidinyl)ethyl]-N²-(3,4-dichlorophenyl)-N¹,N²-dimethylglycinamide | 556/558 |
| 50 | 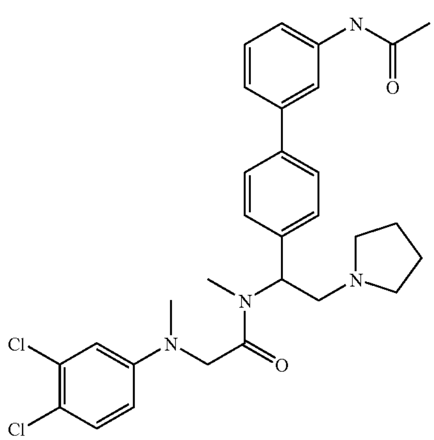 | N¹-[1-[3'-(acetylamino)-4-biphenylyl]-2-(1-pyrrolidinyl)ethyl]-N²-(3,4-dichlorophenyl)-N¹,N²-dimethylglycinamide | 553/555 |

TABLE 3-continued

| Ex # | Structure | Name | MS [M + H]+ |
|---|---|---|---|
| 51 | 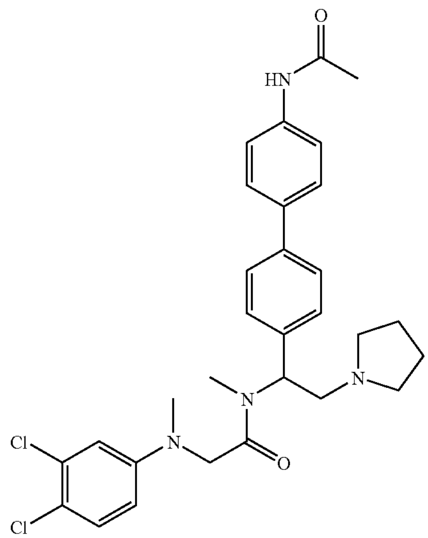 | $N^1$-[1-[4'-(acetylamino)-4-biphenylyl]-2-(1-pyrrolidinyl)ethyl]-$N^2$-(3,4-dichlorophenyl)-$N^1$,$N^2$-dimethylglycinamide | 553/555 |
| 52 | 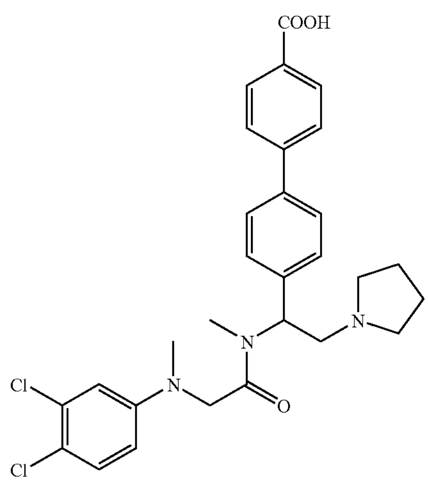 | 4'-[1-[[N-(3,4-dichlorophenyl)-N-methylglycyl](methyl)amino]-2-(1-pyrrolidinyl)ethyl]-4-biphenylcarboxylic acid | 540/542 |
| 53 | 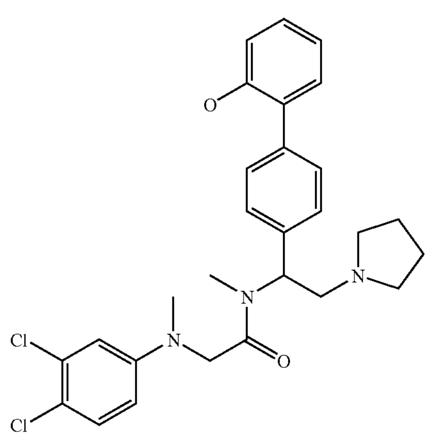 | $N^2$-(3,4-dichlorophenyl)-$N^1$-[1-(2'-hydroxy-4-biphenylyl)-2-(1-pyrrolidinyl)ethyl]-$N^1$,$N^2$-dimethylglycinamide | 512/514 |

TABLE 3-continued

| Ex # | Structure | Name | MS [M + H]+ |
|---|---|---|---|
| 54 | 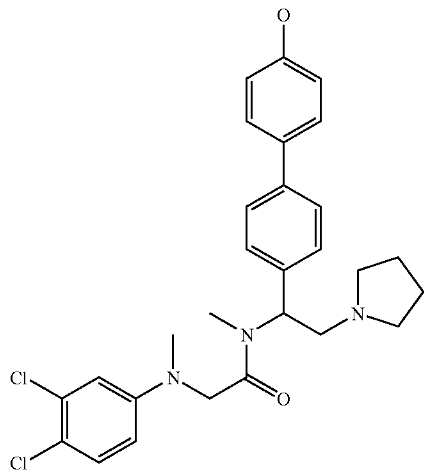 | $N^2$-(3,4-dichlorophenyl)-$N^1$-[1-(4'-hydroxy-4-biphenylyl)-2-(1-pyrrolidinyl)ethyl]-$N^1$,$N^2$-dimethylglycinamide | 512/514 |
| 55 | 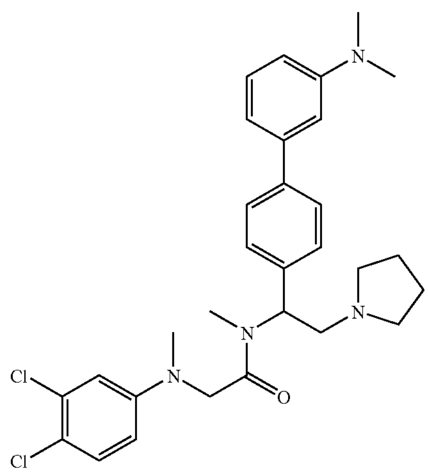 | $N^2$-(3,4-dichlorophenyl)-$N^1$-[1-[3'-(dimethylamino)-4-biphenylyl]-2-(1-pyrrolidinyl)ethyl]-$N^1$,$N^2$-dimethylglycinamide | 539/541 |
| 56 | 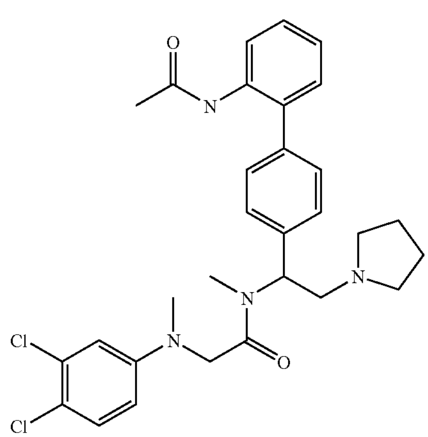 | $N^1$-[1-[2'-(acetylamino)-4-biphenylyl]-2-(1-pyrrolidinyl)ethyl]-$N^2$-(3,4-dichlorophenyl)-$N^1$,$N^2$-dimethylglycinamide | 553/555 |

TABLE 3-continued

| Ex # | Structure | Name | MS [M + H]+ |
|---|---|---|---|
| 57 | 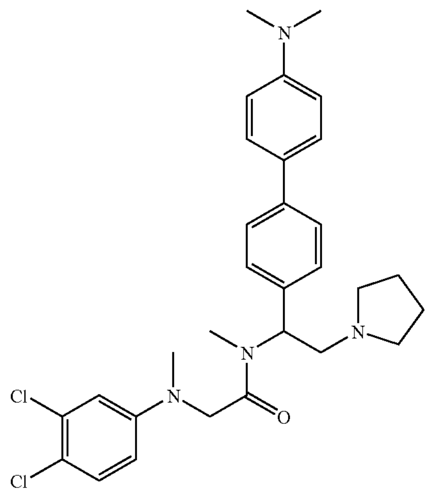 | N²-(3,4-dichlorophenyl)-N¹-[1-[4'-(dimethylamino)-4-biphenylyl]-2-(1-pyrrolidinyl)ethyl]-N¹,N²-dimethylglycinamide | 539/541 |
| 58 | 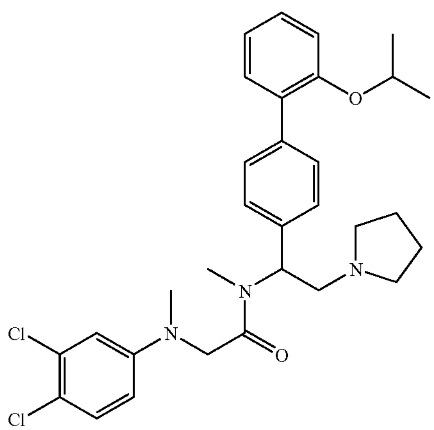 | N²-(3,4-dichlorophenyl)-N¹,N²-dimethyl-N¹-[1-{2'-[(1-methylethyl)oxy]-4-biphenylyl}-2-(1-pyrrolidinyl)ethyl]glycinamide | 554/556 |
| 59 | 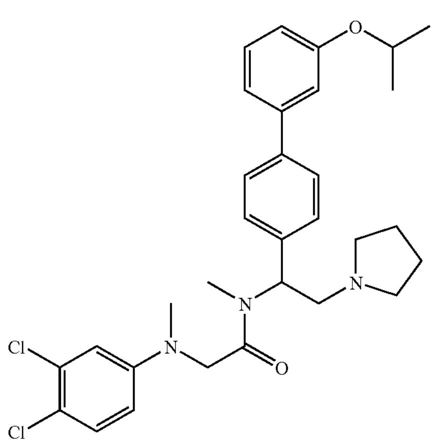 | N²-(3,4-dichlorophenyl)-N¹,N²-dimethyl-N¹-[1-{3'-[(1-methylethyl)oxy]-4-biphenylyl}-2-(1-pyrrolidinyl)ethyl]glycinamide | 554/556 |

TABLE 3-continued

| Ex # | Structure | Name | MS [M + H]+ |
|---|---|---|---|
| 60 | 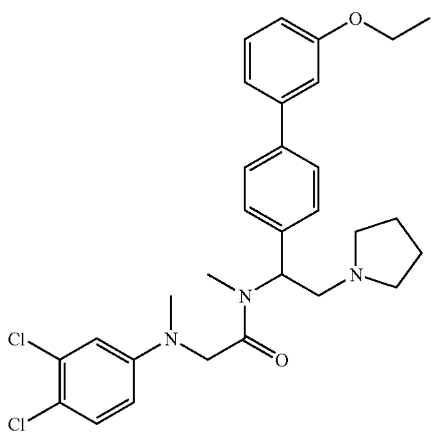 | $N^2$-(3,4-dichlorophenyl)-$N^1$-[1-[3'-(ethyloxy)-4-biphenylyl]-2-(1-pyrrolidinyl)ethyl]-$N^1$,$N^2$-dimethylglycinamide | 540/542 |
| 61 | 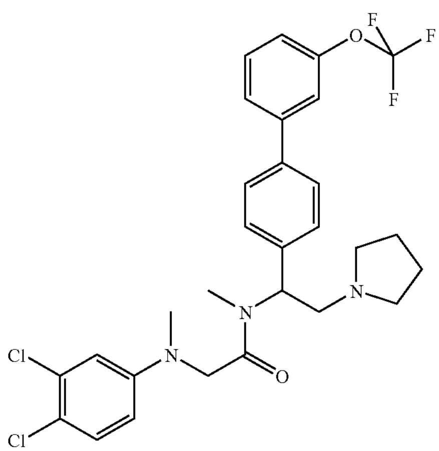 | $N^2$-(3,4-dichlorophenyl)-$N^1$,$N^2$-dimethyl-$N^1$-(2-(1-pyrrolidinyl)-1-{3'-[(trifluoromethyl)oxy]-4-biphenylyl}ethyl)glycinamide | 580/582 |
| 62 | 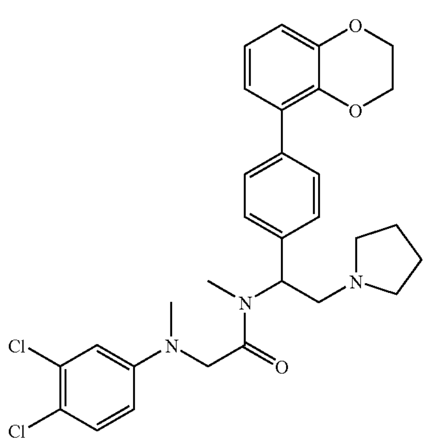 | $N^2$-(3,4-dichlorophenyl)-$N^1$-[1-[4-(2,3-dihydro-1,4-benzodioxin-5-yl)phenyl]-2-(1-pyrrolidinyl)ethyl]-$N^1$,$N^2$-dimethylglycinamide | 554/556 |

TABLE 3-continued

| Ex # | Structure | Name | MS [M + H]+ |
|---|---|---|---|
| 63 | 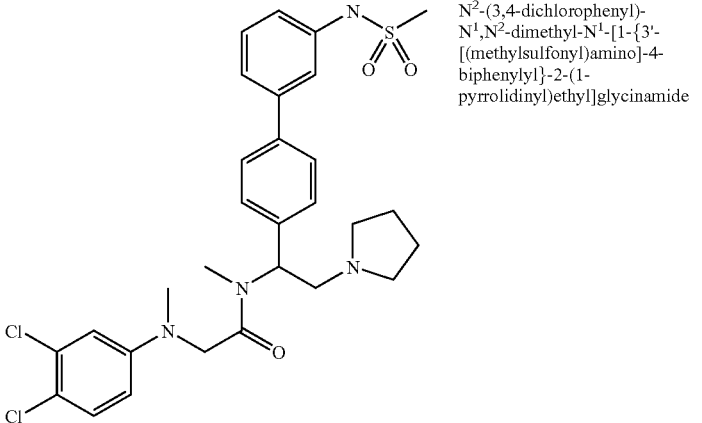 | $N^2$-(3,4-dichlorophenyl)-$N^1,N^2$-dimethyl-$N^1$-[1-{3'-[(methylsulfonyl)amino]-4-biphenylyl}-2-(1-pyrrolidinyl)ethyl]glycinamide | 589/591 |
| 64 | 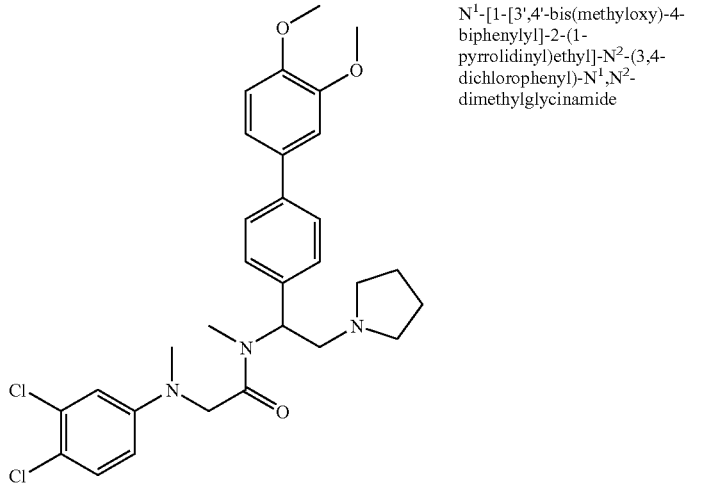 | $N^1$-[1-[3',4'-bis(methyloxy)-4-biphenylyl]-2-(1-pyrrolidinyl)ethyl]-$N^2$-(3,4-dichlorophenyl)-$N^1,N^2$-dimethylglycinamide | 556/558 |
| 65 | 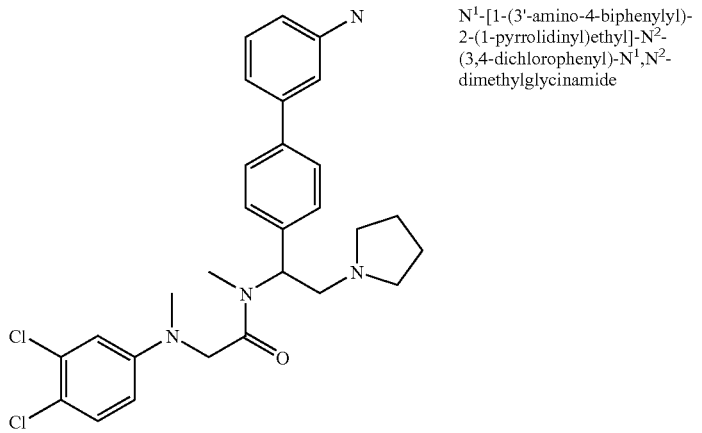 | $N^1$-[1-(3'-amino-4-biphenylyl)-2-(1-pyrrolidinyl)ethyl]-$N^2$-(3,4-dichlorophenyl)-$N^1,N^2$-dimethylglycinamide | 511/513 |

TABLE 3-continued

| Ex # | Structure | Name | MS [M + H]+ |
|---|---|---|---|
| 66 | 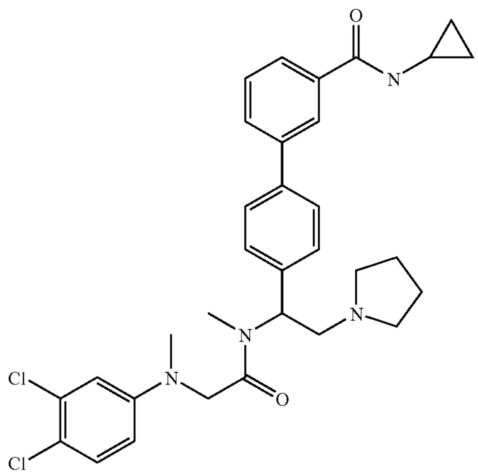 | N-cyclopropyl-4'-[1-[[N-(3,4-dichlorophenyl)-N-methylglycyl](methyl)amino]-2-(1-pyrrolidinyl)ethyl]-3-biphenylcarboxamide | 579/581 |
| 67 | 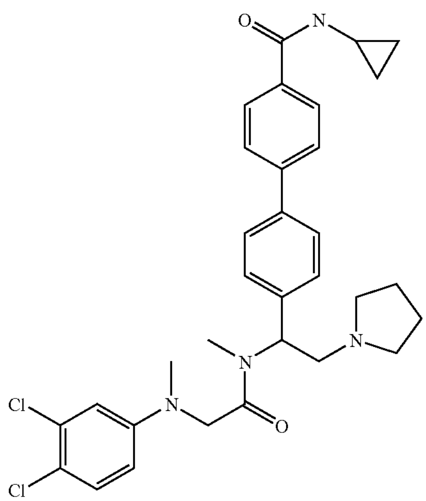 | N-cyclopropyl-4'-[1-[[N-(3,4-dichlorophenyl)-N-methylglycyl](methyl)amino]-2-(1-pyrrolidinyl)ethyl]-4-biphenylcarboxamide | 579/581 |
| 68 | 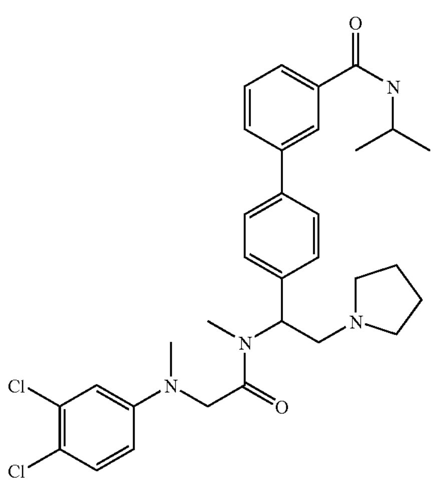 | 4'-[1-[[N-(3,4-dichlorophenyl)-N-methylglycyl](methyl)amino]-2-(1-pyrrolidinyl)ethyl]-N-(1-methylethyl)-3-biphenylcarboxamide | 581/583 |

TABLE 3-continued

| Ex # | Structure | Name | MS [M + H]+ |
|---|---|---|---|
| 69 | 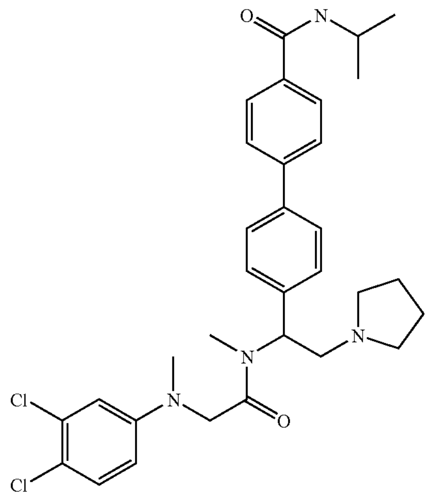 | 4'-[1-[[N-(3,4-dichlorophenyl)-N-methylglycyl](methyl)amino]-2-(1-pyrrolidinyl)ethyl]-N-(1-methylethyl)-4-biphenylcarboxamide | 581/583 |
| 70 | 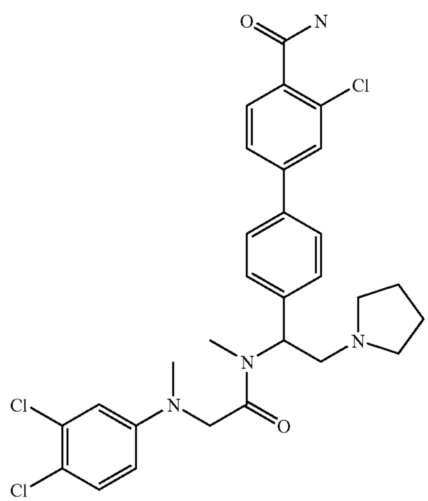 | 3-chloro-4'-[1-[[N-(3,4-dichlorophenyl)-N-methylglycyl](methyl)amino]-2-(1-pyrrolidinyl)ethyl]-4-biphenylcarboxamide | 573/575 |
| 71 | 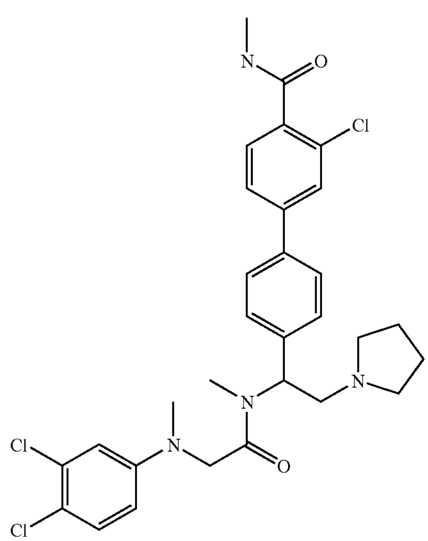 | 3-chloro-4'-[1-[[N-(3,4-dichlorophenyl)-N-methylglycyl](methyl)amino]-2-(1-pyrrolidinyl)ethyl]-N-methyl-4-biphenylcarboxamide | 587/589 |

TABLE 3-continued

| Ex # | Structure | Name | MS [M + H]+ |
|---|---|---|---|
| 72 | 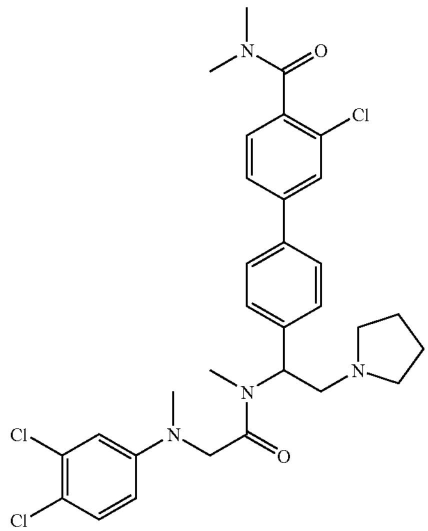 | 3-chloro-4'-[1-[[N-(3,4-dichlorophenyl)-N-methylglycyl](methyl)amino]-2-(1-pyrrolidinyl)ethyl]-N,N-dimethyl-4-biphenylcarboxamide | 601/603 |
| 73 | 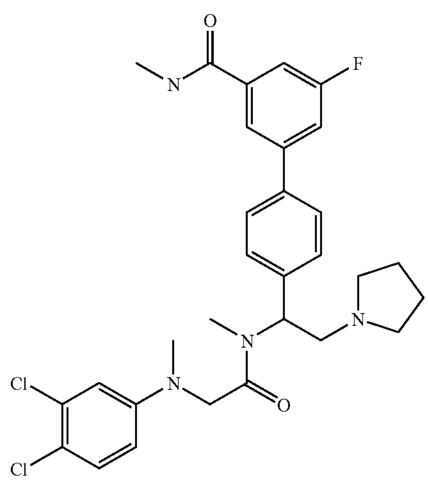 | 4'-[1-[[N-(3,4-dichlorophenyl)-N-methylglycyl](methyl)amino]-2-(1-pyrrolidinyl)ethyl]-5-fluoro-N-methyl-3-biphenylcarboxamide | 571/573 |
| 74 | 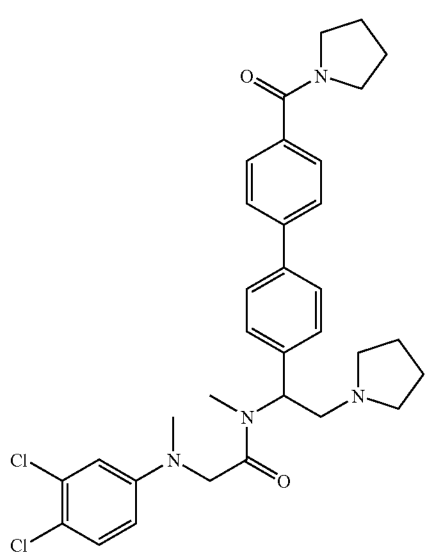 | $N^2$-(3,4-dichlorophenyl)-$N^1$,$N^2$-dimethyl-$N^1$-{2-(1-pyrrolidinyl)-1-[4'-(1-pyrrolidinylcarbonyl)-4-biphenylyl]ethyl}glycinamide | 593/595 |

TABLE 3-continued

| Ex # | Structure | Name | MS [M + H]+ |
|---|---|---|---|
| 75 | 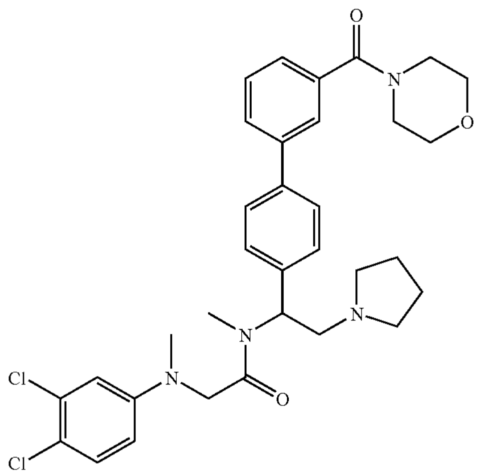 | N²-(3,4-dichlorophenyl)-N¹,N²-dimethyl-N¹-[1-[3'-(4-morpholinylcarbonyl)-4-biphenylyl]-2-(1-pyrrolidinyl)ethyl]glycinamide | 609/611 |
| 76 | 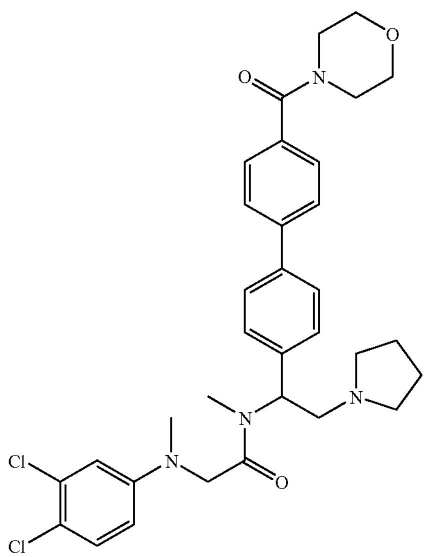 | N²-(3,4-dichlorophenyl)-N¹,N²-dimethyl-N¹-[1-[4'-(4-morpholinylcarbonyl)-4-biphenylyl]-2-(1-pyrrolidinyl)ethyl]glycinamide | 609/611 |
| 77 | 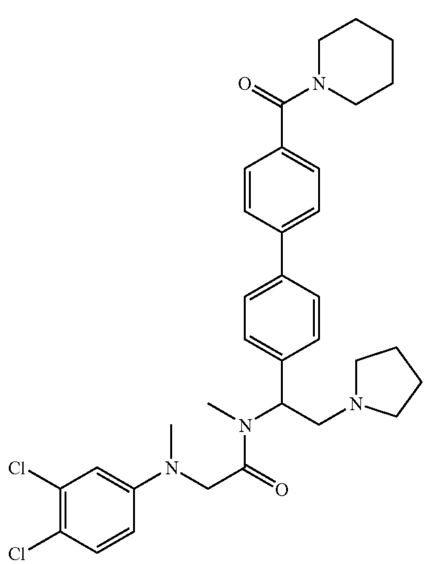 | N²-(3,4-dichlorophenyl)-N¹,N²-dimethyl-N¹-[1-[4'-(1-piperidinylcarbonyl)-4-biphenylyl]-2-(1-pyrrolidinyl)ethyl]glycinamide | 607/609 |

TABLE 3-continued

| Ex # | Structure | Name | MS [M + H]+ |
|---|---|---|---|
| 78 | 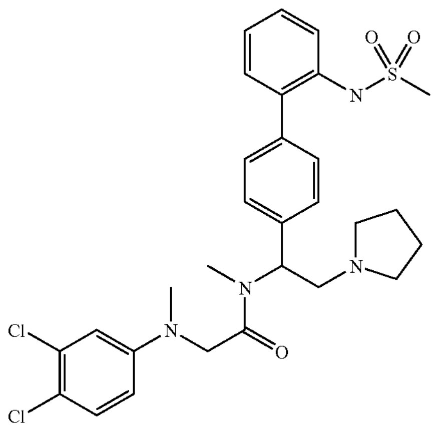 | $N^2$-(3,4-dichlorophenyl)-$N^1$,$N^2$-dimethyl-$N^1$-[1-{2'-[(methylsulfonyl)amino]-4-biphenylyl}-2-(1-pyrrolidinyl)ethyl]glycinamide | 589/591 |
| 79 | 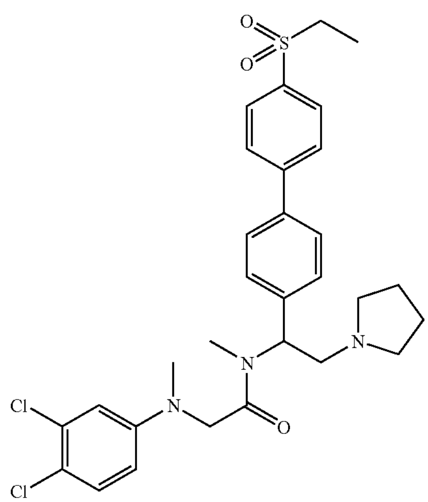 | $N^2$-(3,4-dichlorophenyl)-$N^1$-[1-[4'-(ethylsulfonyl)-4-biphenylyl]-2-(1-pyrrolidinyl)ethyl]-$N^1$,$N^2$-dimethylglycinamide | 588/590 |
| 80 | 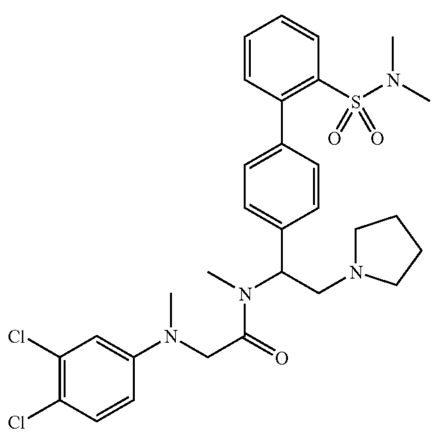 | $N^2$-(3,4-dichlorophenyl)-$N^1$-[1-{2'-[(dimethylamino)sulfonyl]-4-biphenylyl}-2-(1-pyrrolidinyl)ethyl]-$N^1$,$N^2$-dimethylglycinamide | 603/605 |

TABLE 3-continued

| Ex # | Structure | Name | MS [M + H]+ |
|---|---|---|---|
| 81 | 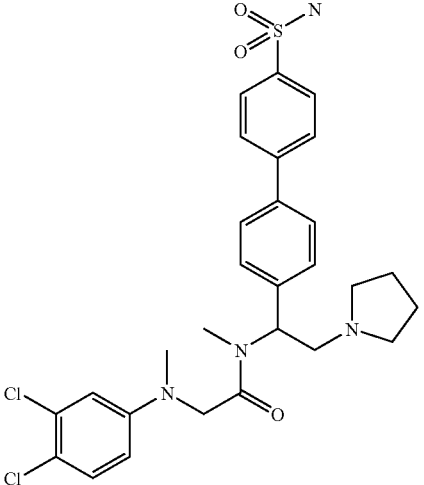 | $N^1$-[1-[4'-(aminosulfonyl)-4-biphenylyl]-2-(1-pyrrolidinyl)ethyl]-$N^2$-(3,4-dichlorophenyl)-$N^1,N^2$-dimethylglycinamide | 575/577 |
| 82 | 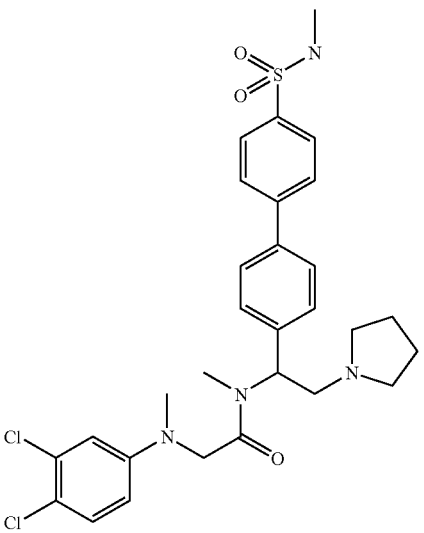 | $N^2$-(3,4-dichlorophenyl)-$N^1,N^2$-dimethyl-$N^1$-[1-{4'-[(methylamino)sulfonyl]-4-biphenylyl}-2-(1-pyrrolidinyl)ethyl]glycinamide | 589/591 |
| 83 | 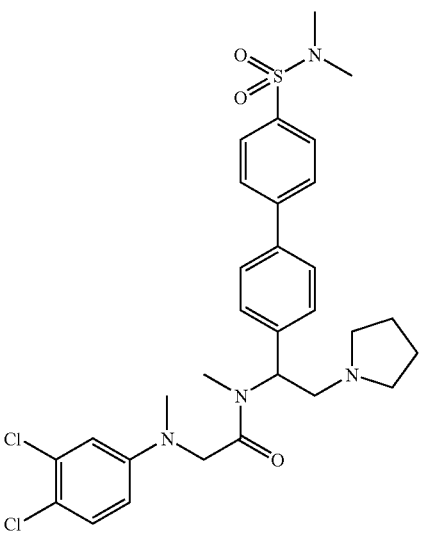 | $N^2$-(3,4-dichlorophenyl)-$N^1$-[1-{4'-[(dimethylamino)sulfonyl]-4-biphenylyl}-2-(1-pyrrolidinyl)ethyl]-$N^1,N^2$-dimethylglycinamide | 603/605 |

TABLE 3-continued

| Ex # | Structure | Name | MS [M + H]+ |
|---|---|---|---|
| 84 | 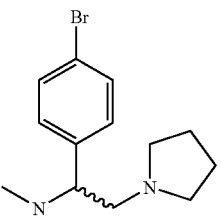 | N²-(3,4-dichlorophenyl)-N¹,N²-dimethyl-N¹-[1-[4'-(methylsulfonyl)-4-biphenylyl]-2-(1-pyrrolidinyl)ethyl]glycinamide | 574/576 |

Example 85

N-[1-[3',4'-bis(methyloxy)-4-biphenylyl]-2-(1-pyrrolidinyl)ethyl]-2-(6,7-dichloro-3-oxo-2,3-dihydro-4H-1,4-benzoxazin-4-yl)-N-methylacetamide

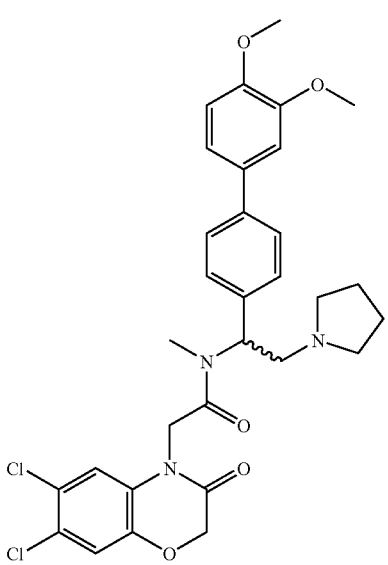

a) N-[1-(4-bromophenyl)-2-(1-pyrrolidinyl)ethyl]-2-(6,7-dichloro-3-oxo-2,3-dihydro-4H-1,4-benzoxazin-4-yl)-N-methylacetamide

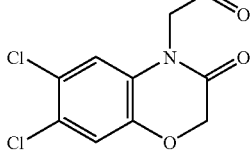

To a solution of [1-(4-bromophenyl)-2-(1-pyrrolidinyl)ethyl]methylamine (1.61 g, 5.68 mmol) and (6,7-dichloro-2-oxo-3,4-dihydro-1(2H)-quinolinyl)acetic acid (1.73 g, 6.25 mmol) in DMF (20 mL) was added BOP Reagent (3.77 g, 8.52 mmol) and triethylamine (1.72 g, 17.3 mmol). The resultant mixture was stirred at room temperature for 16 h. The mixture was concentrated under reduce pressure. The residue was diluted with ethyl acetate (100 mL) and extracted with 5% NaHCO₃ (100 mL) and brine (100 mL). The organic layer was dried (MgSO₄) and concentrated. The residue was purified by silica gel chromatography (120 g redisep column, silica 40 um, 60 A, 85 ml/min, A: MeOH, B: CH₂Cl₂, A: 1% for 20 min) to give 0.76 g (25%) title compound as yellow solid. MS (ES) m/e 545.4 [M+H]⁺.

b) N-[1-[3',4'-bis(methyloxy)-4-biphenylyl]-2-(1-pyrrolidinyl)ethyl]-2-(6,7-dichloro-3-oxo-2,3-dihydro-4H-1,4-benzoxazin-4-yl)-N-methylacetamide

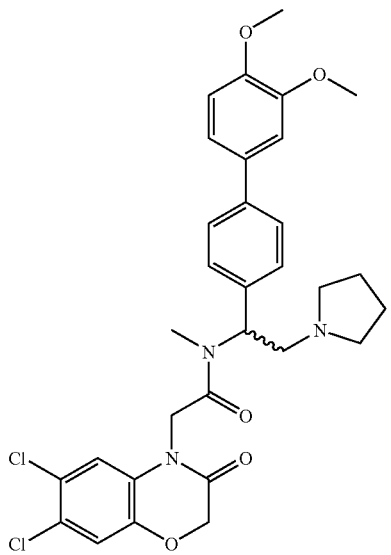

To a solution of N-[1-(4-bromophenyl)-2-(1-pyrrolidinyl)ethyl]-2-(6,7-dichloro-3-oxo-2,3-dihydro-4H-1,4-benzoxazin-4-yl)-N-methylacetamide (70 mg, 0.13 mmol) and 3,4-dimethoxyphenylboronic acid (26 mg, 0.14 mmol) in DMF (1 mL) was added Pd(dppf)Cl$_2$ (5.3 mg, 0.0065 mmol) followed by a 2M aqueous solution of Na$_2$CO$_3$ (0.26 mL, 0.52 mmol). The resultant mixture was stirred at 80° C. for 16 h. The mixture was filtered through a 0.45 um polypropylene filter and purified by Gilson Preparation HPLC (Xterra Prep RP, 19×150 mm, 18 mL/min, PH 10 with NH$_4$OH, A: acetonitrile B: water, A: 40 to 99% over 15 min, UV detection at 214 nm) to give 30.1 mg (39%) of the title compound as an off white solid. MS (ES) m/e 598.1 [M+H]$^+$.

Examples 86-105

Proceeding in a similar manner to example 85, but replacing 3,4-dimethoxyphenylboronic acid with the appropriate boronic acids and replacing (6,7-dichloro-2-oxo-3,4-dihydro-1(2H)-quinolinyl)acetic acid with appropriate acetic acids; the compounds listed in table 4 were prepared. As is appreciated by those skilled in the art, these analogous examples may involve variations in synthetic procedure.

TABLE 4

| Ex # | Structure | Name | MS [M + H]$^+$ |
|---|---|---|---|
| 86 | 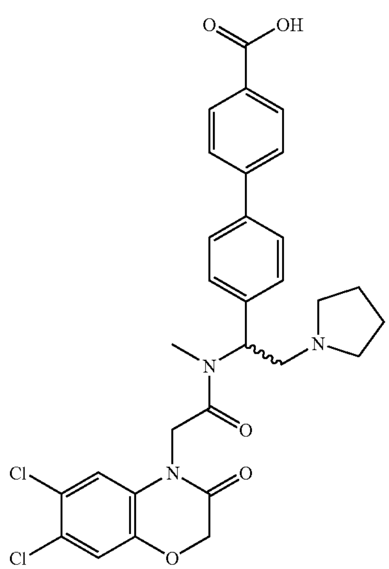 | 4'-[1-[[(6,7-dichloro-3-oxo-2,3-dihydro-4H-1,4-benzoxazin-4-yl)acetyl]-methyl)amino]-2-(1-pyrrolidinyl)ethyl]-4-biphenylcarboxylic acid | 582.1 |

TABLE 4-continued

| Ex # | Structure | Name | MS [M + H]+ |
|---|---|---|---|
| 87 | 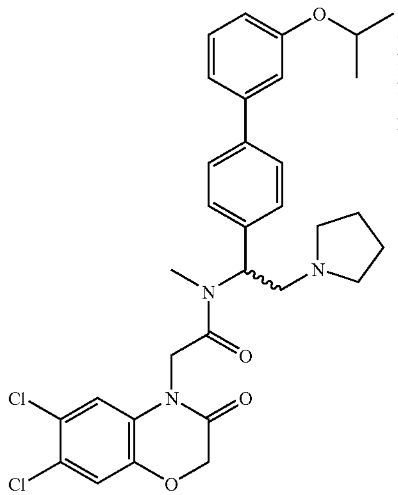 | 2-(6,7-dichloro-3-oxo-2,3-dihydro-4H-1,4-benzoxazin-4-yl)-N-methyl-N-[1-{3'-[(1-methylethyl)oxy]-4-biphenylyl}-2-(1-pyrrolidinyl)ethyl]acetamide | 596.2 |
| 88 | 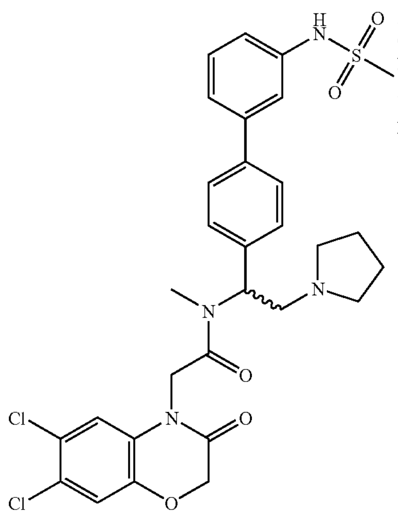 | 2-(6,7-dichloro-3-oxo-2,3-dihydro-4H-1,4-benzoxazin-4-yl)-N-methyl-N-[1-{3'-[(methylsulfonyl)amino]-4-biphenylyl}-2-(1-pyrrolidinyl)ethyl]acetamide | 631.1 |
| 89 | 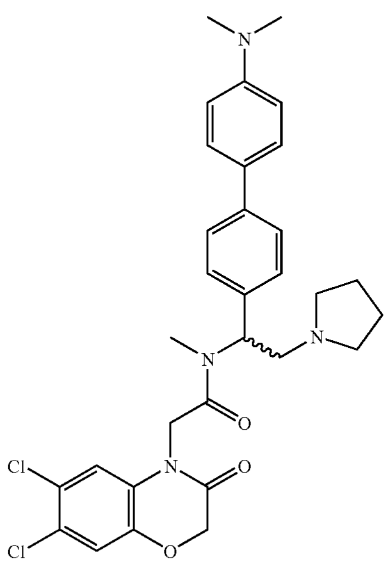 | 2-(6,7-dichloro-3-oxo-2,3-dihydro-4H-1,4-benzoxazin-4-yl)-N-[1-[4'-(dimethylamino)-4-biphenylyl]-2-(1-pyrrolidinyl)ethyl]-N-methylacetamide | 580.0 |

TABLE 4-continued
| Ex # | Structure | Name | MS [M + H]+ |
|---|---|---|---|
| 90 | 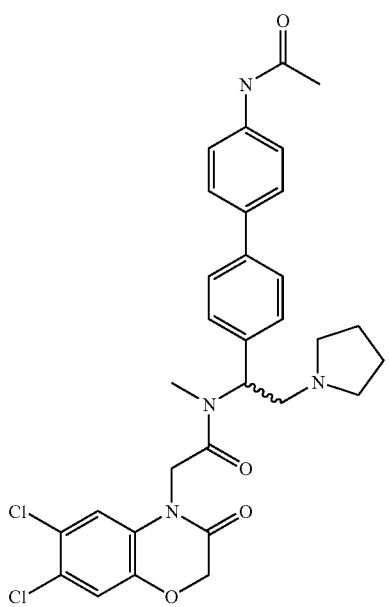 | N-[1-[4'-(acetylamino)-4-biphenylyl]-2-(1-pyrrolidinyl)ethyl]-2-(6,7-dichloro-3-oxo-2,3-dihydro-4H-1,4-benzoxazin-4-yl)-N-methylacetamide | 595.1 |
| 91 | 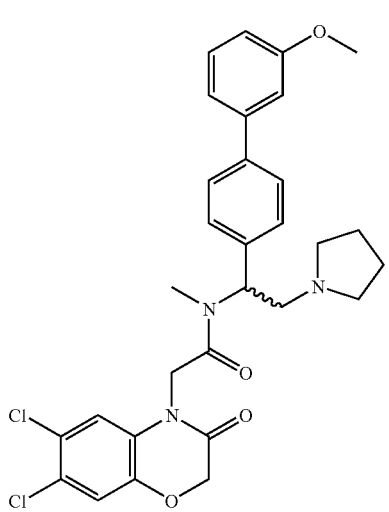 | 2-(6,7-dichloro-3-oxo-2,3-dihydro-4H-1,4-benzoxazin-4-yl)-N-methyl-N-[1-[3'-(methyloxy)-4-biphenylyl]-2-(1-pyrrolidinyl)ethyl]acetamide | 568.1 |

TABLE 4-continued

| Ex # | Structure | Name | MS [M + H]+ |
|---|---|---|---|
| 92 | 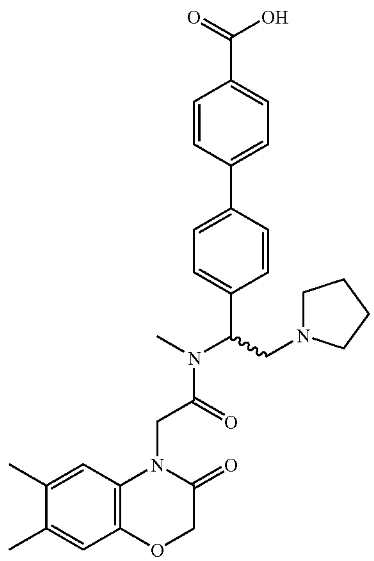 | 4'-[1-[[(6,7-dimethyl-3-oxo-2,3-dihydro-4H-1,4-benzoxazin-4-yl)acetyl](methyl)amino]-2-(1-pyrrolidinyl)ethyl]-4-biphenylcarboxylic acid | 542.2 |
| 93 | 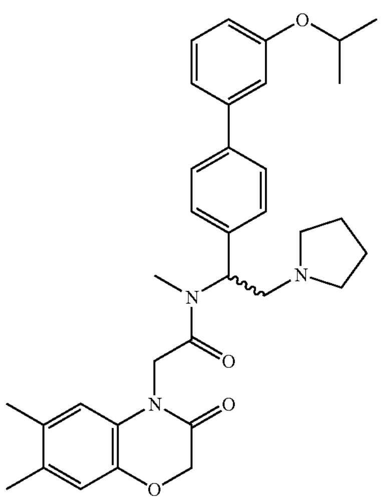 | 2-(6,7-dimethyl-3-oxo-2,3-dihydro-4H-1,4-benzoxazin-4-yl)-N-methyl-N-[1-{3'-[(1-methylethyl)oxy]-4-biphenylyl}-2-(1-pyrrolidinyl)ethyl]acetamide | 556.3 |
| 94 | 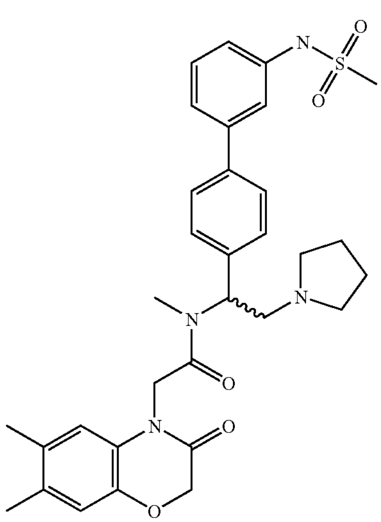 | 2-(6,7-dimethyl-3-oxo-2,3-dihydro-4H-1,4-benzoxazin-4-yl)-N-methyl-N-[1-{3'-[(methylsulfonyl)amino]-4-biphenylyl}-2-(1-pyrrolidinyl)ethyl]acetamide | 591.2 |

TABLE 4-continued

| Ex # | Structure | Name | MS [M + H]+ |
|---|---|---|---|
| 95 | 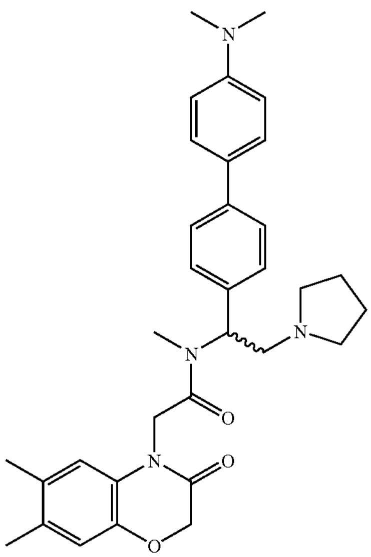 | N-[1-[4'-(dimethylamino)-4-biphenylyl]-2-(1-pyrrolidinyl)ethyl]-2-(6,7-dimethyl-3-oxo-2,3-dihydro-4H-1,4-benzoxazin-4-yl)-N-methylacetamide | 540.0 |
| 96 | 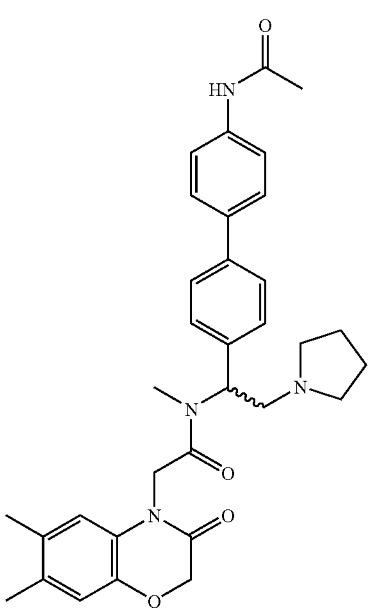 | N-[1-[4'-(acetylamino)-4-biphenylyl]-2-(1-pyrrolidinyl)ethyl]-2-(6,7-dimethyl-3-oxo-2,3-dihydro-4H-1,4-benzoxazin-4-yl)-N-methylacetamide | 555.3 |

TABLE 4-continued
| Ex # | Structure | Name | MS [M + H]+ |
|---|---|---|---|
| 97 | 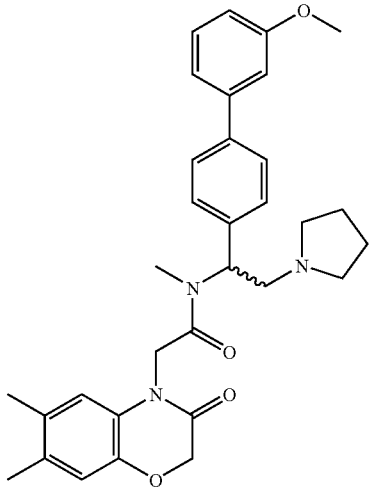 | 2-(6,7-dimethyl-3-oxo-2,3-dihydro-4H-1,4-benzoxazin-4-yl)-N-methyl-N-[1-[3'-(methyloxy)-4-biphenylyl]-2-(1-pyrrolidinyl)ethyl]acetamide | 528.3 |
| 98 | 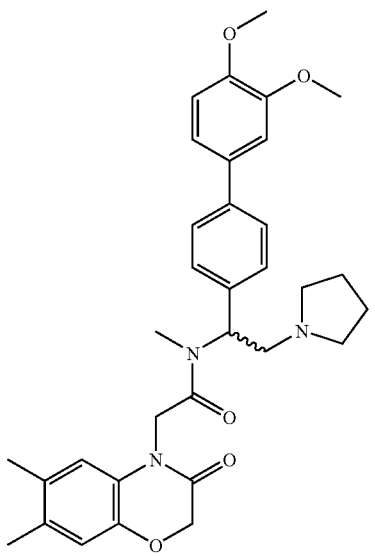 | N-[1-[3',4'-bis(methyloxy)-4-biphenylyl]-2-(1-pyrrolidinyl)ethyl]-2-(6,7-dimethyl-3-oxo-2,3-dihydro-4H-1,4-benzoxazin-4-yl)-N-methylacetamide | 558.3 |

TABLE 4-continued
| Ex # | Structure | Name | MS [M + H]+ |
|---|---|---|---|
| 99 | 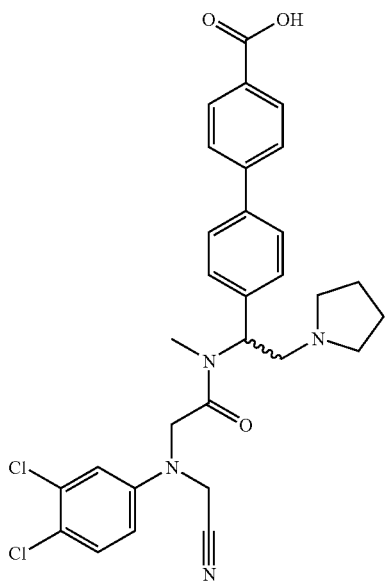 | 4'-[1-[[N-(cyanomethyl)-N-(3,4-dichlorophenyl)glycyl](methyl)amino]-2-(1-pyrrolidinyl)ethyl]-4-biphenylcarboxylic acid | 565.1 |
| 100 | 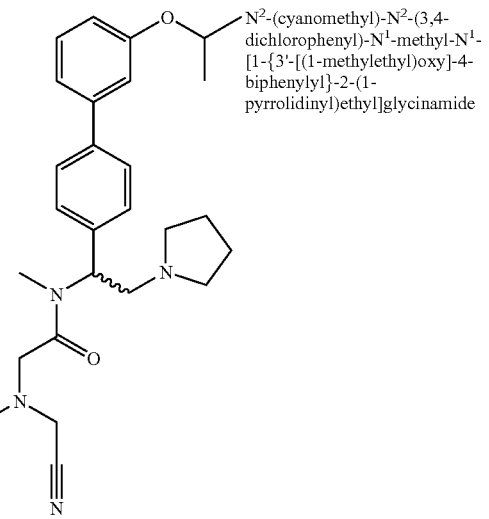 | N²-(cyanomethyl)-N²-(3,4-dichlorophenyl)-N¹-methyl-N¹-[1-{3'-[(1-methylethyl)oxy]-4-biphenylyl}-2-(1-pyrrolidinyl)ethyl]glycinamide | 579.1 |

TABLE 4-continued

| Ex # | Structure | Name | MS [M + H]+ |
|---|---|---|---|
| 101 | 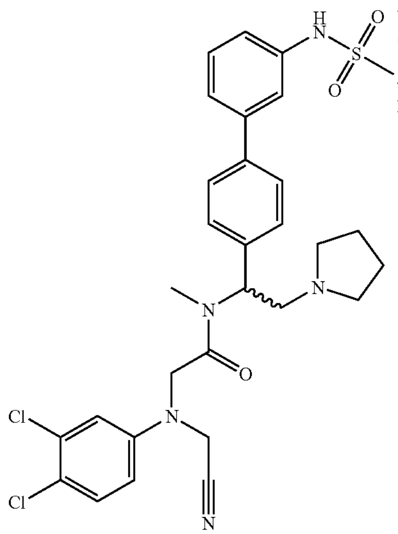 | N²-(cyanomethyl)-N²-(3,4-dichlorophenyl)-N¹-methyl-N¹-[1-{3'-[(methylsulfonyl)amino]-4-biphenylyl}-2-(1-pyrrolidinyl)ethyl]glycinamide | 614.1 |
| 102 | 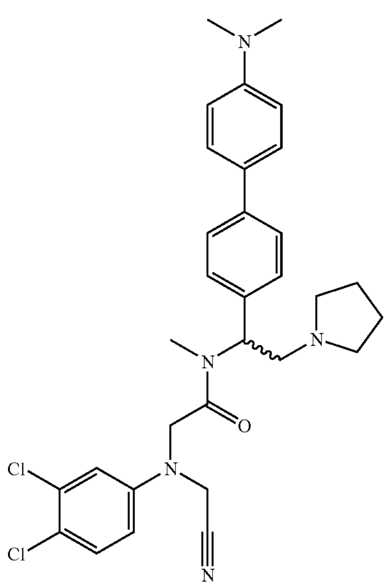 | N²-(cyanomethyl)-N²-(3,4-dichlorophenyl)-N¹-[1-[4'-(dimethylamino)-4-biphenylyl]-2-(1-pyrrolidinyl)ethyl]-N¹-methylglycinamide | 564.1 |

TABLE 4-continued
| Ex # | Structure | Name | MS [M + H]+ |
|---|---|---|---|
| 103 | 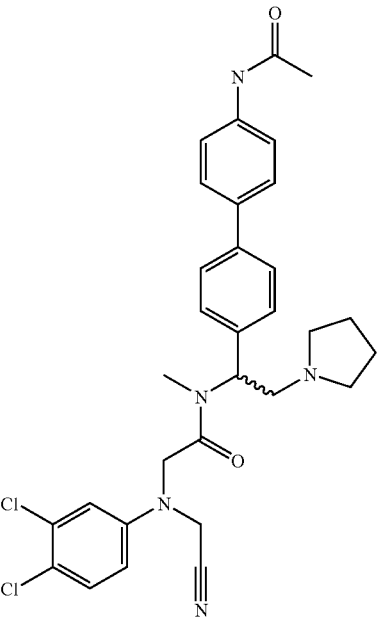 | $N^1$-[1-[4'-(acetylamino)-4-biphenylyl]-2-(1-pyrrolidinyl)ethyl]-$N^2$-(cyanomethyl)-$N^2$-(3,4-dichlorophenyl)-$N^1$-methylglycinamide | 578.1 |
| 104 | 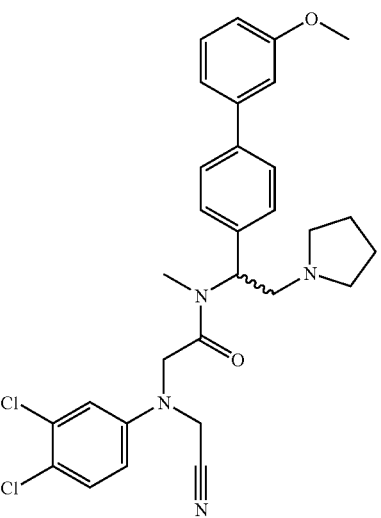 | $N^2$-(cyanomethyl)-$N^2$-(3,4-dichlorophenyl)-$N^1$-methyl-$N^1$-[1-[3'-(methyloxy)-4-biphenylyl]-2-(1-pyrrolidinyl)ethyl]glycinamide | 551.1 |

TABLE 4-continued

| Ex # | Structure | Name | MS [M + H]+ |
|---|---|---|---|
| 105 | 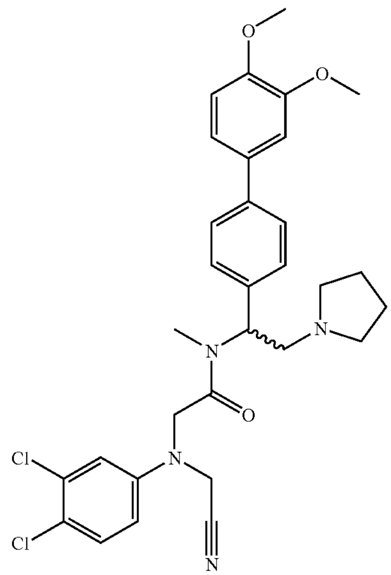 | N¹-[1-[3',4'-bis(methyloxy)-4-biphenylyl]-2-(1-pyrrolidinyl)ethyl]-N²-(cyanomethyl)-N²-(3,4-dichlorophenyl)-N¹-methylglycinamide | 581.1 |

Example 106

4'-[1-[[N-(3,4-dichlorophenyl)-N-methylglycyl](methyl)amino]-2-(1-pyrrolidinyl)ethyl]-2-biphenylcarboxamide

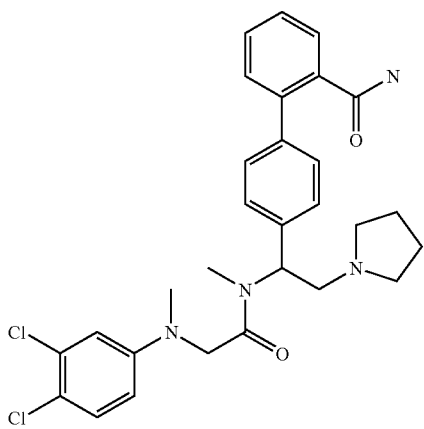

N¹-[1-(4-bromophenyl)-2-(1-pyrrolidinyl)ethyl]-N²-(3,4-dichlorophenyl)-N¹,N²-dimethylglycinamide (100 mg, 0.200 mmol) was dissolved in 1.5 mL of DMF and combined with [2-(aminocarbonyl)phenyl]boronic acid (40 mg, 0.240 mmol), Pd(dppf)₂Cl₂ (8 mg, 0.01 mmol), and 400 uL of 2M Na₂CO₃ in water. The reaction mixture was heated to at 80° C. and stirred for 18 h. Ethyl acetate (4 mL) and brine (4 mL) were added and the reaction mixture was filtered. The organic layer was separated and the solvent was removed under reduced pressure. The residue was dissolved in 1.0 mL DMSO and purified by preparative HPLC (Phenomenex 75×30 mm column, 40 mL/min flow rate, A: 0.1% TFA in acetonitrile B: 0.1% TFA in water, A: 10 to 100% over 15 min, UV detection at 215 nm) to give 51 mg (47%) of the title compound as a yellow solid. MS (ES) m/e 539/541 [M+H]⁺.

Examples 107-112

Proceeding in a similar manner to example 106, but replacing [2-(aminocarbonyl)phenyl]boronic acid with the appropriate boronic acids or esters, the compounds listed in table 5 were prepared. As is appreciated by those skilled in the art, these analogous examples may involve variations in synthetic procedure.

TABLE 5

| Ex # | Structure | Name | MS [M + H]+ |
|---|---|---|---|
| 107 | 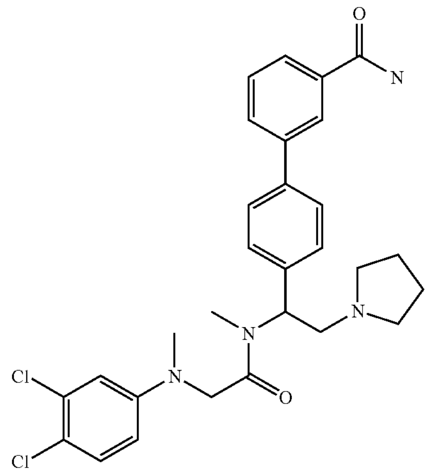 | 4'-[1-[[N-(3,4-dichlorophenyl)-N-methylglycyl](methyl)amino]-2-(1-pyrrolidinyl)ethyl]-3-biphenylcarboxamide | 539/541 |
| 108 | 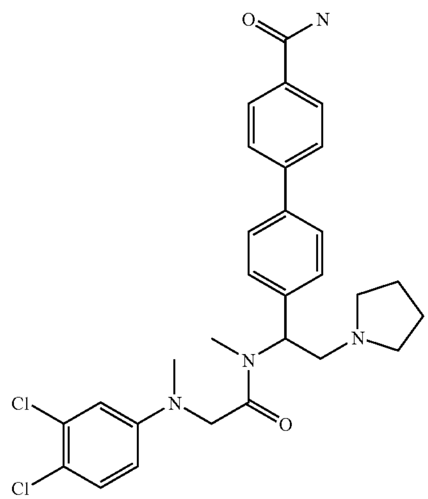 | 4'-[1-[[N-(3,4-dichlorophenyl)-N-methylglycyl](methyl)amino]-2-(1-pyrrolidinyl)ethyl]-4-biphenylcarboxamide | 539/541 |
| 109 | 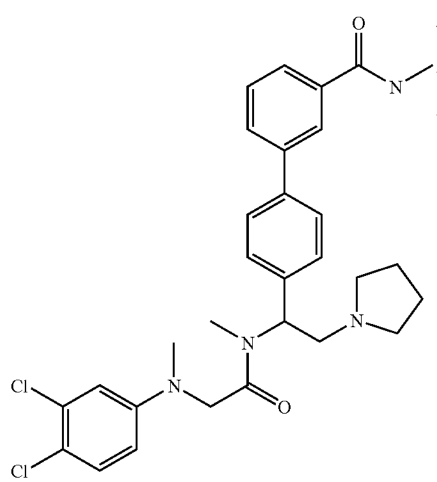 | 4'-[1-[[N-(3,4-dichlorophenyl)-N-methylglycyl](methyl)amino]-2-(1-pyrrolidinyl)ethyl]-N-methyl-3-biphenylcarboxamide | 553/555 |

TABLE 5-continued

| Ex # | Structure | Name | MS [M + H]+ |
|---|---|---|---|
| 110 | 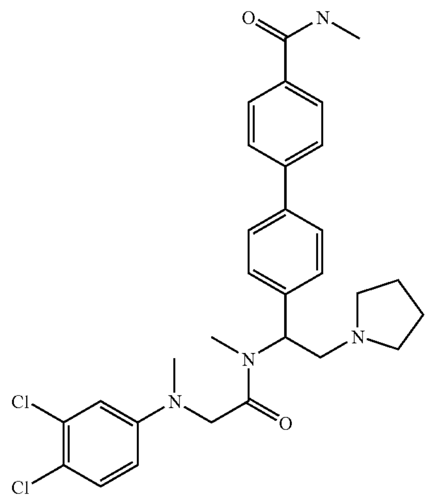 | 4'-[1-[[N-(3,4-dichlorophenyl)-N-methylglycyl](methyl)amino]-2-(1-pyrrolidinyl)ethyl]-N-methyl-4-biphenylcarboxamide | 553/555 |
| 111 | 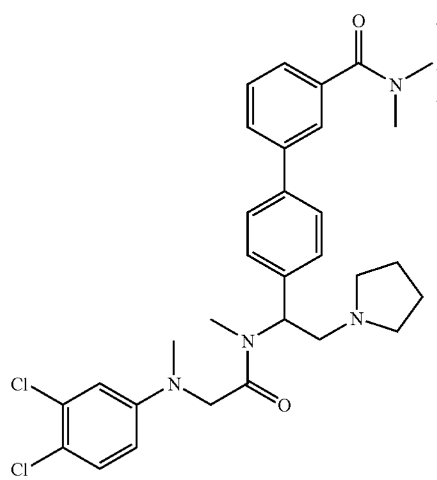 | 4'-[1-[[N-(3,4-dichlorophenyl)-N-methylglycyl](methyl)amino]-2-(1-pyrrolidinyl)ethyl]-N,N-dimethyl-3-biphenylcarboxamide | 567/569 |
| 112 | 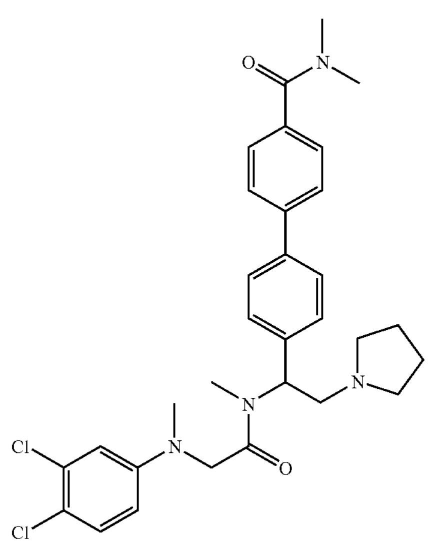 | 4'-[1-[[N-(3,4-dichlorophenyl)-N-methylglycyl](methyl)amino]-2-(1-pyrrolidinyl)ethyl]-N,N-dimethyl-4-biphenylcarboxamide | 567/569 |

Example 113

N[1]-[1-(4'-chloro-3-biphenylyl)-2-(1-pyrrolidinyl)ethyl]-N[2]-(3,4-dichlorophenyl)-N[1],N[2]-dimethylglycinamide

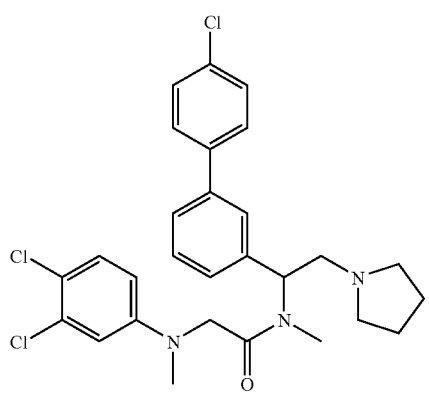

a) 1-(3-bromophenyl)-2-(1-pyrrolidinyl)ethanone

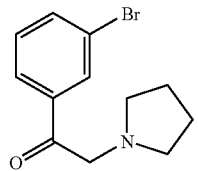

2-bromo-1-(3-bromophenyl)ethanone (4.0 g, 14.39 mmol) in anhydrous ether (50 mL) was added dropwise to a solution of pyrrolidine (2.05 g, 28.78 mmol) in anhydrous ether (20 mL) at 0° C. The reaction mixture was then warmed to room temperature. After stirring for 2 h, water (80 mL) was added and the aqueous layer was extracted with ethyl acetate (2×80 mL). The combined organic layers were dried over MgSO₄ and concentrated to yield 1-(3-bromophenyl)-2-(1-pyrrolidinyl)ethanone as a light yellow oil (3.6 g, 94%), which was used without purification. MS (ES) m/e 268 [M+H]⁺.

b [1-(3-bromophenyl)-2-(1-pyrrolidinyl)ethyl]methylamine

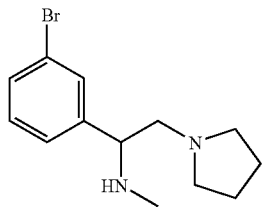

2.0 M methylamine solution in THF (55 mL, 110.0 mmol) was added to a solution of 1-(3-bromophenyl)-2-(1-pyrrolidinyl)ethanone (7.40 g, 27.62 mmol) in anhydrous THF (30 mL) at room temperature. The reaction mixture was stirred for 1 h and then sodium cyanoborohydride (5.21 g, 82.86 mmol) and acetic acid (3 mL) were added. The resulting reaction mixture was continually stirred at room temperature for 96 h until the starting material was consumed completely. Saturated K₂CO₃ solution (100 mL) was added and after stirring for 15 min, the solution was extracted with ethyl acetate (2×80 mL). The organic layers were combined, dried over Na₂SO₄, and concentrated. The resulting residue was isolated by column chromatography on silica gel (MeOH/EtOAc, 1:10) to yield the title compound as a yellow oil (3.75 g, 48%), MS (ES) m/e 283[M+H]⁺.

c) (N[1]-[1-(3-bromophenyl)-2-(1-pyrrolidinyl)ethyl]-N[2]-(3,4-dichlorophenyl)-N[1],N[2]-dimethylglycinamide

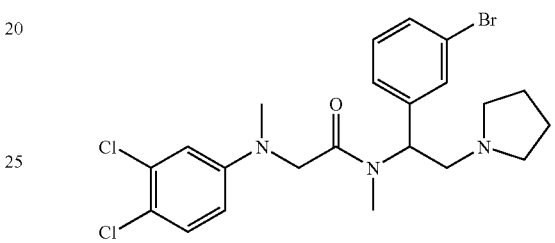

[1-(3-Bromophenyl)-2-(1-pyrrolidinyl)ethyl]methylamine (0.65 g, 2.30 mmol) was added to a solution of N-(3,4-dichlorophenyl)-N-methylglycine (0.65 g, 2.30 mmol), (benzotriazol-1-yloxy) tris(dimethylamino)phosphoniumhexafluorophosphate (BOP) (1.52 g, 3.40 mmol) and triethylamine (TEA) (0.70 g, 6.90 mmol) in N,N-dimethyl-formamide (DMF) (10 mL). The reaction mixture was stirred at RT for 12 h. Water (10 mL) was then added an the crude compound precipitated, was filtered and crystallized from ether and hexane to give the title compound as an off-white solid (0.62 g, 54%). MS (ES) m/e 499[M+H]⁺.

d) N[1]-[1-(4'-chloro-3-biphenylyl)-2-(1-pyrrolidinyl)ethyl]-N[2]-(3,4-dichlorophenyl)-N[1],N[2]-dimethylglycinamide

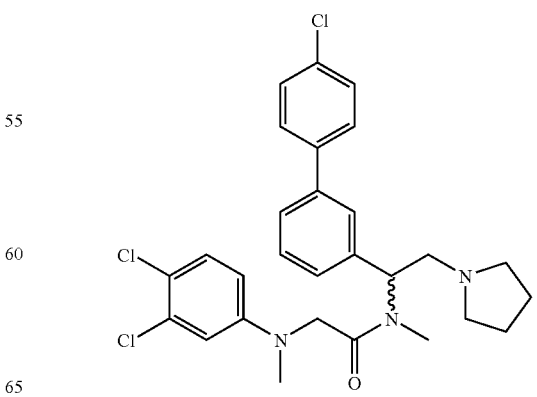

The title compound was prepared according to the procedure described for example 33, using 4-chlorophenylboronic acid and the intermediate from step c) above. MS (ES) m/e 532 [M+H]⁺.

Example 114

N-[1-(3-bromophenyl)-2-(1-pyrrolidinyl)ethyl]-2-(6,7-dichloro-3-oxo-2,3-dihydro-4H-1,4-benzoxazin-4-yl)-N-methylacetamide

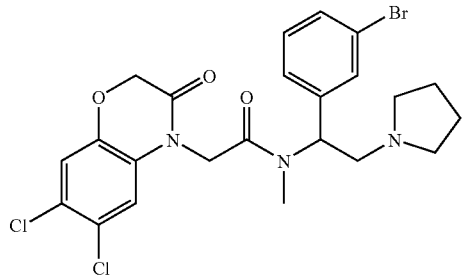

The title compound was prepared according to the procedure described in step 111c) above, replacing N-(3,4-dichlorophenyl)-N-methylglycine with (6,7-dichloro-3-oxo-2,3-dihydro-4H-1,4-benzoxazin-4-yl)acetic acid. MS (ES) m/e 541 [M+H]⁺.

Examples 115-129

Proceeding in a similar manner as in example 113c, but replacing 4-chlorophenylboronic acid with the appropriate boronic acids and/or replacing (N¹-[1-(3-bromophenyl)-2-(1-pyrrolidinyl)ethyl]-N²-(3,4-dichlorophenyl)-N¹,N²-dimethylglycinamide with N-[1-(3-bromophenyl)-2-(1-pyrrolidinyl)ethyl]-2-(6,7-dichloro-3-oxo-2,3-dihydro-4H-1,4-benzoxazin-4-yl)-N-methylacetamide, the compounds listed in table 6 were prepared. As is appreciated by those skilled in the art, these analogous examples may involve variations in synthetic procedure.

TABLE 6

| Ex # | Structure | Name | MS [M + H]⁺ |
|---|---|---|---|
| 115 | 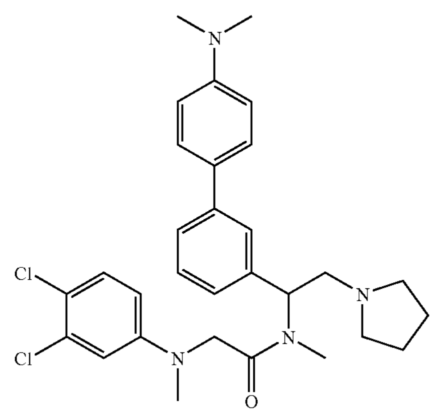 | N²-(3,4-dichlorophenyl)-N¹-[1-[4'-(dimethylamino)-3-biphenylyl]-2-(1-pyrrolidinyl)ethyl]-N¹,N²-dimethylglycinamide | 539 |
| 116 | 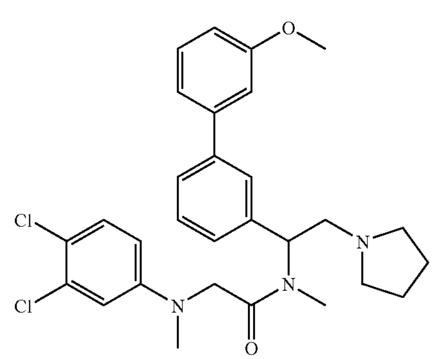 | N²-(3,4-dichlorophenyl)-N¹,N²-dimethyl-N¹-[1-[3'-(methyloxy)-3-biphenylyl]-2-(1-pyrrolidinyl)ethyl]glycinamide | 526 |

TABLE 6-continued

| Ex # | Structure | Name | MS [M + H]+ |
|---|---|---|---|
| 117 | 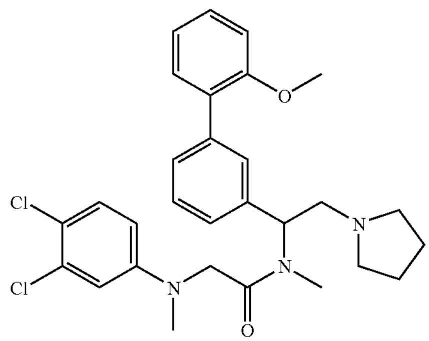 | $N^2$-(3,4-dichlorophenyl)-$N^1$,$N^2$-dimethyl-$N^1$-[1-[2'-(methyloxy)-3-biphenylyl]-2-(1-pyrrolidinyl)ethyl]glycinamide | 526 |
| 118 | 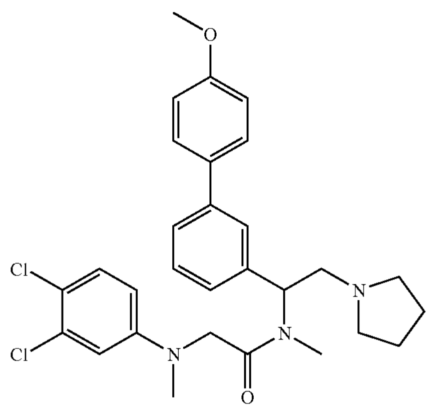 | $N^2$-(3,4-dichlorophenyl)-$N^1$,$N^2$-dimethyl-$N^1$-[1-[4'-(methyloxy)-3-biphenylyl]-2-(1-pyrrolidinyl)ethyl]glycinamide | 526 |
| 119 | 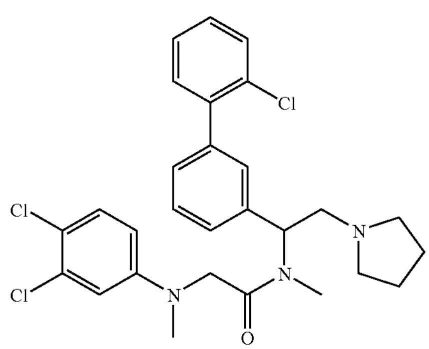 | N'-[1-(2'-chloro-3-biphenylyl)-2-(1-pyrrolidinyl)ethyl]-$N^2$-(3,4-dichlorophenyl)-$N^1$,$N^2$-dimethylglycinamide | 530 |
| 120 | 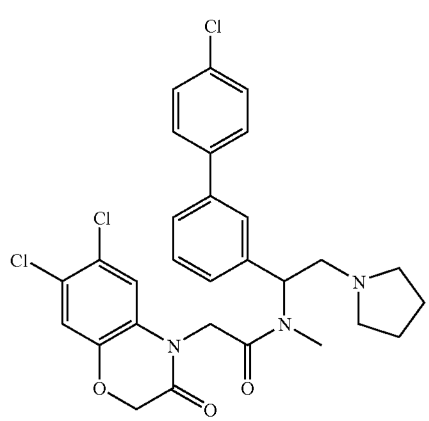 | N-[1-(4'-chloro-3-biphenylyl)-2-(1-pyrrolidinyl)ethyl]-2-(6,7-dichloro-3-oxo-2,3-dihydro-4H-1,4-benzoxazin-4-yl)-N-methylacetamide | 572 |

TABLE 6-continued

| Ex # | Structure | Name | MS [M + H]+ |
|---|---|---|---|
| 121 | 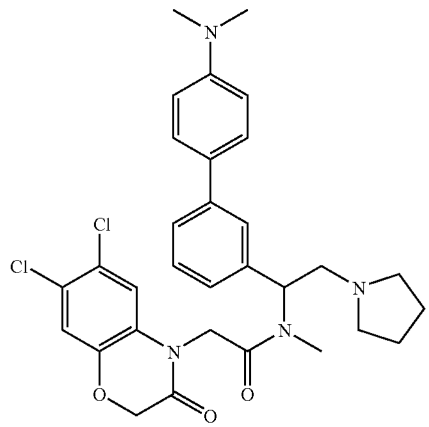 | 2-(6,7-dichloro-3-oxo-2,3-dihydro-4H-1,4-benzoxazin-4-yl)-N-[1-[4'-(dimethylamino)-3-biphenylyl]-2-(1-pyrrolidinyl)ethyl]-N-methylacetamide | 581 |
| 122 | 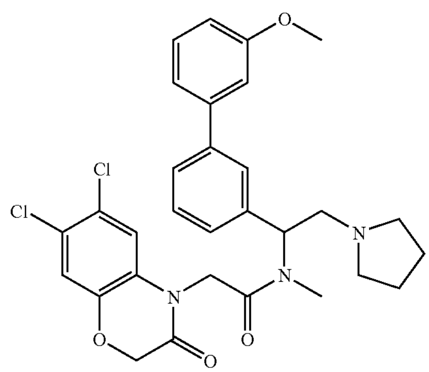 | 2-(6,7-dichloro-3-oxo-2,3-dihydro-4H-1,4-benzoxazin-4-yl)-N-methyl-N-[1-[3'-(methyloxy)-3-biphenylyl]-2-(1-pyrrolidinyl)ethyl]acetamide | 568 |
| 123 | 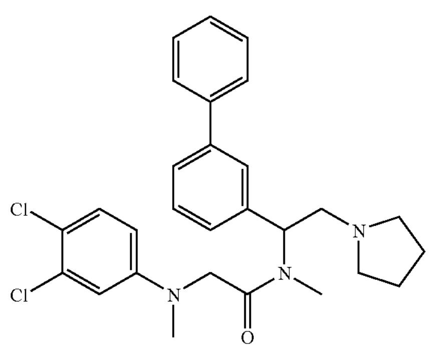 | $N^1$-[1-(3-biphenylyl)-2-(1-pyrrolidinyl)ethyl]-$N^2$-(3,4-dichlorophenyl)-$N^1$,$N^2$-dimethylglycinamide | 498 |
| 124 | 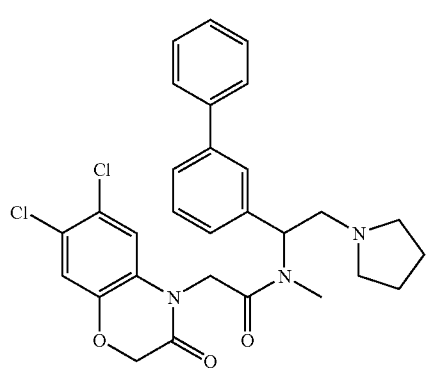 | N-[1-(3-biphenylyl)-2-(1-pyrrolidinyl)ethyl]-2-(6,7-dichloro-3-oxo-2,3-dihydro-4H-1,4-benzoxazin-4-yl)-N-methylacetamide | 538 |

TABLE 6-continued

| Ex # | Structure | Name | MS [M + H]+ |
|---|---|---|---|
| 125 | 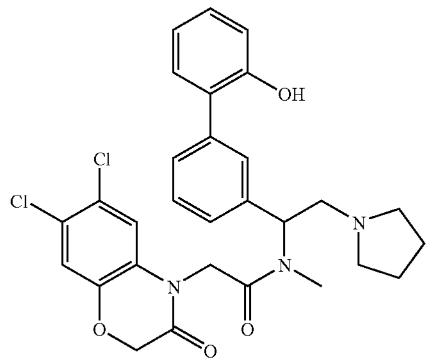 | 2-(6,7-dichloro-3-oxo-2,3-dihydro-4H-1,4-benzoxazin-4-yl)-N-[1-(2'-hydroxy-3-biphenylyl)-2-(1-pyrrolidinyl)ethyl]-N-methylacetamide | 554 |
| 126 | 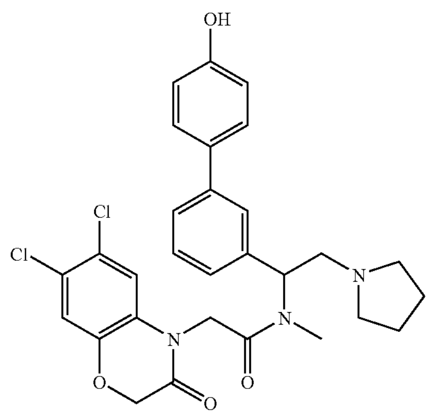 | 2-(6,7-dichloro-3-oxo-2,3-dihydro-4H-1,4-benzoxazin-4-yl)-N-[1-(4'-hydroxy-3-biphenylyl)-2-(1-pyrrolidinyl)ethyl]-N-methylacetamide | 554 |
| 127 | 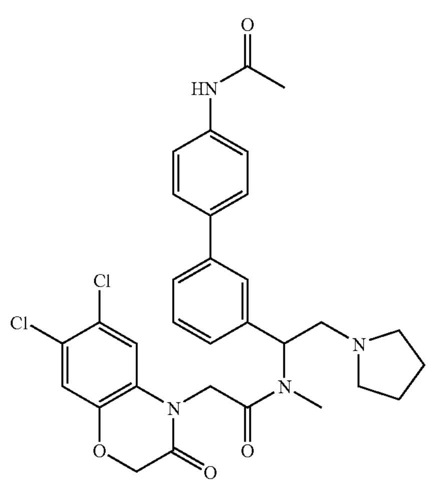 | N-[1-[4'-(acetylamino)-3-biphenylyl]-2-(1-pyrrolidinyl)ethyl]-2-(6,7-dichloro-3-oxo-2,3-dihydro-4H-1,4-benzoxazin-4-yl)-N-methylacetamide | 595 |

TABLE 6-continued

| Ex # | Structure | Name | MS [M + H]+ |
|---|---|---|---|
| 128 | 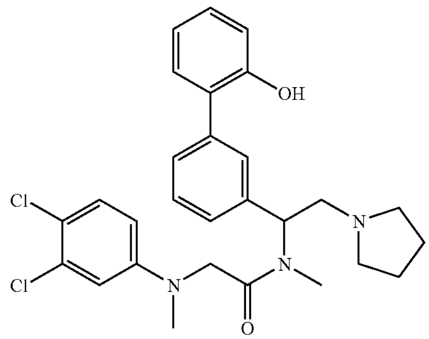 | $N^2$-(3,4-dichlorophenyl)-$N^1$-[1-(2'-hydroxy-3-biphenylyl)-2-(1-pyrrolidinyl)ethyl]-$N^1$,$N^2$-dimethylglycinamide | 512 |
| 129 | 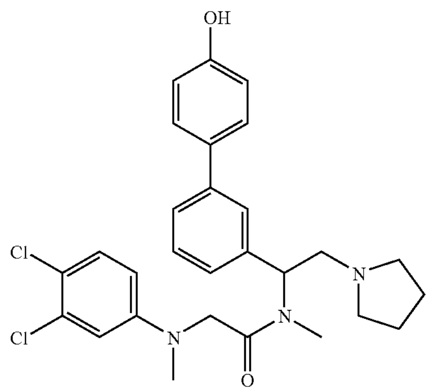 | $N^2$-(3,4-dichlorophenyl)-$N^1$-[1-(4'-hydroxy-3-biphenylyl)-2-(1-pyrrolidinyl)ethyl]-$N^1$,$N^2$-dimethylglycinamide | 512 |

Example 130

2-(6,7-dichloro-3-oxo-2,3-dihydro-4H-1,4-benzoxazin-4-yl)-N-methyl-N-[1-{4'-[(methylsulfonyl)amino]-4-biphenylyl}-2-(4-morpholinyl)ethyl]acetamide

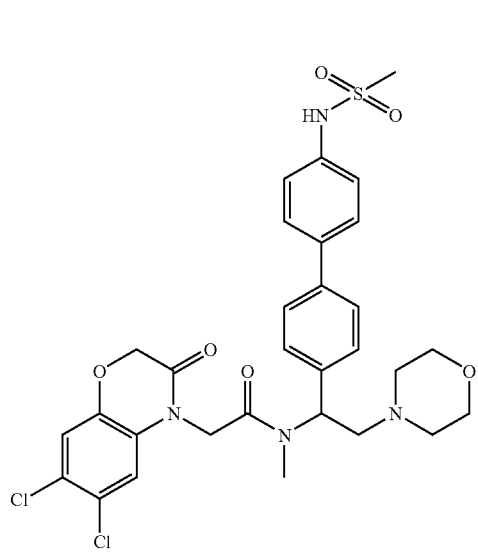

a) 1-(4-bromophenyl)-2-(4-morpholinyl)ethanone

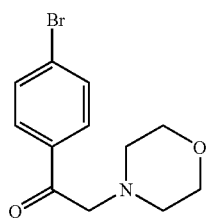

The title compound was prepared according to the procedure described in example 113, replacing 2-bromo-1-(3-bromophenyl)ethanone with 2-bromo-1-(4-bromophenyl)ethanone and pyrrolidine with morpholine. MS (ES) m/e 284 [M+H]+.

b) [1-(4-bromophenyl)-2-(4-morpholinyl)ethyl]methylamine

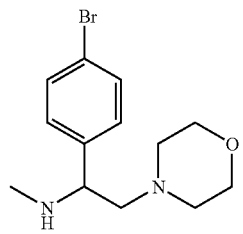

The desired compound was prepared according to the procedure described in example 113, replacing 1-(3-bromophenyl)-2-(1-pyrrolidinyl)ethanone with 1-(4-bromophenyl)-2-(4-morpholinyl)ethanone. MS (ES) m/e 299 [M+H]$^+$.

c) N-[1-(4-bromophenyl)-2-(4-morpholinyl)ethyl]-2-(6,7-dichloro-3-oxo-2,3-dihydro-4H-1,4-benzoxazin-4-yl)-N-methylacetamide

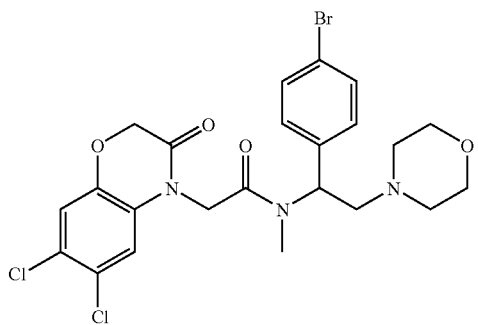

The desired compound was prepared according to the method described in example 113, replacing [1-(3-bromophenyl)-2-(1-pyrrolidinyl)ethyl]methylamine with [1-(4-bromophenyl)-2-(4-morpholinyl)ethyl]methylamine MS (ES) m/e 557 [M+H]$^+$.

d) 2-(6,7-dichloro-3-oxo-2,3-dihydro-4H-1,4-benzoxazin-4-yl)-N-methyl-N-[1-{4'-[(methylsulfonyl)amino]-4-biphenylyl}-2-(4-morpholinyl)ethyl]acetamide

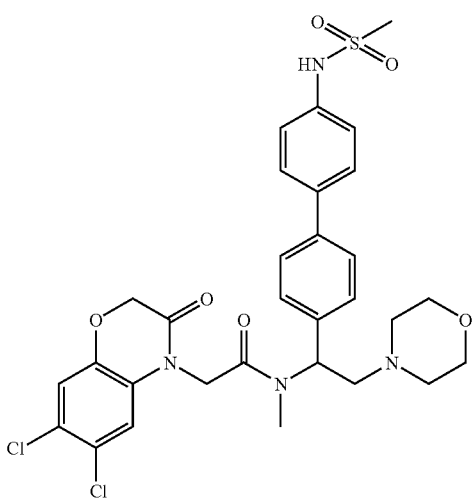

The title compound was prepared according to example 33, using the intermediate from step c) and {4-[(methylsulfonyl)amino]-phenyl}boronic acid, MS (ES) m/e 647 [M+H]$^+$.

Examples 131-178

Proceeding in a similar manner as in example 130, but replacing (6,7-dichloro-3-oxo-2,3-dihydro-4H-1,4-benzoxazin-4-yl)acetic acid with N-(cyanomethyl)-N-(3,4-dichlorophenyl)glycine or (6,7-dimethyl-3-oxo-2,3-dihydro-4H-1,4-benzoxazin-4-yl)acetic acid and/or {4[(methylsulfonyl)amino]-phenyl}boronic acid with the appropriate boronic acids, the compounds listed in table 7 were prepared. Note that with N-(cyanomethyl)-N-(3,4-dichlorophenyl)glycine, cross coupling is accompanied by hydrolysis to the primary amide. As is appreciated by those skilled in the art, these analogous examples may involve variations in synthetic procedure.

TABLE 7

| Ex # | Structure | Name | MS [M + H]+ |
|---|---|---|---|
| 131 | 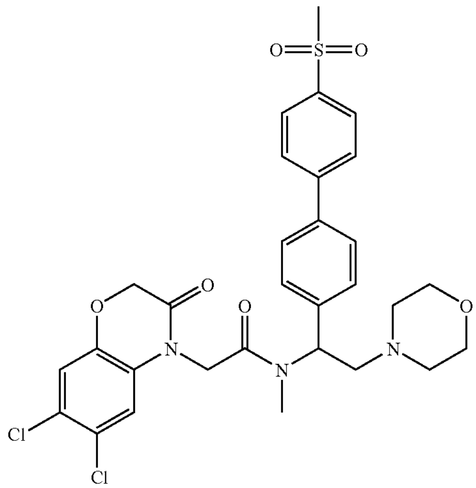 | 2-(6,7-dichloro-3-oxo-2,3-dihydro-4H-1,4-benzoxazin-4-yl)-N-methyl-N-[1-[4'-(methylsulfonyl)-4-biphenylyl]-2-(4-morpholinyl)ethyl]acetamide | 632 |
| 132 | 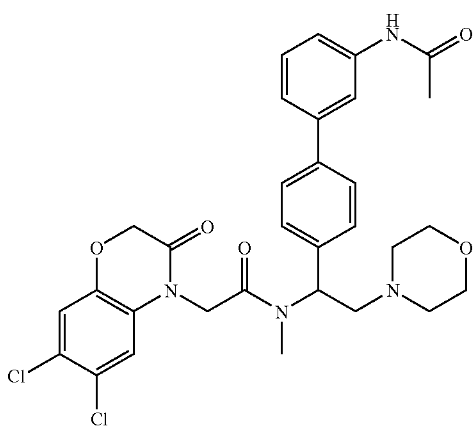 | N-{1-[3'-(acetylamino)biphenyl-4-yl]-2-morpholin-4-ylethyl}-2-(6,7-dichloro-3-oxo-2,3-dihydro-4H-1,4-benzoxazin-4-yl)-N-methylacetamide | 611 |
| 133 | 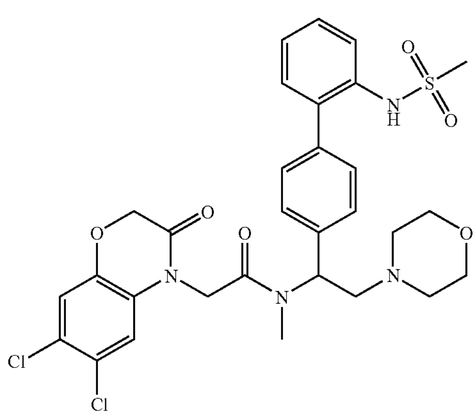 | 2-(6,7-dichloro-3-oxo-2,3-dihydro-4H-1,4-benzoxazin-4-yl)-N-methyl-N-[1-{2'-[(methylsulfonyl)amino]-4-biphenylyl}-2-(4-morpholinyl)ethyl]acetamide | 647 |

TABLE 7-continued

| Ex # | Structure | Name | MS [M + H]+ |
|---|---|---|---|
| 134 | 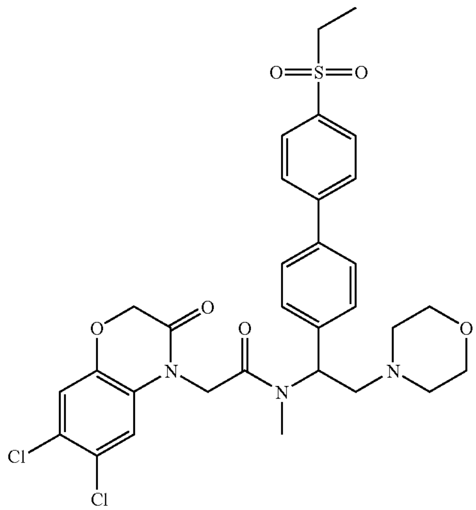 | 2-(6,7-dichloro-3-oxo-2,3-dihydro-4H-1,4-benzoxazin-4-yl)-N-[1-[4'-(ethylsulfonyl)-4-biphenylyl]-2-(4-morpholinyl)ethyl]-N-methylacetamide | 646 |
| 135 | 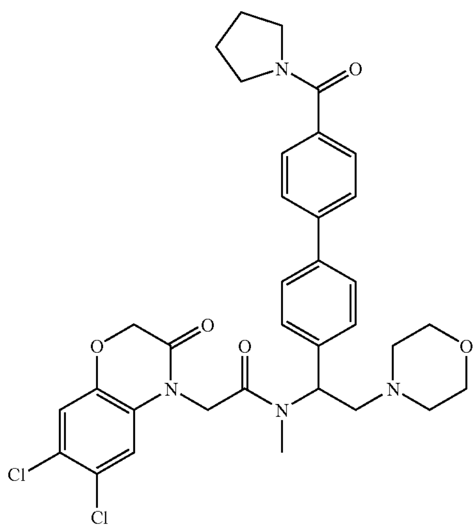 | 2-(6,7-dichloro-3-oxo-2,3-dihydro-4H-1,4-benzoxazin-4-yl)-N-methyl-N-{2-(4-morpholinyl)-1-[4'-(1-pyrrolidinylcarbonyl)-4-biphenylyl]ethyl}acetamide | 651 |
| 136 | 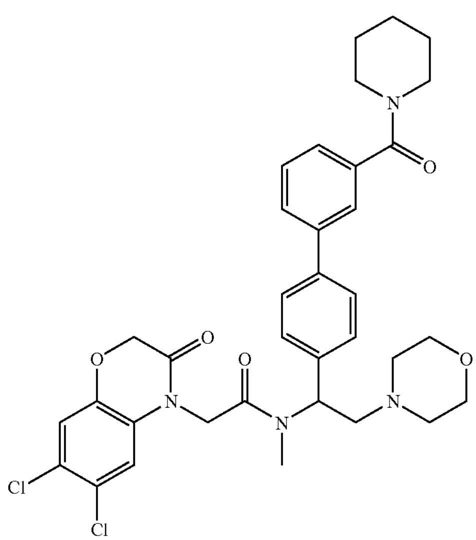 | 2-(6,7-dichloro-3-oxo-2,3-dihydro-4H-1,4-benzoxazin-4-yl)-N-methyl-N-{2-(4-morpholinyl)-1-[3'-(1-piperidinylcarbonyl)-4-biphenylyl]ethyl}acetamide | 665 |

TABLE 7-continued

| Ex # | Structure | Name | MS [M + H]+ |
|---|---|---|---|
| 137 | 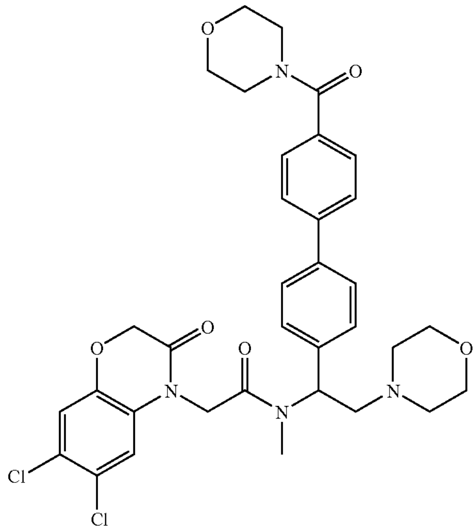 | 2-(6,7-dichloro-3-oxo-2,3-dihydro-4H-1,4-benzoxazin-4-yl)-N-methyl-N-{2-(4-morpholinyl)-1-[4'-(4-morpholinylcarbonyl)-4-biphenylyl]ethyl}acetamide | 667 |
| 138 | 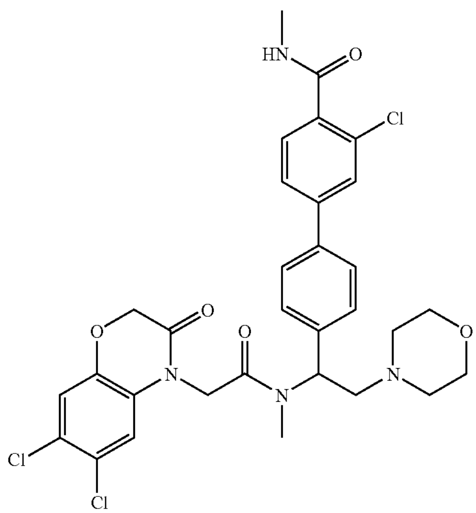 | 3-chloro-4'-[1-[[(6,7-dichloro-3-oxo-2,3-dihydro-4H-1,4-benzoxazin-4-yl)acetyl](methyl)amino]-2-(4-morpholinyl)ethyl]-N-methyl-4-biphenylcarboxamide | 645 |
| 139 | 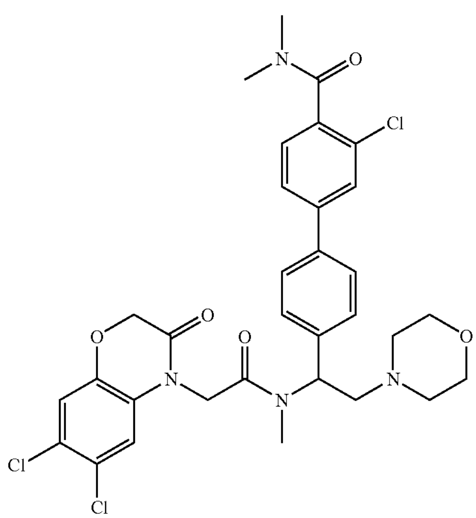 | 3-chloro-4'-[1-[[(6,7-dichloro-3-oxo-2,3-dihydro-4H-1,4-benzoxazin-4-yl)acetyl](methyl)amino]-2-(4-morpholinyl)ethyl]-N,N-dimethyl-4-biphenylcarboxamide | 659 |

TABLE 7-continued

| Ex # | Structure | Name | MS [M + H]+ |
|---|---|---|---|
| 140 | 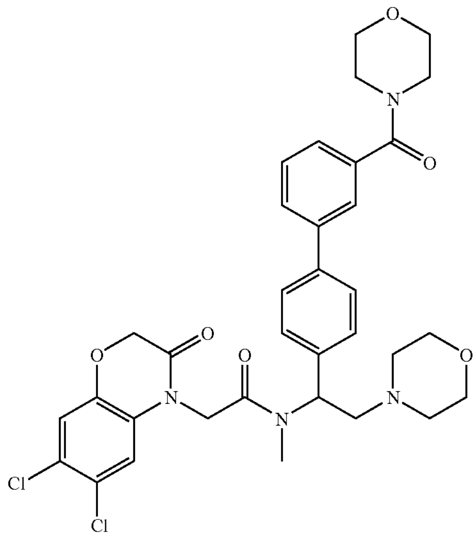 | 2-(6,7-dichloro-3-oxo-2,3-dihydro-4H-1,4-benzoxazin-4-yl)-N-methyl-N-{2-(4-morpholinyl)-1-[3'-(4-morpholinylcarbonyl)-4-biphenylyl]ethyl}acetamide | 667 |
| 141 | 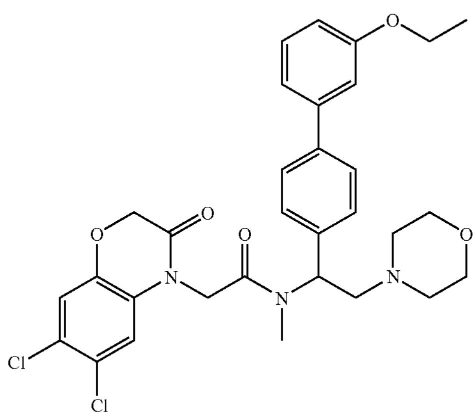 | 2-(6,7-dichloro-3-oxo-2,3-dihydro-4H-1,4-benzoxazin-4-yl)-N-[1-[3'-(ethyloxy)-4-biphenylyl]-2-(4-morpholinyl)ethyl]-N-methylacetamide | 598 |
| 142 | 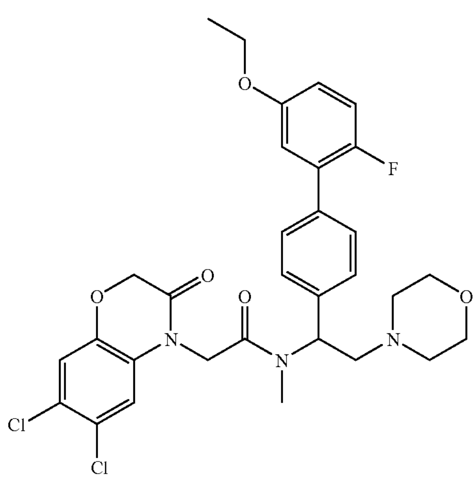 | 2-(6,7-dichloro-3-oxo-2,3-dihydro-4H-1,4-benzoxazin-4-yl)-N-[1-[5'-(ethyloxy)-2'-fluoro-4-biphenylyl]-2-(4-morpholinyl)ethyl]-N-methylacetamide | 616 |

TABLE 7-continued

| Ex # | Structure | Name | MS [M + H]+ |
|---|---|---|---|
| 143 | 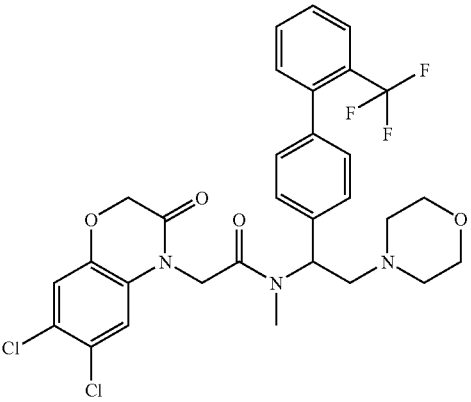 | 2-(6,7-dichloro-3-oxo-2,3-dihydro-4H-1,4-benzoxazin-4-yl)-N-methyl-N-{2-(4-morpholinyl)-1-[2'-(trifluoromethyl)-4-biphenylyl]ethyl}acetamide | 622 |
| 144 | 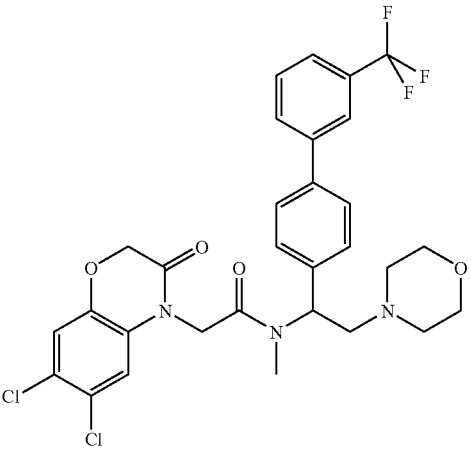 | 2-(6,7-dichloro-3-oxo-2,3-dihydro-4H-1,4-benzoxazin-4-yl)-N-methyl-N-{2-(4-morpholinyl)-1-[3'-(trifluoromethyl)-4-biphenylyl]ethyl}acetamide | 622 |
| 145 | 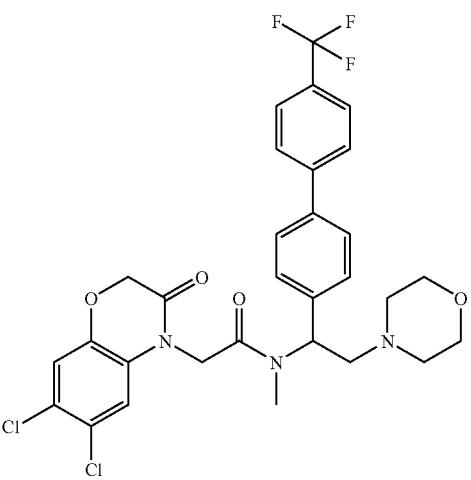 | 2-(6,7-dichloro-3-oxo-2,3-dihydro-4H-1,4-benzoxazin-4-yl)-N-methyl-N-{2-(4-morpholinyl)-1-[4'-(trifluoromethyl)-4-biphenylyl]ethyl}acetamide | 622 |

TABLE 7-continued

| Ex # | Structure | Name | MS [M + H]+ |
|---|---|---|---|
| 146 | 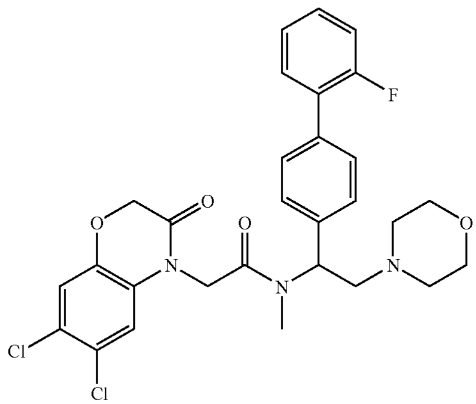 | 2-(6,7-dichloro-3-oxo-2,3-dihydro-4H-1,4-benzoxazin-4-yl)-N-[1-(2'-fluoro-4-biphenylyl)-2-(4-morpholinyl)ethyl]-N-methylacetamide | 572 |
| 147 | 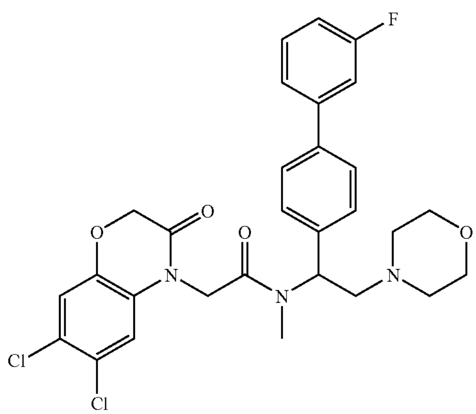 | 2-(6,7-dichloro-3-oxo-2,3-dihydro-4H-1,4-benzoxazin-4-yl)-N-[1-(3'-fluoro-4-biphenylyl)-2-(4-morpholinyl)ethyl]-N-methylacetamide | 572 |
| 148 | 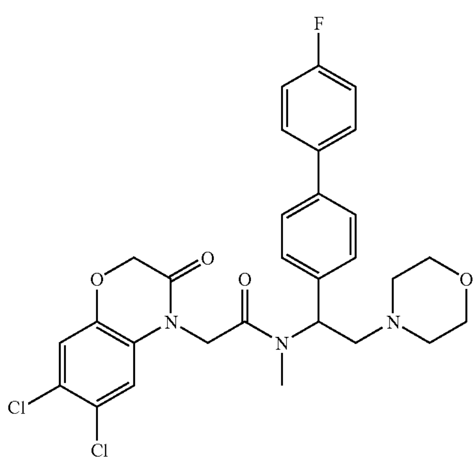 | 2-(6,7-dichloro-3-oxo-2,3-dihydro-4H-1,4-benzoxazin-4-yl)-N-[1-(4'-fluoro-4-biphenylyl)-2-(4-morpholinyl)ethyl]-N-methylacetamide | 572 |

TABLE 7-continued

| Ex # | Structure | Name | MS [M + H]+ |
|---|---|---|---|
| 149 | 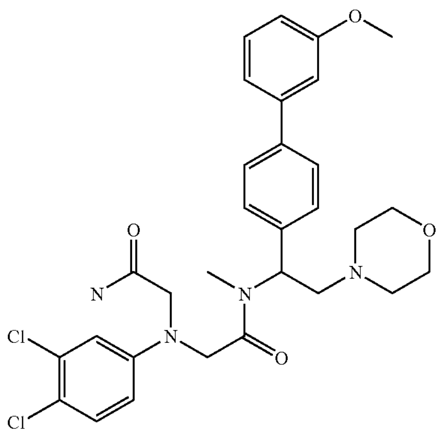 | 2-[(2-amino-2-oxoethyl)(3,4-dichlorophenyl)amino]-N-methyl-N-[1-[3'-(methyloxy)-4-biphenylyl]-2-(4-morpholinyl)ethyl]acetamide | 585/587 |
| 150 | 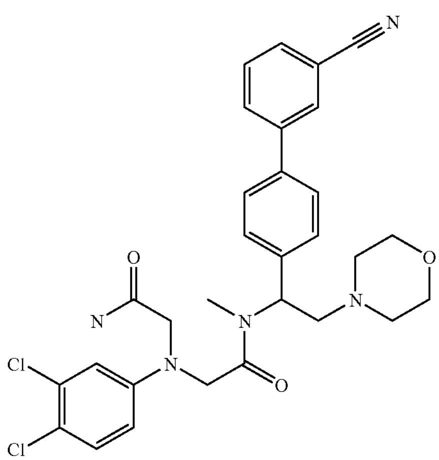 | 2-[(2-amino-2-oxoethyl)(3,4-dichlorophenyl)amino]-N-[1-(3'-cyano-4-biphenylyl)-2-(4-morpholinyl)ethyl]-N-methylacetamide | 580/582 |
| 151 | 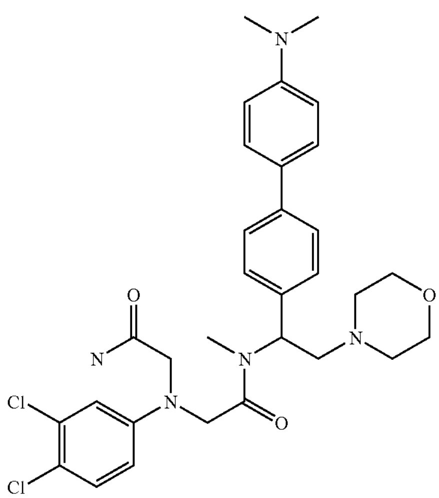 | 2-[(2-amino-2-oxoethyl)(3,4-dichlorophenyl)amino]-N-[1-[4'-(dimethylamino)-4-biphenylyl]-2-(4-morpholinyl)ethyl]-N-methylacetamide | 598/600 |

TABLE 7-continued
| Ex # | Structure | Name | MS [M + H]+ |
|---|---|---|---|
| 152 | 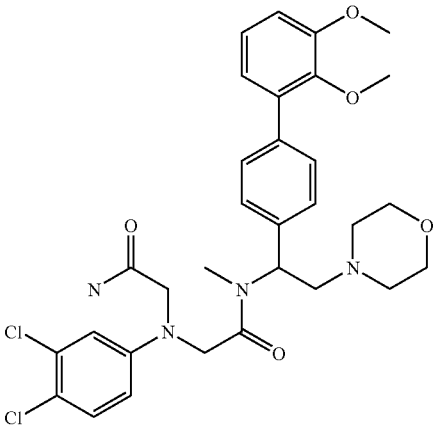 | 2-[(2-amino-2-oxoethyl)(3,4-dichlorophenyl)amino]-N-[1-[2',3'-bis(methyloxy)-4-biphenylyl]-2-(4-morpholinyl)ethyl]-N-methylacetamide | 615/617 |
| 153 | 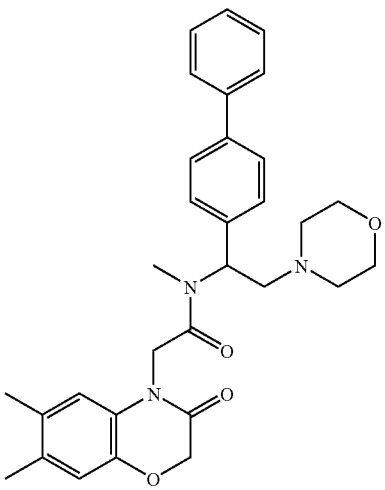 | N-[1-(4-biphenylyl)-2-(4-morpholinyl)ethyl]-2-(6,7-dimethyl-3-oxo-2,3-dihydro-4H-1,4-benzoxazin-4-yl)-N-methylacetamide | 514 |
| 154 | 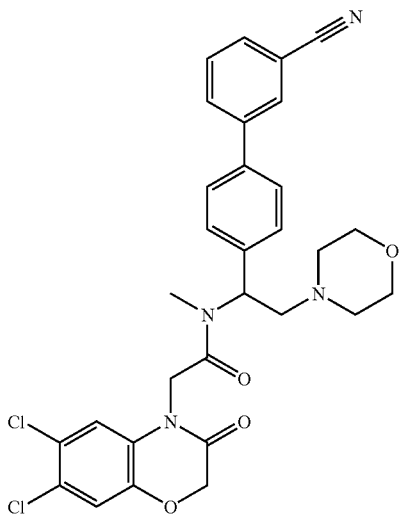 | N-[1-(3'-cyano-4-biphenylyl)-2-(4-morpholinyl)ethyl]-2-(6,7-dichloro-3-oxo-2,3-dihydro-4H-1,4-benzoxazin-4-yl)-N-methylacetamide | 579/581 |

TABLE 7-continued

| Ex # | Structure | Name | MS [M + H]+ |
|---|---|---|---|
| 155 | 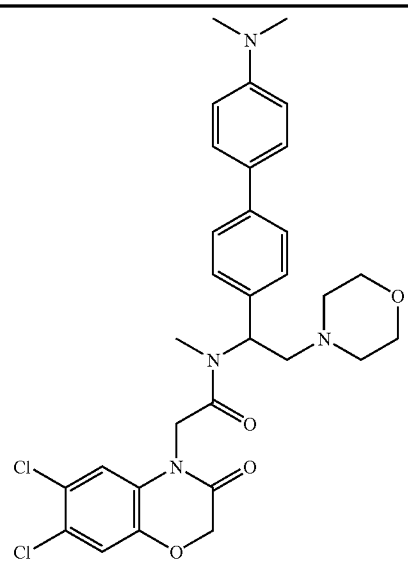 | 2-(6,7-dichloro-3-oxo-2,3-dihydro-4H-1,4-benzoxazin-4-yl)-N-[1-[4'-(dimethylamino)-4-biphenylyl]-2-(4-morpholinyl)ethyl]-N-methylacetamide | 597/599 |
| 156 | 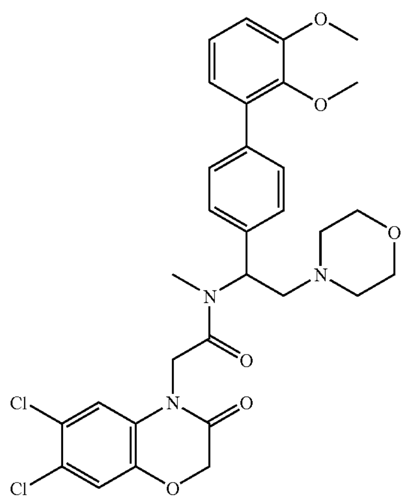 | N-[1-[2',3'-bis(methyloxy)-4-biphenylyl]-2-(4-morpholinyl)ethyl]-2-(6,7-dichloro-3-oxo-2,3-dihydro-4H-1,4-benzoxazin-4-yl)-N-methylacetamide | 614/616 |
| 157 | 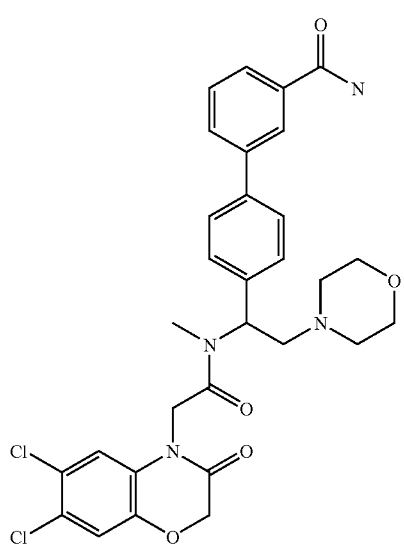 | 4'-[1-[[(6,7-dichloro-3-oxo-2,3-dihydro-4H-1,4-benzoxazin-4-yl)acetyl](methyl)amino]-2-(4-morpholinyl)ethyl]-3-biphenylcarboxamide | 597/599 |

TABLE 7-continued
| Ex # | Structure | Name | MS [M + H]+ |
|---|---|---|---|
| 158 | 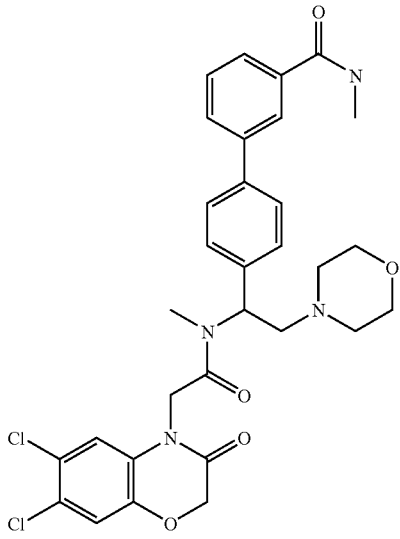 | 4'-[1-[[(6,7-dichloro-3-oxo-2,3-dihydro-4H-1,4-benzoxazin-4-yl)acetyl](methyl)amino]-2-(4-morpholinyl)ethyl]-N-methyl-3-biphenylcarboxamide | 611/613 |
| 159 | 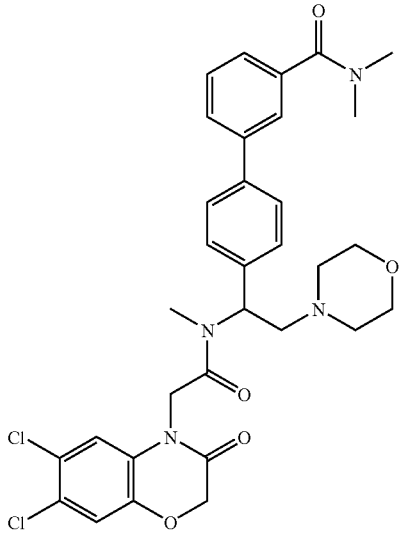 | 4'-[1-[[(6,7-dichloro-3-oxo-2,3-dihydro-4H-1,4-benzoxazin-4-yl)acetyl](methyl)amino]-2-(4-morpholinyl)ethyl]-N,N-dimethyl-3-biphenylcarboxamide | 625/627 |

TABLE 7-continued

| Ex # | Structure | Name | MS [M + H]+ |
|---|---|---|---|
| 160 | 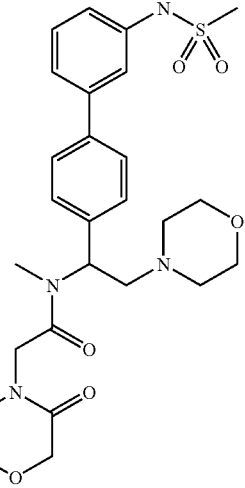 | 2-(6,7-dichloro-3-oxo-2,3-dihydro-4H-1,4-benzoxazin-4-yl)-N-methyl-N-[1-{3'-[(methylsulfonyl)amino]-4-biphenylyl}-2-(4-morpholinyl)ethyl]acetamide | 647/649 |
| 161 | 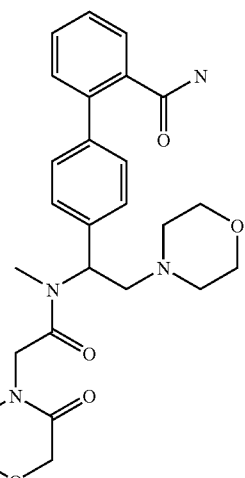 | 4'-[1-[[(6,7-dichloro-3-oxo-2,3-dihydro-4H-1,4-benzoxazin-4-yl)acetyl](methyl)amino]-2-(4-morpholinyl)ethyl]-2-biphenylcarboxamide | 597/599 |
| 162 | 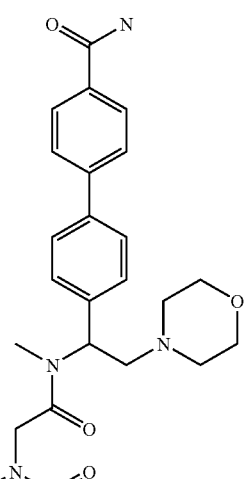 | 4'-[1-[[(6,7-dichloro-3-oxo-2,3-dihydro-4H-1,4-benzoxazin-4-yl)acetyl](methyl)amino]-2-(4-morpholinyl)ethyl]-4-biphenylcarboxamide | 597/599 |

TABLE 7-continued
| Ex # | Structure | Name | MS [M + H]+ |
|---|---|---|---|
| 163 | 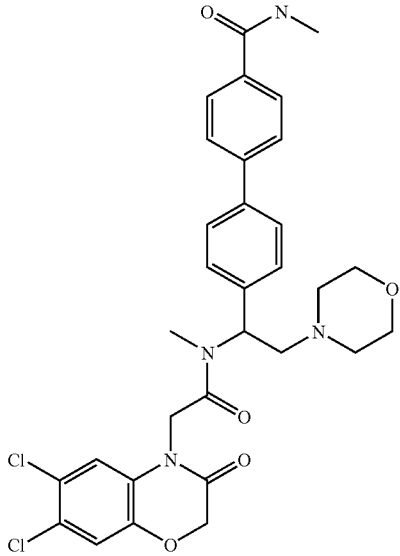 | 4'-[1-[[(6,7-dichloro-3-oxo-2,3-dihydro-4H-1,4-benzoxazin-4-yl)acetyl](methyl)amino]-2-(4-morpholinyl)ethyl]-N-methyl-4-biphenylcarboxamide | 611/613 |
| 164 | 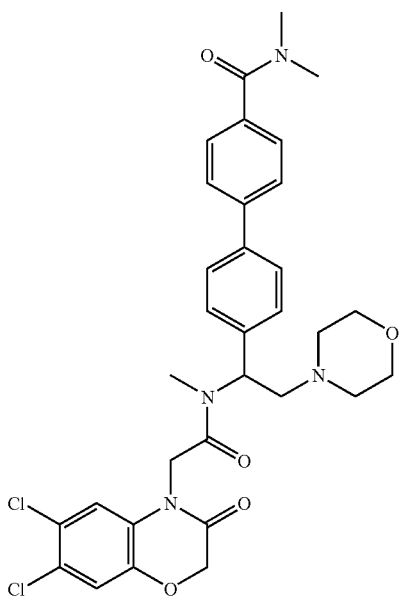 | 4'-[1-[[(6,7-dichloro-3-oxo-2,3-dihydro-4H-1,4-benzoxazin-4-yl)acetyl](methyl)amino]-2-(4-morpholinyl)ethyl]-N,N-dimethyl-4-biphenylcarboxamide | 625/627 |

TABLE 7-continued

| Ex # | Structure | Name | MS [M + H]+ |
|---|---|---|---|
| 165 | 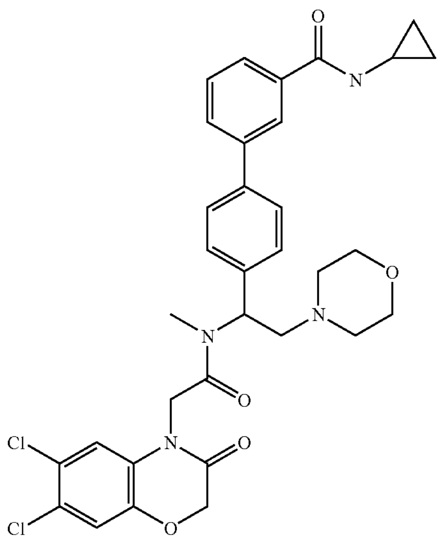 | N-cyclopropyl-4'-[1-[[(6,7-dichloro-3-oxo-2,3-dihydro-4H-1,4-benzoxazin-4-yl)acetyl](methyl)amino]-2-(4-morpholinyl)ethyl]-3-biphenylcarboxamide | 637/639 |
| 166 | 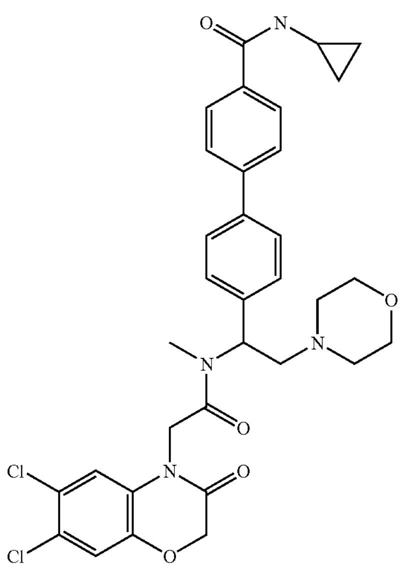 | N-cyclopropyl-4'-[1-[[(6,7-dichloro-3-oxo-2,3-dihydro-4H-1,4-benzoxazin-4-yl)acetyl](methyl)amino]-2-(4-morpholinyl)ethyl]-4-biphenylcarboxamide | 637/639 |

TABLE 7-continued
| Ex # | Structure | Name | MS [M + H]+ |
|---|---|---|---|
| 167 | 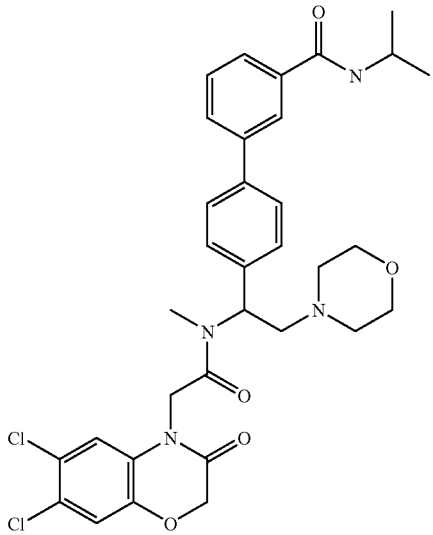 | 4'-[1-[[(6,7-dichloro-3-oxo-2,3-dihydro-4H-1,4-benzoxazin-4-yl)acetyl](methyl)amino]-2-(4-morpholinyl)ethyl]-N-(1-methylethyl)-3-biphenylcarboxamide | 639/641 |
| 168 | 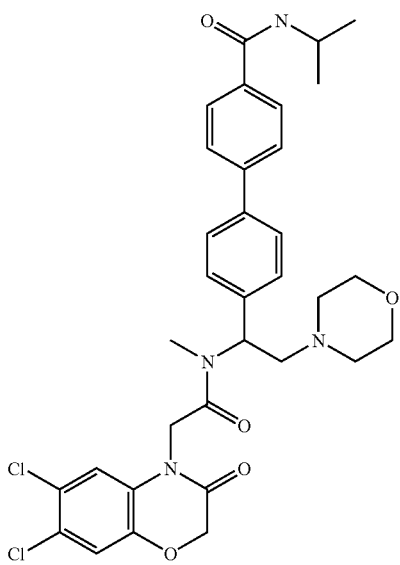 | 4'-[1-[[(6,7-dichloro-3-oxo-2,3-dihydro-4H-1,4-benzoxazin-4-yl)acetyl](methyl)amino]-2-(4-morpholinyl)ethyl]-N-(1-methylethyl)-4-biphenylcarboxamide | 639/641 |

TABLE 7-continued

| Ex # | Structure | Name | MS [M + H]+ |
|---|---|---|---|
| 169 | 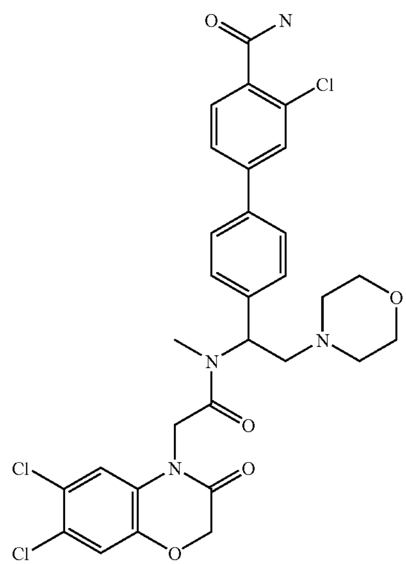 | 3-chloro-4'-[1-[[(6,7-dichloro-3-oxo-2,3-dihydro-4H-1,4-benzoxazin-4-yl)acetyl](methyl)amino]-2-(4-morpholinyl)ethyl]-4-biphenylcarboxamide | 631/633 |
| 170 | 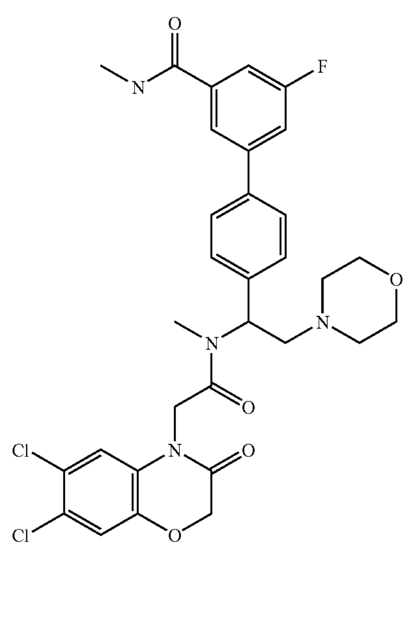 | 4'-[1-[[(6,7-dichloro-3-oxo-2,3-dihydro-4H-1,4-benzoxazin-4-yl)acetyl](methyl)amino]-2-(4-morpholinyl)ethyl]-5-fluoro-N-methyl-3-biphenylcarboxamide | 629/631 |

| Ex # | Structure | Name | MS [M + H]+ |
|---|---|---|---|
| 171 | 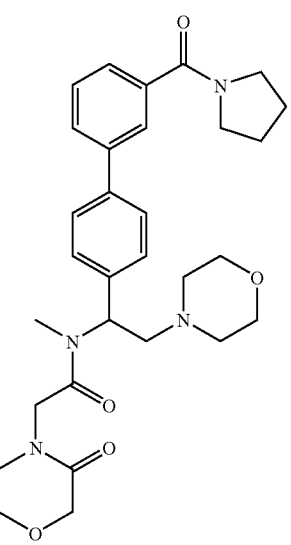 | 2-(6,7-dichloro-3-oxo-2,3-dihydro-4H-1,4-benzoxazin-4-yl)-N-methyl-N-{2-(4-morpholinyl)-1-[3'-(1-pyrrolidinylcarbonyl)-4-biphenylyl]ethyl}acetamide | 651/653 |
| 172 | 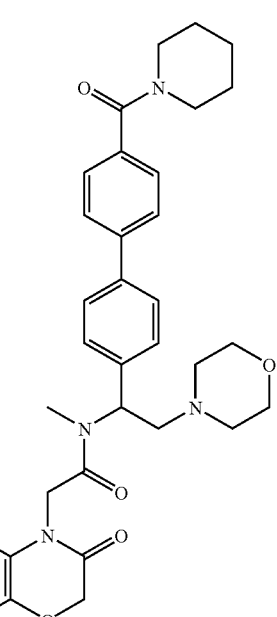 | 2-(6,7-dichloro-3-oxo-2,3-dihydro-4H-1,4-benzoxazin-4-yl)-N-methyl-N-{2-(4-morpholinyl)-1-[4'-(1-piperidinylcarbonyl)-4-biphenylyl]ethyl}acetamide | 665/667 |

TABLE 7-continued
| Ex # | Structure | Name | MS [M + H]+ |
|---|---|---|---|
| 173 | 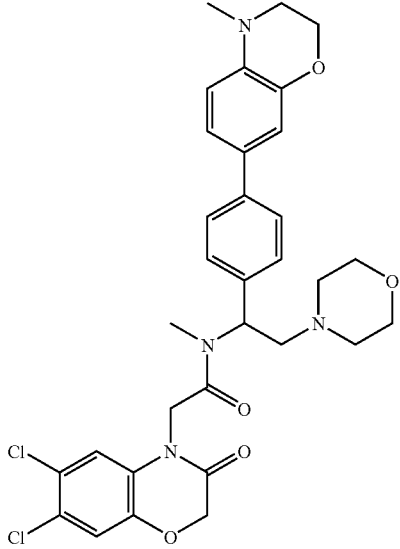 | 2-(6,7-dichloro-3-oxo-2,3-dihydro-4H-1,4-benzoxazin-4-yl)-N-methyl-N-[1-[4-(4-methyl-3,4-dihydro-2H-1,4-benzoxazin-7-yl)phenyl]-2-(4-morpholinyl)ethyl]acetamide | 625/627 |
| 174 | 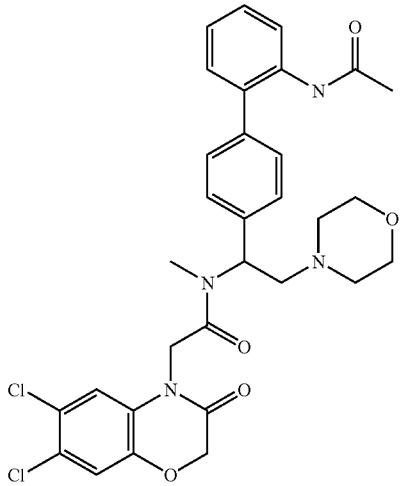 | N-[1-[2'-(acetylamino)-4-biphenylyl]-2-(4-morpholinyl)ethyl]-2-(6,7-dichloro-3-oxo-2,3-dihydro-4H-1,4-benzoxazin-4-yl)-N-methylacetamide | 611/613 |

TABLE 7-continued
| Ex # | Structure | Name | MS [M + H]+ |
|---|---|---|---|
| 175 | 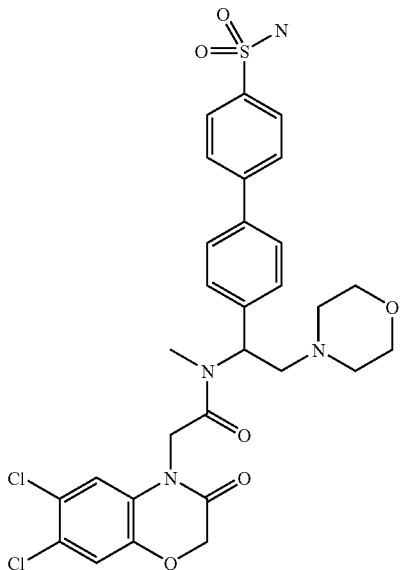 | N-[1-[4'-(aminosulfonyl)-4-biphenylyl]-2-(4-morpholinyl)ethyl]-2-(6,7-dichloro-3-oxo-2,3-dihydro-4H-1,4-benzoxazin-4-yl)-N-methylacetamide | 633/635 |
| 176 | 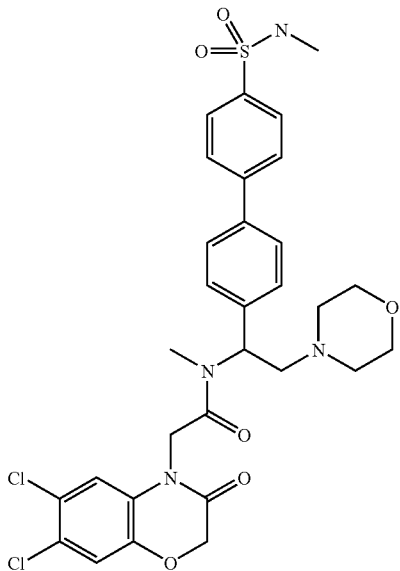 | 2-(6,7-dichloro-3-oxo-2,3-dihydro-4H-1,4-benzoxazin-4-yl)-N-methyl-N-[1-{4'-[(methylamino)sulfonyl]-4-biphenylyl}-2-(4-morpholinyl)ethyl]acetamide | 647/649 |

TABLE 7-continued
| Ex # | Structure | Name | MS [M + H]+ |
|---|---|---|---|
| 177 | 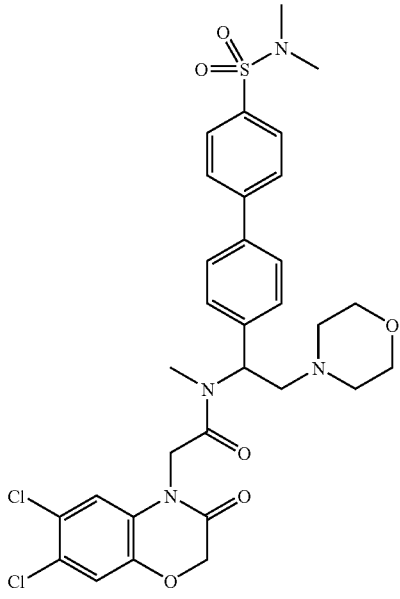 | 2-(6,7-dichloro-3-oxo-2,3-dihydro-4H-1,4-benzoxazin-4-yl)-N-[1-{4'-[(dimethylamino)sulfonyl]-4-biphenylyl}-2-(4-morpholinyl)ethyl]-N-methylacetamide | 661/663 |
| 178 | 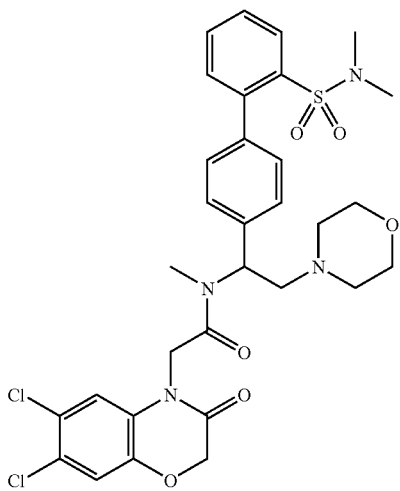 | 2-(6,7-dichloro-3-oxo-2,3-dihydro-4H-1,4-benzoxazin-4-yl)-N-[1-{2'-[(dimethylamino)sulfonyl]-4-biphenylyl}-2-(4-morpholinyl)ethyl]-N-methylacetamide | 661/663 |

Example 179

2-(6,7-dichloro-3-oxo-2,3-dihydro-4H-1,4-benzoxazin-4-yl)-N-methyl-N-{2-(4-morpholinyl)-1-[3'-(1-piperidinylcarbonyl)-3-biphenylyl]ethyl}acetamide

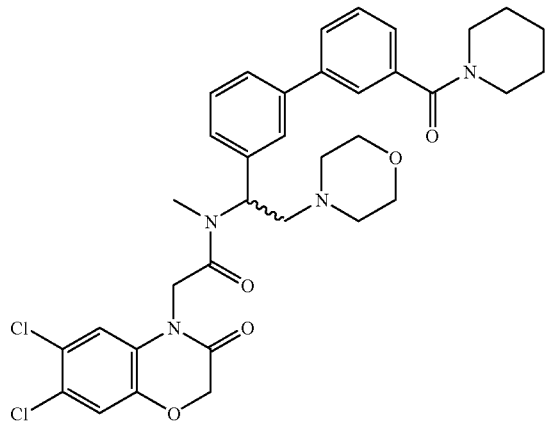

a) 1-(3-bromophenyl)-2-(4-morpholinyl)ethanone

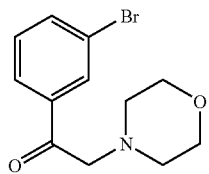

To a solution of morpholine (4.72 mL, 54.0 mmol) in ether (40 mL) cooled at 0° C., was added dropwise 2-bromo-1-(3-bromophenyl)ethanone (7.53 g, 27.0 mmol) in a mixture of ether (100 mL) and dichloromethane (100 mL). The reaction mixture was then warmed to room temperature, stirred at room temperature for 1 h, and concentrated under reduced pressure to give white solid. The white solid was dissolved in dichloromethane (200 mL) and washed with 5% NaHCO₃ (200 mL) and brine (200 mL). The organic layer was dried (MgSO₄) and concentrated to yield 1-(3-bromophenyl)-2-(4-morpholinyl)ethanone 7.8 g (100%) as a white solid, which was used without purification. MS (ESI): 284.2 [M+H]⁺.

b) [1-(3-bromophenyl)-2-(4-morpholinyl)ethyl]methylamine

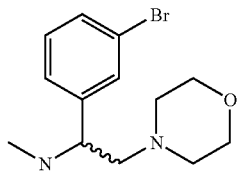

To a solution of 1-(3-bromophenyl)-2-(4-morpholinyl) ethanone (7.8 g, 27.0 mmol) in THF (50 mL) was added methylamine (100 mL, 200 mmol, 2M solution in THF). After stirring for 15 min at room temperature, sodium cyanoborohydride (3.40 g, 54 mmol) was added followed by acetic acid (2 mL). The resultant mixture was stirred at RT for 5 days. The mixture was concentrated under reduced pressure. The residue was dissolved in ethyl acetate (200 mL) and washed with 5% NaHCO₃ (200 mL) and brine (200 mL). The organic layer was dried (MgSO₄) and concentrated to give [1-(3-bromophenyl)-2-(4-morpholinyl)ethyl]methylamine as yellow oil (8.10 g, 100%) which solidified after standing at room temperature. MS (ESI): 299.6 [M+H]⁺.

c) N-[1-(3-bromophenyl)-2-(4-morpholinyl)ethyl]-2-(6,7-dichloro-3-oxo-2,3-dihydro-4H-1,4-benzoxazin-4-yl)-N-methylacetamide

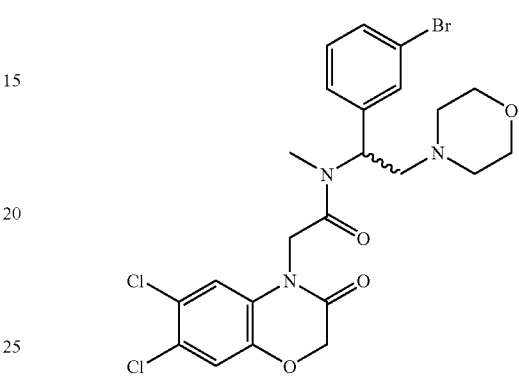

A mixture of [1-(3-bromophenyl)-2-(4-morpholinyl) ethyl]methylamine (3.06 g, 10.2 mmol) and (6,7-dichloro-2, 3-dihydro-4H-1,4-benzoxazin-4-yl)acetic acid (2.82 g, 10.2 mmol) was dissolved in a mixture of dichloromethane and DMF (1:1, 100 mL). BOP Reagent (7.16 g, 16.6 mmol) was added followed by triethylamine (4.36 g, 43.2 mmol). The resultant mixture was stirred at room temperature for 16 h. The mixture was concentrated under reduced pressure. The residue was dissolved in ethyl acetate (150 mL) and extracted with 5% NaHCO₃ (150 mL) and brine (150 mL). The organic layer was dried over MgSO₄, and concentrated. The residue was recrystallized in ether, and the crystal was collected by filtration to give the title compound as a white solid (3.17 g, 56%). MS (ESI): 556.2 [M+H]⁺.

d) 2-(6,7-dichloro-3-oxo-2,3-dihydro-4H-1,4-benzoxazin-4-yl)-N-methyl-N-{2-(4-morpholinyl)-1-[3'-(1-piperidinylcarbonyl)-3-biphenylyl]ethyl}acetamide

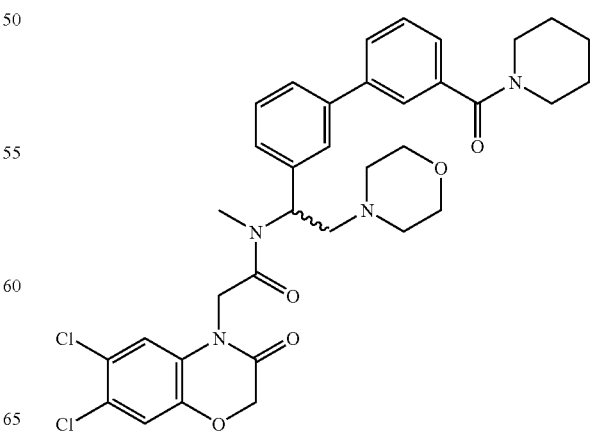

To a solution of N-[1-(3-bromophenyl)-2-(4-morpholinyl)ethyl]-2-(6,7-dichloro-3-oxo-2,3-dihydro-4H-1,4-benzoxazin-4-yl)-N-methylacetamide (75.0 mg, 0.13 mmol) and [3-(1-piperidinylcarbonyl)phenyl]boronic acid (35.0 mg, 0.15 mmol) in DMF (1.5 mL) was added Pd(dppf)Cl$_2$ (5.5 mg, 0.0067 mmol) and a 2M aqueous solution of Na$_2$CO$_3$ (0.26 mL, 0.52 mmol). The resultant mixture was stirred at 80° C. for 16 h. The mixture was filtered through a 0.45 uM filter and was purified using a Gilson preparative HPLC (Xterra Prep RP, 30×100 mm, 45 mL/min, A: acetonitrile B: water, A: 30 to 70% over 10 min, PH 10 with NH$_4$OH, UV detection at 214 nm) to give 65.4 mg (76%) of the title compound as off white solid. MS (ES) m/e 665.3 [M+H]$^+$.

Examples 180-225

Proceeding in a similar manner as in example 179d, but replacing [3-(1-piperidinylcarbonyl)phenyl]boronic acid with the appropriate boronic acids and/or N-[1-(3-bromophenyl)-2-(4-morpholinyl)ethyl]-2-(6,7-dichloro-3-oxo-2,3-dihydro-4H-1,4-benzoxazin-4-yl)-N-methylacetamide with N-[1-(4-bromophenyl)-2-(4-morpholinyl)ethyl]-2-(6,7-dimethyl-3-oxo-2,3-dihydro-4H-1,4-benzoxazin-4-yl)-N-methylacetamide or N-[1-(4-bromophenyl)-2-(4-morpholinyl)ethyl]-2-(6,7-dichloro-3-oxo-2,3-dihydro-4H-1,4-benzoxazin-4-yl)-N-methylacetamide, the compounds listed in table 8 were prepared. As is appreciated by those skilled in the art, these analogous examples may involve variations in synthetic procedure.

TABLE 8

| Ex # | Structure | Name | MS [M + H]$^+$ |
|---|---|---|---|
| 180 | 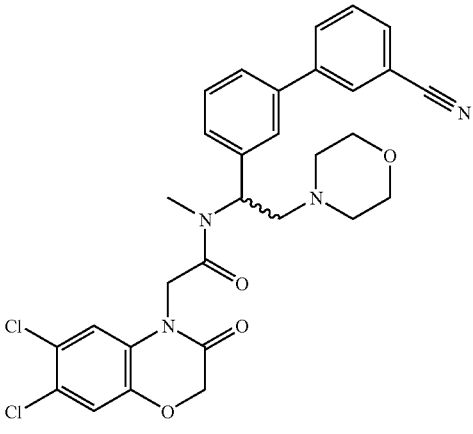 | N-[1-(3'-cyano-3-biphenylyl)-2-(4-morpholinyl)ethyl]-2-(6,7-dichloro-3-oxo-2,3-dihydro-4H-1,4-benzoxazin-4-yl)-N-methylacetamide | 579.2 |
| 181 | 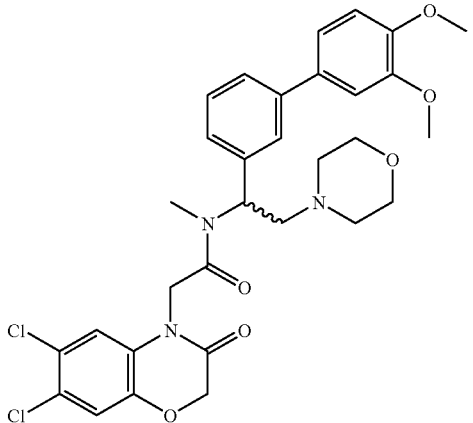 | N-[1-[3',4'-bis(methyloxy)-3-biphenylyl]-2-(4-morpholinyl)ethyl]-2-(6,7-dichloro-3-oxo-2,3-dihydro-4H-1,4-benzoxazin-4-yl)-N-methylacetamide | 614.2 |

TABLE 8-continued
| Ex # | Structure | Name | MS [M + H]+ |
|---|---|---|---|
| 182 | 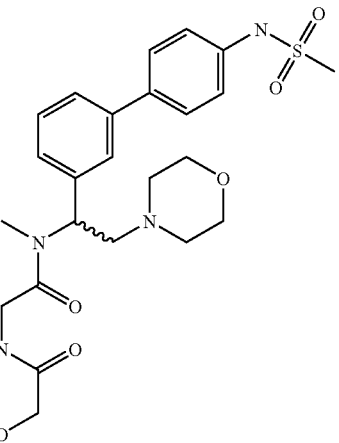 | 2-(6,7-dichloro-3-oxo-2,3-dihydro-4H-1,4-benzoxazin-4-yl)-N-methyl-N-[1-{4'-[(methylsulfonyl)amino]-3-biphenylyl}-2-(4-morpholinyl)ethyl]acetamide | 647.2 |
| 183 | 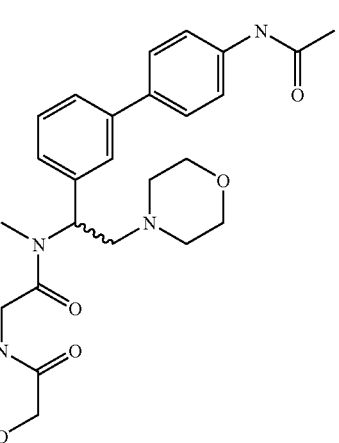 | N-[1-[4'-(acetylamino)-3-biphenylyl]-2-(4-morpholinyl)ethyl]-2-(6,7-dichloro-3-oxo-2,3-dihydro-4H-1,4-benzoxazin-4-yl)-N-methylacetamide | 611.2 |
| 184 | 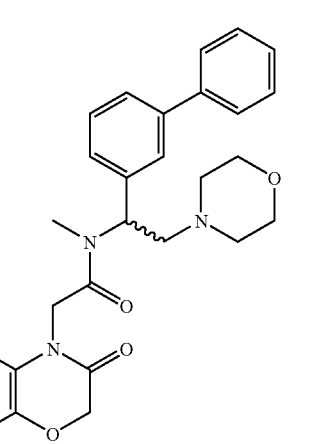 | N-[1-(3-biphenylyl)-2-(4-morpholinyl)ethyl]-2-(6,7-dichloro-3-oxo-2,3-dihydro-4H-1,4-benzoxazin-4-yl)-N-methylacetamide | 554.2 |

TABLE 8-continued

| Ex # | Structure | Name | MS [M + H]+ |
|---|---|---|---|
| 185 | 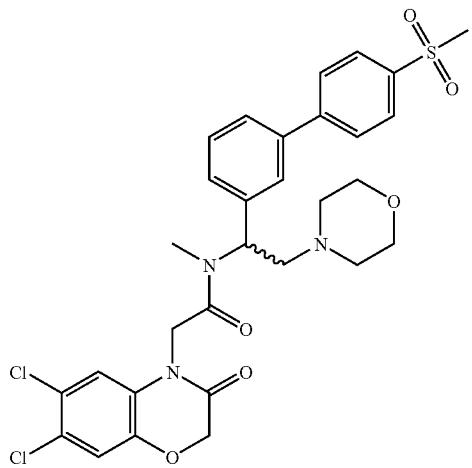 | 2-(6,7-dichloro-3-oxo-2,3-dihydro-4H-1,4-benzoxazin-4-yl)-N-methyl-N-[1-[4'-(methylsulfonyl)-3-biphenylyl]-2-(4-morpholinyl)ethyl]acetamide | 632.2 |
| 186 | 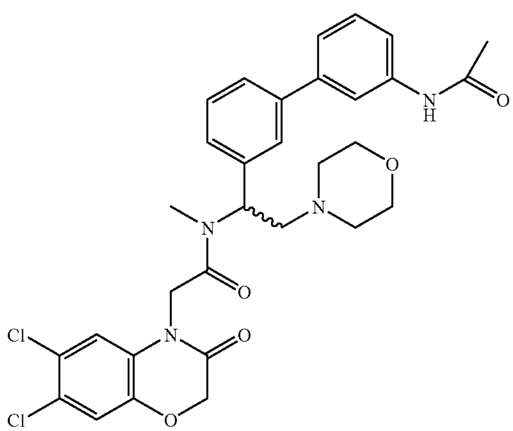 | N-[1-[3'-(acetylamino)-3-biphenylyl]-2-(4-morpholinyl)ethyl]-2-(6,7-dichloro-3-oxo-2,3-dihydro-4H-1,4-benzoxazin-4-yl)-N-methylacetamide | 611.2 |
| 187 | 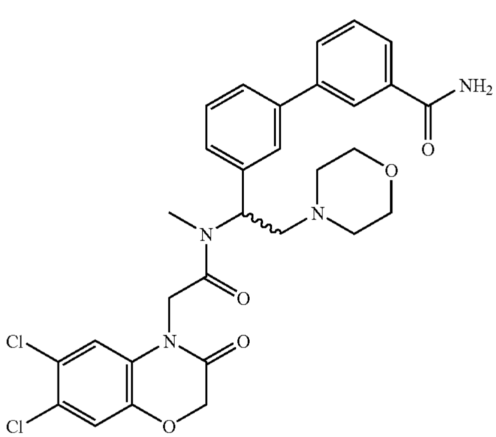 | 3'-[1-[[(6,7-dichloro-3-oxo-2,3-dihydro-4H-1,4-benzoxazin-4-yl)acetyl](methyl)amino]-2-(4-morpholinyl)ethyl]-3-biphenylcarboxamide | 597.4 |

TABLE 8-continued
| Ex # | Structure | Name | MS [M + H]+ |
|---|---|---|---|
| 188 | 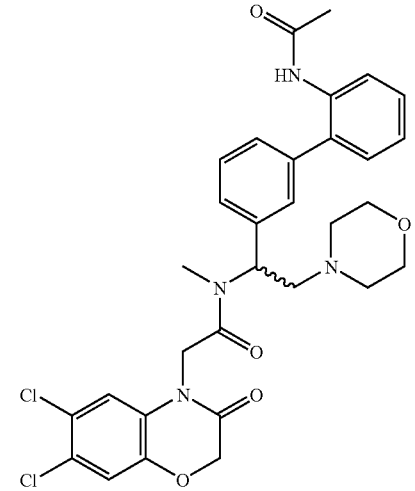 | N-[1-[2'-(acetylamino)-3-biphenylyl]-2-(4-morpholinyl)ethyl]-2-(6,7-dichloro-3-oxo-2,3-dihydro-4H-1,4-benzoxazin-4-yl)-N-methylacetamide | 611.2 |
| 189 | 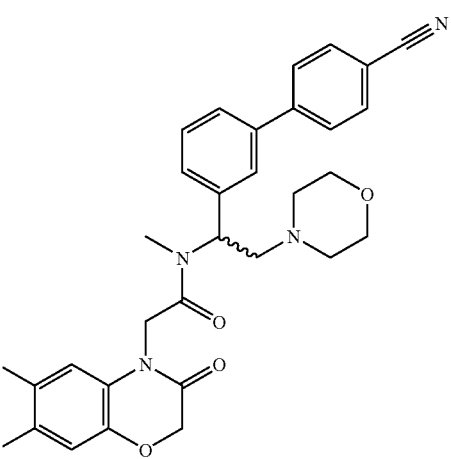 | N-[1-(4'-cyano-3-biphenylyl)-2-(4-morpholinyl)ethyl]-2-(6,7-dichloro-3-oxo-2,3-dihydro-4H-1,4-benzoxazin-4-yl)-N-methylacetamide | 579.2 |
| 190 | 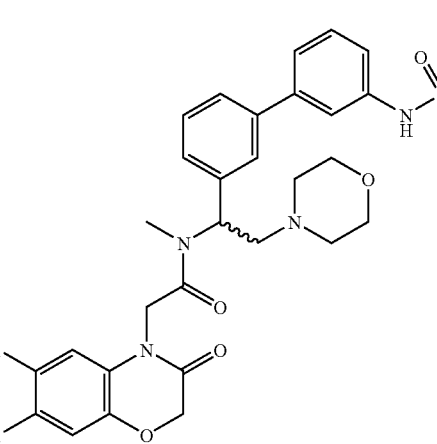 | 2-(6,7-dichloro-3-oxo-2,3-dihydro-4H-1,4-benzoxazin-4-yl)-N-methyl-N-[1-{3'-[(methylsulfonyl)amino]-3-biphenylyl}-2-(4-morpholinyl)ethyl]acetamide | 647.2 |

TABLE 8-continued

| Ex # | Structure | Name | MS [M + H]+ |
|---|---|---|---|
| 191 | 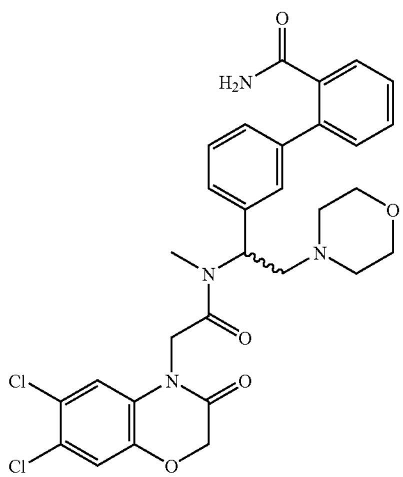 | 3'-[1-[[(6,7-dichloro-3-oxo-2,3-dihydro-4H-1,4-benzoxazin-4-yl)acetyl](methyl)amino]-2-(4-morpholinyl)ethyl]-2-biphenylcarboxamide | 597.2 |
| 192 | 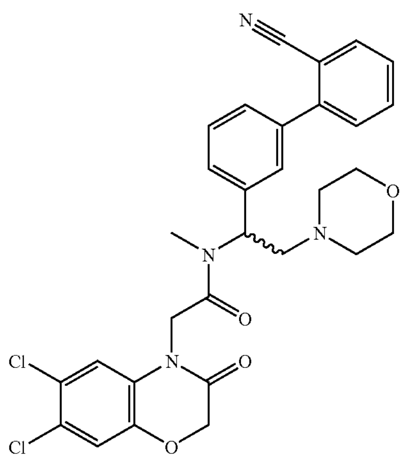 | N-[1-(2'-cyano-3-biphenylyl)-2-(4-morpholinyl)ethyl]-2-(6,7-dichloro-3-oxo-2,3-dihydro-4H-1,4-benzoxazin-4-yl)-N-methylacetamide | 579.2 |
| 193 | 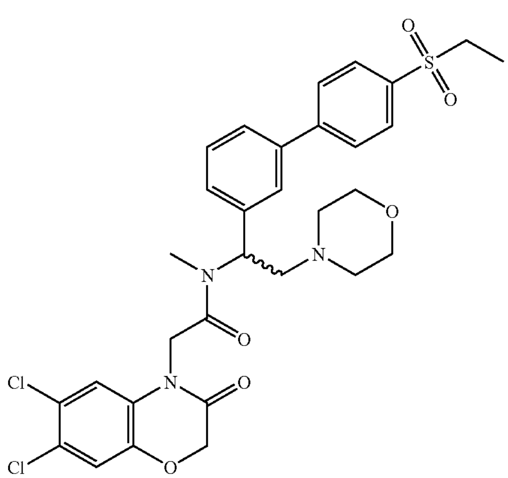 | 2-(6,7-dichloro-3-oxo-2,3-dihydro-4H-1,4-benzoxazin-4-yl)-N-[1-[4'-(ethylsulfonyl)-3-biphenylyl]-2-(4-morpholinyl)ethyl]-N-methylacetamide | 646.2 |

TABLE 8-continued

| Ex # | Structure | Name | MS [M + H]+ |
|---|---|---|---|
| 194 | 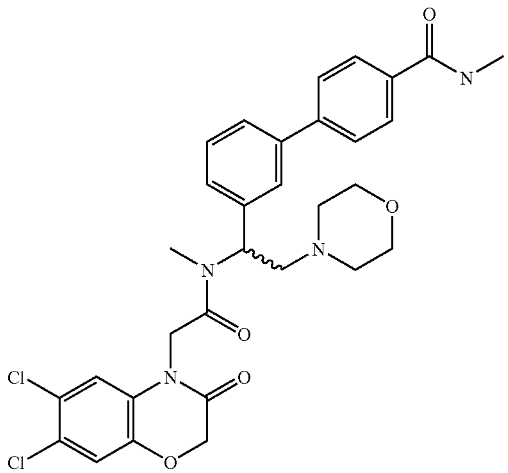 | 3'-[1-[[(6,7-dichloro-3-oxo-2,3-dihydro-4H-1,4-benzoxazin-4-yl)acetyl](methyl)amino]-2-(4-morpholinyl)ethyl]-N-methyl-4-biphenylcarboxamide | 611.2 |
| 195 | 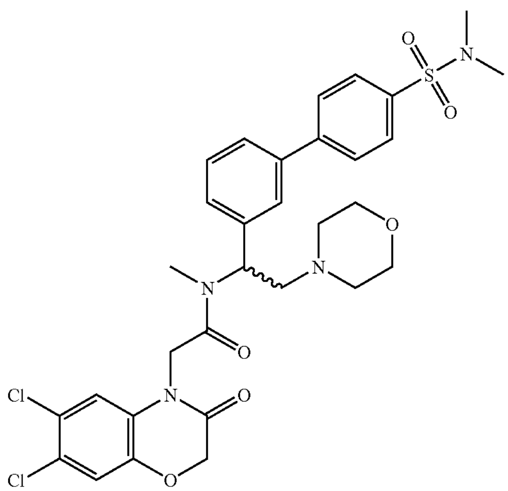 | 2-(6,7-dichloro-3-oxo-2,3-dihydro-4H-1,4-benzoxazin-4-yl)-N-[1-{4'-[(dimethylamino)sulfonyl]-3-biphenylyl}-2-(4-morpholinyl)ethyl]-N-methylacetamide | 661.2 |
| 196 | 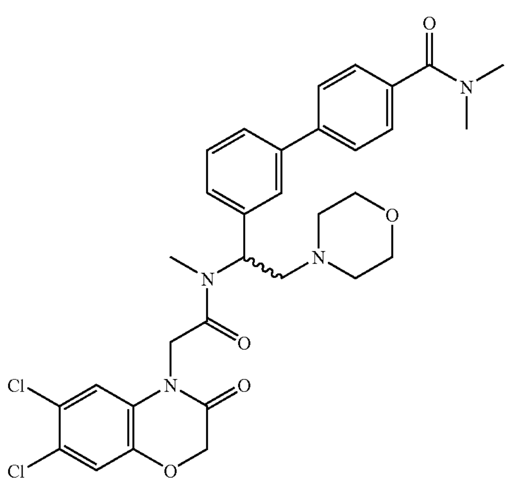 | 3'-[1-[[(6,7-dichloro-3-oxo-2,3-dihydro-4H-1,4-benzoxazin-4-yl)acetyl](methyl)amino]-2-(4-morpholinyl)ethyl]-N,N-dimethyl-4-biphenylcarboxamide | 625.2 |

TABLE 8-continued

| Ex # | Structure | Name | MS [M + H]+ |
|---|---|---|---|
| 197 | 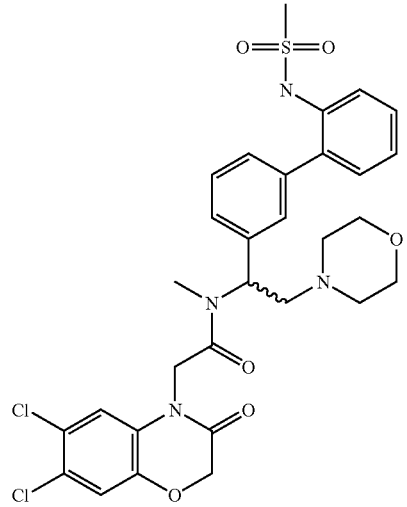 | 2-(6,7-dichloro-3-oxo-2,3-dihydro-4H-1,4-benzoxazin-4-yl)-N-methyl-N-[1-{2'-[(methylsulfonyl)amino]-3-biphenylyl}-2-(4-morpholinyl)ethyl]acetamide | 647.2 |
| 198 | 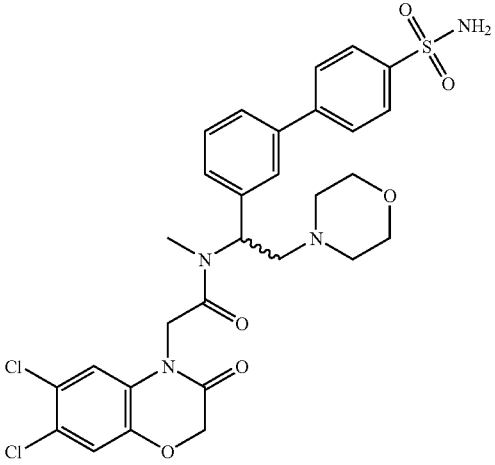 | N-[1-[4'-(aminosulfonyl)-3-biphenylyl]-2-(4-morpholinyl)ethyl]-2-(6,7-dichloro-3-oxo-2,3-dihydro-4H-1,4-benzoxazin-4-yl)-N-methylacetamide | 633.4 |
| 199 | 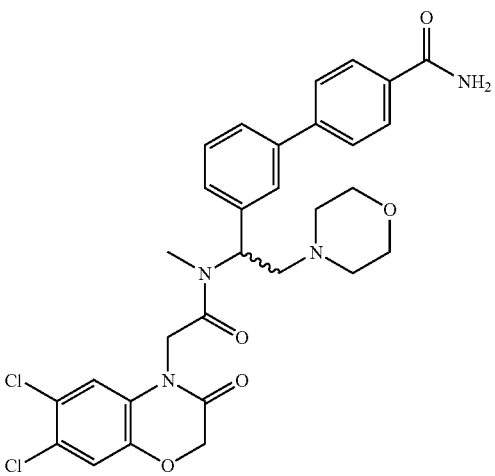 | 3'-[1-[[(6,7-dichloro-3-oxo-2,3-dihydro-4H-1,4-benzoxazin-4-yl)acetyl](methyl)amino]-2-(4-morpholinyl)ethyl]-4-biphenylcarboxamide | 597.4 |

TABLE 8-continued

| Ex # | Name | MS [M + H]+ |
|---|---|---|
| 200 | 3'-[1-[[(6,7-dichloro-3-oxo-2,3-dihydro-4H-1,4-benzoxazin-4-yl)acetyl](methyl)amino]-2-(4-morpholinyl)ethyl]-N,N-dimethyl-3-biphenylcarboxamide | 625.4 |
| 201 | 3'-[1-[[(6,7-dichloro-3-oxo-2,3-dihydro-4H-1,4-benzoxazin-4-yl)acetyl](methyl)amino]-2-(4-morpholinyl)ethyl]-N-methyl-3-biphenylcarboxamide | 611.4 |
| 202 | 2-(6,7-dichloro-3-oxo-2,3-dihydro-4H-1,4-benzoxazin-4-yl)-N-methyl-N-{2-(4-morpholinyl)-1-[4'-(1-pyrrolidinylcarbonyl)-3-biphenylyl]ethyl}acetamide | 651.6 |

TABLE 8-continued

| Ex # | Structure | Name | MS [M + H]+ |
|---|---|---|---|
| 203 | 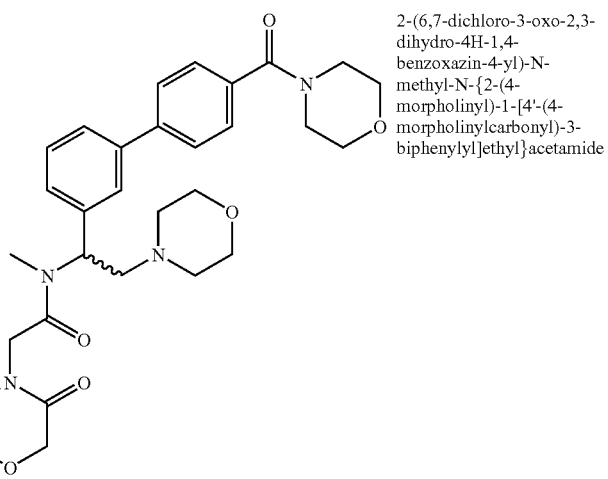 | 2-(6,7-dichloro-3-oxo-2,3-dihydro-4H-1,4-benzoxazin-4-yl)-N-methyl-N-{2-(4-morpholinyl)-1-[4'-(4-morpholinylcarbonyl)-3-biphenylyl]ethyl}acetamide | 667.4 |
| 204 | 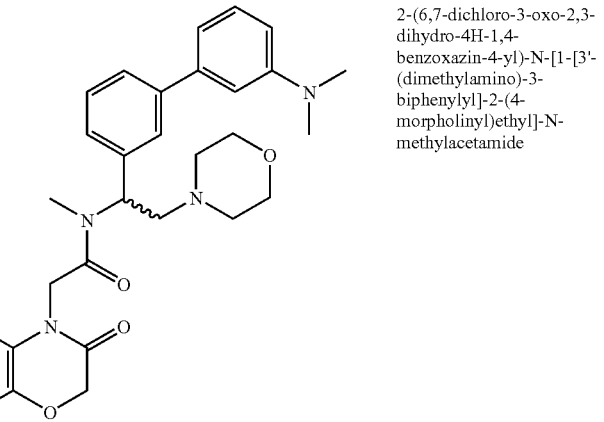 | 2-(6,7-dichloro-3-oxo-2,3-dihydro-4H-1,4-benzoxazin-4-yl)-N-[1-[3'-(dimethylamino)-3-biphenylyl]-2-(4-morpholinyl)ethyl]-N-methylacetamide | 597.4 |
| 205 | 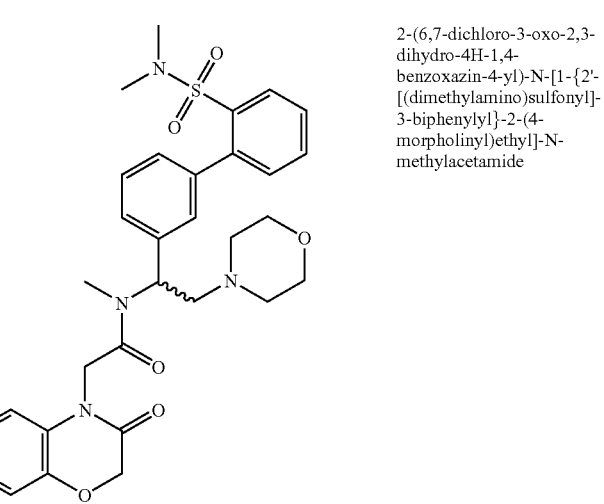 | 2-(6,7-dichloro-3-oxo-2,3-dihydro-4H-1,4-benzoxazin-4-yl)-N-[1-{2'-[(dimethylamino)sulfonyl]-3-biphenylyl}-2-(4-morpholinyl)ethyl]-N-methylacetamide | 661.2 |

TABLE 8-continued

| Ex # | Structure | Name | MS [M + H]+ |
|---|---|---|---|
| 206 | 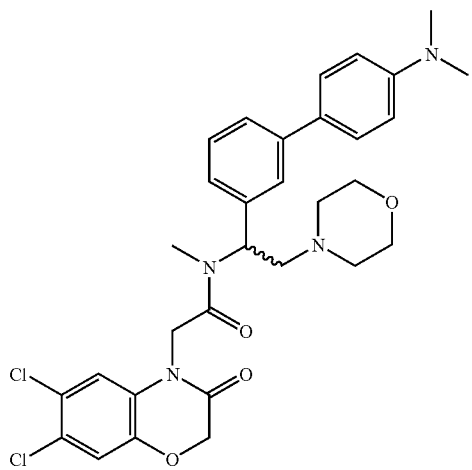 | 2-(6,7-dichloro-3-oxo-2,3-dihydro-4H-1,4-benzoxazin-4-yl)-N-[1-[4'-(dimethylamino)-3-biphenylyl]-2-(4-morpholinyl)ethyl]-N-methylacetamide | 597.1 |
| 207 | 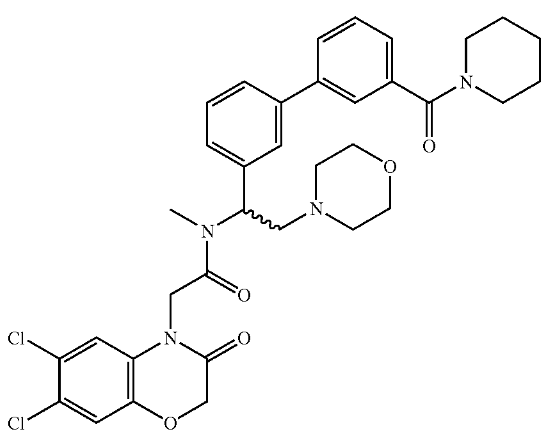 | 2-(6,7-dichloro-3-oxo-2,3-dihydro-4H-1,4-benzoxazin-4-yl)-N-methyl-N-{2-(4-morpholinyl)-1-[3'-(1-piperidinylcarbonyl)-3-biphenylyl]ethyl}acetamide | 665.3 |
| 208 | 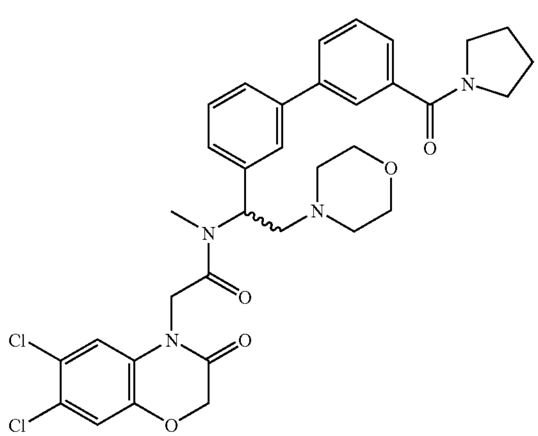 | 2-(6,7-dichloro-3-oxo-2,3-dihydro-4H-1,4-benzoxazin-4-yl)-N-methyl-N-{2-(4-morpholinyl)-1-[3'-(1-pyrrolidinylcarbonyl)-3-biphenylyl]ethyl}acetamide | 651.3 |

TABLE 8-continued

| Ex # | Structure | Name | MS [M + H]+ |
|---|---|---|---|
| 209 | 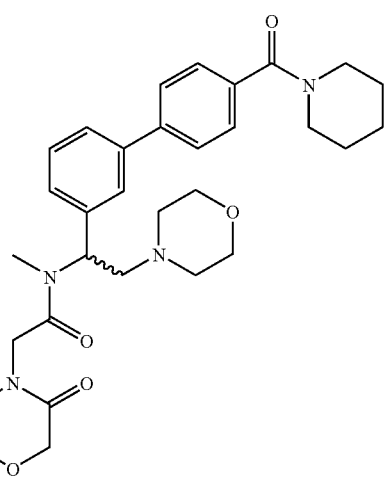 | 2-(6,7-dichloro-3-oxo-2,3-dihydro-4H-1,4-benzoxazin-4-yl)-N-methyl-N-{2-(4-morpholinyl)-1-[4'-(1-piperidinylcarbonyl)-3-biphenylyl]ethyl}acetamide | 665.3 |
| 210 | 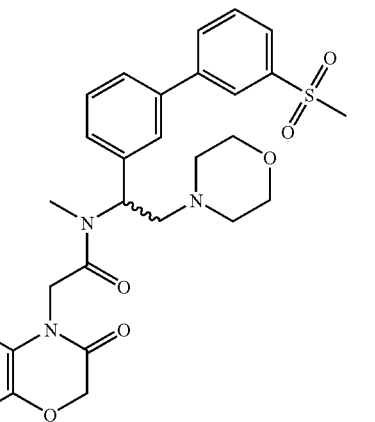 | 2-(6,7-dichloro-3-oxo-2,3-dihydro-4H-1,4-benzoxazin-4-yl)-N-methyl-N-[1-[3'-(methylsulfonyl)-3-biphenylyl]-2-(4-morpholinyl)ethyl]acetamide | 632.3 |
| 211 | 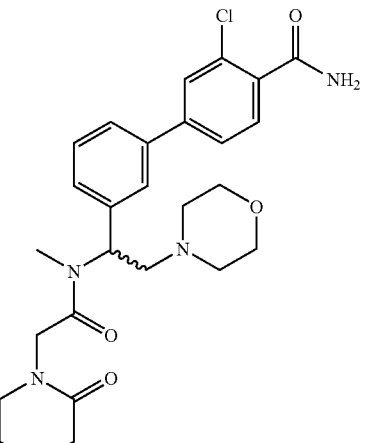 | 3-chloro-3'-[1-[[(6,7-dichloro-3-oxo-2,3-dihydro-4H-1,4-benzoxazin-4-yl)acetyl](methyl)amino]-2-(4-morpholinyl)ethyl]-4-biphenylcarboxamide | 631.4 |

TABLE 8-continued

| Ex # | Structure | Name | MS [M + H]+ |
|---|---|---|---|
| 212 | 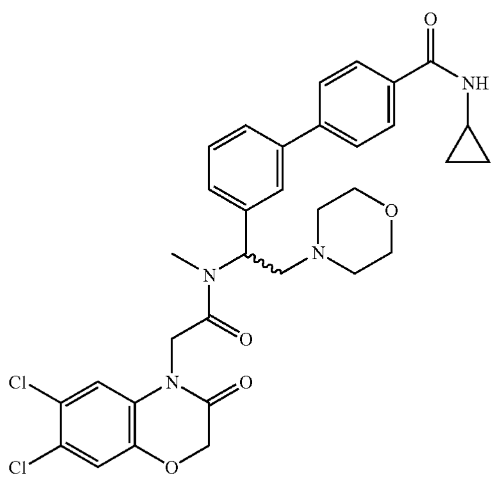 | N-cyclopropyl-3'-[1-[[(6,7-dichloro-3-oxo-2,3-dihydro-4H-1,4-benzoxazin-4-yl)acetyl](methyl)amino]-2-(4-morpholinyl)ethyl]-4-biphenylcarboxamide | 637.3 |
| 213 | 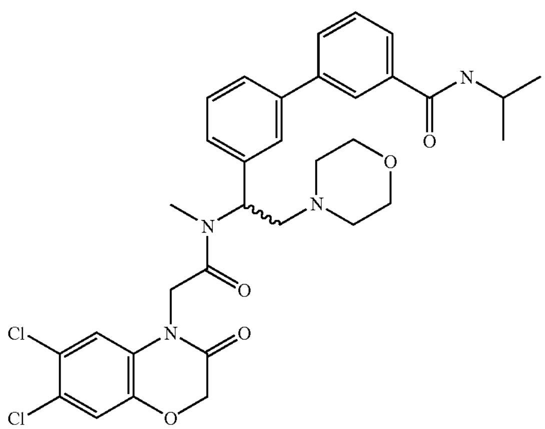 | 3'-[1-[[(6,7-dichloro-3-oxo-2,3-dihydro-4H-1,4-benzoxazin-4-yl)acetyl](methyl)amino]-2-(4-morpholinyl)ethyl]-N-(1-methylethyl)-3-biphenylcarboxamide | 641.2 |
| 214 | 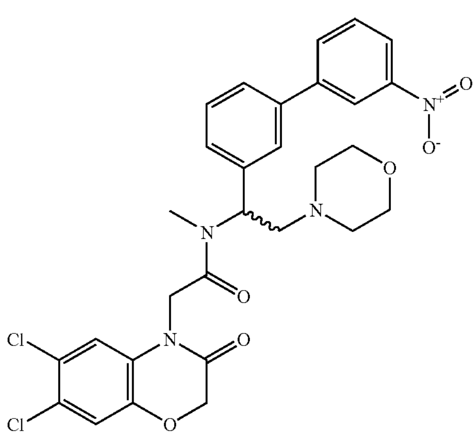 | 2-(6,7-dichloro-3-oxo-2,3-dihydro-4H-1,4-benzoxazin-4-yl)-N-methyl-N-[2-(4-morpholinyl)-1-(3'-nitro-3-biphenylyl)ethyl]acetamide | 600.1 |

TABLE 8-continued

| Ex # | Structure | Name | MS [M + H]+ |
|---|---|---|---|
| 215 | 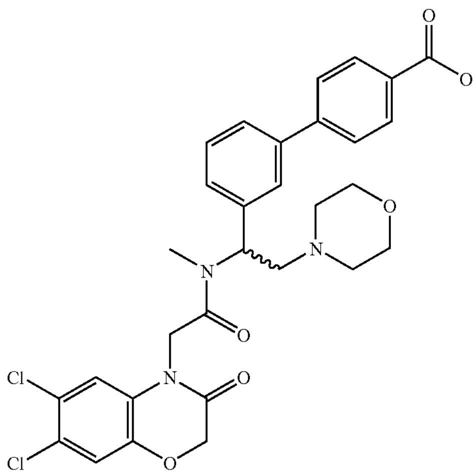 | 3'-[1-[[(6,7-dichloro-3-oxo-2,3-dihydro-4H-1,4-benzoxazin-4-yl)acetyl](methyl)amino]-2-(4-morpholinyl)ethyl]-4-biphenylcarboxylic acid | 598.1 |
| 216 | 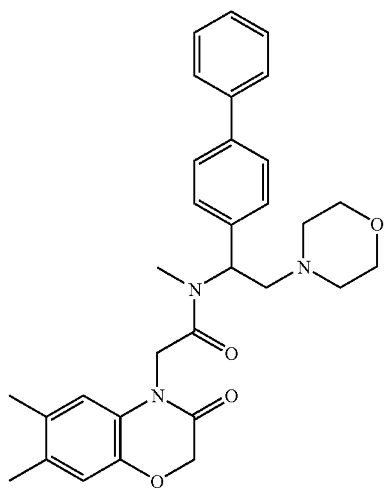 | N-[1-(4-biphenylyl)-2-(4-morpholinyl)ethyl]-2-(6,7-dimethyl-3-oxo-2,3-dihydro-4H-1,4-benzoxazin-4-yl)-N-methylacetamide | 514 |
| 217 | 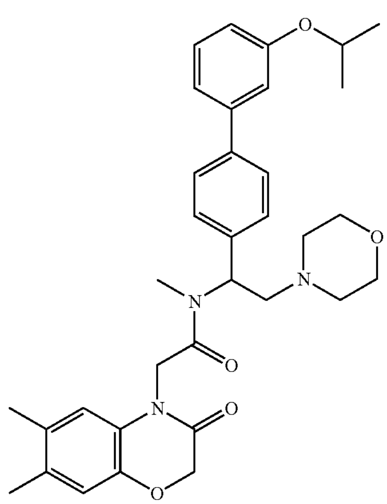 | 2-(6,7-dimethyl-3-oxo-2,3-dihydro-4H-1,4-benzoxazin-4-yl)-N-methyl-N-[1-{3'-[(1-methylethyl)oxy]-4-biphenylyl}-2-(4-morpholinyl)ethyl]acetamide | 572 |

| Ex # | Structure | Name | MS [M + H]+ |
|---|---|---|---|
| 218 | 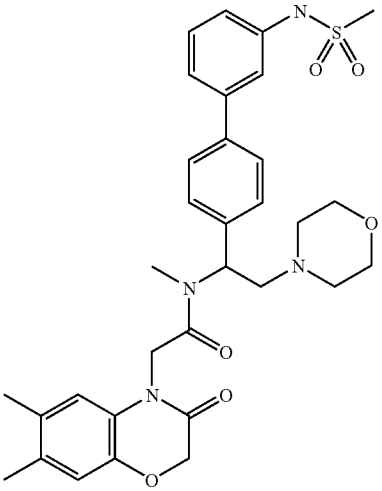 | 2-(6,7-dimethyl-3-oxo-2,3-dihydro-4H-1,4-benzoxazin-4-yl)-N-methyl-N-[1-{3'-[(methylsulfonyl)amino]-4-biphenylyl}-2-(4-morpholinyl)ethyl]acetamide | 607 |
| 219 | 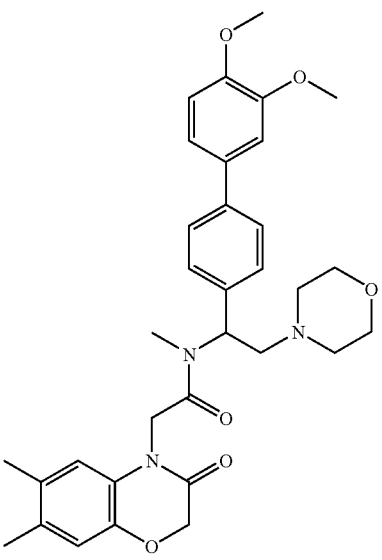 | N-[1-[3',4'-bis(methyloxy)-4-biphenylyl]-2-(4-morpholinyl)ethyl]-2-(6,7-dimethyl-3-oxo-2,3-dihydro-4H-1,4-benzoxazin-4-yl)-N-methylacetamide | 574 |

TABLE 8-continued

| Ex # | Structure | Name | MS [M + H]+ |
|---|---|---|---|
| 220 | 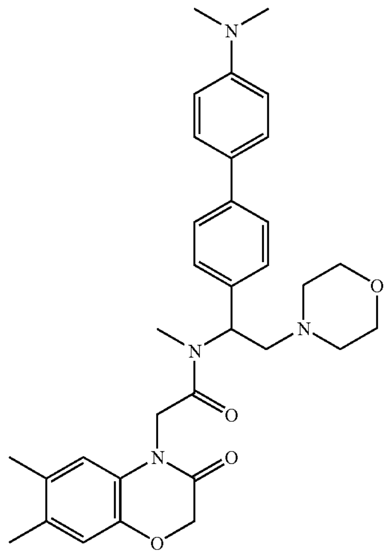 | N-[1-[4'-(dimethylamino)-4-biphenylyl]-2-(4-morpholinyl)ethyl]-2-(6,7-dimethyl-3-oxo-2,3-dihydro-4H-1,4-benzoxazin-4-yl)-N-methylacetamide | 557 |
| 221 | 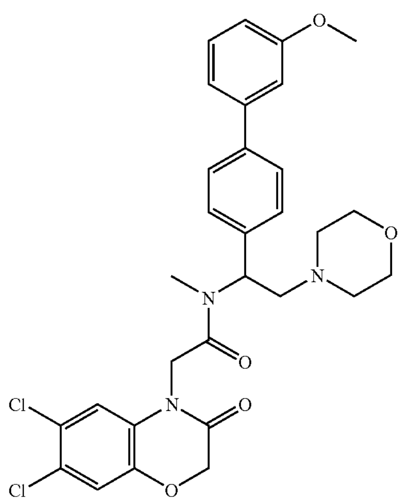 | 2-(6,7-dichloro-3-oxo-2,3-dihydro-4H-1,4-benzoxazin-4-yl)-N-methyl-N-[1-[3'-(methyloxy)-4-biphenylyl]-2-(4-morpholinyl)ethyl]acetamide | 584/586 |
| 222 | 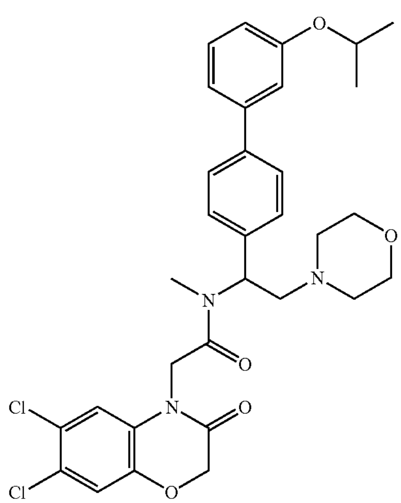 | 2-(6,7-dichloro-3-oxo-2,3-dihydro-4H-1,4-benzoxazin-4-yl)-N-methyl-N-[1-{3'-[(1-methylethyl)oxy]-4-biphenylyl}-2-(4-morpholinyl)ethyl]acetamide | 612/614 |

TABLE 8-continued
| Ex # | Structure | Name | MS [M + H]+ |
|---|---|---|---|
| 223 | 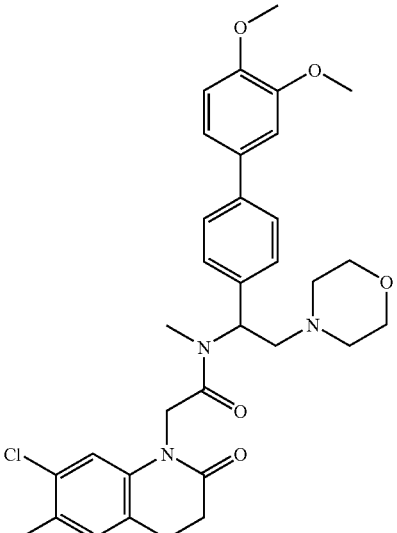 | N-[1-[3',4'-bis(methyloxy)-4-biphenylyl]-2-(4-morpholinyl)ethyl]-2-(6,7-dichloro-3-oxo-2,3-dihydro-4H-1,4-benzoxazin-4-yl)-N-methylacetamide | 614/616 |
| 224 | 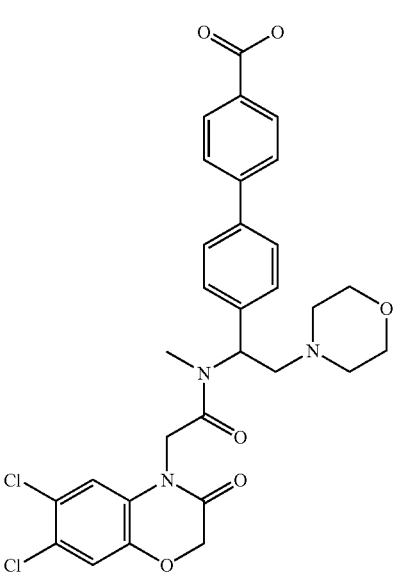 | 4'-[1-[[(6,7-dichloro-3-oxo-2,3-dihydro-4H-1,4-benzoxazin-4-yl)acetyl](methyl)amino]-2-(4-morpholinyl)ethyl]-4-biphenylcarboxylic acid | 598/600 |

TABLE 8-continued

| Ex # | Structure | Name | MS [M + H]+ |
|---|---|---|---|
| 225 | 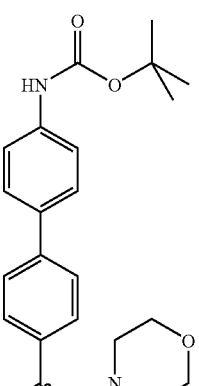 | N-[1-[4'-(acetylamino)-4-biphenylyl]-2-(4-morpholinyl)ethyl]-2-(6,7-dichloro-3-oxo-2,3-dihydro-4H-1,4-benzoxazin-4-yl)-N-methylacetamide | 611/613 |

Example 226

N-{4'-[1-[[(6,7-dichloro-3-oxo-2,3-dihydro-4H-1,4-benzoxazin-4-yl)acetyl](methyl)amino]-2-(4-morpholinyl)ethyl]-4-biphenylyl}propanamide

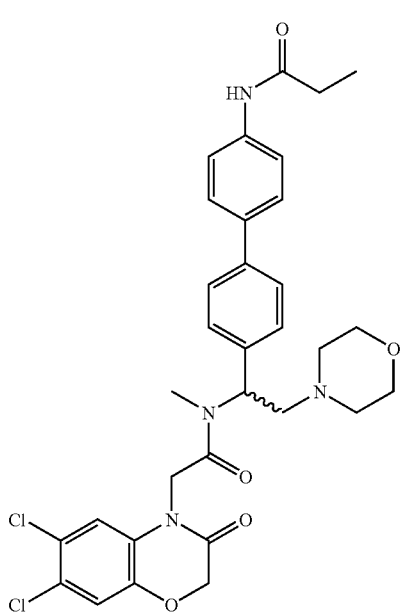

a) 1,1-dimethylethyl {4'-[1-[[(6,7-dichloro-3-oxo-2,3-dihydro-4H-1,4-benzoxazin-4-yl)acetyl](methyl)amino]-2-(4-morpholinyl)ethyl]-4-biphenylyl}carbamate

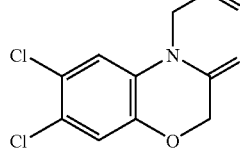

To a solution of N-[1-(4-bromophenyl)-2-(4-morpholinyl)ethyl]-2-(6,7-dichloro-3-oxo-2,3-dihydro-4H-1,4-benzoxazin-4-yl)-N-methylacetamide (1.64 g, 2.9 mmol) and [4-({[(1,1-dimethylethyl)oxy]carbonyl}amino)phenyl]boronic acid (0.77 g, 3.2 mmol) in DMF (10 mL) was added Pd(dppf)Cl$_2$ (0.12 g, 0.15 mmol) and 2N aqueous solution of Na$_2$CO$_3$ (0.26 mL, 0.52 mmol). The resultant mixture was stirred at 80° C. for 16 h. The mixture was filtered through a 0.45 uM filter and concentrated under reduce pressure. The residue was dissolved in ethyl acetate (100 mL) and washed with 5% NaHCO$_3$ (100 mL) and brine (100 mL). The organic layer was dried over MgSO$_4$ and concentrated. The residue was recrystallized in methanol to give 0.77 g (40%) white solid. The mother liquid was concentrated and was purified by using a Gilson preparative HPLC (Phenomenex, 100×50 mm, 10 micron, 90 mL/min, A: acetonitrile B: water, A: 10 to 90% over 15 min, UV detection at 214 nm) to give 0.10 g (5%) of the title compound as yellow oil. Total yield 45%. MS (ES) m/e 669.4 [M+H]$^+$.

b) N-[1-(4'-amino-4-biphenylyl)-2-(4-morpholinyl)ethyl]-2-(6,7-dichloro-3-oxo-2,3-dihydro-4H-1,4-benzoxazin-4-yl)-N-methylacetamide c) N-{4'-[1-[[(6,7-dichloro-3-oxo-2,3-dihydro-4H-1,4-benzoxazin-4-yl)acetyl](methyl)amino]-2-(4-morpholinyl)ethyl]-4-biphenylyl}propanamide

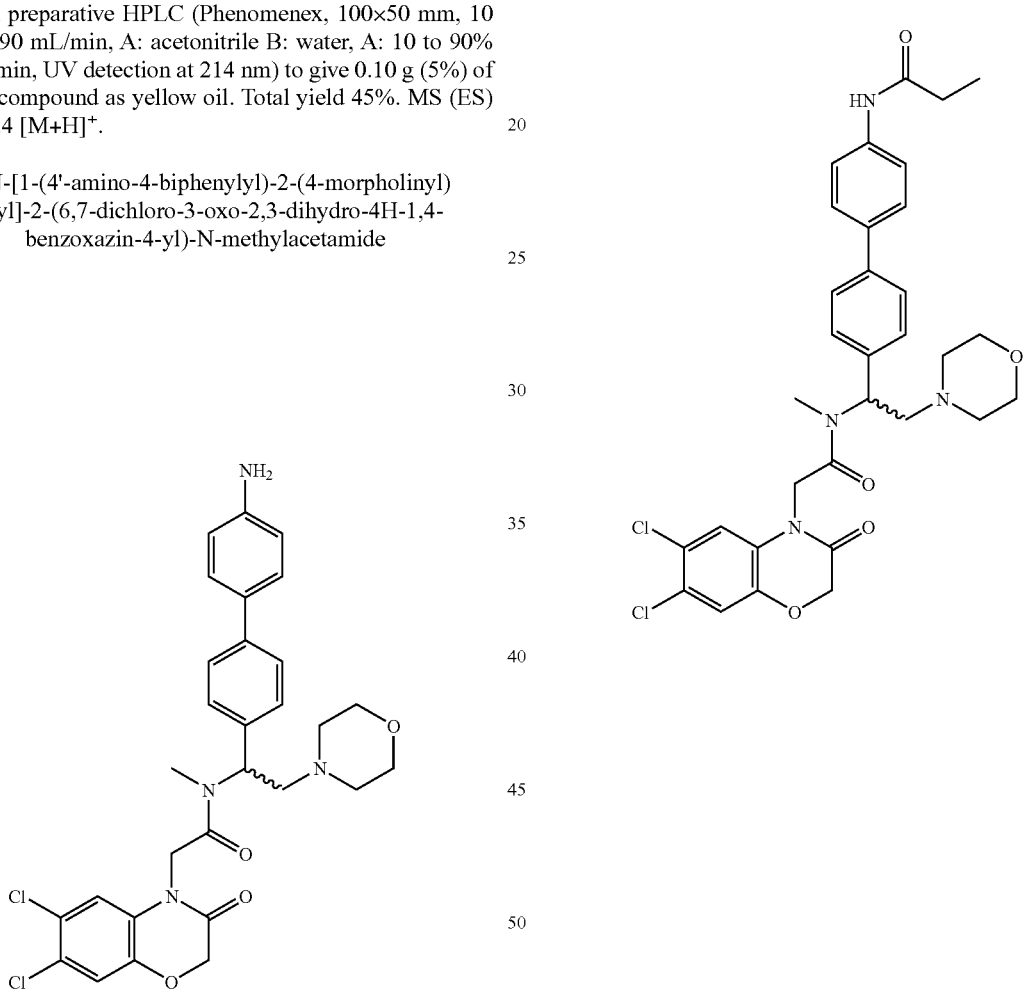

To a solution of 1,1-dimethylethyl {4'-[1-[[(6,7-dichloro-3-oxo-2,3-dihydro-4H-1,4-benzoxazin-4-yl)acetyl](methyl)amino]-2-(4-morpholinyl)ethyl]-4-biphenylyl}carbamate (0.64 g, 0.96 mmol) in dichloromethane (4 mL) was added trifluoroacetic acid (4 mL). The resultant mixture was stirred at room temperature for 1 h. The mixture was concentrated under reduced pressure to give 0.55 g (100%) of the title compound as tan solid MS (ES) m/e 569.4 [M+H]$^+$.

To a solution of N-[1-(4'-amino-4-biphenylyl)-2-(4-morpholinyl)ethyl]-2-(6,7-dichloro-3-oxo-2,3-dihydro-4H-1,4-benzoxazin-4-yl)-N-methylacetamide (85 mg, 0.15 mmol) in dichloromethane (2 mL) was added propanoyl chloride (15.6 mg, 0.17 mmol). Triethylamine (30 mg, 0.30 mmol) was added, and the resultant mixture was stirred at room temperature for 1 h. The mixture was concentrated under reduced pressure and the residue was purified by Gilson preparative HPLC (Xterra Prep RP, 30×100 mm, 45 mL/min, A: acetonitrile with 0.1% TFA B: water with 0.1% TFA, A: 25 to 55% over 15 min, UV detection at 214 nm) to give 15.7 mg (17%) of the title compound as an off white solid. MS (ES) m/e 625.1 [M+H]$^+$.

Example 227

2-(6,7-dichloro-3-oxo-2,3-dihydro-4H-1,4-benzoxazin-4-yl)-N-[1-{4'-[(ethylsulfonyl)amino]-4-biphenylyl}-2-(4-morpholinyl)ethyl]-N-methylacetamide

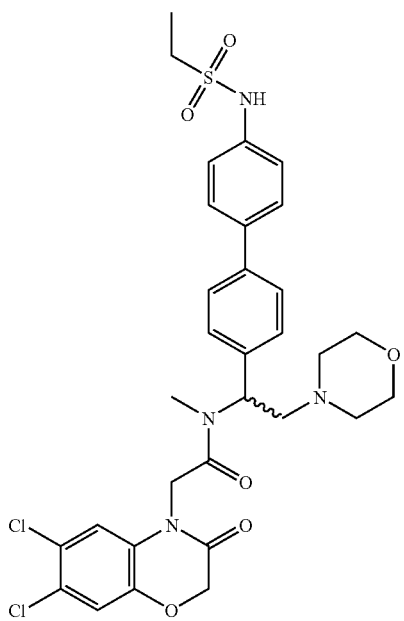

To a solution of N-[1-(4'-amino-4-biphenylyl)-2-(4-morpholinyl)ethyl]-2-(6,7-dichloro-3-oxo-2,3-dihydro-4H-1,4-benzoxazin-4-yl)-N-methylacetamide (68 mg, 0.12 mmol) in dichloromethane (2 mL) was added ethanesulfonyl chloride (18.5 mg, 0.14 mmol). Triethylamine (24 mg, 0.24 mmol) was added, and the resultant mixture was stirred at room temperature for 2 h. The mixture was concentrated under reduced pressure, and the residue was purified by Gilson preparative HPLC (Xterra Prep RP, 30×100 mm, 45 mL/min, A: acetonitrile with 0.1% TFA B: water with 0.1% TFA, A: 25 to 55% over 15 min, UV detection at 214 nm) to give 18.3 mg (23%) of the title compound as an off white solid. MS (ES) m/e 661.1 [M+H]$^+$.

Example 228

2-(6,7-dichloro-3-oxo-2,3-dihydro-4H-1,4-benzoxazin-4-yl)-N—[1-(4'-{[(ethylamino)carbonyl]amino}-4-biphenylyl)-2-(4-morpholinyl)ethyl]-N-methylacetamide

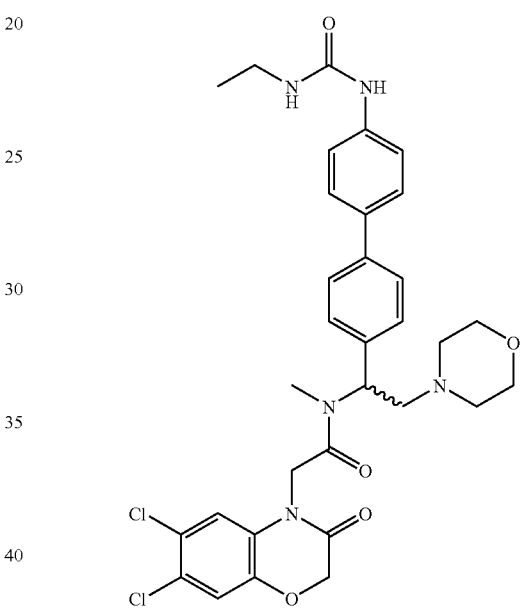

To a solution of N-[1-(4'-amino-4-biphenylyl)-2-(4-morpholinyl)ethyl]-2-(6,7-dichloro-3-oxo-2,3-dihydro-4H-1,4-benzoxazin-4-yl)-N-methylacetamide (68 mg, 0.12 mmol) in dichloromethane (2 mL) was added isocyanatoethane (36.5 mg, 0.51 mmol). Triethylamine (36 mg, 0.36 mmol) was added, and the resultant mixture was stirred at room temperature for 18 h. The mixture was concentrated under reduced pressure, and the residue was purified by Gilson preparative HPLC (Xterra Prep RP, 30×100 mm, 45 mL/min, A: acetonitrile with 0.1% TFA B: water with 0.1% TFA, A: 20 to 50% over 15 min, UV detection at 214 nm) to give 53.5 mg (70%) of the title compound as an off white solid. MS (ES) m/e 640.2 [M+H]$^+$.

Example 229

[N-[1-(4-biphenylyl)-2-(1-pyrrolidinyl)ethyl]-N-methyl-2-[7-methyl-6-(methyloxy)-3-oxo-2,3-dihydro-4H-1,4-benzoxazin-4-yl]acetamide

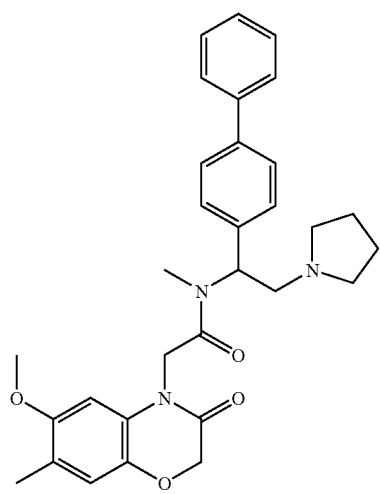

a) 1-Methyl-2,5-bis(methyloxy)-4-nitrobenzene

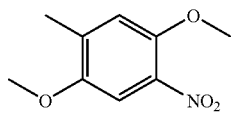

2-Methyl-1,4-bis(methyloxy)benzene (6.12 g, 40 mmol) was dissolved in acetic acid (20 mL) and heated at 40° C. A solution of nitric acid (4.32 g) in acetic acid (10 mL) was added to above solution drop wise over 5 minutes. The reaction mixture was stirred at 40° C. for 30 min (yellow precipitates formed), then room temperature for 30 min and then diluted with water (300 mL). The precipitate was collected by filtration, washed with water, and dried in the air for 16 h to afford the title compound (7.56 g, 96%) as a yellow solid. MS (ES) m/e 198 [M+H]$^+$.

b) 5-Methyl-4-(methyloxy)-2-nitrophenol

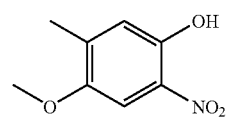

1-Methyl-2,5-bis(methyloxy)-4-nitrobenzene (3.96 g, 20 mmol) was dissolved in CH$_2$Cl$_2$ (20 mL) and cooled to −20° C. A solution of BCl$_3$ (1.0 M) in CH$_2$Cl$_2$ (20 mL) was added to above solution drop wise over 5 minutes. A purple solution was obtained. The reaction mixture was slowly warmed to room temperature and stirred for 20 h. The mixture was then quenched with saturated Na$_2$CO$_3$, stirred for 10 minutes and then extracted with EtOAc (3×100 mL). The organic extracts were combined, washed with water, brine, and dried (Na$_2$SO$_4$). The solvent was removed via rotovap to give the title compound (3.65 g, 99%) as a yellow solid. MS (ES) m/e 184 [M+H]$^+$.

c) 2-Amino-5-methyl-4-(methyloxy)phenol

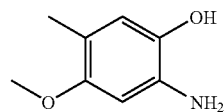

5-Methyl-4-(methyloxy)-2-nitrophenol (3.65 g, 20 mmol) was dissolved in EtOAc (100 mL) and 200 mg of 5% Pd/C was added. The reaction vessel was evacuated and filled with N$_2$. This process was repeated twice then filled with H$_2$ at 1 atm, and stirred for 16 h. The mixture was filtered through a pad of celite, washed with EtOAc, and the solvent was removed via rotovap to give the title compound (3.0 g, 98%) as a white solid. MS (ES) m/e 154 [M+H]$^+$.

d) 7-Methyl-6-(methyloxy)-2H-1,4-benzoxazin-3(4H)-one

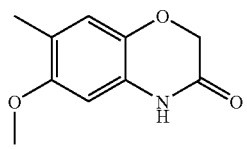

To a solution of 2-amino-5-methyl-4-(methyloxy)phenol (3.0 g, 19 mmol) in CHCl$_3$ (100 mL) were added saturated NaHCO$_3$ (60 mL) and bromoacetyl bromide (5.78 g, 28.5 mmol) sequentially. The reaction mixture was vigorously stirred for 2 hours at room temperature, diluted with EtOAc (300 mL), washed with H$_2$O, brine, and dried (Na$_2$SO$_4$). The solvent was removed via rotovap to give a brown solid. This brown solid was dissolved in DMF (200 mL), Cs$_2$CO$_3$ (6.19 g, 19 mmol) was added, and the reaction mixture was heated at 80° C. for 3 h. It was then poured into cold water (300 mL) and extracted with EtOAc (3×250 mL). The organic extracts were combined, washed with water, brine, and dried (MgSO$_4$). The solvent was removed via rotovap, and the residue was purified on silica gel, using 50% EtOAc-Hexane, to give the title compound (2.13 g, 58%) as a brown solid. MS (ES) m/e 194 [M+H]$^+$.

e) [7-Methyl-6-(methyloxy)-3-oxo-2,3-dihydro-4H-1,4-benzoxazin-4-yl]acetic acid

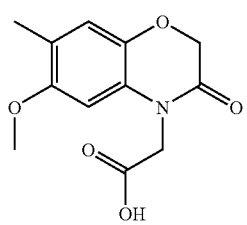

To a solution of 7-methyl-6-(methyloxy)-2H-1,4-benzoxazin-3(4H)-one (2.13 g, 11 mmol) in DMF (20 mL) was added NaH (528 mg, 13.2 mmol) in two portions. The reaction mixture was stirred for 30 minutes at room temperature, and ethyl bromoacetate (1.22 mL, 11 mmol) was added. The reaction mixture was stirred for 3 hour until all starting material was consumed, then poured into cold water (200 mL). The precipitate was collected by filtration, washed with water, and dried in the air to afford a pale solid. This solid was dissolved in THF (22 mL) and NaOH (2.0 M, 5.5 mL) was added, and the reaction mixture was stirred at room temperature for 2 h, poured into cold water (100 mL), and extracted with EtOAc (2×100 mL). The aqueous layer was acidified with HCl (6 N) to pH~1, extracted with EtOAc (3×100 mL). The organic extracts were combined, washed with brine, and dried ($Na_2SO_4$). The solvent was removed via rotovap to give the title compound (2.35 g, 85%) as a pale solid. MS (ES) m/e 252 [M+H]$^+$.

f) [N-[1-(4-biphenylyl)-2-(1-pyrrolidinyl)ethyl]-N-methyl-2-[7-methyl-6-(methyloxy)-3-oxo-2,3-dihydro-4H-1,4-benzoxazin-4-yl]acetamide

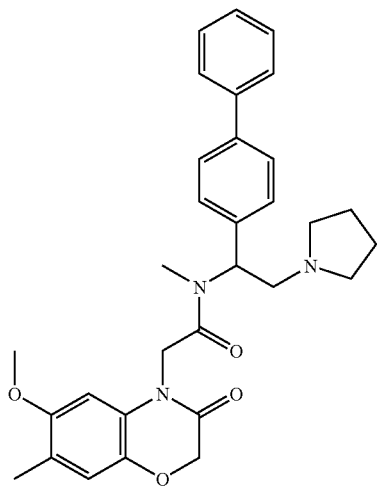

7-Methyl-6-(methyloxy)-3-oxo-2,3-dihydro-4H-1,4-benzoxazin-4-yl]acetic acid (63 mg, 0.25 mmol) and BOP reagent (133 mg, 0.30 mmol) were dissolved in $CH_2Cl_2$ (1 mL), and diisopropylethylamine (32 mg, 0.25 mmol) was added. The resulting mixture was stirred at room temperature for 5 min and then 1-(4-biphenylyl)-N-methyl-2-(1-pyrrolidinyl)ethanamine (70 mg, 0.25 mmol) was added. Stirring was continued for 16 h and then the mixture was concentrated. The residue was dissolved in $CH_3OH$, and purified by preparative HPLC (YMC CombiPrep ODS-A, 50×50 mm, 50 mL/min, A: acetonitrile B: water with $NH_4OH$ at pH=10, A: 20% to 70% during 12 min, UV detection at 214 nm) to give 101 mg (79%) of the title compound as a white solid. MS (ES) m/e 514 [M+H]$^+$.

Example 230 a) N-[1-(4-biphenylyl)-2-(4-morpholinyl)ethyl]-N-methyl-2-[7-methyl-6-(methyloxy)-3-oxo-2,3-dihydro-4H-1,4-benzoxazin-4-yl]acetamide

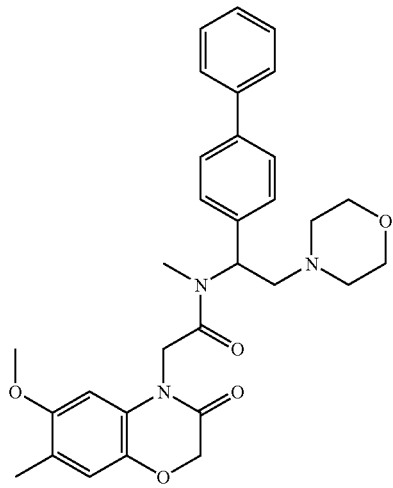

7-Methyl-6-(methyloxy)-3-oxo-2,3-dihydro-4H-1,4-benzoxazin-4-yl]acetic acid (63 mg, 0.25 mmol) and BOP reagent (133 mg, 0.30 mmol) were dissolved in $CH_2Cl_2$ (1 mL), and diisopropylethylamine (32 mg, 0.25 mmol) was added. The resulting mixture was stirred at room temperature for 5 min, then 1-(4-biphenylyl)-N-methyl-2-(4-morpholinyl)ethanamine (74 mg, 0.25 mmol) was added. Stirring was continued for 16 hours and then the mixture was concentrated. The residue was dissolved in $CH_3OH$, and purified by preparative HPLC (YMC CombiPrep ODS-A, 50×50 mm, 50 mL/min, A: acetonitrile B: water with $NH_4OH$ at pH=10, A: 20% to 70% during 12 min, UV detection at 214 nm) to give 57 mg (43%) of the title compound as a white solid. MS (ES) m/e 530 [M+H]$^+$.

Example 231

N-[1-(4-biphenylyl)-2-(1-pyrrolidinyl)ethyl]-N-methyl-2-[6-methyl-5-(methyloxy)-2-oxo-1,3-benzoxazol-3(2H)-yl]acetamide

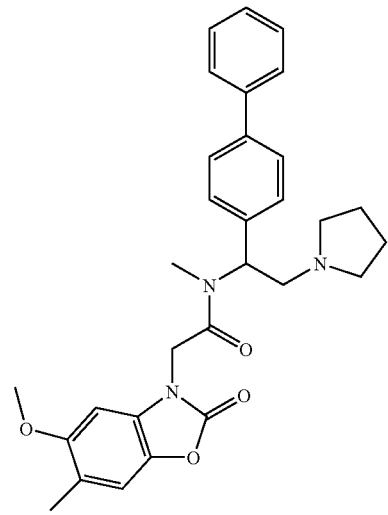

211 a) 6-Methyl-5-(methyloxy)-1,3-benzoxazol-2(3H)-one

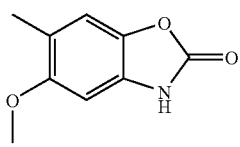

To a solution of 2-amino-5-methyl-4-(methyloxy)phenol (1.54 g, 10 mmol) in THF (60 mL) was added carbodiimidazole (1.94 g, 12 mmol). The reaction mixture was stirred for 3 hours at room temperature, concentrated, diluted with EtOAc (100 mL), washed with 1N HCl, H$_2$O, brine, and dried (Na$_2$SO$_4$). The solvent was removed via rotovap to give the title compound (1.76 g, 98%) as a white solid. MS (ES) m/e 180 [M+H]$^+$.

b) [6-Methyl-5-(methyloxy)-2-oxo-1,3-benzoxazol-3(2H)-yl]acetic acid

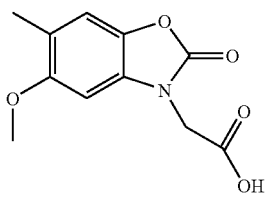

To a solution of 6-methyl-5-(methyloxy)-1,3-benzoxazol-2(3H)-one (1.76 g, 9.8 mmol) in DMF (20 mL) was added NaH (470 mg, 11.8 mmol) in two portions. The reaction mixture was stirred for 30 minutes at room temperature, and ethyl bromoacetate (1.09 mL, 9.8 mmol) was added. The reaction mixture was stirred for 3 hour until all starting material was consumed, then poured into cold water (100 mL). The precipitate which formed was collected by filtration, washed with water, and dried in the air to afford a pale solid. This solid was dissolved in THF (20 mL) and NaOH (2.0 M, 4.9 mL) was added, and the reaction mixture was stirred at room temperature for 2 hours, poured into cold water (100 mL), and extracted with EtOAc (2×100 mL). The aqueous layer was acidified with HCl (6 N) to pH~1, extracted with EtOAc (3×100 mL). The organic extracts were combined, washed with brine, and dried (Na$_2$SO$_4$). The solvent was removed via rotovap to give the title compound (2.16 g, 93%) as a pale solid. MS (ES) m/e 238 [M+H]$^+$.

212 c) N-[1-(4-biphenylyl)-2-(1-pyrrolidinyl)ethyl]-N-methyl-2-[6-methyl-5-(methyloxy)-2-oxo-1,3-benzoxazol-3(2H)-yl]acetamide

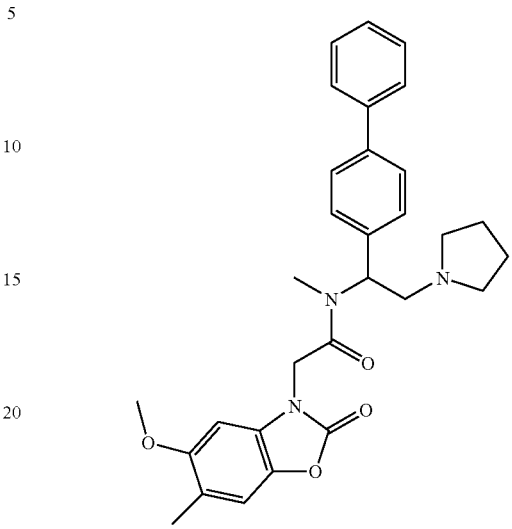

[6-Methyl-5-(methyloxy)-2-oxo-1,3-benzoxazol-3(2H)-yl]acetic acid (59 mg, 0.25 mmol) and BOP reagent (133 mg, 0.30 mmol) were dissolved in CH$_2$Cl$_2$ (1 mL), and diisopropylethylamine (32 mg, 0.25 mmol) was added to it. The resulting mixture was stirred at room temperature for 5 min, then 1-(4-biphenylyl)-N-methyl-2-(1-pyrrolidinyl)ethanamine (70 mg, 0.25 mmol) was added. Stirring was continued for 16 h and then the mixture was concentrated. The residue was dissolved in CH$_3$OH, and purified by preparative HPLC (YMC CombiPrep ODS-A, 50×50 mm, 50 mL/min, A: acetonitrile B: water with NH$_4$OH at pH=10, A: 20% to 70% during 12 min, UV detection at 214 nm) to give 92 mg (74%) of the title compound as a white solid. MS (ES) m/e 500 [M+H]$^+$.

Example 232

N-[1-(4-biphenylyl)-2-(4-morpholinyl)ethyl]-N-methyl-2-[6-methyl-5-(methyloxy)-2-oxo-1,3-benzoxazol-3(2H)-yl]acetamide

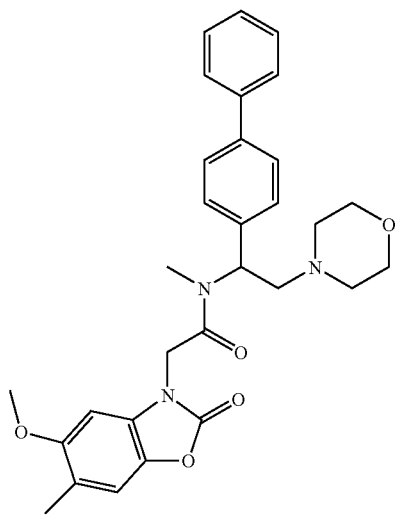

[6-Methyl-5-(methyloxy)-2-oxo-1,3-benzoxazol-3(2H)-yl]acetic acid (59 mg, 0.25 mmol) and BOP reagent (133 mg, 0.30 mmol) were dissolved in CH₂Cl₂ (1 mL), and diisopropylethylamine (32 mg, 0.25 mmol) was added. The resulting mixture was stirred at room temperature for 5 min, then 1-(4-biphenylyl)-N-methyl-2-(4-morpholinyl)ethanamine (74 mg, 0.25 mmol) was added. Stirring was continued for 16 h and then the mixture was concentrated. The residue was dissolved in CH₃OH, and purified by preparative HPLC (YMC CombiPrep ODS-A, 50×50 mm, 50 mL/min, A: acetonitrile B: water with NH₄OH at pH=10, A: 20% to 70% during 12 min, UV detection at 214 nm) to give 32 mg (25%) of the title compound as a white solid. MS (ES) m/e 516 [M+H]⁺.

Example 233

N-[1-(4-biphenylyl)-1-methyl-2-(1-pyrrolidinyl)ethyl]-2-(5-chloro-2-oxo-1,3-benzoxazol-3(2H)-yl)-N-methylacetamide

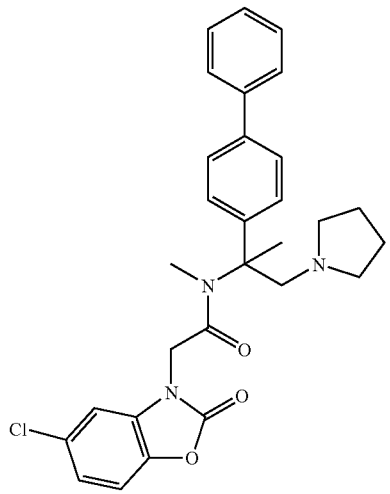

a) 1,1-dimethylethyl [1-(4-bromophenyl)ethyl]carbamate

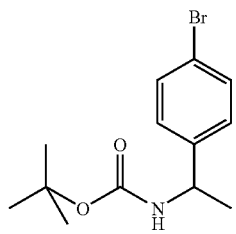

A solution of di-tert-butyl dicarbonate (10.9 g, 50 mmol) in CH₂Cl₂ (50 ml) was added dropwise to an ice-cooled solution of 4-bromo-alpha-methylbenzylamine (10 g, 50 mmol) in CH₂Cl₂ (50 ml). After the mixture was stirred at room temperature for 30 min, the solvent was removed under reduced pressure which left a white solid. The mixture of this material, phenyl boronic acid (7.32 g, 60 mmol) and potassium carbonate (27.6 g, 200 mmol) in dioxane (300 ml) and water (120 ml) was deoxygenated, and then Pd(dppf)Cl₂ (4.08 g, 5 mmol) was added. The resulting mix was heated under argon at reflux for 18 h. Catalyst was removed by filtration and the filtrate was concentrated, the residue was taken into EtOAc and washed with brine, dried (MgSO₄) and concentrated. This material was purified by silica gel chromatography (330 g Redisep column, silica, 40 um, 60 Å, 100 mL/min, A: hexane, B: ethyl acetate, B: 2% for 2 min, 8% for 30 min, detection at 254 nm) to give 7.09 g (48%) of the title compound as a white solid. MS (ES) m/e (M−C₄H₈⁺)=242.0 b) Bis(1,1-dimethylethyl) [1-(4-biphenylyl)ethyl]imidodicarbonate

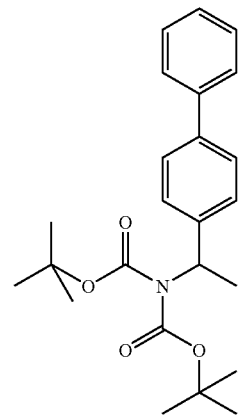

A mixture of 1,1-dimethylethyl [1-(4-bromophenyl)ethyl]carbamate (7.09 g, 23.9 mmol), di-tert-butyl dicarbonate (7.82 g, 35.9 mmol) and DMAP (1.0 g) was stirred at 80° C. for 2.5 h. The product was isolated by silica gel chromatography (330 g Redisep column, silica, 40 um, 60 Å, 100 mL/min, A: hexane, B: ethyl acetate, B: 10% for 1 min, 50% for 30 min, detection at 214 nm) gave 1.29 g (13.6%) as a clear oil. ¹H NMR (CDCl₃): delta 7.36-7.62 (m, 9H, arom), 5.59 (q, J=6.88 Hz, 1H), 1.76 (d, J=7.05 Hz, 3H), 1.41 (s, 18H).

c) 1,1-Dimethylethyl 2-(4-biphenylyl)-N-{[(1,1-dimethylethyl)oxy]carbonyl}alaninate

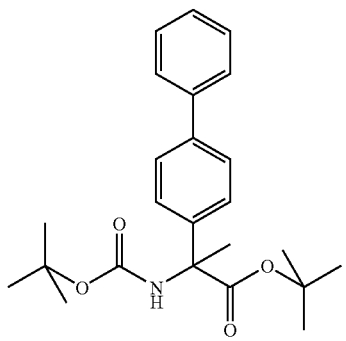

n-BuLi (4.09 ml, 6.5 mmol, 1.6 M in hexane) was added to a suspension of t-BuOK (735 mg, 6.55 mmol) and diisopropyl amine (926 ul, 6.55 mmol) in THF (20 ml) at −78° C. The mixture was stirred at −78° C. for 15 min. before a solution of bis(1,1-dimethylethyl) [1-(4-biphenylyl)ethyl]imidodicarbonate (2.08 g, 5.24 mmol) in THF (20 ml) was added dropwise and stirring was continued for 30 min at −78° C. The reaction mixture was diluted with HCl (2M, 50 ml) and the product was extracted with ether (3×30 ml). The ether extracts were concentrated and then purified by silica gel chromatography (120 g Redisep column, silica, 40 um, 60 Å, 85 mL/min, A: hexane, B: ethyl acetate, B: 4% for 2 min, 10% for 30 min, detection at 214 nm) which gave 1.15 g (55%) as a clear oil. $^1$H NMR (CDCl$_3$): delta 7.38-7.63 (m, 9H, arom), 5.95 (1H), 2.01 (3H), 1.41 (S, 18H).

d) Methyl 2-(4-biphenylyl)alaninate

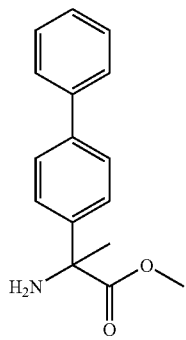

HCl (7.2 ml, 4M in dioxane) was added dropwise to a solution of 1,1-dimethylethyl 2-(4-biphenylyl)-N-{[(1,1-dimethylethyl)oxy]carbonyl}alaninate (1.14 g, 2.87 mmol) in CH$_2$Cl$_2$ (10 ml) at 0° C. under argon. The resulting mix was stirred at room temperature for 16 h. The reaction mixture was concentrated leaving a white solid which was refluxed in methanolic HCl (30 mL) for 16 h. The reaction mixture was concentrated and the residue was taken into Na$_2$CO$_3$ (10%, 100 ml) and the product was extracted by EtOAc (3×20 ml). The combined extracts were washed by water then brine, dried and concentrated left 830 mg as a clear oil. MS (ES) m/e 256.2 [M+H]$^+$.

e) Methyl 2-(4-biphenylyl)-N-{[(1,1-dimethylethyl)oxy]carbonyl}alaninate

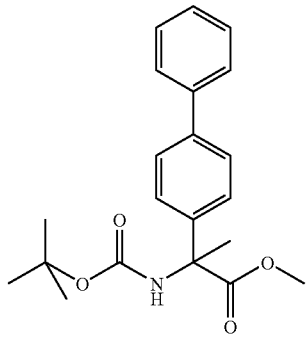

Di-tert-butyl dicarbonate (780 mg, 3.58 mmol) was added to a solution containing methyl 2-(4-biphenylyl)alaninate (830 mg, 3.25 mmol) and Et$_3$N (682 uL, 4.88 mmol) in CH$_2$Cl$_2$ (20 mL). The mixture was stirred at rt for 16 h. The reaction was concentrated to give 1.29 g of crude product which was purified by column chromatography (51 g silica gel 60, 230-400 mesh, 5% EtOAc in hexane as eluent) to give 533 mg (46%) as a white solid. MS (ES) m/e 356.4 [M+H]$^+$.

f) 2-(4-biphenylyl)-N-{[(1,1-dimethylethyl)oxy]carbonyl}alanine

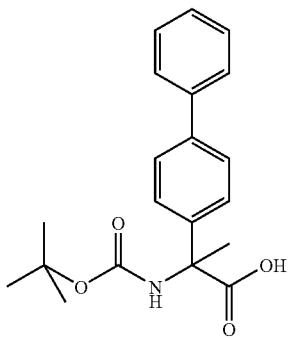

LiOH (1.63 ml, 1M) was added dropwise to a solution of methyl-N-Boc-2-(4-biphenylyl)alaninate (482 mg, 1.36 mmol) in THF (3 ml). The resulting mixture was stirred at rt for 16 h. Solvent was removed under reduced pressure and the residue was taken up in water (10 ml) and washed with EtOAc. The aqueous layer was acidified with HCl (1M) to pH ~2 and the product was extracted by EtOAc (3×10 ml). The combined extracts were washed with water and brine, dried and concentrated which left 470 mg (90%) as a white solid. MS (ES) m/e 342.4 [M+H]+ g) 1,1-dimethylethyl [1-(4-biphenylyl)-1-methyl-2-oxo-2-(1-pyrrolidinyl)ethyl]carbamate

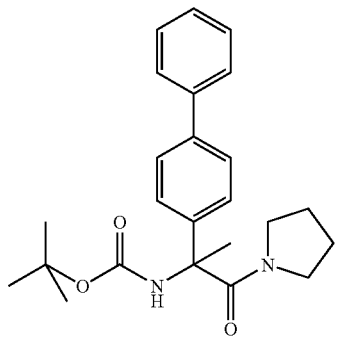

BOP (880 mg, 2.0 mmol) was added to a mixture containing pyrrolidine (142 mg, 2.0 mmol), Et₃N (279 ul, 2.0 mmol) and N-Boc-2-phenylalanine (570 mg, 1.67 mmol) in DMF (10 ml) and the resulting mixture was stirred at room temperature for 16 h. The solvent was removed under reduced pressure and the residue was taken up in EtOAc and washed with brine, dried and concentrated. The crude product was purified by column chromatography (48 g silica gel 60, 230-400 mesh, 20% EtOAc in hexane as eluent) to give 581 mg (75%) of the title compound as a white solid. MS (ES) m/e 395.6 [M+H]+ h) 2-(4-biphenylyl)-N-methyl-1-(1-pyrrolidinyl)-2-propanamine

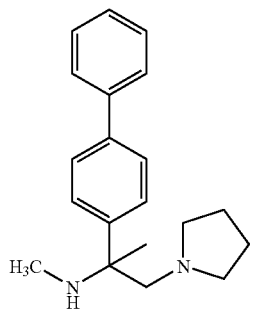

LAH (447 mg, 11.8 mmol) was added to a solution of 1,1-dimethylethyl [1-(4-biphenylyl)-1-methyl-2-oxo-2-(1-pyrrolidinyl)ethyl]carbamate (580 mg, 1.47 mmol) in THF (20 ml) at 0° C. under argon. The resulting mixture was then refluxed for 2.5 h. The reaction mixture was then cooled in and ice bath and diluted with toluene (20 ml). Water (847 ul, 47 mmol) was added followed by NaF (1.48 g, 35.3 mmol) and the mixture was stirred at 0° C. for 30 min, filtered and the filter pad was washed with THF. The combined filtrates were concentrated to give 417 mg (96%) as a light brown oil. MS (ES) m/e 295.4 [M+H]+.

i) N-[1-(4-biphenylyl)-1-methyl-2-(1-pyrrolidinyl)ethyl]-2-(5-chloro-2-oxo-1,3-benzoxazol-3(2H)-yl)-N-methylacetamide

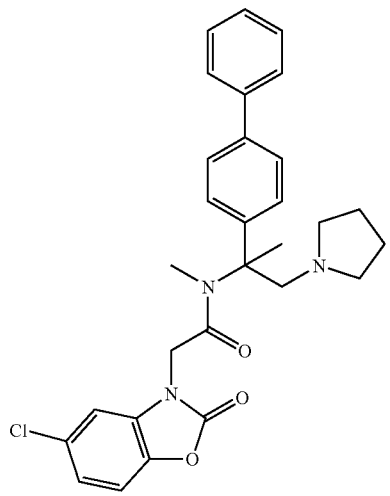

BOP (133 mg, 0.30 mmol) was added to a mixture containing (5-chloro-2-oxo-1,3-benzoxazol-3(2H)-yl)acetic acid (68 mg, 0.30 mmol), 2-(4-biphenylyl)-N-methyl-1-(1-pyrrolidinyl)-2-propanamine (74 mg, 0.25 mmol) and Et₃N (0.042 ml, 0.30 mmol) in DMF (3 ml) and the resulting mixture was stirred at room temperature for 16 h. The crude reaction mixture was purified by preparative HPLC (Xterra PrepRP 30×100 mm, 45 mL/min, A: acetonitrile B: water, PH 10, A: 50 to 90% over 12 min, UV detection at 214 nm) to give 17.5 mg (13.9%) as a white solid. MS (ES) m/e 504.4 [M+H]+.

Examples 234-236

Proceeding in a manner similar example 233i, but replacing (5-chloro-2-oxo-1,3-benzoxazol-3(2H)-yl)acetic acid with the appropriate acids, the compounds in table 9 were prepared. As is appreciated by those skilled in the art, these analogous examples may involve variations in synthetic procedure.

TABLE 9
| Ex # | Structure | Name | MS [M + H]$^+$ |
|---|---|---|---|
| 234 | 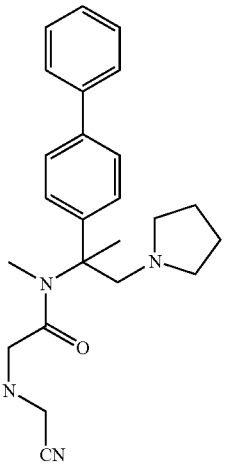 | N$^1$-[1-(4-biphenylyl)-1-methyl-2-(1-pyrrolidinyl)ethyl]-N$^2$-(cyanomethyl)-N$^2$-(3,4-dichlorophenyl)-N$^1$-methylglycinamide | 535.2 |
| 235 | 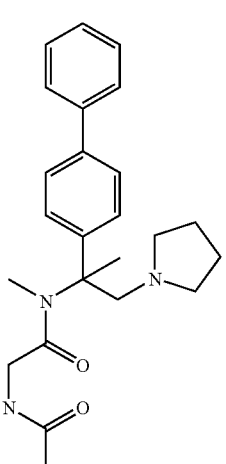 | N-[1-(4-biphenylyl)-1-methyl-2-(1-pyrrolidinyl)ethyl]-2-(6,7-dichloro-3-oxo-2,3-dihydro-4H-1,4-benzoxazin-4-yl)-N-methylacetamide | 552.4 |
| 236 | 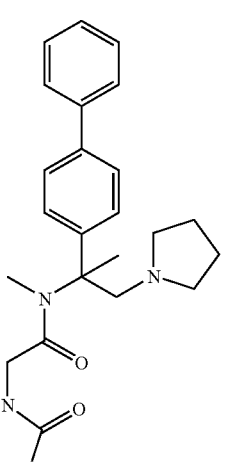 | N-[1-(4-biphenylyl)-1-methyl-2-(1-pyrrolidinyl)ethyl]-2-(5-chloro-2-oxo-1,3-benzothiazol-3(2H)-yl)-N-methylacetamide | 520.2 |

Example 237

N-[1-(4-biphenylyl)-2-(1-pyrrolidinyl)ethyl]-N-methyl-2-[6-(methyloxy)-2-oxo-1,3-benzoxazol-3(2H)-yl]acetamide

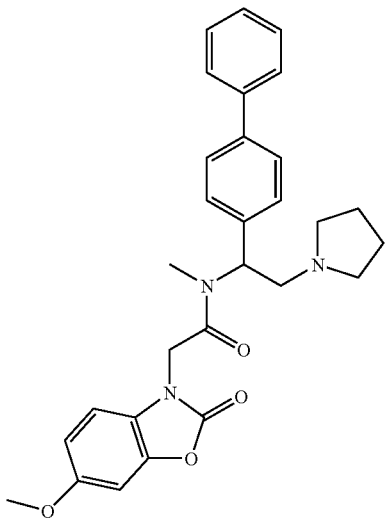

a) ethyl[6-(methyloxy)-2-oxo-1,3-benzoxazol-3(2H)-yl]acetate

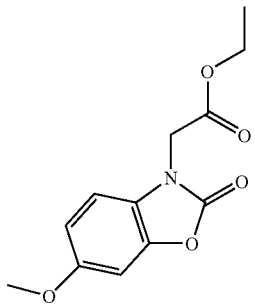

A solution of 6-methoxy-2-benzoxazolinone (0.78 g, 4.72 mmol) dissolved in 5 mL of anhydrous THF was added to a suspension of sodium hydride (0.208 g of a 60% dispersion in mineral oil, 5.2 mmol) in 10 mL of anhydrous THF at room temperature and stirred for 10 minutes. Then, ethyl bromoacetate (0.629 mL, 5.67 mmol) was added and stirred at room temperature for two hours. HPLC (Eclipse XDB-C18, 4.6× 250 mm, 5 micron, 1-99% CH$_3$CN/H$_2$O with 0.1% trifluoroacetic acid) showed that almost all of the starting material (R$_t$=4.36 min) was gone and that a new peak (R$_t$=6.0 min) had formed. The reaction was quenched with 2 mL of 4.0M HCl in dioxane. The solvent was removed by rotary evaporation and the residue was adsorbed onto approximately 10 g of silica gel and purified by column chromatography (40 g silica gel 40 um, gradient elution from 100% dichloromethane to 35% methanol/65% dichloromethane over 40 minutes) to give ethyl[6-(methyloxy)-2-oxo-1,3-benzoxazol-3(2H)-yl]acetate (0.96 g, 3.84 mmol, 81%) as a white crystalline solid. MS (ES) m/e 252 [M+H]$^+$.

b) [6-(methyloxy)-2-oxo-1,3-benzoxazol-3(2H)-yl]acetic acid, lithium salt

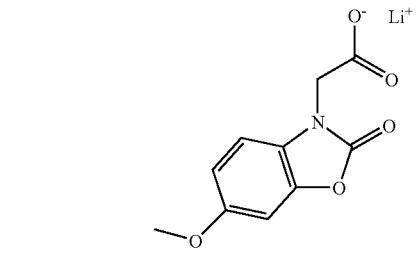

Ethyl[6-(methyloxy)-2-oxo-1,3-benzoxazol-3(2H)-yl]acetate (0.96 g, 3.84 mmol) was dissolved in 10 mL of THF and treated with a solution of LiOH (0.0919 g, 3.84 mmol) dissolved in 1 mL of water. The reaction was stirred vigorously at room temperature, and after one hour, HPLC (Eclipse XDB-C18, 4.6×250 mm, 5 micron, 1-99% CH$_3$CN/H$_2$O with 0.1% trifluoroacetic acid) showed that all of the starting material (R$_t$=6.0 min) was gone and that a single new product had formed (4.4 min). The solvent was removed by rotary evaporation and the residue was suspended in 20 mL of anhydrous dioxane. The dioxane was then removed by rotary evaporation to drive off any traces of water and the residue was dried under high vacuum, resulting in 6-(methyloxy)-2-oxo-1,3-benzoxazol-3(2H)-yl]acetic acid, lithium salt (0.870 g, 3.80 mmol, 99%) as an off-white solid. MS (ES) m/e 224 [M+H]$^+$.

c) N-[1-(4-biphenylyl)-2-(1-pyrrolidinyl)ethyl]-N-methyl-2-[6-(methyloxy)-2-oxo-1,3-benzoxazol-3(2H)-yl]acetamide

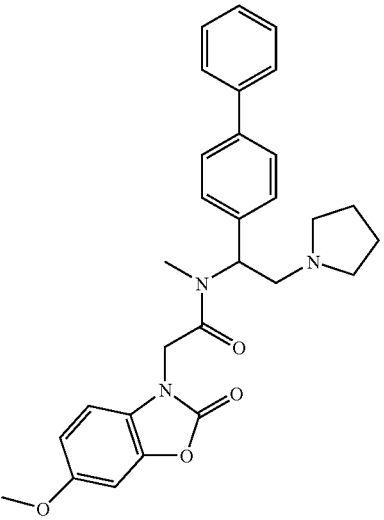

6-(methyloxy)-2-oxo-1,3-benzoxazol-3(2H)-yl]acetic acid, lithium salt (100 mg, 0.44 mmol), [1-(4-biphenylyl)-2-(1-pyrrolidinyl)ethyl]methylamine (122 mg, 0.44 mmol), triethylamine (91 uL, 0.66 mmol), and (1H-1,2,3-benzotriazol-1-yloxy)[tris(dimethylamino)]phosphonium hexafluorophosphate (BOP Reagent, 232 mg, 0.524 mmol) were added in that order to a 4 mL screw capped vial that contained 1 mL of anhydrous DMF. The reaction mixture was stirred for 20 hours at room temperature, after which time HPLC (Eclipse XDB-C18, 4.6×250 mm, 5 micron, 1-99% CH₃CN/H₂O with 0.1% trifluoroacetic acid) showed that the reaction was complete. The solvent was removed under vacuum and the residue was dissolved in 2 mL of DMSO, filtered through a 0.2 um PTFE Acrodisk, and purified by reverse-phase HPLC (Phenomenex C-18, 50×100 mm, 80 mL/min, A: acetonitrile (0.1% TFA) B: water (0.1% TFA), A: 15 to 98% over 20 min, UV detection at 214 nm) to give the title compound (107 mg, 0.220 mmol, 51%) as the TFA salt in the form of an off-white solid. MS (ES) m/e 486 [M+H]⁺.

Example 238

N-[1-(4-biphenylyl)-2-(1-pyrrolidinyl)ethyl]-N-methyl-2-[7-(methyloxy)-3-oxo-2,3-dihydro-4H-1,4-benzoxazin-4-yl]acetamide

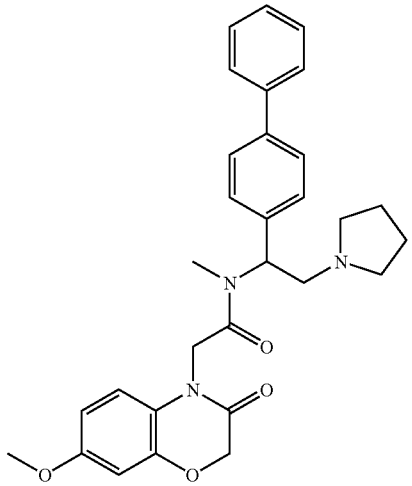

a) 7-(methyloxy)-2H-1,4-benzoxazin-3(4H)-one

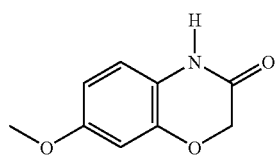

2-amino-5-methoxy-phenol hydrochloride (4.0 g, 22.8 mmol) was dissolved in 100 mL of chloroform in a 500 mL round-bottom flask and treated with 80 mL of saturated sodium bicarbonate solution. This mixture was stirred rapidly and was cooled to 0° C. in an ice bath. A solution of bromoacetyl bromide (2.98 mL, 34.2 mmol) in 20 mL of chloroform was added slowly. After 2 hours, HPLC (Eclipse XDB-C18, 4.6×250 mm, 5 micron, 1-99% CH₃CN/H₂O with 0.1% trifluoroacetic acid) showed that all of the starting material ($R_t$=2.4 min) was consumed and that a major product peak had formed ($R_t$=4.5 min). The reaction was diluted with 200 mL of chloroform and 200 mL of water. The layers were separated and the aqueous layer was extracted with chloroform (3×150 mL). The combined organic layers were dried over magnesium sulfate, filtered, and concentrated to a red-brown solid. This solid was dissolved in 200 mL of anhydrous DMF, treated with potassium carbonate (3.2 g, 22.8 mmol) and heated to 85° C. After two hours, HPLC showed that all of the material had converted to a new product ($R_t$=4.4 min), so the reaction mixture was allowed to cool to room temperature and was poured into 700 mL of water. The aqueous phase was extracted with ethyl acetate (3×200 mL) and the combined organic layers were washed with water (3×500 mL) and saturated NaCl (1×200 mL), dried over magnesium sulfate, filtered, and concentrated to give 7-(methyloxy)-2H-1,4-benzoxazin-3(4H)-one (1.42 g, 7.9 mmol, 34%) as a red-orange solid. MS (ES) m/e 180 [M+H]⁺.

b) Ethyl[7-(methyloxy)-3-oxo-2,3-dihydro-4H-1,4-benzoxazin-4-yl]acetate

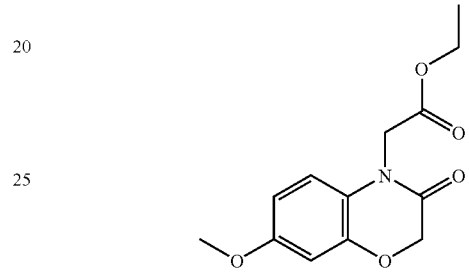

A solution of 7-(methyloxy)-2H-1,4-benzoxazin-3(4H)-one (1.42 g, 7.9 mmol) dissolved in 5 mL of anhydrous THF was added to a suspension of sodium hydride (0.349 g of a 60% dispersion in mineral oil, 8.7 mmol) in 10 mL of anhydrous THF at room temperature and stirred for 10 minutes. Then, ethyl bromoacetate (1.06 mL, 9.52 mmol) was added and stirred at room temperature for two hours. HPLC (Eclipse XDB-C18, 4.6×250 mm, 5 micron, 1-99% CH₃CN/H₂O with 0.1% trifluoroacetic acid) showed that all of the starting material ($R_t$=4.4 min) was gone and that a new peak ($R_t$=6.5 min) had formed. The reaction was quenched with 5 mL of 4.0M HCl in dioxane. The solvent was removed by rotary evaporation and the residue was adsorbed onto approximately 10 g of silica gel and purified by column chromatography (120 g silica gel 40 um, gradient elution from 100% dichloromethane to 10% methanol/90% dichloromethane over 40 minutes) to give ethyl [7-(methyloxy)-3-oxo-2,3-dihydro-4H-1,4-benzoxazin-4-yl]acetate (1.35 g, 5.1 mmol, 64%) as a white crystalline solid. MS (ES) m/e 266 [M+H]⁺.

c) [7-(methyloxy)-3-oxo-2,3-dihydro-4H-1,4-benzoxazin-4-yl]acetic acid, lithium salt

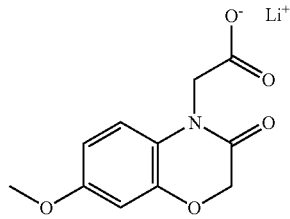

Ethyl[7-(methyloxy)-3-oxo-2,3-dihydro-4H-1,4-benzoxazin-4-yl]acetate (1.35 g, 5.1 mmol) was dissolved in 10 mL of THF and treated with a solution of LiOH (0.122 g, 5.1 mmol) dissolved in 1 mL of water. The reaction was stirred vigorously at room temperature, and after 20 hours, HPLC (Eclipse XDB-C18, 4.6×250 mm, 5 micron, 1-99% $CH_3CN/H_2O$ with 0.1% trifluoroacetic acid) showed that all of the starting material ($R_t$=6.5 min) was gone and that a single new product had formed (4.6 min). The solvent was removed by rotary evaporation and the residue was suspended in 20 mL of anhydrous dioxane. The dioxane was then removed by rotary evaporation to drive off any traces of water and the residue was dried under high vacuum, resulting in [7-(methyloxy)-3-oxo-2,3-dihydro-4H-1,4-benzoxazin-4-yl]acetic acid, lithium salt (1.0 g, 4.1 mmol, 81%) as a white solid. MS (ES) m/e 238 $[M+H]^+$.

d) N-[1-(4-biphenylyl)-2-(1-pyrrolidinyl)ethyl]-N-methyl-2-[7-(methyloxy)-3-oxo-2,3-dihydro-4H-1,4-benzoxazin-4-yl]acetamide

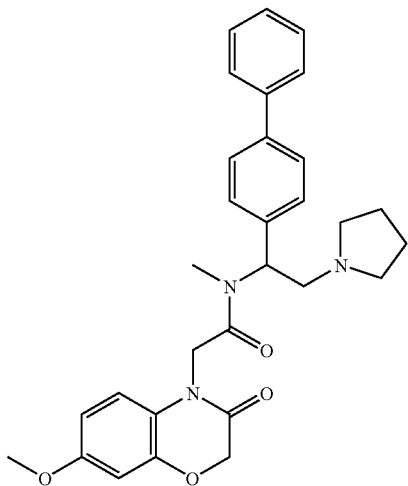

[7-(methyloxy)-3-oxo-2,3-dihydro-4H-1,4-benzoxazin-4-yl]acetic acid, lithium salt (106 mg, 0.44 mmol), [1-(4-biphenylyl)-2-(1-pyrrolidinyl)ethyl]methylamine (122 mg, 0.44 mmol), triethylamine (91 uL, 0.66 mmol), and (1H-1,2,3-benzotriazol-1-yloxy)[tris(dimethylamino)]phosphonium hexafluorophosphate (BOP Reagent, 232 mg, 0.524 mmol) were added in that order to a 4 mL screw capped vial that contained 1 mL of anhydrous DMF. The reaction mixture was stirred for 20 hours at room temperature, after which time HPLC (Eclipse XDB-C18, 4.6×250 mm, 5 micron, 1-99% $CH_3CN/H_2O$ with 0.1% trifluoroacetic acid) showed that the reaction was complete. The solvent was removed under vacuum and the residue was dissolved in 2 mL of DMSO, filtered through a 0.2 um PTFE Acrodisk, and purified by reverse-phase HPLC (Phenomenex C-18, 50×100 mm, 80 mL/min, A: acetonitrile (0.1% TFA) B: water (0.1% TFA), A: 15 to 98% over 20 min, UV detection at 214 nm) to give the title compound (123 mg, 0.246 mmol, 56%) as the TFA salt in the form of an off-white solid. MS (ES) m/e 501 $[M+H]^+$.

Example 239

$N^1$-[1-(4-biphenylyl)-2-(1-pyrrolidinyl)ethyl]-$N^2$-(3,4-dichlorophenyl)-$N^1$-methyl-N-[2-(methyloxy)ethyl]glycinamide

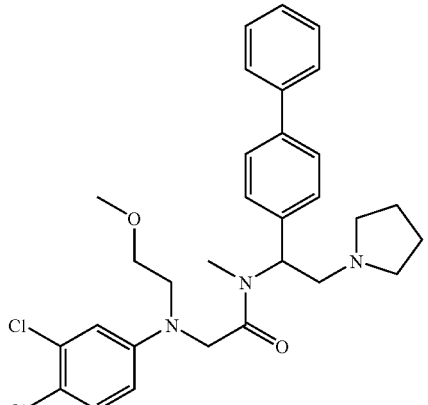

a) ethyl N-(3,4-dichlorophenyl)glycinate

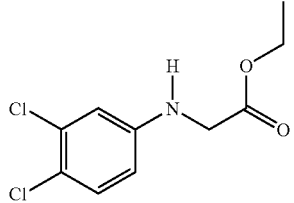

3,4-dichloroaniline (100 g, 0.617 mol), ethyl bromoacetate (68.4 mL, 0.617 mol), and di-isopropylethylamine (129.0 mL, 0.740 mol) were combined in 300 mL of dry N-methyl pyrrolidinone and stirred at room temperature for 18 hours. HPLC (Eclipse XDB-C18, 4.6×250 mm, 5 micron, 1-99% $CH_3CN/H_2O$ with 0.1% trifluoroacetic acid) after 18 hours at room temperature showed that most of the starting material ($R_t$=5.2 min) was gone and that a new peak had formed ($R_t$=7.9 min). The reaction was heated to 90° C. to push it to completion, which was achieved after one hour at 90° C., as shown by HPLC. The reaction was allowed to cool to room temperature and then poured onto 2.5 L of ice, 1.5 L of water, and 240 g of $NaHCO_3$. A tan precipitate formed immediately and this suspension was stirred vigorously for 10 minutes and then filtered through a fritted glass funnel. The tan solid was air-dried for 20 hours in a crystallizing dish and then transferred to a 1 L flask and dried by rotary evaporation to remove the bulk of the remaining water. The tan solid was then dried under high vacuum to give 147.8 g (0.596 mol, 97%) of ethyl N-(3,4-dichlorophenyl)glycinate. LC/MS (APCI) m/e 248 $[M+H]^+$.

b) ethyl N-(3,4-dichlorophenyl)-N-[2-(methyloxy)ethyl]glycinate

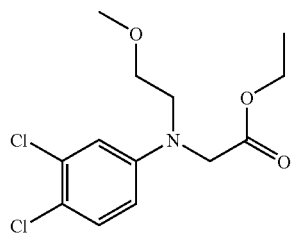

Ethyl N-(3,4-dichlorophenyl)glycinate (3.0 g, 12.1 mmol) was suspended in 2-bromoethyl methyl ether (9.09 mL, 96.7 mmol) and treated with sodium iodide (1.81 g, 12.1 mmol), sodium bicarbonate (1.02 g, 12.1 mmol), and 10 mL of DMF. The reaction was stirred for 20 hours at room temperature, but HPLC (Eclipse XDB-C18, 4.6×250 mm, 5 micron, 1-99% $CH_3CN/H_2O$ with 0.1% trifluoroacetic acid) indicated that only starting material ($R_t$=8.0 min) was present and that no reaction had taken place. The reaction was heated to 125° C. for 24 hours, after which time HPLC showed that all of the starting material was gone and that a new product peak had formed ($R_t$=8.7 min). The reaction mixture was poured into 200 mL of ethyl acetate, 100 mL of ether, and 250 mL of water and shaken vigorously. The layers were separated and the organic layer was washed with water (1×400 mL), dried over magnesium sulfate, filtered, and concentrated to a black oil. The oil was adsorbed onto approximately 50 g of silica gel and purified by column chromatography (300 g silica gel 40 um, gradient elution from 10% ethyl acetate/90% hexanes to 100% ethyl acetate over 110 minutes) to give ethyl N-(3,4-dichlorophenyl)-N-[2-(methyloxy)ethyl]glycinate (0.73 g, 2.39 mmol, 20%) as a brown oil. MS (ES) m/e 306 [M+H]$^+$.

c) N-(3,4-dichlorophenyl)-N-[2-(methyloxy)ethyl]glycine, lithium salt

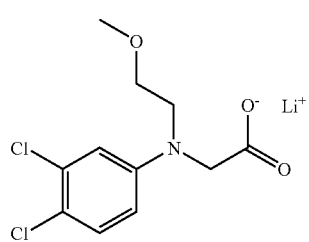

Ethyl N-(3,4-dichlorophenyl)-N-[2-(methyloxy)ethyl]glycinate (0.73 g, 2.39 mmol) was dissolved in 10 mL of THF and treated with a solution of LiOH (0.0572 g, 2.39 mmol) dissolved in 1 mL of water. The reaction was stirred vigorously at room temperature, and after 20 hours HPLC (Eclipse XDB-C18, 4.6×250 mm, 5 micron, 1-99% $CH_3CN/H_2O$ with 0.1% trifluoroacetic acid) showed that most of the starting material (Rt=8.7 min) had been converted to a new product peak (Rt=6.9 min). An additional 16 mg (0.28 eq.) of LiOH was added to the reaction in an attempt to push the hydrolysis to completion, but after 20 hours, the reaction mixture remained unchanged, so the reaction was quenched with 5 mL of 4.0 M HCl in dioxane and concentrated to dryness by rotary evaporation. The brown powder was dried under high vacuum to give N-(3,4-dichlorophenyl)-N-[2-(methyloxy)ethyl]glycine, lithium salt mixed with LiCl (0.74 g total mass of product and LiCl) which was used without further purification in the next step. MS (ES) m/e 278 [M+H]$^+$.

d) $N^1$-[1-(4-biphenylyl)-2-(1-pyrrolidinyl)ethyl]-$N^2$-(3,4-dichlorophenyl)-$N^1$-methyl-$N^2$-[2-(methyloxy)ethyl]glycinamide

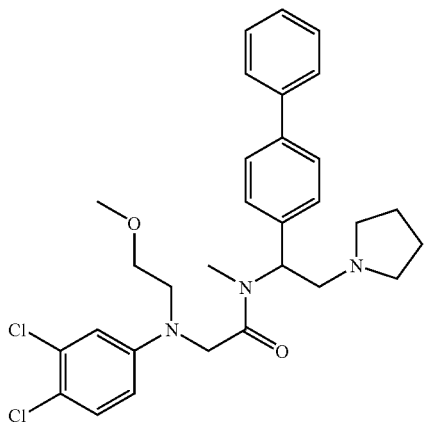

N-(3,4-dichlorophenyl)-N-[2-(methyloxy)ethyl]glycine, lithium salt (100 mg, 0.35 mmol) [1-(4-biphenylyl)-2-(1-pyrrolidinyl)ethyl]methylamine (98 mg, 0.35 mmol), triethylamine (73 uL, 0.53 mmol), and (1H-1,2,3-benzotriazol-1-yloxy)[tris(dimethylamino)]phosphonium hexafluorophosphate (BOP Reagent, 186 mg, 0.42 mmol) were added in that order to a 4 mL screw capped vial that contained 1 mL of anhydrous DMF. The reaction mixture was stirred for 20 hours at room temperature, after which time HPLC (Eclipse XDB-C18, 4.6×250 mm, 5 micron, 1-99% $CH_3CN/H_2O$ with 0.1% trifluoroacetic acid) showed that the reaction was complete. The solvent was removed under vacuum and the residue was dissolved in 2 mL of DMSO, filtered through a 0.2 um PTFE Acrodisk, and purified by reverse-phase HPLC (Xterra Prep RP, 30×150 mm, 35 mL/min, A: acetonitrile B: water (adjusted to pH 10 with $NH_4OH$), A: 35 to 99% over 14 min, UV detection at 214 nm) to give the title compound (117 mg, 0.216 mmol, 61%) as a white solid. MS (ES) m/e 540 [M+H]$^+$.

Example 240

$N^1$-[1-(4-biphenylyl)-2-(1-pyrrolidinyl)ethyl]-$N^2$-(3,4-dichlorophenyl)-$N^1$,2-dimethylalaninamide

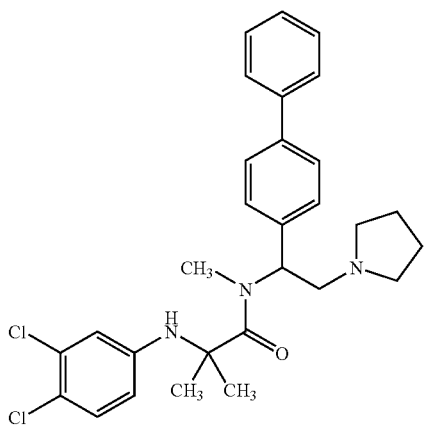

229 a) Ethyl N-(3,4-dichlorophenyl)-2-methylalaninate

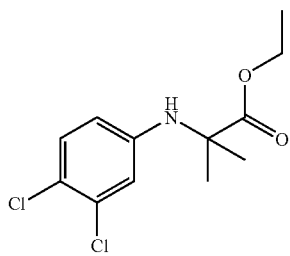

A 15-mL sealed tube equipped with a magnetic stirring bar was charged with 3,4-dichloroaniline (1.63 g, 10.0 mmol) and treated with ethyl-2-bromoisobutyrate (1.6 mL, 11 mmol), diisopropylethylamine (1.9 mL, 11.0 mmol), and NaI (824 mg, 0.600 mmol). The vessel was sealed tightly, heated to 110° C. and maintained at that temperature for 48 h. After allowing the reaction mixture to cool to room temperature, the reaction was diluted with THF and the solids were filtered off. The filtrate was collected and concentrated under vacuum. The crude oil was purified by silica gel chromatography (35 g Redisep column, silica 40 um, 35 mL/min, A: $CH_2Cl_2$, B: MeOH, B: 0% for 20 min, 5% for 5 min, 10% for 5 min; detection at 214 nm) to give 1.71 g (55%) of ethyl N-(3,4-dichlorophenyl)-2-methylalaninate as a brown oil. MS (ES) m/z 276 [M+H]$^+$ b) N-(3,4-Dichlorophenyl)-2-methylalanine lithium salt

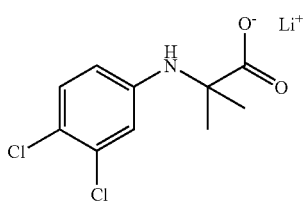

A 50-mL round bottom flask equipped with a magnetic stirring bar was charged with ethyl N-(3,4-dichlorophenyl)-2-methylalaninate (790 mg, 2.9 mmol) and dissolved in 3 mL of THF. A solution of LiOH (132 mg, 5.8 mmol) dissolved in 1.0 mL of $H_2O$ was added and the mixture was stirred at room temperature for 24 h. The solvent was removed under reduced pressure. A total of 846 mg (90%) of N-(3,4-dichlorophenyl)-2-methylalanine as a yellow solid was recovered as the lithium salt, after drying under vacuum for 24 h. MS (ES) m/z 248 [M+H]$^+$

230 c) $N^1$-[1-(4-biphenylyl)-2-(1-pyrrolidinyl)ethyl]-$N^2$-(3,4-dichlorophenyl)-$N^1$,2-dimethylalaninamide

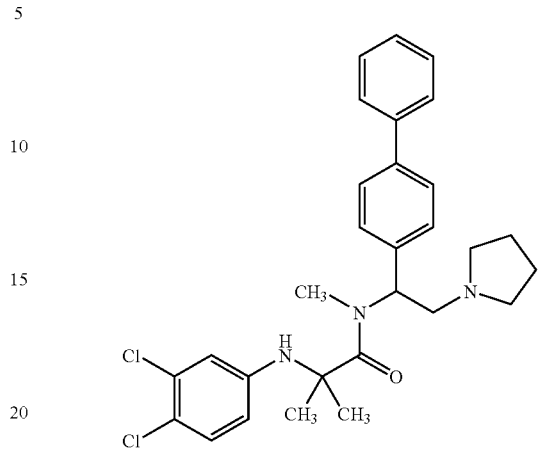

N-(3,4-dichlorophenyl)-2-methylalanine, lithium salt (100 mg, 0.4 mmol), [1-(4-biphenylyl)-2-(1-pyrrolidinyl)ethyl] methylamine (124 mg, 0.44 mmol), triethylamine (246 uL, 1.77 mmol), and (1H-1,2,3-benzotriazol-1-yloxy)[tris(dimethylamino)]phosphonium hexafluorophosphate (BOP Reagent, 215 mg, 0.486 mmol) were added in that order to a 4 mL screw capped vial that contained 2 mL of anhydrous DMF. The reaction mixture was stirred for 20 hours at room temperature, then filtered through a 0.45 um PTFE Acrodisk, and purified by reverse-phase HPLC (Xterra Prep RP C-18, 30×150 mm, 50 mL/min, A: acetonitrile B: water, pH 10 w/$NH_4OH$, A: 20 to 99% over 9 min, UV detection at 214 nm) to give the title compound as a white solid. MS (ES) m/e 510 [M+H]$^+$.

Example 241 and 242

(R) and (S)N-[1-(4-biphenylyl)-2-(4-morpholinyl)ethyl]-2-(6,7-dichloro-3-oxo-2,3-dihydro-4H-1,4-benzoxazin-4-yl)-N-methylacetamide

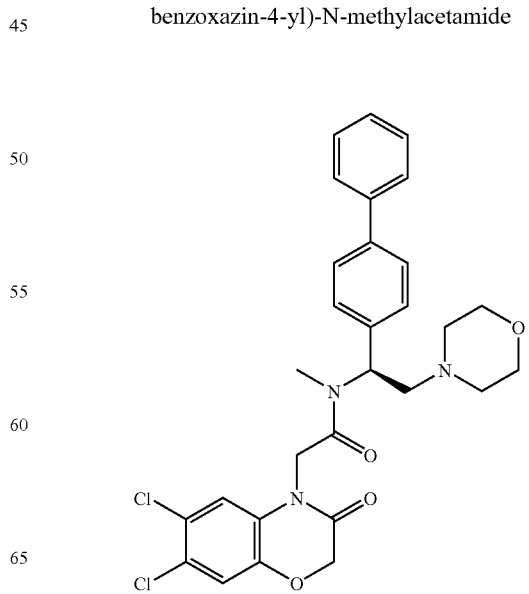

-continued

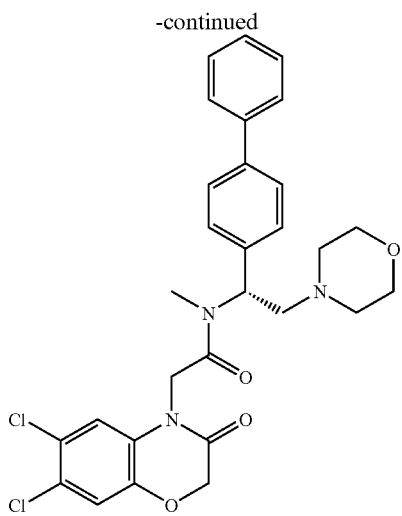

a) 1-(4-biphenylyl)-2-(4-morpholinyl)ethanone

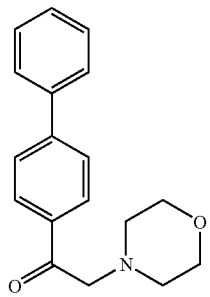

To a cooled (0° C.) solution of morpholine (5.99 g, 68.7 mmol) in ether (20 mL) was added the solution of 1-(4-biphenylyl)-2-bromoethanone (9.47 g, 34.4 mmol) in a mixture of ether (100 mL) and dichloromethane (100 mL) dropwise at 0° C. After the addition was over, the reaction mixture was allowed to warm to room temperature and stirred at room temperature for 1 h. The mixture was concentrated under reduced pressure. The residue was dissolved in dichloromethane (150 mL) and extracted with 5% NaHCO$_3$ (150 mL) and brine (100 mL). The organic layer was dried (MgSO$_4$) and concentrated to give 9.70 g (100%) of the title compound as a white solid. MS (ES) m/e 281.2 [M+H]$^+$.

b) [1-(4-biphenylyl)-2-(4-morpholinyl)ethyl]methylamine

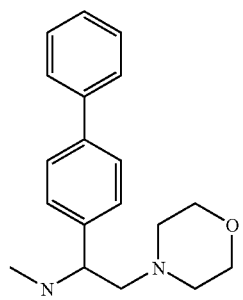

To a solution of 1-(4-biphenylyl)-2-(4-morpholinyl)ethanone (9.70 g, 34.4 mmol) in THF (100 mL) was added methylamine (2M solution in THF, 100 mL, 200 mmol). The mixture was stirred at room temperature for 15 min and then sodium cyanoborohydride (8.34 g, 133 mmol) and acetic acid (2.0 mL) were added. The resultant mixture was stirred at room temperature for 48 h. The mixture was diluted with ethyl acetate (200 mL) and washed with 5% NaHCO$_3$ (200 mL) and water (200 mL). The organic layer was dried (MgSO$_4$) and concentrated to give 10.59 g (100%) of the title compound as a yellow oil which solidified upon standing at room temperature. MS (ES) m/e 297.6 [M+H]$^+$ c) N-[1-(4-biphenylyl)-2-(4-morpholinyl)ethyl]-2-(6,7-dichloro-3-oxo-2,3-dihydro-4H-1,4-benzoxazin-4-yl)-N-methylacetamide

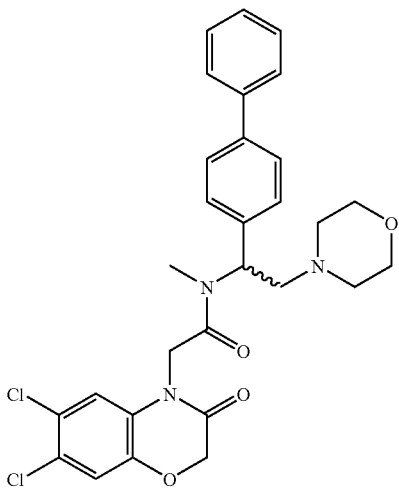

To a solution of [1-(4-biphenylyl)-2-(4-morpholinyl)ethyl]methylamine (3.67 g, 12.4 mmol) and (6,7-dichloro-2,3-dihydro-4H-1,4-benzoxazin-4-yl)acetic acid (3.42 g, 12.4 mmol) in DMF (50 mL) was added BOP Reagent (8.23 g, 18.6 mmol) followed by triethylamine (3.76 g, 37.2 mmol). The resultant mixture was stirred at room temperature for 16 h. The mixture was concentrated under reduced pressure, diluted with ethyl acetate (150 mL), and extracted with 5% NaHCO$_3$ (100 mL) and brine (100 mL). The organic layer was dried (MgSO$_4$) and concentrated. The residue was purified by silica gel chromatography (330 g redisep column, silica 40 um, 60 A, 100 ml/min, A: MeOH, B: CH$_2$Cl$_2$, A: 1% for 30 min) to give 4.08 g (59%) of title compound as a white solid. MS (ES) m/e 554.4 [M+H]$^+$.

d) N-[1-(4-biphenylyl)-2-(4-morpholinyl)ethyl]-2-(6,7-dichloro-3-oxo-2,3-dihydro-4H-1,4-benzoxazin-4-yl)-N-methylacetamide

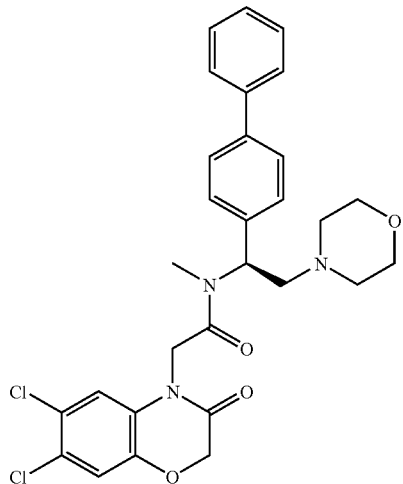

Separation of the Enantiomers:

Prep column: Varian Rampak self-packed 41 mm I.D. column containing whelk 02 (Regis Technologies), 250 g slurry packed in IPA under 1400 psi dynamic axial composition. Switched to the desired mobile phase of 0.1 Et₃N/EtOH at 50 mL/min, UV at 285 nm. Racemate (2.0 g) in CHCl₃ (10 mL) was filtered through a 0.45 um polypropylene filter and injected into the column. Enantiomer 1(0.85 g, 99% e.e., Optical Rotation (−)183,) eluted from 17.1 min to 20.2 min; Enantiomer 2 (0.79 g, 99% e.e., Optical Rotation (+)171.) eluted from 20.2 min to 27 min.

Example 243

Ethyl 4-[2-[[1-(4-biphenylyl)-2-(1-pyrrolidinyl)ethyl](methyl)amino]-2-oxoethyl]-3-oxo-3,4-dihydro-2H-1,4-benzoxazine-6-carboxylate a) 3-oxo-3,4-dihydro-2H-1,4-benzoxazine-6-carboxylic acid 3-amino-4-hydroxybenzoic acid (4.0 g, 26.0 mmol) was dissolved in 168 mL of chloroform. 92 mL of saturated sodium bicarbonate solution was added and the new bi-phase mixture was stirred vigorously and cooled to 0° C. using an ice bath. Bromoacetylbromide (3.42 mL, 39 mmol) was added drop-wise. Fifteen minutes later the solution was removed from the ice bath and maintained at room temperature for 48 hours. HPLC (Eclipse XDB-C18, 4.6×250 mm, 5 micron, 1-99% CH₃CN/H₂O with 0.1% trifluoroacetic acid) chromatogram indicated that all of the starting material was gone and a new peak (R$_t$=3.7 min) had formed. The reaction mixture was quenched using concentrated hydrochloric acid until the solution reached a pH of 2. The organic layer was separated and the aqueous phase was extracted with 100 mL of chloroform. The combined organic layers were treated with 75 mL of 10% hydrochloric acid solution and separated once again. The organic phase was dried over Na₂SO₄, filtered and concentrated to give 3-oxo-3,4-dihydro-2H-1,4- benzoxazine-6-carboxylic acid (4.8 g, 24.7 mmol, 95%) as an off-white amorphous solid. MS (ES) m/e 194 [M+H]⁺.

b) Ethyl 3-oxo-3,4-dihydro-2H-1,4-benzoxazine-6-carboxylate

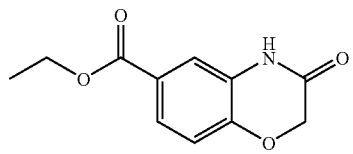

3-oxo-3,4-dihydro-2H-1,4-benzoxazine-6-carboxylic acid, (1.63 g, 8.4 mmol), 1-(3-dimethylaminopropyl)-3-ethylcarbodiimide hydrochloride (1.49 g, 7.8 mmol), 1-hydroxybenzotriazole hydrate (1.05 g, 7.8 mmol), and 4-dimethylaminopyridine (0.43 g, 3.5 mmol), were dissolved in 40 mL of anhydrous dichloromethane under argon. Triethylamine (4.0 mL, 29 mmol) was added to the room temperature mixture via syringe. Absolute ethanol (0.83 mL, 14.2 mmol) was then delivered to the solution, which was maintained at room temperature for 18 hours. HPLC (Eclipse XDB-C18, 4.6×250 mm, 5 micron, 1-99% CH₃CN/H₂O with 0.1% trifluoroacetic acid) chromatogram indicated that all of the starting material (Rt=3.7 min) was gone and that a single new product had formed (Rt=5.5 min). The solvent was removed by rotary evaporation and the residue was dissolved in 200 mL of ethyl acetate. The organic layer was washed with water (3×50 mL), 10% hydrochloric acid solution (3×50 mL), and 50% sodium bicarbonate solution (3×50 mL). The organic phase was dried over Na₂SO₄, filtered and concentrated to give ethyl 3-oxo-3,4-dihydro-2H-1,4-benzoxazine-6-carboxylate (1.6 g, 7.2 mmol, 86%) as a yellow solid. MS (ES) m/e 221 [M+H]⁺.

c) Ethyl 4-{2-[(1,1-dimethylethyl)oxy]-2-oxoethyl}-3-oxo-3,4-dihydro-2H-1,4-benzoxazine-6-carboxylate

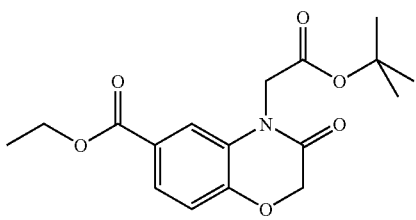

Several smaller batches of ethyl 3-oxo-3,4-dihydro-2H-1,4-benzoxazine-6-carboxylate were combined. A solution of ethyl 3-oxo-3,4-dihydro-2H-1,4-benzoxazine-6-carboxylate (4.1 g, 19.0 mmol) dissolved in 30 mL of anhydrous tetrahydrofuran was added drop-wise to a mixture of sodium hydride (60% by weight in mineral oil, 0.8 g, 20 mmol) suspended in 60 mL of anhydrous tetrahydrofuran under argon. The mixture was allowed to stir at room temperature for 10 minutes before t-butyl-2-bromoacetate (3.4 mL, 23 mmol) was added to the mixture and stirred vigorously for 2 hours. HPLC (Eclipse XDB-C18, 4.6×250 mm, 5 micron, 1-99% CH₃CN/H₂O with 0.1% trifluoroacetic acid) chromatogram indicated that all of the starting material (R_t=5.5 min) was consumed and only a single new product had formed (R_t=7.7 min). The reaction was quenched by adding 8 mL of a 4 M solution of hydrochloric acid in dioxane. After allowing the mixture to stir for one hour, all of the volatiles were removed by rotary evaporation to give ethyl 4-{2-[(1,1-dimethylethyl)oxy]-2-oxoethyl}-3-oxo-3,4-dihydro-2H-1,4-benzoxazine-6-carboxylate (6.14 g, 18.0 mmol, 96%). MS (ES) m/e 280 [M−t-butyl C₄H₉]⁺.

d) {6-[(ethyloxy)carbonyl]-3-oxo-2,3-dihydro-4H-1,4-benzoxazin-4-yl}acetic acid

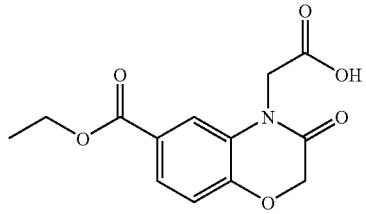

Ethyl 4-{2-[(1,1-dimethylethyl)oxy]-2-oxoethyl}-3-oxo-3,4-dihydro-2H-1,4-benzoxazine-6-carboxylate (6.14 g, 18.0 mmol) was dissolved in 60 mL of a 1:1 solution of methylene chloride and trifluoroacetic acid. The mixture was allowed to stir at room temperature for three hours before it was determined to be complete by HPLC (Eclipse XDB-C18, 4.6×250 mm, 5 micron, 1-99% CH₃CN/H₂O with 0.1% trifluoroacetic acid). The chromatogram indicated that all of the starting material (Rt=7.7 min) was consumed and converted to the desired product (Rt=5.3 min). The volatiles were removed by rotary evaporation and the resulting residue was taken up in a minimal amount of methylene chloride and treated with a 2 M solution of hydrochloric acid in ethyl ether. After allowing the mixture to stir for several minutes, the mixture was concentrated once again by rotary evaporation to yield {6-[(ethyloxy)carbonyl]-3-oxo-2,3-dihydro-4H-1,4-benzoxazin-4-yl}acetic acid (5.28 g, 17.9 mmol, 99%) as a brown amorphous solid. MS (ES) m/e 280 [M+H]⁺.

Ethyl 4-{2-[[1-(4-biphenylyl)-2-(1-pyrrolidinyl)ethyl](methyl)amino]-2-oxoethyl}-3-oxo-3,4-dihydro-2H-1,4-benzoxazine-6-carboxylate

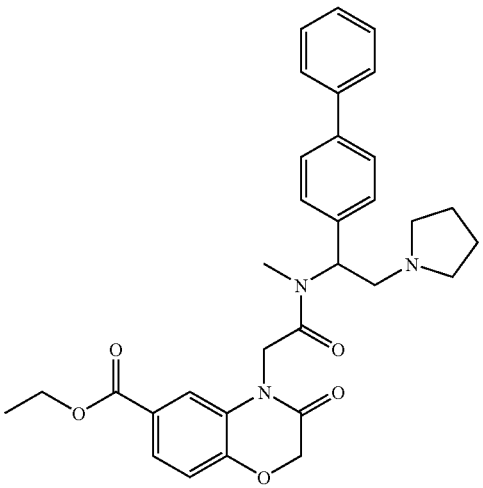

[1-(4-biphenylyl)-2-(1-pyrrolidinyl)ethyl]methylamine (0.5 g, 1.8 mmol) and {6-[(ethyloxy)carbonyl]-3-oxo-2,3- dihydro-4H-1,4-benzoxazin-4-yl}acetic acid (0.63 g, 2.0 mmol) were dissolved in 10 mL of methylene chloride. Triethylamine (1.0 mL, 7.1 mmol) was delivered to the room temperature mixture, and the solution was allowed to stir for several minutes before a separate solution of 1H-1,2,3-benzotriazol-1-yloxy-tris(dimethylamino)-phosphonium hexafluorophosphate (BOP reagent, 0.89 g, 2.0 mmol) dissolved in 4 mL of methylene chloride was added at room temperature to the mixture. The reaction was maintained at that temperature for 72 hours, before it was determined to be complete by LCMS (two Aquasil C18, 20×1 mm columns were run in sequence, 4 minutes at 0.1 mL/min, 1-99% $CH_3CN/H_2O$ with 0.018% trifluoroacetic acid, ES) Rt=2.7 min and m/e 542 [M+1]$^+$. Solvent was removed by rotary evaporation and the crude residue was purified by prep HPLC (Waters, 50×100 mm, 84 mL/min, A: acetonitrile B: water (pH=10, $NH_4OH$), A: 10 to 99% over 15 min, UV detection at 214 nm) to give the title compound (0.75 g. 1.4 mmol, 77%) as a pale yellow amorphous solid. MS (ES) m/e 542 [M+H]$^+$.

Example 244

4-{2-[[1-(4-biphenylyl)-2-(1-pyrrolidinyl)ethyl](methyl)amino]-2-oxoethyl}-3-oxo-3,4-dihydro-2H-1,4-benzoxazine-6-carboxylic acid

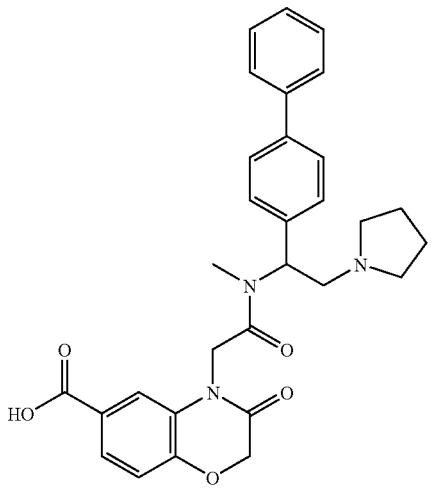

Ethyl 4-{2-[[1-(4-biphenylyl)-2-(1-pyrrolidinyl)ethyl](methyl)amino]-2-oxoethyl}-3-oxo-3,4-dihydro-2H-1,4-benzoxazine-6-carboxylate (0.75 g, 1.4 mmol) was dissolved in 7 mL of tetrahydrofuran. The mixture was refluxed at 75° C. and then a separate solution of LiOH (0.034 g, 1.4 mmol) dissolved in 0.7 mL of $H_2O$ was added to the mixture. The reaction was refluxed for 2 hours before it was determined to be complete by HPLC (Eclipse XDB-C18, 4.6×250 mm, 5 micron, 1-99% $CH_3CN/H_2O$ with 0.1% trifluoroacetic acid). The chromatogram indicated that all of the starting material (Rt=6.9 min) was consumed and converted to a mixture of the desired product (Rt=5.8 min) and a di-acid form of the product (Rt=5.6 min) resulting from the benzoxazinone ring opening. Solvent was removed by rotary evaporation and the crude residue was purified by prep HPLC (Waters, 50×100 mm, 84 mL/min, A: acetonitrile B: water (pH=10, $NH_4OH$), A: 10 to 99% over 15 min, UV detection at 214 nm). The isolated mixture was treated with a solution of 4 M hydrochloric acid in dioxane, in order to close the di-acid component to the desired product. The solvent was removed by rotary evaporation and then placed under high vacuum to give the title compound as the HCl salt (0.3 g, 0.5 mmol, 37%) in the form of an off white amorphous solid. MS (ES) m/e 514 [M+H]$^+$.

Example 245

Ethyl 4-{2-[[1-(4-biphenylyl)-2-(4-morpholinyl)ethyl](methyl)amino]-2-oxoethyl}-3-oxo-3,4-dihydro-2H-1,4-benzoxazine-6-carboxylate

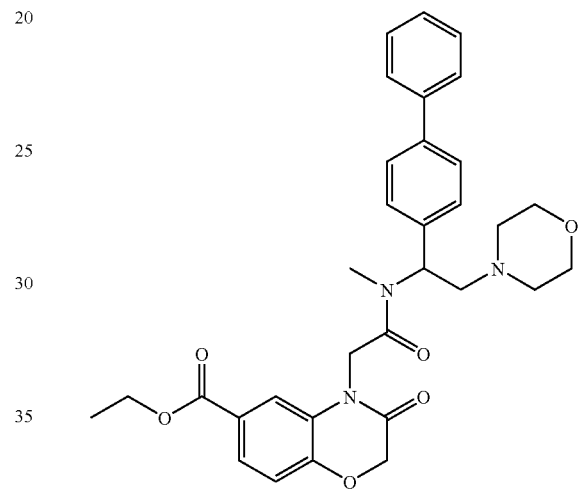

1-(4-biphenylyl)-N-methyl-2-(4-morpholinyl)ethanamine (0.68 g, 2.3 mmol) and {6-[(ethyloxy)carbonyl]-3-oxo-2,3-dihydro-4H-1,4-benzoxazin-4-yl}acetic acid (0.8 g, 2.5 mmol) were dissolved in 12 mL of methylene chloride. Triethylamine (1.3 mL, 9.2 mmol) was delivered to the room temperature mixture, and the solution was allowed to stir for several minutes before a separate solution of 1H-1,2,3-benzotriazol-1-yloxy-tris(dimethylamino)-phosphonium hexafluorophosphate (BOP reagent, 1.11 g, 2.5 mmol) dissolved in 5 mL of methylene chloride was added to the mixture at room temperature. The reaction was maintained at that temperature for 18 hours, before it was determined to be complete by LCMS (two Aquasil C18, 20×1 mm columns were run in sequence, 4 minutes at 0.1 mL/min, 1-99% $CH_3CN/H_2O$ with 0.018% trifluoroacetic acid, ES) Rt=2.7 min and m/e 558 [M+1]$^+$. Solvent was removed by rotary evaporation and the crude residue was purified by prep HPLC (Waters, 50×100 mm, 84 mL/min, A: acetonitrile B: water (pH=10, $NH_4OH$), A: 10 to 99% over 15 min, UV detection at 214 nm) to give the title compound (0.58 g. 1.0 mmol, 43%) as an off-white amorphous solid. MS (ES) m/e 558 [M+H]$^+$.

Example 246

4-{2-[[1-(4-biphenylyl)-2-(4-morpholinyl)ethyl](methyl)amino]-2-oxoethyl}-3-oxo-3,4-dihydro-2H-1,4-benzoxazine-6-carboxylic acid

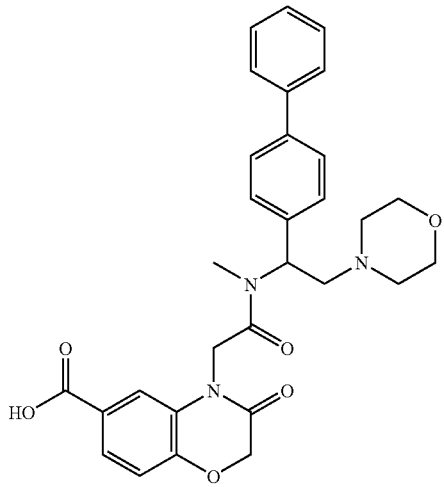

Ethyl 4-{2-[[1-(4-biphenylyl)-2-(4-morpholinyl)ethyl](methyl)amino]-2-oxoethyl}-3-oxo-3,4-dihydro-2H-1,4-benzoxazine-6-carboxylate (0.58 g, 1.0 mmol) was dissolved in 10 mL of tetrahydrofuran. The mixture was refluxed at 75° C. and then a separate solution of LiOH (0.075 g, 1.4 mmol) suspended in 2.0 mL of H₂O was added to the mixture. The reaction was refluxed for 2 hours before it was determined to be complete by HPLC (Eclipse XDB-C18, 4.6×250 mm, 5 micron, 1-99% CH₃CN/H₂O with 0.1% trifluoroacetic acid). The chromatogram indicated that all of the starting material (Rt=6.7 min) was consumed and converted to a mixture of the desired product (Rt=5.6 min) and a di-acid form of the product (Rt=5.4 min) resulting form the benzoxazinone ring opening. The mixture was purified by prep HPLC (Waters, 50×100 mm, 84 mL/min, A: acetonitrile B: water (pH=10, NH₄OH), A: 10 to 99% over 15 min, UV detection at 214 nm). The isolated mixture was treated with a solution of 4 M hydrochloric acid in dioxane, in order to close the di-acid component to the desired product. The solvent was removed by rotary evaporation and then placed under high vacuum to give the title compound (0.3 g, 0.5 mmol, 50%) as an off white amorphous solid. MS (ES) m/e 530 [M+H]⁺.

Example 247

4-{2-[[1-(4-biphenylyl)-2-(1-pyrrolidinyl)ethyl](methyl)amino]-2-oxoethyl}-N-methyl-3-oxo-3,4-dihydro-2H-1,4-benzoxazine-6-carboxamide

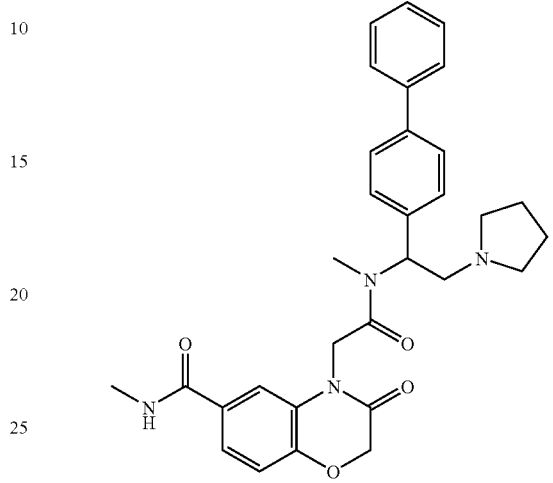

4-{2-[[1-(4-biphenylyl)-2-(1-pyrrolidinyl)ethyl] (methyl)amino]-2-oxoethyl}-3-oxo-3,4-dihydro-2H-1,4-benzoxazine-6-carboxylic acid, HCl salt (0.074 g, 0.14 mmol) was dissolved along with methylamine hydrochloride (0.01 g, 0.15 mmol) in 1 mL of dimethylformamide. Triethylamine (0.08 mL, 0.55 mmol) was delivered to the room temperature mixture, and the solution was allowed to stir for several minutes before a separate solution of 1H-1,2,3-benzotriazol-1-yloxy-tris(dimethylamino)-phosphonium hexafluorophosphate (BOP reagent, 0.066 g, 0.15 mmol) dissolved in 0.5 mL of dimethylformamide was added to the mixture at room temperature. The reaction was maintained at that temperature for 18 hours, before it was determined to be complete by LCMS (two Aquasil C18, 20×1 mm columns were run in sequence, 4 minutes at 0.1 mL/min, 1-99% CH₃CN/H₂O with 0.018% trifluoroacetic acid, ES) Rt=2.16 min and m/e 528 [M+1]⁺. The reaction mixture was filtered through a 0.45 μm PTFE Acrodisk and the crude residue was purified by prep HPLC (Waters, 50×100 mm, 84 mL/min, A: acetonitrile B: water (pH=10, NH₄OH), A: 10 to 99% over 15 min, UV detection at 214 nm) to give the title compound (0.025 g, 0.05 mmol, 34%) as an off-white amorphous solid. MS (ES) m/e 528 [M+H]⁺.

Examples 248-250

The compounds in table 10 were prepared by a method similar to the one described for the preparation of 4-{2-[[1-(4-biphenylyl)-2-(1-pyrrolidinyl)ethyl](methyl)amino]-2-oxoethyl}-N-methyl-3-oxo-3,4-dihydro-2H-1,4-benzoxazine-6-carboxamide (example 247) using amine hydrochloride, ethylamine hydrochloride and ammonia in place of methylamine hydrochloride. As is appreciated by those skilled in the art, these analogous examples may involve variations in synthetic procedure.

TABLE 10

| Ex # | Structure | Name | MS [M + H]+ |
|---|---|---|---|
| 248 | 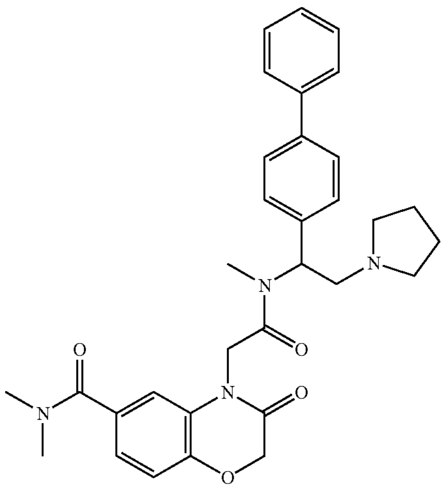 | 4-{2-[[1-(4-biphenylyl)-2-(1-pyrrolidinyl)ethyl](methyl)amino]-2-oxoethyl}-N,N-dimethyl-3-oxo-3,4-dihydro-2H-1,4-benzoxazine-6-carboxamide | 541 |
| 249 | 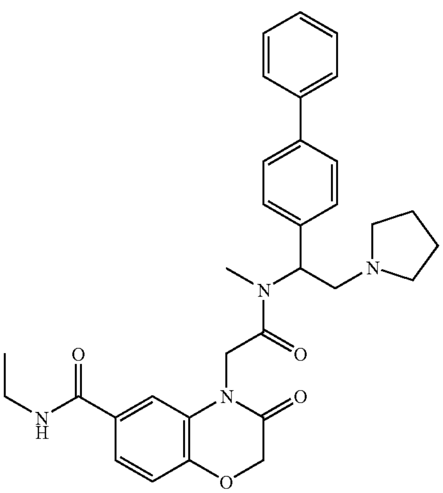 | 4-{2-[[1-(4-biphenylyl)-2-(1-pyrrolidinyl)ethyl](methyl)amino]-2-oxoethyl}-N-ethyl-3-oxo-3,4-dihydro-2H-1,4-benzoxazine-6-carboxamide | 541 |
| 250 | 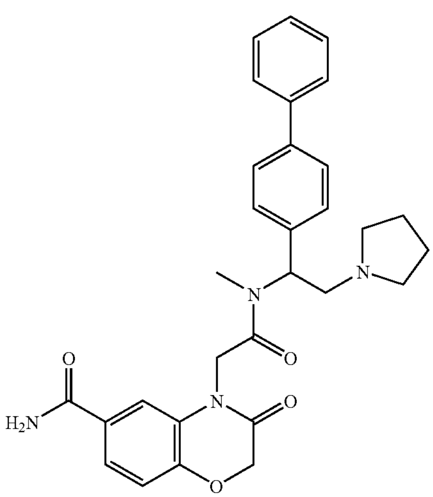 | 4-{2-[[1-(4-biphenylyl)-2-(1-pyrrolidinyl)ethyl](methyl)amino]-2-oxoethyl}-3-oxo-3,4-dihydro-2H-1,4-benzoxazine-6-carboxamide | 513 |

Example 251

4-{2-[[1-(4-biphenylyl)-2-(4-morpholinyl)ethyl](methyl)amino]-2-oxoethyl}-3-oxo-3,4-dihydro-2H-1,4-benzoxazine-6-carboxamide

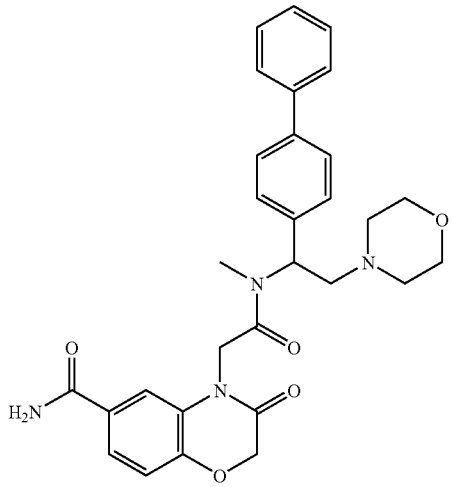

4-{2-[[1-(4-biphenylyl)-2-(4-morpholinyl)ethyl] (methyl)amino]-2-oxoethyl}-3-oxo-3,4-dihydro-2H-1,4-benzoxazine-6-carboxylic acid, HCl salt (0.08 g, 0.1.4 mmol) was dissolved along with an excess of ammonia gas (bubbled into solution for 20 minutes) in 1 mL of dimethylformamide. The room temperature solution was allowed to stir for one minute before a separate solution of 1H-1,2,3-benzotriazol-1-yloxy-tris(dimethylamino)-phosphonium hexafluorophosphate (BOP reagent, 0.066 g, 0.15 mmol) dissolved in 0.5 mL of dimethylformamide was added to the mixture at room temperature. The reaction was maintained at that temperature for 18 hours, before it was determined to be complete by LCMS (two Aquasil C18, 20×1 mm columns were run in sequence, 4 minutes at 0.1 mL/min, 1-99% CH$_3$CN/H$_2$O with 0.018% trifluoroacetic acid, ES) Rt=2.1 min and m/e 529 [M+1]$^+$. The reaction mixture was filtered through a 0.45 μm PTFE Acrodisk and the crude residue was purified by prep HPLC (Waters, 50×100 mm, 84 mL/min, A: acetonitrile B: water (pH=10, NH$_4$OH), A: 10 to 99% over 15 min, UV detection at 214 nm) to give the title compound (0.017 g. 0.03 mmol, 21%) as an off-white amorphous solid. MS (ES) m/e 529 [M+H]$^+$.

Example 252

2-Bromo-1-(4-bromo-2-fluorophenyl)ethanone

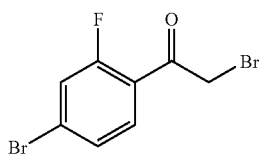

a) 4-[(4-Bromo-2-fluorophenyl)carbonyl]morpholine

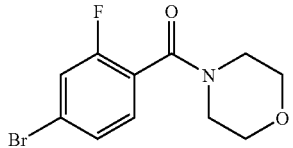

4-Bromo-2-fluorobenzoic acid (5.00 g, 22.8 mmol, 1.00 equiv) and EDC (5.23 g, 27.4 mmol, 1.20 equiv) were dissolved in dichloromethane (100 mL). Morpholine (4.77 mL, 54.8 mmol, 2.40 equiv) was added and the solution was maintained at room temperature for 19 h. The reaction mixture was concentrated en vacuo and diluted with EtOAc and 1N HCl. The phases were separated and the organic phase was washed sequentially with water, saturated NaHCO$_3$, and saturated NaCl. The organic phase was subsequently dried over Na$_2$SO$_4$, filtered and concentrated to afford 5.06 g (81%) of a colorless oil which was used without further purification in the next step. MS (ES) m/e 289 [M+H]$^+$.

b) 1-(4-Bromo-2-fluorophenyl)ethanone

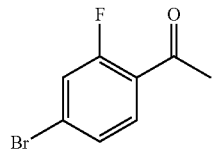

4-[(4-Bromo-2-fluorophenyl)carbonyl]morpholine (5.06 g, 17.6 mmol, 1.00 equiv) was dissolved in 150 mL of THF and the resultant solution was cooled to 0° C. Methyl magnesium bromide (17.6 mL, 3.0 M in Et$_2$O, 52.7 mmol, 3.00 equiv) was added over 5 minutes via syringe. The reaction mixture was maintained for 30 minutes, an additional portion of methyl magnesium bromide was added (10 mL, 29.9 mmol, 1.70 equiv) and the reaction mixture was allowed to warm to room temperature. After an additional 1.5 h, the reaction mixture was poured into saturated NH$_4$Cl. The mixture was diluted with EtOAc and the phases were separated. The organic phase was washed with 1N HCl, saturated NaHCO$_3$, and saturated NaCl, then dried over Na$_2$SO$_4$, filtered and concentrated en vacuo. The resulting residue was purified by column chromatography (40 g SiO$_2$, 0→10% EtOAc/Hexanes) to afford 2.59 g (68%) of a colorless oil. $^1$H NMR (CDCl$_3$) δ 7.79 (t, J=8.2 Hz, 1H), 7.42-7.36 (m, 2H), 2.66 (d, J=5.0 Hz, 3H).

c) 2-Bromo-1-(4-bromo-2-fluorophenyl)ethanone

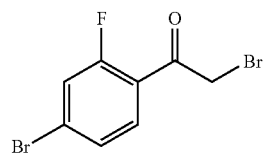

1-(4-Bromo-2-fluorophenyl)ethanone (2.59 g, 11.9 mmol, 1.00 equiv) was dissolved in chloroform (5 mL) and cooled to 5° C. Bromine (0.613 mL, 11.9 mmol, 1.00 equiv) was added dropwise via syringe. On completion of the addition, the bath was removed and the reaction was allowed to warm to room temperature. After two hours, the reaction was poured onto ice and diluted with EtOAc. The mixture was washed sequentially with saturated NaHCO$_3$, water, and saturated NaCl. The organic phase was dried over Na$_2$SO$_4$, filtered and concentrated to afford 3.14 g (89%) of a white solid. $^1$H NMR (CDCl$_3$) δ 17.92-7.83 (m, 1H), 7.51-40 (m, 2H), 4.50 (s, 2H).

Example 253

2-(6,7-dichloro-3-oxo-2,3-dihydro-4H-1,4-benzoxazin-4-yl)-N-[1-(3-fluoro-4-biphenylyl)-2-(4-morpholinyl)ethyl]-N-methylacetamide

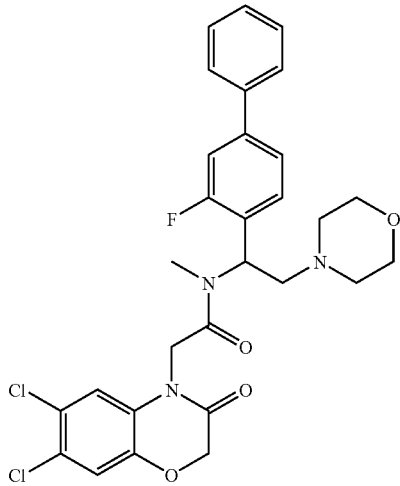

Following the procedure in example 22 except replacing 1-(4-Biphenylyl)-2-(4-morpholinyl)ethanone with the product of example 252 and using the appropriate carboxylic acid the title compound was prepared. MS (ES) m/e 572 [M+H]$^+$.

Example 254

N-[1-(3-chloro-4-biphenylyl)-2-(4-morpholinyl)ethyl]-2-(6,7-dichloro-3-oxo-2,3-dihydro-4H-1,4-benzoxazin-4-yl)-N-methylacetamide

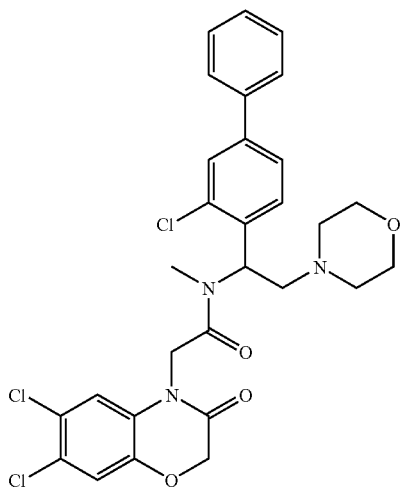

Following the procedures in examples 252 and 253, except starting with 4-bromo-2-chlorobenzoic acid in stead of 4-bromo-2-fluorobenzoic acid, the title compound was prepared. MS (ES) m/e 590 [M+H]$^+$.

Example 255

N-[1-(4-biphenylyl)-2-(1-pyrrolidinyl)ethyl]-N-methyl-2-[6-(methyloxy)-3-oxo-2,3-dihydro-4H-1,4-benzoxazin-4-yl]acetamide

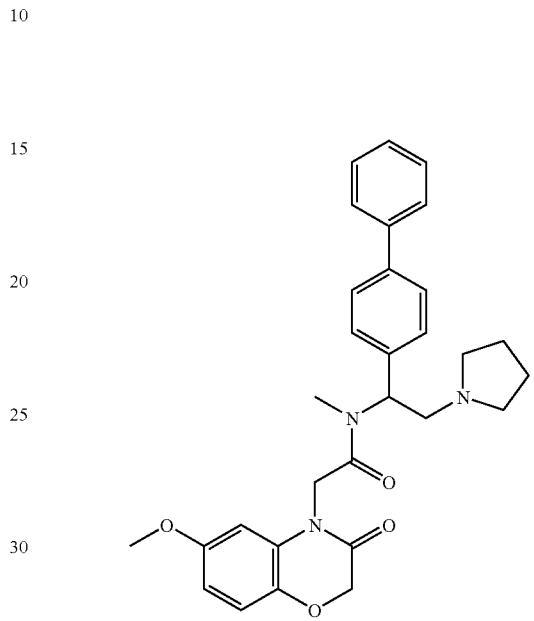

a)
2-bromo-N-[2-hydroxy-5-(methyloxy)phenyl]acetamide

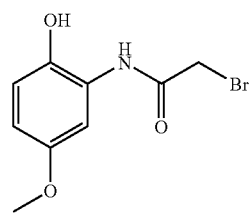

4-methoxy-2-aminophenol (3.0 g, 17.1 mmol) was dissolved in 100 mL of chloroform. 62 mL of saturated sodium bicarbonate solution was added and the new bi-phase mixture was stirred vigorously and cooled to 0° C. using an ice bath. Bromoacetylbromide (3.42 mL, 39 mmol) was added dropwise. Fifteen minutes later the solution was removed from the ice bath and maintained at room temperature for 1.5 hours. HPLC (Eclipse XDB-C18, 4.6×250 mm, 5 micron, 1-99% CH$_3$CN/H$_2$O with 0.1% trifluoroacetic acid) indicated that all of the starting material was gone and a new peak (Rt=4.9 min) had formed. The organic layer was separated and the aqueous phase was extracted with 100 mL of chloroform. The combined organic phases were dried over Na$_2$SO$_4$, filtered and concentrated to give 2-bromo-N-[2-hydroxy-5-(methyloxy)phenyl]acetamide (3.42 g, 13.1 mmol, 77%) as a brown amorphous solid. MS (ES) m/e 260 [M+H]$^+$.

b) 6-(methyloxy)-2H-1,4-benzoxazin-3(4H)-one

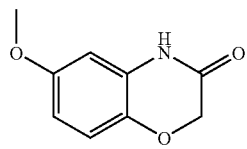

2-bromo-N-[2-hydroxy-5-(methyloxy)phenyl]acetamide (3.42 g, 13.1 mmol), was dissolved in 120 mL of anhydrous dimethylformamide under argon. Potassium carbonate was added and suspended in the solution at room temperature. The mixture was warmed to 85° C. and refluxed for one hour before it was determined to be complete by LCMS (two Aquasil C18, 20×1 mm columns were run in sequence, 4 minutes at 0.1 mL/min, 1-99% CH$_3$CN/H$_2$O with 0.018% trifluoroacetic acid, ES) Rt=1.1 min and m/e 180 [M+1]$^+$. The mixture was allowed to cool to room temperature before it was diluted with 600 mL of ethyl acetate and washed with water (2×150 mL) and brine (2×150 mL). The organic phase was dried over Na$_2$SO$_4$, filtered and concentrated to give 6-(methyloxy)-2H-1,4-benzoxazin-3(4H)-one (2.08 g, 11.6 mmol, 88%) as a brown amorphous solid. MS (ES) m/e 180 [M+H]$^+$.

c) Ethyl[6-(methyloxy)-3-oxo-2,3-dihydro-4H-1,4-benzoxazin-4-yl]acetate

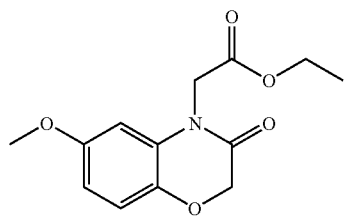

A solution of 6-(methyloxy)-2H-1,4-benzoxazin-3(4H)-one (2.08 g, 11.6 mmol) dissolved in 12.5 mL of anhydrous tetrahydrofuran was added drop-wise to a mixture of sodium hydride (60% by weight in mineral oil, 0.52 g, 12.8 mmol) suspended in 25 mL of anhydrous tetrahydrofuran under argon. The mixture was allowed to stir at room temperature for 10 minutes and then ethyl bromoacetate (1.54 mL, 13.9 mmol) was added to the mixture and stirred vigorously for 1.5 hours before it was determined to be complete by LCMS (two Aquasil C18, 20×1 mm columns were run in sequence, 4 minutes at 0.1 mL/min, 1-99% CH$_3$CN/H$_2$O with 0.018% trifluoroacetic acid, ES) Rt=1.5 min and m/e 265 [M+1]$^+$. The reaction was quenched by adding 5 mL of a 4 M solution of hydrochloric acid in dioxane. After allowing the mixture to stir for one hour, all of the volatiles were removed by rotary evaporation, and the crude residue was purified by silica gel chromatography (120 g Redisep column, silica, 40 um, 60 Å, 50 mL/min, A: methylene chloride, B: methanol, B: 10% for 5 min, 80% for 30 min; detection at 214 nm) to give ethyl[6-(methyloxy)-3-oxo-2,3-dihydro-4H-1,4-benzoxazin-4-yl]acetate (1.82 g, 6.9 mmol, 60%). MS (ES) m/e 265 [M+1]$^+$.

d) [6-(methyloxy)-3-oxo-2,3-dihydro-4H-1,4-benzoxazin-4-yl]acetic acid, lithium salt

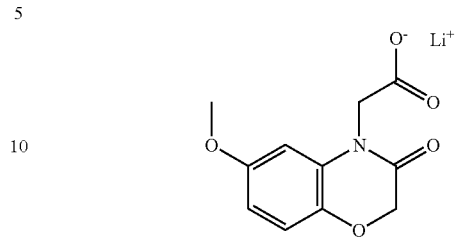

Ethyl[6-(methyloxy)-3-oxo-2,3-dihydro-4H-1,4-benzoxazin-4-yl]acetate (1.82 g, 6.9 mmol) was dissolved in 25 mL of tetrahydrofuran and treated with a solution of LiOH (0.0919 g, 3.84 mmol) dissolved in 1 mL of water. The reaction was stirred vigorously at room temperature for one hour before it was determined to be complete by LCMS (two Aquasil C18, 20×1 mm columns were run in sequence, 4 minutes at 0.1 mL/min, 1-99% CH$_3$CN/H$_2$O with 0.018% trifluoroacetic acid, ES) Rt=1.0 min and m/e 238 [M+1]$^+$. The solvent was removed by rotary evaporation and the residue was suspended in 25 mL of anhydrous dioxane. The dioxane was then removed by rotary evaporation to drive off any traces of water and the residue was dried under high vacuum, resulting in [6-(methyloxy)-3-oxo-2,3-dihydro-4H-1,4-benzoxazin-4-yl]acetic acid as the lithium salt (1.6 g, 6.5 mmol, 95%) in the form of an off-white solid. MS (ES) m/e 238 [M+H]$^+$.

e) N-[1-(4-biphenylyl)-2-(1-pyrrolidinyl)ethyl]-N-methyl-2-[6-(methyloxy)-3-oxo-2,3-dihydro-4H-1,4-benzoxazin-4-yl]acetamide

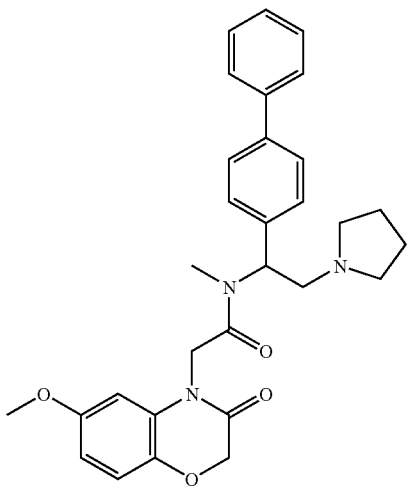

[1-(4-biphenylyl)-2-(1-pyrrolidinyl)ethyl]methylamine (0.107 g, 0.38 mmol) and [6-(methyloxy)-3-oxo-2,3-dihydro-4H-1,4-benzoxazin-4-yl]acetic acid, lithium salt, (0.1 g, 0.42 mmol) were dissolved in 1 mL of dimethylformamide. Triethylamine (0.16 mL, 1.1 mmol) was delivered to the room temperature mixture, and the solution was allowed to stir for several minutes before a separate solution of 1H-1,2,3-benzotriazol-1-yloxy-tris(dimethylamino)-phosphonium hexafluorophosphate (BOP reagent, 0.186 g, 0.42 mmol) dissolved in 1 mL of dimethylformamide was added to the mixture at room temperature. The reaction was maintained at that temperature for 72 hours, before it was determined to be complete by LCMS (two Aquasil C18, 20×1 mm columns were run in sequence, 4 minutes at 0.1 mL/min, 1-99% CH₃CN/H₂O with 0.018% trifluoroacetic acid, ES) Rt=1.9 min and m/e 500 [M+1]⁺. The reaction mixture was filtered through a 0.45 μm PTFE Acrodisk and the crude residue was purified by prep HPLC (Phenomenex, 75×30 mm, 40 mL/min, A: acetonitrile (0.1% TFA) B: water (0.1% TFA), A: 10 to 99% over 15 min, UV detection at 214 nm). The TFA salt form of the desired product was dissolved in a minimal amount of methanol and acidified with a solution on 4 M hydrochloric acid in dioxane. The mixture was concentrated using rotary evaporation and then placed under high vacuum to give the title compound as the HCl salt (0.065 g, 0.13 mmol, 31%) in the form of a pale purple amorphous solid. MS (ES) m/e 500 [M+H]⁺.

Example 256

N-[1-(4-biphenylyl)-2-(1-pyrrolidinyl)ethyl]-N-methyl-2-{3-oxo-6-[(trifluoromethyl)oxy]-2,3-dihydro-4H-1,4-benzoxazin-4-yl}acetamide

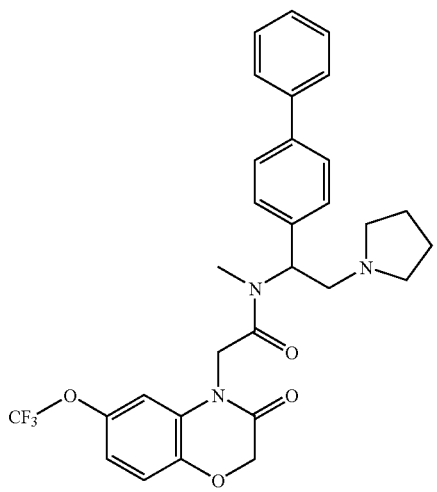

a) 2-bromo-N-{2-hydroxy-5-[(trifluoromethyl)oxy]phenyl}acetamide

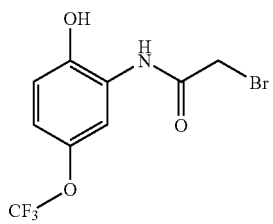

2-amino-4-[(trifluoromethyl)oxy]phenol (3.0 g, 15.5 mmol) was dissolved in 100 mL of chloroform. 54 mL of saturated sodium bicarbonate solution was added and the new bi-phase mixture was stirred vigorously and cooled to 0° C. using an ice bath. Bromoacetylbromide (2.1 mL, 23.3 mmol) was added drop-wise. Fifteen minutes later the solution was removed from the ice bath and maintained at room temperature for 2 hours before it was determined to be complete by LCMS (two Aquasil C18, 20×1 mm columns were run in sequence, 4 minutes at 0.1 mL/min, 1-99% CH₃CN/H₂O with 0.018% trifluoroacetic acid, ES) Rt=1.77 min and m/e 314 [M+1]⁺. The organic layer was separated and the aqueous phase was extracted with 100 mL of chloroform. The combined organic phases were dried over Na₂SO₄, filtered and concentrated to give 2-bromo-N-{2-hydroxy-5-[(trifluoromethyl)oxy]phenyl}acetamide (4.23 g, 13.5 mmol, 87%) as a brown amorphous solid. MS (ES) m/e 314 [M+H]⁺.

b) 6-[(trifluoromethyl)oxy]-2H-1,4-benzoxazin-3(4H)-one

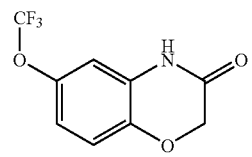

2-bromo-N-{2-hydroxy-5-[(trifluoromethyl)oxy]phenyl}acetamide (4.23 g, 13.5 mmol), was dissolved in 140 mL of anhydrous dimethylformamide under argon. Potassium carbonate was added and suspended in the solution at room temperature. The mixture was warmed to 85° C. and was refluxed for one hour. HPLC (Eclipse XDB-C18, 4.6× 250 mm, 5 micron, 1-99% CH₃CN/H₂O with 0.1% trifluoroacetic acid) indicated that all of the starting material (Rt=6.5 min) was consumed and a new single peak formed (Rt=6.2 min). The mixture was allowed to cool to room temperature before it was diluted with 600 mL of ethyl acetate and washed with water (2×150 mL) and brine (2×150 mL). The organic phase was dried over Na₂SO₄, filtered and concentrated to give 6-[(trifluoromethyl)oxy]-2H-1,4-benzoxazin-3(4H)-one (2.86 g, 12.3 mmol, 91%) as a brown amorphous solid. MS (ES) m/e 233 [M+H]⁺.

c) Ethyl {3-oxo-6-[(trifluoromethyl)oxy]-2,3-dihydro-4H-1,4-benzoxazin-4-yl}acetate

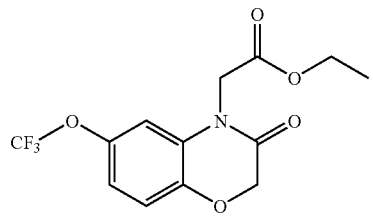

A solution of 6-[(trifluoromethyl)oxy]-2H-1,4-benzoxazin-3(4H)-one (2.86 g, 12.3 mmol) dissolved in 13 mL of anhydrous tetrahydrofuran was added drop-wise to a mixture of sodium hydride (60% by weight in mineral oil, 0.54 g, 13.5 mmol) suspended in 26 mL of anhydrous tetrahydrofuran under argon. The mixture was allowed to stir at room temperature for 10 minutes and then ethyl bromoacetate (1.63 mL, 14.7 mmol) was added to the mixture and stirred vigorously for 1.5 hours before it was determined to be complete by LCMS (two Aquasil C18, 20×1 mm columns were run in sequence, 4 minutes at 0.1 mL/min, 1-99% CH₃CN/H₂O with 0.018% trifluoroacetic acid, ES) Rt=2.77 min and m/e 320 [M+1]⁺. The reaction was quenched by adding 5 mL of a 4 M solution of hydrochloric acid in dioxane. After allowing the mixture to stir for one hour, all of the volatiles were removed by rotary evaporation, and the crude residue was purified by silica gel chromatography (120 g Redisep column, silica, 40 um, 60 Å, 50 mL/min, A: methylene chloride, B: methanol, B: 0% to 35% over 30 min; detection at 214 nm) to give ethyl {3-oxo-6-[(trifluoromethyl)oxy]-2,3-dihydro-4H-1,4-benzoxazin-4-yl}acetate (2.85 g, 8.9 mmol, 73%) as an orange oil. MS (ES) m/e 320 [M+1]$^+$.

d) {3-oxo-6-[(trifluoromethyl)oxy]-2,3-dihydro-4H-1,4-benzoxazin-4-yl}acetic acid

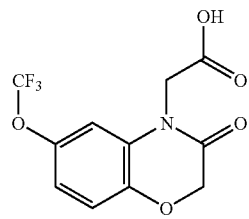

Ethyl {3-oxo-6-[(trifluoromethyl)oxy]-2,3-dihydro-4H-1,4-benzoxazin-4-yl}acetate (2.85 g, 9.0 mmol) was dissolved in 30 mL of tetrahydrofuran and treated with a solution of LiOH (0.283 g, 9.8 mmol) dissolved in 3 mL of water. The reaction was stirred vigorously at room temperature for one hour before it was determined to be complete by HPLC (Eclipse XDB-C18, 4.6×250 mm, 5 micron, 1-99% CH$_3$CN/H$_2$O with 0.1% trifluoroacetic acid). The chromatogram indicated that all of the starting material was consumed and converted to a mixture of the desired product (Rt=5.92 min) and a di-acid form of the product (Rt=5.65 min) resulting from the benzoxazinone ring opening. The solvent was removed by rotary evaporation and the residue was then dissolved in 250 mL of ethyl acetate. The organic layer was washed with a 10% hydrochloric acid solution (3×75 mL) and the organic phase was then dried over Na$_2$SO$_4$, filtered and concentrated to give {3-oxo-6-[(trifluoromethyl)oxy]-2,3-dihydro-4H-1,4-benzoxazin-4-yl}acetic acid (2.23 g, 7.7 mmol, 85%) as a brown solid. MS (ES) m/e 292 [M+H]$^+$.

e) N-[1-(4-biphenylyl)-2-(1-pyrrolidinyl)ethyl]-N-methyl-2-{3-oxo-6-[(trifluoromethyl)oxy]-2,3-dihydro-4H-1,4-benzoxazin-4-yl}acetamide

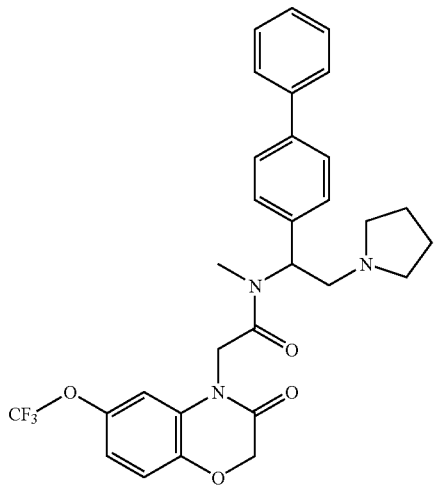

[1-(4-biphenylyl)-2-(1-pyrrolidinyl)ethyl]methylamine (0.087 g, 0.31 mmol) and {3-oxo-6-[(trifluoromethyl)oxy]-2,3-dihydro-4H-1,4-benzoxazin-4-yl}acetic acid (0.1 g, 0.34 mmol) were dissolved in 1 mL of dimethylformamide. Triethylamine (0.13 mL, 0.93 mmol) was delivered to the room temperature mixture, and the solution was allowed to stir for several minutes before a separate solution of 1H-1,2,3-benzotriazol-1-yloxy-tris(dimethylamino)-phosphonium hexafluorophosphate (BOP reagent, 0.150 g, 0.34 mmol) dissolved in 1 mL of dimethylformamide was added at room temperature to the mixture. The reaction was maintained at that temperature for 18 hours, before it was determined to be complete by LCMS (two Aquasil C18, 20×1 mm columns were run in sequence, 4 minutes at 0.1 mL/min, 1-99% CH$_3$CN/H$_2$O with 0.018% trifluoroacetic acid, ES) Rt=2.0 min and m/e 554 [M+1]$^+$. The reaction mixture was filtered through a 0.45 μm PTFE Acrodisk and the crude residue was purified by prep HPLC (Waters, 50×100 mm, 84 mL/min, A: acetonitrile B: water (pH=10, NH$_4$OH), A: 10 to 99% over 15 min, UV detection at 214 nm) to give the title compound (0.087 g. 0.16 mmol, 46%) as an off-white amorphous solid. MS (ES) m/e 554 [M+H]$^+$.

Example 257

N-[1-(4-biphenylyl)-2-(4-morpholinyl)ethyl]-N-methyl-2-{3-oxo-6-[(trifluoromethyl)oxy]-2,3-dihydro-4H-1,4-benzoxazin-4-yl}acetamide

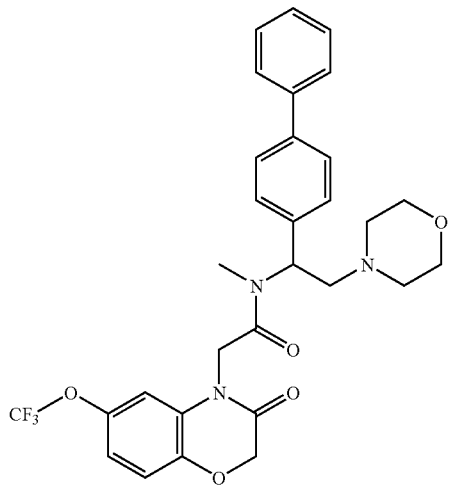

[1-(4-biphenylyl)-2-(4-morpholinyl)ethyl]methylamine (0.1 g, 0.34 mmol) and {3-oxo-6-[(trifluoromethyl)oxy]-2,3-dihydro-4H-1,4-benzoxazin-4-yl}acetic acid (0.108 g, 0.37 mmol) were dissolved in 1 mL of dimethylformamide. Triethylamine (0.13 mL, 0.93 mmol) was delivered to the room temperature mixture, and the solution was allowed to stir for several minutes before a separate solution of 1H-1,2,3-benzotriazol-1-yloxy-tris(dimethylamino)-phosphonium hexafluorophosphate (BOP reagent, 0.164 g, 0.37 mmol) dissolved in 1 mL of dimethylformamide was added to the mixture at room temperature. The reaction was maintained at that temperature for 18 hours, before it was determined to be complete by LCMS (two Aquasil C18, 20×1 mm columns were run in sequence, 4 minutes at 0.1 mL/min, 1-99% CH$_3$CN/H$_2$O with 0.018% trifluoroacetic acid, ES) Rt=2.52 min and m/e 570 [M+1]$^+$. The reaction mixture was filtered through a 0.45 μm PTFE Acrodisk and the crude residue was purified by prep HPLC (Waters, 50×100 mm, 84 mL/min, A: acetonitrile B: water (pH=10, NH$_4$OH), A: 10 to 99% over 15 min, UV detection at 214 nm) to give the title compound (0.089 g. 0.16 mmol, 42%) as an off-white amorphous solid. MS (ES) m/e 570 [M+H]⁺.

Example 258

N-[1-(4-biphenylyl)-2-(1-pyrrolidinyl)ethyl]-N-methyl-2-[7-(methyloxy)-3-oxo-6-(trifluoromethyl)-2,3-dihydro-4H-1,4-benzoxazin-4-yl]acetamide

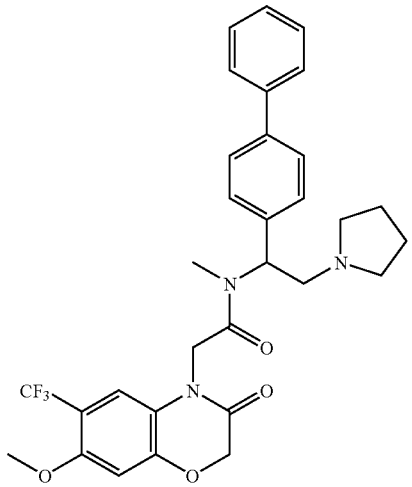

a) Ethyl {[5-(methyloxy)-2-nitro-4-(trifluoromethyl)phenyl]oxy}acetate

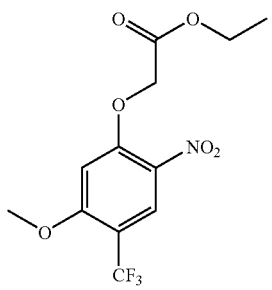

5-(methyloxy)-2-nitro-4-(trifluoromethyl)phenol (0.5 g, 2.1 mmol) was dissolved in 1 mL of dimethylformamide under argon. Potassium carbonate was added and the mixture was allowed to stir for 5 minutes before ethyl bromoacetate (2.3 mL, 21.0 mmol) was slowly delivered to the flask. The mixture was warmed to 80° C. and maintained at that temperature for one hour. The reaction was determined to be complete by LCMS (two Aquasil C18, 20×1 mm columns were run in sequence, 4 minutes at 0.1 mL/min, 1-99% CH₃CN/H₂O with 0.018% trifluoroacetic acid, ES) Rt=2.1 min and m/e 324 [M+1]⁺. The mixture was allowed to cool to room temperature before it was diluted with 50 mL of ethyl acetate. The organic layer was washed with water (3×20 mL) and brine (3×20 mL). The organic phase was dried over Na₂SO₄, filtered and concentrated to give ethyl {[5-(methyloxy)-2-nitro-4-(trifluoromethyl)phenyl]oxy}acetate (0.71 g, 2.2 mmol, 95%) as a brown amorphous solid. MS (ES) m/e 324 [M+H]⁺.

b) 7-(methyloxy)-6-(trifluoromethyl)-2H-1,4-benzoxazin-3(4H)-one

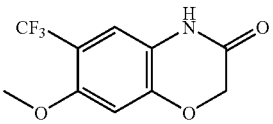

Ethyl {[5-(methyloxy)-2-nitro-4-(trifluoromethyl)phenyl]oxy}acetate (0.71 g, 2.2 mmol), was dissolved in 20 mL of ethanol. Tin chloride dihydrate (2.97 g, 12.5 mmol) was added to the solution and the mixture was stirred and maintained at room temperature for 18 hours. HPLC (Eclipse XDB-C18, 4.6×250 mm, 5 micron, 1-99% CH₃CN/H₂O with 0.1% trifluoroacetic acid) indicated that all of the starting material (Rt=7.65 min) was consumed and a new single peak formed (Rt=5.9 min). The mixture was allowed to cool to room temperature before all volatiles were removed by rotary evaporation. The crude residue was dissolved in 100 mL of ethyl acetate and washed with 10% hydrochloric acid solution (3×30 mL). The organic layer was dried over Na₂SO₄, filtered and concentrated. The crude material was purified by silica gel chromatography (40 g Redisep column, silica, 40 um, 60 Å, 35 mL/min, A: hexanes, B: ethyl acetate, B: 0% to 85% over 40 min; detection at 214 nm) to give 7-(methyloxy)-6-(trifluoromethyl)-2H-1,4-benzoxazin-3(4H)-one (0.39 g, 1.6 mmol, 73%) as an off-white amorphous solid. MS (ES) m/e 248 [M+H]⁺.

c) Ethyl[7-(methyloxy)-3-oxo-6-(trifluoromethyl)-2,3-dihydro-4H-1,4-benzoxazin-4-yl]acetate

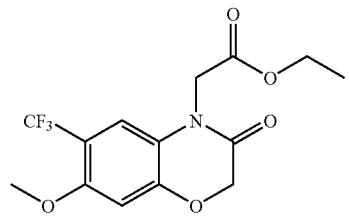

A solution of 7-(methyloxy)-6-(trifluoromethyl)-2H-1,4-benzoxazin-3(4H)-one (0.39 g, 1.6 mmol) dissolved in 1 mL of anhydrous tetrahydrofuran was added drop-wise to a mixture of sodium hydride (60% by weight in mineral oil, 0.068 g, 1.7 mmol) suspended in 2 mL of anhydrous tetrahydrofuran under argon. The mixture was allowed to stir at room temperature for 10 minutes and then ethyl bromoacetate (0.21 mL, 1.9 mmol) was added to the mixture and stirred vigorously for 18 hours before it was determined to be complete by LCMS (two Aquasil C18, 20×1 mm columns were run in sequence, 4 minutes at 0.1 mL/min, 1-99% CH₃CN/H₂O with 0.018% trifluoroacetic acid, ES) Rt=2.0 min and m/e 334 [M+1]⁺. The reaction was quenched by adding 5 mL of a 4 M solution of hydrochloric acid in dioxane. After allowing the mixture to stir for one hour, all of the volatiles were removed by rotary evaporation, and the crude residue was purified by silica gel chromatography (40 g Redisep column, silica, 40 um, 60 Å, 35 mL/min, A: methylene chloride, B: methanol, B: 0% to 10% over 30 min; detection at 214 nm) to give ethyl [7-(methyloxy)-3-oxo-6-(trifluoromethyl)-2,3-dihydro-4H-

1,4-benzoxazin-4-yl]acetate (0.36 g, 1.1 mmol, 69%) of an off-white amorphous solid. MS (ES) m/e 334 [M+1]+.

d) [7-(methyloxy)-3-oxo-6-(trifluoromethyl)-2,3-dihydro-4H-1,4-benzoxazin-4-yl]acetic acid

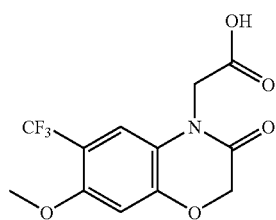

Ethyl[7-(methyloxy)-3-oxo-6-(trifluoromethyl)-2,3-dihydro-4H-1,4-benzoxazin-4-yl]acetate (0.36 g, 1.1 mmol) was dissolved in 4 mL of tetrahydrofuran and treated with a solution of LiOH (0.028 g, 1.2 mmol) dissolved in 0.5 mL of water. The reaction was stirred vigorously at room temperature for 18 hours before it was determined to be complete by LCMS (two Aquasil C18, 20×1 mm columns were run in sequence, 4 minutes at 0.1 mL/min, 1-99% CH$_3$CN/H$_2$O with 0.018% trifluoroacetic acid, ES) Rt=1.62 min and m/e 306 [M+1]+. The solvent was removed by rotary evaporation and the residue was then dissolved in 50 mL of ethyl acetate. The organic layer was washed with a 10% hydrochloric acid solution (3×10 mL) and the organic phase was then dried over Na$_2$SO$_4$, filtered and concentrated to give [7-(methyloxy)-3-oxo-6-(trifluoromethyl)-2,3-dihydro-4H-1,4-benzoxazin-4-yl]acetic acid (0.31 g, 1.0 mmol, 91%) as an off-white amorphous solid. MS (ES) m/e 306 [M+H]+.

e) N-[1-(4-biphenylyl)-2-(1-pyrrolidinyl)ethyl]-N-methyl-2-[7-(methyloxy)-3-oxo-6-(trifluoromethyl)-2,3-dihydro-4H-1,4-benzoxazin-4-yl]acetamide

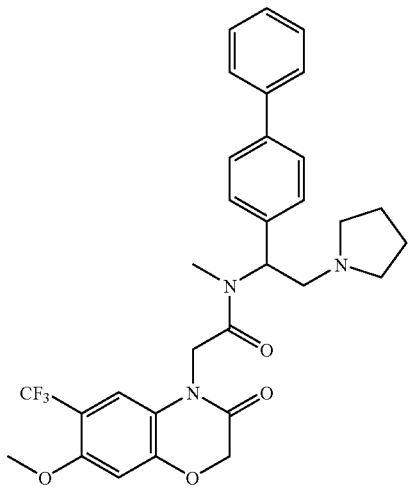

[1-(4-biphenylyl)-2-(1-pyrrolidinyl)ethyl]methylamine (0.084 g, 0.30 mmol) and [7-(methyloxy)-3-oxo-6-(trifluoromethyl)-2,3-dihydro-4H-1,4-benzoxazin-4-yl]acetic acid (0.1 g, 0.33 mmol) were dissolved in 1 mL of dimethylformamide. Triethylamine (0.13 mL, 0.9 mmol) was delivered to the room temperature mixture, and the solution was allowed to stir for several minutes before a separate solution of 1H-1,2,3-benzotriazol-1-yloxy-tris(dimethylamino)-phosphonium hexafluorophosphate (BOP reagent, 0.146 g, 0.33 mmol) dissolved in 1 mL of dimethylformamide was added to the mixture at room temperature. The reaction was maintained at that temperature for 18 hours, before it was determined to be complete by LCMS (two Aquasil C18, 20×1 mm columns were run in sequence, 4 minutes at 0.1 mL/min, 1-99% CH$_3$CN/H$_2$O with 0.018% trifluoroacetic acid, ES) Rt=2.1 min and m/e 568 [M+1]+. The reaction mixture was filtered through a 0.45 µm PTFE Acrodisk and the crude residue was purified by prep HPLC (Waters, 50×100 mm, 84 mL/min, A: acetonitrile B: water (pH=10, NH$_4$OH), A: 10 to 99% over 15 min, UV detection at 214 nm) to give the title compound (0.070 g. 0.12 mmol, 41%) as an off-white amorphous solid. MS (ES) m/e 568 [M+H]+.

Example 259

N-[1-(4-biphenylyl)-2-(1-pyrrolidinyl)ethyl]-N-methyl-2-[5-(methyloxy)-2-oxo-1,3-benzoxazol-3(2H)-yl]acetamide

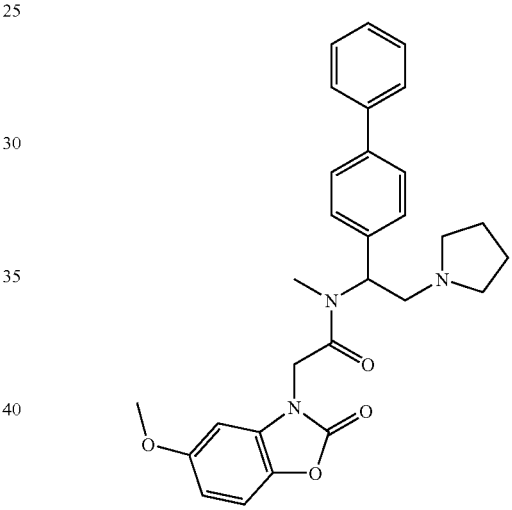

a) 2-amino-4-(methyloxy)phenol, HCl salt

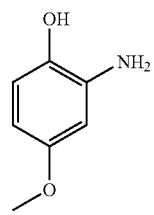

A 1 L round bottom 3-neck flask equipped with a magnetic stir bar was charged with 4-methoxy-2-nitrophenol (10.0 g, 59.0 mmol) and 10% Pd/C (1 g, 10% by weight) under argon. Ethyl acetate (200 mL) was then added very slowly to the mixture under argon. The mixture was stirred vigorously at room temperature for several minutes before 1.8 mL of concentrated hydrochoric acid was added. The argon was evacuated from the flask under reduced pressure and the flask was then charged with 1 atm of hydrogen gas and stirred for 18 hours at room temperature before its progress was checked by HPLC (Eclipse XDB-C18, 4.6×250 mm, 5 micron, 1-99% $CH_3CN/H_2O$ with 0.1% trifluoroacetic acid). The chromatogram indicated that all of the starting material (Rt=5.9 min) was consumed and a new single peak had formed (Rt=2.3 min). The reaction was filtered through 10 g plug of Celite. The organic filtrate was then concentrated by rotary evaporation to give 2-amino-4-(methyloxy)phenol as the HCl salt (6.62 g, 38 mmol, 64%) in the form of a brown amorphous solid. MS (ES) m/e 140 [M+H]$^+$.

b) 5-(methyloxy)-1,3-benzoxazol-2(3H)-one

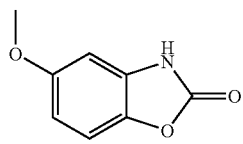

2-amino-4-(methyloxy)phenol, HCl salt (1.0 g, 5.7 mmol) was dissolved in 20 mL of anhydrous tetrahydrofuran under argon. The mixture was heated to reflux (70° C.) and then 1,1'-carbonyldiimidazole (1.2 g, 7.4 mmol) was slowly added in small portions over a one hour period. After the addition was complete, the reaction continued to reflux for another 2.5 hours, before it was determined to be complete by LCMS (two Aquasil C18, 20×1 mm columns were run in sequence, 4 minutes at 0.1 mL/min, 1-99% $CH_3CN/H_2O$ with 0.018% trifluoroacetic acid, ES) Rt=1.0 min and m/e 166 [M+1]$^+$. The mixture was allowed to cool to room temperature before all volatiles were removed by rotary evaporation. The crude residue was dissolved in 100 mL of ethyl ether and washed with water (3×30 mL) and brine (3×30 mL). The organic layer was dried over $Na_2SO_4$, filtered and concentrated to give 5-(methyloxy)-1,3-benzoxazol-2(3H)-one (0.78 g, 4.7 mmol, 82%) as an orange amorphous solid. MS (ES) m/e 166 [M+H]$^+$.

c) Ethyl[5-(methyloxy)-2-oxo-1,3-benzoxazol-3 (2H)-yl]acetate

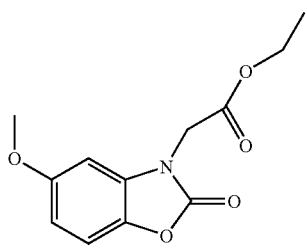

A solution of 5-(methyloxy)-1,3-benzoxazol-2(3H)-one (0.78 g, 4.7 mmol) dissolved in 5 mL of anhydrous tetrahydrofuran was added drop-wise to a mixture of sodium hydride (60% by weight in mineral oil, 0.21 g, 5.2 mmol) suspended in 10 mL of anhydrous tetrahydrofuran under argon. The mixture was allowed to stir at room temperature for 10 minutes and then ethyl bromoacetate (0.63 mL, 5.7 mmol) was added to the mixture and stirred vigorously for 18 hours before it was determined to be complete by LCMS (two Aquasil C18, 20×1 mm columns were run in sequence, 4 minutes at 0.1 mL/min, 1-99% $CH_3CN/H_2O$ with 0.018% trifluoroacetic acid, ES) Rt=1.5 min and m/e 252 [M+1]$^+$. The reaction was quenched by adding 5 mL of a 4 M solution of hydrochloric acid in dioxane. After allowing the mixture to stir for one hour, all of the volatiles were removed by rotary evaporation, and the crude residue was purified by silica gel chromatography (40 g Redisep column, silica, 40 um, 60 Å, 35 mL/min, A: methylene chloride, B: methanol, B: 0% to 10% over 30 min; detection at 214 nm) to give ethyl[5-(methyloxy)-2-oxo-1,3-benzoxazol-3(2H)-yl]acetate (0.98 g, 3.9 mmol, 83%) of a pink oil. MS (ES) m/e 252 [M+1]$^+$.

d) [5-(methyloxy)-2-oxo-1,3-benzoxazol-3(2H)-yl] acetic acid

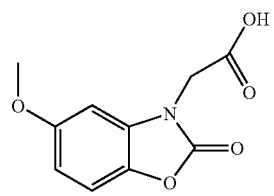

Ethyl[5-(methyloxy)-2-oxo-1,3-benzoxazol-3(2H)-yl]acetate (0.98 g, 3.9 mmol) was dissolved in 12.5 mL of tetrahydrofuran and treated with a solution of LiOH (0.094 g, 3.9 mmol) dissolved in 1.25 mL of water. The reaction was stirred vigorously at room temperature for 18 hours before it was determined to be complete by LCMS (two Aquasil C18, 20×1 mm columns were run in sequence, 4 minutes at 0.1 mL/min, 1-99% $CH_3CN/H_2O$ with 0.018% trifluoroacetic acid, ES) Rt=1.5 min and m/e 224 [M+1]$^+$. The solvent was removed by rotary evaporation and the residue was then dissolved in 100 mL of ethyl acetate. The organic layer was washed with a 10% hydrochloric acid solution (3×30 mL) and the organic phase was then dried over $Na_2SO_4$, filtered and concentrated to give [5-(methyloxy)-2-oxo-1,3-benzoxazol-3(2H)-yl]acetic acid (0.64 g, 2.8 mmol, 73%) as a brown amorphous solid. MS (ES) m/e 224 [M+H]$^+$.

e) N-[1-(4-biphenylyl)-2-(1-pyrrolidinyl)ethyl]-N-methyl-2-[5-(methyloxy)-2-oxo-1,3-benzoxazol-3 (2H)-yl]acetamide

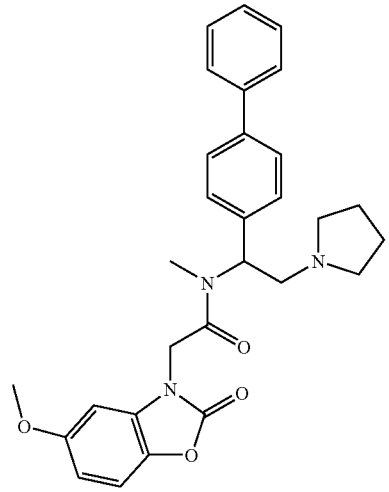

[1-(4-biphenylyl)-2-(1-pyrrolidinyl)ethyl]methylamine (0.12 g, 0.41 mmol) and [5-(methyloxy)-2-oxo-1,3-benzoxazol-3(2H)-yl]acetic acid (0.1 g, 0.43 mmol) were dissolved in 1 mL of dimethylformamide. Triethylamine (0.17 mL, 1.2 mmol) was delivered to the room temperature mixture, and the solution was allowed to stir for several minutes before a separate solution of 1H-1,2,3-benzotriazol-1-yloxy-tris(dimethylamino)-phosphonium hexafluorophosphate (BOP reagent, 0.199 g, 0.45 mmol) dissolved in 1 mL of dimethylformamide was added to the mixture at room temperature. The reaction was maintained at that temperature for 18 hours, before it was determined to be complete by LCMS (two Aquasil C18, 20×1 mm columns were run in sequence, 4 minutes at 0.1 mL/min, 1-99% CH$_3$CN/H$_2$O with 0.018% trifluoroacetic acid, ES) Rt=1.8 min and m/e 486 [M+1]$^+$. The reaction mixture was filtered through a 0.45 μm PTFE Acrodisk and the crude residue was purified by prep HPLC (Phenomenex, 30×75 mm, 40 mL/min, A: acetonitrile (0.1% TFA) B: water (0.1% TFA), A: 10 to 99% over 15 min, UV detection at 214 nm) to give the title compound as the TFA salt (0.076 g. 0.16 mmol, 36%) in the form of a brown amorphous solid. MS (ES) m/e 486 [M+H]$^+$.

Example 260

N-[1-(4-biphenylyl)-2-(1-pyrrolidinyl)ethyl]-N-methyl-2-[2-oxo-5-[(trifluoromethyl)oxy]-1,3-benzoxazol-3(2H)-yl]acetamide

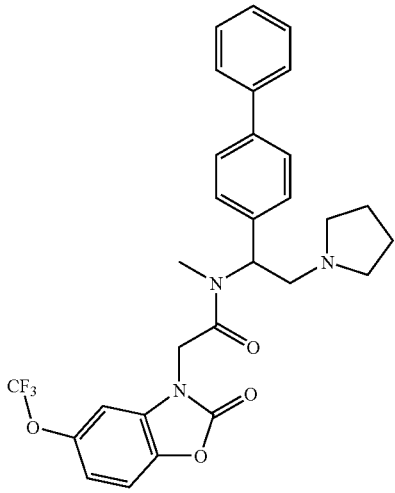

a)
5-[(trifluoromethyl)oxy]-1,3-benzoxazol-2(3H)-one

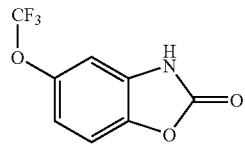

2-amino-4-(trifluoromethyloxy)phenol (1.0 g, 5.2 mmol), was dissolved in 25 mL of anhydrous tetrahydrofuran under argon. The mixture was heated to reflux (70° C.) and then 1,1'-carbonyldiimidazole (1.1 g, 6.7 mmol) was slowly added in small portions over a one hour period. After the addition was complete, the reaction continued to reflux for another 2.5 hours, before it was determined to be complete by LCMS (two Aquasil C18, 20×1 mm columns were run in sequence, 4 minutes at 0.1 mL/min, 1-99% CH$_3$CN/H$_2$O with 0.018% trifluoroacetic acid, ES) Rt=2.3 min and m/e 220 [M+1]$^+$. The mixture was allowed to cool to room temperature before all volatiles were removed by rotary evaporation. The crude residue was dissolved in 100 mL of ethyl ether and washed with water (3×30 mL) and brine (3×30 mL). The organic layer was dried over Na$_2$SO$_4$, filtered and concentrated to give 5-[(trifluoromethyl)oxy]-1,3-benzoxazol-2(3H)-one (1.12 g, 5.1 mmol, 98%) as a brown amorphous solid. MS (ES) m/e 220 [M+H]$^+$.

b) Ethyl[2-oxo-5-[(trifluoromethyl)oxy]-1,3-benzoxazol-3(2H)-yl]acetate

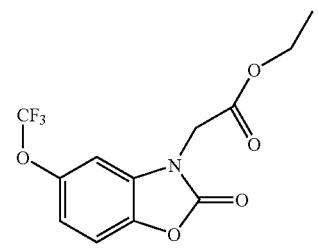

A solution of 5-[(trifluoromethyl)oxy]-1,3-benzoxazol-2(3H)-one (1.12 g, 5.1 mmol) dissolved in 6 mL of anhydrous tetrahydrofuran was added drop-wise to a mixture of sodium hydride (60% by weight in mineral oil, 0.22 g, 5.6 mmol) suspended in 11 mL of anhydrous tetrahydrofuran under argon. The mixture was allowed to stir at room temperature for 10 minutes and then ethyl bromoacetate (0.68 mL, 6.1 mmol) was added to the mixture and stirred vigorously for 18 hours before it was determined to be complete by LCMS (two Aquasil C18, 20×1 mm columns were run in sequence, 4 minutes at 0.1 mL/min, 1-99% CH$_3$CN/H$_2$O with 0.018% trifluoroacetic acid, ES) Rt=2.8 min and m/e 306 [M+1]$^+$. The reaction was quenched by adding 5 mL of a 4 M solution of hydrochloric acid in dioxane. After allowing the mixture to stir for one hour, all of the volatiles were removed by rotary evaporation, and the crude residue was purified by silica gel chromatography (40 g Redisep column, silica, 40 um, 60 Å, 35 mL/min, A: methylene chloride, B: methanol, B: 0% to 35% over 30 min; detection at 214 nm) to give ethyl[2-oxo-5-[(trifluoromethyl)oxy]-1,3-benzoxazol-3(2H)-yl]acetate (0.96 g, 3.0 mmol, 62%) of a pink oil. MS (ES) m/e 306 [M+1]$^+$.

c) [2-oxo-5-[(trifluoromethyl)oxy]-1,3-benzoxazol-3(2H)-yl]acetic acid

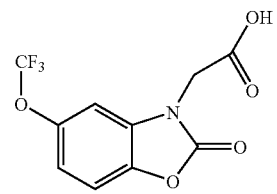

Ethyl[2-oxo-5-[(trifluoromethyl)oxy]-1,3-benzoxazol-3(2H)-yl]acetate (0.96 g, 3.0 mmol) was dissolved in 10 mL of tetrahydrofuran and treated with a solution of LiOH (0.083 g, 3.5 mmol) dissolved in 1.0 mL of water. The reaction was stirred vigorously at room temperature for 18 hours before it was determined to be complete by LCMS (two Aquasil C18, 20×1 mm columns were run in sequence, 4 minutes at 0.1 mL/min, 1-99% CH$_3$CN/H$_2$O with 0.018% trifluoroacetic acid, ES) Rt=2.3 min and m/e 278 [M+1]$^+$. The solvent was removed by rotary evaporation and the residue was then dissolved in 100 mL of ethyl acetate. The organic layer was washed with a 10% hydrochloric acid solution (3×30 mL) and the organic phase was then dried over Na$_2$SO$_4$, filtered and concentrated under vacuum. The crude residue was purified by prep HPLC (Phenomenex, 30×75 mm, 40 mL/min, A: acetonitrile (0.1% TFA) B: water (0.1% TFA), A: 10 to 99% over 15 min, UV detection at 214 nm) to give [2-oxo-5-[(trifluoromethyl)oxy]-1,3-benzoxazol-3(2H)-yl]acetic acid (0.39 g, 1.4 mmol, 47%) as an off-white amorphous solid. MS (ES) m/e 278 [M+H]$^+$.

d) N-[1-(4-biphenylyl)-2-(1-pyrrolidinyl)ethyl]-N-methyl-2-[2-oxo-5-[(trifluoromethyl)oxy]-1,3-benzoxazol-3(2H)-yl]acetamide

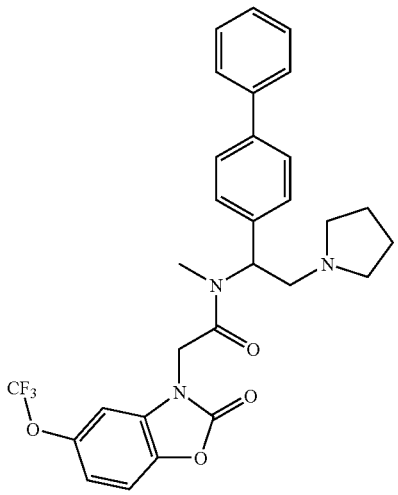

[1-(4-biphenylyl)-2-(1-pyrrolidinyl)ethyl]methylamine (0.09 g, 0.32 mmol) and [2-oxo-5-[(trifluoromethyl)oxy]-1,3-benzoxazol-3(2H)-yl]acetic acid (0.097 g, 0.35 mmol) were dissolved in 1 mL of dimethylformamide. Triethylamine (0.13 mL, 0.96 mmol) was delivered to the room temperature mixture, and the solution was allowed to stir for several minutes before a separate solution of 1H-1,2,3-benzotriazol-1-yloxy-tris(dimethylamino)-phosphonium hexafluorophosphate (BOP reagent, 0.155 g, 0.32 mmol) dissolved in 1 mL of dimethylformamide was added to the mixture at room temperature. The reaction was maintained at that temperature for 18 hours, before it was determined to be complete by LCMS (two Aquasil C18, 20×1 mm columns were run in sequence, 4 minutes at 0.1 mL/min, 1-99% CH$_3$CN/H$_2$O with 0.018% trifluoroacetic acid, ES) Rt=2.0 min and m/e 541 [M+1]$^+$. The reaction mixture was filtered through a 0.45 μm PTFE Acrodisk and the crude residue was purified by prep HPLC (Waters, 30×75 mm, 84 mL/min, A: acetonitrile B: water (pH=10, NH$_4$OH), A: 10 to 99% over 15 min, UV detection at 214 nm) to give the title compound (0.011 g. 0.02 mmol, 6%) as an off-white amorphous solid. MS (ES) m/e 541 [M+H]$^+$.

Example 261

N-[1-(4-biphenylyl)-2-(4-morpholinyl)ethyl]-2-(5,6-dichloro-2-oxo-1(2H)-quinolinyl)-N-methylacetamide

[1-(4-biphenylyl)-2-(4-morpholinyl)ethyl]methylamine (80 mg, 0.26 mmol) was added to a solution of (6,7-dichloro-2-oxo-1(2H)-quinolinyl)acetic acid (50 mg, 0.22 mmol), (benzotriazol-1-yloxy) tris(dimethylamino) phosphoniumhexafluorophosphate (BOP) (110 mg, 0.26 mmol) and diisopropylethylamine (140 mg, 1.1 mmol) in dimethylformamide (DMF) (5 mL). The reaction mixture was stirred at room temperature for 3 h, filtered and solids washed with DMF. The crude mixture was purified by preparative HPLC (YMC CombiPrep ODS-A, 50×20 mm, 20 mL/min, A: acetonitrile B: water, A: 10 to 90% over 10 min, UV detection at 214 nm) to give the title compound (22 mg, 17%), MS (ES) m/e 510 [M+H]$^+$.

Examples 262A and 262B (6,7-dimethyl-2-oxo-1(2H)-quinolinyl)acetic acid (A) (5,6-dimethyl-2-oxo-1(2H)-quinolinyl)acetic acid (B)

A

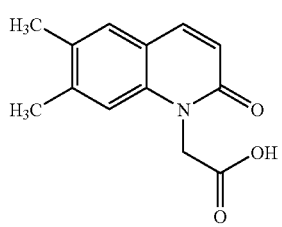

a) (2E)-N-(3,4-dimethylphenyl)-3-phenyl-2-propenamide

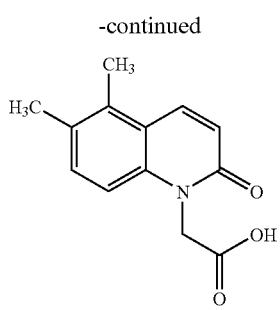

3,4-Dimethylaniline (5.20 g, 42.9 mmol) was dissolved in 150 mL of THF and treated with trans-cinnamoyl chloride (7.5 g, 45 mmol) with vigorous stirring at room temperature. After 2 hours the mixture was quenched with 10 mL of $H_2O$ and extracted with EtOAc (3×100 mL). The combined organics were washed with saturated solution of $Na_2CO_3$, brine, dried over $MgSO_4$ and then concentrated in vacuo to yield the title compound as a pure white crystalline solid (6.2 g, 67%). MS (ES) m/e 252 $[M+H]^+$.

b) 6,7-Dimethyl-2(1H)-quinolinone (A) 5,6-dimethyl-2(1H)-quinolinone (B)

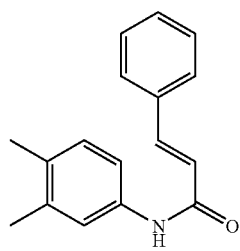

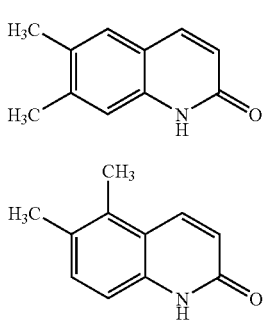

A mixture of (2E)-N-(3,4-dimethylphenyl)-3-phenyl-2-propenamide (5.86 g, 23.3 mmol) and $AlCl_3$ (15.6 g, 116.57 mmol) was heated slowly until the mixture became liquefied and then subsequently congealed to form a solid cake. Ice was slowly added to break up the hardened material. The mixture was vigorously stirred for 2 h. The solid material was collected and washed with 2 N HCl solution, water, and ether to obtain a white mixture of product A and B above (3.8 g, 94%), MS (ES) m/e 176 $[M+H]^+$.

c) Methyl (6,7-dimethyl-2-oxo-1(2H)-quinolinyl)acetate (A) methyl (5,6-dimethyl-2-oxo-1(2H)-quinolinyl)acetate (B)

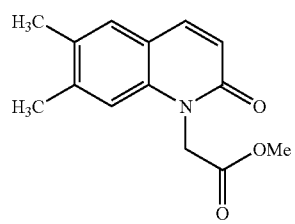

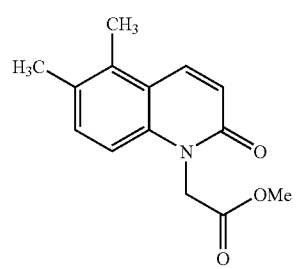

A suspension of NaH (1.75 g, 43.9 mmol) in mineral oil (60%) was added to a mixture of 6,7-dimethyl-2(1H)-quinolinone (A) and 5,6-dimethyl-2(1H)-quinolinone (B) (3.8 g, 21.9 mmol) in THF. The mixture was stirred for 0.5 h and a solution of methyl bromoacetate (4.36 g, 28.5 mmol) was added. The reaction mixture was continued stirring for 3 h, quenched with $H_2O$ and then concentrated in vacuo. The residue was extracted with EtOAc (2×100 mL), washed with a saturated solution of $Na_2CO_3$, brine, dried over $MgSO_4$ and then concentrated in vacuo to yield the title compounds as a white crystalline solid (4.1 g, 76%), MS (ES) m/e 246 $[M+H]^+$.

d) (6,7-dimethyl-2-oxo-1(2H)-quinolinyl)acetic acid (A) (5,6-dimethyl-2-oxo-1(2H)-quinolinyl)acetic acid (B)

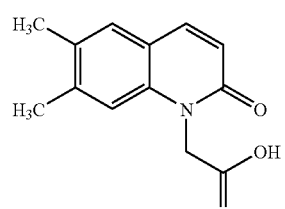

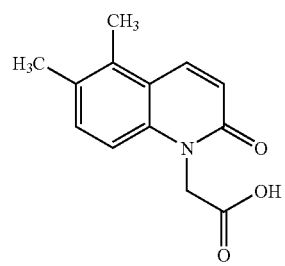

LiOH.H2O (1.7 g, 41 mmol) was added to a solution of (6,7-dichloro-2-oxo-1(2H)-quinolinyl)acetic acid (A) and (5,6-dimethyl-2-oxo-1(2H)-quinolinyl)acetic acid (B) (2.0 g, 8.2 mmol) in MeOH. The resulting reaction mixture was heated under reflux for 2 h and then concentrated in vacuo. The residue was washed with H$_2$O several times and purified by preparative HPLC (YMC CombiPrep ODS-A, 50×20 mm, 20 mL/min, A: acetonitrile B: water, A: 10 to 90% over 10 min, UV detection at 214 nm) to give the title compounds A (0.5 g 25%), B (0.4 g, 21%), MS (ES) m/e 232 [M+H]$^+$ Example 263

N-[1-(4-biphenylyl)-2-(4-morpholinyl)ethyl]-2-(6,7-dimethyl-2-oxo-1(2H)-quinolinyl)-N-methylacetamide

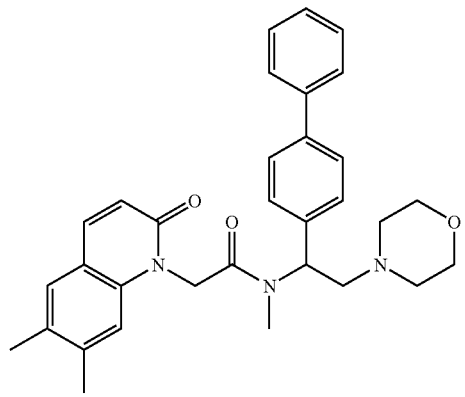

[1-(4-biphenylyl)-2-(4-morpholinyl)ethyl]methylamine (150 mg, 0.52 mmol) was added to a solution of (6,7-dimethyl-2-oxo-1(2H)-quinolinyl)acetic acid (100 mg, 0.43 mmol), (benzotriazol-1-yloxy) tris(dimethylamino) phosphonium-hexafluorophosphate (BOP) (230 mg, 0.52 mmol) and diisopropylethylamine (280 mg, 2.15 mmol) in dimethylformamide (DMF) (5 mL). The reaction mixture was stirred at room temperature for 3 h, filtered and washed with DMF. The crude was purified by preparative HPLC (YMC Combi-Prep ODS-A, 50×20 mm, 20 mL/min, A: acetonitrile B: water, A: 10 to 90% over 10 min, UV detection at 214 nm) to give the title compound (43 mg, 16%), MS (ES) m/e 510 [M+H]$^+$.

Example 264

N-[1-(4-biphenylyl)-2-(4-morpholinyl)ethyl]-2-(5,6-dimethyl-2-oxo-1(2H)-quinolinyl)-N-methylacetamide

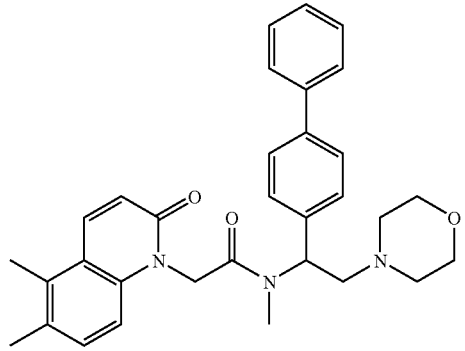

[1-(4-biphenylyl)-2-(4-morpholinyl)ethyl]methylamine (80 mg, 0.26 mmol) was added to a solution of (6,7-dimethyl-2-oxo-1(2H)-quinolinyl)acetic acid (50 mg, 0.22 mmol), (benzotriazol-1-yloxy) tris(dimethylamino) phosphonium-hexafluorophosphate (BOP) (110 mg, 0.26 mmol) and diisopropylethylamine (140 mg, 1.1 mmol) in dimethylformamide (DMF) (5 mL). The reaction mixture was stirred at room temperature for 3 h, filtered and washed with DMF. The crude was purified by preparative HPLC (YMC CombiPrep ODS-A, 50×20 mm, 20 mL/min, A: acetonitrile B: water, A: 10 to 90% over 10 min, UV detection at 214 nm) to give the title compound (22 mg, 17%), MS (ES) m/e 510 [M+H]$^+$.

Example 265

N-[1-(4-biphenylyl)-2-(4-morpholinyl)ethyl]-2-(6,7-dimethyl-2-oxo-1(2H)-quinoxalinyl)-N-methylacetamide

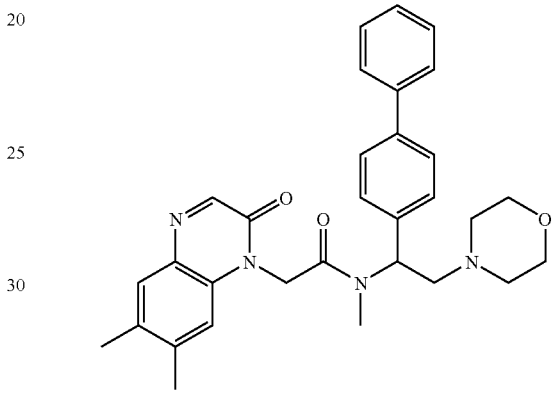

[1-(4-biphenylyl)-2-(4-morpholinyl)ethyl]methylamine (180 mg, 0.62 mmol) was added to a solution of (6,7-dimethyl-2-oxo-1(2H)-quinoxalinyl)acetic acid (120 mg, 0.52 mmol), (benzotriazol-1-yloxy) tris(dimethylamino) phosphonium-hexafluorophosphate (BOP) (270 mg, 0.62 mmol) and diisopropylethylamine (340 mg, 2.6 mmol) in dimethylformamide (DMF) (5 mL). The reaction mixture was stirred at room temperature for 3 h, filtered and washed with DMF. The crude was purified by preparative HPLC (YMC Combi-Prep ODS-A, 50×20 mm, 20 mL/min, A: acetonitrile B: water, A: 10 to 90% over 10 min, UV detection at 214 nm) to give the title compound (43 mg, 14%), MS (ES) m/e 511 [M+H]$^+$.

Example 266 a) (2R)-2-(4-bromophenyl)oxirane

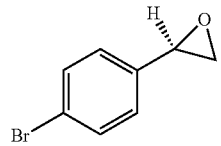

(R,R)-(−)-N,N'-Bis(3,5-di-tert-butyl-salicylidene-1,2-cyclohexane-diaminocobalt(II) (9.7 g, 0.016 mol) was dissolved in 100 mL of toluene in an open flask at 0° C. with magnetic stirring and acetic acid (9.2 mL, 0.16 mol) was added. The bath was removed and then the mixture was maintained at room temperature for 1 h with vigorous stirring. The mixture was concentrated in vacuo to a brown solid, and then the residue was put under high vacuum overnight. The brown residue was dissolved in 100 mL of THF, and to the resulting solution was added to 2-(4-bromophenyl)oxirane (400 g, 2 mol) dissolved in THF (300 mL). The reaction mixture was cooled to 0° C. and distilled water (19.8 g, 1.1 mol) was added slowly into the mixture. The resulting mixture was maintained at room temperature for 16 h with magnetic stirring, concentrated and the 1 L 5% EtOAc/Hexane was added to the residue. The resulting mixture was maintained at room temperature for 1 h with vigorous magnetic stirring. The insoluble solid material was filtered away (100% diol by HPLC). The filtrate was concentrated and dissolved in 1 L hexane. The resulting mixture was maintained at room temperature for 1 h with vigorous magnetic stirring. The insoluble solid was filtered off. The filtrate was concentrated, and put under high vacuum for 2 h to yield a brown oil (250 g, a mixture of desired product, trace amount of diol, and Co Salen catalyst).

b) (1R)-1-(4-bromophenyl)-2-(4-morpholinyl)ethanol

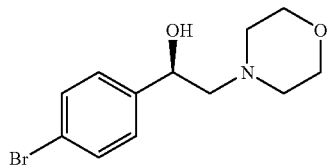

(2R)-2-(4-Bromophenyl)oxirane crude (250 g) was added to morpholine (8 mL, 1 mol) in 100 mL $CH_2Cl_2$ solution at 0° C. with magnetic stirring. Montmorillonite K10 clay (20 g) was added portionwise to the brown mixture and the resulting dark brown mixture was maintained under argon for 60 h at room temperature with magnetic stirring. The clay was filtered off and the filtrate was concentrated to a brown oil. The oil was loaded onto a 3 inch plug of silica gel. 12 L of 30% EtOAc/Hexane was used to elute off less polar impurities and then 40 L of 30%-40% EtOAc/Hexane with 1% ammonia was used to elute off the desired product. The fractions were combined, concentrated, and then crystallized from $Et_2O$. The white crystals were filtered and dried to yield the title compound (109 g, 41.6%). MS (ES) m/e 287 $[M+H]^+$. Chiral HPLC analysis (Chiralpak AD-RH, 5 micron, 150×4.6 mm, mobile phase: 50% CH3CN/50% aqueous borate buffer (pH 9.0), 0.50 mL/min, UV 220 nm, 5 uL inj in MeOH) confirmed the product is a single enantiomer (>99% ee).

c) 4-[(2R)-2-(4-bromophenyl)-2-chloroethyl]morpholine

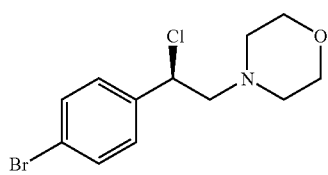

(1R)-1-(4-Bromophenyl)-2-(4-morpholinyl)ethanol (48.5 g, 0.17 mol) was dissolved in 200 mL $CH_2Cl_2$ at room temperature with magnetic stirring and triethylamine (52 mL. 0.37 mol, 2.2 equiv) was added. The resulting solution was cooled to 0° C. and treated with methanesulfonyl chloride (16 mL, 0.20 mol, 1.2 equiv) through an addition funnel. After the addition, the reaction mixture was maintained at 40° C. for 48 h with magnetic stirring. The reaction mixture was concentrated and the residue was partitioned between EtOAc and saturated aqueous $NaHCO_3$. The organic layer was washed with brine, dried over $MgSO_4$, filtered and concentrated. The crude brown oil was purified by silica gel chromatography (800 g silica gel 60, 230-400 mesh, 5% EtOAc/$CH_2Cl_2$ as eluent). Concentration of the pure fractions yielded the title compound as a yellow oil (34.5 g, 67%). MS (ES) m/e 304 $[M+H]^+$.

d) [(1R)-1-(4-bromophenyl)-2-(4-morpholinyl)ethyl]methylamine

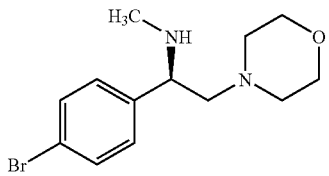

Crude 4-[(2R)-2-(4-Bromophenyl)-2-chloroethyl]morpholine (34.5 g) was dissolved in 200 mL of EtOH at room temperature with magnetic stirring. The resulting solution was cooled to 0° C. and treated with $MeNH_2$ (71 mL, 33 wt % in EtOH) under $N_2$. The reaction flask was capped with a rubber septum and the reaction mixture maintained at room temperature for 48 h. The mixture was then concentrated and the residue was partitioned between EtOAc and saturated aqueous $NaHCO_3$. The organic layer was washed with brine, dried over $MgSO_4$, and filtered. The filtrate was concentrated to yield the title compound as a yellow solid (32 g, 93%). MS (ES) m/e 300 $[M+H]^+$.

e) (1R)—N-methyl-1-[3'-(methyloxy)-4-biphenylyl]-2-(4-morpholinyl)ethanamine

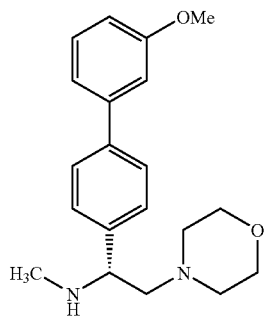

[(1R)-1-(4-Bromophenyl)-2-(4-morpholinyl)ethyl]methylamine (3.5 g, 11.7 mmol) was dissolved in a dioxane/$H_2O$ solution (140 mL, 5:2 volume ratio) at room temperature with magnetic stirring. The resulting solution was treated with 3-methoxylbenzene boronic acid (1.76 g, 12.9 mmol) followed by $K_2CO_3$ (4.85 g, 3.51 mmol) and $PdCl_2$(dppf)$_2$·$CH_2Cl_2$ (0.48 g, 0.59 mmol). The reaction was maintained at 100° C. for 5 h. The reaction mixture was cooled to room

269 temperature and then filtered through celite. The filtrate was concentrated and then partitioned between EtOAc and brine. The organic layer was dried over MgSO₄, and filtered. The filtrate was concentrated, and the residue was purified by silica gel chromatography (120 g Redisep column, silica, 40 um, 60 Å, 80 mL/min, A: MeOH (with 10% NEt₃), B: CH₂Cl₂, A: 2% for 20 min, 5% for 20 min, 10% for 10 min; detection at 254 nm) to give the title compound as a yellow oil (3.3 g, 85%). MS (ES) m/e 327 [M+H]$^+$.

f) 2-(6,7-dichloro-3-oxo-2,3-dihydro-4H-1,4-benzoxazin-4-yl)-N-methyl-N-[(1R)-1-[3'-(methyloxy)-4-biphenylyl]-2-(4-morpholinyl)ethyl]acetamide

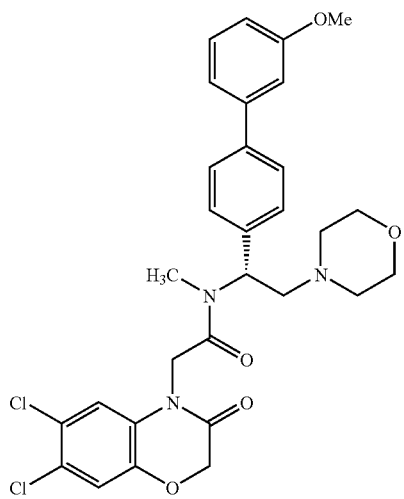

(1R)—N-Methyl-1-[3'-(methyloxy)-4-biphenylyl]-2-(4-morpholinyl)ethanamine (3.3 g, 10 mmol) was dissolved in 100 mL of DMF at room temperature with magnetic stirring. The resulting solution was treated with (6,7-dichloro-3-oxo-2,3-dihydro-4H-1,4-benzoxazin-4-yl)acetic acid (4.3 g, 12 mmol, with 23 wt % LiCl) followed by triethylamine (2.8 mL, 20 mmol) and BOP (5.3 g, 12 mmol). The reaction mixture was maintained at room temperature for 16 h. The reaction mixture was filtered and the filtrate was added slowly to of H₂O (300 mL) with vigorous stirring. The precipitate which formed was collected by filtration and further purified by silica gel chromatography (120 g Redisep column, silica, 40 um, 60 Å, 80 mL/min, A: MeOH (with 10% NEt₃), B: CH₂Cl₂, A: 1% for 20 min, 2% for 20 min, 5% for 10 min; detection at 254 nm). The combined fractions were concentrated, and the resulting residue was triturated with MeOH. The white solid was collected by filtration to give the title compound (2.7 g, 46%). MS (ES) m/e 585 [M+H]$^+$.

270

Example 267

4'-[(1R)-1-[[(6,7-dichloro-3-oxo-2,3-dihydro-4H-1,4-benzoxazin-4-yl)acetyl](methyl)amino]-2-(4-morpholinyl)ethyl]-4-biphenylcarboxamide

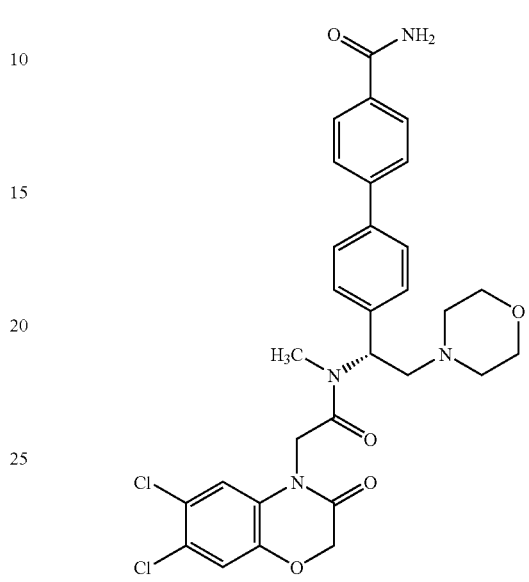

Following the general procedure in example 266 except substituting 4-aminocarbonylphenylboronic acid for 3-methoxylbenzene boronic acid in step e), the title compound was prepared. MS (ES) m/e 597 [M+H]$^+$.

Example 268 (A)

4'-[(1R)-1-[[(6,7-dichloro-3-oxo-2,3-dihydro-4H-1,4-benzoxazin-4-yl)acetyl](methyl)amino]-2-(4-morpholinyl)ethyl]-4-biphenylcarboxylic acid, HCl salt

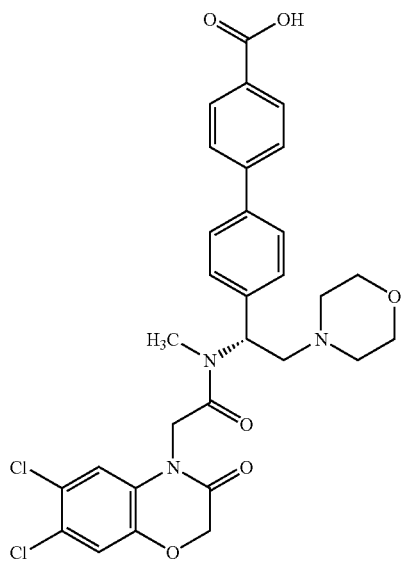

a) N-[(1R)-1-(4-bromophenyl)-2-(4-morpholinyl)ethyl]-2-(6,7-dichloro-3-oxo-2,3-dihydro-4H-1,4-benzoxazin-4-yl)-N-methylacetamide

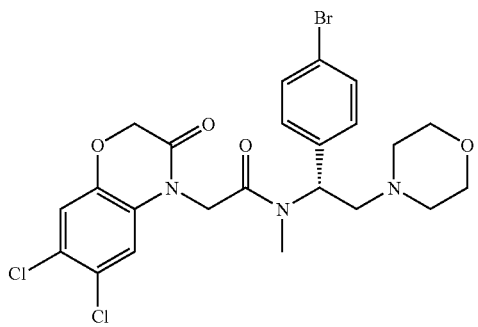

[(1R)-1-(4-Bromophenyl)2-(4-morpholinyl)methylamine (23.95 g, 80 mmol) and (6,7-dichloro-3-oxo-2,3-dihydro-4H-1,4-benzoxazin-4-yl)acetic acid (31.57 g, 88 mmol, 77 wt % pure) were dissolved in a mixture of DMF (200 mL) and dichloromethane (200 mL). (Benzotriazol-1-yloxy)tris(dimethylamino) phosphonium-hexafluorophosphate (BOP) (42.46 g, 96 mmol) was added followed by triethylamine (24.24 g, 240 mmol). The mixture was stirred overnight at room temperature and then concentrated in vacuo. The residue was partitioned between ethyl acetate and 5% sodium carbonate solution upon which a white solid precipitate formed. The solid was filtered off, washed with diethyl ether, and dried in vacuo to yield 40.53 g (73%) of title compound at 80% purity by LC/MS. MS (ES) m/e 556, 558 [M+H]+.

b) 4'-[(1R)-1-[[(6,7-dichloro-3-oxo-2,3-dihydro-4H-1,4-benzoxazin-4-yl)acetyl](methyl)amino]-2-(4-morpholinyl)ethyl]-4-biphenylcarboxylic acid, HCl salt

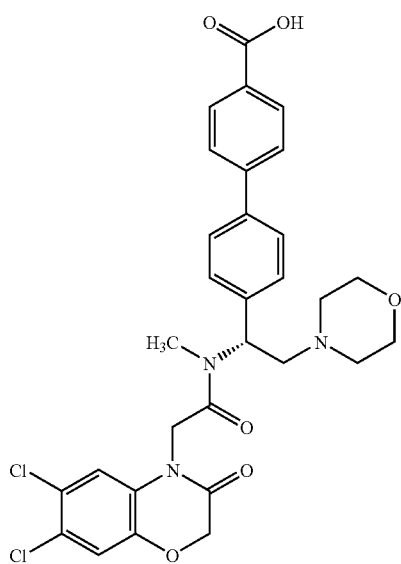

N-[(1R)-1-(4-bromophenyl)-2-(4-morpholinyl)ethyl]-2-(6,7-dichloro-3-oxo-2,3-dihydro-4H-1,4-benzoxazin-4-yl)-N-methylacetamide (40.53 g, 72.7 mmol) and 4-carboxyphenylboronic acid (13.28 g, 80.0 mmol) were dissolved in a dioxane/water solution (700 mL, 5:2 volume ratio) at room temperature with magnetic stirring. Potassium carbonate (30.17 g, 218 mmol) and Pd(dppf)Cl$_2$ (2.97 g, 3.64 mmol) were added. The mixture was stirred at 100° C. for 5 h. The mixture was cooled to room temperature and filtered through a pad of celite. The filter cake was washed with water, and the eluent was added dropwise to an aqueous HCl solution while maintaining the pH at approximately 2. After the addition, the mixture was stirred at room temperature overnight upon which substantial solid had formed. The solid was collected, washed with water, and redissolved in methanol. The methanol solution was filtered through a frit and concentrated to a solid which was washed with water and dried. The solid was redissolved in 1.5 L tetrahydrofuran. The THF solution was heated to reflux. Insoluble material was filtered off and the mixture was cooled to room temperature. The filtered solid was washed with ether and dried in vacuo to yield 15.0 g (35%) of title compound at 97.2% purity by LC/MS.

The mother liquor was concentrated in vacuo and redissolved in minimum amount of tetrahydrofuran. Diethyl ether was added dropwise until a maximum amount of solid formed. The solid was collected by filtration, washed with diethyl ether, and redissolved in minimum amount of dioxane. Water was added dropwise to the dioxane solution. The mixture was stirred at room temperature overnight upon which a solid formed. The solid was collected by filtration and dried in vacuo to yield 13.0 g (30%) of title compound as a yellow solid at 95% purity by LC/MS.

The combined batches of title compound (15.0 g and 13.0 g) were combined and dried further in the vacuum oven at 70° C. overnight to yield 27.79 g of title compound. MS (ES) m/e 598.8 [M+H]+.

Example 268 (B)

Alternate synthetic method for 4'-[(1R)-1-[[(6,7-dichloro-3-oxo-2,3-dihydro-4H-1,4-benzoxazin-4-yl)acetyl](methyl)amino]-2-(4-morpholinyl)ethyl]-4-biphenylcarboxylic acid, HCl salt

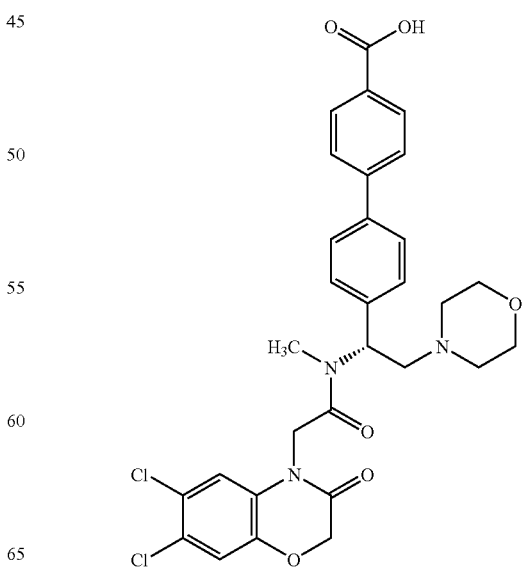

c) (2R)-2-(4-bromophenyl)oxirane

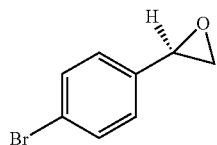

(R,R)-(−)-N,N'-Bis(3,5-di-tert-butyl-salicylidene-1,2-cyclohexane-diaminocobalt(II) (9.7 g, 0.016 mol) was dissolved in 100 mL of toluene in an open flask with magnetic stirring, and acetic acid (9.2 mL, 0.16 mol) was added. The mixture was maintained at room temperature for 1 h with vigorous magnetic stirring. The mixture was concentrated to a brown solid, and then the residue was put under high vacuum overnight. The brown residue was dissolved in 100 mL of THF, and the resulting solution was added to 2-(4-bromophenyl)oxirane (400 g, 2 mol) in 300 mL THF solution. The reaction mixture was cooled to 0° C. Distilled water (19.8 g, 1.1 mol) was added slowly into the mixture. The resulting mixture was maintained at room temperature overnight with magnetic stirring. The reaction mixture was concentrated and 1 L 5% EtOAc/Hexane was added to the residue. The insoluble solid was filtered off (100% diol by HPLC). The filtrate was concentrated, and put under high vacuum for 2 h to yield a brown oil (250 g, a mixture of desired product, trace amount of diol byproduct, and Co Salen catalyst) which was carried on to the next step without further purification.

d) (1R)-1-(4-bromophenyl)-2-(4-morpholinyl)ethanol

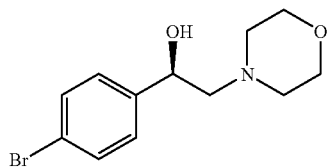

(2R)-2-(4-Bromophenyl)oxirane crude (200 g) was added to 88 mL morpholine (1 mol) in 100 mL CH$_2$Cl$_2$ solution at 0° C. with magnetic stirring, then 20 g of Montmorillonite K10 clay was added portionwise to the brown mixture. The resulting dark brown mixture was maintained under Argon for 60 h at room temperature with magnetic stirring. The clay was filtered off and the filtrate was concentrated to a brown oil. The oil was loaded onto a 3 inch plug of silica gel. 12 L of 30% EtOAc/Hexane was used to elute off less polar impurities. 40 L of 30%-40% EtOAc/Hexane with 1% ammonia was used to elute off the desired product. The fractions were combined, concentrated, and then crystallized in Et$_2$O to afford 61 g of a yellow-white solid. The mother liquor was concentrated and the residue recrystallized from Et$_2$O a second time to afford 48.5 g of solid. The two crops were combined yielding 109 g of the title compound (41.6%). MS (ES) m/e 286, 288 [M+H]$^+$. Chiral HPLC analysis (Chiralpak AD-RH, 5 micron, 150×4.6 mm, mobile phase: 50% CH$_3$CN/50% aqueous borate buffer (pH 9.0), 0.50 mL/min, UV 220 nm, 5 uL inj in MeOH) confirmed the product is a single enantiomer (>99% ee).

e) 4-[(2R)-2-(4-bromophenyl)-2-chloroethyl]morpholine

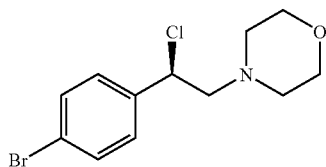

To a stirred 0° C. solution of (1R)-1-(4-Bromophenyl)-2-(4-morpholinyl)ethanol (48.5 g, 0.17 mol) in 200 mL CH$_2$Cl$_2$ was added 52 mL of triethylamine (0.37 mol, 2.2 equiv). Following the addition of triethylamine, 15.8 mL of methanesulfonyl chloride (0.2 mol, 1.2 equiv) was added to the reaction mixture through an addition funnel. After the addition, the reaction mixture was stirred at room temperature overnight. HPLC analysis indicated a 5:1 ratio of starting material to product and an additional 6.58 mL of methanesulfonyl chloride (0.085 mols) and 11.8 mL of triethylamine (0.085 mol) were added. After stirring overnight at ambient temperature, the reaction was heated to 40° C. and stirred for 48 h. The reaction mixture was concentrated, and the residue was partitioned between EtOAc and saturated aqueous NaHCO$_3$. The organic layer was washed with brine, dried over MgSO$_4$, filtered and concentrated. The crude brown oil was purified by silica gel chromatography (800 g silica gel 60, 230-400 mesh, 20-50% EtOAc/CH$_2$Cl$_2$ as eluent). Concentration of the pure fractions yielded the title compound as a yellow oil (34.5 g, 67%). MS (ES) m/e 304, 306 [M+H]$^+$.

f) [(1R)-1-(4-bromophenyl)-2-(4-morpholinyl)ethyl]methylamine

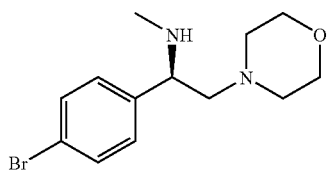

Crude 4-[(2R)-2-(4-Bromophenyl)-2-chloroethyl]morpholine (34.5 g) was dissolved in 200 mL of EtOH at room temperature with magnetic stirring. The resulting solution was cooled to 0° C. and treated with 71 ml of MeNH$_2$ (33 wt % in EtOH) under N$_2$. The reaction flask was capped by a rubber septum, and the reaction mixture was maintained at room temperature for 48 h. The reaction mixture was concentrated, and the residue was partitioned between EtOAc and sat NaHCO$_3$(aq). The organic layer was washed by brine, dried over MgSO$_4$, and filtered. The filtrate was concentrated to yield the title compound as a yellow solid (31.6 g, 93%). MS (ES) m/e 300, 301 [M+H]$^+$.

g) Ethyl 4'-[(1R)-1-(methylamino)-2-(4-morpholinyl)ethyl]-4-biphenylcarboxylate

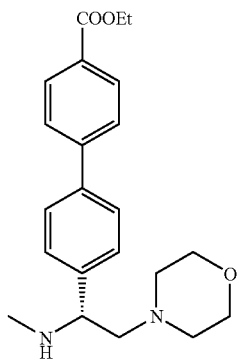

[(1R)-1-(4-Bromophenyl)-2-(4-morpholinyl)ethyl]methylamine (20.0 g, 66.9 mmol) was dissolved in EtOH (500 mL) at room temperature with magnetic stirring. The resulting solution was treated with {4-[(ethyloxy)carbonyl]phenyl}boronic acid (14.5 g, 73.6 mmol) followed by $K_2CO_3$ (27.7 g, 200.7 mmol) and $PdCl_2(dppf)_2 \cdot CH_2Cl_2$ (2.73 g, 3.34 mmol). The reaction was maintained at 80° C. overnight. The reaction mixture was cooled to room temperature and then filtered through celite. The filtrate was concentrated and then partitioned between EtOAc and brine. The organic layer was dried over $MgSO_4$, and filtered. The filtrate was concentrated to give the title compound as a brown oil (26.5 g, 80% purity). MS (ES) m/e 369 [M+H]+.

h) Ethyl 4'-[(1R)-1-[[(6,7-dichloro-3-oxo-2,3-dihydro-4H-1,4-benzoxazin-4-yl)acetyl](methyl)amino]-2-(4-morpholinyl)ethyl]-4-biphenylcarboxylate

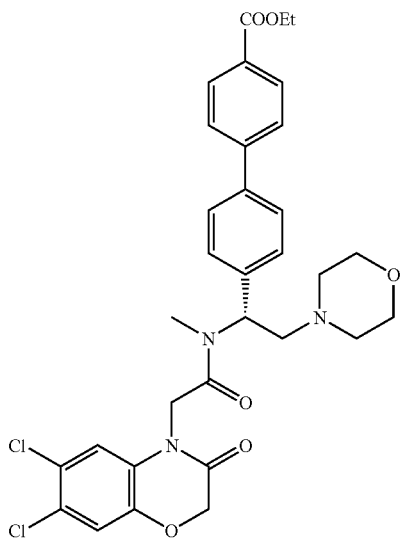

Ethyl 4'-[(1R)-1-(methylamino)-2-(4-morpholinyl)ethyl]-4-biphenylcarboxylate (crude, 26.5 g) was dissolved in 500 mL of DMF at room temperature with magnetic stirring. The resulting solution was treated with (6,7-dichloro-3-oxo-2,3-dihydro-4H-1,4-benzoxazin-4-yl)acetic acid (28.8 g, 80.4 mmol, with 23 wt % LiCl) and cooled to 0° C. To this solution was added triethylamine (20.5 mL, 147.4 mmol) and BOP (35.5 g, 80.4 mmol). The reaction mixture was maintained at room temperature overnight. The reaction mixture was filtered. The filtrate was slowly added to 2500 mL of $H_2O$ with vigorous stirring. The resulting precipitate was collected by filtration and partitioned between 300 mL of brine solution and 1000 mL of DCM. The organic layer was dried over $MgSO_4$, filtered, and concentrated. The brown residue was purified by column chromatography (250 g silica gel 60, 230-400 mesh, 2% MeOH and 0.5% $NEt_3$ in $CH_2Cl_2$ as eluent) to give the title compound as a brown solid (31.3 g, 75% yield). MS (ES) m/e 626 [M+H]+.

i) 4'-[(1R)-1-[[(6,7-dichloro-3-oxo-2,3-dihydro-4H-1,4-benzoxazin-4-yl)acetyl](methyl)amino]-2-(4-morpholinyl)ethyl]-4-biphenylcarboxylic acid, HCl salt

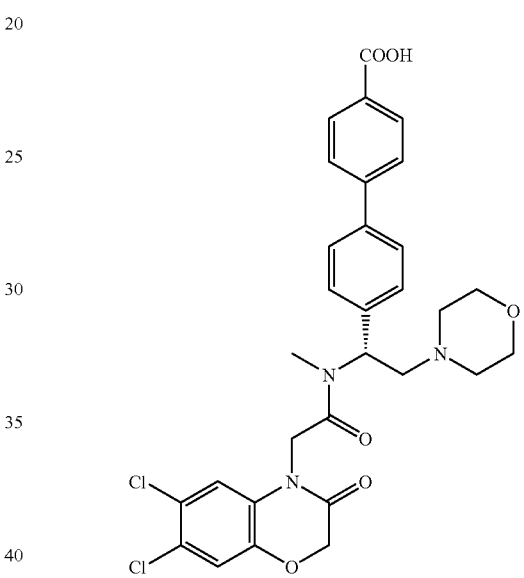

Ethyl 4'-[(1R)-1-[[(6,7-dichloro-3-oxo-2,3-dihydro-4H-1,4-benzoxazin-4-yl)acetyl](methyl)amino]-2-(4-morpholinyl)ethyl]-4-biphenylcarboxylate (30.1 g, 48.2 mmol) was dissolved in 500 mL of THF at room temperature with magnetic stirring. LiOH monohydrate (4.45 g, 106.1 mmol) was dissolved in 60 mL of $H_2O$. The LiOH aqueous solution was added to the ethylcarboxylate in THF solution at room temperature. The resulting solution was maintained at 60° C. overnight with magnetic stirring, cooled to room temperature, and then treated slowly with 16.9 mL of conc. HCl solution. The reaction mixture was maintained at room temperature for 3 h with magnetic stirring. The reaction mixture was slowly added to 1000 mL of $H_2O$ with vigorous stirring. The precipitate was collected by filtration and washed with 300 mL of MeOH. The light yellow solid was recrystallized in a mixture of MeOH/$CH_2Cl_2$ (1:8). The light yellow crystal was collected by filtration, washed with 1000 mL of hot acetone, and dried. The acetone mixture was then concentrated to one third of its original volume, and cooled to room temperature. The light yellow solid was collected by filtration, and then dried in vacuum oven for 16 h to give the title compound (15.5 g, 51% yield). MS (ES) m/e 598 [M+H]+. $^1$H NMR (400 MHz, $d_6$-DMSO) δ 2.74 (s, $d_6$-DMSO residue), 2.96 (s, 3H), 3.21 (m, 2H), 3.52 (d, J=12 Hz, 1H), 3.64 (d, J=12 Hz, 1H), 3.74 (d, J=12 Hz, 1H), 4.03 (m, 3H), 4.26 (m, 2H), 4.80 (m, 3H); 5.13 (d, J=20 Hz, 1H), 6.26 (d, J=8 Hz, 1H), 7.38 (m, 3H), 7.84 (d, J=8 Hz, 4H), 7.97 (s, 1H), 8.03 (d, J=8 Hz, 2H), 11.21 (s, 1H).

$^{13}$C NMR (100 MHz, d$_6$-DMSO) δ 29.26, 43.68, 49.04, 50.36, 53.04, 54.30, 62.55, 62.82, 66.87, 110.76, 113.63, 116.50, 117.50, 117.96, 119.37, 124.72, 126.80, 127.38, 128.03, 129.71, 129.80, 129.94, 135.55, 138.93, 143.34, 143.93, 164.35, 167.04, 167.74.

Example 268 (C)

4'-[(1R)-1-[[(6,7-dichloro-3-oxo-2,3-dihydro-4H-1,4-benzoxazin-4-yl)acetyl](methyl)amino]-2-(4-morpholinyl)ethyl]-4-biphenylcarboxylic acid, Trifluoroacetate salt

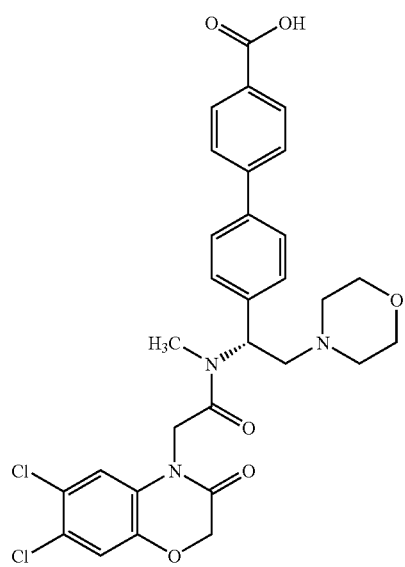

a) N-[(1R)-1-(4-bromophenyl)-2-(4-morpholinyl)ethyl]-2-(6,7-dichloro-3-oxo-2,3-dihydro-4H-1,4-benzoxazin-4-yl)-N-methylacetamide

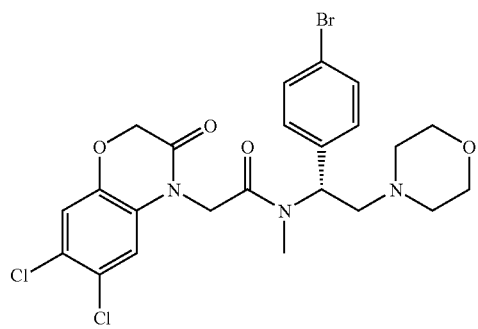

The title compound is the (R) enantiomer of the compound prepared in 130c) and was prepared in the same manner except starting with the product of example 266d)

b) 4'-[(1R)-1-[[(6,7-dichloro-3-oxo-2,3-dihydro-4H-1,4-benzoxazin-4-yl)acetyl](methyl)amino]-2-(4-morpholinyl)ethyl]-4-biphenylcarboxylic acid, Trifluoroacetate salt

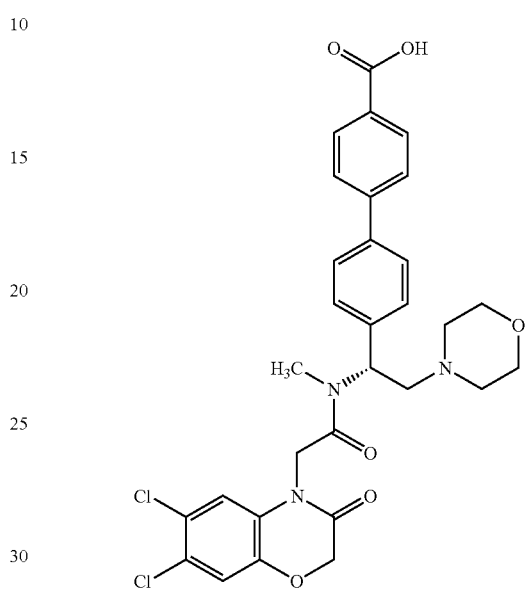

Following the procedure in example 85a) except substituting the product from 268a) for N-[1-(4-bromophenyl)-2-(1-pyrrolidinyl)ethyl]-2-(6,7-dichloro-3-oxo-2,3-dihydro-4H-1,4-benzoxazin-4-yl)-N-methylacetamide and 4-carboxyphenyl boronic acid for 3,4-dimethoxyphenylboronic acid and using modified purification conditions (preparative HPLC (Waters Sunfire RP column, 30×150 mm, 25 mL/min, A: (acetonitrile with 0.1% trifluoroacetic acid) B: (water with 0.1% trifluoroacetic acid), gradient from 10%-85% of A in B, 20 min run)) the title compound was prepared. As is appreciated by those skilled in the art, this analogous example may involve variations in synthetic procedure. MS (ES) m/e 598 [M+H]$^+$.

Example 268 (D)

4'-[(1R)-1-[[(6,7-dichloro-3-oxo-2,3-dihydro-4H-1,4-benzoxazin-4-yl)acetyl](methyl)amino]-2-(4-morpholinyl)ethyl]-4-biphenylcarboxylic acid Free-base is generated by slurrying the HCl salt in solvent followed by sodium hydroxide. One equivalent of sodium hydroxide is used because excess base is known to hydrolyze the amide and open the ring.

Acetonitrile (25.6 mL) is added to crystalline HCl salt of GSK1440115 (5.11 g; 8.05 mmol), and the resulting mixture is heated to 50° C. Aqueous 1M sodium hydroxide is added (1.0 eq; 8.05 mL). The mixture becomes very thick upon addition of base, and additional acetonitrile (15 mL) and water (40 mL) are added. The mixture is cooled to room temperature, and product is filtered and dried overnight in a vacuum oven at 50° C. with a slow nitrogen bleed. The yield is 81.7% (6.58 mmol; 3.94 g) of crystalline free-base.

Example 269

(6,7-dimethyl-2-oxo-1(2H)-quinoxalinyl)acetic acid a) 6,7-dimethyl-2(1H)-quinoxalinone

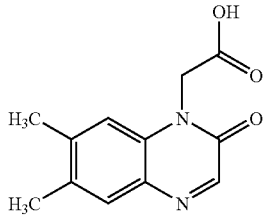

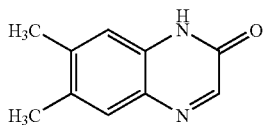

Following the procedure in example 6 except replacing 4,5-dichlorophenylenediamine with 4,5-dimethylphenylenediamine, the title compound was prepared MS (ES) m/e 175 [M+H]+.

b) (6,7-dimethyl-2-oxo-1(2H)-quinoxalinyl)acetic acid

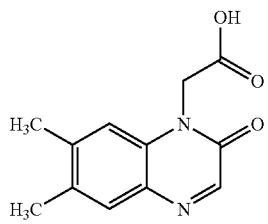

Following the procedure in example 3c and 3d except replacing 6,7-dichloro-2(1H)-quinoxalinone with 6,7-dimethyl-2(1H)-quinoxalinone, the title compound was prepared. MS (ES) m/e 233 [M+H]+.

Examples 270-391

Proceeding in a similar manner as in example 130, but replacing (6,7-dichloro-3-oxo-2,3-dihydro-4H-1,4-benzoxazin-4-yl)acetic acid with the appropriate acids and/or {4[(methylsulfonyl)amino]-phenyl}boronic acid with the appropriate boronic acids, the compounds listed in table 11 were prepared. Note that with N-(cyanomethyl)-N-(3,4-dichlorophenyl)glycine, cross coupling is accompanied by hydrolysis to the primary amide. As is appreciated by those skilled in the art, these analogous examples may involve variations in synthetic procedure.

TABLE 11

| Ex # | Structure | Name | MS [M + H]+ |
|---|---|---|---|
| 270 | 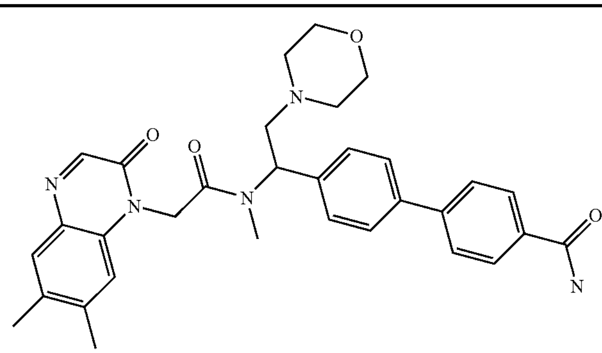 | 4'-[1-[[(6,7-dimethyl-2-oxo-1(2H)-quinoxalinyl)acetyl](methyl)amino]-2-(4-morpholinyl)ethyl]-4-biphenylcarboxamide | 554 |
| 271 | 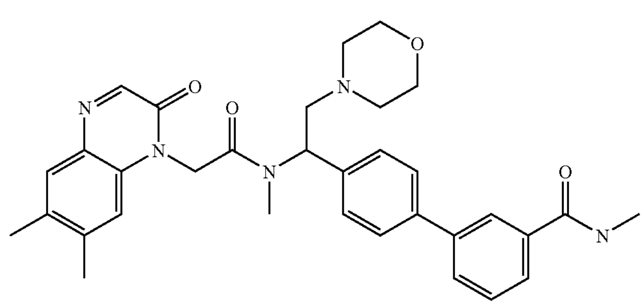 | 4'-[1-[[(6,7-dimethyl-2-oxo-1(2H)-quinoxalinyl)acetyl](methyl)amino]-2-(4-morpholinyl)ethyl]-N-methyl-3-biphenylcarboxamide | 568 |

TABLE 11-continued

| Ex # | Structure | Name | MS [M + H]+ |
|---|---|---|---|
| 272 | 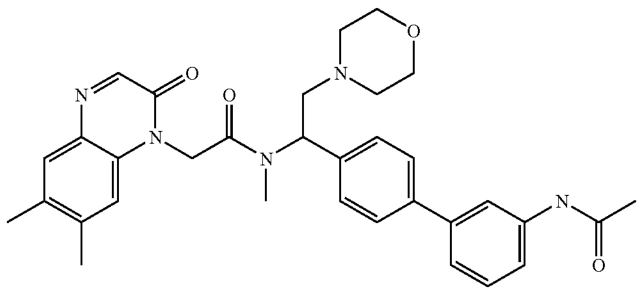 | N-[1-[3'-(acetylamino)-4-biphenylyl]-2-(4-morpholinyl)ethyl]-2-(6,7-dimethyl-2-oxo-1(2H)-quinoxalinyl)-N-methylacetamide | 568 |
| 273 | 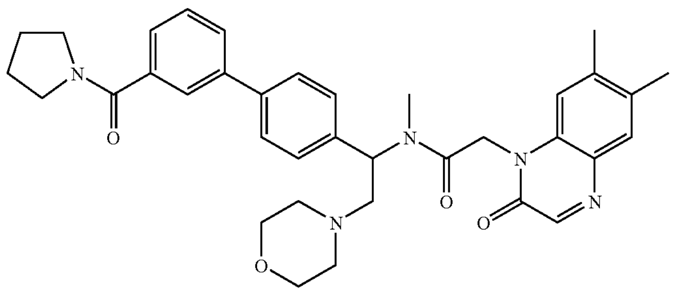 | 2-(6,7-dimethyl-2-oxo-1(2H)-quinoxalinyl)-N-methyl-N-{2-(4-morpholinyl)-1-[3'-(1-pyrrolidinylcarbonyl)-4-biphenylyl]ethyl}acetamide | 608 |
| 274 | 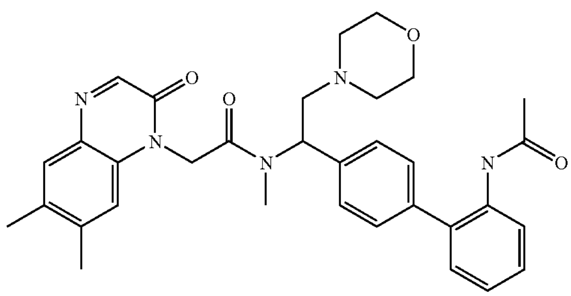 | N-[1-[2'-(acetylamino)-4-biphenylyl]-2-(4-morpholinyl)ethyl]-2-(6,7-dimethyl-2-oxo-1(2H)-quinoxalinyl)-N-methylacetamide | 568 |
| 275 | 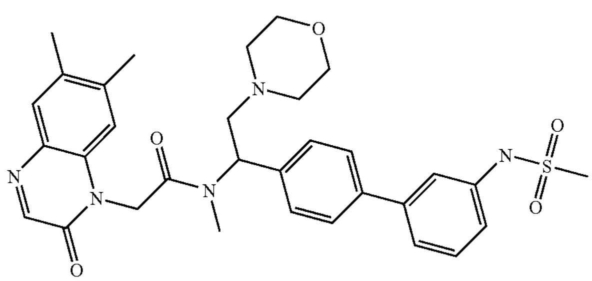 | 2-(6,7-dimethyl-2-oxo-1(2H)-quinoxalinyl)-N-methyl-N-[1-{3'-[(methylsulfonyl)amino]-4-biphenylyl}-2-(4-morpholinyl)ethyl]acetamide | 604 |
| 276 | 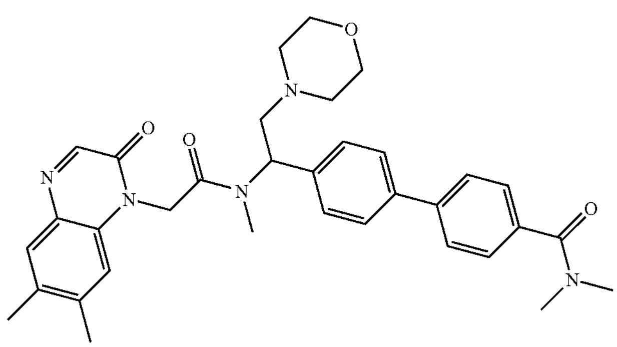 | 4'-[1-[[(6,7-dimethyl-2-oxo-1(2H)-quinoxalinyl)acetyl](methyl)amino]-2-(4-morpholinyl)ethyl]-N,N-dimethyl-4-biphenylcarboxamide | 582 |

TABLE 11-continued

| Ex # | Structure | Name | MS [M + H]+ |
|---|---|---|---|
| 277 | 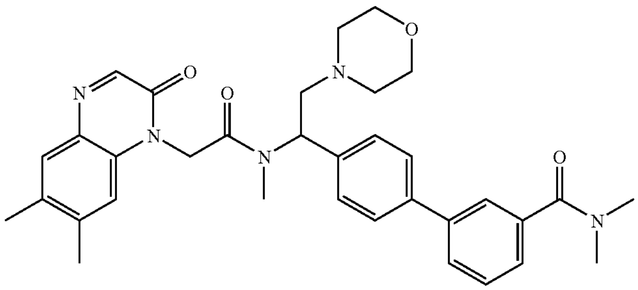 | 4'-[1-[[(6,7-dimethyl-2-oxo-1(2H)-quinoxalinyl)acetyl](methyl)amino]-2-(4-morpholinyl)ethyl]-N,N-dimethyl-3-biphenylcarboxamide | 582 |
| 278 | 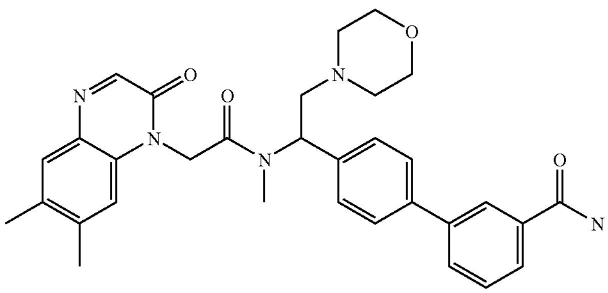 | 4'-[1-[[(6,7-dimethyl-2-oxo-1(2H)-quinoxalinyl)acetyl](methyl)amino]-2-(4-morpholinyl)ethyl]-3-biphenylcarboxamide | 554 |
| 279 | 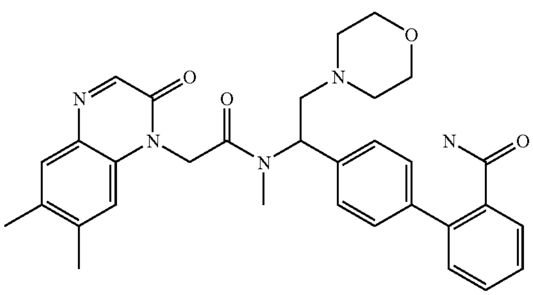 | 4'-[1-[[(6,7-dimethyl-2-oxo-1(2H)-quinoxalinyl)acetyl](methyl)amino]-2-(4-morpholinyl)ethyl]-2-biphenylcarboxamide | 554 |
| 280 | 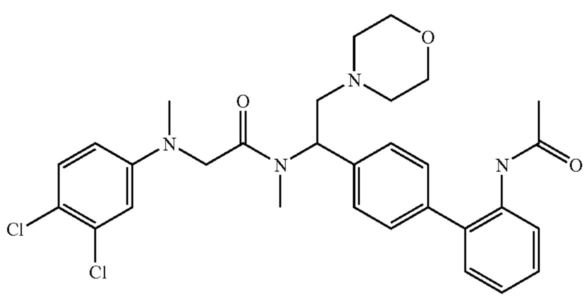 | $N^1$-[1-[2'-(acetylamino)-4-biphenylyl]-2-(4-morpholinyl)ethyl]-$N^2$-(3,4-dichlorophenyl)-$N^1$,$N^2$-dimethylglycinamide | 568 |
| 281 | 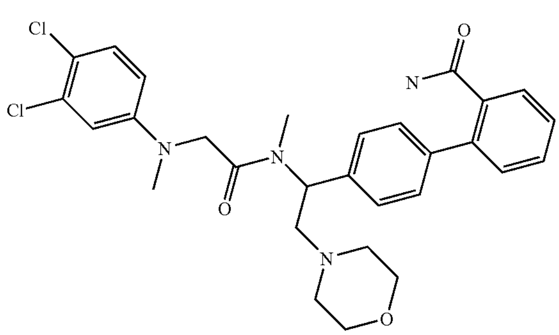 | 4'-[1-[[N-(3,4-dichlorophenyl)-N-methylglycyl](methyl)amino]-2-(4-morpholinyl)ethyl]-2-biphenylcarboxamide | 554 |

TABLE 11-continued

| Ex # | Structure | Name | MS [M + H]+ |
|---|---|---|---|
| 282 | 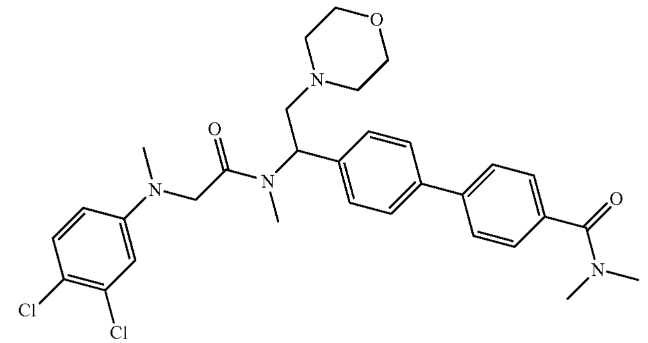 | 4'-[1-[[N-(3,4-dichlorophenyl)-N-methylglycyl](methyl)amino]-2-(4-morpholinyl)ethyl]-N,N-dimethyl-4-biphenylcarboxamide | 583 |
| 283 | 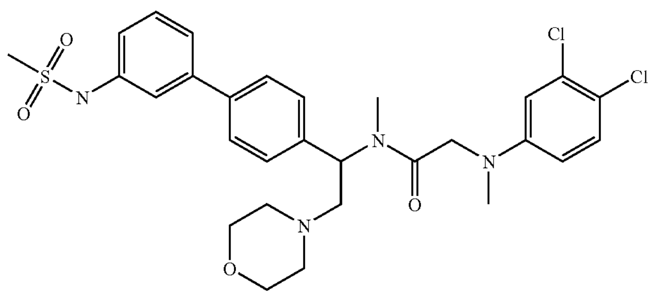 | N²-(3,4-dichlorophenyl)-N¹,N²-dimethyl-N¹-[1-{3'-[(methylsulfonyl)amino]-4-biphenylyl}-2-(4-morpholinyl)ethyl]glycinamide | 604 |
| 284 | 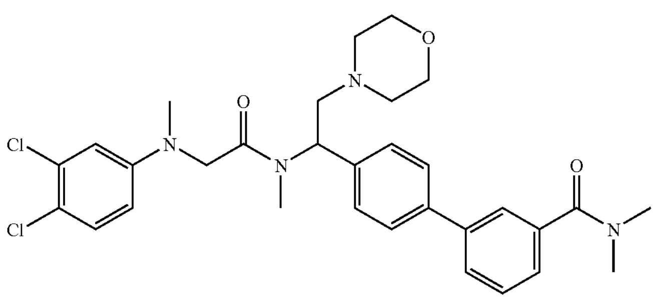 | 4'-[1-[[N-(3,4-dichlorophenyl)-N-methylglycyl](methyl)amino]-2-(4-morpholinyl)ethyl]-N,N-dimethyl-3-biphenylcarboxamide | 583 |
| 285 | 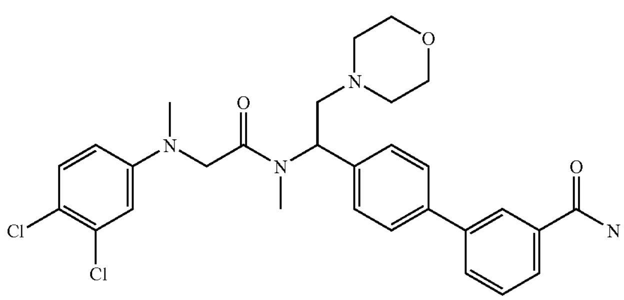 | 4'-[1-[[N-(3,4-dichlorophenyl)-N-methylglycyl](methyl)amino]-2-(4-morpholinyl)ethyl]-3-biphenylcarboxamide | 554 |
| 286 | 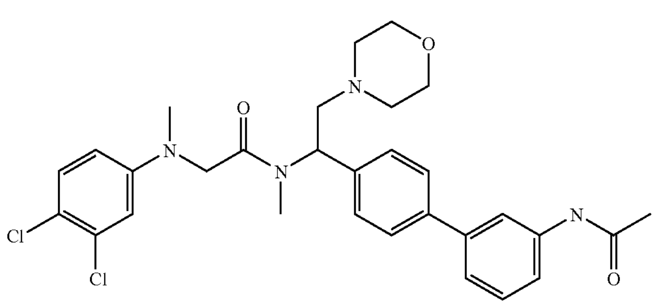 | N¹-[1-[3'-(acetylamino)-4-biphenylyl]-2-(4-morpholinyl)ethyl]-N²-(3,4-dichlorophenyl)-N¹,N²-dimethylglycinamide | 569 |

TABLE 11-continued

| Ex # | Structure | Name | MS [M + H]+ |
|---|---|---|---|
| 287 | 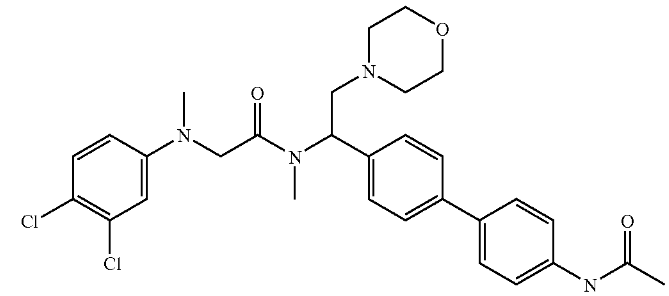 | $N^1$-[1-[4'-(acetylamino)-4-biphenylyl]-2-(4-morpholinyl)ethyl]-$N^2$-(3,4-dichlorophenyl)-$N^1$,$N^2$-dimethylglycinamide | 569 |
| 288 | 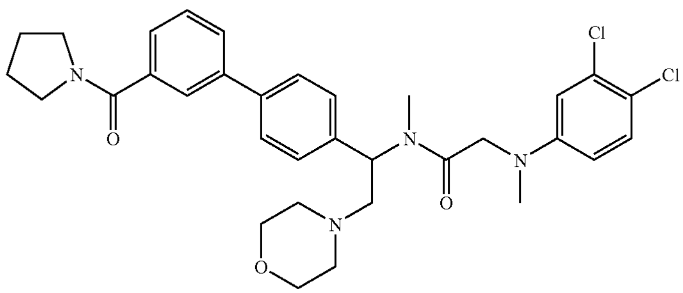 | $N^2$-(3,4-dichlorophenyl)-$N^1$,$N^2$-dimethyl-$N^1$-{2-(4-morpholinyl)-1-[3'-(1-pyrrolidinylcarbonyl)-4-biphenylyl]ethyl}glycinamide | 609 |
| 289 | 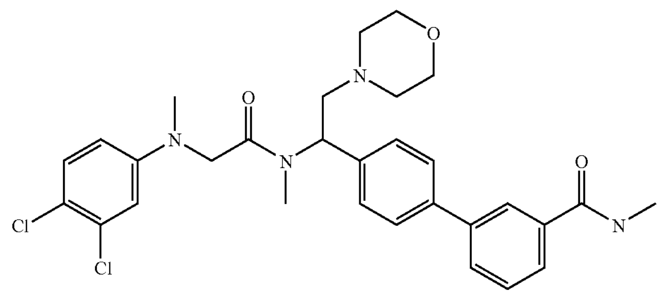 | 4'-[1-[[N-(3,4-dichlorophenyl)-N-methylglycyl](methyl)amino]-2-(4-morpholinyl)ethyl]-N-methyl-3-biphenylcarboxamide | 569 |
| 290 | 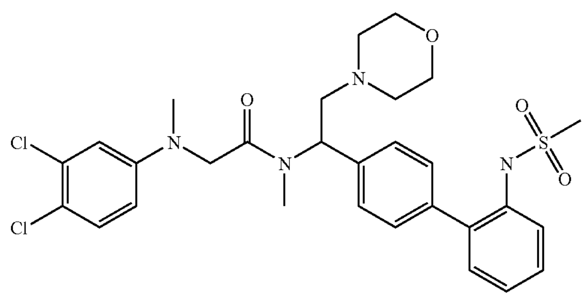 | $N^2$-(3,4-dichlorophenyl)-$N^1$,$N^2$-dimethyl-$N^1$-[1-{2'-[(methylsulfonyl)amino]-4-biphenylyl}-2-(4-morpholinyl)ethyl]glycinamide | 604 |
| 291 | 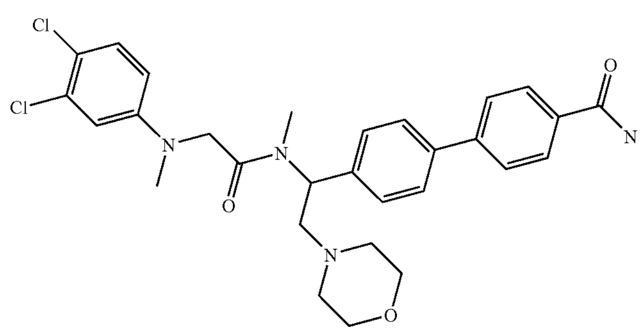 | 4'-[1-[[N-(3,4-dichlorophenyl)-N-methylglycyl](methyl)amino]-2-(4-morpholinyl)ethyl]-4-biphenylcarboxamide | 554 |

TABLE 11-continued

| Ex # | Structure | Name | MS [M + H]+ |
|---|---|---|---|
| 292 | 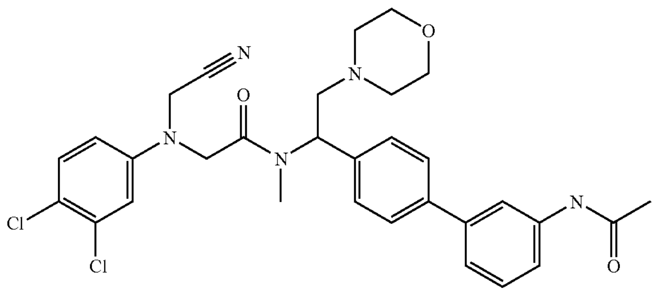 | N1-[1-[3'-(acetylamino)-4-biphenylyl]-2-(4-morpholinyl)ethyl]-N2-(cyanomethyl)-N2-(3,4-dichlorophenyl)-N1-methylglycinamide | 594 |
| 293 | 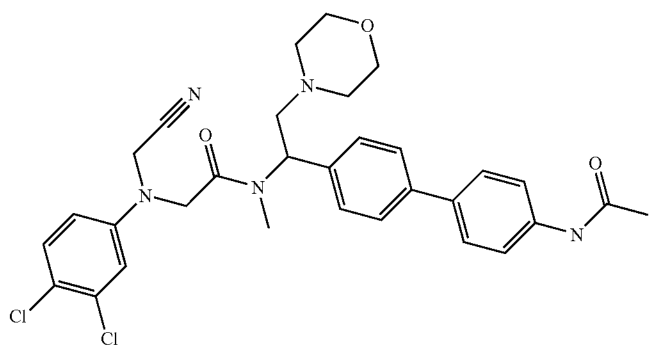 | N1-[1-[4'-(acetylamino)-4-biphenylyl]-2-(4-morpholinyl)ethyl]-N2-(4-morpholinyl)ethyl]-N2-(cyanomethyl)-N2-(3,4-dichlorophenyl)-N1-methylglycinamide | 594 |
| 294 | 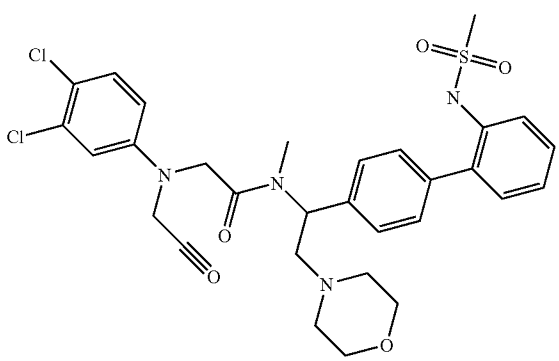 | N2-(cyanomethyl)-N2-(3,4-dichlorophenyl)-N1-methyl-N1-[1-{2'-[(methylsulfonyl)amino]-4-biphenylyl}-2-(4-morpholinyl)ethyl]glycinamide | 630 |
| 295 | 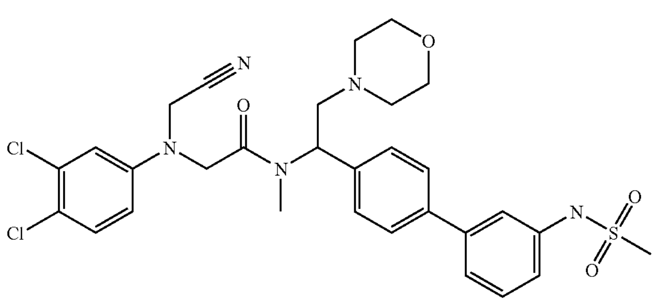 | N2-(cyanomethyl)-N2-(3,4-dichlorophenyl)-N1-methyl-N1-[1-{3'-[(methylsulfonyl)amino]-4-biphenylyl}-2-(4-morpholinyl)ethyl]glycinamide | 630 |

TABLE 11-continued

| Ex # | Structure | Name | MS [M + H]+ |
|---|---|---|---|
| 296 | 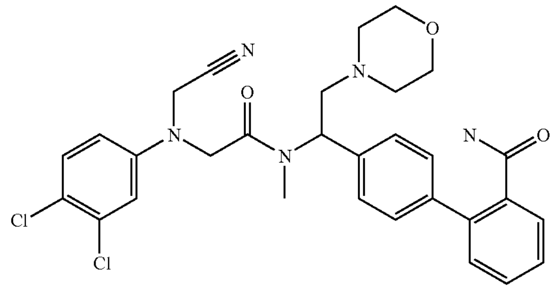 | 4'-[1-[[N-(cyanomethyl)-N-(3,4-dichlorophenyl)glycyl](methyl)amino]-2-(4-morpholinyl)ethyl]-2-biphenylcarboxamide | 580 |
| 297 | 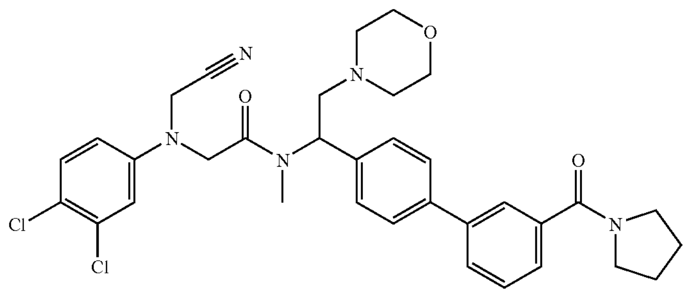 | N²-(cyanomethyl)-N²-(3,4-dichlorophenyl)-N¹-methyl-N¹-{2-(4-morpholinyl)-1-[3'-(1-pyrrolidinylcarbonyl)-4-biphenylyl]ethyl}glycinamide | 634 |
| 298 | 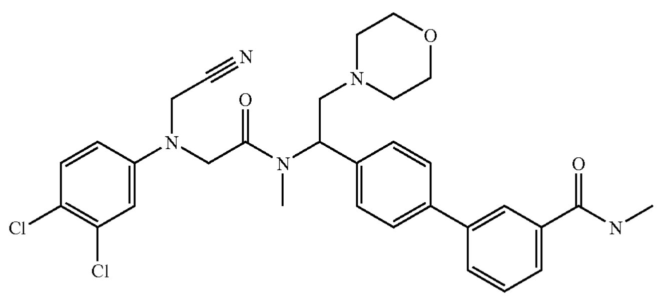 | 4'-[1-[[N-(cyanomethyl)-N-(3,4-dichlorophenyl)glycyl](methyl)amino]-2-(4-morpholinyl)ethyl]-N-methyl-3-biphenylcarboxamide | 594 |
| 299 | 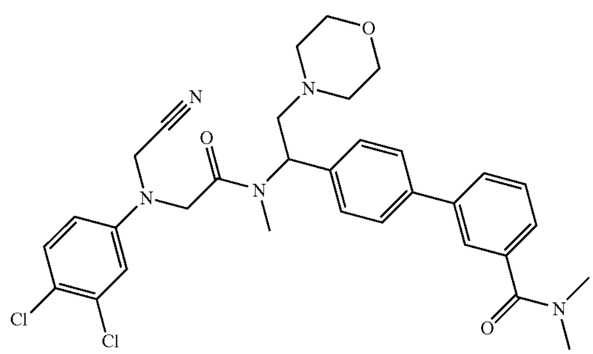 | 4'-[1-[[N-(cyanomethyl)-N-(3,4-dichlorophenyl)glycyl](methyl)amino]-2-(4-morpholinyl)ethyl]-N,N-dimethyl-3-biphenylcarboxamide | 608 |
| 300 | 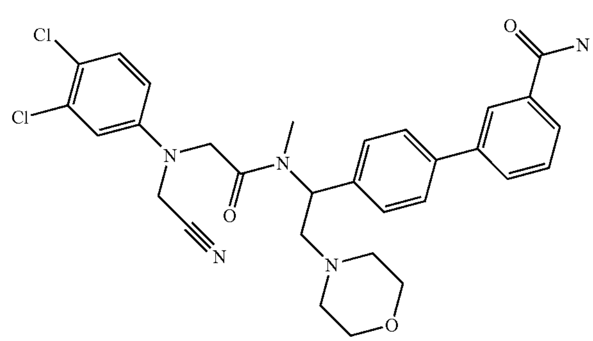 | 4'-[1-[[N-(cyanomethyl)-N-(3,4-dichlorophenyl)glycyl](methyl)amino]-2-(4-morpholinyl)ethyl]-3-biphenylcarboxamide | 580 |

TABLE 11-continued

| Ex # | Structure | Name | MS [M + H]+ |
|---|---|---|---|
| 301 | 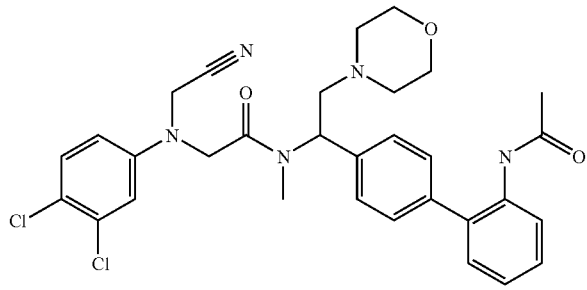 | N¹-[1-[2'-(acetylamino)-4-biphenylyl]-2-(4-morpholinyl)ethyl]-N²-(cyanomethyl)-N²-(3,4-dichlorophenyl)-N¹-methylglycinamide | 594 |
| 302 | 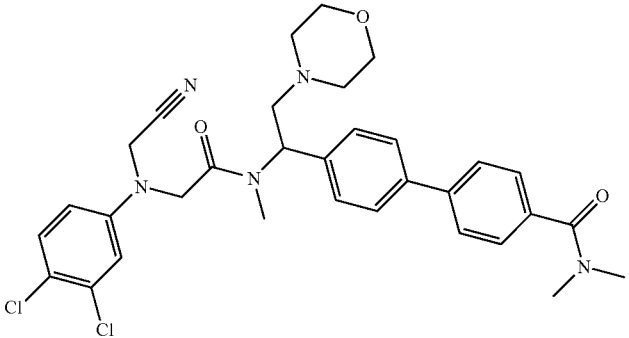 | 4'-[1-[[N-(cyanomethyl)-N-(3,4-dichlorophenyl)glycyl](methyl)amino]-2-(4-morpholinyl)ethyl]-N,N-dimethyl-4-biphenylcarboxamide | 608 |
| 303 | 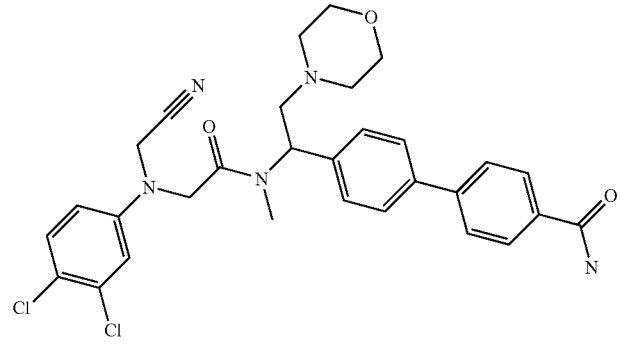 | 4'-[1-[[N-(cyanomethyl)-N-(3,4-dichlorophenyl)glycyl](methyl)amino]-2-(4-morpholinyl)ethyl]-4-biphenylcarboxamide | 580 |
| 304 | 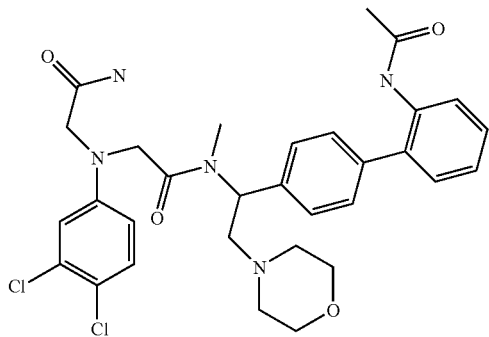 | 2-[{2-[[1-[2'-(acetylamino)-4-biphenylyl]-2-(4-morpholinyl)ethyl](methyl)amino]-2-oxoethyl}(3,4-dichlorophenyl)amino]acetamide | 612 |

TABLE 11-continued

| Ex # | Structure | Name | MS [M + H]+ |
|---|---|---|---|
| 305 | 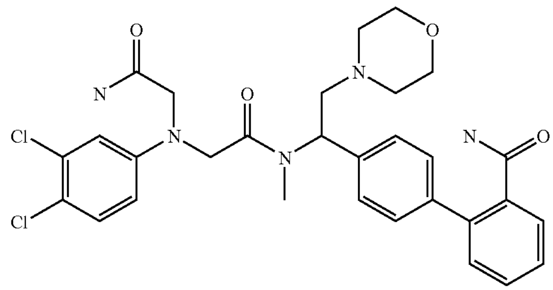 | 4'-[1-[{[(2-amino-2-oxoethyl)(3,4-dichlorophenyl)amino]acetyl}(methyl)amino]-2-(4-morpholinyl)ethyl]-2-biphenylcarboxamide | 598 |
| 306 | 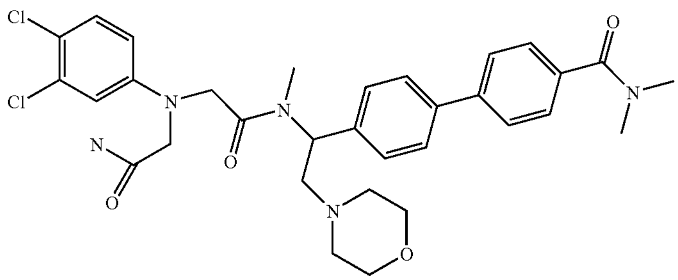 | 4'-[1-[{[(2-amino-2-oxoethyl)(3,4-dichlorophenyl)amino]acetyl}(methyl)amino]-2-(4-morpholinyl)ethyl]-N,N-dimethyl-4-biphenylcarboxamide | 626 |
| 307 | 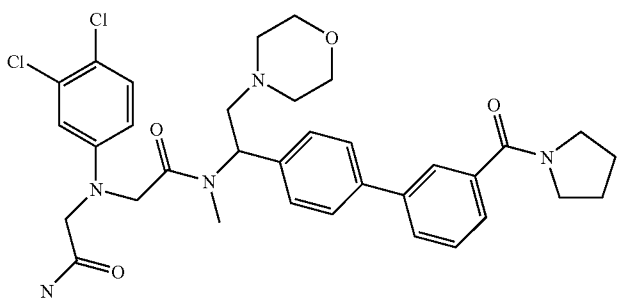 | 2-[(2-amino-2-oxoethyl)(3,4-dichlorophenyl)amino]-N-methyl-N-{2-(4-morpholinyl)-1-[3'-(1-pyrrolidinylcarbonyl)-4-biphenylyl]ethyl}acetamide | 652 |
| 308 | 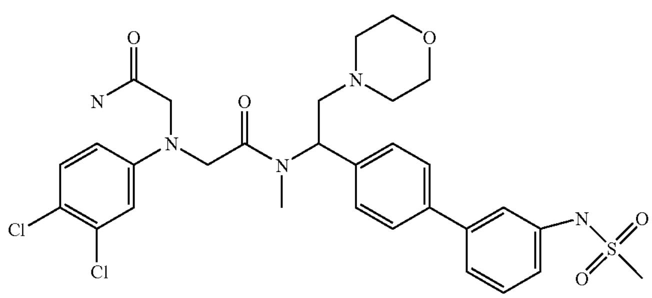 | 2-[(2-amino-2-oxoethyl)(3,4-dichlorophenyl)amino]-N-methyl-N-[1-{3'-[(methylsulfonyl)amino]-4-biphenylyl}-2-(4-morpholinyl)ethyl]acetamide | 648 |
| 309 | 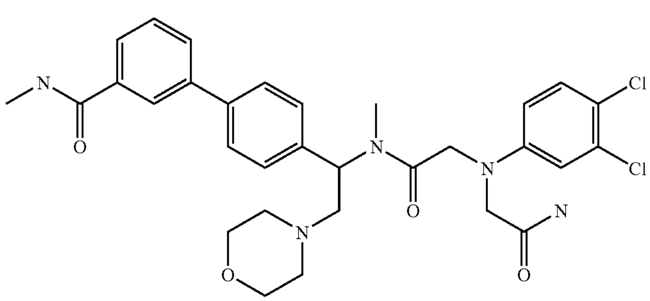 | 4'-[1-[{[(2-amino-2-oxoethyl)(3,4-dichlorophenyl)amino]acetyl}(methyl)amino]-2-(4-morpholinyl)ethyl]-N-methyl-3-biphenylcarboxamide | 612 |

TABLE 11-continued

| Ex # | Structure | Name | MS [M + H]+ |
|---|---|---|---|
| 310 | 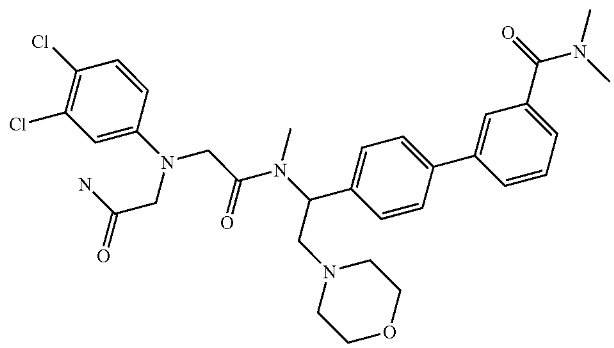 | 4'-[1-[{[(2-amino-2-oxoethyl)(3,4-dichlorophenyl)amino]acetyl}(methyl)amino]-2-(4-morpholinyl)ethyl]-N,N-dimethyl-3-biphenylcarboxamide | 626 |
| 311 | 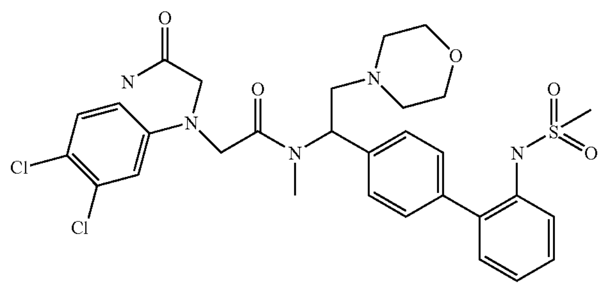 | 2-[(2-amino-2-oxoethyl)(3,4-dichlorophenyl)amino]-N-methyl-N-[1-{2'-[(methylsulfonyl)amino]-4-biphenylyl}-2-(4-morpholinyl)ethyl]acetamide | 648 |
| 312 | 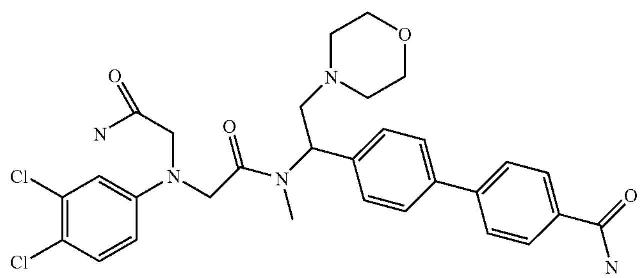 | 4'-[1-[{[(2-amino-2-oxoethyl)(3,4-dichlorophenyl)amino]acetyl}(methyl)amino]-2-(4-morpholinyl)ethyl]-4-biphenylcarboxamide | 598 |
| 313 | 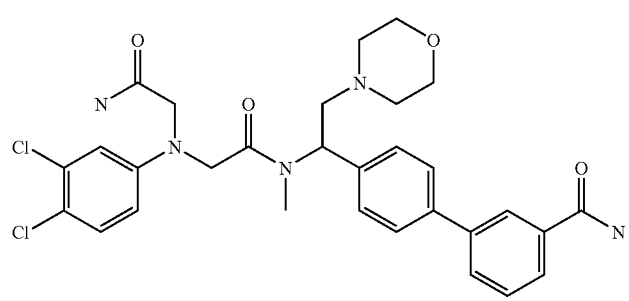 | 4'-[1-[{[(2-amino-2-oxoethyl)(3,4-dichlorophenyl)amino]acetyl}(methyl)amino]-2-(4-morpholinyl)ethyl]-3-biphenylcarboxamide | 598 |
| 314 | 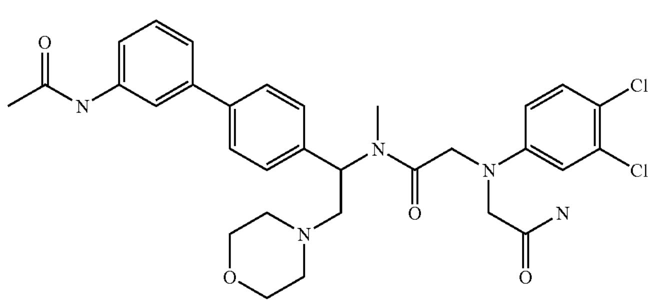 | 2-[{2-[[1-[3'-(acetylamino)-4-biphenylyl]-2-(4-morpholinyl)ethyl](methyl)amino]-2-oxoethyl}(3,4-dichlorophenyl)amino]acetamide | 612 |

TABLE 11-continued

| Ex # | Structure | Name | MS [M + H]+ |
|---|---|---|---|
| 315 | 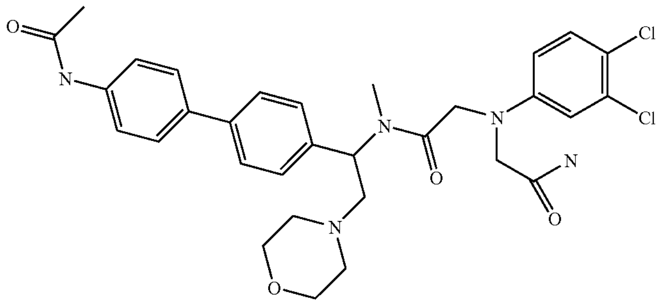 | 2-[{2-[[1-[4'-(acetylamino)-4-biphenylyl]-2-(4-morpholinyl)ethyl](methyl)amino]-2-oxoethyl}(3,4-dichlorophenyl)amino]acetamide | 612 |
| 316 | 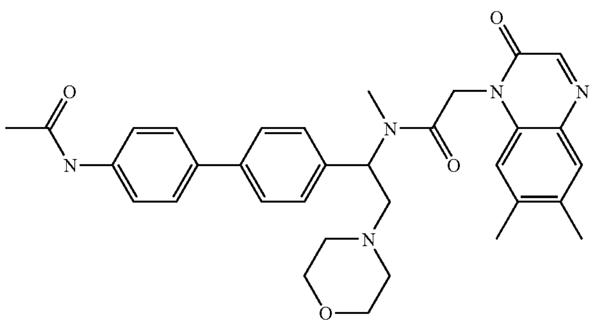 | N-[1-[4'-(acetylamino)-4-biphenylyl]-2-(4-morpholinyl)ethyl]-2-(6,7-dimethyl-2-oxo-1(2H)-quinoxalinyl)-N-methylacetamide | 568 |
| 317 | 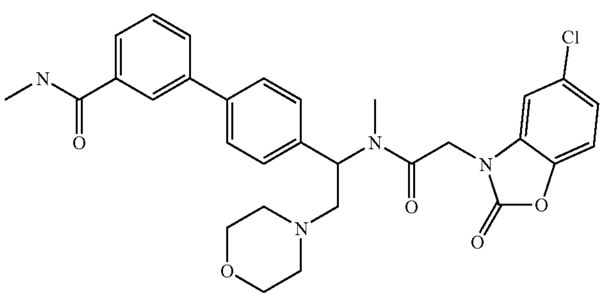 | 4'-[1-[[(5-chloro-2-oxo-1,3-benzoxazol-3(2H)-yl)acetyl](methyl)amino]-2-(4-morpholinyl)ethyl]-N-methyl-3-biphenylcarboxamide | 562 |
| 318 | 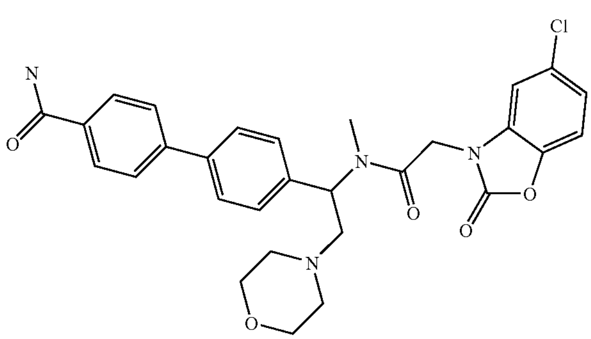 | 4'-[1-[[(5-chloro-2-oxo-1,3-benzoxazol-3(2H)-yl)acetyl](methyl)amino]-2-(4-morpholinyl)ethyl]-4-biphenylcarboxamide | 548 |

TABLE 11-continued

| Ex # | Structure | Name | MS [M + H]+ |
|---|---|---|---|
| 319 | 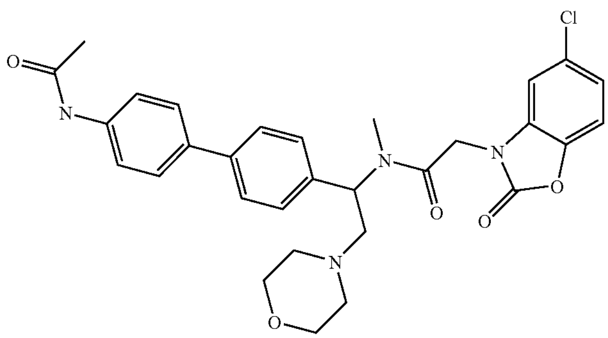 | N-[1-[4'-(acetylamino)-4-biphenylyl]-2-(4-morpholinyl)ethyl]-2-(5-chloro-2-oxo-1,3-benzoxazol-3(2H)-yl)-N-methylacetamide | 562 |
| 320 | 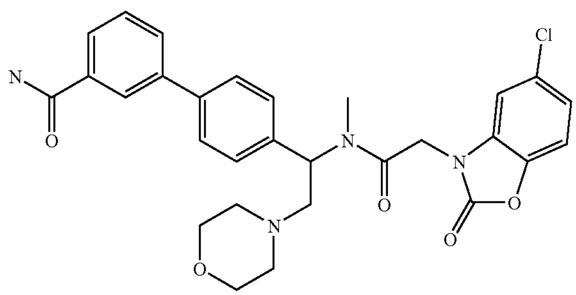 | 4'-[1-[[(5-chloro-2-oxo-1,3-benzoxazol-3(2H)-yl)acetyl](methyl)amino]-2-(4-morpholinyl)ethyl]-3-biphenylcarboxamide | 548 |
| 321 | 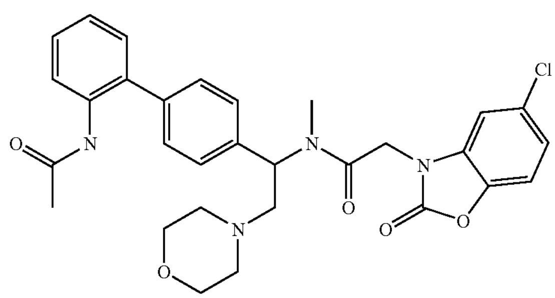 | N-[1-[2'-(acetylamino)-4-biphenylyl]-2-(4-morpholinyl)ethyl]-2-(5-chloro-2-oxo-1,3-benzoxazol-3(2H)-yl)-N-methylacetamide | 562 |
| 322 | 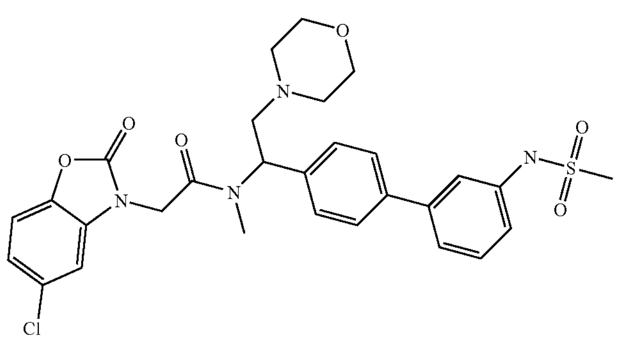 | 2-(5-chloro-2-oxo-1,3-benzoxazol-3(2H)-yl)-N-methyl-N-[1-{3'-[(methylsulfonyl)amino]-4-biphenylyl}-2-(4-morpholinyl)ethyl]acetamide | 598 |

TABLE 11-continued

| Ex # | Structure | Name | MS [M + H]+ |
|---|---|---|---|
| 323 | 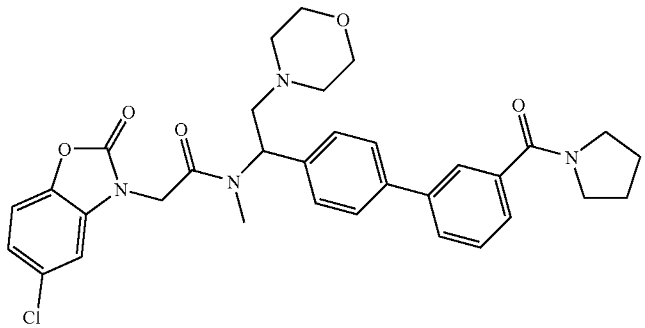 | 2-(5-chloro-2-oxo-1,3-benzoxazol-3(2H)-yl)-N-methyl-N-{2-(4-morpholinyl)-1-[3'-(1-pyrrolidinylcarbonyl)-4-biphenylyl]ethyl}acetamide | 602 |
| 324 | 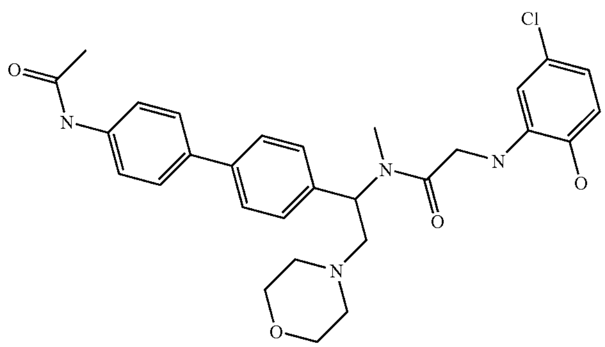 | $N^1$-[1-[4'-(acetylamino)-4-biphenylyl]-2-(4-morpholinyl)ethyl]-$N^2$-(5-chloro-2-hydroxyphenyl)-$N^1$-methylglycinamide | 536 |
| 325 | 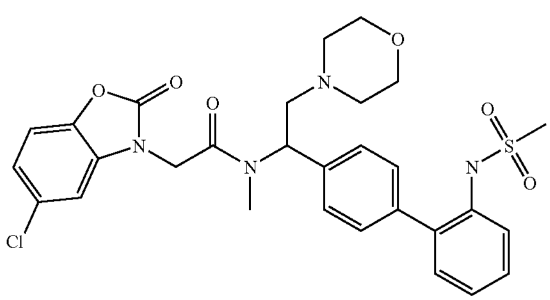 | 2-(5-chloro-2-oxo-1,3-benzoxazol-3(2H)-yl)-N-methyl-N-[1-{2'-[(methylsulfonyl)amino]-4-biphenylyl}-2-(4-morpholinyl)ethyl]acetamide | 598 |
| 326 | 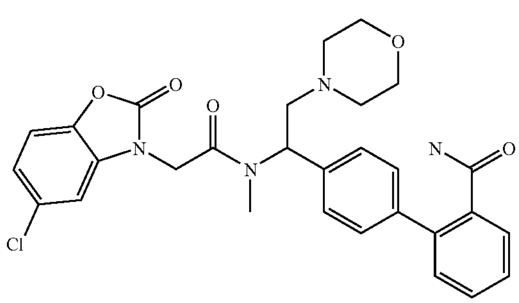 | 4'-[1-[[(5-chloro-2-oxo-1,3-benzoxazol-3(2H)-yl)acetyl](methyl)amino]-2-(4-morpholinyl)ethyl]-2-biphenylcarboxamide | 548 |

TABLE 11-continued

| Ex # | Structure | Name | MS [M + H]+ |
|---|---|---|---|
| 327 | 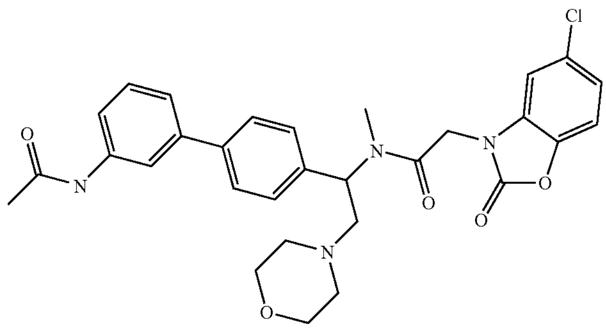 | N-[1-[3'-(acetylamino)-4-biphenylyl]-2-(4-morpholinyl)ethyl]-2-(5-chloro-2-oxo-1,3-benzoxazol-3(2H)-yl)-N-methylacetamide | 563 |
| 328 | 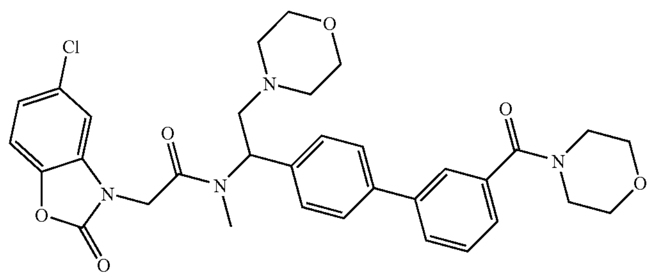 | 2-(5-chloro-2-oxo-1,3-benzoxazol-3(2H)-yl)-N-methyl-N-{2-(4-morpholinyl)-1-[3'-(4-morpholinylcarbonyl)-4-biphenylyl]ethyl}acetamide | 619 |
| 329 | 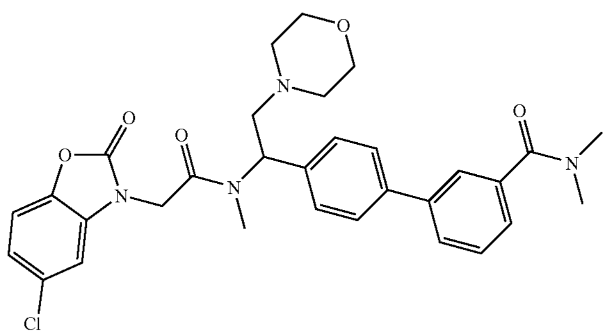 | 4'-[1-[[(5-chloro-2-oxo-1,3-benzoxazol-3(2H)-yl)acetyl](methyl)amino]-2-(4-morpholinyl)ethyl]-N,N-dimethyl-3-biphenylcarboxamide | 577 |
| 330 | 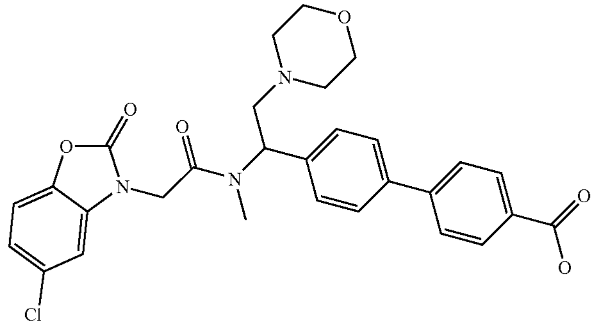 | 4'-[1-[[(5-chloro-2-oxo-1,3-benzoxazol-3(2H)-yl)acetyl](methyl)amino]-2-(4-morpholinyl)ethyl]-4-biphenylcarboxylic acid | 550 |

TABLE 11-continued

| Ex # | Structure | Name | MS [M + H]+ |
|---|---|---|---|
| 331 | 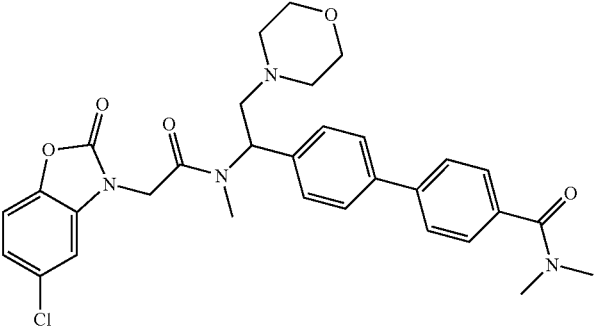 | 4'-[1-[[(5-chloro-2-oxo-1,3-benzoxazol-3(2H)-yl)acetyl](methyl)amino]-2-(4-morpholinyl)ethyl]-N,N-dimethyl-4-biphenylcarboxamide | 577 |
| 332 | 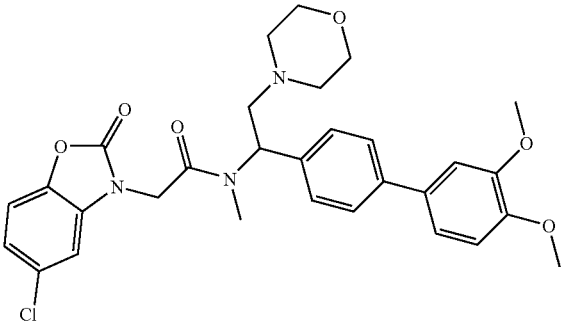 | N-[1-[3',4'-bis(methyloxy)-4-biphenylyl]-2-(4-morpholinyl)ethyl]-2-(5-chloro-2-oxo-1,3-benzoxazol-3(2H)-yl)-N-methylacetamide | 566 |
| 333 | 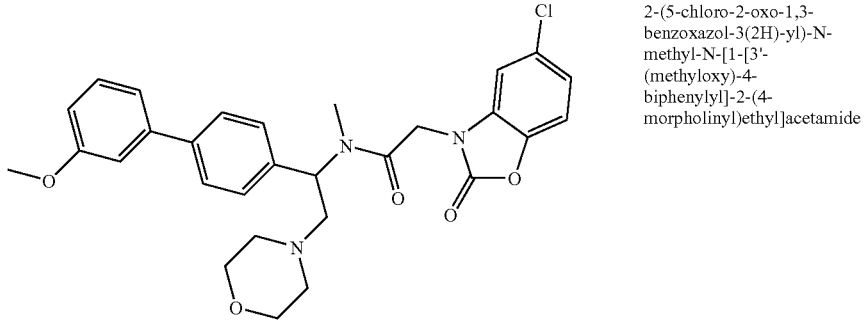 | 2-(5-chloro-2-oxo-1,3-benzoxazol-3(2H)-yl)-N-methyl-N-[1-[3'-(methyloxy)-4-biphenylyl]-2-(4-morpholinyl)ethyl]acetamide | 536 |
| 334 | 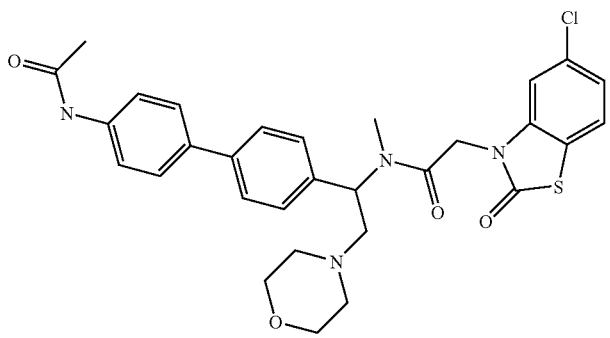 | N-[1-[4'-(acetylamino)-4-biphenylyl]-2-(4-morpholinyl)ethyl]-2-(5-chloro-2-oxo-1,3-benzothiazol-3(2H)-yl)-N-methylacetamide | 579 |

TABLE 11-continued

| Ex # | Structure | Name | MS [M + H]+ |
|---|---|---|---|
| 335 | 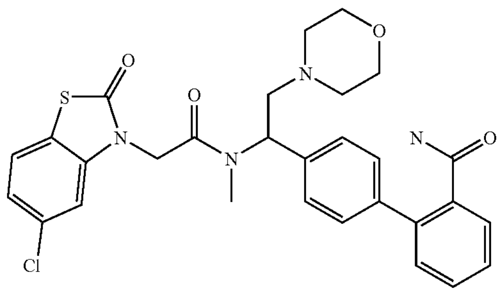 | 4'-[1-[[(5-chloro-2-oxo-1,3-benzothiazol-3(2H)-yl)acetyl](methyl)amino]-2-(4-morpholinyl)ethyl]-2-biphenylcarboxamide | 565 |
| 336 | 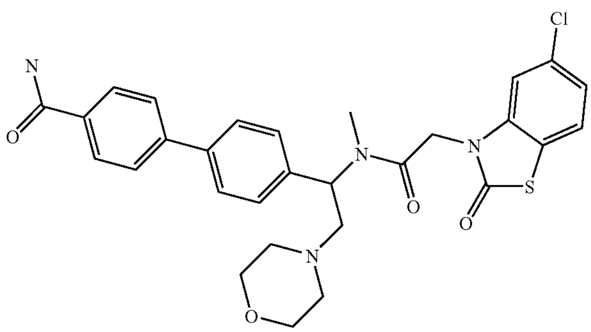 | 4'-[1-[[(5-chloro-2-oxo-1,3-benzothiazol-3(2H)-yl)acetyl](methyl)amino]-2-(4-morpholinyl)ethyl]-4-biphenylcarboxamide | 565 |
| 337 | 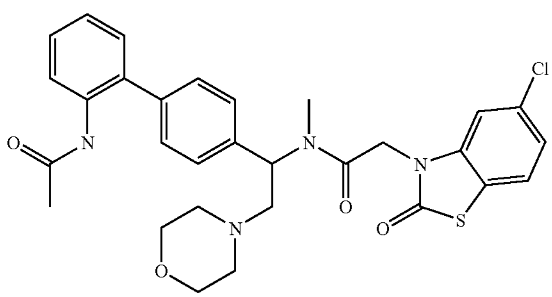 | N-[1-[2'-(acetylamino)-4-biphenylyl]-2-(4-morpholinyl)ethyl]-2-(5-chloro-2-oxo-1,3-benzothiazol-3(2H)-yl)-N-methylacetamide | 579 |
| 338 | 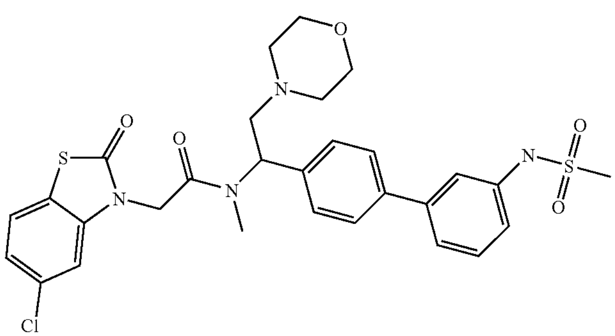 | 2-(5-chloro-2-oxo-1,3-benzothiazol-3(2H)-yl)-N-methyl-N-[1-{3'-[(methylsulfonyl)amino]-4-biphenylyl}-2-(4-morpholinyl)ethyl]acetamide | 615 |

TABLE 11-continued

| Ex # | Structure | Name | MS [M + H]+ |
|---|---|---|---|
| 339 | 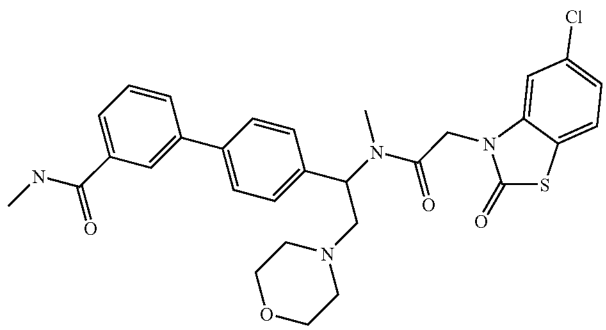 | 4'-[1-[[(5-chloro-2-oxo-1,3-benzothiazol-3(2H)-yl)acetyl](methyl)amino]-2-(4-morpholinyl)ethyl]-N-methyl-3-biphenylcarboxamide | 579 |
| 340 | 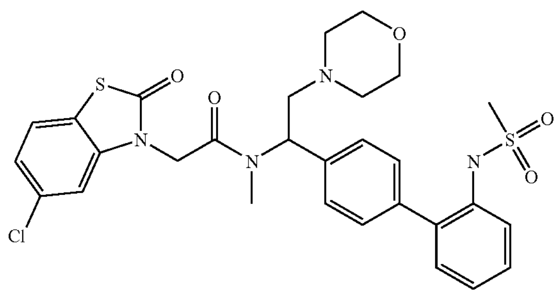 | 2-(5-chloro-2-oxo-1,3-benzothiazol-3(2H)-yl)-N-methyl-N-[1-{2'-[(methylsulfonyl)amino]-4-biphenylyl}-2-(4-morpholinyl)ethyl]acetamide | 615 |
| 341 | 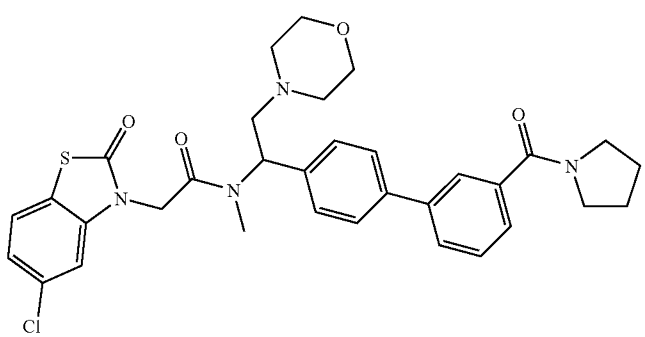 | 2-(5-chloro-2-oxo-1,3-benzothiazol-3(2H)-yl)-N-methyl-N-{2-(4-morpholinyl)-1-[3'-(1-pyrrolidinylcarbonyl)-4-biphenylyl]ethyl}acetamide | 619 |
| 342 | 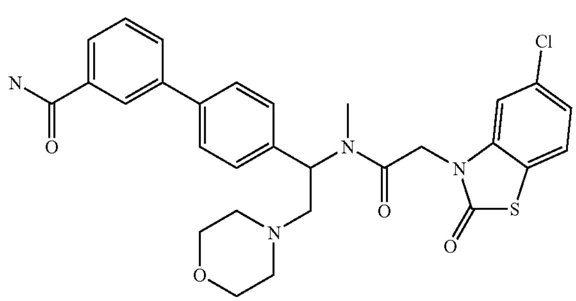 | 4'-[1-[[(5-chloro-2-oxo-1,3-benzothiazol-3(2H)-yl)acetyl](methyl)amino]-2-(4-morpholinyl)ethyl]-3-biphenylcarboxamide | 565 |

TABLE 11-continued

| Ex # | Structure | Name | MS [M + H]+ |
|---|---|---|---|
| 343 | 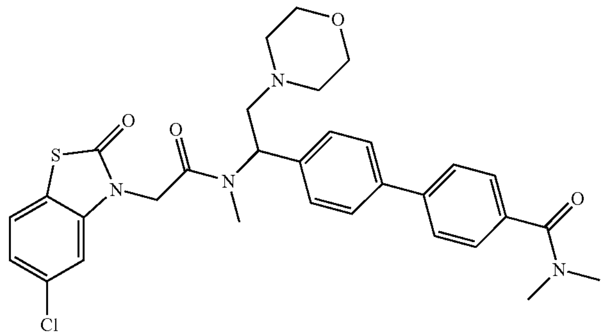 | 4'-[1-[[(5-chloro-2-oxo-1,3-benzothiazol-3(2H)-yl)acetyl](methyl)amino]-2-(4-morpholinyl)ethyl]-N,N-dimethyl-4-biphenylcarboxamide | 592 |
| 344 | 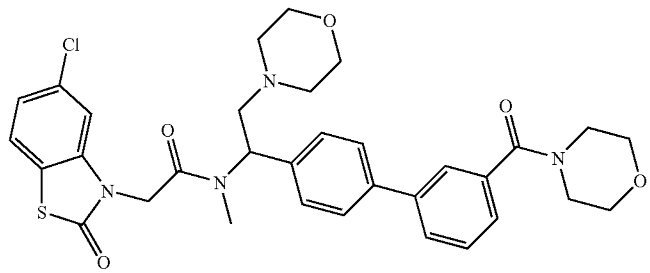 | 2-(5-chloro-2-oxo-1,3-benzothiazol-3(2H)-yl)-N-methyl-N-{2-(4-morpholinyl)-1-[3'-(4-morpholinylcarbonyl)-4-biphenylyl]ethyl}acetamide | 634 |
| 345 | 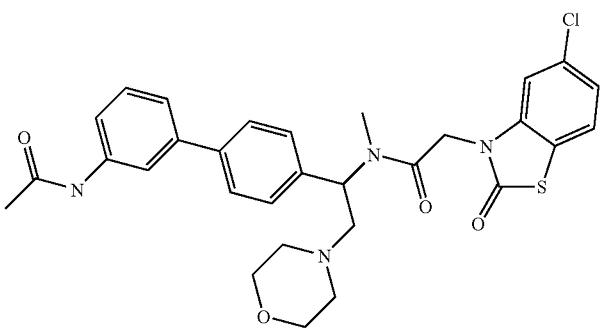 | N-[1-[3'-(acetylamino)-4-biphenylyl]-2-(4-morpholinyl)ethyl]-2-(5-chloro-2-oxo-1,3-benzothiazol-3(2H)-yl)-N-methylacetamide | 578 |
| 346 | 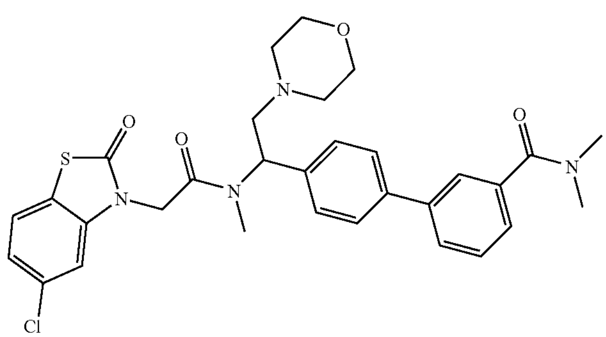 | 4'-[1-[[(5-chloro-2-oxo-1,3-benzothiazol-3(2H)-yl)acetyl](methyl)amino]-2-(4-morpholinyl)ethyl]-N,N-dimethyl-3-biphenylcarboxamide | 592 |
| 347 | 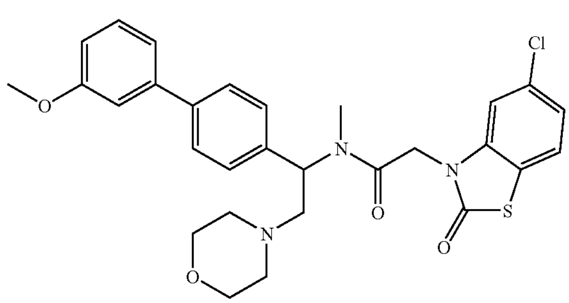 | 2-(5-chloro-2-oxo-1,3-benzothiazol-3(2H)-yl)-N-methyl-N-[1-[3'-(methyloxy)-4-biphenylyl]-2-(4-morpholinyl)ethyl]acetamide | 552 |

TABLE 11-continued

| Ex # | Structure | Name | MS [M + H]+ |
|---|---|---|---|
| 348 | 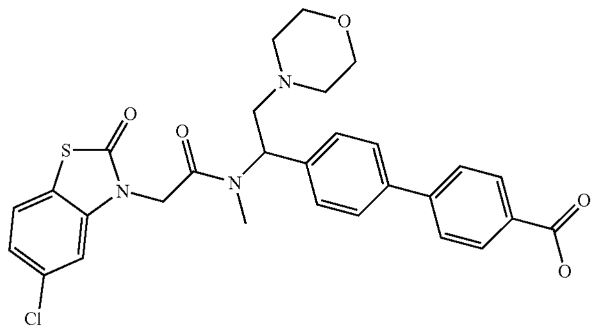 | 4'-[1-[[(5-chloro-2-oxo-1,3-benzothiazol-3(2H)-yl)acetyl](methyl)amino]-2-(4-morpholinyl)ethyl]-4-biphenylcarboxylic acid | 566 |
| 349 | 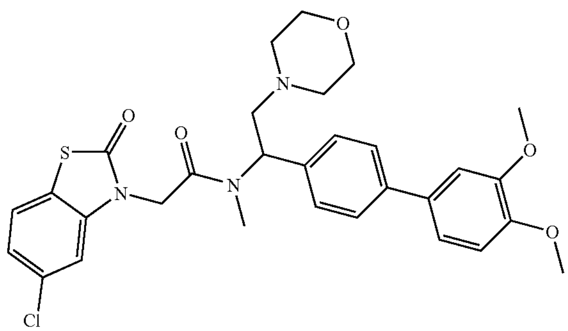 | N-[1-[3',4'-bis(methyloxy)-4-biphenylyl]-2-(4-morpholinyl)ethyl]-2-(5-chloro-2-oxo-1,3-benzothiazol-3(2H)-yl)-N-methylacetamide | 582 |
| 350 | 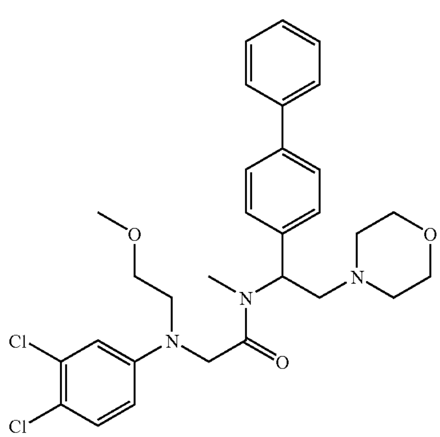 | N$^1$-[1-(4-biphenylyl)-2-(4-morpholinyl)ethyl]-N$^2$-(3,4-dichlorophenyl)-N$^1$-methyl-N$^2$-[2-(methyloxy)ethyl]glycinamide | 556.3, 558.4 |

TABLE 11-continued

| Ex # | Structure | Name | MS [M + H]+ |
|---|---|---|---|
| 351 | 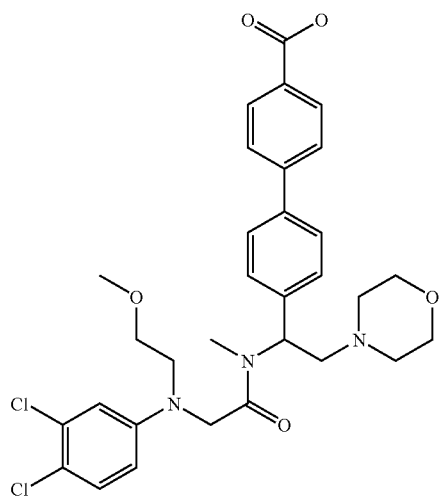 | 4'-[1-[{N-(3,4-dichlorophenyl)-N-[2-(methyloxy)ethyl]glycyl}(methyl)amino]-2-(4-morpholinyl)ethyl]-4-biphenylcarboxylic acid | 600.3, 602.3 |
| 352 | 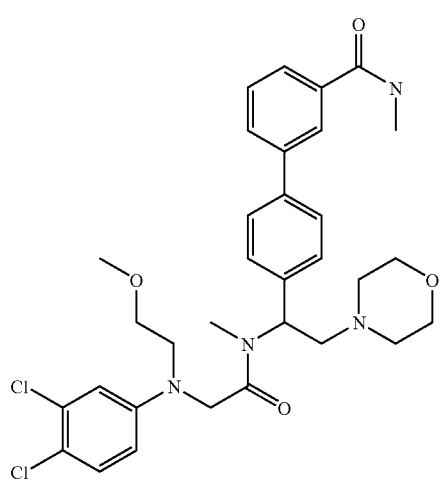 | 4'-[1-[{N-(3,4-dichlorophenyl)-N-[2-(methyloxy)ethyl]glycyl}(methyl)amino]-2-(4-morpholinyl)ethyl]-N-methyl-3-biphenylcarboxamide | 613.4, 615.4 |
| 353 | 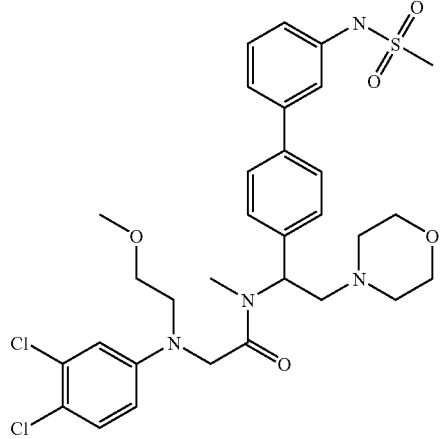 | $N^2$-(3,4-dichlorophenyl)-$N^1$-methyl-$N^2$-[2-(methyloxy)ethyl]-$N^1$-[1-{3'-[(methylsulfonyl)amino]-4-biphenylyl}-2-(4-morpholinyl)ethyl]glycinamide | 651.5 |

TABLE 11-continued

| Ex # | Structure | Name | MS [M + H]+ |
|---|---|---|---|
| 354 | 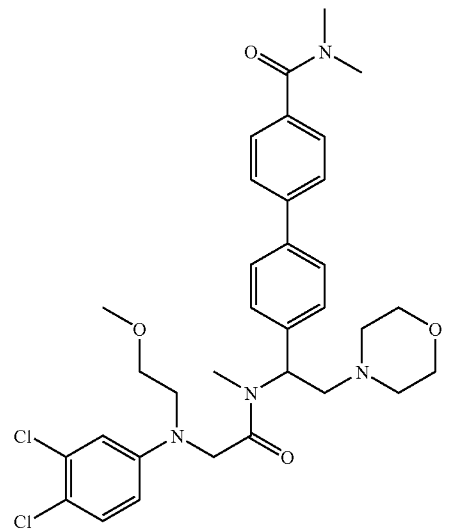 | 4'-[1-[{N-(3,4-dichlorophenyl)-N-[2-(methyloxy)ethyl]glycyl}(methyl)amino]-2-(4-morpholinyl)ethyl]-N,N-dimethyl-4-biphenylcarboxamide | 627.4, 629.4 |
| 355 | 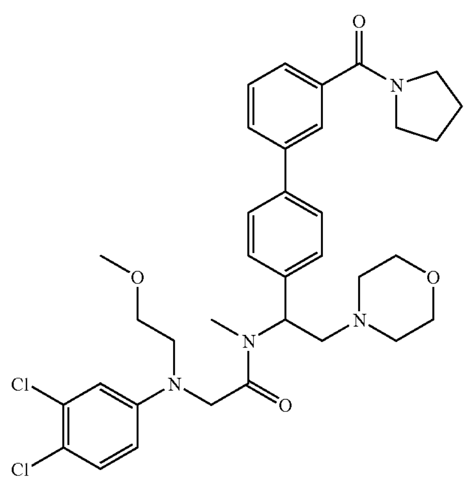 | $N^2$-(3,4-dichlorophenyl)-$N^1$-methyl-$N^2$-[2-(methyloxy)ethyl]-$N^1$-{2-(4-morpholinyl)-1-[3'-(1-pyrrolidinylcarbonyl)-4-biphenylyl]ethyl}glycinamide | 653.4, 655.4 |
| 356 | 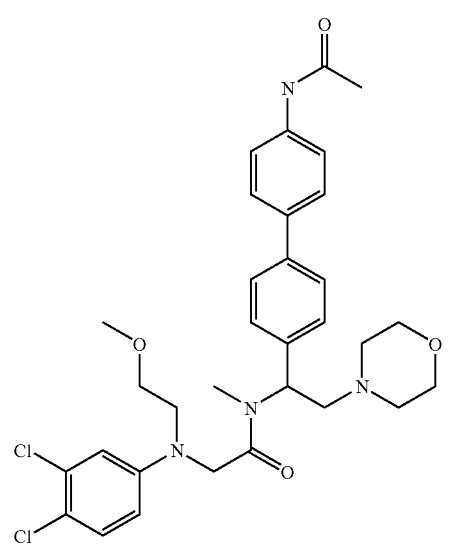 | $N^1$-[1-[4'-(acetylamino)-4-biphenylyl]-2-(4-morpholinyl)ethyl]-$N^2$-(3,4-dichlorophenyl)-$N^1$-methyl-$N^2$-[2-(methyloxy)ethyl]glycinamide | 613.4, 615.4 |

TABLE 11-continued
| Ex # | Structure | Name | MS [M + H]+ |
|---|---|---|---|
| 357 | 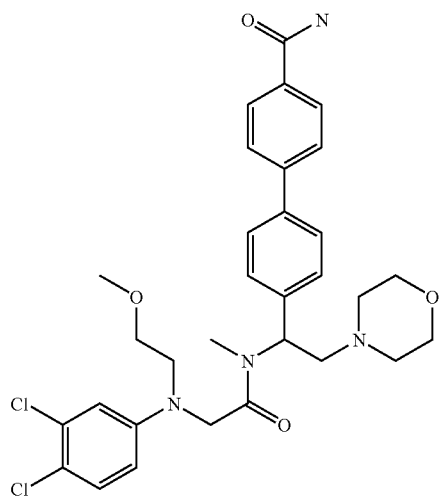 | 4'-[1-[{N-(3,4-dichlorophenyl)-N-[2-(methyloxy)ethyl]glycyl}(methyl)amino]-2-(4-morpholinyl)ethyl]-4-biphenylcarboxamide | 599.3, 601.4 |
| 358 | 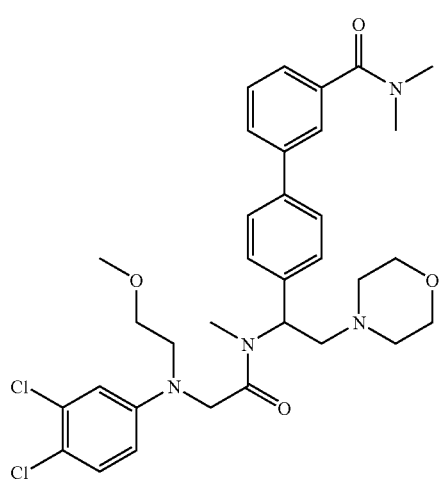 | 4'-[1-[{N-(3,4-dichlorophenyl)-N-[2-(methyloxy)ethyl]glycyl}(methyl)amino]-2-(4-morpholinyl)ethyl]-N,N-dimethyl-3-biphenylcarboxamide | 627.4, 629.5 |
| 359 | 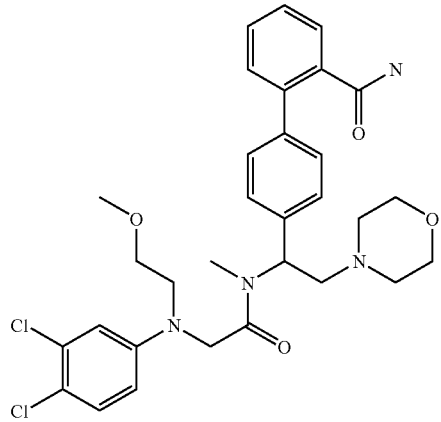 | 4'-[1-[{N-(3,4-dichlorophenyl)-N-[2-(methyloxy)ethyl]glycyl}(methyl)amino]-2-(4-morpholinyl)ethyl]-2-biphenylcarboxamide | 599.3, 601.4 |

TABLE 11-continued

| Ex # | Structure | Name | MS [M + H]+ |
|---|---|---|---|
| 360 | 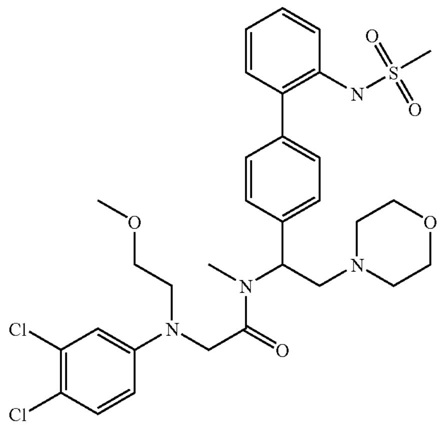 | $N^2$-(3,4-dichlorophenyl)-$N^1$-methyl-$N^2$-[2-(methyloxy)ethyl]-$N^1$-[1-{2'-[(methylsulfonyl)amino]-4-biphenylyl}-2-(4-morpholinyl)ethyl]glycinamide | 649.5, 651.3 |
| 361 | 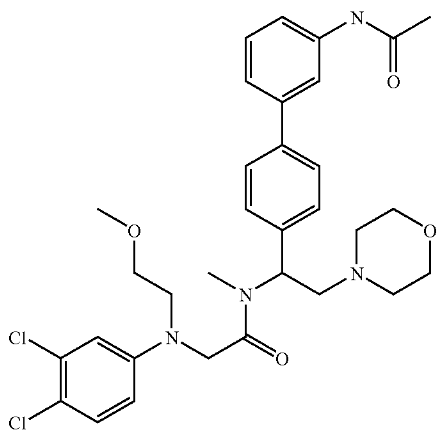 | $N^1$-[1-[3'-(acetylamino)-4-biphenylyl]-2-(4-morpholinyl)ethyl]-$N^2$-(3,4-dichlorophenyl)-$N^1$-methyl-$N^2$-[2-(methyloxy)ethyl]glycinamide | 613.3, 615.4 |
| 362 | 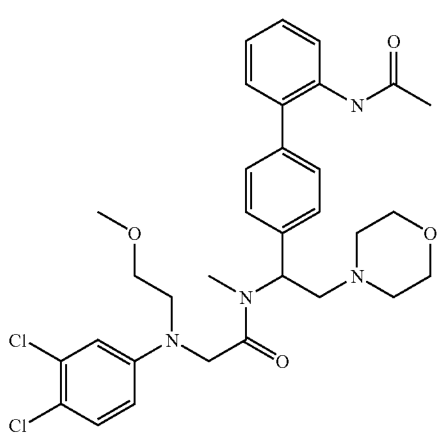 | $N^1$-[1-[2'-(acetylamino)-4-biphenylyl]-2-(4-morpholinyl)ethyl]-$N^2$-(3,4-dichlorophenyl)-$N^1$-methyl-$N^2$-[2-(methyloxy)ethyl]glycinamide | 613.3, 615.4 |

TABLE 11-continued

| Ex # | Structure | Name | MS [M + H]+ |
|---|---|---|---|
| 363 | 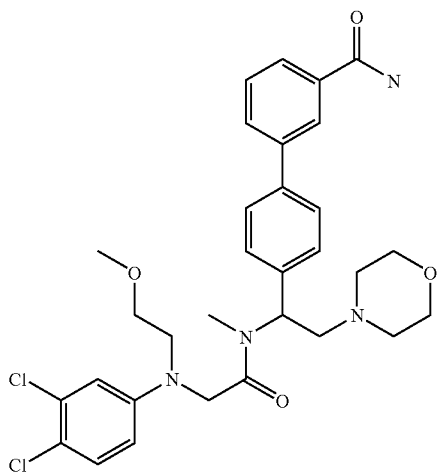 | 4'-[1-[{N-(3,4-dichlorophenyl)-N-[2-(methyloxy)ethyl]glycyl}(methyl)amino]-2-(4-morpholinyl)ethyl]-3-biphenylcarboxamide | 599.3, 601.4 |
| 364 | 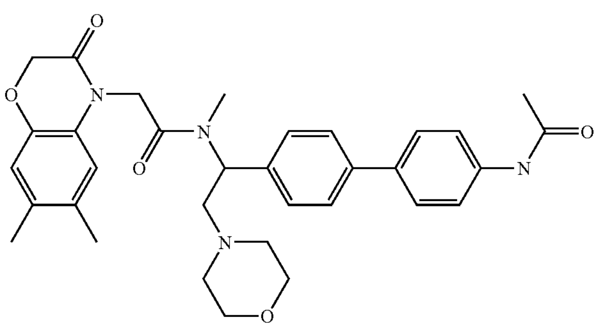 | N-[1-[4'-(acetylamino)-4-biphenylyl]-2-(4-morpholinyl)ethyl]-2-(6,7-dimethyl-3-oxo-2,3-dihydro-4H-1,4-benzoxazin-4-yl)-N-methylacetamide | 571.5 |
| 365 | 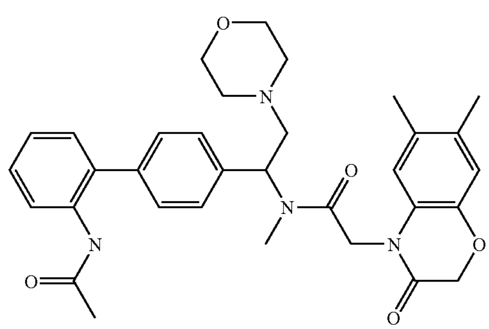 | N-[1-[2'-(acetylamino)-4-biphenylyl]-2-(4-morpholinyl)ethyl]-2-(6,7-dimethyl-3-oxo-2,3-dihydro-4H-1,4-benzoxazin-4-yl)-N-methylacetamide | 571.5 |
| 366 | 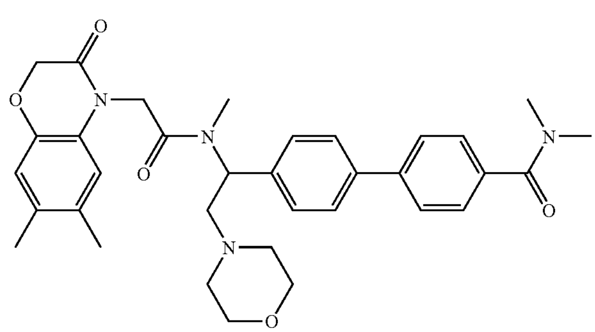 | 4'-[1-[[(6,7-dimethyl-3-oxo-2,3-dihydro-4H-1,4-benzoxazin-4-yl)acetyl](methyl)amino]-2-(4-morpholinyl)ethyl]-N,N-dimethyl-4-biphenylcarboxamide | 585.5 |

TABLE 11-continued

| Ex # | Structure | Name | MS [M + H]+ |
|---|---|---|---|
| 367 | 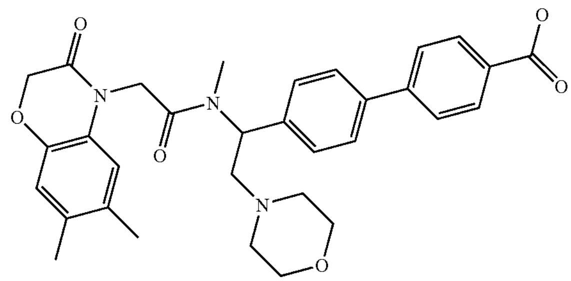 | 4'-[1-[[(6,7-dimethyl-3-oxo-2,3-dihydro-4H-1,4-benzoxazin-4-yl)acetyl](methyl)amino]-2-(4-morpholinyl)ethyl]-4-biphenylcarboxylic acid | 558.2 |
| 368 | 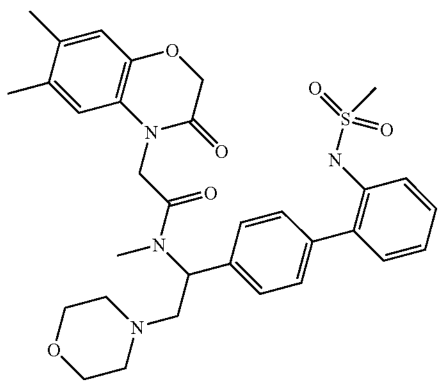 | 2-(6,7-dimethyl-3-oxo-2,3-dihydro-4H-1,4-benzoxazin-4-yl)-N-methyl-N-[1-{2'-[(methylsulfonyl)amino]-4-biphenylyl}-2-(4-morpholinyl)ethyl]acetamide | 607.4 |
| 369 | 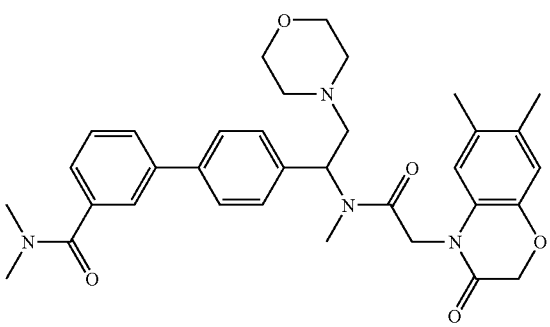 | 4'-[1-[[(6,7-dimethyl-3-oxo-2,3-dihydro-4H-1,4-benzoxazin-4-yl)acetyl](methyl)amino]-2-(4-morpholinyl)ethyl]-N,N-dimethyl-3-biphenylcarboxamide | 585.5 |
| 370 | 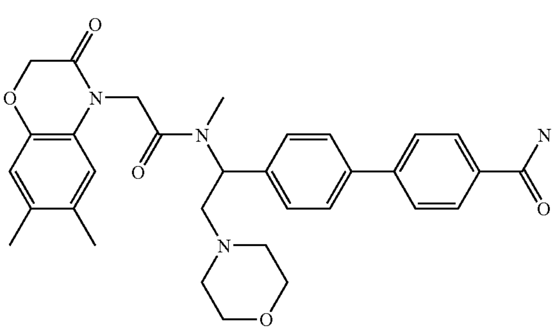 | 4'-[1-[[(6,7-dimethyl-3-oxo-2,3-dihydro-4H-1,4-benzoxazin-4-yl)acetyl](methyl)amino]-2-(4-morpholinyl)ethyl]-4-biphenylcarboxamide | 557.2 |

TABLE 11-continued

| Ex # | Structure | Name | MS [M + H]+ |
|---|---|---|---|
| 371 | 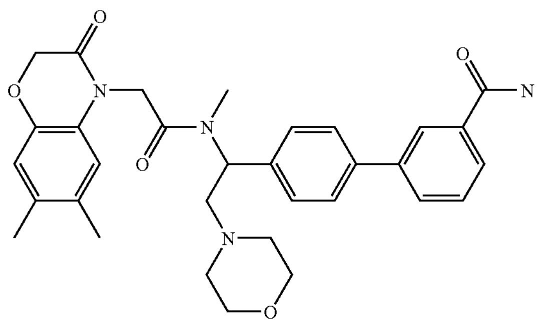 | 4'-[1-[[(6,7-dimethyl-3-oxo-2,3-dihydro-4H-1,4-benzoxazin-4-yl)acetyl](methyl)amino]-2-(4-morpholinyl)ethyl]-3-biphenylcarboxamide | 557.2 |
| 372 | 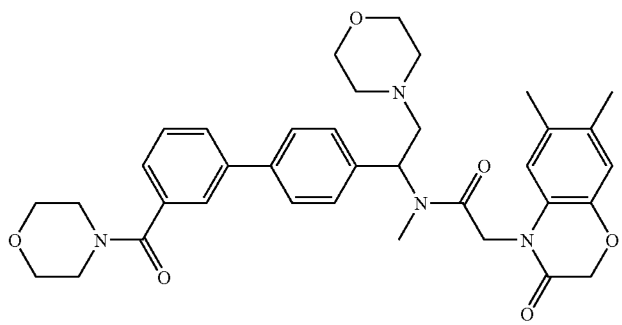 | 2-(6,7-dimethyl-3-oxo-2,3-dihydro-4H-1,4-benzoxazin-4-yl)-N-methyl-N-{2-(4-morpholinyl)-1-[3'-(4-morpholinylcarbonyl)-4-biphenylyl]ethyl}acetamide | 627.5 |
| 373 | 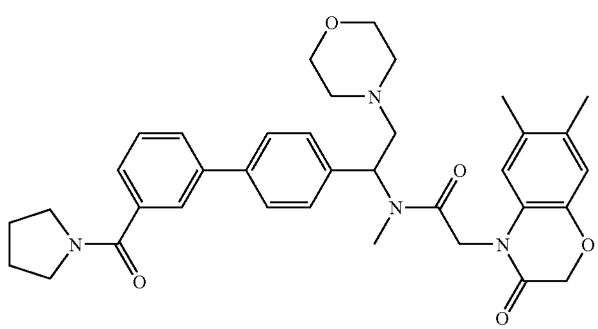 | 2-(6,7-dimethyl-3-oxo-2,3-dihydro-4H-1,4-benzoxazin-4-yl)-N-methyl-N-{2-(4-morpholinyl)-1-[3'-(1-pyrrolidinylcarbonyl)-4-biphenylyl]ethyl}acetamide | 611.5 |
| 374 | 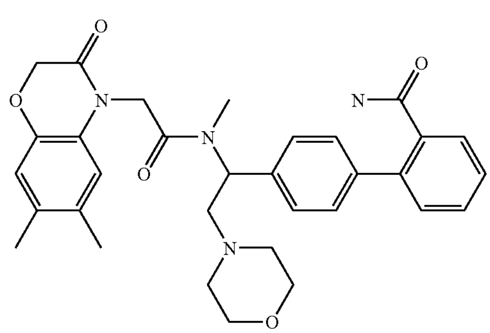 | 4'-[1-[[(6,7-dimethyl-3-oxo-2,3-dihydro-4H-1,4-benzoxazin-4-yl)acetyl](methyl)amino]-2-(4-morpholinyl)ethyl]-2-biphenylcarboxamide | 557.2 |

TABLE 11-continued

| Ex # | Structure | Name | MS [M + H]+ |
|---|---|---|---|
| 375 | 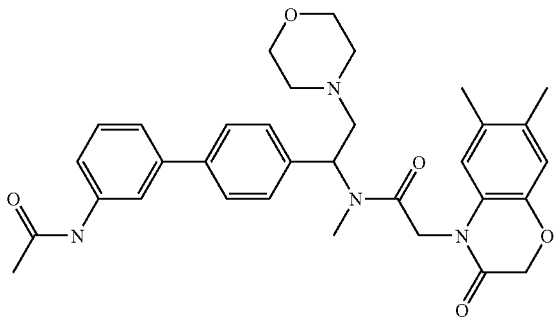 | N-[1-[3'-(acetylamino)-4-biphenylyl]-2-(4-morpholinyl)ethyl]-2-(6,7-dimethyl-3-oxo-2,3-dihydro-4H-1,4-benzoxazin-4-yl)-N-methylacetamide | 571.5 |
| 376 | 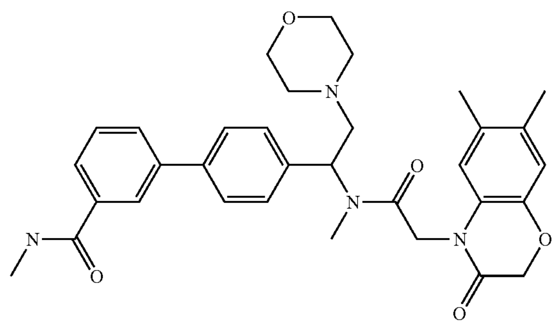 | 4'-[1-[[(6,7-dimethyl-3-oxo-2,3-dihydro-4H-1,4-benzoxazin-4-yl)acetyl](methyl)amino]-2-(4-morpholinyl)ethyl]-N-methyl-3-biphenylcarboxamide | 571.5 |
| 377 | 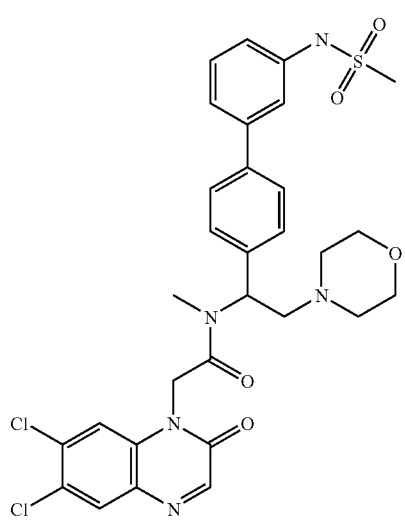 | 2-(6,7-dichloro-2-oxo-1(2H)-quinoxalinyl)-N-methyl-N-[1-{3'-[(methylsulfonyl)amino]-4-biphenylyl}-2-(4-morpholinyl)ethyl]acetamide | 644.1 |

TABLE 11-continued
| Ex # | Structure | Name | MS [M + H]+ |
|---|---|---|---|
| 378 | 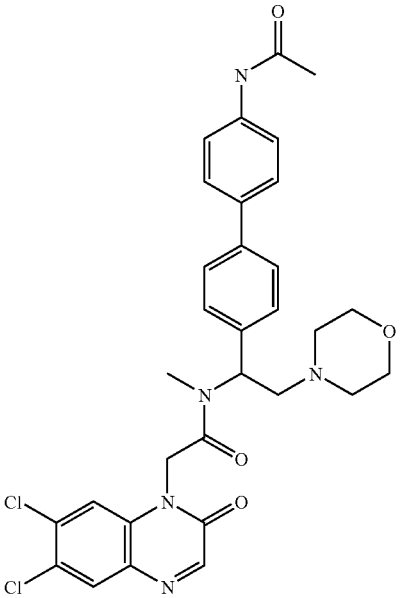 | N-[1-[4'-(acetylamino)-4-biphenylyl]-2-(4-morpholinyl)ethyl]-2-(6,7-dichloro-2-oxo-1(2H)-quinoxalinyl)-N-methylacetamide | 608.4 |
| 379 | 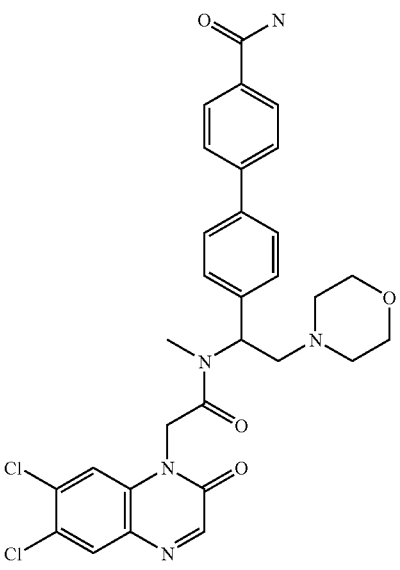 | 4'-[1-[[(6,7-dichloro-2-oxo-1(2H)-quinoxalinyl)acetyl](methyl)amino]-2-(4-morpholinyl)ethyl]-4-biphenylcarboxamide | 594.4 |

TABLE 11-continued

| Ex # | Structure | Name | MS [M + H]+ |
|---|---|---|---|
| 380 | 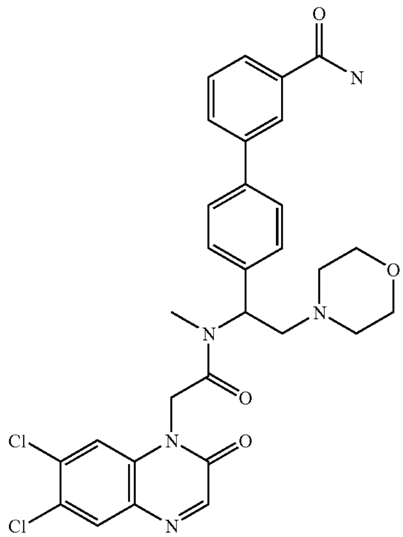 | 4'-[1-[[(6,7-dichloro-2-oxo-1(2H)-quinoxalinyl)acetyl](methyl)amino]-2-(4-morpholinyl)ethyl]-3-biphenylcarboxamide | 594.1 |
| 381 | 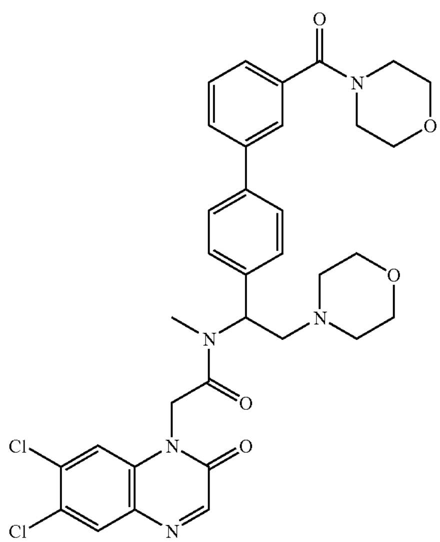 | 2-(6,7-dichloro-2-oxo-1(2H)-quinoxalinyl)-N-methyl-N-{2-(4-morpholinyl)-1-[3'-(4-morpholinylcarbonyl)-4-biphenylyl]ethyl}acetamide | 664.4 |
| 382 | 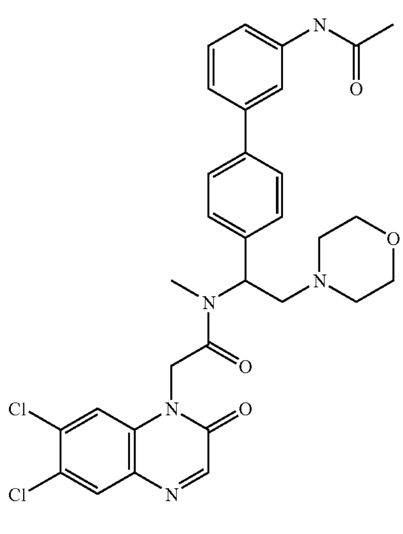 | N-[1-[3'-(acetylamino)-4-biphenylyl]-2-(4-morpholinyl)ethyl]-2-(6,7-dichloro-2-oxo-1(2H)-quinoxalinyl)-N-methylacetamide | 608.1 |

TABLE 11-continued

| Ex # | Structure | Name | MS [M + H]+ |
|---|---|---|---|
| 383 | 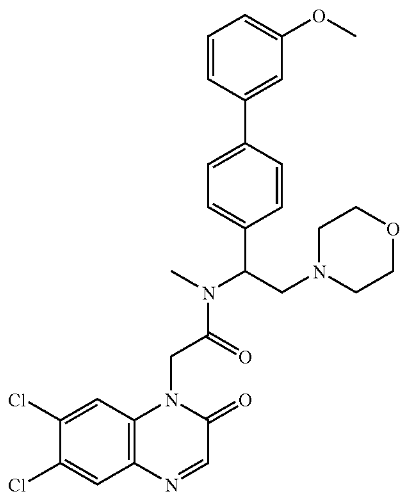 | 2-(6,7-dichloro-2-oxo-1(2H)-quinoxalinyl)-N-methyl-N-[1-[3'-methyloxy)-4-biphenylyl]-2-(4-morpholinyl)ethyl]acetamide | 581.4 |
| 384 | 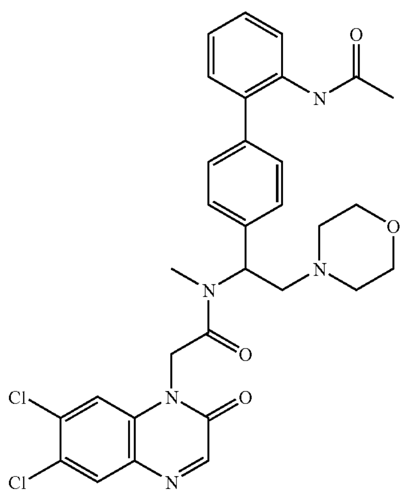 | N-[1-[2'-(acetylamino)-4-biphenylyl]-2-(4-morpholinyl)ethyl]-2-(6,7-dichloro-2-oxo-1(2H)-quinoxalinyl)-N-methylacetamide | 608.1 |
| 385 | 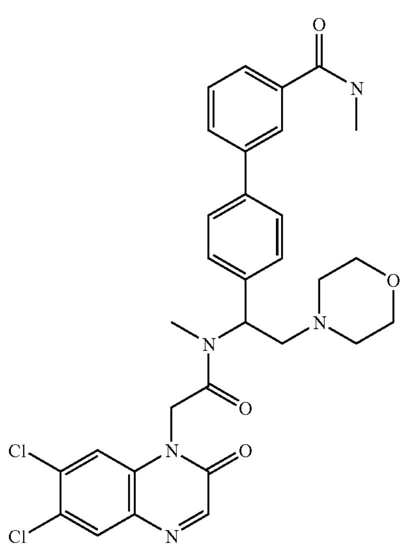 | 4'-[1-[[(6,7-dichloro-2-oxo-1(2H)-quinoxalinyl)acetyl](methyl)amino]-2-(4-morpholinyl)ethyl]-N-methyl-3-biphenylcarboxamide | 608.4 |

TABLE 11-continued
| Ex # | Structure | Name | MS [M + H]+ |
|---|---|---|---|
| 386 | 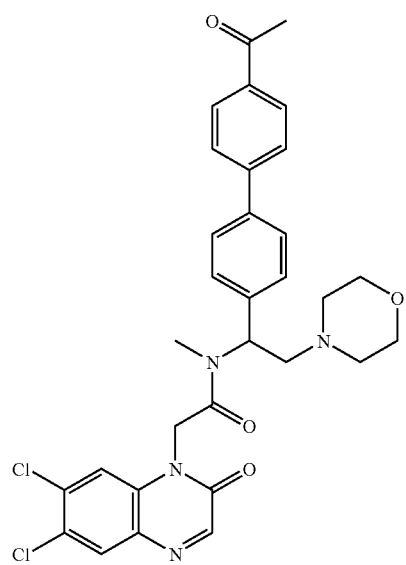 | 4'-[1-[[(6,7-dichloro-2-oxo-1(2H)-quinoxalinyl)acetyl](methyl)amino]-2-(4-morpholinyl)ethyl]-4-biphenylcarboxylic acid | 551.2 [M − COOH] |
| 387 | 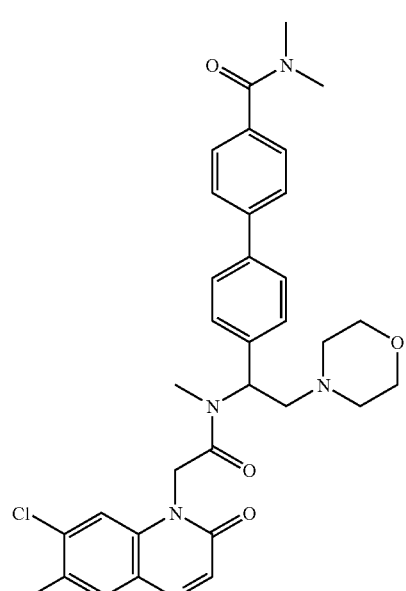 | 4'-[1-[[(6,7-dichloro-2-oxo-1(2H)-quinoxalinyl)acetyl](methyl)amino]-2-(4-morpholinyl)ethyl]-N,N-dimethyl-4-biphenylcarboxamide | 622.4 |

TABLE 11-continued

| Ex # | Structure | Name | MS [M + H]+ |
|---|---|---|---|
| 388 | 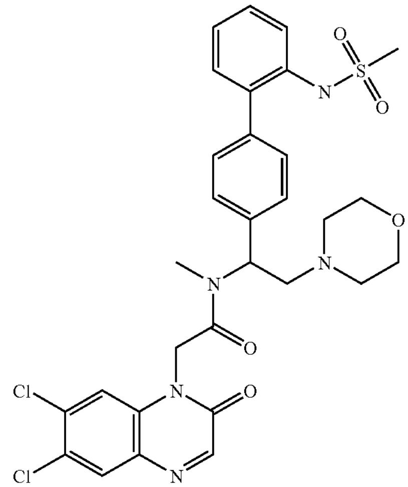 | 2-(6,7-dichloro-2-oxo-1(2H)-quinoxalinyl)-N-methyl-N-[1-{2'-[(methylsulfonyl)amino]-4-biphenylyl}-2-(4-morpholinyl)ethyl]acetamide | 644.3 |
| 389 | 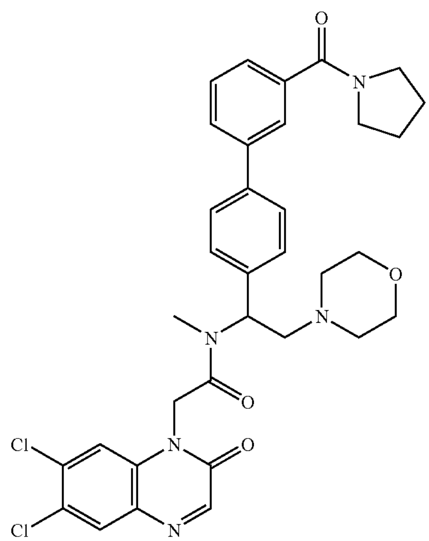 | 2-(6,7-dichloro-2-oxo-1(2H)-quinoxalinyl)-N-methyl-N-{2-(4-morpholinyl)-1-[3'-(1-pyrrolidinylcarbonyl)-4-biphenylyl]ethyl}acetamide | 648.4 |
| 390 | 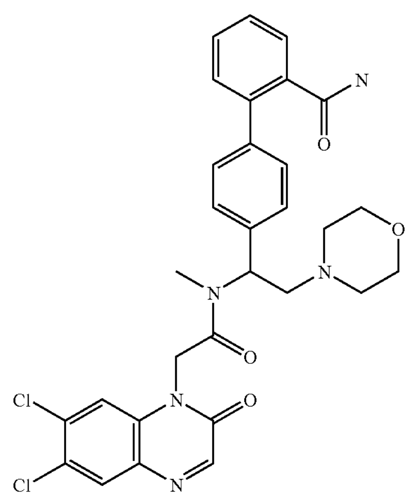 | 4'-[1-[[(6,7-dichloro-2-oxo-1(2H)-quinoxalinyl)acetyl](methyl)amino]-2-(4-morpholinyl)ethyl]-2-biphenylcarboxamide | 594.4 |

| Ex # | Structure | Name | MS [M + H]+ |
|---|---|---|---|
| 391 | 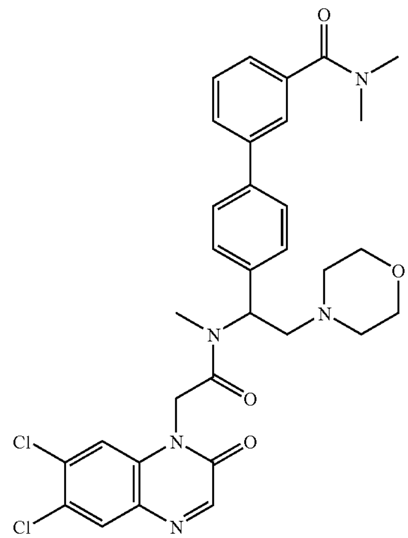 | 4'-[1-[[(6,7-dichloro-2-oxo-1(2H)-quinoxalinyl)acetyl](methyl)amino]-2-(4-morpholinyl)ethyl]-N,N-dimethyl-3-biphenylcarboxamide | 622.4 |

Example 392

$N^1$-[1-[4'-(acetylamino)-4-biphenylyl]-2-(1-pyrrolidinyl)ethyl]-$N^2$-(3,4-dichlorophenyl)-$N^1$-methyl-$N^2$-[2-(methyloxy)ethyl]glycinamide

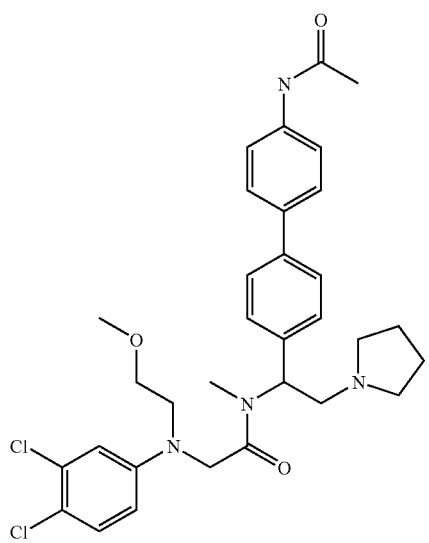

a) $N^1$-[1-(4-bromophenyl)-2-(1-pyrrolidinyl)ethyl]-$N^2$-(3,4-dichlorophenyl)-$N^1$-methyl-$N^2$-[2-(methyloxy)ethyl]glycinamide

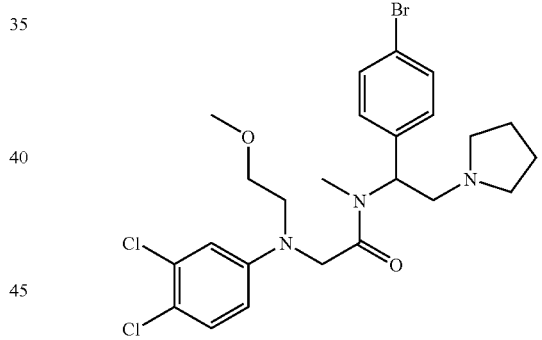

1-(4-bromophenyl)-N-methyl-2-(1-pyrrolidinyl)ethanamine (6.0 g of 50% purity, 10.5 mmol) was dissolved in 30 mL of anhydrous DMF and treated with N-(3,4-dichlorophenyl)-N-[2-(methyloxy)ethyl]glycine, lithium salt (3.0 g, 10.5 mmol), triethyl amine (2.9 mL, 21.0 mmol), and (1H-1,2,3-benzotriazol-1-yloxy) [tris(dimethylamino)]phosphonium hexafluorophosphate (BOP Reagent, 5.6 g, 12.6 mmol). The reaction mixture was stirred for 2 hours at room temperature, after which time HPLC (Eclipse XDB-C18, 4.6×250 mm, 5 micron, 1-99% $CH_3CN/H_2O$ with 0.1% trifluoroacetic acid) showed that the reaction was complete. The reaction mixture was treated with 50 mL of 50% saturated aqueous sodium bicarbonate solution and stirred for 30 minutes. The mixture was poured into 100 mL of water and 300 mL of a 1:1 ether/ethyl acetate mixture. The layers were separated and the organic phase was washed with 50% saturated aqueous sodium bicarbonate solution (2×300 mL), 1M HCl (1×300 mL), 50% saturated aqueous sodium bicarbonate solution (1×300 mL), saturated NaCl (1×200 mL), dried over magnesium sulphate, filtered, and concentrated to an orange foam. The compound was adsorbed onto approximately 30 g of silica gel and purified by column chromatography (300 g silica gel 40 um, 20 minute isocratic flush with ethyl acetate followed by gradient elution from 0% MeOH/100% $CH_2Cl_2$ to 30% MeOH/70% $CH_2Cl_2$ over 90 minutes) to give $N^1$-[1-(4-bromophenyl)-2-(1-pyrrolidinyl)ethyl]-$N^2$-(3,4-dichlorophenyl)-$N^1$-methyl-$N^2$-[2-(methyloxy)ethyl]glycinamide (3.85 g, 7.1 mmol, 67%) as a yellow glass. MS (ES) m/e 542, 544 [M+H]$^+$.

b) $N^1$-[1-[4'-(acetylamino)-4-biphenylyl]-2-(1-pyrrolidinyl)ethyl]-$N^2$-(3,4-dichlorophenyl)-$N^1$-methyl-$N^2$-[2-(methyloxy)ethyl]glycinamide

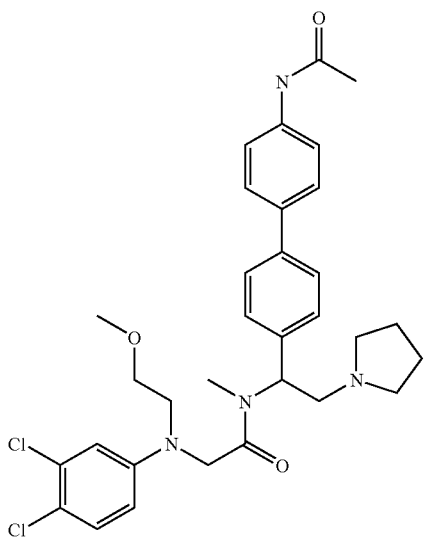

$N^1$-[1-(4-bromophenyl)-2-(1-pyrrolidinyl)ethyl]-$N^2$-(3,4-dichlorophenyl)-$N^1$-methyl-$N^2$-[2-(methyloxy)ethyl]glycinamide (150 mg, 0.276 mmol) was dissolved in 1 mL of 1,4-dioxane and combined with [4-(acetylamino)phenyl]boronic acid (74 mg, 0.413 mmol), Pd(dppf)$_2$Cl$_2$ (6.8 mg, 0.008 mmol), and 825 uL of 1M Na$_2$CO$_3$ in water in a glass reaction tube (0.5-2.0 mL Smith Process Vial) that was equipped with a magnetic stir bar. The tube was fitted with a rubber septum and hermetically sealed with a crimped metal foil seal. Using a Personal Chemistry Emrys Optimizer microwave unit, the reaction mixture was magnetically stirred and irradiated with microwave energy of dynamically adjusted power in order to maintain a temperature of 160° C. for 360 seconds. The reaction mixture was diluted with 2 mL of DMSO and filtered through a 0.2 micron PTFE filter and purified by preparative HPLC (Waters C18RP Xterra 5 micron 50×100 mm column, 45 mL/min flow rate, A: 0.1% TFA in acetonitrile B: 0.1% TFA in water, A: 10 to 95% over 20 min, UV detection at 215 nm) to give 47.7 mg (19%) of the title compound as a brown solid. MS (ES) m/e 598, 600 [M+H]$^+$.

Examples 393-454

Proceeding in a similar manner as in example 392, but replacing N-(3,4-dichlorophenyl)-N-[2-(methyloxy)ethyl] glycine, lithium salt with the appropriate acids and/or [4-(acetylamino)phenyl]boronic acid with the appropriate boronic acids, the compounds listed in table 12 were prepared. Note that with N-(cyanomethyl)-N-(3,4-dichlorophenyl)glycine, cross coupling is accompanied by hydrolysis to the primary amide. As is appreciated by those skilled in the art, these analogous examples may involve variations in synthetic procedure.

TABLE 12

| Ex # | Structure | Name | MS [M + H]$^+$ |
|---|---|---|---|
| 393 | 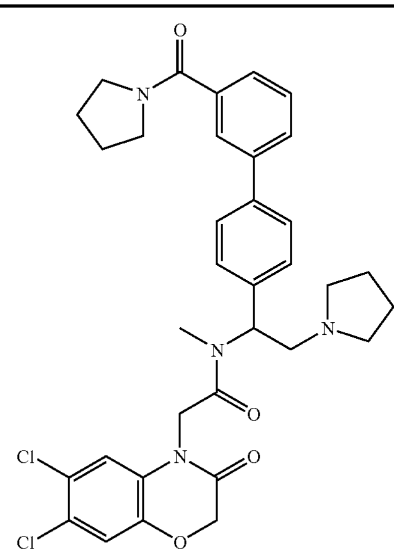 | 2-(6,7-dichloro-3-oxo-2,3-dihydro-4H-1,4-benzoxazin-4-yl)-N-methyl-N-{2-(1-pyrrolidinyl)-1-[3'-(1-pyrrolidinylcarbonyl)-4-biphenylyl]ethyl}acetamide | 635 |

TABLE 12-continued
| Ex # | Structure | Name | MS [M + H]+ |
|---|---|---|---|
| 394 | 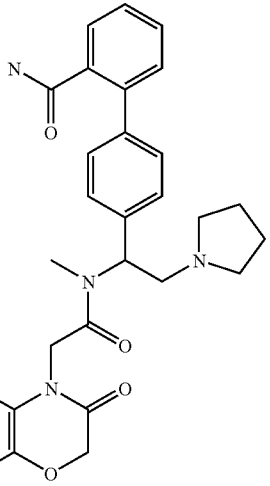 | 4'-[1-[[(6,7-dichloro-3-oxo-2,3-dihydro-4H-1,4-benzoxazin-4-yl)acetyl](methyl)amino]-2-(1-pyrrolidinyl)ethyl]-2-biphenylcarboxamide | 581 |
| 395 | 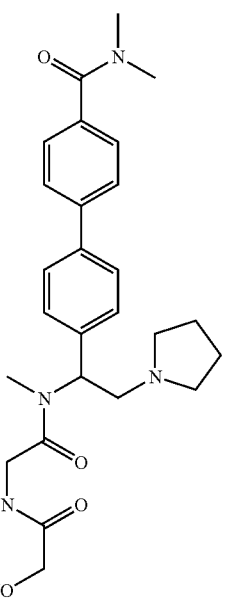 | 4'-[1-[[(6,7-dichloro-3-oxo-2,3-dihydro-4H-1,4-benzoxazin-4-yl)acetyl-methyl)amino]-2-(1-biphenylcarboxamide | 609 |

TABLE 12-continued

| Ex # | Structure | Name | MS [M + H]+ |
|---|---|---|---|
| 396 | 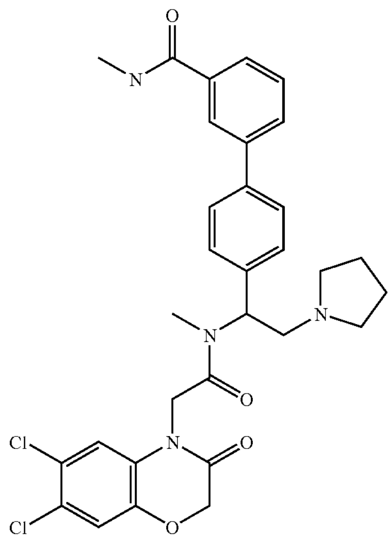 | 4'-[1-[[(6,7-dichloro-3-oxo-2,3-dihydro-4H-1,4-benzoxazin-4-yl)acetyl](methyl)amino]-2-(1-pyrrolidinyl)ethyl]-N-methyl-3-biphenylcarboxamide | 595 |
| 397 | 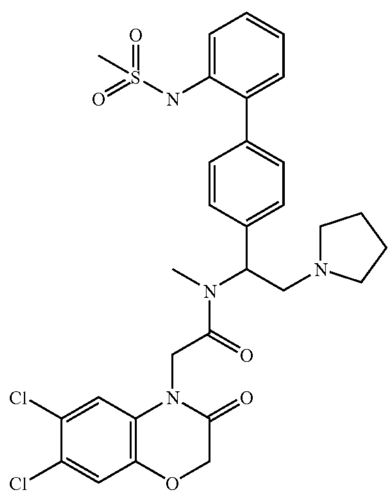 | 2-(6,7-dichloro-3-oxo-2,3-dihydro 4H-1,4-benzoxazin-4-yl)-N-methyl-N-[1-{2'-[(methylsulfonyl)amino]-4-biphenylyl}-2-(1-pyrrolidinyl)ethyl]acetamide | 631 |
| 398 | 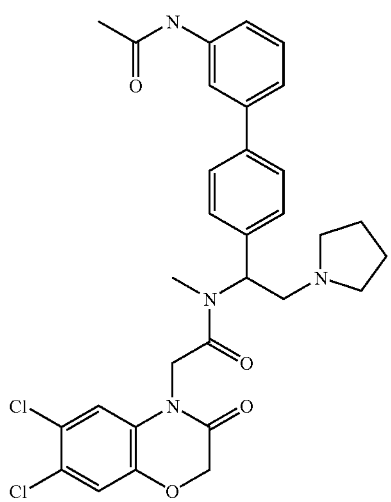 | N-[1-[3'-(acetylamino)-4-biphenylyl]-2-(1-pyrrolidinyl)ethyl]-2-(6,7-dichloro-benzoxazin-4-yl)-N-methylacetamide | 595 |

TABLE 12-continued
| Ex # | Structure | Name | MS [M + H]+ |
|---|---|---|---|
| 399 | 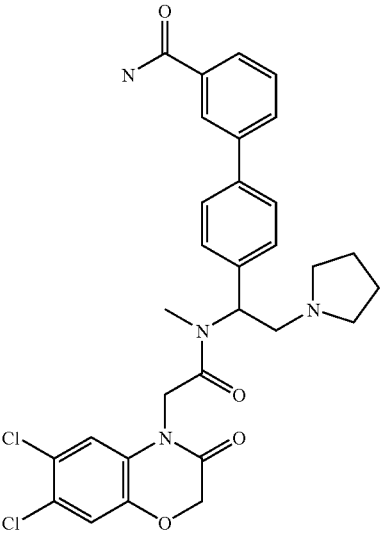 | 4'-[1-[[(6,7-dichloro-3-oxo-2,3-dihydro-4H-1,4-benzoxazin-4-yl)acetyl](methyl)amino]-2-(1-pyrrolidinyl)ethyl]-3-biphenylcarboxamide | 581 |
| 400 | 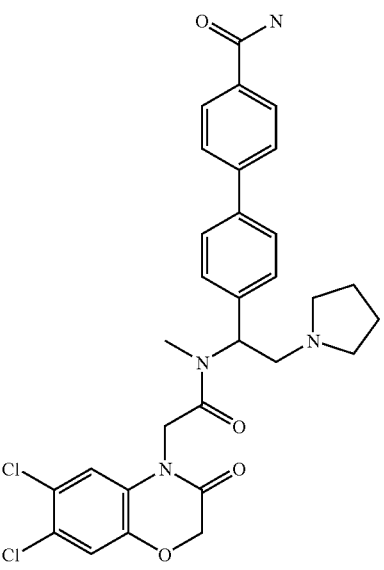 | 4'-[1-[[(6,7-dichloro-3-oxo-2,3-dihydro-4H-1,4-benzoxazin-4-yl)acetyl](methyl)amino]-2-(1-pyrrolidinyl)ethyl]-4-biphenylcarboxamide | 581 |

TABLE 12-continued

| Ex # | Structure | Name | MS [M + H]+ |
|---|---|---|---|
| 401 | 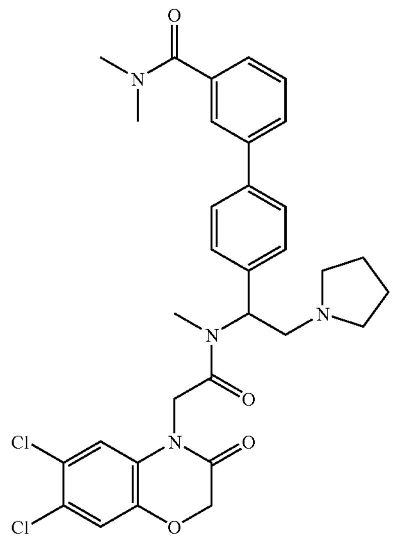 | 4'-[1-[[(6,7-dichloro-3-oxo-2,3-dihydro-4H-1,4-benzoxazin-4-yl)acetyl](methyl)amino]-2-(1-pyrrolidinyl)ethyl]-N,N-dimethyl-3-biphenylcarboxamide | 609 |
| 402 | 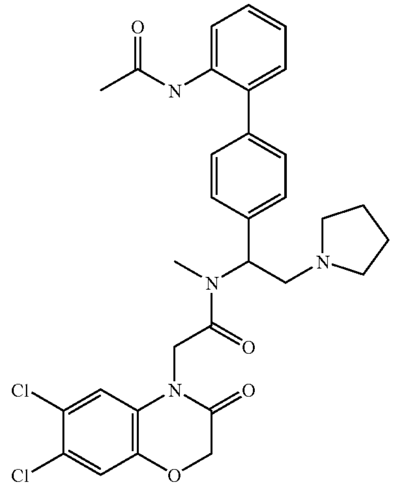 | N-[1-[2'-(acetylamino)-4-biphenylyl]-2-(1-pyrrolidinyl)ethyl]-2-(6,7-dichloro-3-oxo-2,3-dihydro-4H-1,4-benzoxazin-4-yl)-N-methylacetamide | 595 |
| 403 | 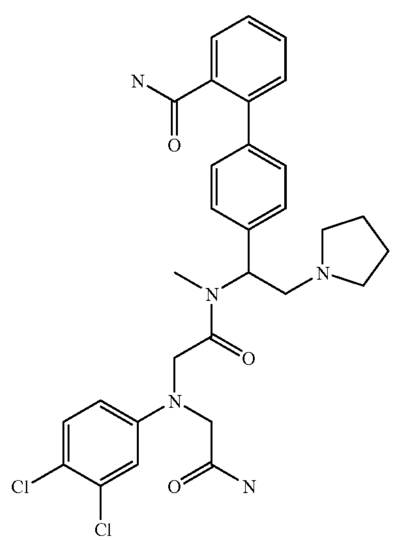 | 4'[1-[{[(2-amino-2-oxoethyl)(3,4-dichlorophenyl)amino]acetyl}(methyl)amino]-2-(1-pyrrolidinyl)ethyl]-2-biphenylcarboxamide | 582 |

| Ex # | Structure | Name | MS [M + H]+ |
|---|---|---|---|
| 404 | 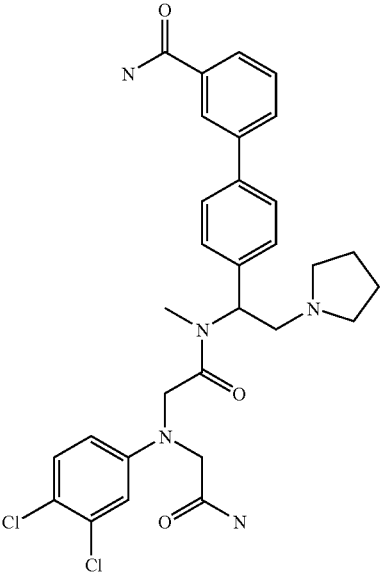 | 4'-[1-[{[(2-amino-2-oxoethyl)(3,4-dichlorophenyl)amino]acetyl}(methyl)amino]-2-(1-pyrrolidinyl)ethyl]-3-biphenylcarboxamide | 582 |
| 405 | 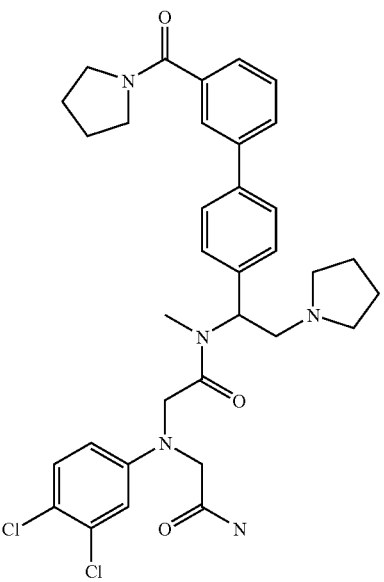 | 2-[(2-amino-2-oxoethyl)(3,4-dichlorophenyl)amino]-N-methyl-N-{2-(1-pyrrolidinyl)-1-[3'-(1-pyrrolidinylcarbonyl)-4-biphenylyl]ethyl}acetamide | 636 |

TABLE 12-continued

| Ex # | Structure | Name | MS [M + H]+ |
|---|---|---|---|
| 406 | 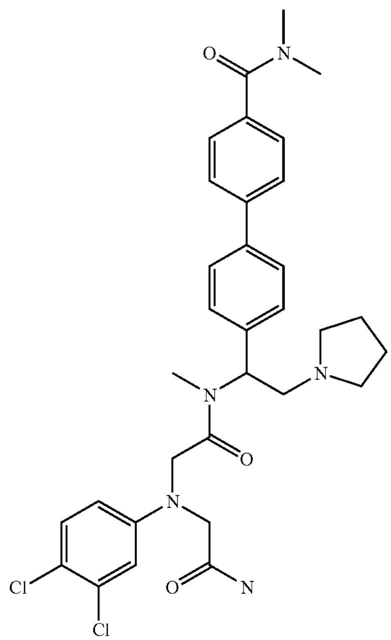 | 4'-[1-[{[(2-amino-2-oxoethyl)(3,4-dichlorophenyl)amino]acetyl}(methyl)amino]-2-(1-pyrrolidinyl)ethyl]-N,N-dimethyl-4-biphenylcarboxamide | 610 |
| 407 | 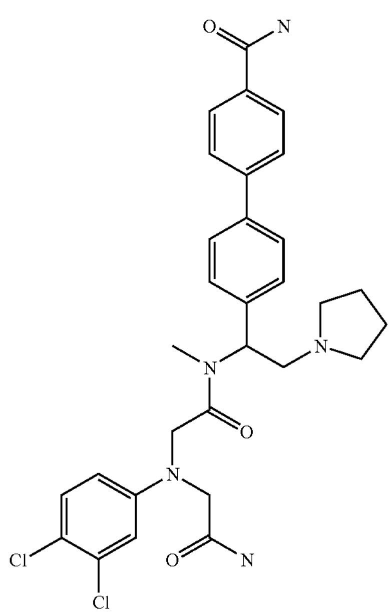 | 4'-[1-[{[(2-amino-2-oxoethyl)(3,4-dichlorophenyl)amino]acetyl}(methyl)amino]-2-(1-pyrrolidinyl)ethyl]-4-biphenylcarboxamide | 582 |

TABLE 12-continued

| Ex # | Structure | Name | MS [M + H]+ |
|---|---|---|---|
| 408 | 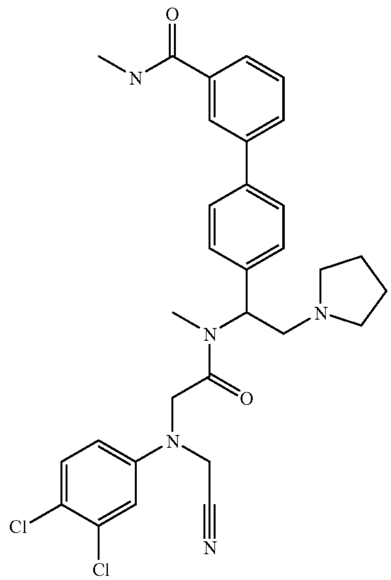 | 4'-[1-[[N-(cyanomethyl)-N-(3,4-dichlorophenyl)glycyl](methyl)amino]-2-(1-pyrrolidinyl)ethyl]-N-methyl-3-biphenylcarboxamide | 578 |
| 409 | 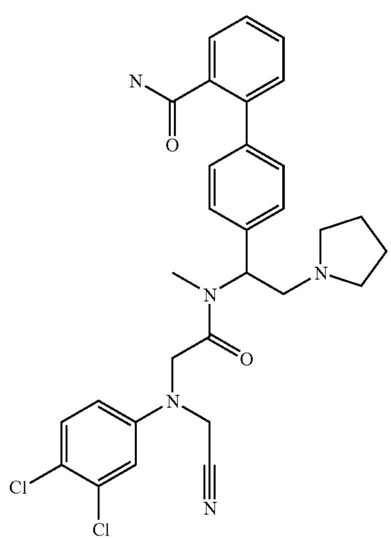 | 4'-[1-[[N-(cyanomethyl)-N-(3,4-dichlorophenyl)glycyl](methyl)amino]-2-(1-pyrrolidinyl)ethyl]-2-biphenylcarboxamide | 564 |

TABLE 12-continued

| Ex # | Structure | Name | MS [M + H]+ |
|---|---|---|---|
| 410 | 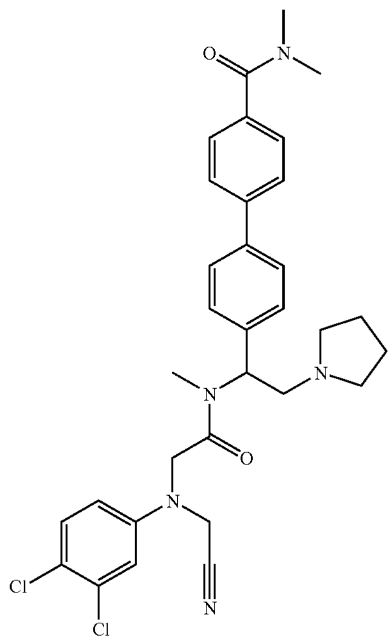 | 4'-[1-[[N-(cyanomethyl)-N-(3,4-dichlorophenyl)glycyl](methyl)amino]-2-(1-pyrrohdinyl)ethyl]-N,N-dimethyl-4-biphenylcarboxamide | 592 |
| 411 | 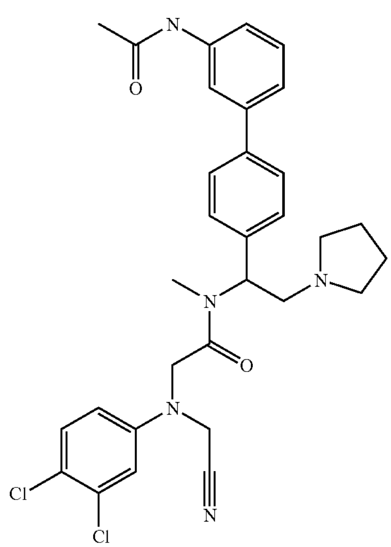 | N¹-[1-[3'-(acetylamino)-4-biphenylyl]-2-(1-pyrrolidinyl)ethyl]-N²-(cyanomethyl)-N²-(3,4-dichlorophenyl)-N¹-methylglycinamide 578 | |

TABLE 12-continued

| Ex # | Structure | Name | MS [M + H]+ |
|---|---|---|---|
| 412 | 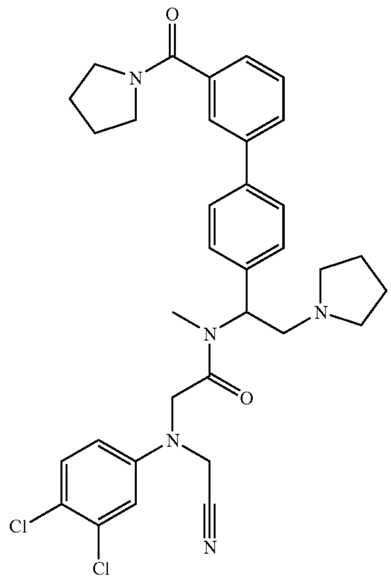 | N²-(cyanomethyl)-N²-(3,4-dichlorophenyl)-N¹-methyl-N¹-{2-(1-pyrrolidinyl)-1-[3'-(1-pyrrolidinylcarbonyl)-4-biphenylyl]ethyl}glycinamide | 618 |
| 413 | 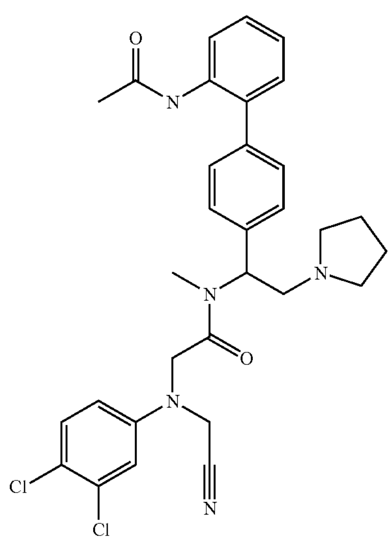 | N¹-[1-[2'-(acetylamino)-4-biphenylyl]-2-(1-2 pyrrolidinyl)ethyl]N²-(cyanomethyl)-N²-(3,4-dichlorophenyl)-N¹-methylglycinamide | 578 |

TABLE 12-continued
| Ex # | Structure | Name | MS [M + H]+ |
|---|---|---|---|
| 414 | 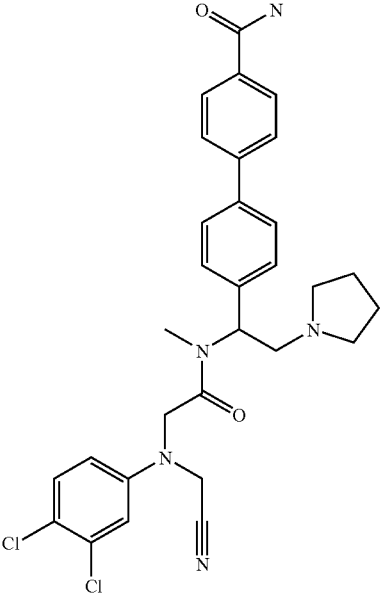 | 4'-[1-[[N-(cyanomethyl)-N-(3,4-dichlorophenyl)glycyl](methyl)amino]-2-(1-pyrrolidinyl)ethyl]-4-biphenylcarboxamide | 564 |
| 415 | 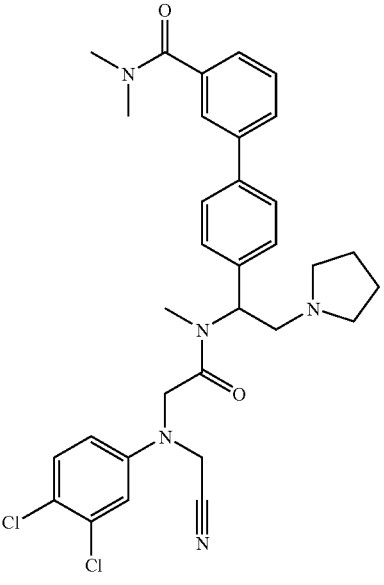 | 4'-[1-[[N-(cyanomethyl)-N-(3,4-dichlorophenyl)glycyl](methyl)amino]-2-(1-pyrrolidinyl)ethyl]-N,N-dimethyl-3-biphenylcarboxamide | 592 |

TABLE 12-continued

| Ex # | Structure | Name | MS [M + H]$^+$ |
|---|---|---|---|
| 416 | 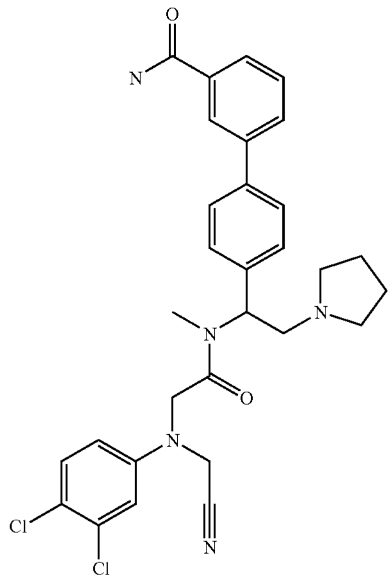 | 4'-[1-[[N-(cyanomethyl)-N-(3,4-dichlorophenyl)glycyl](methyl)amino]-2-(1-pyrrolidinyl)ethyl]-3-biphenylcarboxamide | 564 |
| 417 | 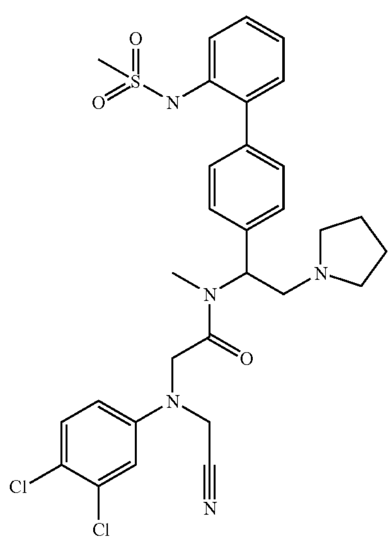 | N$^2$-(cyanomethyl)-N$^2$-(3,4-dichlorophenyl)-N$^1$-methyl-N$^1$-[1-{2'-[(methylsulfonyl)amino]-4-biphenylyl}-2-(1-pyrrolidinyl)ethyl]glycinamide | 614 |

TABLE 12-continued

| Ex # | Structure | Name | MS [M + H]+ |
|---|---|---|---|
| 418 | 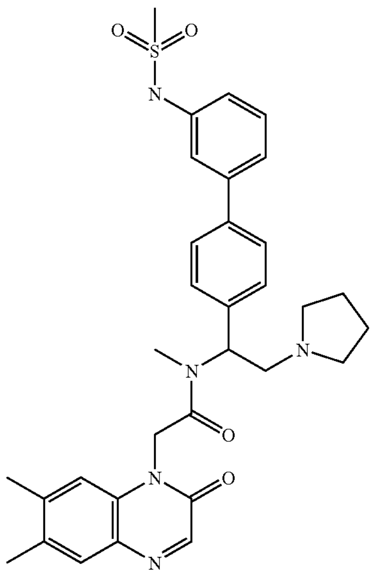 | 2-(6,7-dimethyl-2-oxo-1(2H)-quinoxalinyl)-N-methyl-N-[1-{3'-[(methylsulfonyl)amino]-4-biphenylyl}-2-(1-pyrrolidinyl)ethyl]acetamide | 588 |
| 419 | 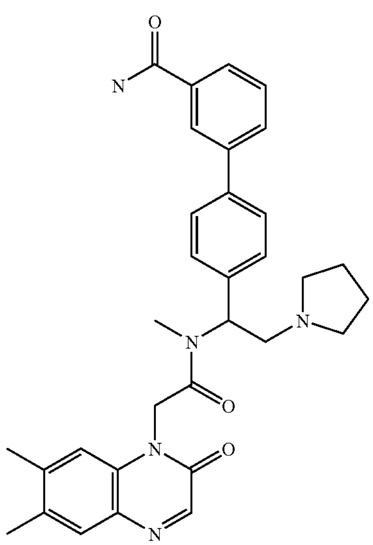 | 4'-[1-[[(6,7-dimethyl-2-oxo-1(2H)-quinoxalinyl)acetyl](methyl)amino]-2-(1-pyrrolidinyl)ethyl]-3-biphenylcarboxamide | 538 |

TABLE 12-continued

| Ex # | Structure | Name | MS [M + H]+ |
|---|---|---|---|
| 420 | 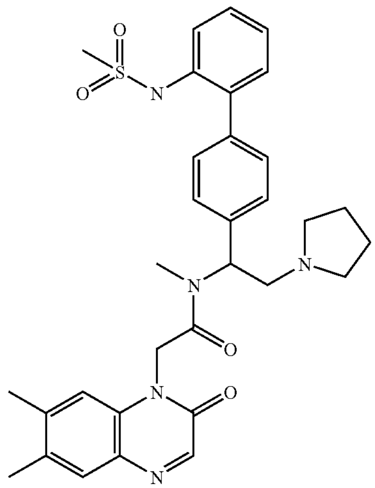 | 2-(6,7-dimethyl-2-oxo-1(2H)-quinoxalinyl)-N-methyl-N-[1-{2'-[(methylsulfonyl)amino]-4-biphenylyl}-2-(1-pyrrolidinyl)ethyl]acetamide | 588 |
| 421 | 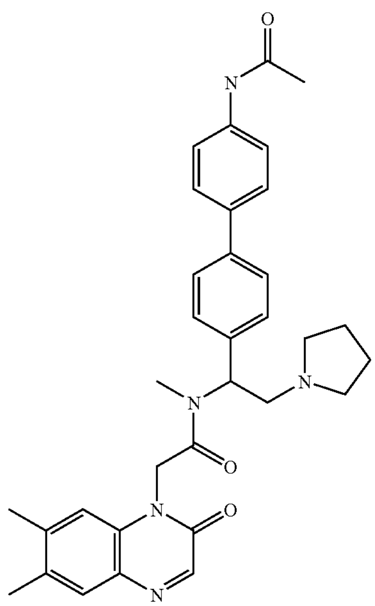 | N-[1-[4'-(acetylamino)-4-biphenylyl]-2-(1-pyrrolidinyl)ethyl]-2-(6,7-dimethyl-2-oxo-1(2H)-quinoxalinyl)-N-methylacetamide | 552 |
| 422 | 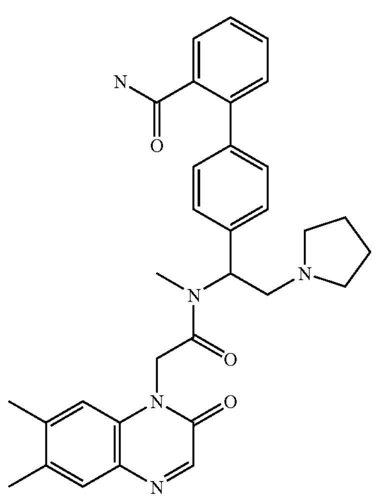 | 4'-[1-[[(6,7-dimethyl-2-oxo-1(2H)-quinoxalinyl)acetyl](methyl)amino]-2-(1-pyrrolidinyl)ethyl]-2-biphenylcarboxamide | 538 |

TABLE 12-continued
| Ex # | Structure | Name | MS [M + H]+ |
|---|---|---|---|
| 423 | 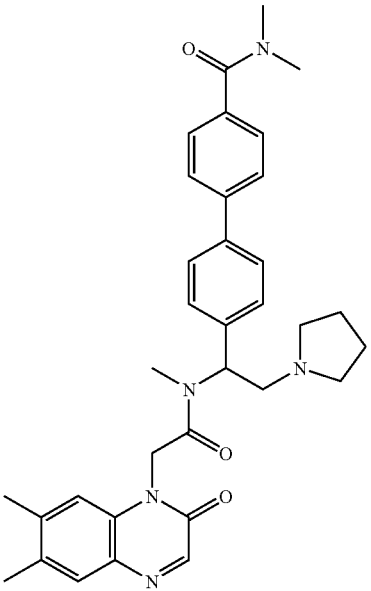 | 4'-[1-[[(6,7-dimethyl-2-oxo-1(2H)-quinoxalinyl)acetyl](methyl)amino]-2-(1-pyrrolidinyl)ethyl]-N,N-dimethyl-4-biphenylcarboxamide | 566 |
| 424 | 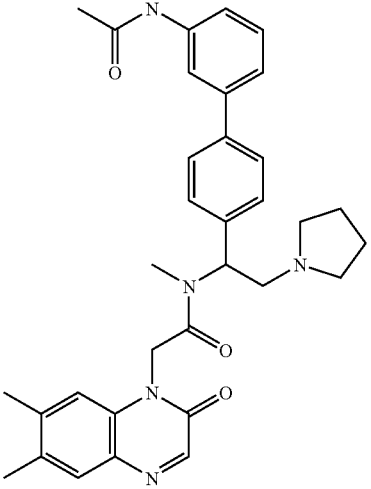 | N-[1-[3'-(acetylamino)-4-biphenylyl]-2-(1-pyrrolidinyl)ethyl]-2-(6,7-dimethyl-2-oxo-1(2H)-quinoxalinyl)-N-methylacetamide | 552 |

TABLE 12-continued

| Ex # | Structure | Name | MS [M + H]+ |
|---|---|---|---|
| 425 | 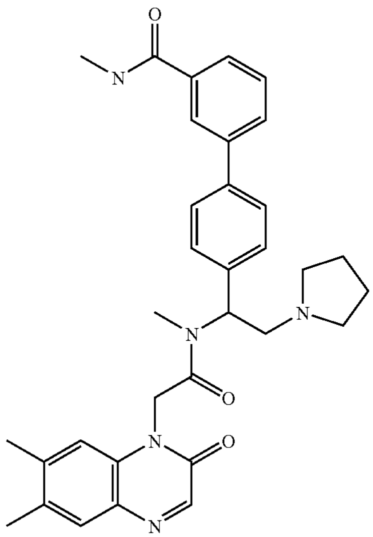 | 4'-[1-[[(6,7-dimethyl-2-oxo-1(2H)-quinoxalinyl)acetyl](methyl)amino]-2-(1-pyrrolidinyl)ethyl]-N-methyl-3-biphenylcarboxamide | 552 |
| 426 | 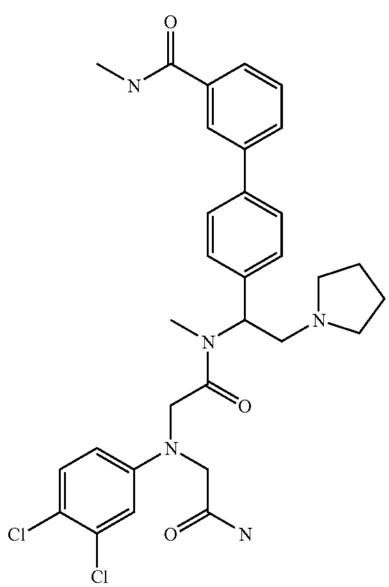 | 4'-[1-[{[(2-amino-2-oxoethyl)(3,4-dichlorophenyl)amino]acetyl}(methyl)amino]-2-(1-pyrrolidinyl)ethyl]-N-methyl-3-biphenylcarboxamide | 596 |

TABLE 12-continued

| Ex # | Structure | Name | MS [M + H]+ |
|---|---|---|---|
| 427 | 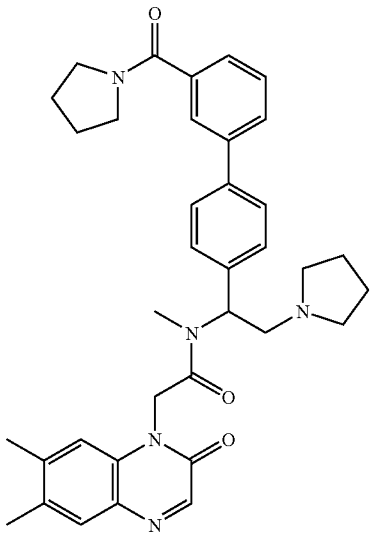 | 2-(6,7-dimethyl-2-oxo-1(2H)-quinoxalinyl)-N-methyl-N-{2-(1-pyrrolidinyl)-1-[3'-(1-pyrrolidinylcarbonyl)-4-biphenylyl]ethyl}acetamide | 592 |
| 428 | 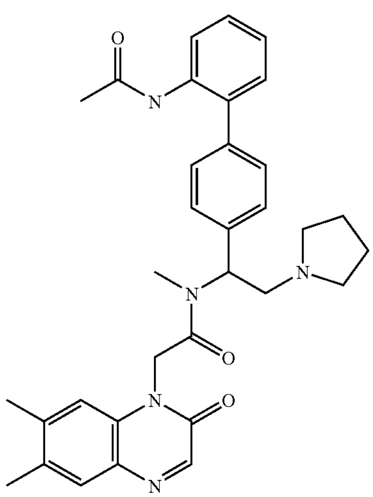 | N-[1-[2'-(acetylamino)-4-biphenylyl]-2-(1-pyrrolidinyl)ethyl]-2-(6,7-dimethyl-2-oxo-1(2H)-quinoxalinyl)-N-methylacetamide | 552 |
| 429 | 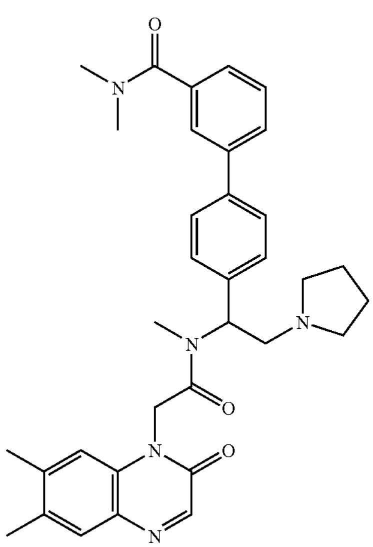 | 4'-[1-[[(6,7-dimethyl-2-oxo-1(2H)-quinoxalinyl)acetyl](methyl)amino]-2-(1-pyrrolidinyl)ethyl]-N,N-dimethyl-3-biphenylcarboxamide | 566 |

TABLE 12-continued
| Ex # | Structure | Name | MS [M + H]+ |
|---|---|---|---|
| 430 | 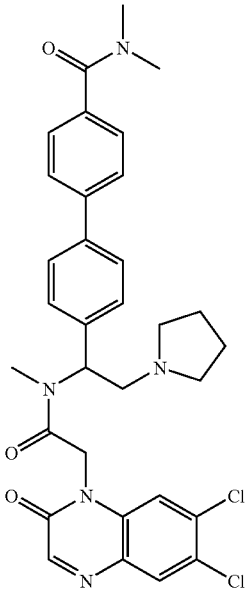 | 4'-[1-[[(6,7-dichloro-2-oxo-1(2H)-quinoxalinyl)acetyl](methyl)amino]-2-(1-pyrrolidinyl)ethyl]-N,N-dimethyl-4-biphenylcarboxamide | 609 |
| 431 | 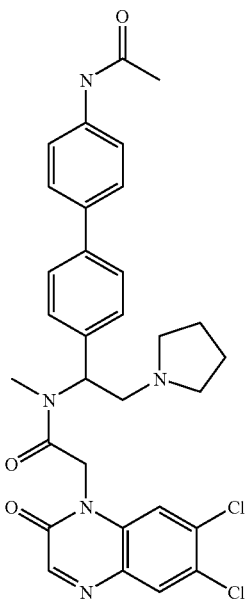 | N-[1-[4'-(acetylamino)-4-biphenylyl]-2-(1-pyrrolidinyl)ethyl]-2-(6,7-dichloro-2-oxo-1(2H)-quinoxalinyl)-N-methylacetamide | 592 |

TABLE 12-continued

| Ex # | Structure | Name | MS [M + H]+ |
|---|---|---|---|
| 432 | 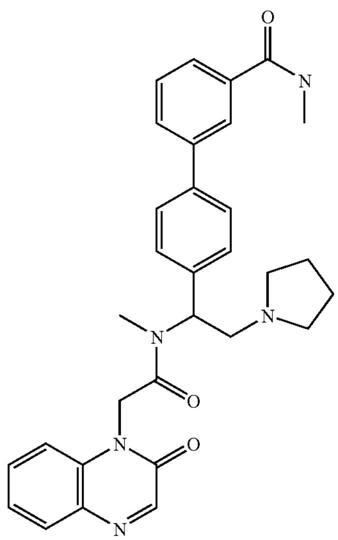 | N-methyl-4'-[1-{methyl[(2-oxo-1(2H)-quinoxalinyl)acetyl]amino}-2-(1-pyrrolidinyl)ethyl]-3-biphenylcarboxamide | 524 |
| 433 | 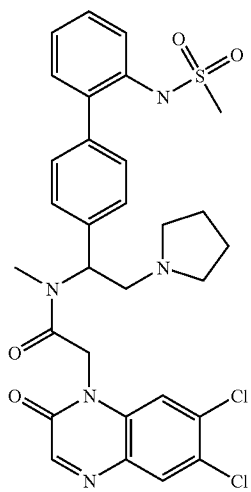 | 2-(6,7-dichloro-2-oxo-1(2H)-quinoxalinyl)-N-methyl-N-[1-{2'-[(methylsulfonyl)amino]-4-biphenylyl}-2-(1-pyrrolidinyl)ethyl]acetamide | 631 |
| 434 | 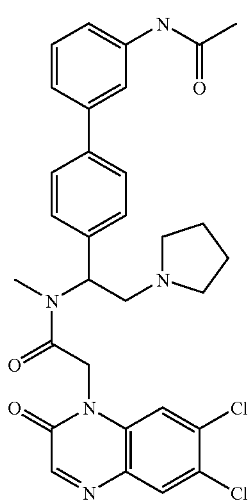 | N-[1-[3'-(acetylamino)-4-biphenylyl]-2-(1-pyrrolidinyl)ethyl]-2-(6,7-dichloro-2-oxo-1(2H)-quinoxalinyl)-N-methylacetamide | 595 |

TABLE 12-continued
| Ex # | Structure | Name | MS [M + H]+ |
|---|---|---|---|
| 435 | 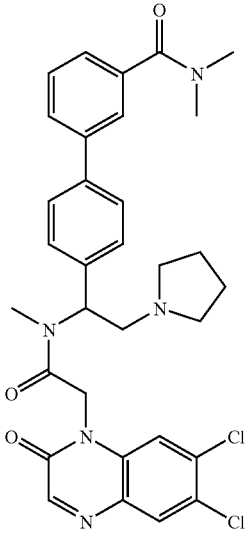 | 4'-[1-[[(6,7-dichloro-2-oxo-1(2H)-quinoxalinyl)acetyl](methyl)amino]-2-(1-pyrrolidinyl)ethyl]-N,N-dimethyl-3-biphenylcarboxamide | 609 |
| 436 | 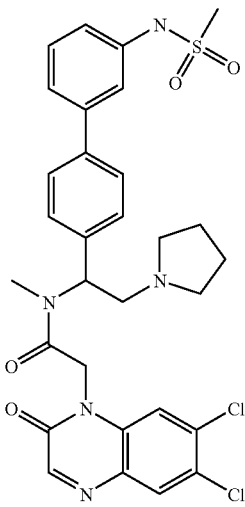 | 2-(6,7-dichloro-2-oxo-1(2H)-quinoxalinyl)-N-methyl-N-[1-{3'-[(methylsulfonyl)amino]-4-biphenylyl}-2-(1-pyrrolidinyl)ethyl]acetamide | 631 |

TABLE 12-continued

| Ex # | Structure | Name | MS [M + H]+ |
|------|-----------|------|-------------|
| 437 | 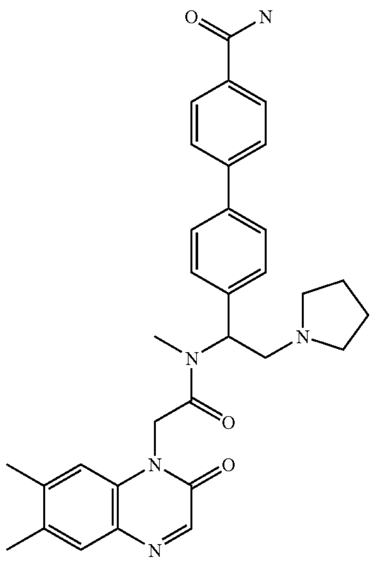 | 4'-[1-[[(6,7-dimethyl-2-oxo-1(2H)-quinoxalinyl)acetyl](methyl)amino]-2-(1-pyrrolidinyl)ethyl]-4-biphenylcarboxamide | 538 |
| 438 | 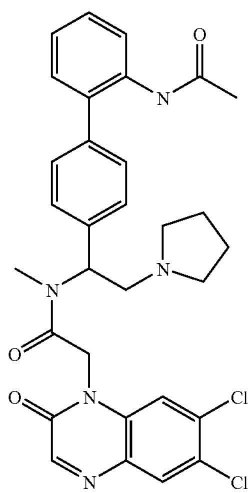 | N-[1-[2'-(acetylamino)-4-biphenylyl]-2-(1-pyrrolidinyl)ethyl]-2-(6,7-dichloro-2-oxo-1(2H)-quinoxalinyl)-N-methylacetamide | 592 |
| 439 | 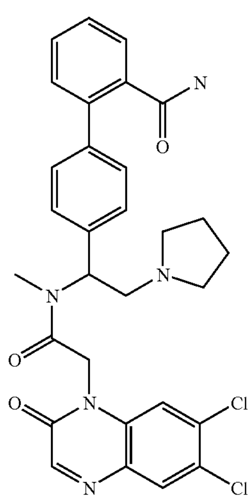 | 4'-[1-[[(6,7-dichloro-2-oxo-1(2H)-quinoxalinyl)acetyl](methyl)amino]-2-(1-pyrrolidinyl)ethyl]-2-biphenylcarboxamide | 578 |

TABLE 12-continued
| Ex # | Structure | Name | MS [M + H]+ |
|---|---|---|---|
| 440 | 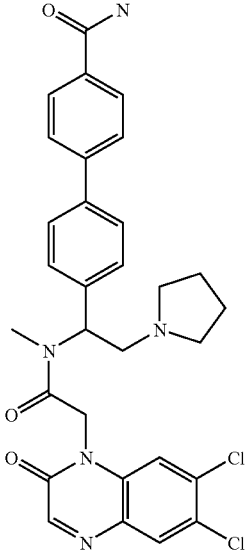 | 4'-[1-[[(6,7-dichloro-2-oxo-1(2H)-quinoxalinyl)acetyl](methyl)amino]-2-(1-pyrrolidinyl)ethyl]-4-biphenylcarboxamide | 578 |
| 441 | 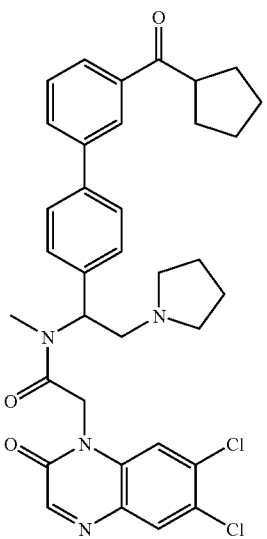 | 2-(6,7-dichloro-2-oxo-1(2H)-quinoxalinyl)-N-methyl-N-{2-(1-pyrrolidinyl)-1-[3'-(1-pyrrolidinylcarbonyl)-4-biphenylyl]ethyl}acetamide | 632 |

TABLE 12-continued

| Ex # | Structure | Name | MS [M + H]+ |
|---|---|---|---|
| 442 | 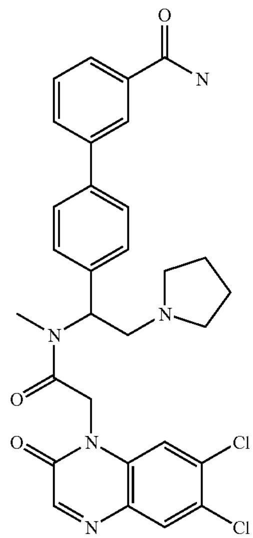 | 4'-[1-[[(6,7-dichloro-2-oxo-1(2H)-quinoxalinyl)acetyl](methyl)amino]-2-(1-pyrrolidinyl)ethyl]-3-biphenylcarboxamide | 578 |
| 443 | 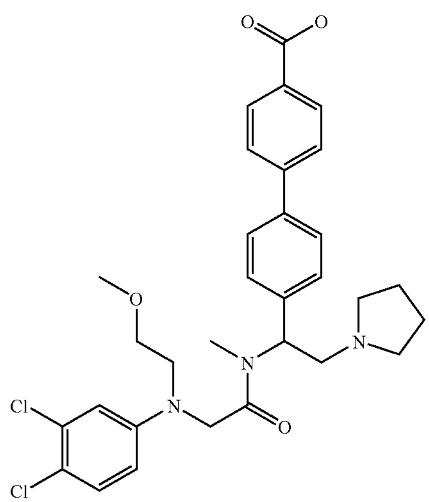 | 4'-[1-[{N-(3,4-dichlorophenyl)-N-[2-(methyloxy)ethyl]glycyl}(methyl)amino]-2-(1-pyrrolidinyl)ethyl]-4-biphenylcarboxylic acid | 584.3, 586.4 |
| 444 | 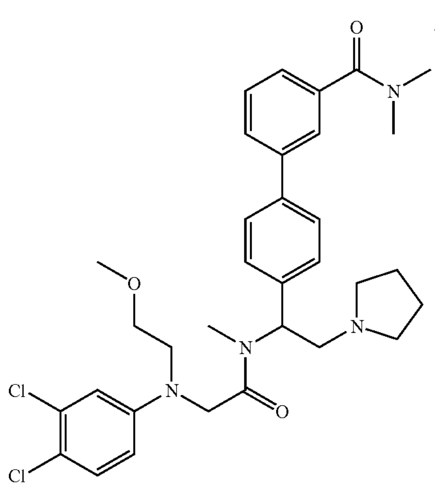 | 4'-[1-[{N-(3,4-dichlorophenyl)-N-[2-(methyloxy)ethyl]glycyl}(methyl)amino]-2-(1-pyrrolidinyl)ethyl]-N,N-dimethyl-3-biphenylcarboxamide | 611.4, 613.4 |

TABLE 12-continued

| Ex # | Structure | Name | MS [M + H]+ |
|---|---|---|---|
| 445 | 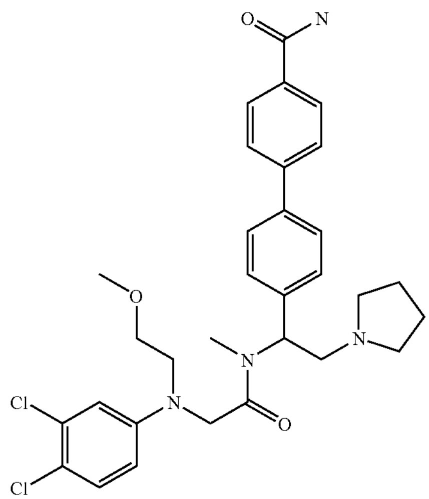 | 4'-[1-[{N-(3,4-dichlorophenyl)-N-[2-(methyloxy)ethyl]glycyl}(methyl)amino]-2-(1-pyrrolidinyl)ethyl]-4-biphenylcarboxamide | 583.3, 585.4 |
| 446 | 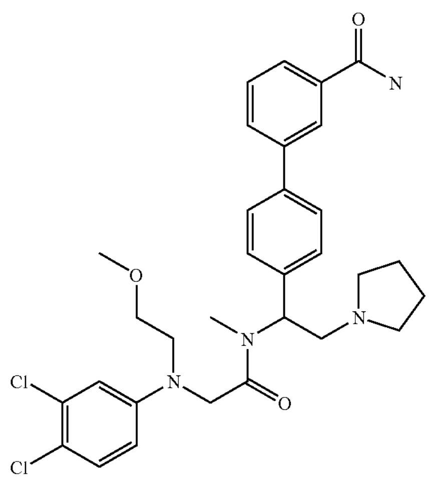 | 4'-[1-[{N-(3,4-dichlorophenyl)-N-[2-(methyloxy)ethyl]glycyl}(methyl)amino]-2-(1-pyrrolidinyl)ethyl]-3-biphenylcarboxamide pyrrolidinyl)ethyl]glycinamide | 583.4, 585.4 |
| 447 | 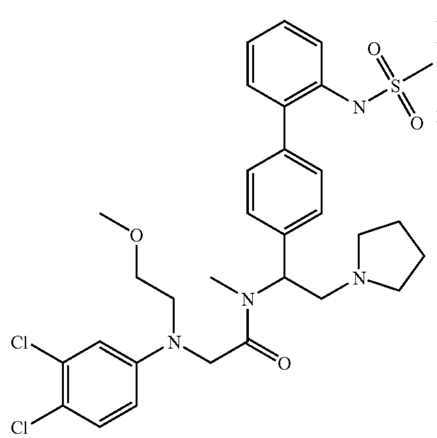 | $N^2$-(3,4-dichlorophenyl)-N-$^1$methyl-$N^2$-[2-(methyloxy)ethyl]-$N^1$-[1-{2'-[(methylsulfonyl)amino]-4-biphenylyl}-2-(1-pyrrolidinyl)ethyl]glycinamide | 633.4, 635.6 |

TABLE 12-continued

| Ex # | Structure | Name | MS [M + H]+ |
|---|---|---|---|
| 448 | 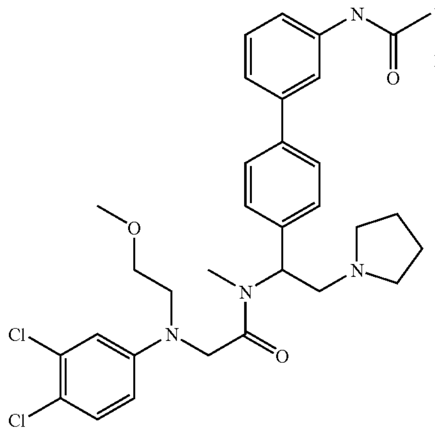 | N¹-[1-[3'-(acetylamino)-4-biphenylyl]-2-(1-pyrrolidinyl)ethyl]-N²-(3,4-2 dichlorophenyl)-N¹-methyl-N²-[2-(methyloxy)ethyl]glycinamide | 597.5, 599.4 |
| 449 | 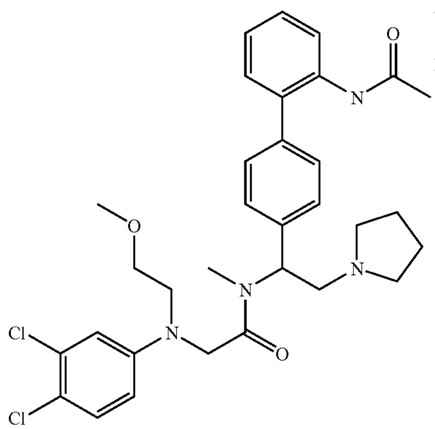 | N¹-[1-[2'-(acetylamino)-4-biphenylyl]-2-(1-pyrrolidinyl)ethyl]-N²-(3,4-2 dichlorophenyl)-N¹-methyl-N²-[2-(methyloxy)ethyl]glycinamide | 597.5, 599.4 |
| 450 | 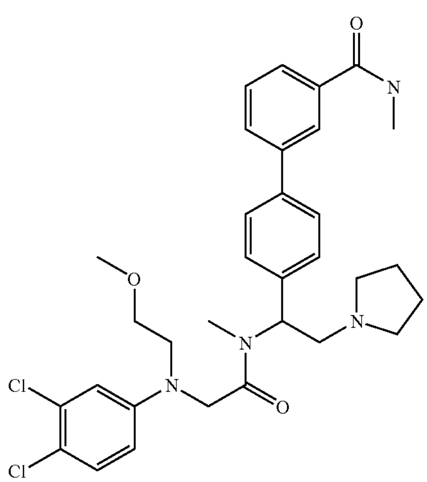 | 4'-[1-[{N-(3,4-dichlorophenyl)-N-[2-(methyloxy)ethyl]glycyl}(methyl)amino]-2-(1-pyrrolidinyl)ethyl]-N-methyl-3-biphenylcarboxamide | 597.5, 599.4 |

TABLE 12-continued

| Ex # | Structure | Name | MS [M + H]+ |
|---|---|---|---|
| 451 | 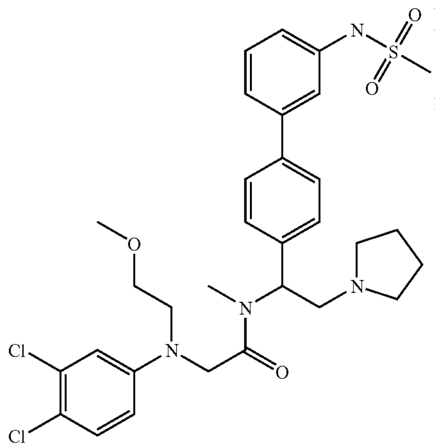 | N²-(3,4-dichlorophenyl)-N¹-methyl-N²-[2-(methyloxy)ethyl]-N-¹[1-{3'-[(methylsulfonyl)amino]-4-biphenylyl}-2-(1-pyrrolidinyl)ethyl]glycinamide | 633.4 |
| 452 | 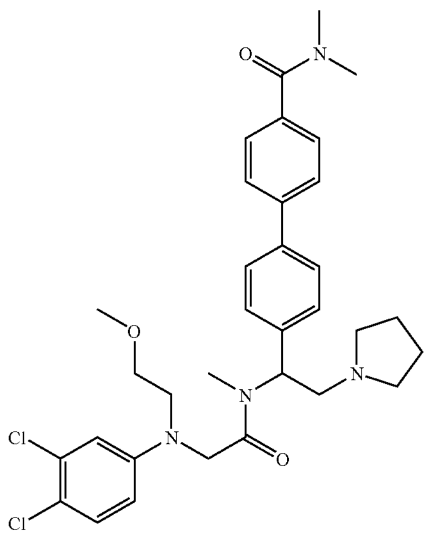 | 4'-[1-[{N-(3,4-dichlorophenyl)-N-[2-(methyloxy)ethyl]glycyl}(methyl)amino]-2-(1-pyrrolidinyl)ethyl]-N,N-dimethyl-4-biphenylcarboxamide | 611.4, 613.4 |
| 453 | 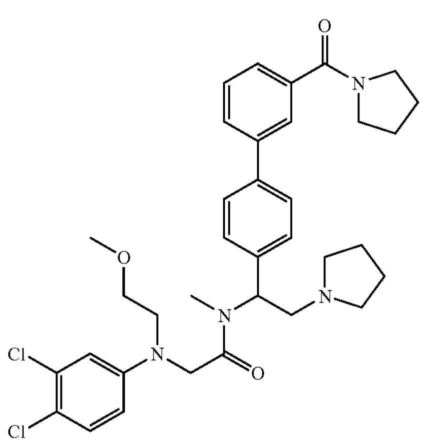 | N²-(3,4-dichlorophenyl)-N¹-methyl-N²-[2-(methyloxy)ethyl]-N-¹{2-(1-pyrrolidinyl)-1-[3'-(1-pyrrolidinylcarbonyl)-4-biphenylyl]ethyl}glycinamide | 637.4 |

TABLE 12-continued

| Ex # | Structure | Name | MS [M + H]+ |
|---|---|---|---|
| 454 | 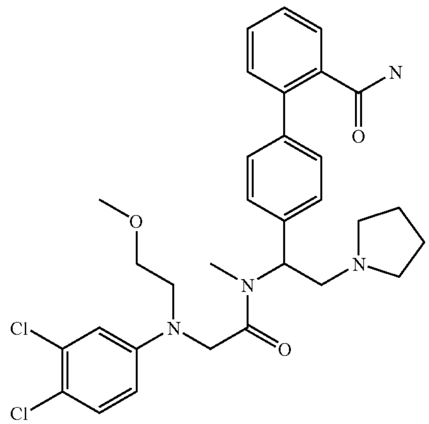 | 4'-[1-[{N-(3,4-dichlorophenyl)-N-[2-(methyloxy)ethyl]glycyl}(methyl)amino]-2-(1-pyrrolidinyl)ethyl]-2-biphenylcarboxamide | 583.3, 585.5 |

Examples 455-458

Proceeding in a similar manner as in example 392, but replacing 1-(4-bromophenyl)-N-methyl-2-(1-pyrrolidinyl)ethanamine with (1R)-1-(4-bromophenyl)-N-methyl-2-(1-pyrrolidinyl)ethanamine and/or replacing N-(3,4-dichlorophenyl)-N-[2-(methyloxy)ethyl]glycine, lithium salt with the appropriate acids and/or replacing [4-(acetylamino)phenyl]boronic acid with the appropriate boronic acids, the compounds listed in table 13 were prepared. As is appreciated by those skilled in the art, these analogous examples may involve variations in synthetic procedure.

TABLE 13

| Ex # | Structure | Name | MS [M + H]+ |
|---|---|---|---|
| 455 | 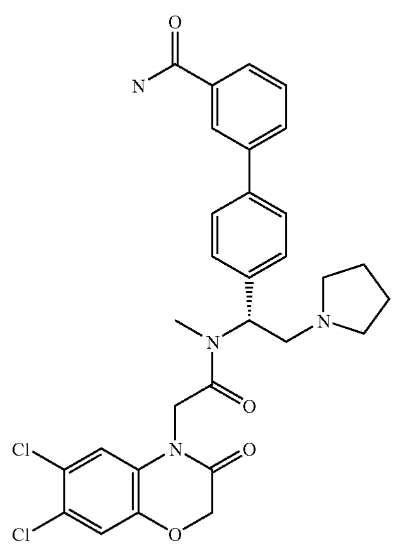 | 4'-[(1R)-1-[[(6,7-dichloro-3-oxo-2,3-dihydro-4H-1,4-benzoxazin-4-yl)acetyl](methyl)amino]-2-(1-pyrrolidinyl)ethyl]-3-biphenylcarboxamide | 581 |

TABLE 13-continued

| Ex # | Structure | Name | MS [M + H]+ |
|---|---|---|---|
| 456 | 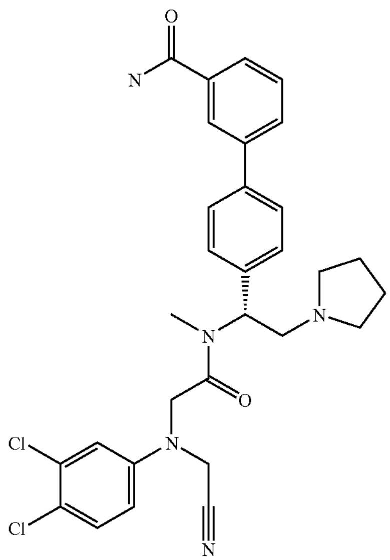 | 4'-[(1R)-1-[[N-(cyanomethyl)-N-(3,4-dichlorophenyl)glycyl](methyl)amino]-2-(1-pyrrolidinyl)ethyl]-3-biphenylcarboxamide | 564 |
| 457 | 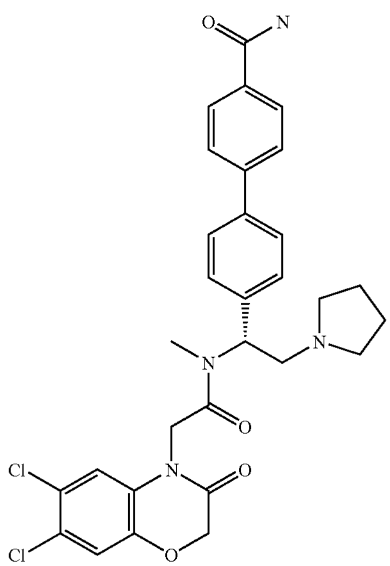 | 4'-[(1R)-1-[[(6,7-dichloro-3-oxo-2,3-dihydro-4H-1,4-benzoxazin-4-yl)acetyl](methyl)amino]-2-(1-pyrrolidinyl)ethyl]-4-biphenylcarboxamide | 581 |

TABLE 13-continued

| Ex # | Structure | Name | MS [M + H]+ |
|---|---|---|---|
| 458 | 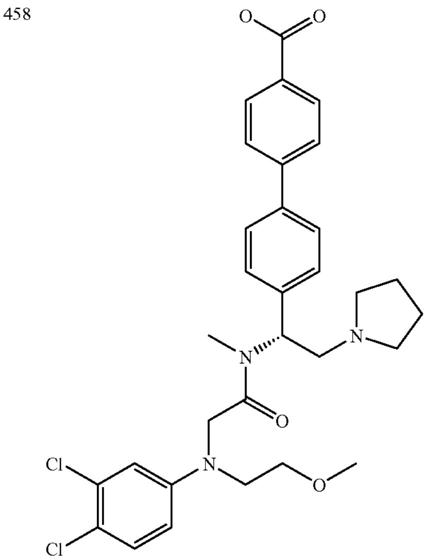 | 4'-[(1R)-1-[{N-(3,4-dichlorophenyl)-N-[2-(methyloxy)ethyl]glycyl}(methyl)amino]-2-(1-pyrrolidinyl)ethyl]-4-biphenylcarboxylic acid | 584 |

Example 459

$N^1$-[(1R)-1-[4'-(acetylamino)-4-biphenylyl]-2-(1-pyrrolidinyl)ethyl]-$N^2$-(cyanomethyl)-$N^2$-(3,4-dichlorophenyl)-$N^1$-methylglycinamide

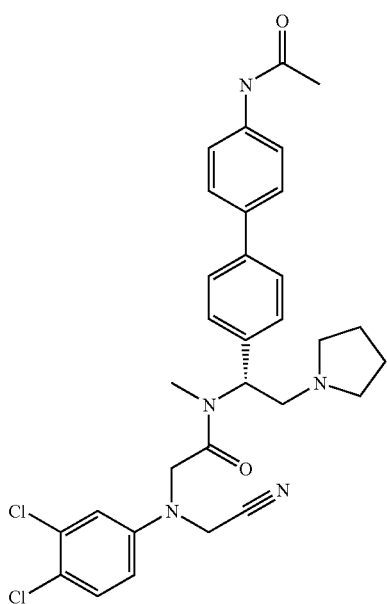

Proceeding in a similar manner as in example 85, but replacing 1-(4-bromophenyl)-N-methyl-2-(1-pyrrolidinyl)ethanamine with (1R)-1-(4-bromophenyl)-N-methyl-2-(1-pyrrolidinyl)ethanamine and replacing (6,7-dichloro-3-oxo-2,3-dihydro-4H-1,4-benzoxazin-4-yl)acetic acid with N-(cyanomethyl)-N-(3,4-dichlorophenyl)glycine in step a) and replacing 3,4-dimethoxyphenylboronic acid with [4-(acetylamino)phenyl]boronic acid in step b), the title compound was prepared. MS (ES) m/e 578 [M+H]+.

Example 460

4'-[(1R)-1-[[(6,7-dichloro-3-oxo-2,3-dihydro-4H-1,4-benzoxazin-4-yl)acetyl](methyl)amino]-2-(1-pyrrolidinyl)ethyl]-4-biphenylcarboxylic acid

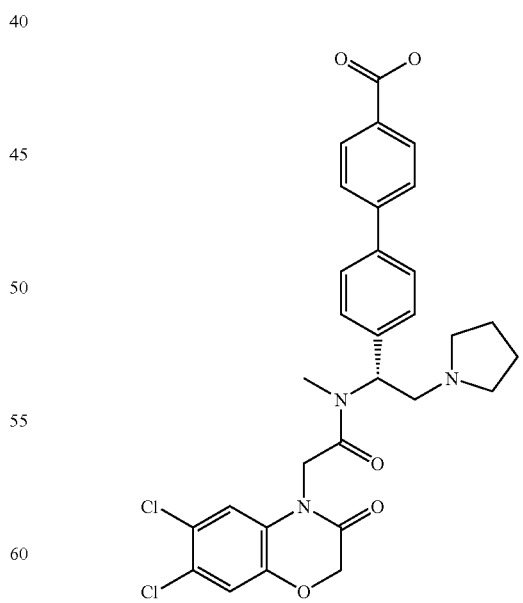

Proceeding in a similar manner as in example 85, but replacing 1-(4-bromophenyl)-N-methyl-2-(1-pyrrolidinyl)ethanamine with (1R)-1-(4-bromophenyl)-N-methyl-2-(1-pyrrolidinyl)ethanamine in step a) and replacing 3,4- dimethoxyphenylboronic acid with 4-(dihydroxyboranyl)benzoic acid in step b), the title compound was prepared. MS (ES) m/e 582 [M+H]+.

Examples 461-462

Proceeding in a similar manner as in example 130, but replacing 1-(4-bromophenyl)-N-methyl-2-(4-morpholinyl)ethanamine with (1R)-1-(4-bromophenyl)-N-methyl-2-(4-morpholinyl)ethanamine and replacing {4[(methylsulfonyl)amino]-phenyl}boronic acid with the appropriate boronic acids, the compounds listed in table 14 were prepared. As is appreciated by those skilled in the art, these analogous examples may involve variations in synthetic procedure.

TABLE 14

| Ex # | Structure | Name | MS [M + H]+ |
|---|---|---|---|
| 461 | 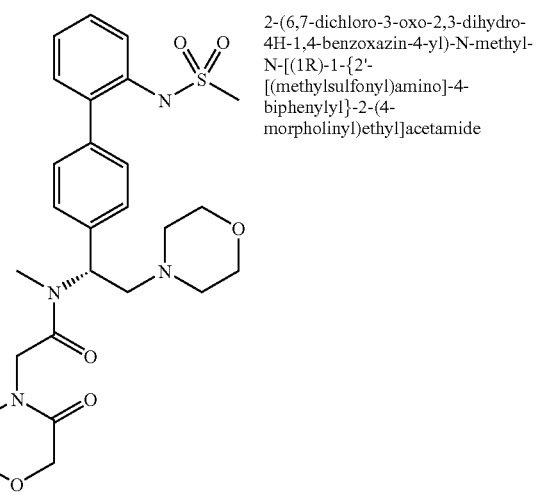 | 2-(6,7-dichloro-3-oxo-2,3-dihydro-4H-1,4-benzoxazin-4-yl)-N-methyl-N-[(1R)-1-{2'-[(methylsulfonyl)amino]-4-biphenylyl}-2-(4-morpholinyl)ethyl]acetamide | 647 |
| 462 | 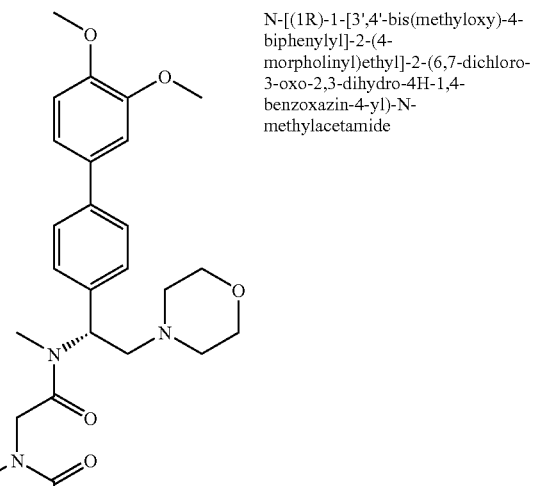 | N-[(1R)-1-[3',4'-bis(methyloxy)-4-biphenylyl]-2-(4-morpholinyl)ethyl]-2-(6,7-dichloro-3-oxo-2,3-dihydro-4H-1,4-benzoxazin-4-yl)-N-methylacetamide | 614 |

Examples 463-466

Proceeding in a similar manner as in example 85, but replacing 1-(4-bromophenyl)-N-methyl-2-(1-pyrrolidinyl)ethanamine with (1R)-1-(4-bromophenyl)-N-methyl-2-(4-morpholinyl)ethanamine and/or replacing 3,4-dimethoxyphenylboronic acid with the appropriate boronic acids, the compounds listed in table 15 were prepared. As is appreciated by those skilled in the art, these analogous examples may involve variations in synthetic procedure.

TABLE 15

| Ex # | Structure | Name | MS [M + H]+ |
|------|-----------|------|-------------|
| 463 | 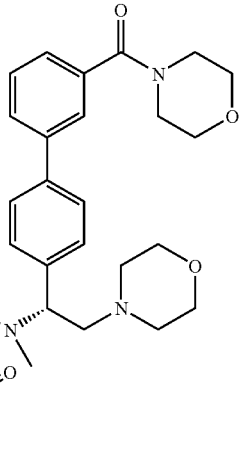 | 2-(6,7-dichloro-3-oxo-2,3-dihydro-4H-1,4-benzoxazin-4-yl)-N-methyl-N-{(1R)-2-(4-morpholinyl)-1-[3'-(4-morpholinylcarbonyl)-4-biphenylyl]ethyl}acetamide | 668 |
| 464 | 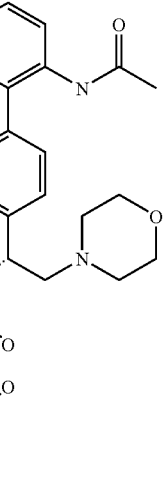 | N-[(1R)-1-[2'-(acetylamino)-4-biphenylyl]-2-(4-morpholinyl)ethyl]-2-(6,7-dichloro-3-oxo-2,3-dihydro-4H-1,4-benzoxazin-4-yl)-N-methylacetamide | 612 |

TABLE 15-continued
| Ex # | Structure | Name | MS [M + H]+ |
|---|---|---|---|
| 465 | 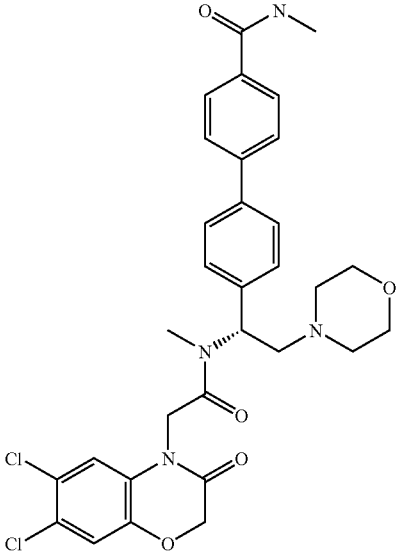 | 4'-[(1R)-1-[[(6,7-dichloro-3-oxo-2,3-dihydro-4H-1,4-benzoxazin-4-yl)acetyl](methyl)amino]-2-(4-morpholinyl)ethyl]-N-methyl-4-biphenylcarboxamide | 612 |
| 466 | 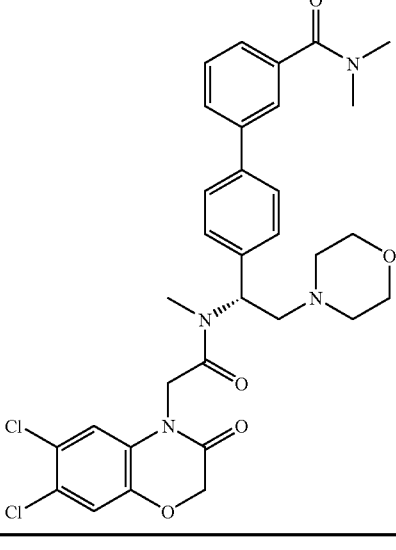 | 4'-[(1R)-1-[[(6,7-dichloro-3-oxo-2,3-dihydro-4H-1,4-benzoxazin-4-yl)acetyl](methyl)amino]-2-(4-morpholinyl)ethyl]-N,N-dimethyl-3-biphenylcarboxamide | 627 |

Example 467

Ethyl 4'-[(1R)-1-[[(6,7-dichloro-3-oxo-2,3-dihydro-4H-1,4-benzoxazin-4-yl)acetyl](methyl)amino]-2-(4-morpholinyl)ethyl]-4-biphenylcarboxylate

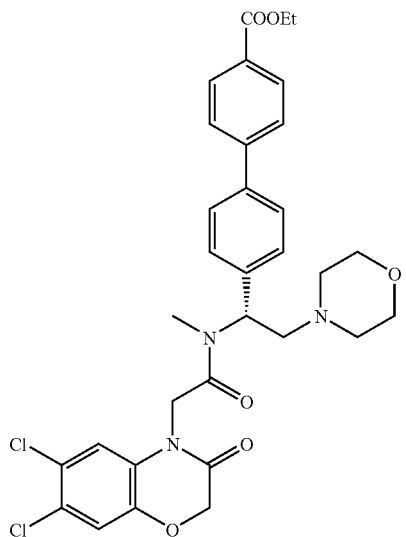

a) Ethyl 4'-[(1R)-1-(methylamino)-2-(4-morpholinyl)ethyl]-4-biphenylcarboxylate

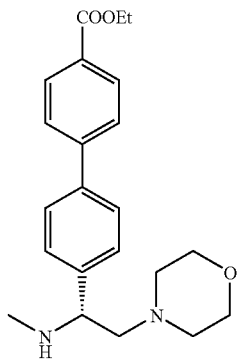

[(1R)-1-(4-Bromophenyl)-2-(4-morpholinyl)ethyl]methylamine (100 mg, 0.29 mmol) was dissolved in EtOH (5 mL) at room temperature with magnetic stirring. The resulting solution was treated with {4-[(ethyloxy)carbonyl]phenyl}boronic acid (62.9 mg, 0.32 mmol) followed by K$_2$CO$_3$ (122.3 mg, 0.88 mmol) and PdCl$_2$(dppf)$_2$·CH$_2$Cl$_2$ (12.0 mg, 0.015 mmol). The reaction mixture was maintained at 80° C. for 16 h. The reaction mixture was cooled to room temperature and then filtered through celite. The filtrate was concentrated and then partitioned between EtOAc and brine. The organic layer was dried over MgSO$_4$, filtered and then concentrated. The residue was purified by silica gel chromatography (40 g Redisep column, silica, 40 um, 60 Å, 40 mL/min, A: MeOH (with 10% NEt$_3$), B: CH$_2$Cl$_2$, A: 2% for 20 min, 5% for 20 min, detection at 254 nm) to give the title compound as a yellow oil (59.7 mg, 48% yield). MS (ES) m/e 369 [M+H]$^+$.

b) Ethyl 4'-[(1R)-1-[[(6,7-dichloro-3-oxo-2,3-dihydro-4H-1,4-benzoxazin-4-yl)acetyl](methyl)amino]-2-(4-morpholinyl)ethyl]-4-biphenylcarboxylate

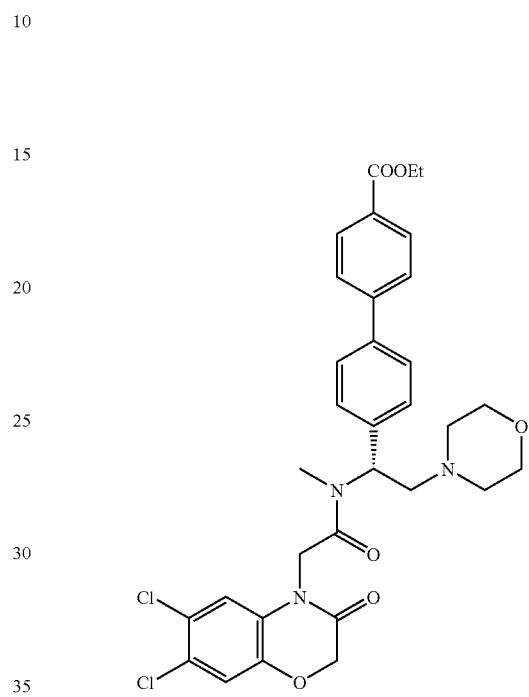

Ethyl 4'-[(1R)-1-(methylamino)-2-(4-morpholinyl)ethyl]-4-biphenylcarboxylate (59.7 mg, 0.16 mmol) was dissolved in 10 mL of DMF at room temperature with magnetic stirring. The resulting solution was treated with (6,7-dichloro-3-oxo-2,3-dihydro-4H-1,4-benzoxazin-4-yl)acetic acid (63.8 mg, 0.18 mmol, with 23 wt % LiCl) followed by triethylamine (32.4 mg, 0.32 mmol) and BOP (78.7 mg, 0.18 mmol), and then the reaction mixture was maintained at room temperature for 16 h. The reaction mixture was concentrated and the residue was partitioned between EtOAc and saturated aqueous NaHCO$_3$ solution. The organic layer was washed by brine, dried over MgSO$_4$, filtered and then concentrated. The residue was dissolved in 2 mL of DMSO and purified by preparative HPLC (Xterra Prep RP, 30×100 mm, 25 mL/min, A: acetonitrile with 0.1% TFA, B: water with 0.1% TFA, A: 15% to 90% during 20 min, UV detection at 214 nm) to give 44 mg (37% yield) of the title compound as a yellow solid. MS (ES) m/e 626 [M+H]$^+$.

Example 468

N-{4'-[1-[[(6,7-dichloro-3-oxo-2,3-dihydro-4H-1,4-benzoxazin-4 yl)acetyl](methyl)amino]-2-(4-morpholinyl)ethyl]-4-biphenylyl}-2-methylpropanamide

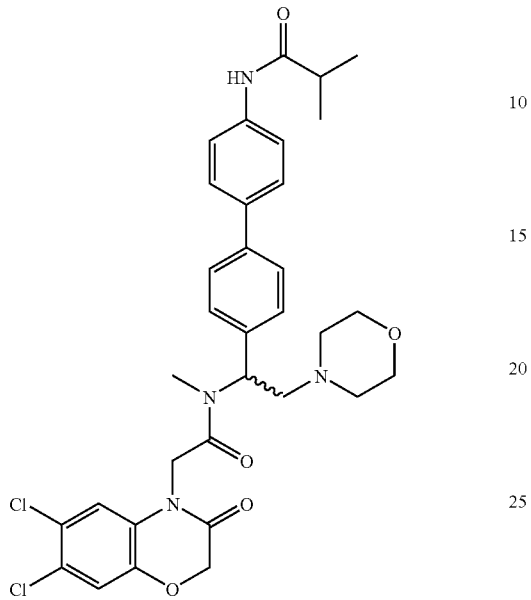

Proceeding in a similar manner as in example 226, but replacing propanoyl chloride with 2-methylpropanoyl chloride in step c), the title compound was prepared. MS (ES) m/e 639 [M+H]⁺.

Example 469

2-(6,7-dichloro-3-oxo-2,3-dihydro-4H-1,4-benzoxazin-4-yl)-N-methyl-N-(2-(4-morpholinyl)-1-{4'-[(phenylsulfonyl)amino]-4-biphenylyl}ethyl)acetamide

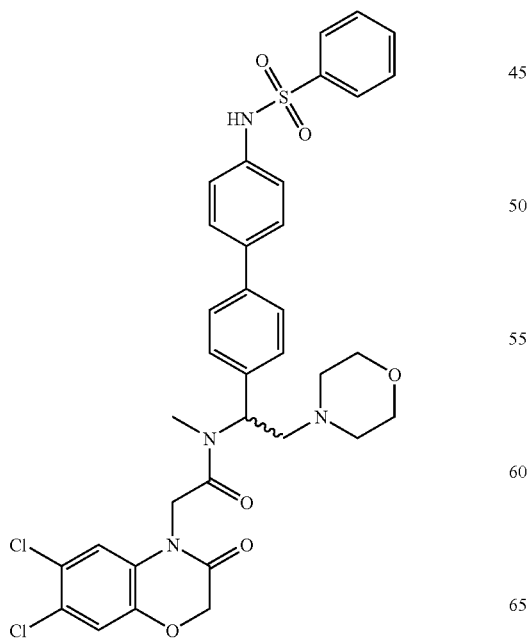

Proceeding in a similar manner as in example 227, but replacing ethanesulfonyl chloride with benzenesulfonyl chloride, the title compound was prepared. MS (ES) m/e 709 [M+H]⁺.

Example 470

2-(6,7-dichloro-3-oxo-2,3-dihydro-4H-1,4-benzoxazin-4-yl)-N-methyl-N-[1-[4'-({[(1-methylethyl)amino]carbonyl}amino)-4-biphenylyl]-2-(4-morpholinyl)ethyl]acetamide

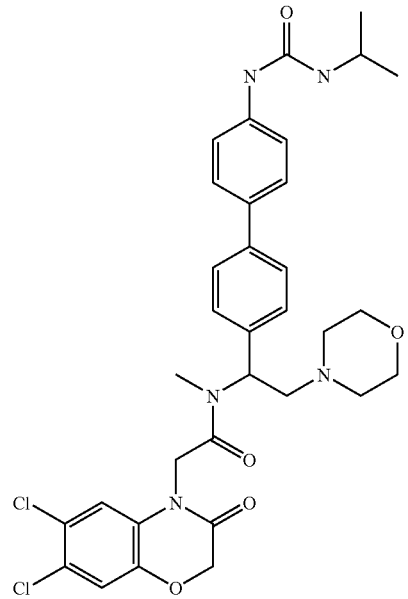

Proceeding in a similar manner as in example 228, but replacing isocyanatoethane with 2-isocyanatopropane, the title compound was prepared. MS (ES) m/e 654 [M+H]⁺.

Example 471

2-(6,7-dichloro-3-oxo-2,3-dihydro-4H-1,4-benzox-azin-4-yl)-N-methyl-N-[1-(4'-{[(methylamino)carbonyl]amino}-4-biphenylyl)-2-(4-morpholinyl)ethyl]acetamide

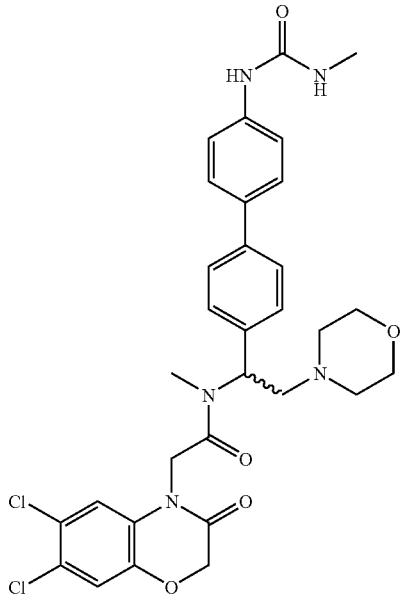

Proceeding in a similar manner as in example 228, but replacing isocyanatoethane with isocyanatomethane, the title compound was prepared. MS (ES) m/e 626 [M+H]$^+$.

Example 472

N-[1-(3'-amino-4-biphenylyl)-2-(4-morpholinyl)ethyl]-2-(6,7-dichloro-3-oxo-2,3-dihydro-4H-1,4-benzoxazin-4-yl)-N-methylacetamide

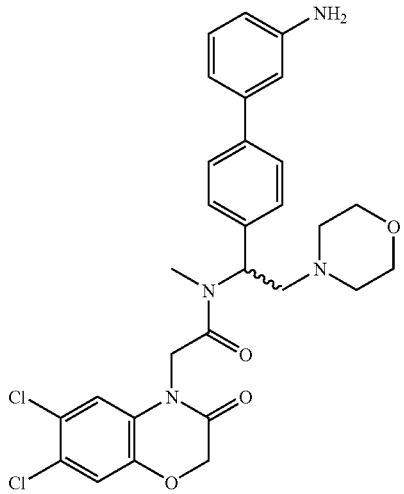

a) 1,1-dimethylethyl {4'-[1-[[(6,7-dichloro-3-oxo-2,3-dihydro-4H-1,4-benzoxazin-4-yl)acetyl](methyl)amino]-2-(4-morpholinyl)ethyl]-3-biphenylyl}carbamate

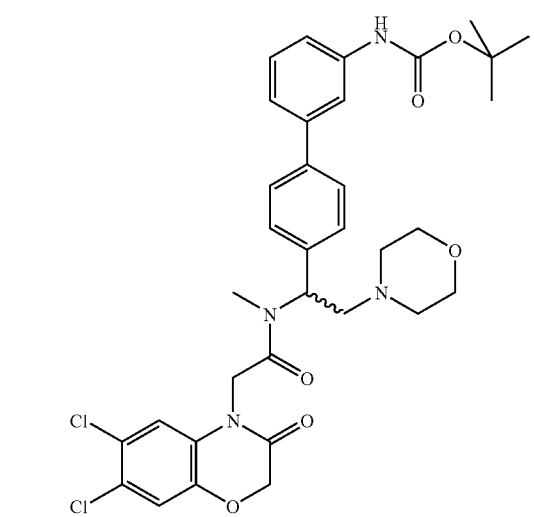

To a solution of N-[1-(4-bromophenyl)-2-(4-morpholinyl)ethyl]-2-(6,7-dichloro-3-oxo-2,3-dihydro-4H-1,4-benzoxazin-4-yl)-N-methylacetamide (3.28 g, 5.8 mmol) and [3-({[(1,1-dimethylethyl)oxy]carbonyl}amino)phenyl]boronic acid (2.00 g, 8.4 mmol) in DMF (15 mL) was added Pd(dppf)Cl$_2$ (0.24 g, 0.29 mmol) and 2N solution of Na$_2$CO$_3$ (11.6 mL, 23.2 mmol). The resultant mixture was stirred at 80° C. for 16 h. The mixture was filtered through a bed of celite and the filtrate was concentrated under reduced pressure. The residue was dissolved in ethyl acetate (100 mL) and washed with 5% NaHCO$_3$ (100 mL) and brine (100 mL). The organic layer was dried over MgSO$_4$ and concentrated. The residue was dissolved in methanol, and water was added to precipitate a tan solid. The solid was collected by filtration and air dried to give 1.55 g (40%) of the title compound a tan solid. MS (ES) m/e 669 [M+H]$^+$ b) N-[1-(3'-amino-4-biphenylyl)-2-(4-morpholinyl)ethyl]-2-(6,7-dichloro-3-oxo-2,3-dihydro-4H-1,4-benzoxazin-4-yl)-N-methylacetamide

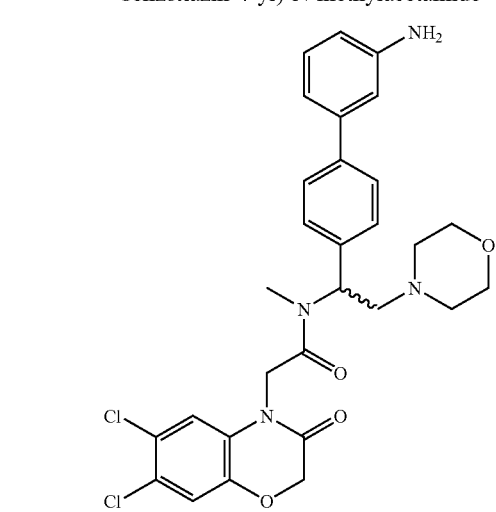

To a solution of 1,1-dimethylethyl {4'-[1-[[(6,7-dichloro-3-oxo-2,3-dihydro-4H-1,4-benzoxazin-4-yl)acetyl](methyl)amino]-2-(4-morpholinyl)ethyl]-3-biphenylyl}carbamate (1.55 g, 2.3 mmol) in dichloromethane (8 mL) was added trifluoro acetic acid (8 mL). The resultant mixture was stirred at room temperature for 2 h. The mixture was concentrated under reduced pressure. The residue was purified by using a Gilson preparative HPLC (Phenomenex, 100×50 mm, 10 micron, 90 mL/min, A: acetonitrile, 0.1% TFA B: water, 0.1% TFA, A: 10 to 90% over 15 min, UV detection at 214 nm) to give 0.66 g (50%) of the title compound as tan solid MS (ES) m/e 569.1 [M+H]$^+$

Example 473

N-{4'-[1-[[(6,7-dichloro-3-oxo-2,3-dihydro-4H-1,4-benzoxazin-4-yl)acetyl](methyl)amino]-2-(4-morpholinyl)ethyl]-3-biphenylyl}propanamide

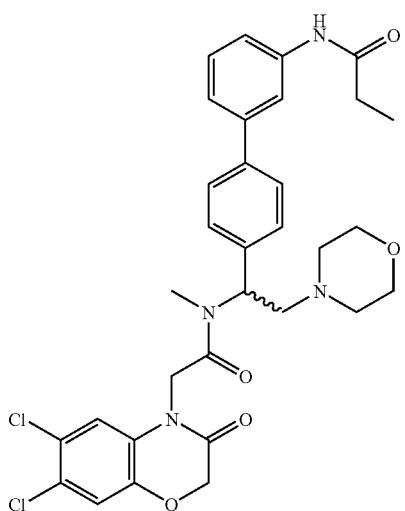

To a solution of N-[1-(3'-amino-4-biphenylyl)-2-(4-morpholinyl)ethyl]-2-(6,7-dichloro-3-oxo-2,3-dihydro-4H-1,4-benzoxazin-4-yl)-N-methylacetamide (70.8 mg, 0.12 mmol) in dichloromethane (1 mL) was added propanoyl chloride (11.5 mg, 0.12 mmol). Triethylamine (50 mg, 0.50 mmol) was added and the resultant mixture was stirred at room temperature for 16 h. The mixture was concentrated under reduced pressure and the residue was purified by Gilson preparative HPLC (Sunfire Prep C18, 30×150 mm, 50 mL/min, A: acetonitrile with 0.1% TFA B: water with 0.1% TFA, A: 30 to 60% over 12 min, UV detection at 214 nm) to give 42.4 mg (56%) of the title compound as off white solid. MS (ES) m/e 625.2 [M+H]$^+$.

Example 474

N-{4'-[1-[[(6,7-dichloro-3-oxo-2,3-dihydro-4H-1,4-benzoxazin-4-yl)acetyl](methyl)amino]-2-(4-morpholinyl)ethyl]-3-biphenylyl}-2-methylpropanamide

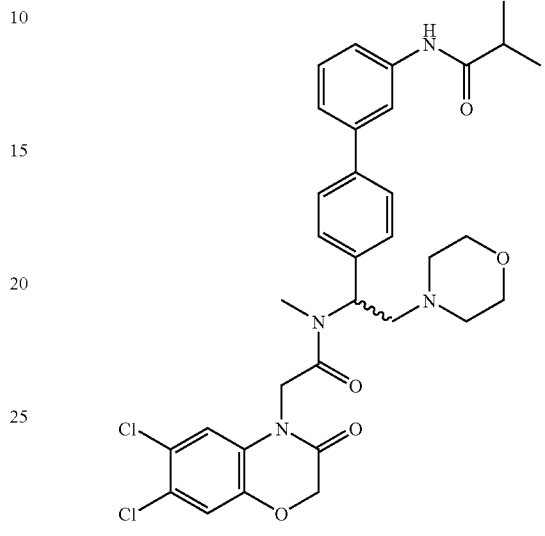

Proceeding in a similar manner as in example 473, but replacing propanoyl chloride with 2-methylpropanoyl chloride, the title compound was prepared. MS (ES) m/e 639 [M+H]$^+$.

Example 475

2-(6,7-dichloro-3-oxo-2,3-dihydro-4H-1,4-benzoxazin-4-yl)-N-[1-{3'-[(ethylsulfonyl)amino]-4-biphenylyl}-2-(4-morpholinyl)ethyl]-N-methylacetamide

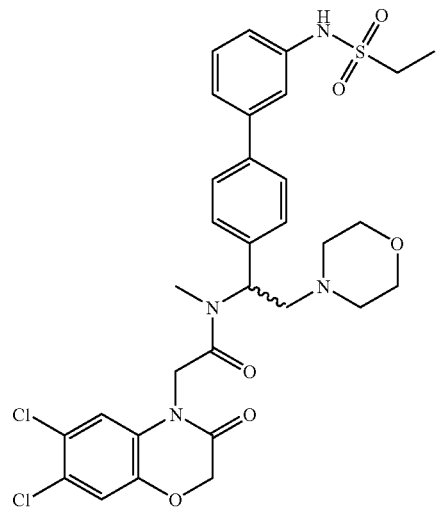

To a solution of N-[1-(3'-amino-4-biphenylyl)-2-(4-morpholinyl)ethyl]-2-(6,7-dichloro-3-oxo-2,3-dihydro-4H-1,4-benzoxazin-4-yl)-N-methylacetamide (70.1 mg, 0.12 mmol) in dichloromethane (1 mL) was added ethanesulfonyl chloride (32 mg, 0.24 mmol). Triethylamine (50 mg, 0.50 mmol) was added and the resultant mixture was stirred at room temperature for 16 h. The mixture was concentrated under reduced pressure and the residue was purified by Gilson preparative HPLC (Sunfire Prep C18, 30×150 mm, 50 mL/min, A: acetonitrile with 0.1% TFA B: water with 0.1% TFA, A: 30 to 60% over 12 min, UV detection at 214 nm) to give 26.4 mg (33%) of the title compound as off white solid. MS (ES) m/e 661.2 [M+H]$^+$.

Example 476

2-(6,7-dichloro-3-oxo-2,3-dihydro-4H-1,4-benzoxazin-4-yl)-N-methyl-N-[1-[3'-({[(1-methylethyl)amino]carbonyl}amino)-4-biphenylyl]-2-(4-morpholinyl)ethyl]acetamide

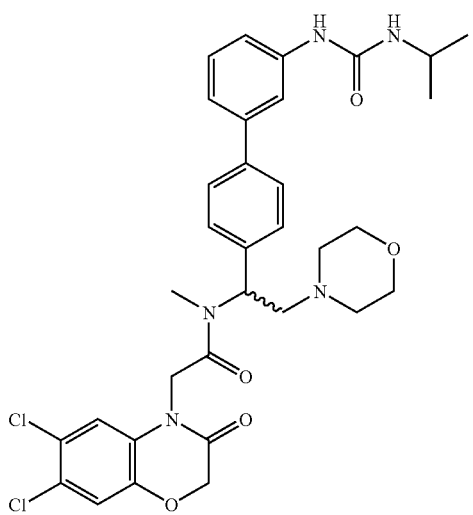

To a solution of N-[1-(3'-amino-4-biphenylyl)-2-(4-morpholinyl)ethyl]-2-(6,7-dichloro-3-oxo-2,3-dihydro-4H-1,4-benzoxazin-4-yl)-N-methylacetamide (52 mg, 0.6 mmol) in dichloromethane (1 mL) was added isopropylisocyanate (36.5 mg, 0.51 mmol). Triethylamine (60 mg, 0.60 mmol) was added and the resultant mixture was stirred at room temperature for 18 h. The mixture was concentrated under reduced pressure and the residue was purified by Gilson preparative HPLC (Sunfire Prep C18, 30×150 mm, 50 mL/min, A: acetonitrile with 0.1% TFA B: water with 0.1% TFA, A: 30 to 60% over 12 min, UV detection at 214 nm) to give 40.8 mg (52%) of the title compound as off white solid. MS (ES) m/e 654.3 [M+H]$^+$.

Example 477

2-(6,7-dichloro-3-oxo-2,3-dihydro-4H-1,4-benzoxazin-4-yl)-N-methyl-N-[1-(3'-{[(methylamino)carbonyl]amino}-4-biphenylyl)-2-(4-morpholinyl)ethyl]acetamide

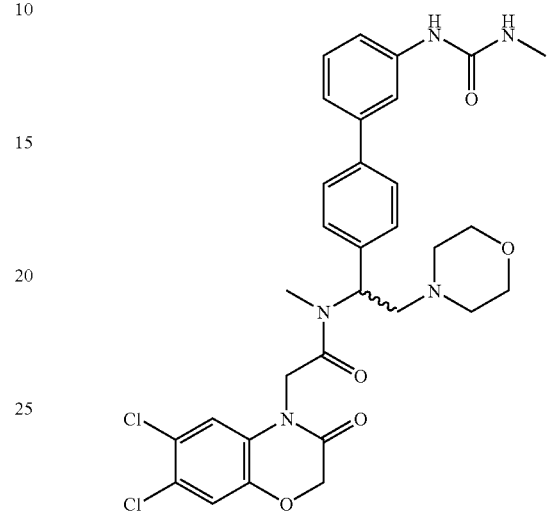

Proceeding in a similar manner as in example 476, but replacing isopropylisocyanate with isocyanatomethane, the title compound was prepared. MS (ES) m/e 626 [M+H]$^+$.

Example 478

2-[(2-amino-2-oxoethyl)(3,4-dichlorophenyl)amino]-N-methyl-N-[(1R)-1-[3'-(4-morpholinylcarbonyl)-4-biphenylyl]-2-(1-pyrrolidinyl)ethyl]acetamide

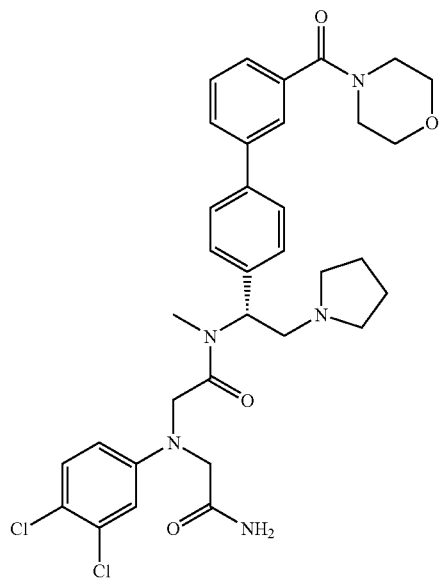

419 a) N$^1$-[(1R)-1-(4-bromophenyl)-2-(1-pyrrolidinyl)ethyl]-N$^2$-(cyanomethyl)-N$^2$-(3,4-dichlorophenyl)-N$^1$-methylglycinamide

420 b) 2-[(2-amino-2-oxoethyl)(3,4-dichlorophenyl)amino]-N-[(1R)-1-(4-bromophenyl)-2-(1-pyrrolidinyl)ethyl]-N-methylacetamide

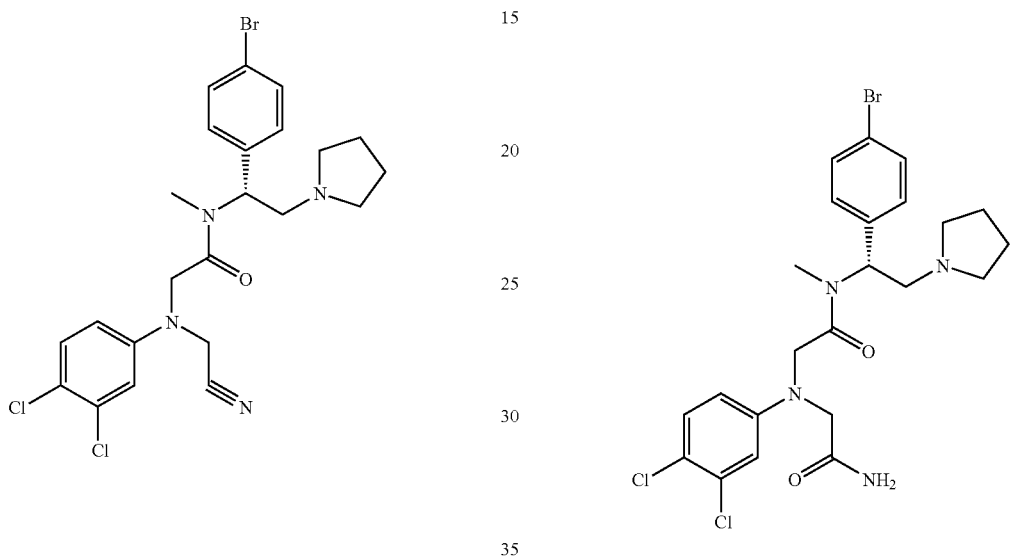

[(1R)-1-(4-bromophenyl)-2-(1-pyrrolidinyl)ethyl]methylamine (3.03 g, 10.7 mmol) and N-(cyanomethyl)-N-(3,4-dichlorophenyl)glycine (2.77 g, 10.7 mmol) were dissolved in 100 mL of dimethylformamide. Triethylamine (4.47 mL, 32.1 mmol) was delivered to the room temperature mixture, and the solution was allowed to stir for several minutes before a separate solution of 1H-1,2,3-benzotriazol-1-yloxy-tris(dimethylamino)-phosphonium hexafluorophosphate (BOP reagent, 4.73 g, 10.7 mmol) dissolved in 10 mL of dimethylformamide was added to the mixture at room temperature. The reaction was maintained at that temperature for 2 hours, before it was determined to be complete by LCMS (Eclipse XDB C18 (4.6×250 mm); trifluoroacetic acid: 1-99% B for 10 min, ES) Rt=8.4 min and m/e 525 [M+1]$^+$. The reaction mixture was treated with 100 mL of 50% H$_2$O and 50% saturated sodium bicarbonate solution and was allowed to stir at room temperature for one hour. After transferring the mixture to a 1 L separatory funnel, the aqueous layer was extracted three times with 200 mL portions of ethyl acetate. The organic layers were combined and washed once with 100 mL of H$_2$O and once with 100 mL of brine. The organic layer was dried over MgSO$_4$, filtered, and concentrated using rotary evaporation and then placed under high vacuum to give 6.1 g of N$^1$-[(1R)-1-(4-bromophenyl)-2-(1-pyrrolidinyl)ethyl]-N$^2$-(cyanomethyl)-N$^2$-(3,4-dichlorophenyl)-N$^1$-methylglycinamide, which was carried onto the next step as crude material. MS (ES) m/e 525 [M+H]$^+$.

N$^1$-[(1R)-1-(4-bromophenyl)-2-(1-pyrrolidinyl)ethyl]-N$^2$-(cyanomethyl)-N$^2$-(3,4-dichlorophenyl)-N$^1$-methylglycinamide (6.1 g, crude) was dissolved in 25 mL of tetrahydrofuran and treated with a solution of LiOH (3.14 g, 74.9 mmol) suspended in 10.8 mL of water. The reaction was stirred vigorously and allowed to reflux at 77° C. for 24 hours before it was determined to be complete by LCMS (Eclipse XDB C18 (4.6×250 mm); trifluoroacetic acid: 1-99% B for 10 min, ES) Rt=7.8 min and m/e 543 [M+1]$^+$. The solvent was removed by rotary evaporation and the crude residue was purified by silica gel chromatography (330 g Redisep column, silica, 40 um, 60 Å, 90 mL/min, A: methylene chloride, B: methanol, B: 0% for 5 min, 10% for 60 min; detection at 214 nm) to give 2-[(2-amino-2-oxoethyl)(3,4-dichlorophenyl)amino]-N-[(1R)-1-(4-bromophenyl)-2-(1-pyrrolidinyl)ethyl]-N-methylacetamide (2.82 g, 5.2 mmol). MS (ES) m/e 543 [M+H]$^+$.

c) 2-[(2-amino-2-oxoethyl)(3,4-dichlorophenyl) amino]-N-methyl-N-[(1R)-1-[3'-(4-morpholinylcarbonyl)-4-biphenylyl]-2-(1-pyrrolidinyl)ethyl]acetamide

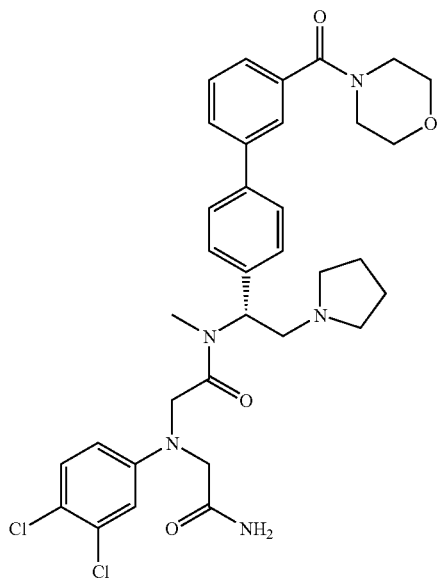

2-[(2-amino-2-oxoethyl)(3,4-dichlorophenyl)amino]-N-[(1R)-1-(4-bromophenyl)-2-(1-pyrrolidinyl)ethyl]-N-methylacetamide (138 mg, 0.254 mmol) was dissolved in 1 mL of 1,4-Dioxane and combined with [3-(4-morpholinylcarbonyl)phenyl]boronic acid (89.8 mg, 0.382 mmol), Pd(dppf)$_2$Cl$_2$ (6.23 mg, 0.0076 mmol), and 400 uL of 2 M Na$_2$CO$_3$ in water in a glass reaction tube (0.5-2.0 mL Smith Process Vial) that was equipped with a magnetic stir bar. The tube was fitted with a rubber septum and hermetically sealed with a crimped metal foil seal. Using a Personal Chemistry Emrys Optimizer microwave unit, the reaction mixture was magnetically stirred and irradiated with microwave energy of dynamically adjusted power in order to maintain a temperature of 160° C. for 360 seconds. After allowing the mixture to cool to room temperature, it was diluted with 1.0 mL DMSO, acidified with trifluoroacetic acid and filtered through a 0.45 μm PTFE Acrodisk. The crude residue was purified by preparative HPLC (Phenomenex 75×30 mm column, 40 mL/min flow rate, A: 0.1% TFA in acetonitrile B: 0.1% TFA in water, A: 10 to 100% over 15 min, UV detection at 215 nm) to give 96 mg (0.15 mmol) of the title compound as an off-white amorphous solid. MS (ES) m/e 651 [M+H]$^+$.

Examples 479-496

Proceeding in a similar manner as in example 478, but replacing [3-(4-morpholinylcarbonyl)phenyl]boronic acid in step c) with the appropriate boronic acids, the compounds listed in table 16 were prepared. As is appreciated by those skilled in the art, these analogous examples may involve variations in synthetic procedure.

TABLE 16

| Ex # | Structure | Name | MS [M + H]$^+$ |
|---|---|---|---|
| 479 | ![structure] | 2-[{2-[[(1R)-1-[4'-(acetylamino)-4-biphenylyl]-2-(1-pyrrolidinyl)ethyl](methyl)amino]-2-oxoethyl}(3,4-dichlorophenyl)amino]acetamide | 596 |

TABLE 16-continued

| Ex # | Structure | Name | MS [M + H]+ |
|---|---|---|---|
| 480 | 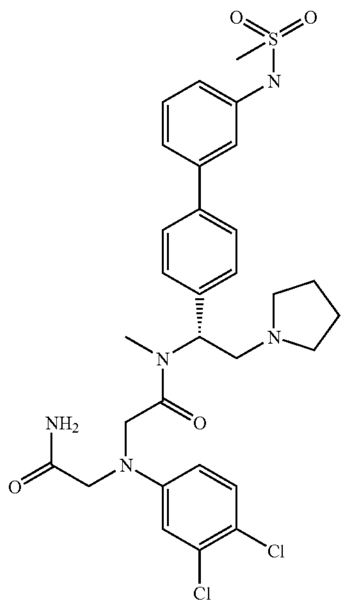 | 2-[(2-amino-2-oxoethyl)(3,4-dichlorophenyl)amino]-N-methyl-N-[(1R)-1-{3'-[(methylsulfonyl)amino]-4-biphenylyl}-2-(1-pyrrolidinyl)ethyl]acetamide | 632 |
| 481 | 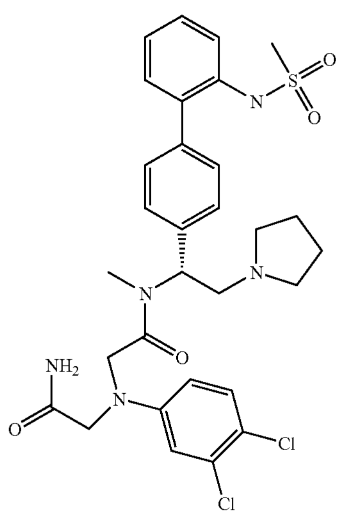 | 2-[(2-amino-2-oxoethyl)(3,4-dichlorophenyl)amino]-N-methyl-N-[(1R)-1-{2'-[(methylsulfonyl)amino]-4-biphenylyl}-2-(1-pyrrolidinyl)ethyl]acetamide | 632 |

TABLE 16-continued
| Ex # | Structure | Name | MS [M + H]+ |
|---|---|---|---|
| 482 | 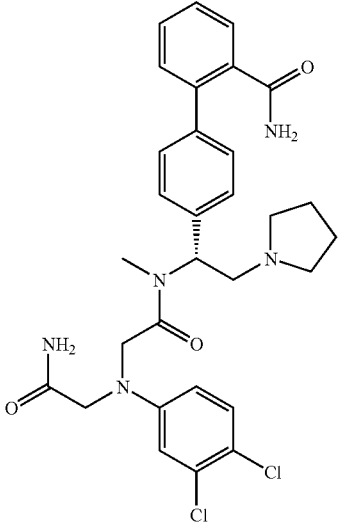 | 4'-[(1R)-1-[{[(2-amino-2-oxoethyl)(3,4-dichlorophenyl)amino]acetyl}(methyl)amino]-2-(1-pyrrolidinyl)ethyl]-2-biphenylcarboxamide | 582 |
| 483 | 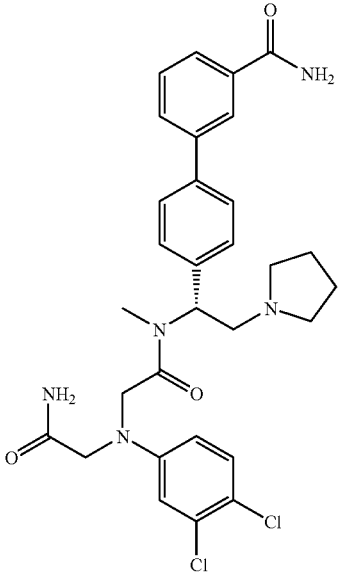 | 4'-[(1R)-1-[{[(2-amino-2-oxoethyl)(3,4-dichlorophenyl)amino]acetyl}(methyl)amino]-2-(1-pyrrolidinyl)ethyl]-3-biphenylcarboxamide | 582 |

TABLE 16-continued

| Ex # | Structure | Name | MS [M + H]+ |
|---|---|---|---|
| 484 | 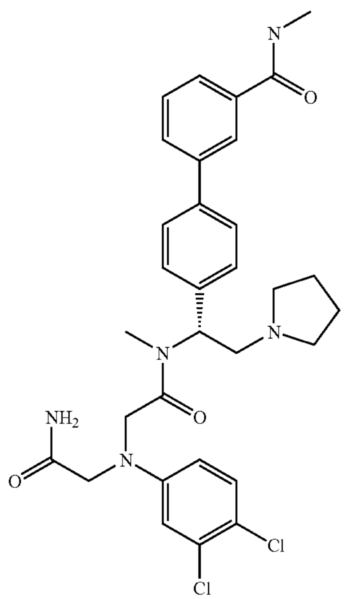 | 4'-[(1R)-1-[{[(2-amino-2-oxoethyl)(3,4-dichlorophenyl)amino]acetyl}(methyl)amino]-2-(1-pyrrolidinyl)ethyl]-N-methyl-3-biphenylcarboxamide | 596 |
| 485 | 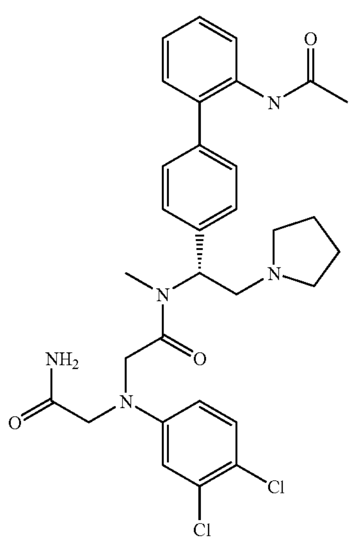 | 2-[{2-[[(1R)-1-[2'-(acetylamino)-4-biphenylyl]-2-(1-pyrrolidinyl)ethyl](methyl)amino]-2-oxoethyl}(3,4-dichlorophenyl)amino]acetamide | 596 |

TABLE 16-continued

| Ex # | Structure | Name | MS [M + H]+ |
|---|---|---|---|
| 486 | 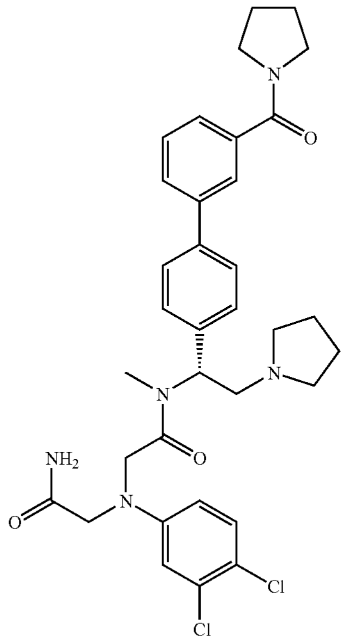 | 2-[(2-amino-2-oxoethyl)(3,4-dichlorophenyl)amino]-N-methyl-N-{(1R)-2-(1-pyrrolidinyl)-1-[3'-(1-pyrrolidinylcarbonyl)-4-biphenylyl]ethyl}acetamide | 636 |
| 487 | 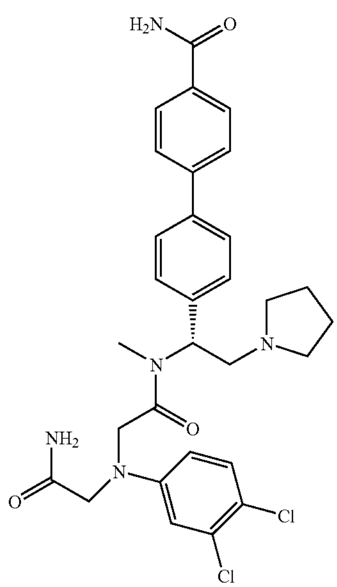 | 4'-[(1R)-1-[{[(2-amino-2-oxoethyl)(3,4-dichlorophenyl)amino]acetyl}(methyl)amino]-2-(1-pyrrolidinyl)ethyl]-4-biphenylcarboxamide | 582 |

TABLE 16-continued

| Ex # | Structure | Name | MS [M + H]+ |
|---|---|---|---|
| 488 | 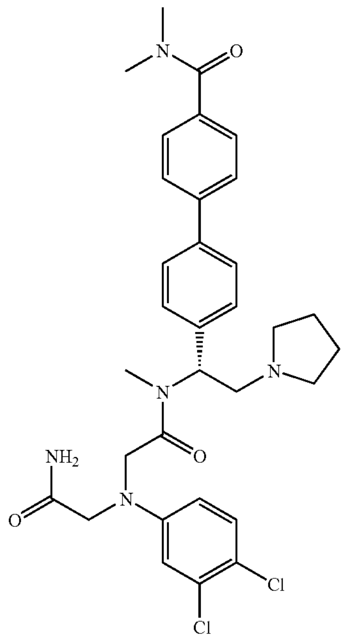 | 4'-[(1R)-1-[{[(2-amino-2-oxoethyl)(3,4-dichlorophenyl)amino]acetyl}(methyl)amino]-2-(1-pyrrolidinyl)ethyl]-N,N-dimethyl-4-biphenylcarboxamide | 610 |
| 489 | 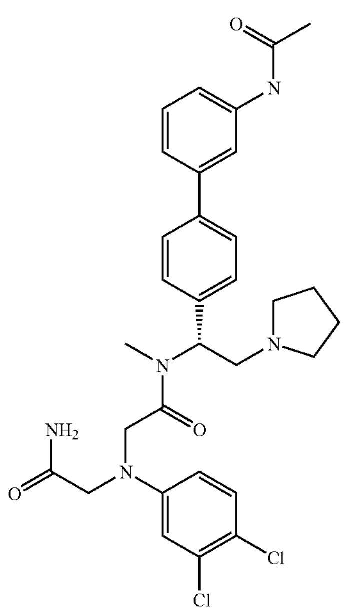 | 2-[{2-[[(1R)-1-[3'-(acetylamino)-4-biphenylyl]-2-(1-pyrrolidinyl)ethyl](methyl)amino]-2-oxoethyl}(3,4-dichlorophenyl)amino]acetamide | 596 |

TABLE 16-continued

| Ex # | Structure | Name | MS [M + H]+ |
|---|---|---|---|
| 490 | 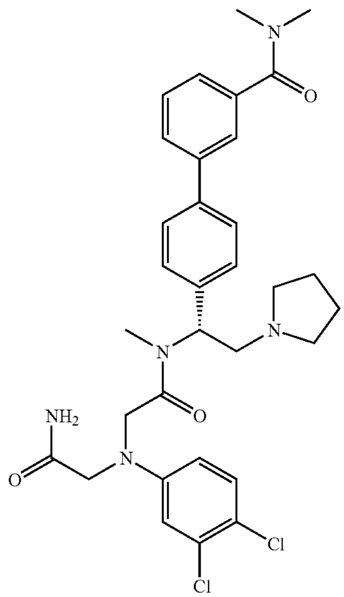 | 4'-[(1R)-1-[{[(2-amino-2-oxoethyl)(3,4-dichlorophenyl)amino]acetyl}(methyl)amino]-2-(1-pyrrolidinyl)ethyl]-N,N-dimethyl-3-biphenylcarboxamide | 610 |
| 491 | 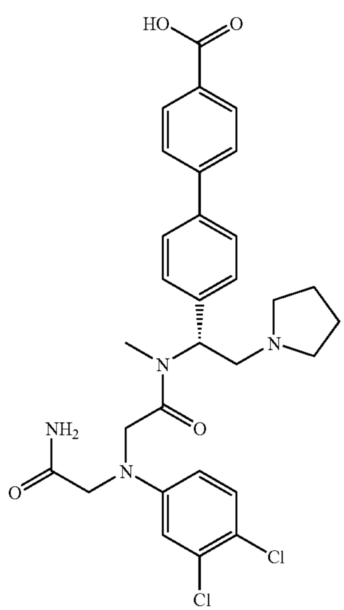 | 4'-[(1R)-1-[{[(2-amino-2-oxoethyl)(3,4-dichlorophenyl)amino]acetyl}(methyl)amino]-2-(1-pyrrolidinyl)ethyl]-4-biphenylcarboxylic acid | 583 |

TABLE 16-continued
| Ex # | Structure | Name | MS [M + H]+ |
|---|---|---|---|
| 492 | 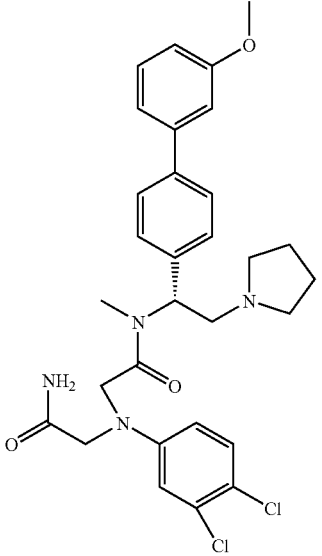 | 2-[(2-amino-2-oxoethyl)(3,4-dichlorophenyl)amino]-N-methyl-N-[(1R)-1-[3'-(methyloxy)-4-biphenylyl]-2-(1-pyrrolidinyl)ethyl]acetamide | 569 |
| 493 | 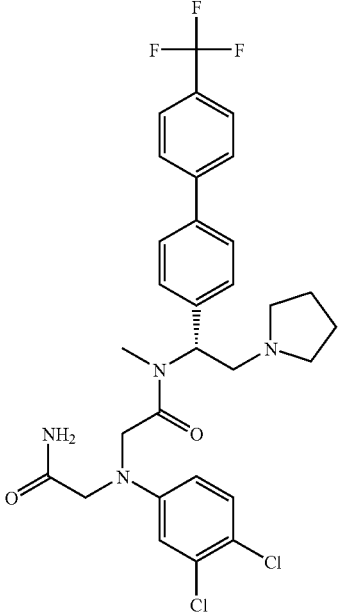 | 2-[(2-amino-2-oxoethyl)(3,4-dichlorophenyl)amino]-N-methyl-N-{(1R)-2-(1-pyrrolidinyl)-1-[4'-(trifluoromethyl)-4-biphenylyl]ethyl}acetamide | 607 |

TABLE 16-continued
| Ex # | Structure | Name | MS [M + H]+ |
|---|---|---|---|
| 494 | 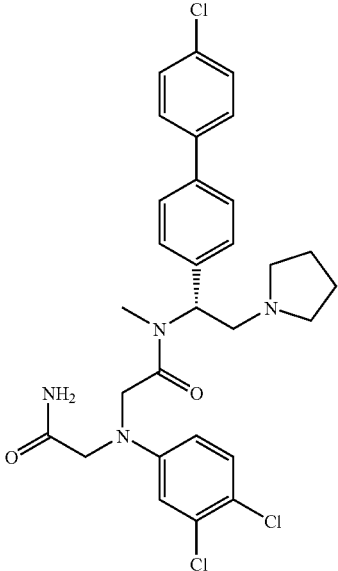 | 2-[(2-amino-2-oxoethyl)(3,4-dichlorophenyl)amino]-N-[(1R)-1-(4'-chloro-4-biphenylyl)-2-(1-pyrrolidinyl)ethyl]-N-methylacetamide | 573 |
| 495 | 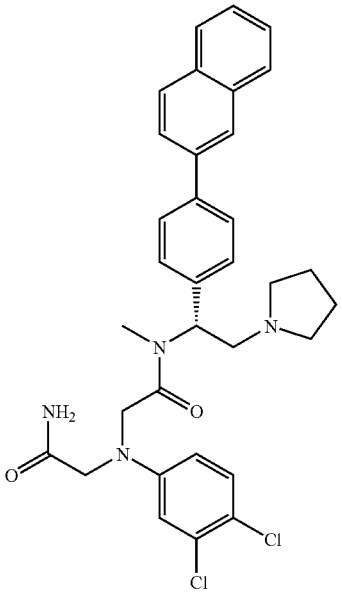 | 2-[(2-amino-2-oxoethyl)(3,4-dichlorophenyl)amino]-N-methyl-N-[(1R)-1-[4-(2-naphthalenyl)phenyl]-2-(1-pyrrolidinyl)ethyl]acetamide | 589 |

TABLE 16-continued

| Ex # | Structure | Name | MS [M + H]+ |
|---|---|---|---|
| 496 | 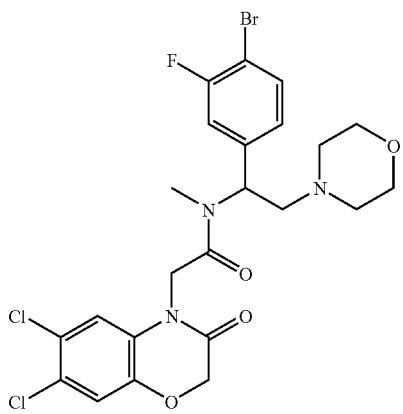 | 2-[(2-amino-2-oxoethyl)(3,4-dichlorophenyl)amino]-N-[(1R)-1-(2',4'-dichloro-4-biphenylyl)-2-(1-pyrrolidinyl)ethyl]-N-methylacetamide | 609 |

Example 497

N-[1-(4-bromo-3-fluorophenyl)-2-(4-morpholinyl)ethyl]-2-(6,7-dichloro-3-oxo-2,3-dihydro-4H-1,4-benzoxazin-4-yl)-N-methylacetamide

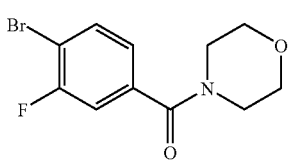

a) 4-[(4-bromo-3-fluorophenyl)carbonyl]morpholine

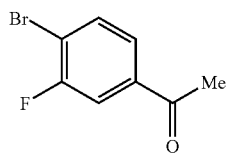

To a room temperature solution containing 10 g of 4-bromo-3-fluorobenzoic acid (45.7 mmols) in 228 mL of dichloromethane was added 1.67 g of DMAP (13.7 mmols), 11.3 g of EDCI (59.2 mmols), and 5.11 mL of morpholine (59.4 mmols). After stirring at ambient temperature for 18 h, 20 mL of water was added to the reaction mixture. The layers were separated, and the organic layer was washed with water (3×20 mL), dried over MgSO$_4$, and filtered through a frit. The resulting solution was concentrated to a pale yellow oil which was purified by silica gel chromatography (120 g redisep column, silica 40 um, 60 A, 85 ml/min, A: EtOAc, B: hexanes, A: 50% for 5 min, then 50-70% for 8 min) to give 8.62 g (66%) of title compound as a yellow oil. MS (ES) m/e 288 [M+]+.

b) 1-(4-bromo-3-fluorophenyl)ethanone

To a 0° C. solution containing 8.62 g of 4-[(4-bromo-3-fluorophenyl)carbonyl]morpholine (30 mmols) in 150 mL THF was added 15 mL of methylmagnesium bromide (45 mmols, 3M solution in Et$_2$O). The reaction mixture was allowed to warm slowly to ambient temperature. After 18 h the reaction mixture was quenched with 20 mL saturated aqueous NH$_4$Cl solution. The layers were separated, and the organic layer was dried over MgSO$_4$, filtered through a frit, and concentrated. The crude product was purified by silica gel chromatography (120 g redisep column, silica 40 um, 60 A, 85 ml/min, A: EtOAc, B: hexanes, A: 8% for 14 min) to give 2.40 g (37%) of title compound as a yellow oil.

c) 2-bromo-1-(4-bromo-3-fluorophenyl)ethanone

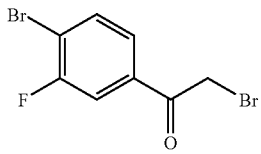

To a 0° C. solution containing 2.4 g of 1-(4-bromo-3-fluorophenyl)ethanone (11.1 mmols) in 56 mL of CHCl$_3$ was added dropwise 0.57 mL of bromine (11.1 mmols). The reaction was stirred at 0° C. for three hours and then allowed to warm to ambient temperature. The reaction mixture was quenched with 10 mL of saturated aqueous Na$_2$S$_2$O$_3$. The layers were separated, and the organics were dried over MgSO$_4$, filtered through a frit, and concentrated to a yellow solid which was used without further purification.

d) 1-(4-bromo-3-fluorophenyl)-2-(4-morpholinyl)ethanone

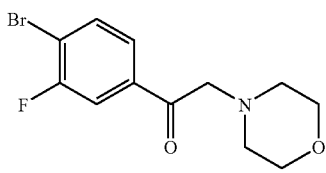

To a 0° C. solution containing 0.55 g of 2-bromo-1-(4-bromo-3-fluorophenyl)ethanone (1.86 mmols) in 9 mL of THF was added 0.32 mL of morpholine (3.72 mmols). After 18 h the reaction mixture was diluted with 100 mL of dichloromethane and washed with water (1×10 mL) and saturated brine solution (1×10 mL). The organic layer was dried over MgSO$_4$, filtered through a frit, and concentrated to a yellow-orange oil which was used without further purification. MS (ES) m/e 302, 303 [M+H]$^+$.

e) 1-(4-bromo-3-fluorophenyl)-N-methyl-2-(4-morpholinyl)ethanamine

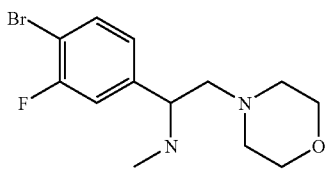

To an ambient temperature solution containing 1.52 g of 1-(4-bromo-3-fluorophenyl)-2-(4-morpholinyl)ethanone (5.04 mmols) in 25 mL of THF was added 10.1 mL of MeNH$_2$ (20.2 mmols, 2M solution in THF). After stirring for 15 min. 0.66 mL of acetic acid and 1.27 g of NaCNBH$_3$ (20.2 mmols) were added to the reaction mixture. The reaction mixture was then warmed to 40° C. and stirred for 24 h. The reaction mixture was quenched with 10% aqueous Na$_2$CO$_3$ (10 mL). The reaction was diluted with 100 mL of EtOAc, and the layers were separated. The organic layer was washed with 10% aqueous Na$_2$CO$_3$ (1×10 mL) and saturated aqueous brine solution (1×10 mL). The organics were then dried over MgSO$_4$, filtered through a frit, and concentrated. The crude title product was isolated as a brown solid (1.6 g, ~100%) and used without further purification. MS (ES) m/e 317 [M+H]$^+$.

f) N-[1-(4-bromo-3-fluorophenyl)-2-(4-morpholinyl)ethyl]-2-(6,7-dichloro-3-oxo-2,3-dihydro-4H-1,4-benzoxazin-4-yl)-N-methylacetamide

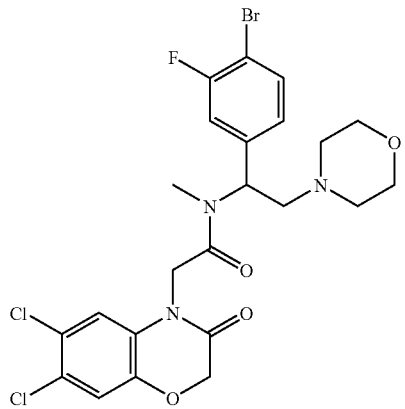

To a room temperature solution containing 1.59 g of 1-(4-bromo-3-fluorophenyl)-N-methyl-2-(4-morpholinyl)ethanamine (5.02 mmols) in 17 mL of dry DMF was added 2 g of (6,7-dichloro-3-oxo-2,3-dihydro-4H-1,4-benzoxazin-4-yl) acetic acid (7.25 mmols), 2.66 g of BOP reagent (6.02 mmols), and 1.4 mL of triethylamine (10.04 mmols). The reaction mixture was stirred at ambient temperature. After 24 h 10 mL of saturated aqueous NaHCO$_3$ was added. The resulting precipitate was collected, washed with water, and dried in vacuo to afford an off-white solid. MS (ES) m/e 574, 576 [M+H]$^+$.

Example 498

2-(6,7-dichloro-3-oxo-2,3-dihydro-4H-1,4-benzoxazin-4-yl)-N-[1-[2-fluoro-4'-[(methylsulfonyl)amino]-4-biphenylyl]-2-(4-morpholinyl)ethyl]-N-methylacetamide

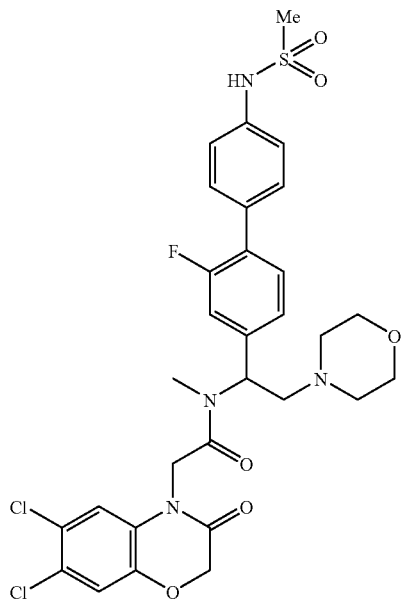

To a room temperature solution under nitrogen containing 0.20 g of N-[1-(4-bromo-3-fluorophenyl)-2-(4-morpholinyl)

ethyl]-2-(6,7-dichloro-3-oxo-2,3-dihydro-4H-1,4-benzoxazin-4-yl)-N-methylacetamide (0.348 mmols) in 3.5 mL of dry DMF was added 0.09 g of {4-[(methylsulfonyl)amino]phenyl}boronic acid (0.418 mmols), 0.014 g of (dppf)PdCl$_2$ (0.017 mmols), and 0.70 mL of Na$_2$CO$_3$ solution (2M in water). The reaction mixture was heated to 80° C. After 18 h the reaction was cooled to ambient temperature and filtered through a 0.2 □m syringe filter. The resulting DMF solution was purified by preparative HPLC (Phenomenex 50×100 mm column, 90 mL/min flow rate, A: 0.1% TFA in acetonitrile B: 0.1% TFA in water, A: 10 to 100% over 15 min, UV detection at 215 nm) to give 0.022 g (9%) of the title compound as a light brown solid. MS (ES) m/e 666, 667 [M+H]$^+$.

Examples 499-503

Proceeding in a similar manner as in example 498 except substituting the appropriate boronic acids for {4-[(methylsulfonyl)amino]phenyl}boronic acid, the compounds listed in table 17 were prepared. As is appreciated by those skilled in the art, these analogous examples may involve variations in synthetic procedure.

TABLE 17

| Ex # | Structure | Name | MS [M + H]$^+$ |
|---|---|---|---|
| 499 | 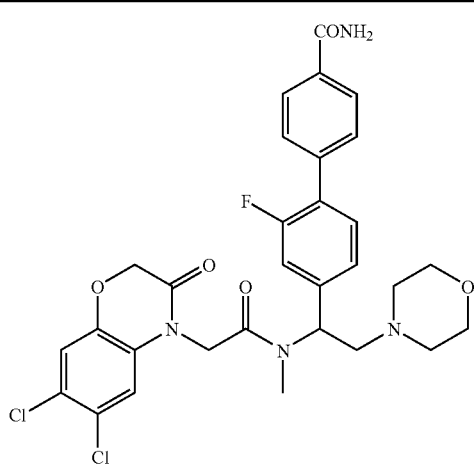 | 4'-[1-[[(6,7-dichloro-3-oxo-2,3-dihydro-4H-1,4-benzoxazin-4-yl)acetyl](methyl)amino]-2-(4-morpholinyl)ethyl]-2'-fluoro-4-biphenylcarboxamide | 615 |
| 500 | 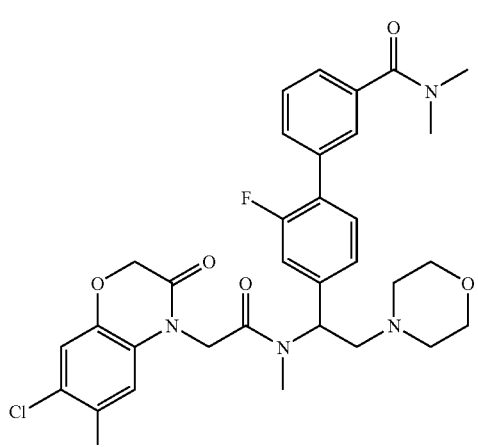 | 4'-[1-[[(6,7-dichloro-3-oxo-2,3-dihydro-4H-1,4-benzoxazin-4-yl)acetyl](methyl)amino]-2-(4-morpholinyl)ethyl]-2'-fluoro-N,N-dimethyl-3-biphenylcarboxamide | 644 |

TABLE 17-continued

| Ex # | Structure | Name | MS [M + H]+ |
|---|---|---|---|
| 501 | 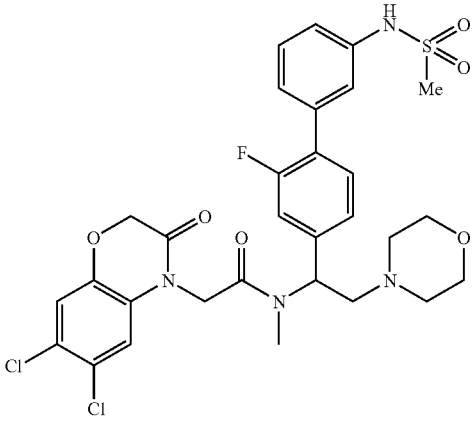 | 2-(6,7-dichloro-3-oxo-2,3-dihydro-4H-1,4-benzoxazin-4-yl)-N-[1-{2-fluoro-3'-[(methyl sulfonyl)amino]-4-biphenylyl}-2-(4-morpholinyl)ethyl]-N-methylacetamide | 666 |
| 502 | 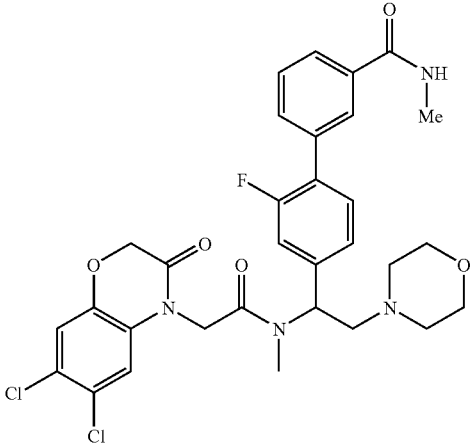 | 4'-[1-[[(6,7-dichloro-3-oxo-2,3-dihydro-4H-1,4-benzoxazin-4-yl)acetyl](methyl)amino]-2-(4-morpholinyl)ethyl]-2'-fluoro-N-methyl-3-biphenylcarboxamide | 629 |
| 503 | 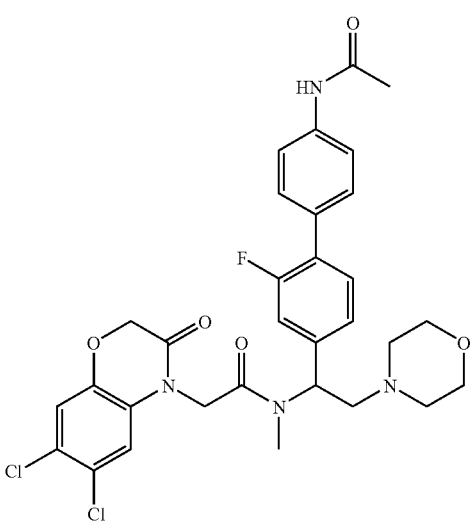 | N-[1-[4'-(acetylamino)-2-fluoro-4-biphenylyl]-2-(4-morpholinyl)ethyl]-2-(6,7-dichloro-3-oxo-2,3-dihydro-4H-1,4-benzoxazin-4-yl)-N-methylacetamide | 629 |

Example 504

4'-[(1R)-1-[[(6,7-dichloro-3-oxo-2,3-dihydro-4H-1,4-benzoxazin-4-yl)acetyl](methyl)amino]-2-(1-pyrrolidinyl)ethyl]-3-biphenylcarboxamide

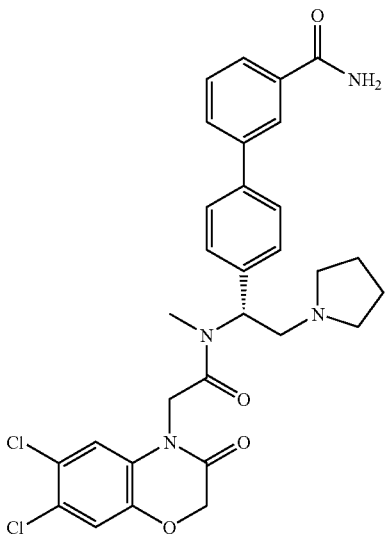

a) (2R)-2-(4-bromophenyl)oxirane

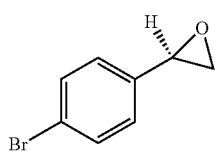

To a magnetically stirred solution of (R,R)-(−)-N,N'-Bis(3,5-di-tert-butyl-salicylidene-1,2-cyclohexane-diaminocobalt (II) (4.88 g, 8.09 mmol) in toluene (50 mL) at room temperature in an open flask, was added acetic acid (4.6 mL, 80.0 mmol). The mixture was stirred for 1 h. The mixture was then concentrated to give a brown solid, which was placed under high vacuum overnight. The brown residue was taken up in THF (50 mL) and the resulting solution was added to 2-(4-bromophenyl)oxirane (199.62 g, 1.0 mol) in THF (150 mL). The reaction mixture was cooled to 0° C. and distilled water (10.0 mL, 556 mmol) was added dropwise over 5 minutes into the mixture. The resulting mixture was warmed to room temperature and stirred for 18 h. The reaction mixture was concentrated and then 5% EtOAc/Hexane (500 mL) was added to the residue. The insoluble material was filtered off. The filtrate was concentrated and the resulting brown oil was diluted with hexane (500 mL). The insoluble material was removed by filtration and the filtrate was concentrated to give a brown oil. The crude material was purified by vacuum distillation at 90° C. to give (2R)-2-(4-bromophenyl)oxirane as a clear oil (72.7 g, 365 mmol, 82%) which solidified upon cooling to a white solid.

$^1$H NMR (400 MHz, CDCl$_3$) δ 7.5 (d, 2H), 7.2 (d, 2H), 3.8 (m, 1H), 3.2 (d, 1H), 2.8 (d, 1H).

b) (1R)-1-(4-bromophenyl)-2-(1-pyrrolidinyl)ethanol

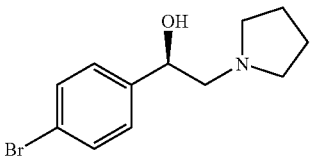

(2R)-2-(4-Bromophenyl)oxirane (49.93 g, 250.8 mmol) was added to pyrrolidine (35 mL, 421.2 mmol) in a CH$_2$Cl$_2$ (150 mL) solution at 0° C. with magnetic stirring. Montmorillonite K10 clay (5.87 g) was added in one portion. The resulting mixture was stirred at room temperature for 16 h. The mixture was then filtered through a pad of Celite and the filtrate was concentrated to give a white solid. The crude material was recrystallized from Et$_2$O to give (1R)-1-(4-bromophenyl)-2-(1-pyrrolidinyl)ethanol as clear crystals (29.43 g, 109 mmol, 43% yield). MS (ES) m/e 272, 270 [M+H]$^+$ c) (1R)-1-(4-bromophenyl)-N-methyl-2-(1-pyrrolidinyl)ethanamine

To a magnetically stirred solution of (1R)-1-(4-bromophenyl)-2-(1-pyrrolidinyl)ethanol (29.43 g, 109 mmol) in CH$_2$Cl$_2$ (300 mL) at 0° C. was added triethylamine (55 mL, 394 mmol). Methanesulfonylchloride (30 mL, 388 mmol) was then added dropwise. The resulting mixture was warmed to room temperature, stirred for 5 h, and then quenched by the addition of H$_2$O (200 mL). The layers were separated and the organic phase was washed with saturated aqueous NaHCO$_3$ and brine, dried over MgSO$_4$, filtered and concentrated under reduced pressure to give an orange oil. The crude oil was taken up in CH$_2$Cl$_2$ (300 mL) and methylamine (33 wt % in EtOH, 135 mL, 1.08 mol) was added at room temperature. The resulting mixture was stirred overnight at room temperature. The mixture was concentrated under reduced pressure and re-dissolved in CH$_2$Cl$_2$. The crude mixture was washed with saturated aqueous NaHCO$_3$ and brine, dried over MgSO$_4$, filtered and concentrated under reduced pressure to give (1R)-1-(4-bromophenyl)-N-methyl-2-(1-pyrrolidinyl)ethanamine as a viscous red/orange oil (25.4 g, 90 mmol, 82% yield).

$^1$H NMR (400 MHz, CDCl$_3$) δ 7.5 (d, 2H), 7.3 (d, 2H), 3.5 (d, 1H), 2.8 (t, 1H), 2.6 (m, 2H), 2.5 (m, 2H), 2.3-2.2 (s and m, overlapping, 4H), 1.8 (bs, 4H)

d) ethyl[(4,5-dichloro-2-nitrophenyl)oxy]acetate

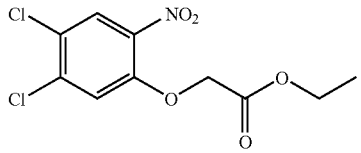

1,2-Dichloro-4-fluoro-5-nitrobenzene (50 g, 0.238 mol), ethyl glycolate (90.1 mL, 0.952 mol), and potassium fluoride (76.1 g, 1.31 mol) were added to a 1 L round-bottom flask containing 200 mL of anhydrous dioxane. The mixture was magnetically stirred and heated to 100° C. in an oil bath. After two hours, HPLC (Eclipse XDB-C18, 4.6×250 mm, 5 micron, 1-99% CH$_3$CN/H$_2$O with 0.1% trifluoroacetic acid) showed that all of the starting material (Rt=7.5 min) was gone and that one major peak (Rt=7.8 min) had formed. The reaction mixture was poured into 4 L of water, which resulted in precipitation of the product. The solid was filtered off and dried under vacuum to give ethyl[(4,5-dichloro-2-nitrophenyl)oxy]acetate (67.4 g, 0.229 mol, 96%) as a tan solid. MS (ES) m/e 294 [M+H]$^+$.

e) 6,7-dichloro-2H-1,4-benzoxazin-3(4H)-one

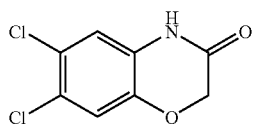

Ethyl[(4,5-dichloro-2-nitrophenyl)oxy]acetate (36.0 g, 0.122 mol) was dissolved in 400 mL of ethanol and treated with SnCl$_2$.2H$_2$O (138.0 g, 0.612 mol). This mixture was magnetically stirred and heated to 85° C. in an oil bath. After stirring overnight, HPLC (Eclipse XDB-C18, 4.6×250 mm, 5 micron, 1-99% CH$_3$CN/H$_2$O with 0.1% trifluoroacetic acid) showed that all of the starting material (Rt=7.8 min) was gone and that two new compounds had formed: the desired product (Rt=6.2 min) and the hydroxamic acid of the desired product (Rt=5.9 min). An additional 138.0 g of SnCl$_2$.2H$_2$O (0.612 mol) and 90 mL of concentrated HCl were added and stirred at 85° C. for seven hours, after which time HPLC showed that only the desired product remained. The reaction mixture was poured into 5.5 L of 5% aqueous HCl and a suspension formed which was stirred for 20 minutes, resulting in a white precipitate. The white solid was filtered off and air-dried on a vacuum funnel for one hour. The white solid was transferred to a 1 L round bottom flask and suspended in 500 mL of absolute ethanol. The solvent was removed by rotary evaporation to azeotrope off the last traces of water. This process of suspending the solid in absolute ethanol and removing the solvent by rotary evaporation was repeated once more. The resulting white solid was dried overnight under high vacuum to give 6,7-dichloro-2H-1,4-benzoxazin-3(4H)-one (22.2 g. 0.102 mol, 83%) as a fine white powder. MS (ES) m/e 218 [M+H]$^+$.

f) ethyl (6,7-dichloro-3-oxo-2,3-dihydro-4H-1,4-benzoxazin-4-yl)acetate

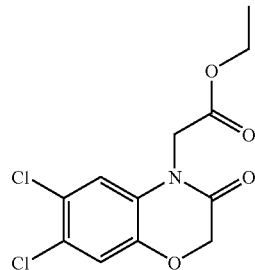

A 1 L round-bottom flask was purged with argon and charged with sodium hydride (6.94 g of a 60% dispersion of NaH in mineral oil, 0.174 mol) and 60 mL of anhydrous DMF. This suspension was magnetically stirred and cooled to 0° C. in an ice-bath and then treated slowly with a suspension of 6,7-dichloro-2H-1,4-benzoxazin-3(4H)-one (22.2 g. 0.102 mol) in 140 mL of anhydrous DMF. The reaction mixture was maintained at 0° C. for one hour and then treated slowly with ethyl bromoacetate (29.4 mL, 0.265 mol) over a period of 5-10 minutes. This reaction mixture was maintained at 0° C. for thirty minutes, allowed to warm to room temperature, and then was maintained at room temperature for thirty minutes. HPLC (Eclipse XDB-C18, 4.6×250 mm, 5 micron, 1-99% CH$_3$CN/H$_2$O with 0.1% trifluoroacetic acid) showed that all of the starting material (Rt=6.2 min) was gone and that a new compound had formed (Rt=7.5 min). The reaction mixture was poured into 5.5 L of 5% aqueous HCl and the product precipitated immediately as a yellow solid. The suspension was stirred for 10 minutes and the solid was filtered off to give a yellow filter cake. The solid was rinsed with ice-cold ethanol (3×200 mL) and hexanes (3×200 mL) and then dried under high vacuum to give ethyl (6,7-dichloro-3-oxo-2,3-dihydro-4H-1,4-benzoxazin-4-yl)acetate (26.0 g, 0.085 mol, 84%) as a white powder. MS (ES) m/e 304 [M+H]$^+$.

g) (6,7-dichloro-3-oxo-2,3-dihydro-4H-1,4-benzoxazin-4-yl)acetic acid

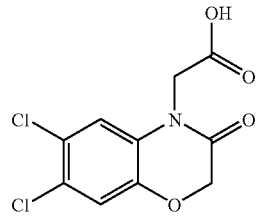

Ethyl (6,7-dichloro-3-oxo-2,3-dihydro-4H-1,4-benzoxazin-4-yl)acetate (22.0 g, 0.072 mol) was suspended in 400 mL of THF and treated with LiOH (3.46 g, 0.144 mol) dissolved in 80 mL of water at room temperature. The reaction was magnetically stirred and maintained at room temperature for 18 hours. The reaction was then quenched with 30 mL of concentrated HCl and stirred for 20 minutes. HPLC (Eclipse XDB-C18, 4.6×250 mm, 5 micron, 1-99% CH$_3$CN/H$_2$O with 0.1% trifluoroacetic acid) showed that all of the starting material (Rt=7.5 min) was gone and that a single product (Rt=6.0 min) had formed. The solvent was removed by rotary evaporation to give an off-white solid that was further dried under high vacuum to give 24.5 g of a mixture of 6,7-dichloro-3-oxo-2,3-dihydro-4H-1,4-benzoxazin-4-yl)acetic acid (77% by mass) and LiCl (23% by mass) which can be used in subsequent reactions without further purification. Actual product yield is 18.9 g (0.068 mol, 95%). MS (ES) m/e 276 [M+H]$^+$.

Alternatively, the product 6,7-dichloro-3-oxo-2,3-dihydro-4H-1,4-benzoxazin-4-yl)acetic acid can be isolated free of LiCl according to the following procedure:

Ethyl (6,7-dichloro-3-oxo-2,3-dihydro-4H-1,4-benzoxazin-4-yl)acetate (52.6 g, 0.173 mol) and LiOH (8.31 g, 0.347 mol) were combined in 750 mL of THF and 150 mL of water and stirred at room temperature for 18 hours, after which time HPLC indicated loss of the starting material. 80 mL of concentrated HCl was added and the mixture was stirred for 1 hour, and then evaporated to dryness. The residue was dissolved in EtOAc and water was added. The layers were separated and the organic layer was washed with water (2×). The organic layer was dried over magnesium sulphate and concentrated to give 45.5 g (0.165 mol, 95%) of 6,7-dichloro-3-oxo-2,3-dihydro-4H-1,4-benzoxazin-4-yl)acetic acid. MS (ES) m/e 278 [M+H]$^+$.

h) 4'-[(1R)-1-(methylamino)-2-(1-pyrrolidinyl)ethyl]-3-biphenylcarboxamide

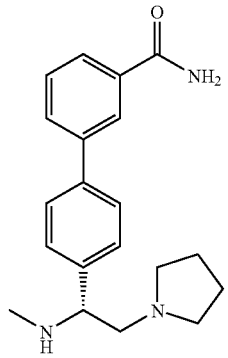

(1R)-1-(4-bromophenyl)-N-methyl-2-(1-pyrrolidinyl)ethanamine (2.65 g, 9.4 mmol) was dissolved in dioxane (100 mL) under argon at room temperature. The resulting solution was magnetically stirred and treated with [3-(aminocarbonyl)phenyl]boronic acid (1.7 g, 10.3 mmol) followed by 15 mL of a 1.88M solution of Na$_2$CO$_3$ (28.2 mmol) and PdCl$_2$(dppf)$_2$·CH$_2$Cl$_2$ (408 mg, 0.5 mmol) all at room temperature. The flask was placed in a preheated 100° C. oil bath and maintained at 100° C. for approximately 18 h after which time it was determined by LCMS to be 60% complete. Additional PdCl$_2$(dppf)$_2$·CH$_2$Cl$_2$, (408 mg, 0.5 mmol) was added and the reaction was allowed to continue at 105° C. for approximately another 6 h. The reaction was determined to be complete by LCMS (Eclipse XDB C18, 4.6×250 mm column, 1.5 mL/min, 10 minutes, gradient from 1-99% CH$_3$CN (0.1% trifluoroacetic acid)/H$_2$O (0.1% trifluoroacetic acid), ES, Rt=4.46 min and m/e 324 [M+1]$^+$). The reaction mixture was cooled to room temperature and filtered through Celite. The filtrate was concentrated under vacuum by rotary evaporation and purified by silica gel chromatography (120 g Redisep silica gel column, 40 um, 60 Å, 50 mL/min, A: (CH$_2$Cl$_2$) B: (Methanol with 1% NH$_4$OH) gradient of 0%-20% B in A, 60 min run; detection at 254 nm) to give 4'-[(1R)-1-(methylamino)-2-(1-pyrrolidinyl)ethyl]-3-biphenylcarboxamide (2.0 g) as a brown oil:

LCMS (Eclipse XDB C18, 4.6×250 mm column, 1.5 mL/min, 10 minutes, gradient from 1-99% CH$_3$CN (0.1% trifluoroacetic acid)/H$_2$O (0.1% trifluoroacetic acid), ES) Rt=4.46 min and m/e 324 [M+1]$^+$;

Analytical HPLC (Eclipse XDB-C18, 4.6×250 mm, 5 micron, 2.5 mL/min, 10 minutes, gradient from 1-99% CH$_3$CN (0.1% trifluoroacetic acid)/H$_2$O (0.1% trifluoroacetic acid), R$_f$=2.88 min, purity >70%;

$^1$H NMR (400 MHz, d$_6$-DMSO) δ 8.2 (s, 1H), 8.1 (s, 1H), 7.8 (m, 2H), 7.65 (d, 2H), 7.5 (t, 1H), 7.5-7.3 (m, 3H), 3.6 (m, 1H), 2.65 (t, 1H), 2.55 (m, 2H), 2.4 (m, 2H), 2.3 (m, 1H), 2.2 (s, 3H), and 1.7 (m, 4H).

i) 4'-[(1R)-1-[[(6,7-dichloro-3-oxo-2,3-dihydro-4H-1,4-benzoxazin-4-yl)acetyl](methyl)amino]-2-(1-pyrrolidinyl)ethyl]-3-biphenylcarboxamide, Trifluoroacetate salt

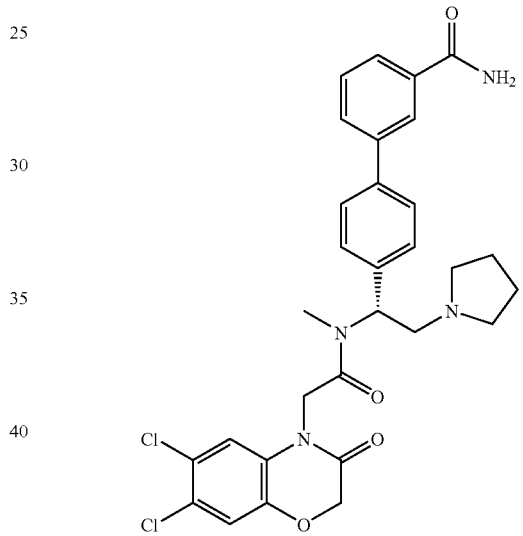

4'-[(1R)-1-(methylamino)-2-(1-pyrrolidinyl)ethyl]-3-biphenylcarboxamide (crude, 2.0 g, estimated 6.2 mmol) was dissolved in 50 mL of DMF at room temperature under argon. The resulting solution was magnetically stirred and treated with (6,7-dichloro-3-oxo-2,3-dihydro-4H-1,4-benzoxazin-4-yl)acetic acid (1.66 g, 6.0 mmol) and triethylamine (2.6 mL, 18.6 mmol) at room temperature. The solution was allowed to stir for several minutes before a separate solution of 1H-1,2,3-benzotriazol-1-yloxy-tris(dimethylamino)-phosphonium hexafluorophosphate (BOP reagent, 2.74 g, 6.2 mmol) dissolved in 10 mL of DMF was added to the mixture at room temperature. The reaction mixture was maintained at room temperature for 90 min, at which time the reaction was determined to be complete by LCMS (Eclipse XDB C18, 4.6×250 mm column, 1.5 mL/min, 10 minutes, gradient from 1-99% CH$_3$CN (0.1% trifluoroacetic acid)/H$_2$O (0.1% trifluoroacetic acid), ES, Rt=7.5 min and m/e 581 [M+1]$^+$). The reaction was quenched by the addition of 60 mL of a 1:1 solution of saturated sodium bicarbonate and H$_2$O. The mixture was allowed to stir for 1 hour before it was extracted with 200 mL of ethyl acetate. The organic layer was washed with the 1:1 solution of saturated sodium bicarbonate and H$_2$O (2×60 mL) and with saturated aqueous NaCl solution (2×60 mL). The organic layer was dried over anhydrous MgSO₄, filtered and concentrated under vacuum to give a brown oil which was purified by preparative HPLC (Phenomenex Luna 10 um Prep C18, 50×100 mm, 10 um, 90 mL/min, A: (acetonitrile with 0.1% trifluoroacetic acid) B: (water with 0.1% trifluoroacetic acid), gradient from 20%-85% of A in B, 10 min run, UV detection at 214 nm) to give 2 grams of 95% pure material which was triturated with water and acetonitrile to give the trifluoroacetate salt of 4'-[(1R)-1-[[(6,7-dichloro-3-oxo-2,3-dihydro-4H-1,4-benzoxazin-4-yl)acetyl](methyl)amino]-2-(1-pyrrolidinyl)ethyl]-3-biphenylcarboxamide (1.92 g, 2.76 mmol) as an off-white amorphous solid.

LCMS (Eclipse XDB C18, 4.6×250 mm column, 1.5 mL/min, 10 minutes, gradient from 1-99% CH₃CN (0.1% trifluoroacetic acid)/H₂O (0.1% trifluoroacetic acid), ES) R$_t$=7.5 min and m/e 581 [M+I]⁺;

Analytical HPLC (Eclipse XDB-C18, 4.6×250 mm, 5 micron, 2.5 mL/min, 10 minutes, gradient from 1-99% CH₃CN (0.1% trifluoroacetic acid)/H₂O (0.1% trifluoroacetic acid) R$_t$=6.4 min and purity=98%;

¹H NMR (400 MHz, d₆-DMSO) δ 9.6 (broad s, 1H), 8.2 (s, 1H), 8.1 (s, 1H), 7.9 (m, 2H), 7.8 (d, 2H), 7.6 (t, 1H), 7.45 (s, 1H), 7.4-7.2 (m, 4H), 6.2 (d, 1H), 5.1 (d, 1H), 4.85-4.7 (m, 3H), 4.3 (t, 1H), 3.75 (m, 2H), 3.5 (broad s, 1H), 3.2 (m, 2H), 2.9 (s, 3H), 2.1-1.8 (broad m, 4H).

Chiral HPLC (Chiralpak IB column, 4.6×250 mm, 1.0 mL/min, 60% ethanol/40% hexanes isocratic elution, 15 min run) R$_t$=9.0 min, 96% ee; Racemic standard shows two peaks, R$_t$=7.8 min and 9.1 min.

Example 505

4'-[(1R)-1-[[(6,7-dichloro-3-oxo-2,3-dihydro-4H-1,4-benzoxazin-4-yl)acetyl](methyl)amino]-2-(1-pyrrolidinyl)ethyl]-3-biphenylcarboxamide, Hydrochloride salt

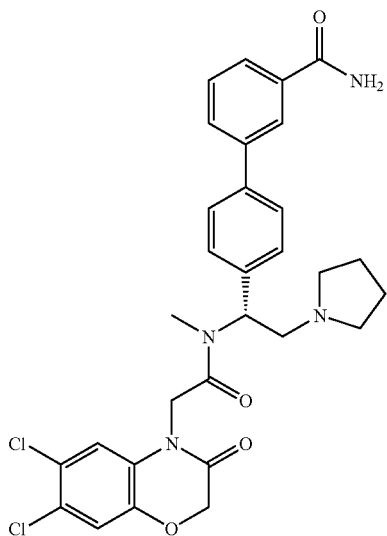

4'-[(1R)-1-[[(6,7-dichloro-3-oxo-2,3-dihydro-4H-1,4-benzoxazin-4-yl)acetyl](methyl)amino]-2-(1-pyrrolidinyl)ethyl]-3-biphenylcarboxamide, Trifluoroacetate salt (94 mg, 0.135 mmol) was dissolved in 20 mL of ethyl acetate. A 1:1 mixture of saturated sodium bicarbonate and water was prepared separately, and 20 mL of this solution was delivered to the flask containing 4'-[(1R)-1-[[(6,7-dichloro-3-oxo-2,3-dihydro-4H-1,4-benzoxazin-4-yl)acetyl](methyl)amino]-2-(1-pyrrolidinyl)ethyl]-3-biphenylcarboxamide, Trifluoroacetate salt. This mixture was magnetically stirred for one hour at room temperature and then the mixture was diluted with 40 mL of ethyl acetate. The organic phase was separated from the aqueous phase, dried over magnesium sulfate, filtered, and concentrated under vacuum. The resulting free base material was taken up in 1 mL of dioxane and then 2 mL of a 4M HCl/dioxane solution was slowly added. A white solid precipitated out of solution and then the flask containing the mixture was transferred to a sonicator and was sonicated for 20 minutes. The mixture was transferred to a vial and dried under vacuum to give 4'-[(1R)-1-[[(6,7-dichloro-3-oxo-2,3-dihydro-4H-1,4-benzoxazin-4-yl)acetyl](methyl)amino]-2-(1-pyrrolidinyl)ethyl]-3-biphenylcarboxamide, Hydrochloride salt (59.3 mg, 0.096 mmol, 71%) as an off-white solid. MS (ES) m/e 583 [M+H]⁺

4'-[(1R)-1-[[(6,7-dichloro-3-oxo-2,3-dihydro-4H-1,4-benzoxazin-4-yl)acetyl](methyl)amino]-2-(1-pyrrolidinyl)ethyl]-4-biphenylcarboxamide

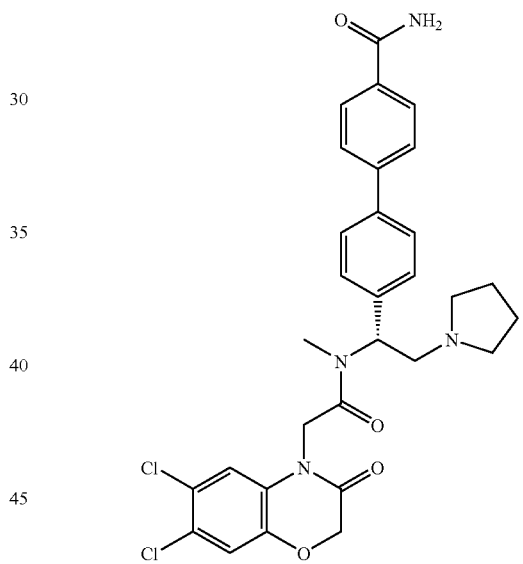

4'-[(1R)-1-[[(6,7-dichloro-3-oxo-2,3-dihydro-4H-1,4-benzoxazin-4-yl)acetyl](methyl)amino]-2-(1-pyrrolidinyl)ethyl]-4-biphenylcarboxamide was prepared in a similar manner as in the preparation of 4'-[(1R)-1-[[(6,7-dichloro-3-oxo-2,3-dihydro-4H-1,4-benzoxazin-4-yl)acetyl](methyl)amino]-2-(1-pyrrolidinyl)ethyl]-3-biphenylcarboxamide except replacing [3-(aminocarbonyl)phenyl]boronic acid with [4-(aminocarbonyl)phenyl]boronic acid. As is appreciated by those skilled in the art, this analogous example may involve variations in synthetic procedure.

LCMS (Eclipse XDB C18, 4.6×250 mm column, 1.5 mL/min, 10 minutes, gradient from 1-99% CH₃CN (0.1% trifluoroacetic acid)/H₂O (0.1% trifluoroacetic acid), ES) R$_t$=7.33 min and m/e 581 [M+1]⁺;

Analytical HPLC (Eclipse XDB-C18, 4.6×250 mm, 5 micron, 2.5 mL/min, 10 minutes, gradient from 1-99% CH₃CN (0.1% trifluoroacetic acid)/H₂O (0.1% trifluoroacetic acid) R$_t$=5.83 min and purity=96%;

$^1$H NMR (400 MHz, d$_6$-DMSO) δ 9.7 (broad s, 1H), 8.1 (s, 1H), 8.0 (d, 2H), 7.9-7.7 (m, 4H), 7.5-7.3 (m, 5H), 6.2 (d, 1H), 5.1 (d, 1H), 4.9-4.7 (m, 3H), 4.3 (t, 1H), 3.8 (m, 2H), 3.4 (1H under H$_2$O peak), 3.2 (m, 2H), 2.9 (s, 3H), and 2.1-1.9 (broad m, 4H).

The invention claimed is:

1. A compound of Formula (I):

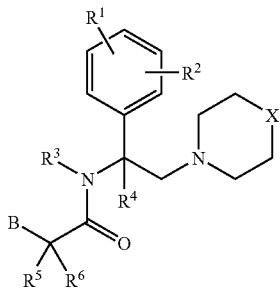

(I)

wherein $R^1$ is:

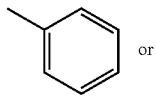

(a)

or

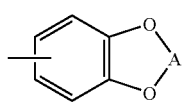

(b)

A is (CH$_2$)$_n$;

n is 1 or 2;

the group (a) may be unsubstituted or substituted by one, two, or three substituents chosen from: halo, OC$_{1-3}$ alkyl, OH, CN, C(O)OH, NR$_7$R$_8$, OCF$_3$, C(O)NR$_9$R$_{10}$, SO$_2$C$_{1-3}$ alkyl, SO$_2$C$_{3-6}$ cycloalkyl, SO$_2$-phenyl, SO$_2$NR$_9$R$_{10}$, CF$_3$, and NO$_2$;

$R^2$ is hydrogen, halo, OC$_{1-3}$ alkyl, NHC(O)C$_{1-3}$ alkyl, NHSO$_2$C$_{1-3}$alkyl, NHSO$_2$-phenyl, NHC(O)C$_{3-6}$ cycloalkyl, or NHC(O)-phenyl;

$R^3$ is C$_{1-3}$ alkyl or C$_{3-6}$ cycloalkyl;

$R^4$, $R^5$, and $R^6$ are independently hydrogen or CH$_3$;

$R^7$ and $R^8$ are independently hydrogen, C(O)C$_{1-3}$ alkyl, C(O)C$_{3-6}$ cycloalkyl, C(O)-phenyl, C$_{1-6}$ alkyl, phenyl, SO$_2$C$_{1-3}$ alkyl, SO$_2$C$_{3-6}$ cycloalkyl, SO$_2$-phenyl, or C(O)NHC$_{1-3}$ alkyl;

$R^9$ and $R^{10}$ are independently hydrogen, C$_{1-3}$ alkyl, C$_{3-6}$ cycloalkyl, phenyl;

or taken together $R^9$ and $R^{10}$ may form a 5 to 7 member ring optionally containing one or two heteroatoms chosen from O, N, and S;

X is O or a bond;

B is:

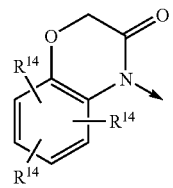

(d)

$R^{14}$ is hydrogen, halo, C$_{1-3}$ alkyl, OC$_{1-3}$ alkyl, OCF$_3$, CF$_3$, C(O)NR$_{15}$R$_{16}$, or C(O)OC$_{1-3}$ alkyl; and $R^{15}$ and $R^{16}$ are independently hydrogen, C$_{1-3}$ alkyl, C$_{3-6}$ cycloalkyl, or phenyl;

or a pharmaceutically acceptable salt thereof.

2. A compound of claim 1 wherein:

$R^1$ is phenyl substituted by one or two halo, OC$_{1-3}$alkyl, CN, C(O)OH, NR$^7$R$^8$, C(O)NR$^9$R$^{10}$, SO$_2$C$_{1-3}$ alkyl, or SO$_2$NR$^{11}$R$^{12}$;

$R^2$ is hydrogen or halo;

$R^3$ is methyl;

$R^4$ is hydrogen or CH$_3$;

$R^5$ and $R^6$ are hydrogen;

$R^7$ and $R^8$ are independently hydrogen, C(O)C$_{1-3}$alkyl, C$_{1-6}$alkyl, SO$_2$C$_{1-3}$ alkyl, or C(O)NHC$_{1-3}$alkyl;

$R^9$ and $R^{10}$ are independently H, C$_{1-3}$alkyl;

or taken together $R^9$ and $R^{10}$ form a pyrrolidine, morpholine, or piperidine group;

X is O or a bond;

B is:

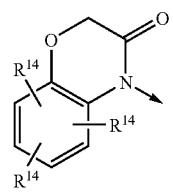

(d)

$R^{14}$ is hydrogen or halo;

or a pharmaceutically acceptable salt thereof.

3. A compound of claim 1 wherein:

$R^1$ is phenyl substituted by one or two OC$_{1-3}$alkyl, C(O)OH, or C(O)NR$^9$R$^{10}$;

$R^2$ is hydrogen or halo;

$R^3$ is methyl;

$R^4$ is hydrogen or CH$_3$;

$R^5$ and $R^6$ are hydrogen;

$R^9$ and $R^{10}$ are independently hydrogen, C$_{1-3}$alkyl;

or taken together $R^9$ and $R^{10}$ form a pyrrolidine, morpholine, or piperidine group;

X is O or a bond;
B is:

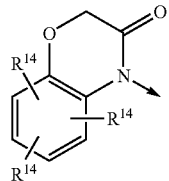

$R^{14}$ is hydrogen or halo;
or a pharmaceutically acceptable salt thereof.

4. A compound of claim 1 selected from:
N-[1-(4-biphenyl)-1)-2-(1-pyrrolidinyl)ethyl]-2-(6,7-dichloro-3-oxo-2,3-dihydro-4H-1,4-benzoxazin-4-yl)-N-methylacetamide;
N-(1-biphenyl-4-yl-2-pyrrolidin-1-ylethyl)-2-(6,7-dibromo-3-oxo-2,3-dihydro-4H-1,4-benzoxazin-4-yl)-N-methylacetamide;
N-[1-(4-biphenylyl)-2-(1-pyrrolidinyl)ethyl]-2-(6,7-dimethyl-3-oxo-2,3-dihydro-4H-1,4-benzoxazin-4-yl)-N-methylacetamide;
(N-[1-(4-biphenylyl)-2-(4-morpholinyl)ethyl]-2-(6,7-dibromo-3-oxo-2,3-dihydro-4H-1,4-benzoxazin-4-yl)-N-methylacetamide;
N-[1-(4-biphenylyl)-2-(4-morpholinyl)ethyl]-2-(6,7-dichloro-3-oxo-2,3-dihydro-4H-1,4-benzoxazin-4-yl)-N-methylacetamide;
N-[1-[3',4'-bis(methyloxy)-4-biphenylyl]-2-(1-pyrrolidinyl)ethyl]-2-(6,7-dichloro-3-oxo-2,3-dihydro-4H-1,4-benzoxazin-4-yl)-N-methylacetamide;
4'-[1-[[(6,7-dichloro-3-oxo-2,3-dihydro-4H-1,4-benzoxazin-4-yl)acetyl](methyl)amino]-2-(1-pyrrolidinyl)ethyl]-4-biphenylcarboxylic acid;
2-(6,7-dichloro-3-oxo-2,3-dihydro-4H-1,4-benzoxazin-4-yl)-N-methyl-N-[1-{3'-[(1-methylethyl)oxy]-4-biphenylyl}-2-(1-pyrrolidinyl)ethyl]acetamide;
2-(6,7-dichloro-3-oxo-2,3-dihydro-4H-1,4-benzoxazin-4-yl)-N-methyl-N-[1-{3'-[(methylsulfonyl)amino]-4-biphenylyl}-2-(1-pyrrolidinyl)ethyl]acetamide;
2-(6,7-dichloro-3-oxo-2,3-dihydro-4H-1,4-benzoxazin-4-yl)-N-[1-[4'-(dimethylamino)-4-biphenylyl]-2-(1-pyrrolidinyl)ethyl]-N-methylacetamide;
N-[1-[4'-(acetylamino)-4-biphenylyl]-2-(1-pyrrolidinyl)ethyl]-2-(6,7-dichloro-3-oxo-2,3-dihydro-4H-1,4-benzoxazin-4-yl)-N-methylacetamide;
2-(6,7-dichloro-3-oxo-2,3-dihydro-4H-1,4-benzoxazin-4-yl)-N-methyl-N-[1-[3'-(methyloxy)-4-biphenylyl]-2-(1-pyrrolidinyl)ethyl]acetamide;
4'-[1-[[(6,7-dimethyl-3-oxo-2,3-dihydro-4H-1,4-benzoxazin-4-yl)acetyl](methyl)amino]-2-(1-pyrrolidinyl)ethyl]-4-biphenylcarboxylic acid;
2-(6,7-dimethyl-3-oxo-2,3-dihydro-4H-1,4-benzoxazin-4-yl)-N-methyl-N-[1-{3'-[(1-methylethyl)oxy]-4-biphenylyl}-2-(1-pyrrolidinyl)ethyl]acetamide;
2-(6,7-dimethyl-3-oxo-2,3-dihydro-4H-1,4-benzoxazin-4-yl)-N-methyl-N-[1-{3'-[(methylsulfonyl)amino]-4-biphenylyl}-2-(1-pyrrolidinyl)ethyl]acetamide;
N-[1-[4'-(dimethylamino)-4-biphenylyl]-2-(1-pyrrolidinyl)ethyl]-2-(6,7-dimethyl-3-oxo-2,3-dihydro-4H-1,4-benzoxazin-4-yl)-N-methylacetamide;
N-[1-[4'-(acetylamino)-4-biphenylyl]-2-(1-pyrrolidinyl)ethyl]-2-(6,7-dimethyl-3-oxo-2,3-dihydro-4H-1,4-benzoxazin-4-yl)-N-methylacetamide;
2-(6,7-dimethyl-3-oxo-2,3-dihydro-4H-1,4-benzoxazin-4-yl)-N-methyl-N-[1-[3'-(methyloxy)-4-biphenylyl]-2-(1-pyrrolidinyl)ethyl]acetamide;
N-[1-[3',4'-bis(methyloxy)-4-biphenylyl]-2-(1-pyrrolidinyl)ethyl]-2-(6,7-dimethyl-3-oxo-2,3-dihydro-4H-1,4-benzoxazin-4-yl)-N-methylacetamide;
N-[1-(4'-chloro-3-biphenylyl)-2-(1-pyrrolidinyl)ethyl]-2-(6,7-dichloro-3-oxo-2,3-dihydro-4H-1,4-benzoxazin-4-yl)-N-methylacetamide;
2-(6,7-dichloro-3-oxo-2,3-dihydro-4H-1,4-benzoxazin-4-yl)-N-[1-[4'-(dimethylamino)-3-biphenylyl]-2-(1-pyrrolidinyl)ethyl]-N-methylacetamide;
2-(6,7-dichloro-3-oxo-2,3-dihydro-4H-1,4-benzoxazin-4-yl)-N-methyl-N-[1-[3'-(methyloxy)-3-biphenylyl]-2-(1-pyrrolidinyl)ethyl]acetamide;
2-(6,7-dichloro-3-oxo-2,3-dihydro-4H-1,4-benzoxazin-4-yl)-N-[1-(2'-hydroxy-3-biphenylyl)-2-(1-pyrrolidinyl)ethyl]-N-methylacetamide;
2-(6,7-dichloro-3-oxo-2,3-dihydro-4H-1,4-benzoxazin-4-yl)-N-[1-(4'-hydroxy-3-biphenylyl)-2-(1-pyrrolidinyl)ethyl]-N-methylacetamide;
N-[1-[4'-(acetylamino)-3-biphenylyl]-2-(1-pyrrolidinyl)ethyl]-2-(6,7-dichloro-3-oxo-2,3-dihydro-4H-1,4-benzoxazin-4-yl)-N-methylacetamide;
2-(6,7-dichloro-3-oxo-2,3-dihydro-4H-1,4-benzoxazin-4-yl)-N-methyl-N-[1-{4'-[(methylsulfonyl)amino]-4-biphenylyl}-2-(4-morpholinyl)ethyl]acetamide;
2-(6,7-dichloro-3-oxo-2,3-dihydro-4H-1,4-benzoxazin-4-yl)-N-methyl-N-[1-{4'-(methylsulfonyl)-4-biphenylyl}-2-(4-morpholinyl)ethyl]acetamide;
N-{1-[3'-(acetylamino)biphenyl-4-yl]-2-morpholin-4-ylethyl}-2-(6,7-dichloro-3-oxo-2,3-dihydro-4H-1,4-benzoxazin-4-yl)-N-methylacetamide;
2-(6,7-dichloro-3-oxo-2,3-dihydro-4H-1,4-benzoxazin-4-yl)-N-methyl-N-[1-{2'-[(methylsulfonyl)amino]-4-biphenylyl}-2-(4-morpholinyl)ethyl]acetamide;
2-(6,7-dichloro-3-oxo-2,3-dihydro-4H-1,4-benzoxazin-4-yl)-N-[1-[4'-(ethylsulfonyl)-4-biphenylyl]-2-(4-morpholinyl)ethyl]-N-methylacetamide;
2-(6,7-dichloro-3-oxo-2,3-dihydro-4H-1,4-benzoxazin-4-yl)-N-methyl-N-{2-(4-morpholinyl)-1-[3'-(1-piperidinylcarbonyl)-4-biphenylyl]ethyl}acetamide;
2-(6,7-dichloro-3-oxo-2,3-dihydro-4H-1,4-benzoxazin-4-yl)-N-methyl-N-{2-(4-morpholinyl)-1-[4'-(4-morpholinylcarbonyl)-4-biphenylyl]ethyl}acetamide;
2-(6,7-dichloro-3-oxo-2,3-dihydro-4H-1,4-benzoxazin-4-yl)-N-methyl-N-{2-(4-morpholinyl)-1-[3'-(4-morpholinylcarbonyl)-4-biphenylyl]ethyl}acetamide;
2-(6,7-dichloro-3-oxo-2,3-dihydro-4H-1,4-benzoxazin-4-yl)-N-[1-[3'-(ethyloxy)-4-biphenylyl]-2-(4-morpholinyl)ethyl]-N-methylacetamide;
2-(6,7-dichloro-3-oxo-2,3-dihydro-4H-1,4-benzoxazin-4-yl)-N-[1-[5'-(ethyloxy)-2'-fluoro-4-biphenylyl]-2-(4-morpholinyl)ethyl]-N-methylacetamide;
2-(6,7-dichloro-3-oxo-2,3-dihydro-4H-1,4-benzoxazin-4-yl)-N-[1-[4'-(dimethylamino)-4-biphenylyl]-2-(4-morpholinyl)ethyl]-N-methylacetamide;
N-[1-[2',3'-bis(methyloxy)-4-biphenylyl]-2-(4-morpholinyl)ethyl]-2-(6,7-dichloro-3-oxo-2,3-dihydro-4H-1,4-benzoxazin-4-yl)-N-methylacetamide;
4'-[1-[[(6,7-dichloro-3-oxo-2,3-dihydro-4H-1,4-benzoxazin-4-yl)acetyl](methyl)amino]-2-(4-morpholinyl)ethyl]-3-biphenylcarboxamide;
4'-[1-[[(6,7-dichloro-3-oxo-2,3-dihydro-4H-1,4-benzoxazin-4-yl)acetyl](methyl)amino]-2-(4-morpholinyl)ethyl]-N-methyl-3-biphenylcarboxamide;

4'-[1-[[(6,7-dichloro-3-oxo-2,3-dihydro-4H-1,4-benzoxazin-4-yl)acetyl](methyl)amino]-2-(4-morpholinyl)ethyl]-N,N-dimethyl-3-biphenylcarboxamide;

2-(6,7-dichloro-3-oxo-2,3-dihydro-4H-1,4-benzoxazin-4-yl)-N-methyl-N-[1-{3'-[(methylsulfonyl)amino]-4-biphenylyl}-2-(4-morpholinyl)ethyl]acetamide;

4'-[1-[[(6,7-dichloro-3-oxo-2,3-dihydro-4H-1,4-benzoxazin-4-yl)acetyl](methyl)amino]-2-(4-morpholinyl)ethyl]-2-biphenylcarboxamide;

4'-[1-[[(6,7-dichloro-3-oxo-2,3-dihydro-4H-1,4-benzoxazin-4-yl)acetyl](methyl)amino]-2-(4-morpholinyl)ethyl]-4-biphenylcarboxamide;

4'-[1-[[(6,7-dichloro-3-oxo-2,3-dihydro-4H-1,4-benzoxazin-4-yl)acetyl](methyl)amino]-2-(4-morpholinyl)ethyl]-N-methyl-4-biphenylcarboxamide;

4'-[1-[[(6,7-dichloro-3-oxo-2,3-dihydro-4H-1,4-benzoxazin-4-yl)acetyl](methyl)amino]-2-(4-morpholinyl)ethyl]-N,N-dimethyl-4-biphenylcarboxamide;

N-cyclopropyl-4'-[1-[[(6,7-dichloro-3-oxo-2,3-dihydro-4H-1,4-benzoxazin-4-yl)acetyl] (methyl)amino]-2-(4-morpholinyl)ethyl]-3-biphenylcarboxamide;

4'-[1-[[(6,7-dichloro-3-oxo-2,3-dihydro-4H-1,4-benzoxazin-4-yl)acetyl] (methyl)amino]-2-(4-morpholinyl)ethyl]-N-(1-methylethyl)-3-biphenylcarboxamide;

4'-[1-[[(6,7-dichloro-3-oxo-2,3-dihydro-4H-1,4-benzoxazin-4-yl)acetyl] (methyl)amino]-2-(4-morpholinyl)ethyl]-5-fluoro-N-methyl-3-biphenylcarboxamide;

2-(6,7-dichloro-3-oxo-2,3-dihydro-4H-1,4-benzoxazin-4-yl)-N-methyl-N-{2-(4-morpholinyl)-1-[3'-(1-pyrrolidinylcarbonyl)-4-biphenylyl]ethyl}acetamide;

N-[1-[2'-(acetylamino)-4-biphenylyl]-2-(4-morpholinyl)ethyl]-2-(6,7-dichloro-3-oxo-2,3-dihydro-4H-1,4-benzoxazin-4-yl)-N-methylacetamide;

2-(6,7-dichloro-3-oxo-2,3-dihydro-4H-1,4-benzoxazin-4-yl)-N-methyl-N-[1-{4'-[(methylamino)sulfonyl]-4-biphenylyl}-2-(4-morpholinyl)ethyl]acetamide;

2-(6,7-dichloro-3-oxo-2,3-dihydro-4H-1,4-benzoxazin-4-yl)-N-[1-{4'-[(dimethylamino)sulfonyl]-4-biphenylyl}-2-(4-morpholinyl)ethyl]-N-methylacetamide;

2-(6,7-dichloro-3-oxo-2,3-dihydro-4H-1,4-benzoxazin-4-yl)-N-[1-{2'-[(dimethylamino)sulfonyl]-4-biphenylyl}-2-(4-morpholinyl)ethyl]-N-methylacetamide;

2-(6,7-dichloro-3-oxo-2,3-dihydro-4H-1,4-benzoxazin-4-yl)-N-methyl-N-{2-(4-morpholinyl)-1-[3'-(1-piperidinylcarbonyl)-3-biphenylyl]ethyl}acetamide;

N-[1-[3',4'-bis(methyloxy)-3-biphenylyl]-2-(4-morpholinyl)ethyl]-2-(6,7-dichloro-3-oxo-2,3-dihydro-4H-1,4-benzoxazin-4-yl)-N-methylacetamide;

2-(6,7-dichloro-3-oxo-2,3-dihydro-4H-1,4-benzoxazin-4-yl)-N-methyl-N-[1-{4'-[(methylsulfonyl)amino]-3-biphenylyl}-2-(4-morpholinyl)ethyl]acetamide;

N-[1-[4'-(acetylamino)-3-biphenylyl]-2-(4-morpholinyl)ethyl]-2-(6,7-dichloro-3-oxo-2,3-dihydro-4H-1,4-benzoxazin-4-yl)-N-methylacetamide;

2-(6,7-dichloro-3-oxo-2,3-dihydro-4H-1,4-benzoxazin-4-yl)-N-methyl-N-[1-[4'-(methylsulfonyl)-3-biphenylyl]-2-(4-morpholinyl)ethyl]acetamide;

N-[1-[4'-(acetylamino)-3-biphenylyl]-2-(4-morpholinyl)ethyl]-2-(6,7-dichloro-3-oxo-2,3-dihydro-4H-1,4-benzoxazin-4-yl)-N-methylacetamide;

3'-[1-[[(6,7-dichloro-3-oxo-2,3-dihydro-4H-1,4-benzoxazin-4-yl)acetyl] (methyl)amino]-2-(4-morpholinyl)ethyl]-3-biphenylcarboxamide;

N-[1-[2'-(acetylamino)-3-biphenylyl]-2-(4-morpholinyl)ethyl]-2-(6,7-dichloro-3-oxo-2,3-dihydro-4H-1,4-benzoxazin-4-yl)-N-methylacetamide;

N-[1-(4'-cyano-3-biphenylyl)-2-(4-morpholinyl)ethyl]-2-(6,7-dichloro-3-oxo-2,3-dihydro-4H-1,4-benzoxazin-4-yl)-N-methylacetamide;

2-(6,7-dichloro-3-oxo-2,3-dihydro-4H-1,4-benzoxazin-4-yl)-N-methyl-N-[1-{3'-[(methylsulfonyl)amino]-3-biphenylyl}-2-(4-morpholinyl)ethyl]acetamide;

3'-[1-[[(6,7-dichloro-3-oxo-2,3-dihydro-4H-1,4-benzoxazin-4-yl)acetyl](methyl)amino]-2-(4-morpholinyl)ethyl]-2-biphenylcarboxamide;

N-[1-(2'-cyano-3-biphenylyl)-2-(4-morpholinyl)ethyl]-2-(6,7-dichloro-3-oxo-2,3-dihydro-4H-1,4-benzoxazin-4-yl)-N-methylacetamide;

2-(6,7-dichloro-3-oxo-2,3-dihydro-4H-1,4-benzoxazin-4-yl)-N-[1-[4'-(ethylsulfonyl)-3-biphenylyl]-2-(4-morpholinyl)ethyl]-N-methylacetamide;

3'-[1-[[(6,7-dichloro-3-oxo-2,3-dihydro-4H-1,4-benzoxazin-4-yl)acetyl](methyl)amino]-2-(4-morpholinyl)ethyl]-N-methyl-4-biphenylcarboxamide;

3'-[1-[[(6,7-dichloro-3-oxo-2,3-dihydro-4H-1,4-benzoxazin-4-yl)acetyl](methyl)amino]-2-(4-morpholinyl)ethyl]-N,N-dimethyl-4-biphenylcarboxamide;

2-(6,7-dichloro-3-oxo-2,3-dihydro-4H-1,4-benzoxazin-4-yl)-N-methyl-N-[1-{2'-[(methylsulfonyl)amino]-3-biphenylyl}-2-(4-morpholinyl)ethyl]acetamide;

N-[1-[4'-(aminosulfonyl)-3-biphenylyl]-2-(4-morpholinyl)ethyl]-2-(6,7-dichloro-3-oxo-2,3-dihydro-4H-1,4-benzoxazin-4-yl)-N-methylacetamide;

3'-[1-[[(6,7-dichloro-3-oxo-2,3-dihydro-4H-1,4-benzoxazin-4-yl)acetyl](methyl)amino]-2-(4-morpholinyl)ethyl]-4-biphenylcarboxamide;

3'-[1-[[(6,7-dichloro-3-oxo-2,3-dihydro-4H-1,4-benzoxazin-4-yl)acetyl](methyl)amino]-2-(4-morpholinyl)ethyl]-N,N-dimethyl-3-biphenylcarboxamide;

3'-[1-[[(6,7-dichloro-3-oxo-2,3-dihydro-4H-1,4-benzoxazin-4-yl)acetyl](methyl)amino]-2-(4-morpholinyl)ethyl]-N-methyl-3-biphenylcarboxamide;

2-(6,7-dichloro-3-oxo-2,3-dihydro-4H-1,4-benzoxazin-4-yl)-N-methyl-N-{2-(4-morpholinyl)-1-[4'-(1-pyrrolidinylcarbonyl)-3-biphenylyl]ethyl}acetamide;

2-(6,7-dichloro-3-oxo-2,3-dihydro-4H-1,4-benzoxazin-4-yl)-N-methyl-N-{2-(4-morpholinyl)-1-[4'-(4-morpholinylcarbonyl)-3-biphenylyl]ethyl}acetamide; 2-(6,7-dichloro-3-oxo-2,3-dihydro-4H-1,4-benzoxazin-4-yl)-N-[1-[3'-(dimethylamino)-3-biphenylyl]-2-(4-morpholinyl)ethyl]-N-methylacetamide;

2-(6,7-dichloro-3-oxo-2,3-dihydro-4H-1,4-benzoxazin-4-yl)-N-[1-{2'-[(dimethylamino)sulfonyl]-3-biphenylyl}-2-(4-morpholinyl)ethyl]-N-methylacetamide;

2-(6,7-dichloro-3-oxo-2,3-dihydro-4H-1,4-benzoxazin-4-yl)-N-methyl-N-{2-(4-morpholinyl)-1-[3'-(1-pyrrolidinylcarbonyl)-3-biphenylyl]ethyl}acetamide;

2-(6,7-dichloro-3-oxo-2,3-dihydro-4H-1,4-benzoxazin-4-yl)-N-methyl-N-{2-(4-morpholinyl)-1-[4'-(1-piperidinylcarbonyl)-3-biphenylyl]ethyl}acetamide;

2-(6,7-dichloro-3-oxo-2,3-dihydro-4H-1,4-benzoxazin-4-yl)-N-methyl-N-[1-[3'-(methylsulfonyl)-3-biphenylyl]-2-(4-morpholinyl)ethyl]acetamide;

3-chloro-3'-[1-[[(6,7-dichloro-3-oxo-2,3-dihydro-4H-1,4-benzoxazin-4-yl)acetyl](methyl)amino]-2-(4-morpholinyl)ethyl]-4-biphenylcarboxamide;

N-cyclopropyl-3'-[1-[[(6,7-dichloro-3-oxo-2,3-dihydro-4H-1,4-benzoxazin-4-yl)acetyl](methyl)amino]-2-(4-morpholinyl)ethyl]-4-biphenylcarboxamide;

3'-[1-[[(6,7-dichloro-3-oxo-2,3-dihydro-4H-1,4-benzoxazin-4-yl)acetyl] (methyl)amino]-2-(4-morpholinyl)ethyl]-N-(1-methylethyl)-3-biphenylcarboxamide;

3'-[1-[[(6,7-dichloro-3-oxo-2,3-dihydro-4H-1,4-benzoxazin-4-yl)acetyl](methyl)amino]-2-(4-morpholinyl)ethyl]-4-biphenylcarboxylic acid;

2-(6,7-dimethyl-3-oxo-2,3-dihydro-4H-1,4-benzoxazin-4-yl)-N-methyl-N-[1-{3'-[(1-methylethyl)oxy]-4-biphenylyl}-2-(4-morpholinyl)ethyl]acetamide;

2-(6,7-dimethyl-3-oxo-2,3-dihydro-4H-1,4-benzoxazin-4-yl)-N-methyl-N-[1-{3'-[(methylsulfonyl)amino]-4-biphenylyl}-2-(4-morpholinyl)ethyl]acetamide;

N-[1-[3',4'-bis(methyloxy)-4-biphenylyl]-2-(4-morpholinyl)ethyl]-2-(6,7-dimethyl-3-oxo-2,3-dihydro-4H-1,4-benzoxazin-4-yl)-N-methylacetamide;

2-(6,7-dichloro-3-oxo-2,3-dihydro-4H-1,4-benzoxazin-4-yl)-N-methyl-N-[1-[3'-(methyloxy)-4-biphenylyl]-2-(4-morpholinyl)ethyl]acetamide;

N-[1-[3',4'-bis(methyloxy)-4-biphenylyl]-2-(4-morpholinyl)ethyl]-2-(6,7-dichloro-3-oxo-2,3-dihydro-4H-1,4-benzoxazin-4-yl)-N-methylacetamide;

4'-[1-[[(6,7-dichloro-3-oxo-2,3-dihydro-4H-1,4-benzoxazin-4-yl)acetyl](methyl)amino]-2-(4-morpholinyl)ethyl]-4-biphenylcarboxylic acid;

N-[1-[4'-(acetylamino)-4-biphenylyl]-2-(4-morpholinyl)ethyl]-2-(6,7-dichloro-3-oxo-2,3-dihydro-4H-1,4-benzoxazin-4-yl)-N-methylacetamide;

N-[1-(4'-amino-4-biphenylyl)-2-(4-morpholinyl)ethyl]-2-(6,7-dichloro-3-oxo-2,3-dihydro-4H-1,4-benzoxazin-4-yl)-N-methylacetamide;

N-{4'-[1-[[(6,7-dichloro-3-oxo-2,3-dihydro-4H-1,4-benzoxazin-4-yl)acetyl](methyl)amino]-2-(4-morpholinyl)ethyl]-4-biphenylyl}propanamide;

2-(6,7-dichloro-3-oxo-2,3-dihydro-4H-1,4-benzoxazin-4-yl)-N-[1-{4'-[(ethylsulfonyl)amino]-4-biphenylyl}-2-(4-morpholinyl)ethyl]-N-methylacetamide;

2-(6,7-dichloro-3-oxo-2,3-dihydro-4H-1,4-benzoxazin-4-yl)-N-[1-(4'-{[(ethylamino)carbonyl]amino}-4-biphenylyl)-2-(4-morpholinyl)ethyl]-N-methylacetamide;

N-[1-(4-biphenylyl)-2-(1-pyrrolidinyl)ethyl]-N-methyl-2-[7-(methyloxy)-3-oxo-2,3-dihydro-4H-1,4-benzoxazin-4-yl]acetamide;

(R) N-[1-(4-biphenylyl)-2-(4-morpholinyl)ethyl]-2-(6,7-dichloro-3-oxo-2,3-dihydro-4H-1,4-benzoxazin-4-yl)-N-methylacetamide;

N-[1-(4-biphenylyl)-2-(1-pyrrolidinyl)ethyl]-N-methyl-2-[6-(methyloxy)-3-oxo-2,3-dihydro-4H-1,4-benzoxazin-4-yl]acetamide; and N-[1-(4-biphenylyl)-2-(1-pyrrolidinyl)ethyl]-N-methyl-2-{3-oxo-6-[(trifluoromethyl)oxy]-2,3-dihydro-4H-1,4-benzoxazin-4-yl}acetamide;

or a pharmaceutically acceptable salt thereof.

5. A compound of claim 1 selected from:

N-[1-(4-biphenylyl)-2-(4-morpholinyl)ethyl]-2-(6,7-dimethyl-3-oxo-2,3-dihydro-4H-1,4-benzoxazin-4-yl)-N-methylacetamide;

3-chloro-4'-[1-[[(6,7-dichloro-3-oxo-2,3-dihydro-4H-1,4-benzoxazin-4-yl)acetyl](methyl)amino]-2-(4-morpholinyl)ethyl]-N-methyl-4-biphenylcarboxamide;

3-chloro-4'-[1-[[(6,7-dichloro-3-oxo-2,3-dihydro-4H-1,4-benzoxazin-4-yl)acetyl](methyl)amino]-2-(4-morpholinyl)ethyl]-N,N-dimethyl-4-biphenylcarboxamide;

2-(6,7-dichloro-3-oxo-2,3-dihydro-4H-1,4-benzoxazin-4-yl)-N-methyl-N-{2-(4-morpholinyl)-1-[2'-(trifluoromethyl)-4-biphenylyl]ethyl}acetamide;

2-(6,7-dichloro-3-oxo-2,3-dihydro-4H-1,4-benzoxazin-4-yl)-N-methyl-N-{2-(4-morpholinyl)-1-[3'-(trifluoromethyl)-4-biphenylyl]ethyl}acetamide;

2-(6,7-dichloro-3-oxo-2,3-dihydro-4H-1,4-benzoxazin-4-yl)-N-methyl-N-{2-(4-morpholinyl)-1-[4'-(trifluoromethyl)-4-biphenylyl]ethyl}acetamide;

2-(6,7-dichloro-3-oxo-2,3-dihydro-4H-1,4-benzoxazin-4-yl)-N-[1-(2'-fluoro-4-biphenylyl)-2-(4-morpholinyl)ethyl]-N-methylacetamide;

2-(6,7-dichloro-3-oxo-2,3-dihydro-4H-1,4-benzoxazin-4-yl)-N-[1-(3'-fluoro-4-biphenylyl)-2-(4-morpholinyl)ethyl]-N-methylacetamide;

2-(6,7-dichloro-3-oxo-2,3-dihydro-4H-1,4-benzoxazin-4-yl)-N-[1-(4'-fluoro-4-biphenylyl)-2-(4-morpholinyl)ethyl]-N-methylacetamide;

N-[1-(4-biphenylyl)-2-(4-morpholinyl)ethyl]-2-(6,7-dimethyl-3-oxo-2,3-dihydro-4H-1,4-benzoxazin-4-yl)-N-methylacetamide;

N-[1-(3'-cyano-4-biphenylyl)-2-(4-morpholinyl)ethyl]-2-(6,7-dichloro-3-oxo-2,3-dihydro-4H-1,4-benzoxazin-4-yl)-N-methylacetamide;

N-cyclopropyl-4'-[1-[[(6,7-dichloro-3-oxo-2,3-dihydro-4H-1,4-benzoxazin-4-yl)acetyl](methyl)amino]-2-(4-morpholinyl)ethyl]-4-biphenylcarboxamide;

4'-[1-[[(6,7-dichloro-3-oxo-2,3-dihydro-4H-1,4-benzoxazin-4-yl)acetyl](methyl)amino]-2-(4-morpholinyl)ethyl]-N-(1-methylethyl)-4-biphenylcarboxamide;

3-chloro-4'-[1-[[(6,7-dichloro-3-oxo-2,3-dihydro-4H-1,4-benzoxazin-4-yl)acetyl](methyl)amino]-2-(4-morpholinyl)ethyl]-4-biphenylcarboxamide;

2-(6,7-dichloro-3-oxo-2,3-dihydro-4H-1,4-benzoxazin-4-yl)-N-methyl-N-{2-(4-morpholinyl)-1-[4'-(1-piperidinylcarbonyl)-4-biphenylyl]ethyl}acetamide;

2-(6,7-dichloro-3-oxo-2,3-dihydro-4H-1,4-benzoxazin-4-yl)-N-methyl-N-[1-[4-(4-methyl-3,4-dihydro-2H-1,4-benzoxazin-7-yl)phenyl]-2-(4-morpholinyl)ethyl]acetamide;

N-[1-[4'-(aminosulfonyl)-4-biphenylyl]-2-(4-morpholinyl)ethyl]-2-(6,7-dichloro-3-oxo-2,3-dihydro-4H-1,4-benzoxazin-4-yl)-N-methylacetamide;

N-[1-(3'-cyano-3-biphenylyl)-2-(4-morpholinyl)ethyl]-2-(6,7-dichloro-3-oxo-2,3-dihydro-4H-1,4-benzoxazin-4-yl)-N-methylacetamide;

N-[1-(3-biphenylyl)-2-(4-morpholinyl)ethyl]-2-(6,7-dichloro-3-oxo-2,3-dihydro-4H-1,4-benzoxazin-4-yl)-N-methylacetamide;

2-(6,7-dichloro-3-oxo-2,3-dihydro-4H-1,4-benzoxazin-4-yl)-N-[1-{4'-[(dimethylamino)sulfonyl]-3-biphenylyl}-2-(4-morpholinyl)ethyl]-N-methylacetamide;

2-(6,7-dichloro-3-oxo-2,3-dihydro-4H-1,4-benzoxazin-4-yl)-N-[1-[4'-(dimethylamino)-3-biphenylyl]-2-(4-morpholinyl)ethyl]-N-methylacetamide;

2-(6,7-dichloro-3-oxo-2,3-dihydro-4H-1,4-benzoxazin-4-yl)-N-methyl-N-{2-(4-morpholinyl)-1-[3'-(1-piperidinylcarbonyl)-3-biphenylyl]ethyl}acetamide;

2-(6,7-dichloro-3-oxo-2,3-dihydro-4H-1,4-benzoxazin-4-yl)-N-methyl-N-[2-(4-morpholinyl)-1-(3'-nitro-3-biphenylyl)ethyl]acetamide;

N-[1-(4-biphenylyl)-2-(4-morpholinyl)ethyl]-2-(6,7-dimethyl-3-oxo-2,3-dihydro-4H-1,4-benzoxazin-4-yl)-N-methylacetamide;

N-[1-[4'-(dimethylamino)-4-biphenylyl]-2-(4-morpholinyl)ethyl]-2-(6,7-dimethyl-3-oxo-2,3-dihydro-4H-1,4-benzoxazin-4-yl)-N-methylacetamide;

2-(6,7-dichloro-3-oxo-2,3-dihydro-4H-1,4-benzoxazin-4-yl)-N-methyl-N-[1-{3'-[(1-methylethyl)oxy]-4-biphenylyl}-2-(4-morpholinyl)ethyl]acetamide;

1,1-dimethylethyl {4'-[1-[[(6,7-dichloro-3-oxo-2,3-dihydro-4H-1,4-benzoxazin-4-yl)acetyl](methyl)amino]-2-(4-morpholinyl)ethyl]-4-biphenylyl}carbamate;

[N-[1-(4-biphenylyl)-2-(1-pyrrolidinyl)ethyl]-N-methyl-2-[7-methyl-6-(methyloxy)-3-oxo-2,3-dihydro-4H-1,4-benzoxazin-4-yl]acetamide;

N-[1-(4-biphenylyl)-2-(4-morpholinyl)ethyl]-N-methyl-2-[7-methyl-6-(methyloxy)-3-oxo-2,3-dihydro-4H-1,4-benzoxazin-4-yl]acetamide;

N-[1-(4-biphenylyl)-1-methyl-2-(1-pyrrolidinyl)ethyl]-2-(6,7-dichloro-3-oxo-2,3-dihydro-4H-1,4-benzoxazin-4-yl)-N-methylacetamide;

(S) N-[1-(4-biphenylyl)-2-(4-morpholinyl)ethyl]-2-(6,7-dichloro-3-oxo-2,3-dihydro-4H-1,4-benzoxazin-4-yl)-N-methylacetamide;

Ethyl 4-{2-[[1-(4-biphenylyl)-2-(1-pyrrolidinyl)ethyl](methyl)amino]-2-oxoethyl}-3-oxo-3,4-dihydro-2H-1,4-benzoxazine-6-carboxylate;

Ethyl 4-{2-[[1-(4-biphenylyl)-2-(4-morpholinyl)ethyl](methyl)amino]-2-oxoethyl}-3-oxo-3,4-dihydro-2H-1,4-benzoxazine-6-carboxylate;

4-{2-[[1-(4-biphenylyl)-2-(1-pyrrolidinyl)ethyl] (methyl)amino]-2-oxoethyl}-N-methyl-3-oxo-3,4-dihydro-2H-1,4-benzoxazine-6-carboxamide;

4-{2-[[1-(4-biphenylyl)-2-(1-pyrrolidinyl)ethyl] (methyl)amino]-2-oxoethyl}-N,N-dimethyl-3-oxo-3,4-dihydro-2H-1,4-benzoxazine-6-carboxamide;

4-{2-[[1-(4-biphenylyl)-2-(1-pyrrolidinyl)ethyl] (methyl)amino]-2-oxoethyl}-N-ethyl-3-oxo-3,4-dihydro-2H-1,4-benzoxazine-6-carboxamide;

4-{2-[[1-(4-biphenylyl)-2-(1-pyrrolidinyl)ethyl] (methyl)amino]-2-oxoethyl}-3-oxo-3,4-dihydro-2H-1,4-benzoxazine-6-carboxamide;

4-{2-[[1-(4-biphenylyl)-2-(4-morpholinyl)ethyl] (methyl)amino]-2-oxoethyl}-3-oxo-3,4-dihydro-2H-1,4-benzoxazine-6-carboxamide;

2-(6,7-dichloro-3-oxo-2,3-dihydro-4H-1,4-benzoxazin-4-yl)-N-[1-(3-fluoro-4-biphenylyl)-2-(4-morpholinyl)ethyl]-N-methylacetamide;

N-[1-(3-chloro-4-biphenylyl)-2-(4-morpholinyl)ethyl]-2-(6,7-dichloro-3-oxo-2,3-dihydro-4H-1,4-benzoxazin-4-yl)-N-methylacetamide;

N-[1-(4-biphenylyl)-2-(4-morpholinyl)ethyl]-N-methyl-2-{3-oxo-6-[(trifluoromethyl)oxy]-2,3-dihydro-4H-1,4-benzoxazin-4-yl}acetamide; and N-[1-(4-biphenylyl)-2-(1-pyrrolidinyl)ethyl]-N-methyl-2-[7-(methyloxy)-3-oxo-6-(trifluoromethyl)-2,3-dihydro-4H-1,4-benzoxazin-4-yl]acetamide; and or a pharmaceutically acceptable salt thereof.

6. A compound of claim 1 selected from:

4'-[(1R)-1-[[(6,7-dichloro-3-oxo-2,3-dihydro-4H-1,4-benzoxazin-4-yl)acetyl] (methyl)amino]-2-(1-pyrrolidinyl)ethyl]-3-biphenylcarboxamide; and 4'-[(1R)-1-[[(6,7-dichloro-3-oxo-2,3-dihydro-4H-1,4-benzoxazin-4-yl)acetyl] (methyl)amino]-2-(1-pyrrolidinyl)ethyl]-4-biphenylcarboxamide;

or a pharmaceutically acceptable salt thereof.

7. A compound of claim 1 which is 4'-[(1R)-1-[[(6,7-dichloro-3-oxo-2,3-dihydro-4H-1,4-benzoxazin-4-yl)acetyl](methyl)amino]-2-(1-pyrrolidinyl)ethyl]-3-biphenylcarboxamide Trifluoroacetate salt.

8. A pharmaceutical composition comprising a compound of formula (I) claim 1 and a pharmaceutically acceptable carrier or excipient.

9. A method of treating congestive heart failure, stroke, ischemic heart disease, angina, myocardial ischemia, overactive bladder, or cardiac arrhythmia which comprises administering to a patient in need thereof, a compound of Formula I of claim 1.

10. A method of treating hypertension which comprises administering to a patient in need thereof, a compound of Formula I of claim 1.

* * * * *